(12) United States Patent  (10) Patent No.: US 9,315,494 B2
Moslin et al.  (45) Date of Patent: Apr. 19, 2016

(54) ALKYL-AMIDE-SUBSTITUTED PYRIDYL COMPOUNDS USEFUL AS MODULATORS OF IL-12, IL-23 AND/OR IFNα RESPONSES

(71) Applicant: Bristol-Myers Squibb Company, Princeton, NJ (US)

(72) Inventors: Ryan M. Moslin, Princeton, NJ (US); Shuqun Lin, Newtown, PA (US); David S. Weinstein, East Windsor, NJ (US); Stephen T. Wrobleski, Flemington, NJ (US); Yanlei Zhang, Princeton Junction, NJ (US); John S. Tokarski, Princeton, NJ (US); Michael E. Mertzman, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/441,193

(22) PCT Filed: Nov. 7, 2013

(86) PCT No.: PCT/US2013/068842
§ 371 (c)(1),
(2) Date: May 7, 2015

(87) PCT Pub. No.: WO2014/074660
PCT Pub. Date: May 15, 2014

(65) Prior Publication Data
US 2015/0307483 A1  Oct. 29, 2015

Related U.S. Application Data

(60) Provisional application No. 61/723,854, filed on Nov. 8, 2012.

(51) Int. Cl.
*C07D 401/12* (2006.01)
*A61K 31/444* (2006.01)
*C07D 413/14* (2006.01)
*C07D 401/14* (2006.01)
*C07D 405/14* (2006.01)
*C07D 417/14* (2006.01)
*C07D 471/04* (2006.01)

(52) U.S. Cl.
CPC ............ *C07D 413/14* (2013.01); *C07D 401/12* (2013.01); *C07D 401/14* (2013.01); *C07D 405/14* (2013.01); *C07D 417/14* (2013.01); *C07D 471/04* (2013.01)

(58) Field of Classification Search
None
See application file for complete search history.

(56) References Cited

U.S. PATENT DOCUMENTS

2011/0230467 A1  9/2011  Shirakami et al.

FOREIGN PATENT DOCUMENTS

WO  WO 2009/044162  4/2009
WO  WO 2012/062704  5/2012

*Primary Examiner* — Zinna Northington Davis
(74) *Attorney, Agent, or Firm* — Elliott Korsen

(57) ABSTRACT

Compounds having the following formula (I): or a stereoisomer or pharmaceutically-acceptable salt thereof, where $R^1$, $R^2$, $R^3$, $R^4$, and $R^5$ are as defined herein, are useful in the modulation of IL-12, IL-23 and/or IFNα, by acting on Tyk-2 to cause signal transduction inhibition.

(I)

11 Claims, No Drawings

ALKYL-AMIDE-SUBSTITUTED PYRIDYL COMPOUNDS USEFUL AS MODULATORS OF IL-12, IL-23 AND/OR IFNα RESPONSES

CONTINUING DATA

This application is a 371 of PCT/US2013/068842 filed Nov. 7, 2013 which claims benefit of 61/723,854 filed Nov. 8, 2012.

FIELD OF THE INVENTION

This invention relates to compounds useful in the modulation of IL-12, IL-23 and/or IFNα by acting on Tyk-2 to cause signal transduction inhibition. Provided herein are alkyl amide-substituted pyridyl compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal.

BACKGROUND OF THE INVENTION

The heterodimeric cytokines interleukin (IL)-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", *Semin. Immunol.*, 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", *Eur. J. Immunol.*, 26:1217-1221 (1996); Schroder, K. et al., "Interferon-gamma: an overview of signals, mechanisms and functions", *J. Leukoc. Biol.*, 75(2):163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", *J. Immunol.*, 184:4605-4609 (2010); Hong, K. et al., "IL-12, independently of IFN-gamma, plays a crucial role in the pathogenesis of a murine psoriasis like skin disorder", *J. Immunol.*, 162:7480-7491 (1999); Hue, S. et al., "Interleukin-23 drives innate and T cell-mediated intestinal inflammation", *J. Exp. Med.*, 203:2473-2483 (2006); Cua, D. J. et al., "Interleukin-23 rather than interleukin-12 is the critical cytokine for autoimmune inflammation of the brain", *Nature*, 421:744-748 (2003); Murphy, C. A. et al., "Divergent pro- and anti-inflammatory roles for IL-23 and IL-12 in joint autoimmune inflammation", *J. Exp. Med.*, 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", *J. Exp. Med.*, 199:125-130 (2004); Tzartos, J. S. et al., "Interleukin-17 production in central nervous system infiltrating T cells and glial cells is associated with active disease in multiple sclerosis", *Am. J. Pathol.*, 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", *Mod. Rheumatol.*, 17:220-223 (2007)), and T cells from lupus patients have a predominant Th1 phenotype (Tucci, M. et al., "Overexpression of interleukin-12 and T helper 1 predominance in lupus nephritis", *Clin. Exp. Immunol.*, 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", *Gut*, 60:1739-1753 (2011); Tao, J. H. et al., "Meta-analysis of TYK2 gene polymorphisms association with susceptibility to autoimmune and inflammatory diseases", *Mol. Biol. Rep.*, 38:4663-4672 (2011); Cho, J. H. et al., "Recent insights into the genetics of inflammatory bowel disease", *Gastroenterology*, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", *Lancet*, 371:1665-1674 (2008); Sandborn, W. J. et al., "Ustekinumab Crohn's Disease Study Group. A randomized trial of Ustekinumab, a human interleukin-12/23 monoclonal antibody, in patients with moderate-to-severe Crohn's disease", *Gastroenterology*, 135:1130-1141 (2008); Gottlieb, A. et al., "Ustekinumab, a human interleukin 12/23 monoclonal antibody, for psoriatic arthritis: randomized, double-blind, placebo-controlled, crossover trial", *Lancet*, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.*, 6:40-49 (2010)).

In patients with systemic lupus erythematosus (SLE), a potentially fatal autoimmune disease, increased serum levels of interferon (IFN)α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.*, 197:711-723 (2003); Peterson, K. S. et al., "Characterization of heterogeneity in the molecular pathogenesis of lupus nephritis from transcriptional profiles of laser-captured glomeruli", *J. Clin. Invest.*, 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus*, 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J. Exp. Med.*, 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.*, 6:683-692 (2010); Sandling, J. K. et al., "A candidate gene study of the type I interferon pathway implicates IKBKE and IL8 as risk loci for SLE", *Eur. J. Hum. Genet.*, 19:479-484 (2011)). In addition to lupus, there is evidence that aberrant activation of type I interferon-mediated pathways are important in the pathobiology of other autoimmune diseases such as Sjögren's syndrome and scleroderma (Båve, U. et al., "Activation of the type I interferon system in primary Sjögren's syndrome: a possible etiopathogenic mechanism", *Arthritis Rheum.*, 52:1185-1195 (2005); Kim, D. et al., "Induction of interferon-alpha by scleroderma sera containing autoantibodies to topoisomerase I: association of higher interferon-alpha activity with lung fibrosis", *Arthritis Rheum.*, 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In vivo", *J. Immunol.*, 187:181-189 (2011); Prchal-Murphy, M. et al., "TYK2 kinase activity is required for functional type I interferon responses in vivo", *PLoS One*, 7:e39141 (2012)) and humans (Minegishi, Y. et al., "Human tyrosine kinase 2 deficiency reveals its requisite roles in multiple cytokine signals involved in innate and acquired immunity", *Immunity*, 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In vivo", *J. Immunol.*, 187:181-189 (2011); Oyamada, A. et al., "Tyrosine kinase 2 plays critical roles in the pathogenic CD4 T cell responses for the development of experimental autoimmune encephalomyelitis", *J. Immunol.*, 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility", *Brain*, 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci", *Am. J. Hum. Genet.*, 90:636-647 (2012); Graham, D. et al., "Association of polymorphisms across the tyrosine kinase gene, TYK2 in UK SLE families", *Rheumatology (Oxford)*, 46:927-930 (2007); Eyre, S. et al., "High-density genetic mapping identifies new susceptibility loci for rheumatoid arthritis", *Nat. Genet.*, 44:1336-1340 (2012)).

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I, infra, that which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating proliferative, metabolic, allergic, autoimmune and inflammatory diseases, comprising administering to a host in need of such treatment a therapeutically effective amount of at least one of the compounds of the present invention.

A preferred embodiment is a method for treating inflammatory and autoimmune diseases or diseases. For the purposes of this invention, an inflammatory and autoimmune disease or disorder includes any disease having an inflammatory or autoimmune component.

An alternate preferred embodiment is a method for treating metabolic diseases, including type 2 diabetes and atherosclerosis.

The present invention also provides the use of the compounds of the present invention for the manufacture of a medicament for the treatment of cancers.

The present invention also provides the compounds of the present invention for use in therapy.

These and other features of the invention will be set forth in the expanded form as the disclosure continues.

DETAILED DESCRIPTION OF THE EMBODIMENTS OF THE INVENTION

Provided herein is at least one chemical entity chosen from compounds of formula I:

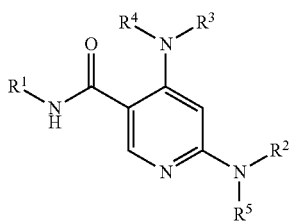

or stereoisomers, tautomers, pharmaceutically-acceptable salts, solvates, or prodrugs thereof, wherein:

$R^1$ is $C_{1-3}$alkyl optionally substituted by 0-7 $R^{1a}$;

$R^{1a}$ at each occurrence is independently hydrogen, deuterium, F, Cl, Br, or CN;

$R^2$ is a 5-14 membered heterocycle containing 1-4 heteroatoms selected from N, O, and S, substituted with 0-4 $R^{2a}$;

$R^{2a}$ at each occurrence is independently hydrogen, =O, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, $CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle substituted with 0-1 $R^a$, —$(CH_2)_r$-5-7 membered heteroaryl comprising carbon atoms and 1-4 heteroatoms selected from N, O, and $S(O)_p$ substituted with 0-2 $R^a$; and —$(CH_2)_r$-5-7 membered heterocycle comprising carbon atoms or 1-4 heteroatoms selected from N, O, and $S(O)_p$ substituted with 0-2 $R^a$;

$R^3$ is $C_{3-10}$ cycloalkyl substituted with 0-3 $R^{3a}$, $C_{6-10}$ aryl substituted with 0-3 $R^{3a}$, a 5-10 membered heterocycle containing 1-4 heteroatoms selected from N, O, and S, substituted with 0-3 $R^{3a}$, or a 5-10 membered heteroaryl containing 1-4 heteroatoms selected from N, O, and S, substituted with 0-3 $R^{3a}$;

$R^{3a}$ at each occurrence is independently hydrogen, =O, halo, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CH_2)_r$-3-14 membered carbocycle substituted with 0-3 $R^a$, a —$(CH_2)_r$-5-7 membered heteroaryl comprising carbon atoms and 1-4 heteroatoms selected from N, S or O substituted with 0-3 $R^a$, or a —$(CH_2)_r$-5-10 membered heterocycle comprising carbon atoms and 1-4 heteroatoms selected from N, O, and $S(O)_p$ substituted with 0-3 $R^a$;

or two $R^{3a}$, together with the atoms to which they are attached, combine to form a fused ring wherein said ring is selected from phenyl and a 5-7 membered heterocycle or heteroaryl, each comprising carbon atoms and 1-4 heteroatoms selected from N, S or O;

$R^4$ and $R^5$ are independently hydrogen, $C_{1-4}$ alkyl substituted with 0-1 $R^f$, $(CH_2)_r$-phenyl substituted with 0-3 $R^d$, or a —$(CH_2)$-5-7 membered heterocycle comprising carbon atoms and 1-4 heteroatoms selected from N, O, and $S(O)_p$;

$R^{11}$ at each occurrence is independently hydrogen, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$, or —$(CH_2)_r$-5-7 membered heterocycle comprising carbon atoms and 1-4 heteroatoms selected from N, O, and $S(O)_p$ substituted with 0-3 $R^d$;

$R^a$ at each occurrence is independently hydrogen, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle, —$(CH_2)_r$-5-7 membered heteroaryl comprising carbon atoms and 1-4 heteroatoms selected from N, O, and $S(O)_p$ substituted with 0-3 $R^f$; or —$(CH_2)_r$-5-7 membered heterocycle comprising carbon atoms and 1-4 heteroatoms selected from N, O, and $S(O)_p$ substituted with 0-3 $R^f$, alternatively two $R^a$ on adjacent or the same carbon atom form a cyclic acetal of the formula —O—$(CH_2)_n$—O—, or —O—$CF_2$—O—, wherein n is selected from 1 or 2;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle comprising carbon atoms and 1-4 heteroatoms selected from N, O, and $S(O)_p$ substituted with 0-3 $R^f$, or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$, $(CH_2)_r$-phenyl substituted with 0-3 $R^f$; or $R^d$ at each occurrence is independently hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl, or $(CH_2)_r$-phenyl substituted with 0-3 $R^f$;

$R^e$ is selected from hydrogen, $C_{1-6}$ alkyl, $C_{3-6}$ cycloalkyl, and $(CH_2)_r$-phenyl substituted with 0-3 $R^f$;

$R^f$ independently at each occurrence is hydrogen, halo, CN, $NH_2$, OH, $C_{3-6}$ cycloalkyl, $CF_3$, $O(C_{1-6}$alkyl) or a —$(CH_2)_r$-5-7 membered heteroaryl comprising carbon atoms and 1-4 heteroatoms selected from N, O, and $S(O)_p$;

p is 0, 1, or 2; and r is 0, 1, 2, 3, or 4;

provided that the compound of formula (I) is not:

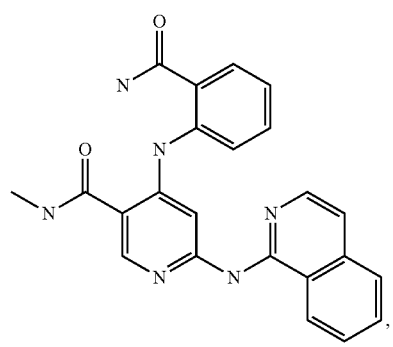

-continued
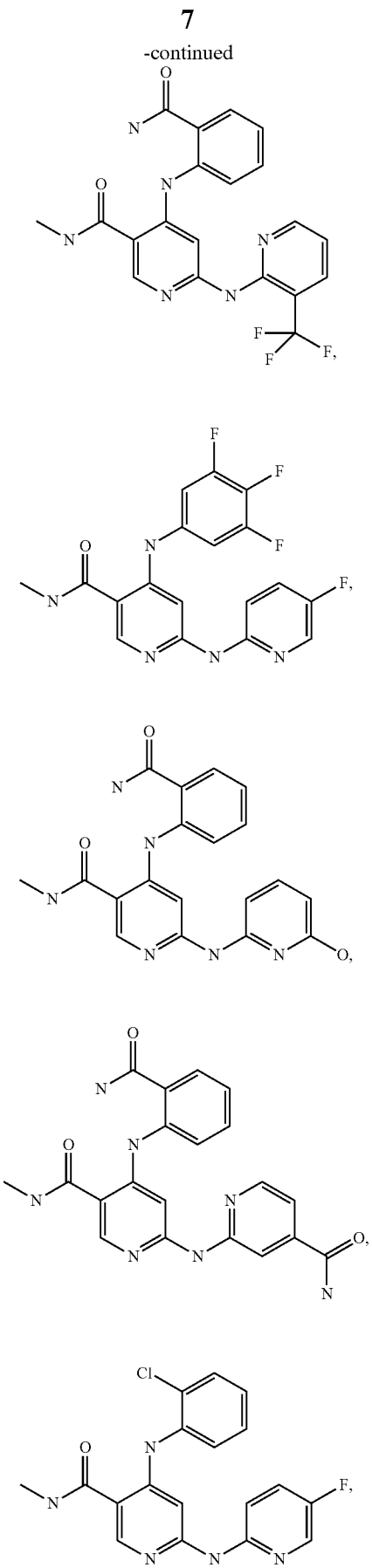
-continued
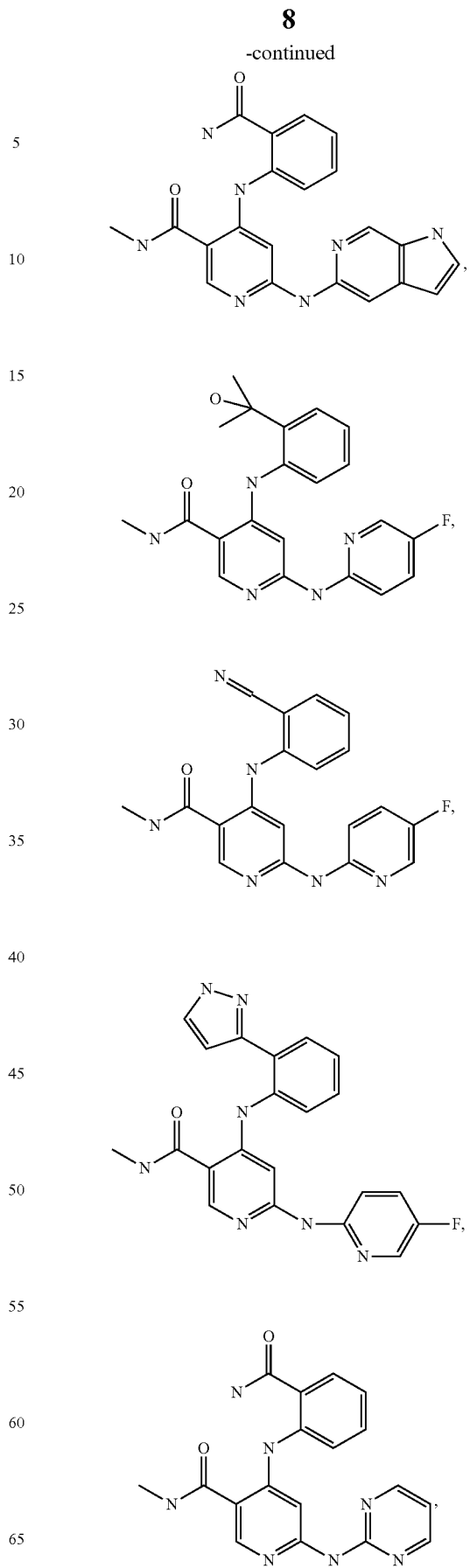

9
-continued
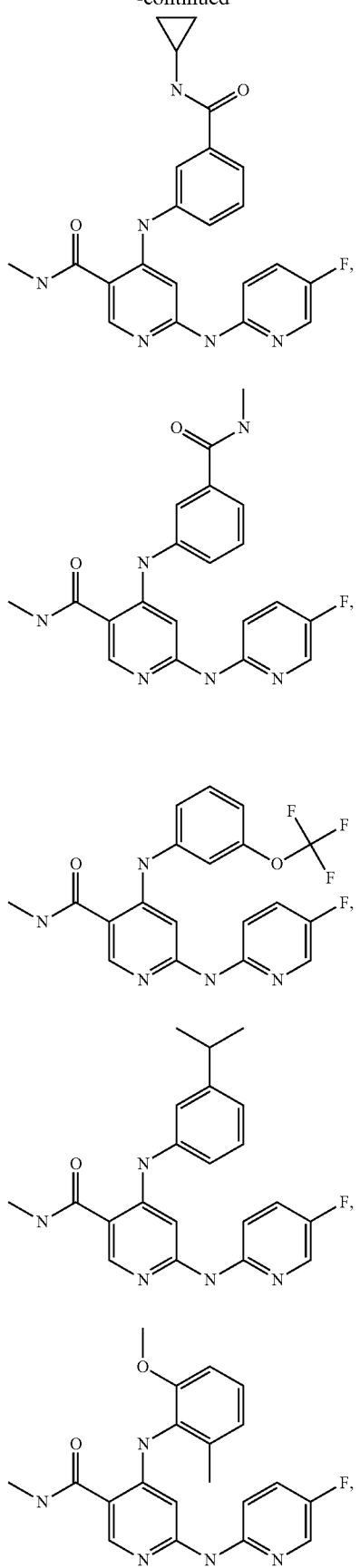
10
-continued
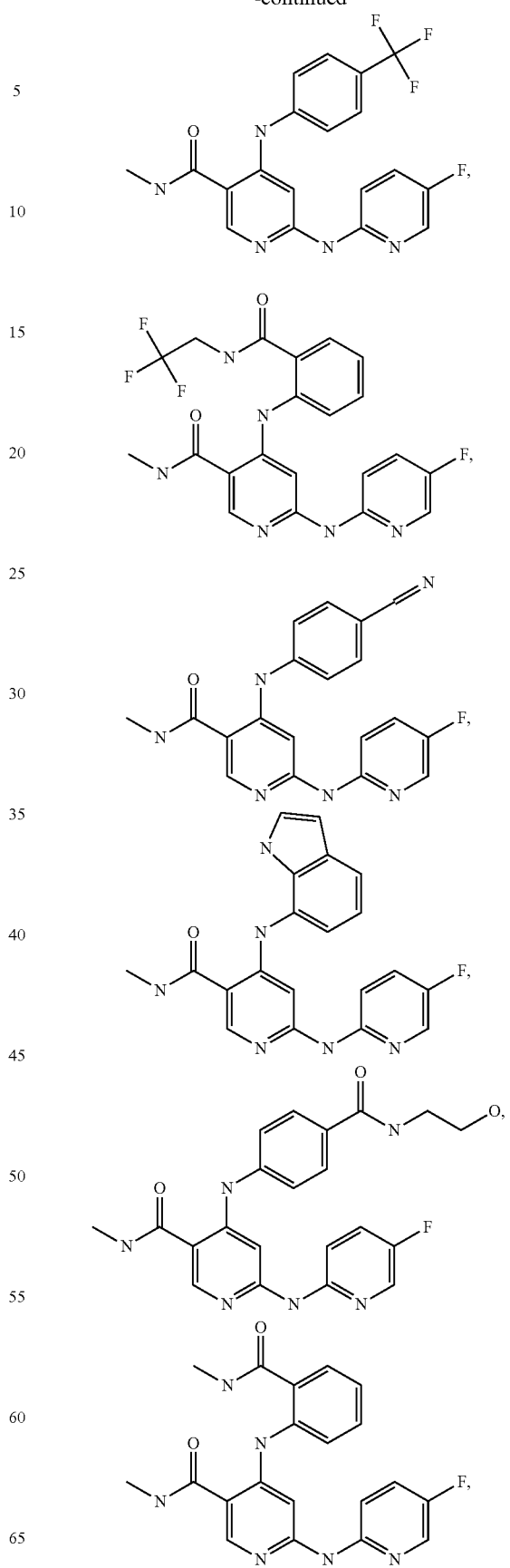

-continued
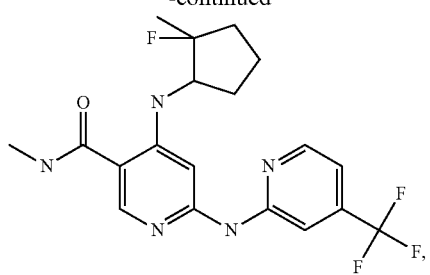
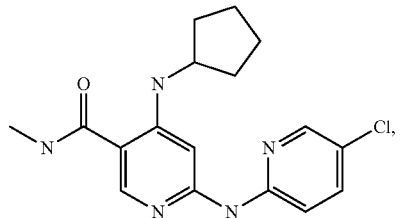
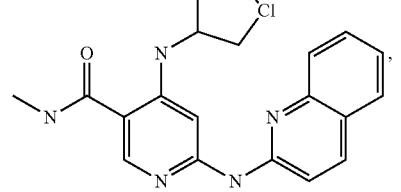
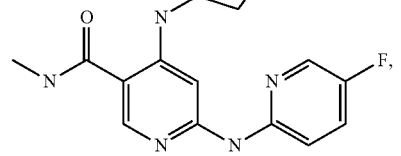
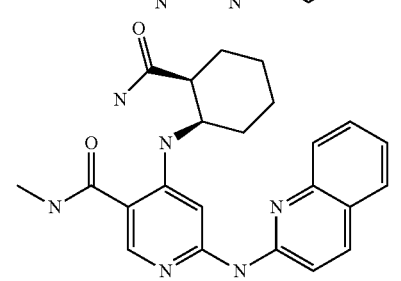
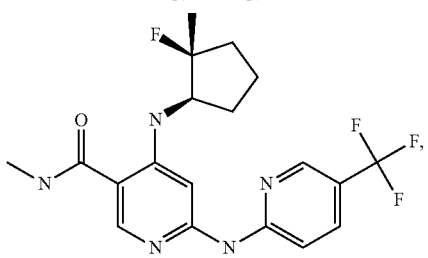
Chiral
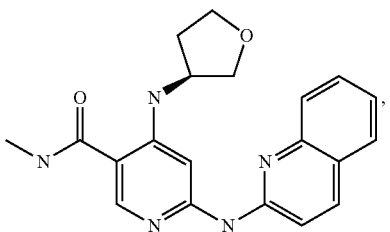
-continued
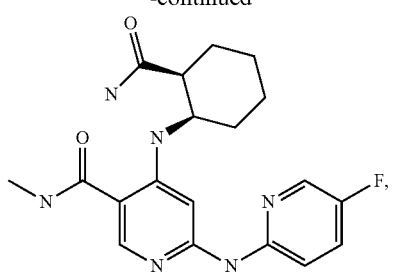
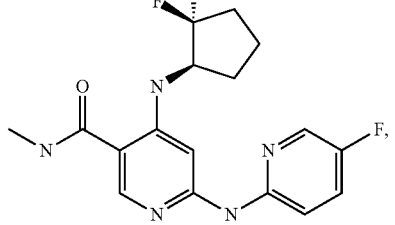
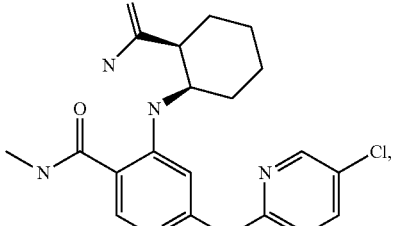
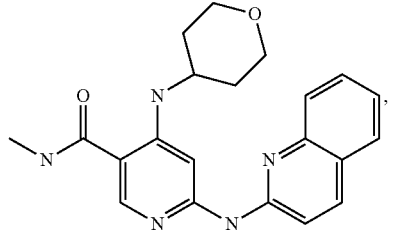
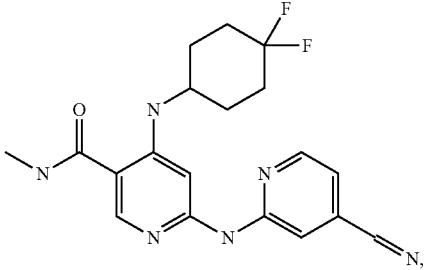
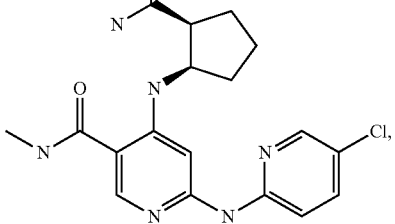

-continued

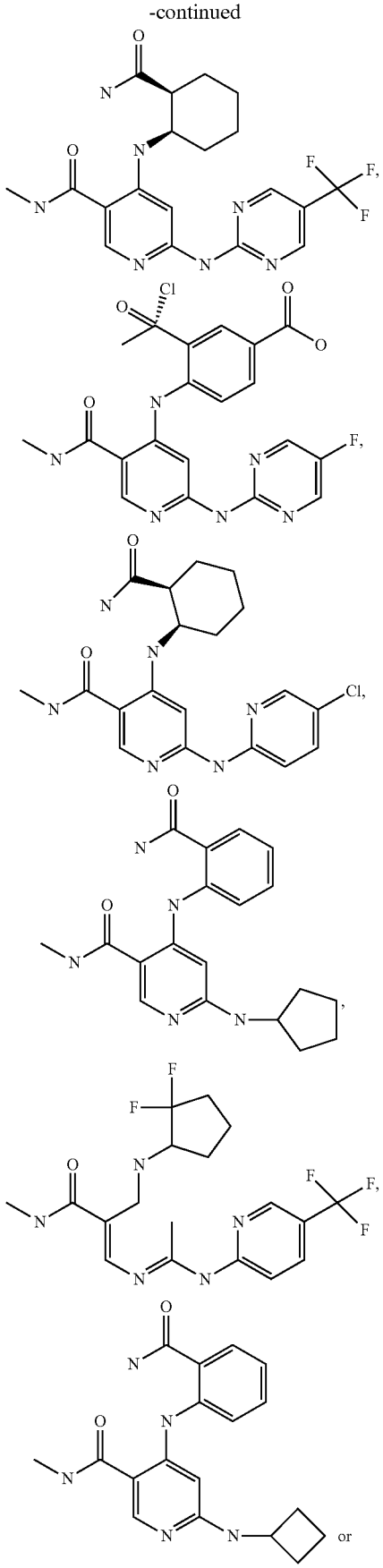

-continued

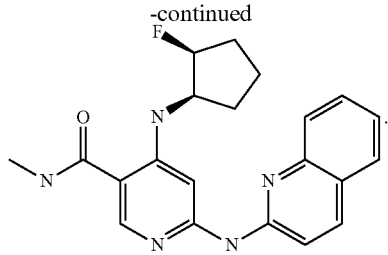

In another embodiment are provided compounds of formula I or stereoisomers, tautomers, pharmaceutically-acceptable salts, solvates, or prodrugs thereof, wherein:

$R^1$ is $C_{1-3}$alkyl optionally substituted by 0-7 $R^{1a}$;

$R^{1a}$ at each occurrence is independently hydrogen, deuterium, F, Cl, Br, $CF_3$ or CN;

$R^2$ is a 5-14 membered heterocycle containing 1-4 heteroatoms selected from N, O, and S, substituted with 0-4 $R^{2a}$;

$R^{2a}$ at each occurrence is independently hydrogen, =O, halo, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle substituted with 0-1 $R^a$, —$(CH_2)_r$-5-7 membered heteroaryl comprising carbon atoms and 1-4 heteroatoms selected from N, O, and $S(O)_p$ substituted with 0-2 $R^a$; and —$(CH_2)_r$-5-7 membered heterocycle comprising carbon atoms or 1-4 heteroatoms selected from N, O, and $S(O)_p$ substituted with 0-2 $R^a$;

$R^3$ is $C_{3-10}$ cycloalkyl substituted with 0-3 $R^{3a}$, $C_{6-10}$ aryl substituted with 0-3 $R^{3a}$, a 5-10 membered heterocycle containing 1-4 heteroatoms selected from N, O, and S, substituted with 0-3 $R^{3a}$, or a 5-10 membered heteroaryl containing 1-4 heteroatoms selected from N, O, and S, substituted with 0-3 $R^{3a}$;

$R^{3a}$ at each occurrence is independently hydrogen, =O, halo, $OCF_3$, $OCHF_2$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CH_2)_r$-3-14 membered carbocycle substituted with 0-3 $R^a$, a —$(CH_2)_r$-5-7 membered heteroaryl comprising carbon atoms and 1-4 heteroatoms selected from N, S or O substituted with 0-3 $R^a$, or a —$(CH_2)_r$-5-10 membered heterocycle comprising carbon atoms and 1-4 heteroatoms selected from N, O, and $S(O)_p$ substituted with 0-3 $R^a$;

or two $R^{3a}$, together with the atoms to which they are attached, combine to form a fused ring wherein said ring is selected from phenyl and a 5-7 membered heterocycle or heteroaryl, each comprising carbon atoms and 1-4 heteroatoms selected from N, S or O;

$R^4$ and $R^5$ are independently hydrogen, $C_{1-4}$ alkyl substituted with 0-1 $R^f$, $(CH_2)_r$-phenyl substituted with 0-3 $R^d$, or a —$(CH_2)$-5-7 membered heterocycle comprising carbon atoms and 1-4 heteroatoms selected from N, O, and $S(O)_p$;

$R^{11}$ at each occurrence is independently hydrogen, $C_{1-6}$ alkyl substituted with 0-3 $R^f$, $CF_3$, $C_{3-10}$ cycloalkyl substituted with 0-3 $R^f$, $(CH)_r$-phenyl substituted with 0-3 $R^d$, or —(CH$_2$)$_r$-5-7 membered heterocycle comprising carbon atoms and 1-4 heteroatoms selected from N, O, and S(O)$_p$ substituted with 0-3 R$^d$;

R$^a$ at each occurrence is independently hydrogen, =O, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle, —(CH$_2$)$_r$-5-7 membered heteroaryl comprising carbon atoms and 1-4 heteroatoms selected from N, O, and S(O)$_p$ substituted with 0-3 R$^f$; or —(CH$_2$)$_r$-5-7 membered heterocycle comprising carbon atoms and 1-4 heteroatoms selected from N, O, and S(O)$_p$ substituted with 0-3 R$^f$, alternatively two R$^a$ on adjacent or the same carbon atom form a cyclic acetal of the formula —O—(CH$_2$)$_n$—O—, or —O—CF$_2$—O—, wherein n is selected from 1 or 2;

R$^b$ is hydrogen, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle comprising carbon atoms and 1-4 heteroatoms selected from N, O, and S(O)$_p$ substituted with 0-3 R$^f$, or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$, (CH$_2$)$_r$-phenyl substituted with 0-3 R$^f$; or R$^d$ at each occurrence is independently hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl, or (CH$_2$)$_r$-phenyl substituted with 0-3 R$^f$;

R$^e$ is selected from hydrogen, C$_{1-6}$ alkyl, C$_{3-6}$ cycloalkyl, and (CH$_2$)$_r$-phenyl substituted with 0-3 R$^f$;

R$^f$ independently at each occurrence is hydrogen, halo, CN, NH$_2$, NH(C$_{1-6}$alkyl), N(C$_{1-6}$alkyl)$_2$, OH, C$_{3-6}$ cycloalkyl, CF$_3$, O(C$_{1-6}$alkyl), phenyl;

or R$^f$ independently at each occurrence is an optionally substituted —(CH$_2$)$_r$-5-10 membered heteroaryl comprising carbon atoms and 1-4 heteroatoms selected from N, O, and S(O) or C$_{3-6}$ cycloalkyl, each group optionally substituted with halo, CN, CF$_3$, C$_{1-6}$ alkyl or O(C$_{1-6}$alkyl);

p is 0, 1, or 2; and r is 0, 1, 2, 3, or 4.

In another embodiment, there is provided a compound of formula I, or stereoisomers, tautomers, pharmaceutically-acceptable salts, solvates, or prodrugs thereof, R$^2$ is pyridyl, pyrimidinyl, pyridazinyl, pyrazinyl, quinolinyl, pyrrolopyridinyl, pyrazolyl, naphthyridinyl, pyrazopyrimidinyl, triazolyl, thiazolyl, thiadiazolyl, isothiadiazolyl, oxazolyl, isooxazolyl, oxdiazolyl, isoxadiazolyl or imidazolyl, each group substituted by 0-4 groups selected from R$^{2a}$. Especially preferred are embodiments providing compounds wherein each R$^2$ has a nitrogen atom adjacent to the point of connection to the pyridyl core ring.

In another embodiment, there is provided a compound of formula I, or stereoisomers, tautomers, pharmaceutically-acceptable salts, solvates, or prodrugs thereof, wherein both R$^4$ and R$^5$ are hydrogen.

In another embodiment, there is provided a compound of formula I, wherein:

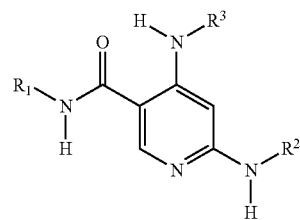

or stereoisomers, tautomers, pharmaceutically-acceptable salts, solvates, or prodrugs thereof, wherein:

R$^1$ is C$_{1-3}$alkyl substituted by 0-7 R$^{1a}$;

R$^{1a}$ at each occurrence is independently hydrogen or deuterium;

R$^2$ is pyridyl, pyrimidinyl, pyridazinyl, pyrazinyl, quinolinyl, pyrrolopyridinyl, pyrazolyl, pyrazopyrimidinyl, triazolyl, thiazolyl, thiadiazolyl, isothiadiazolyl, oxazolyl, isooxazolyl, oxdiazolyl, isoxadiazolyl, and imidazolyl, each group substituted by 0-4 groups selected from R$^{2a}$ (especially where R$^2$ is pyridyl, pyrimidinyl, pyridazinyl, pyrazinyl, quinolinyl, or pyrrolopyridinyl, each groups substituted by 0-4 R$^{2a}$);

R$^{2a}$ at each occurrence is independently halo, CN, —(CH$_2$)$_r$OR$^b$, —(CH$_2$)$_r$C(O)R$^b$, —(CH$_2$)$_r$C(O)NR$^{11}$R$^{11}$, —S(O)$_p$NR$^{11}$R$^{11}$, —C$_{1-6}$alkyl substituted with 0-3 R$^a$, C$_{1-6}$ haloalkyl, —(CH$_2$)$_r$-3-14 membered carbocycle substituted with 0-1 R$^a$, a —(CH$_2$)$_r$-5-7 membered heteroaryl comprising carbon atoms and 1-4 heteroatoms selected from N, O, and S(O)$_p$ substituted with 0-2 R$^a$; or a —(CH$_2$)$_r$-5-7 membered heterocycle comprising carbon atoms and 1-4 heteroatoms selected from N, O, and S(O)$_p$ substituted with 0-2 R$^a$;

R$^3$ is C$_{3-10}$ cycloalkyl substituted with 0-3 R$^{3a}$, a C$_{6-10}$ aryl substituted with 0-3 R$^{3a}$, or a 5-10 membered heterocycle containing 1-4 heteroatoms selected from N, O, and S, substituted with 0-3 R$^{3a}$;

R$^{3a}$ at each occurrence is independently hydrogen, halo, OCF$_3$, CF$_3$, CHF$_2$, CN, —(CH$_2$)$_r$OR$^b$, —(CH$_2$)$_r$SR$^b$, —(CH$_2$)$_r$C(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, a —(CH$_2$)$_r$-3-14 membered carbocycle substituted with 0-3 R$^a$, a —(CH$_2$)$_r$-5-7 membered heteroaryl comprising carbon atoms and 1-4 heteroatoms selected from N, S or O substituted with 0-3 R$^a$, or a —(CH$_2$)$_r$-5-10 membered heterocycle comprising carbon atoms and 1-4 heteroatoms selected from N, O, and S(O)$_p$ substituted with 0-3 R$^a$;

or two R$^{3a}$, together with the atoms to which they are attached, combine to form a fused ring wherein that ring is selected from phenyl, or a 5-7 membered heterocycle or heteroaryl, each comprising carbon atoms and 1-4 heteroatoms selected from N, S or O; and R$^{11}$ at each occurrence is independently hydrogen, C$_{1-4}$ alkyl substituted with 0-3 R$^f$, or C$_{3-10}$ cycloalkyl substituted with 0-1 R$^f$.

In another, preferred embodiment, there is provided a compound of formula I, or stereoisomers, tautomers, pharmaceutically-acceptable salts, solvates, or prodrugs thereof, wherein:

R$^a$ at each occurrence is independently hydrogen, =O, F, —(CH$_2$)$_r$OR$^b$, C$_{1-6}$ alkyl substituted with 0-3 R$^f$;

R$^b$ at each occurrence is independently hydrogen, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle comprising carbon atoms and 1-4 heteroatoms selected from N, O, and S(O)$_p$ substituted with 0-3 R$^f$, or (CH$_2$)$_r$-phenyl substituted with 0-3 R$^d$;

R<sup>c</sup> at each occurrence is independently C$_{1-6}$ alkyl substituted with 0-3 R$^f$;

R$^d$ at each occurrence is independently hydrogen, F or —OH;

R$^f$ at each occurrence is independently hydrogen, halo, CN, OH, O(C$_{1-6}$alkyl), or optionally substituted imidazolyl;

p is 0, 1 or 2; and r is 0, 1 or 2.

In another embodiment, there is provided a compound, or a or stereoisomers, tautomers, pharmaceutically-acceptable salts, solvates, or prodrugs thereof, wherein:

R$^1$ is C$_{1-3}$alkyl substituted by 0-7 deuterium atoms;

R$^2$ is pyridyl, pyrimidinyl, pyridazinyl, pyrazinyl, quinolinyl, pyrrolopyridinyl, naphthyridinyl, pyrazolyl, pyrazopyrimidinyl, triazolyl, thiazolyl, thiadiazolyl, isothiadiazolyl, oxazolyl, isooxazolyl, oxdiazolyl, isoxadiazolyl, and imidazolyl, each group substituted by 0-4 groups selected from R$^{2a}$ (especially where R$^2$ is pyrazolyl, pyridyl, pyrimidinyl, pyridazinyl, pyrazinyl, naphthyridinyl, quinolinyl, or pyrrolopyridinyl, each groups substituted by 0-4 R$^{2a}$);

R$^{2a}$ at each occurrence is independently halo, CN, —(CH$_2$)$_r$OR$^b$, —(CH$_2$)$_r$C(O)R$^b$, —(CH$_2$)$_r$C(O)NR$^{11}$R$^{11}$, —(CH$_2$)$_r$NR$^{11}$R$^{11}$, —S(O)$_p$NR$^{11}$R$^{11}$, —C$_{1-6}$alkyl substituted with 0-3 R$^a$, C$_{1-6}$ haloalkyl, —(CH$_2$)$_r$-3-14 membered carbocycle substituted with 0-1 R$^a$, a —(CH$_2$)$_r$-5-10 membered heteroaryl comprising carbon atoms and 1-4 heteroatoms selected from N, O, and S(O)$_p$ substituted with 0-2 R$^a$; or a —(CH$_2$)$_r$-5-7 membered heterocycle comprising carbon atoms and 1-4 heteroatoms selected from N, O, and S(O)$_p$ substituted with 0-2 R$^a$;

R$^3$ is C$_{3-10}$ cycloalkyl substituted with 0-3 R$^{3a}$, a C$_{6-10}$ aryl substituted with 0-3 R$^{3a}$, or a 5-10 membered heterocycle containing 1-4 heteroatoms selected from N, O, and S, substituted with 0-3 R$^{3a}$;

R$^{3a}$ at each occurrence is independently hydrogen, halo, OCF$_3$, OCHF$_2$, CF$_3$, CHF$_2$, CN, —(CH$_2$)$_r$OR$^b$, —(CH$_2$)$_r$SR$^b$, —(CH$_2$)$_r$C(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, a —(CH$_2$)$_r$-3-14 membered carbocycle substituted with 0-3 R$^a$, a —(CH$_2$)$_r$-5-7 membered heteroaryl comprising carbon atoms and 1-4 heteroatoms selected from N, S or O substituted with 0-3 R$^a$, or a —(CH$_2$)$_r$-5-10 membered heterocycle comprising carbon atoms and 1-4 heteroatoms selected from N, O, and S(O)$_p$ substituted with 0-3 R$^a$;

or two R$^{3a}$, together with the atoms to which they are attached, combine to form a fused ring wherein that ring is selected from phenyl, or a 5-7 membered heterocycle or heteroaryl, each comprising carbon atoms and 1-4 heteroatoms selected from N, S or O; and R$^{11}$ at each occurrence is independently hydrogen;

or R$^{11}$ at each occurrence is independently phenyl, C$_{1-6}$ alkyl, or C$_{3-10}$ cycloalkyl, each group substituted with 0-3 R$^f$.

In a more preferred embodiment, compounds of formula (I), or stereoisomers, tautomers, pharmaceutically-acceptable salts, solvates, or prodrugs thereof, are provided wherein R$^2$ is pyridyl substituted with 0-3 R$^{2a}$.

In a more preferred embodiment compounds of formula (I), or stereoisomers, tautomers, pharmaceutically-acceptable salts, solvates, or prodrugs thereof, are provided wherein R$^2$ is selected from:

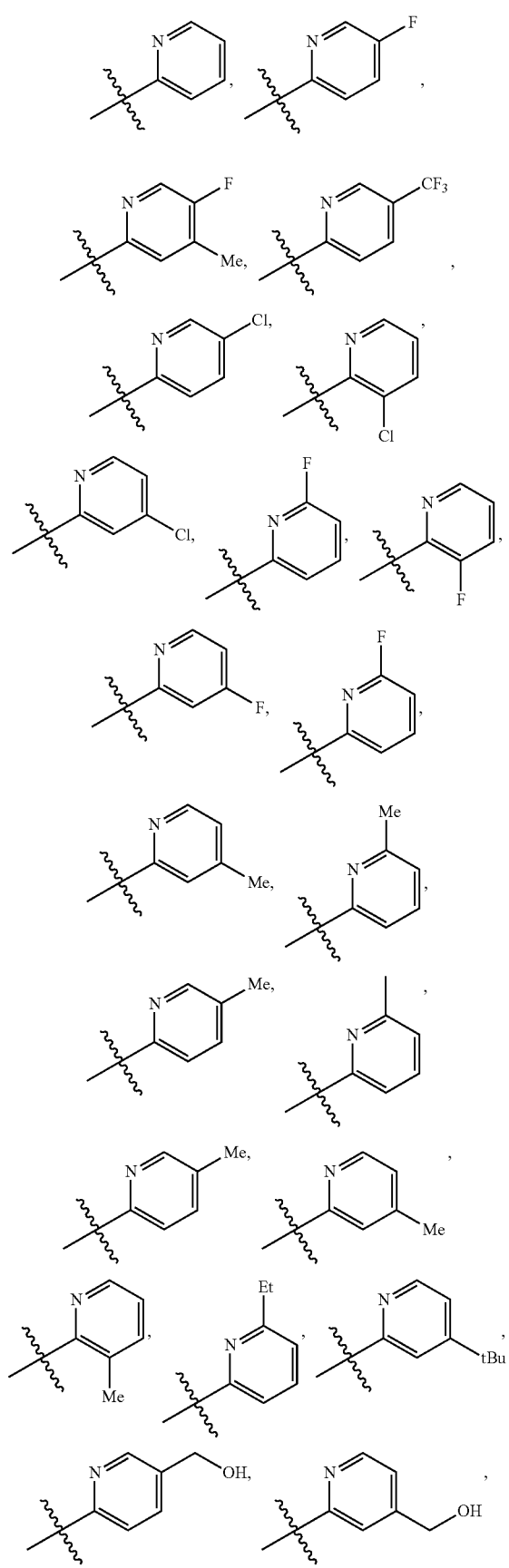

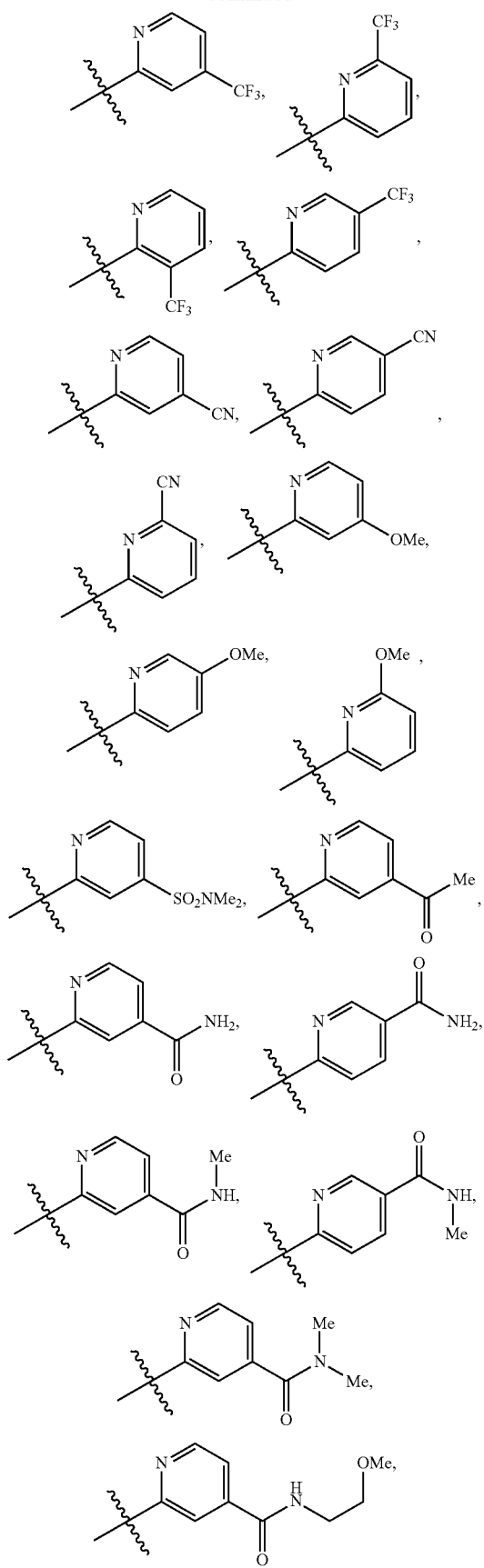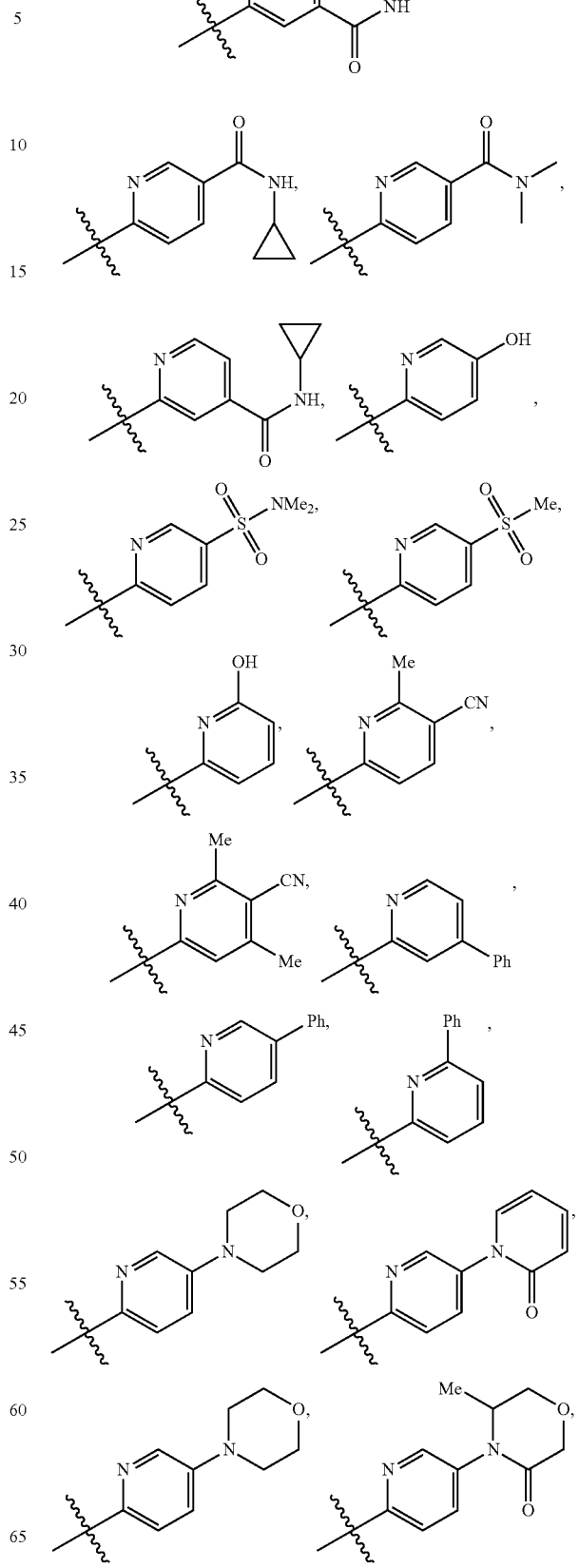

-continued

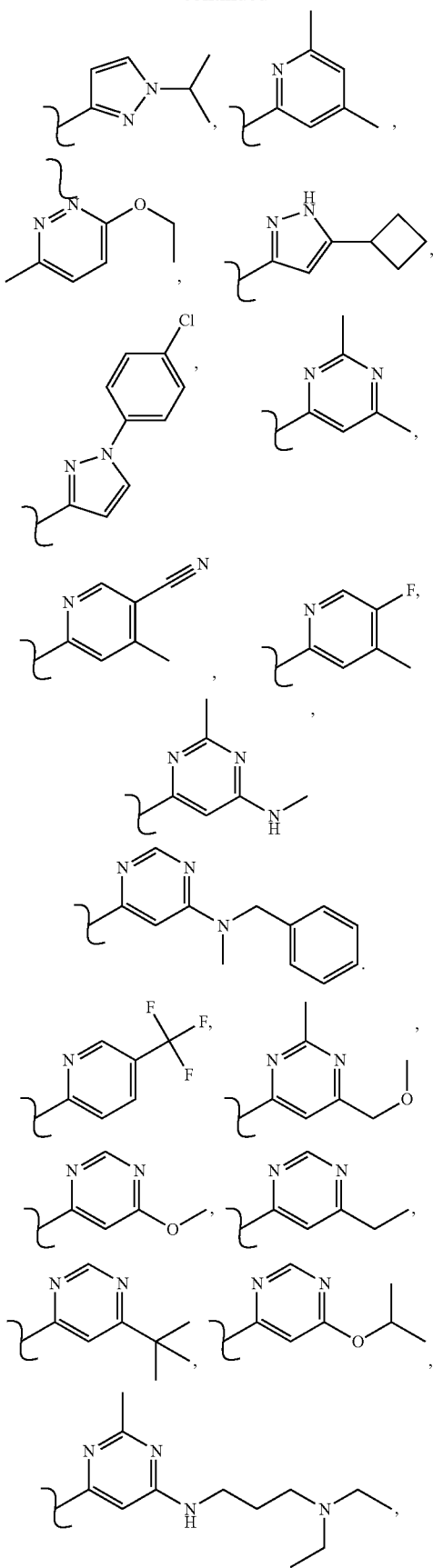
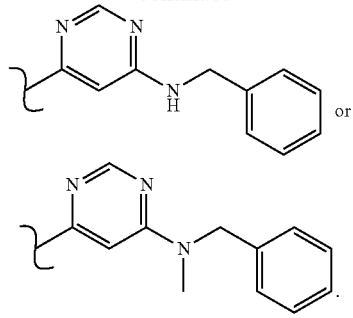

In yet another embodiment there are provided compounds of formula (I), or stereoisomers, tautomers, pharmaceutically-acceptable salts, solvates, or prodrugs thereof, wherein $R^3$ is phenyl, cyclopentyl, cyclohexyl, furanyl, pyridyl or pyranyl, each substituted with 0-3 $R^{3a}$.

In another, more preferred embodiment, there is provided a compound of formula (I), or stereoisomers, tautomers, pharmaceutically-acceptable salts, solvates, or prodrugs thereof, wherein:

$R^{3a}$ at each occurrence independently is hydrogen, Ph, CN, $NH_2$, $OCF_3$, $OCHF_2$, $OR^b$, halo, $C_{3-6}$cycloalkyl, $C(O)NR^{11}R^{11}$ $S(O)_2NR_{11}R_{11}$, $C(O)R^b$, $SO_pR^c$, $NR^bSO_pR^c$, $NR^bC(O)R^c$, haloalkyl, CN, a 5-10 membered heterocycle containing 1-4 heteroatoms selected from N, O, and S substituted with 0-3 $R^a$ and $C_{1-6}$ alkyl substituted with 0-3 $R^a$, or one $R^{3a}$ and a second $R^{3a}$, together with the atoms to which they are attached, combine to form a fused 5-7 membered heterocycle containing 1-4 heteroatoms selected from N, O, and S or fused phenyl;

$R^{11}$ is at each occurrence independently hydrogen, phenyl, cyclopropyl, or $C_{1-6}$alkyl substituted with 0-3 $R^f$;

$R^a$ is at each occurrence independently halo or $OR^b$;

$R^b$ is at each occurrence independently hydrogen, a 5-10 membered heterocycle containing 1-4 heteroatoms selected from N, O, and S substituted with 0-3 $R^f$ or $C_{1-6}$ alkyl substituted with 0-3 $R^d$;

$R^d$ is at each occurrence independently halo or OH;

$R^c$ is at each occurrence independently $C_{1-6}$ alkyl substituted with 0-3 $R^f$;

$R^f$ is at each occurrence independently hydrogen, halo or OH;

or $R^f$ is at each occurrence independently cyclopropyl, cyclohexyl, pyridyl, thiazolyl, indolyl or imidazolyl, each group optionally substituted with CN or OMe; and p is 2.

Also, in another, more preferred embodiment, there is provided a compound of formula (I), or a stereoisomer or pharmaceutically-acceptable salt thereof, wherein:

$R^{3a}$ at each occurrence independently is hydrogen, Ph, CN, $NH_2$, $OCF_3$, $OR^b$, halo, $C_{3-6}$cycloalkyl, $C(O)NR^{11}R^{11}$ $S(O)_2NR_{11}R_{11}$, $C(O)R^b$, $SO_pR^c$, $NR^bSO_pR^c$, $NR^bC(O)R^c$, haloalkyl ($CF_3$), CN, a 5-10 membered heterocycle containing 1-4 heteroatoms selected from N, O, and S substituted with 0-3 $R^a$ (preferably morpholinyl, pyrazolyl, oxazolyl or triazolyl, each substituted with 0-3 $R^a$), and $C_{1-6}$ alkyl substituted with 0-3 $R^a$, or one $R^{3a}$ and a second $R^{3a}$, together with the atoms to which they are attached, combine to form a fused 5-7 membered heterocycle containing 1-4 heteroatoms selected from N, O, and S (preferably said fused heterocycle is pyrrolidinyl or dioxanyl) or fused phenyl;

$R^{11}$ is hydrogen, cyclopropyl, or $C_{1-4}$alkyl substituted with 0-1 $R^f$;

$R^a$ is halo (preferably F) or $OR^b$;

$R^b$ is hydrogen, a 5-10 membered heterocycle containing 1-4 heteroatoms selected from N, O, and S (preferably pyrrolidinyl, piperidinyl, morpholinyl) substituted with 0-3 $R^f$ or $C_{1-6}$ alkyl substituted with 0-3 $R^d$;

$R^d$ is halo (preferably F) or $OR^e$;

$R^e$ is $C_{1-6}$ alkyl substituted with 0-3 $R^f$;

$R^e$ is hydrogen;

$R^f$ is hydrogen, halo (preferably F), OH, or imidazolyl; and p is 2.

In another, embodiment, there is provided a compound of formula (I), or stereoisomers, tautomers, pharmaceutically-acceptable salts, solvates, or prodrugs thereof, wherein:

$R^3$ is

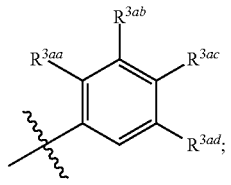

$R^{3aa}$ is $S(O)_pR^c$, $OR^b$, $OCHF_2$, chloro, F, CN, $NH_2$, $C(O)NR^{11}R^{11}$, $NR^bSO_pR^c$, $NR^bC(O)R^c$, $C_{1-6}$ alkyl substituted with 0-3 $R^a$ or a 5- to 6-membered heteroaryl containing 1-3 heteroatoms selected from N, O, and S substituted with 0-3 $R^a$;

$R^{3ab}$, $R^{3ac}$, or $R^{3ad}$ are independently hydrogen, Cl, F, Br, CN, $OR^b$, $C_{1-6}$ alkyl substituted 0-3 $R^a$; $C(O)NR^{11}R^{11}$, $C(O)R^b$, S(O)pRc, or a 4- to 7-membered heterocycle containing 1-3 heteroatoms selected from N, O, and S substituted with 0-3 $R^a$; and p is 0-2.

In an alternate embodiment, there is provided a compound of formula (I), or stereoisomers, tautomers, pharmaceutically-acceptable salts, solvates, or prodrugs thereof, wherein:

$R^3$ is

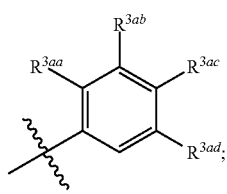

$R^{3aa}$ is $S(O)_pR^c$, $OR^b$, chloro, F, CN, $NH_2$, $C(O)NR^{11}R^{11}$, $NR^bSO_pR^c$, $NR^bC(O)R^c$, $C_{1-6}$ alkyl substituted with 0-3 $R^a$ or a 5- to 6-membered heteroaryl containing 1-3 heteroatoms selected from N, O, and S (preferably pyrazolyl or triazolyl) substituted with 0-3 $R^a$;

$R^{3ab}$, $R^{3ab}$, or $R^{3ad}$ are independently hydrogen, Cl, F, Br, CN, $OR^b$, $C_{1-6}$ alkyl substituted 0-3 $R^a$; $C(O)NR^{11}R^{11}$, $C(O)R^b$, S(O)pRc, or a 4- to 7-membered heterocycle (preferably oxazolyl, morpholinyl or aziridinyl) containing 1-3 heteroatoms selected from N, O, and S substituted with 0-3 $R^a$;

$R^a$ is $OR^b$ or halo;

$R^b$ is hydrogen, $C_{1-6}$ alkyl substituted with 0-2 $R^d$, a 5- to 7-membered heterocycle containing 1-3 heteroatoms selected from N, O and S (preferably piperidinyl or morpholinyl);

$R^{11}$ at each occurrence independently is hydrogen, cyclopropyl substituted with 0-3 $R^f$ or $C_{1-4}$ alkyl substituted with 0-3 $R^f$;

$R^b$ is hydrogen or $C_{1-6}$ alkyl substituted with 0-2 $R^d$;

$R^c$ is $C_{1-6}$ alkyl substituted with 0-3 $R^f$;

$R^d$ independently at each occurrence is F or OH;

$R^f$ is halo (preferably F) or imidazolyl; and p is 0-2.

In a further embodiment, there is provided a compound of formula I, or stereoisomers, tautomers, pharmaceutically-acceptable salts, solvates, or prodrugs thereof, wherein $R^{3aa}$ is $OR^b$.

In a more preferred embodiment, there is provided a compound of formula I, or stereoisomers, tautomers, pharmaceutically-acceptable salts, solvates, or prodrugs thereof, wherein $R^{3aa}$ is OH, OMe, $OCF_3$, $OCHF_2$, $OCH_2F$, or OEt.

In an alternate further embodiment, there is provided a compound of formula I, or stereoisomers, tautomers, pharmaceutically-acceptable salts, solvates, or prodrugs thereof, wherein $R^{3aa}$ is $S(O)_pR^c$. More preferably $R^{3aa}$ is $S(O)C_{1-6}$alkyl or $S(O)_2C_{1-6}$alkyl (especially $SO_2Me$).

In a yet another embodiment, there is provided a compound of formula I, or stereoisomers, tautomers, pharmaceutically-acceptable salts, solvates, or prodrugs thereof, wherein $R^3$ is selected from:

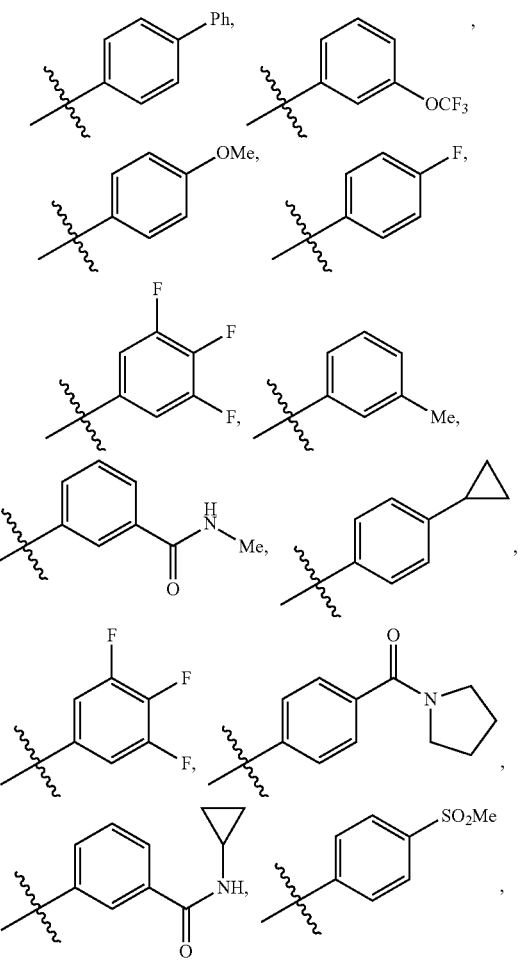

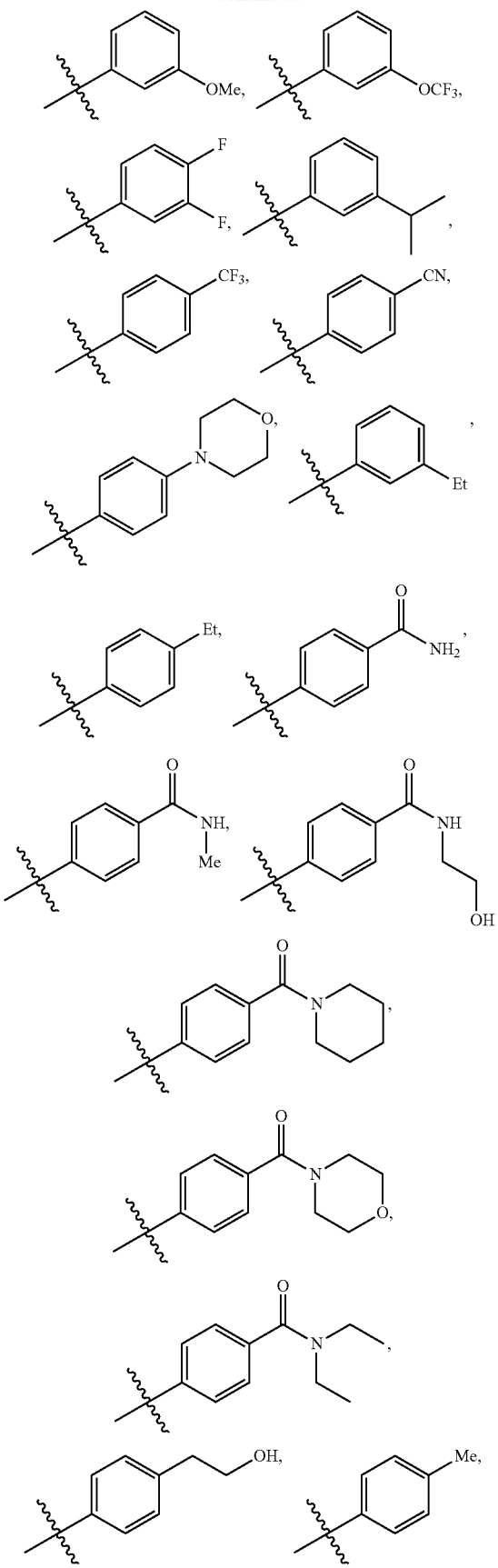
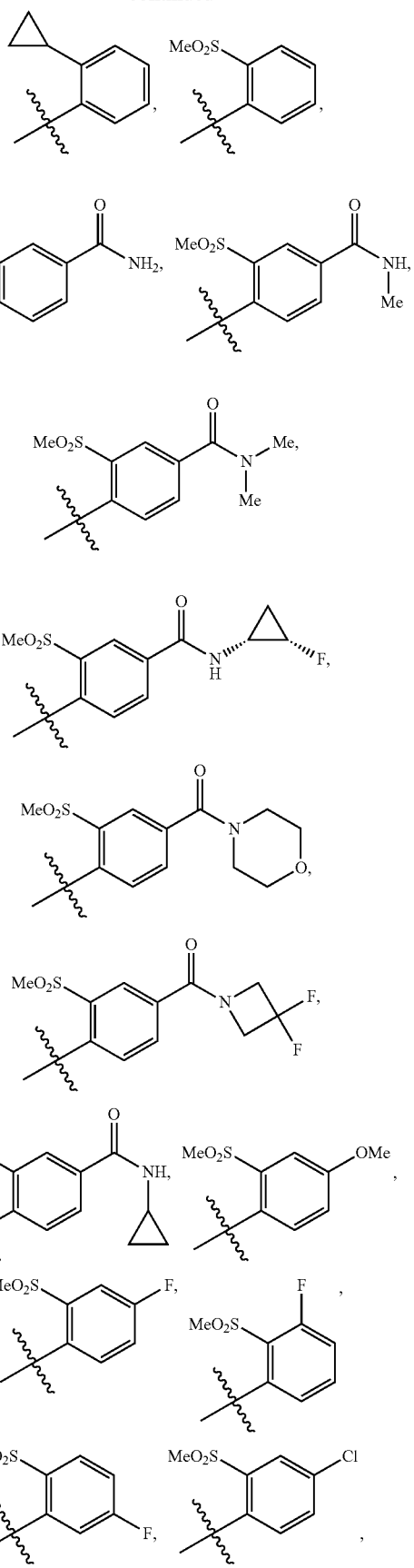

-continued
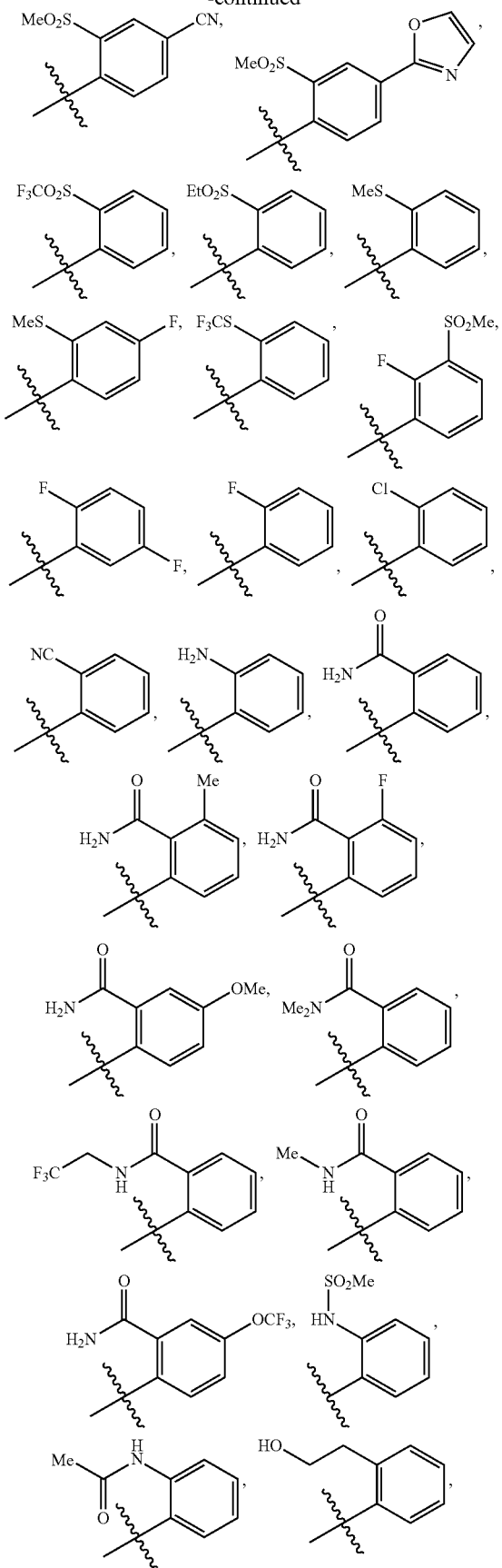
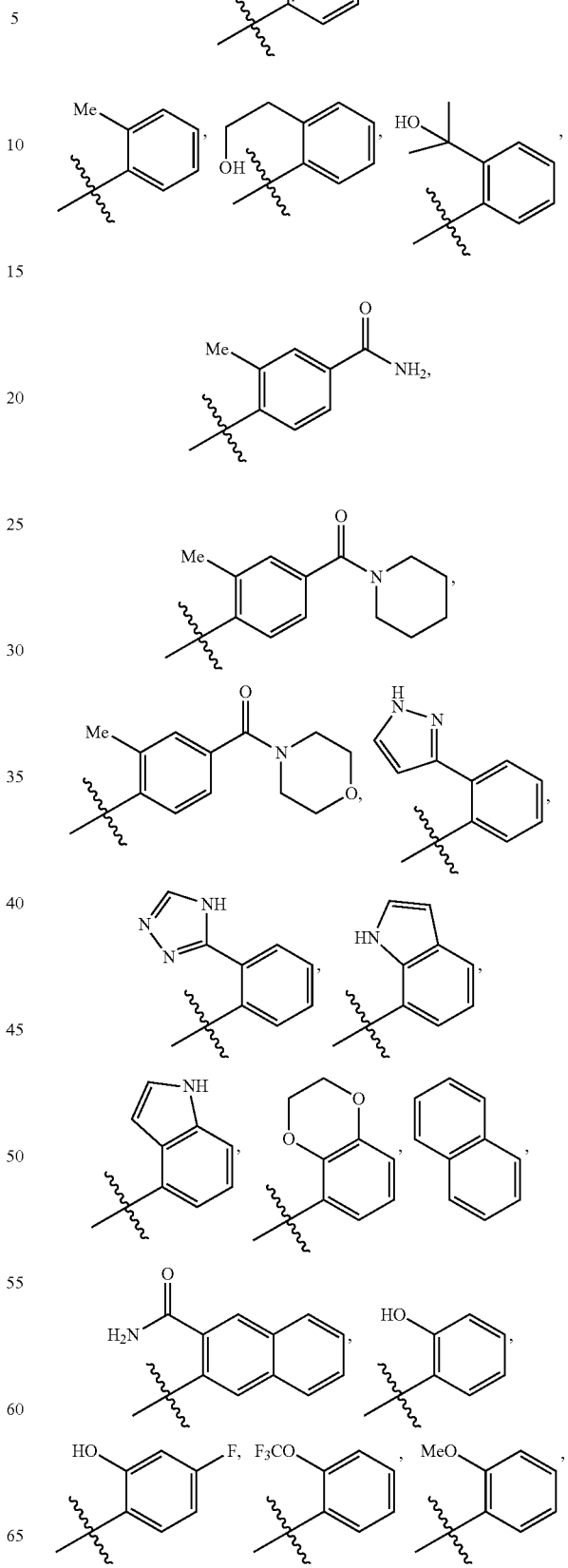

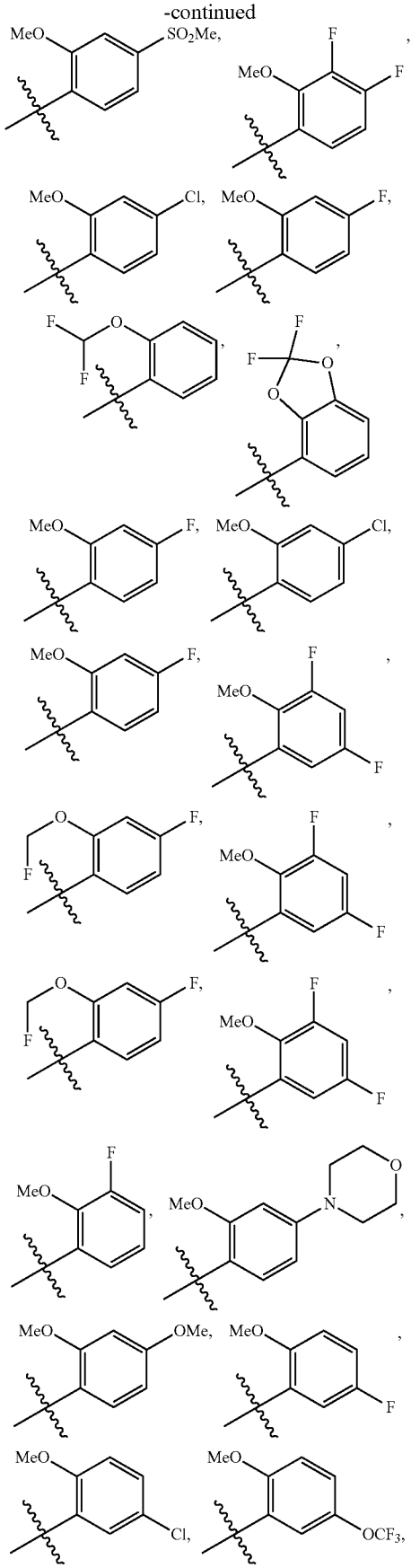
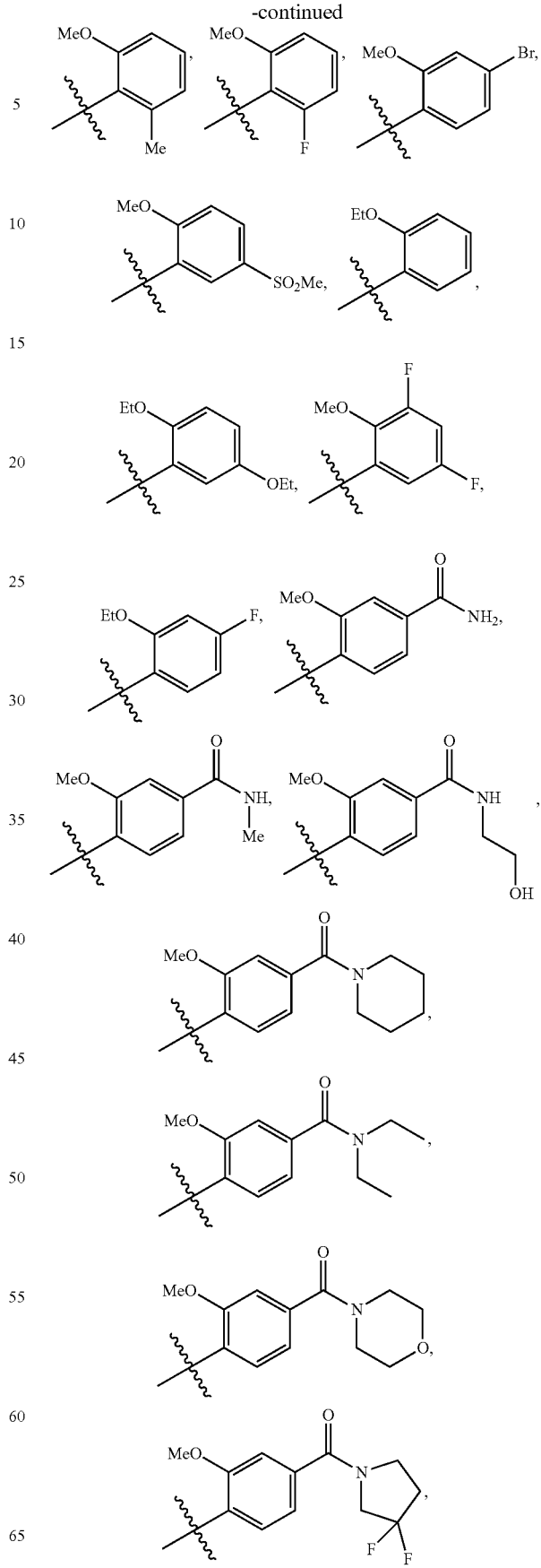

-continued
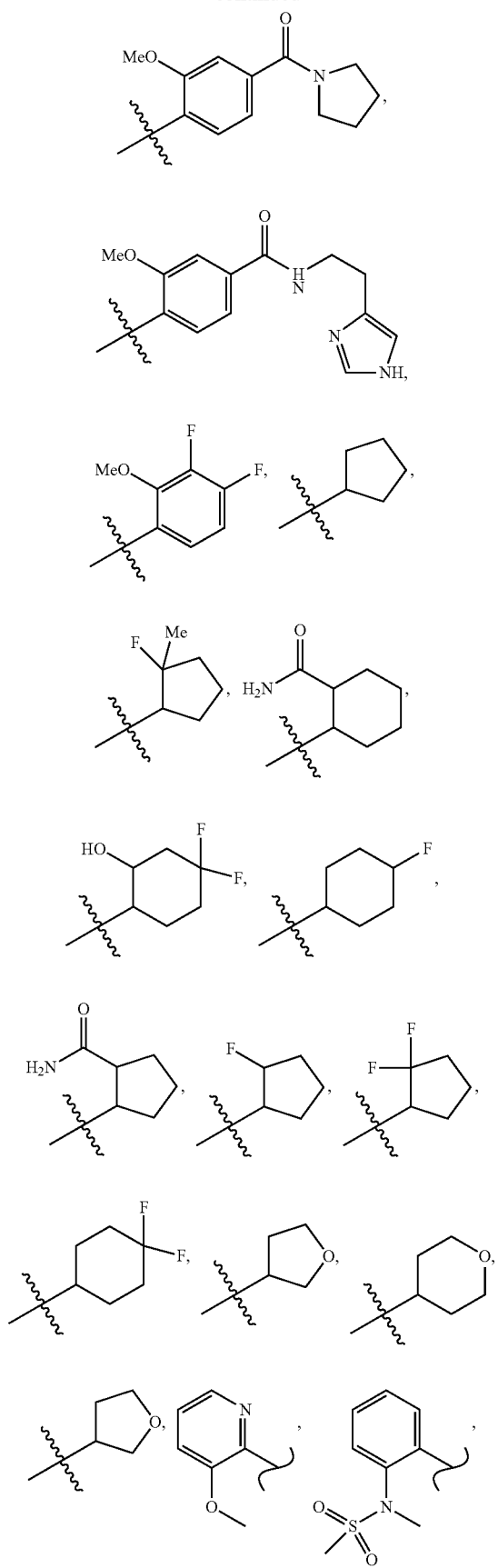
-continued
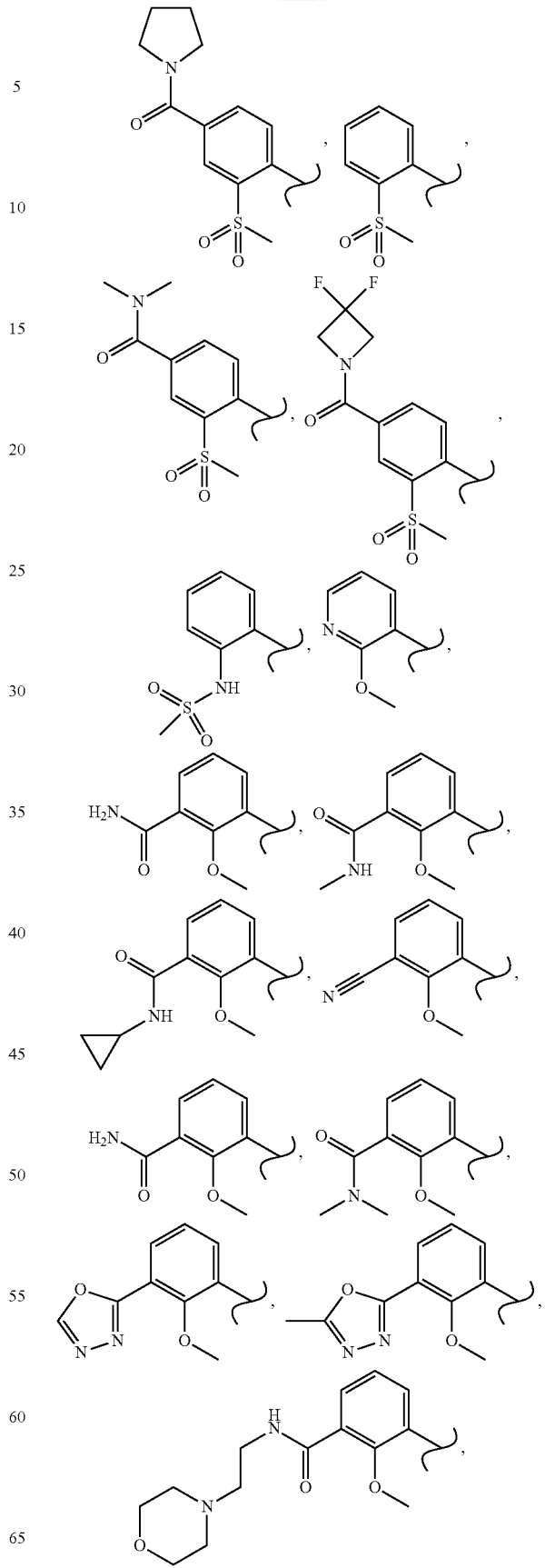

35
-continued
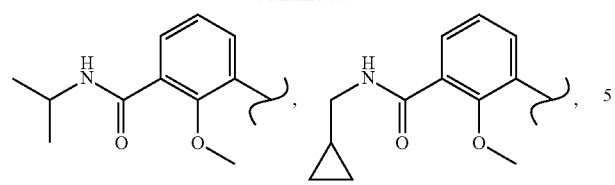
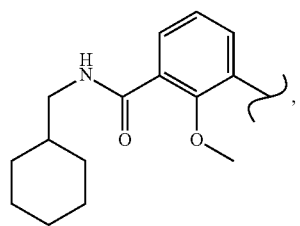
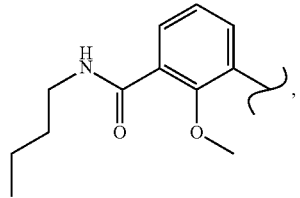
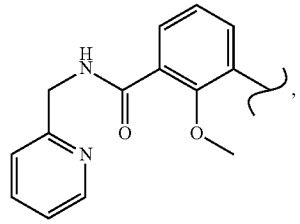
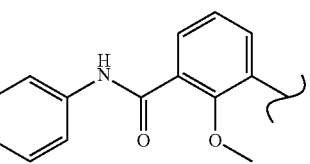
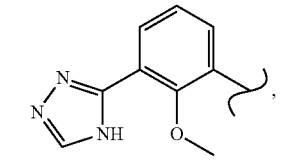
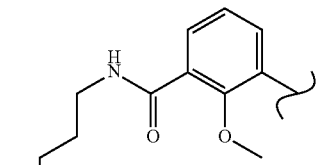

36
-continued
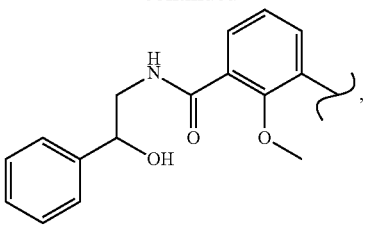
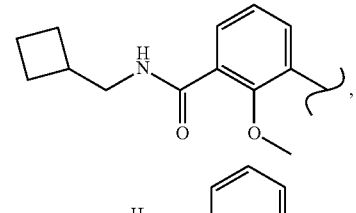
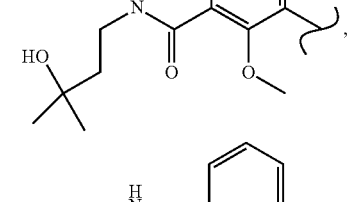
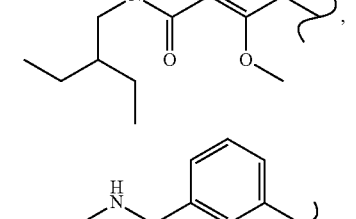
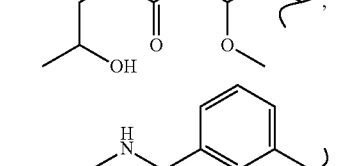
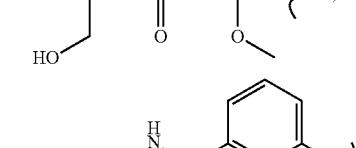
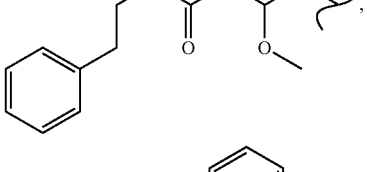
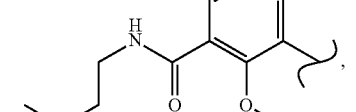
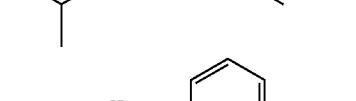
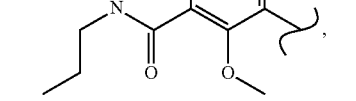

37
-continued
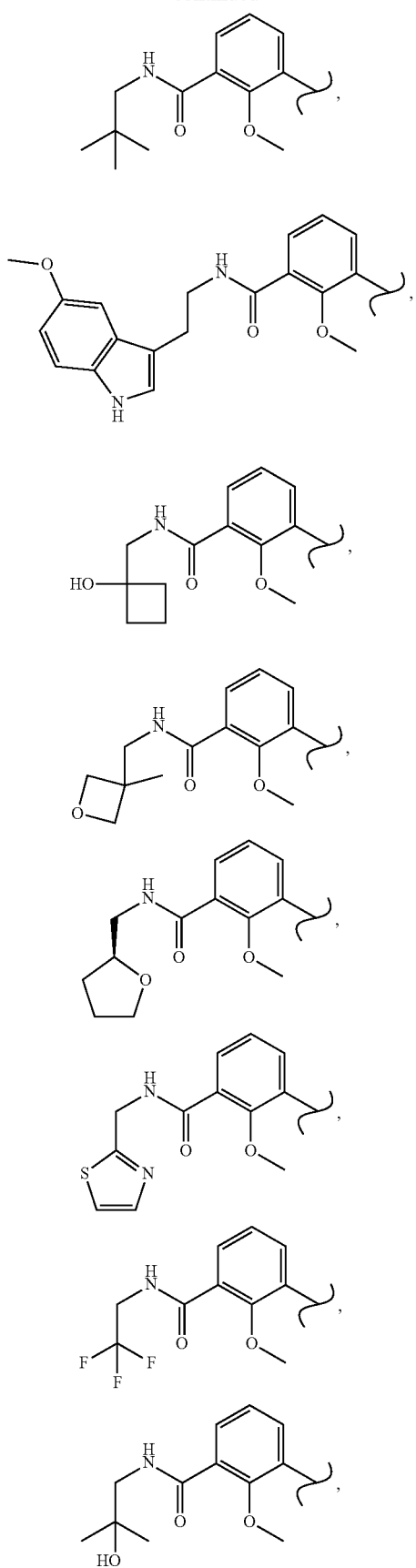
38
-continued
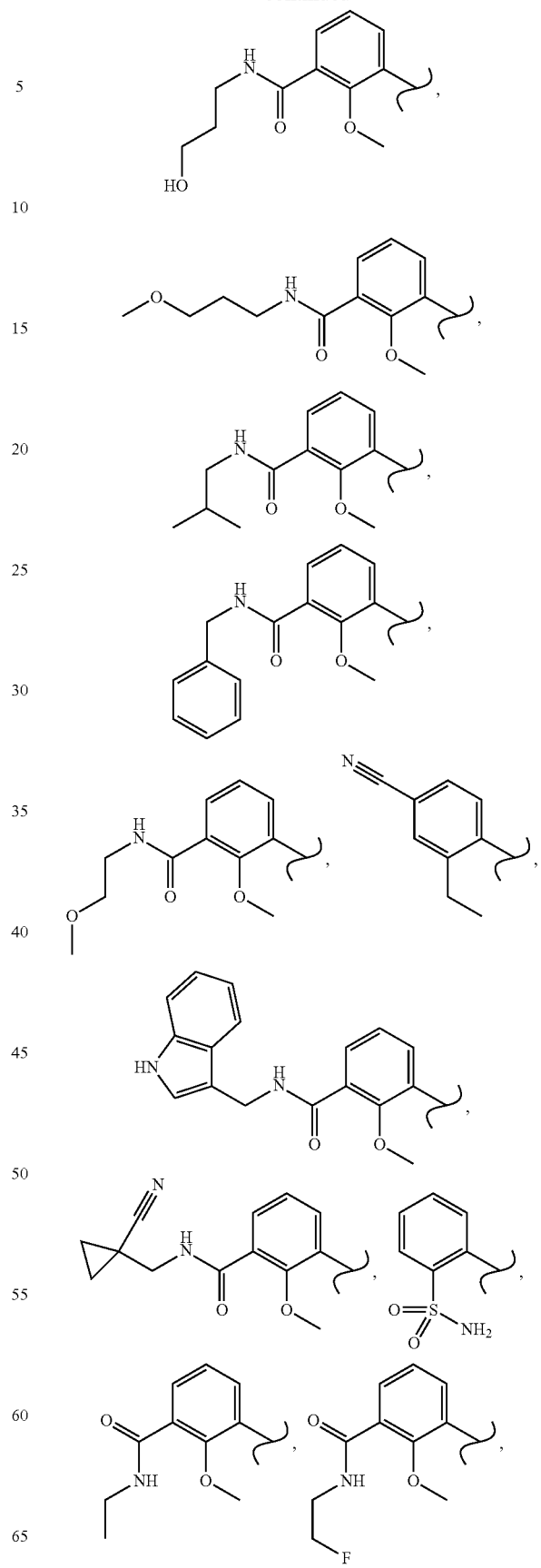

-continued
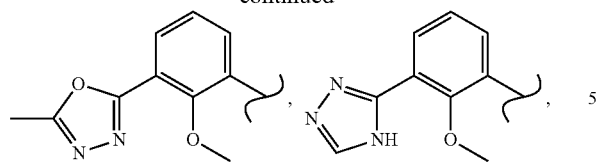
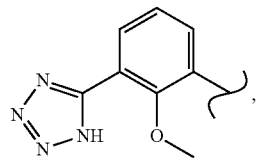
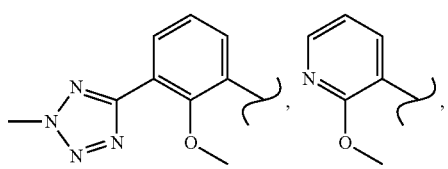
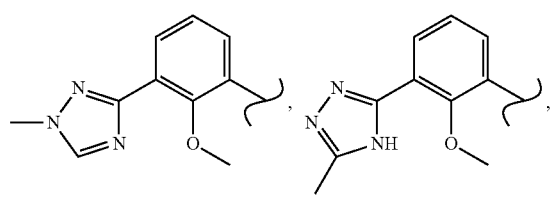
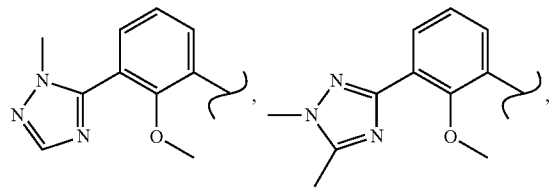
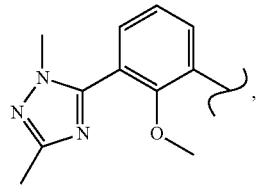
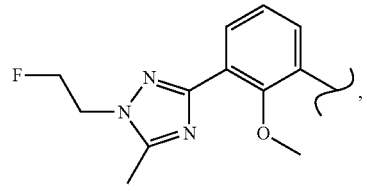
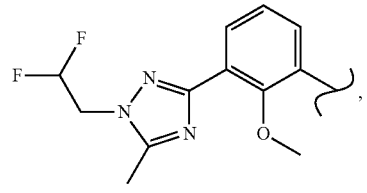
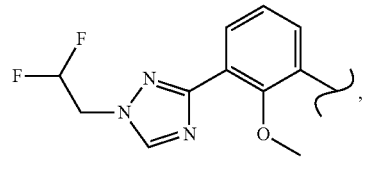
-continued
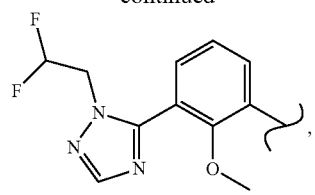
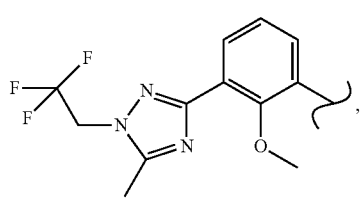
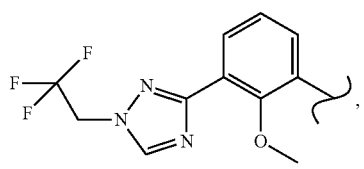
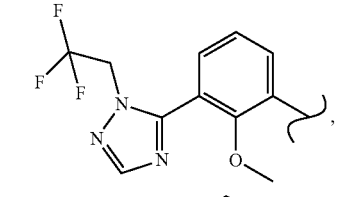
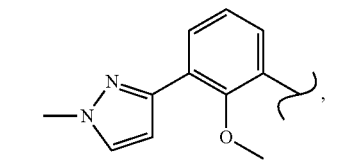
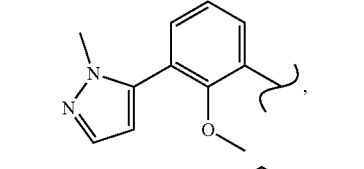
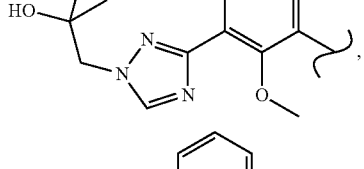
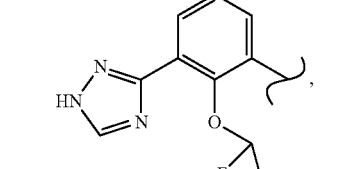
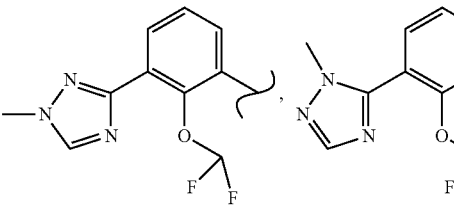

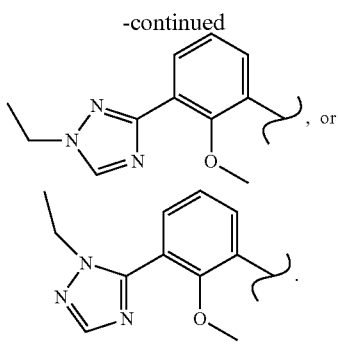

In yet another preferred embodiment, there is provided a compound of formula I, or stereoisomers, tautomers, pharmaceutically-acceptable salts, solvates, or prodrugs thereof, wherein $R^1$ is $CH_3$, $C_2H_5$, $CD_3$, or $CD_2CD_3$ (even more preferred are embodiments wherein $R^1$ is $CH_3$ or $CD_3$).

In another embodiment, there is provided a pharmaceutical composition comprising one or more compounds of formula (I), or stereoisomers, tautomers, pharmaceutically-acceptable salts, solvates, or prodrugs thereof, and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention or stereoisomers, tautomers, pharmaceutically-acceptable salts, solvates, or prodrugs thereof.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating an inflammatory or autoimmune disease (or use of the compounds of the present invention for the manufacture of a medicament for the treatment of these diseases), comprising administering to a patient in need of such treatment a therapeutically-effective amount of a compound of Formula I, wherein the disease is selected from systemic lupus erythematosus (SLE), lupus nephritis, cutaneous lupus, Crohn's Disease, ulcerative colitis, type 1 diabetes, psoriasis, rheumatoid arthritis, systemic onset juvenile idiopathic arthritis, ankylosing spondylitis, and multiple sclerosis.

The present invention also provides a method for treating a rheumatoid arthritis (or use of the compounds of the present invention for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method of treating a IL-12, IL-23, and/or IFNα mediated disease (or use of the compounds of the present invention for the manufacture of a medicament for the treatment of said diseases), comprising administering to a patient in need of such treatment a therapeutically-effective amount of a compound of formula I.

The present invention also provides a method of treating a IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention use in therapy.

In another embodiment, compounds of formula I are selected from exemplified compounds or combinations of exemplified compounds or other embodiments herein.

In another embodiment are compounds having an $IC_{50}$<1000 nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound".

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "CO$_2$" is used herein, this is intended to refer to the group

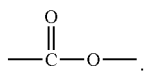

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl (C$_{0-4}$)alkyl includes a substituted lower alkyl having at least one aryl substituent and also includes an aryl directly bonded to another group, i.e., aryl(C$_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—C$_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., ═O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C═C, C═N, or N═N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "cycloalkyl" refers to cyclized alkyl groups, including mono-, bi- or poly-cyclic ring systems. C$_{3-7}$ cycloalkyl is intended to include C$_3$, C$_4$, C$_5$, C$_6$, and C$_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

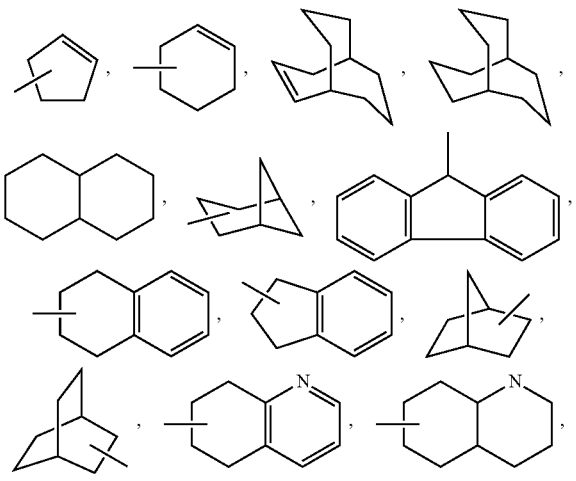

and the like, which optionally may be substituted at any available atoms of the ring(s).

Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

Thus, examples of aryl groups include:

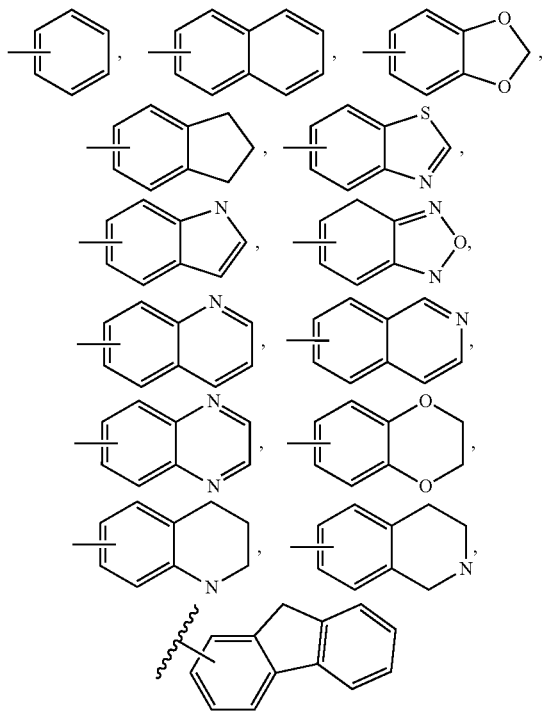

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

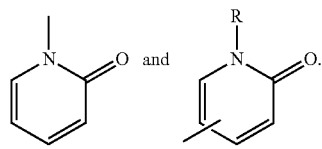

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include:

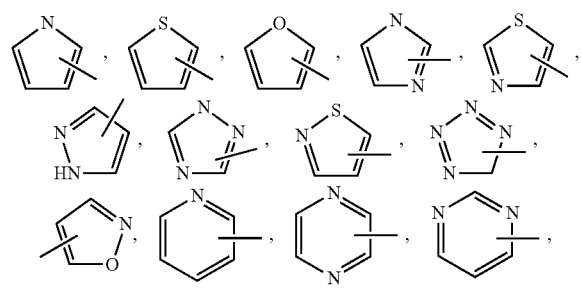

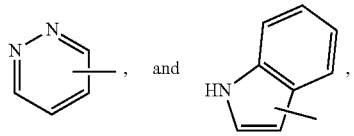

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s)" may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically-acceptable salts include, but are not limited to, mineral or organic acid salts of basic groups such as amines; and alkali or organic salts of acidic groups such as carboxylic acids. The pharmaceutically-acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically-acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) Bundgaard, H., ed., Design of Prodrugs, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans- and cis-isomers.

It should further be understood that solvates (e.g., hydrates) of the compounds of Formula I are also with the scope of the present invention. Methods of solvation are generally known in the art.

Utility

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 or IFNα, and particularly the selective inhibition of function of IL-23, IL-12 and/or IFNα, by acting on Tyk2 to mediate signal transduction. Such conditions include IL-23-, IL-12-, or IFNα-associated diseases in which pathogenic mechanisms are mediated by these cytokines As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and IFNα-stimulated cellular responses, compounds of Formula I are useful in treating IL-23-, IL-12- or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia [should this be hypoxia], vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically-effective amount of at least one compound of Formula I or a salt thereof "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFNα function and/or treat diseases associated with IL-23, IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

Biological Assays

Probe Displacement Assay

The probe displacement assay is conducted as follows: In a 385 well plate, test compounds along with recombinantly expressed His-tagged protein corresponding to amino acids 575-869 of human Tyk2 (sequence shown below) at 2.5 nM, 40 nM ((R)-N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide) (preparation described below) and 80 µg/mL Copper His-Tag scintillation proximity assay beads (Perkin Elmer, Catalog #RPNQ0095) in 50 mM HEPES, pH 7.5, containing 100 µg/mL bovine serum albumin and 5% DMSO were incubated for 30 minutes at room temperature. The amount of radiolabeled probe (preparation described below) bound to Tyk2 was then quantified by scintillation counting, and the inhibition by the test compound calculated by comparison to wells either with no inhibitor (0% inhibition) or without Tyk2 (100% inhibition). The $IC_{50}$ value is defined as the concentration of test compound required to inhibit radiolabeled probe binding by 50%.

Protein Sequence of recombinant Hig-tagged Tyk2 (575-869):

```
MGSSHHHHHH  SSGETVRFQG  HMNLSQLSFH  RVDQKEITQL

SHLGQGTRTN  VYEGRLRVEG  SGDPEEGKMDDEDPLVPGRD

RGQELRVVLK  VLDPSHHDIA  LAFYETASLM  SQVSHTHLAF

VHGVCVRGPE  NIMVTEYVEHGPLDVWLRRE  RGHVPMAWKM

VVAQQLASAL  SYLENKNLVH  GNVCGRNILL  ARLGLAEGTS
```

```
PFIKLSDPGVGLGALSREER VERIPWLAPE CLPGGANSLS

TAMDKWGFGA TLLEICFDGE APLQSRSPSE

KEHFYQRQHRLPEPSCPQLA TLTSQCLTYE

PTQRPSFRTI LRDLTRL.
```

The preparation of radiolabeled probe, (R)-N-(1-(3-(8-methyl-5-(methylamino)-8H-imidazo[4,5-d]thiazolo[5,4-b]pyridin-2-yl)phenyl)ethyl)-2-([$^3$H]methylsulfonyl)benzamide, was performed as described below:

2-([$^3$H]Methylsulfonyl)benzoic acid: 2-Mercaptobenzoic acid (2.3 mg, 0.015 mmol) and cesium carbonate (2 mg, 0.006 mmol) were added to a 5 mL round-bottomed flask. The flask was attached to a ported glass vacuum line and anhydrous DMF (0.5 mL) was introduced with magnetic stirring. An ampoule of tritiated methyl iodide (200 mCi, Perkin-Elmer lot 3643419) was added to the reaction flask and stirring was maintained at rt for 3 h. In-process HPLC analysis with radiometric detection indicated 80% conversion to the desired product by comparison with authentic standard. Without purification, the crude product was reacted with mCPBA (10 mg, 0.058 mmol) pre-dissolved in CH$_2$Cl$_2$ (1 mL) at room temperature with stirring. The reaction was stirred for 7 h and additional mCPBA (10 mg, 0.058 mmol) was added. The reaction was stirred for approximately 24 h and HPLC analysis indicated 35-40% conversion to the desired sulfonate product. The crude product was purified by semi-preparative HPLC (Luna 5 μm C18 (10×250 cm); A: MeOH/H$_2$O=15/85 (0.1% TFA); B: MeOH; 270 nm; 0-8 min 0% B 1 ml/min; 8-10 min 0% B 1-3 ml/min; 10-55 min 0% B 3 ml/min; 55-65 min 0-10% B 3 ml/min; 65-75 min 10-50% B 3 ml/min; 75-80 min 50-100% B 3 ml/min) to give 81 mCi (40% radiochemical yield) of 2-([$^3$H]methylsulfonyl)benzoic acid product identified by its HPLC co-elution with an authentic standard. The radiochemical purity was measured by HPLC to be 99% (Luna 5μ C18 (4.6×150 cm); A: H$_2$O (0.1% TFA); B: MeOH; 1.2 ml/min; 270 nm; 0-10 min 20% B; 10-15 min 20-100% B; 15-25 min 100% B. The product was dissolved in anhydrous acetonitrile to give a final solution activity of 5.8 mCi/mL.

(R)-N-(1-(3-(8-Methyl-5-(methylamino)-8H-imidazo[4,5-d]thiazolo[5,4-b]pyridin-2-yl)phenyl)ethyl)-2-([$^3$H]methylsulfonyl)benzamide: A solution of 2-([$^3$H]methylsulfonyl) benzoic acid (23.2 mCi) in acetonitrile was added to a 5 mL round-bottomed flask which was then attached to a vacuum line and carefully evaporated to dryness. (R)-2-(3-(1-Aminoethyl)phenyl)-N,8-dimethyl-8H-imidazo[4,5-d]thiazolo[5,4-b]pyridin-5-amine (prepared as described in WO 2004/106293 and Dyckman et al., *Bioorganic and Medicinal Chemistry Letters*, 383-386 (2011)) (1.1 mg, 0.0033 mmol) and PyBOP (2 mg, 0.0053 mmol) dissolved in anhydrous DMF (1.5 mL) were added to the flask followed by N,N-diisopropylethylamine (0.010 mL). The resulting clear solution was stirred at room temperature for 18 h. HPLC analysis (Luna 5μ, C18 (4.6×150 cm); A: H$_2$O (0.1% TFA); B: MeOH; 1.2 ml/min; 335 nm; 0-20 min 50% B; 20-25 min 50-100% B; 25-30 min 100% B) indicated approximately a 20% conversion to the desired product by retention time comparison to a sample of non-radiolabeled (R)-N-(1-(3-(8-methyl-5-(methylamino)-8H-imidazo[4,5-d]thiazolo[5,4-b]pyridin-2-yl)phenyl)ethyl)-2-(methylsulfonyl)benzamide. The crude reaction mixture was purified by semi-preparative HPLC (Luna 5μ C18 (10×250 cm); A: MeOH/H$_2$O=50/50 (0.1% TFA); B: MeOH; 335 nm; 0-40 min 0% B 3 ml/min; 40-45 min 0-100% B 3 ml/min). The purification routine was performed a second time to yield a total of 1.7 mCi (7% radiochemical yield) of the desired product in 99.9% radiochemical purity. Mass spectral analysis of the tritiated product (m/z M+H 527.33) was used to establish the specific activity at 80.6 Ci/mmol.

Probe Displacement Data

| Example No. | Probe Displacement (EC$_{50}$, μM) |
|---|---|
| 2 | 0.0132 |
| 42 | 0.0082 |
| 43 | 0.0687 |
| 61 | 0.0164 |
| 62 | 0.0845 |
| 66 | 0.0148 |
| 73 | 0.0120 |
| 79 | 0.0055 |
| 80 | 0.0044 |
| 81 | 0.0227 |
| 87 | 0.0038 |
| 94 | 0.0095 |
| 104 | 0.0177 |
| 107 | 0.0324 |
| 125 | 0.4363 |
| 128 | 0.0213 |
| 134 | 0.0099 |
| 144 | 0.0461 |
| 152 | 0.0406 |
| 165 | 0.7793 |
| 176 | 0.0188 |
| 188 | 0.5570 |
| 194 | 0.3490 |
| 203 | 0.0535 |
| 205 | 0.0251 |
| 211 | 0.2464 |
| 217 | 0.2913 |
| 224 | 0.5968 |
| 226 | 0.0201 |
| 228 | 0.0367 |
| 237 | 0.0291 |
| 238 | 0.0063 |
| 261 | 0.1552 |
| 266 | 0.0065 |
| 283 | 0.6334 |
| 286 | 0.1060 |
| 289 | 0.4951 |
| 298 | 0.0065 |
| 302 | 0.1820 |
| 315 | 0.0050 |
| 325 | 0.0764 |
| 327 | 0.0153 |
| 334 | 0.0140 |
| 345 | 0.0105 |
| 356 | 0.0026 |
| 358 | 0.0053 |
| 363 | 0.0047 |
| 365 | 0.0048 |
| 382 | 0.0046 |
| 383 | 0.0061 |
| 387 | 0.0046 |
| 391 | 0.0060 |
| 393 | 0.0035 |
| 395 | 0.0031 |
| 396 | 0.0065 |
| 409 | 0.0063 |
| 420 | 0.0030 |
| 422 | 0.0057 |
| 426 | 0.0042 |
| 438 | 0.0115 |
| 448 | 0.0080 |
| 449 | 0.0011 |
| 450 | 0.0073 |

Kit225 T Cell Assay

Kit225 T cells with a stably-integrated STAT-dependent luciferase reporter were plated in RPMI (Gibco) containing 10% heat-inactivated FBS (Gibco) and 100 U/mL PenStrep (Gibco). The cells were then stimulated with either 20 ng/mL human recombinant IL-23 or 200 U/mL human recombinant IFNα (PBL InterferonSource) for 5-6 hours. Luciferase expression was measured using the STEADY-GLO® Luciferase Assay System (Promega) according to the manufacturer's instructions. Inhibition data were calculated by comparison to no inhibitor control wells for 0% inhibition and non-stimulated control wells for 100% inhibition. Dose response curves were generated to determine the concentration required to inhibit 50% of cellular response ($IC_{50}$) as derived by non-linear regression analysis.

Kit225 T Cell Inhibition Data

| Example No. | IL23 | IFNα |
| --- | --- | --- |
| 1 | 0.0985 | 0.07 |
| 2 | 0.0574 | 0.03 |
| 3 | 0.0614 | 0.07 |
| 4 | 0.036 | 0.03 |
| 5 | 0.0822 | 0.05 |
| 6 | 0.091 | 0.11 |
| 7 | 0.1536 | 0.1 |
| 8 | 0.1429 | 0.06 |
| 9 | 0.0978 | 0.04 |
| 10 | 0.2176 | 0.12 |
| 11 | 0.1612 | 0.06 |
| 12 | 0.1094 | 0.05 |
| 13 | 0.2574 | 0.12 |
| 14 | 0.1349 | 0.11 |
| 15 | 0.1076 | 0.08 |
| 16 | 0.1797 | 0.1 |
| 17 | 0.1043 | 0.1 |
| 18 | 1.122 | 0.4 |
| 19 | 0.7489 | 0.43 |
| 20 | 0.0507 | 0.04 |
| 21 | 0.0509 | 0.03 |
| 22 | 0.0649 | 0.05 |
| 23 | 0.115 | 0.09 |
| 24 | 0.0352 | 0.04 |
| 25 | 0.0877 | 0.11 |
| 26 | 1.057 | 0.67 |
| 27 | 0.376 | 0.18 |
| 28 | 12.5 | 9.57 |
| 29 | 7.106 | 7.98 |
| 30 | 0.7528 | 0.58 |
| 31 | 1.861 | 1.23 |
| 32 | 2.201 | 1.08 |
| 33 | 0.6116 | 0.66 |
| 34 | 0.1142 | 0.16 |
| 35 | 4.434 | |
| 36 | 1.31 | 0.7 |
| 37 | 0.69 | 1.15 |
| 38 | 0.55 | 0.37 |
| 39 | 1.48 | 1.54 |
| 40 | 0.13 | 0.13 |
| 41 | 6.12 | 1.91 |
| 42 | 0.26 | 0.14 |
| 43 | 0.173 | 0.87 |
| 44 | 1.245 | 1.46 |
| 45 | 4.256 | 1.25 |
| 46 | 2.98 | 1.39 |
| 47 | 2.41 | 1.68 |
| 48 | 1.61 | 0.96 |
| 49 | 0.41 | 0.54 |
| 50 | 1.54 | 2 |
| 51 | 0.27 | 0.2 |
| 52 | 0.2 | 0.09 |
| 53 | 0.09 | 0.08 |
| 54 | 0.19 | 0.16 |
| 55 | 0.13 | 0.17 |
| 56 | 0.12 | 0.05 |
| 57 | 0.16 | 0.19 |
| 58 | 0.22 | 0.14 |
| 59 | 0.37 | 0.12 |
| 60 | 0.06 | 0.04 |
| 61 | 3.53 | 1.03 |
| 62 | 0.8983 | 1.29 |
| 63 | 0.7743 | 0.41 |
| 64 | 5.947 | 9.03 |
| 65 | 0.4806 | 0.37 |
| 66 | 1.772 | 3.17 |
| 67 | 0.2631 | 0.14 |
| 68 | 0.5018 | 0.24 |
| 69 | 1.471 | 1.31 |
| 70 | 0.8198 | 0.73 |
| 71 | 0.5743 | 0.76 |
| 72 | 0.5778 | 0.38 |
| 73 | 0.5061 | 0.29 |
| 74 | 0.2358 | 0.26 |
| 75 | 2.027 | 1.73 |
| 76 | 0.8536 | 0.74 |
| 77 | 0.538 | 0.35 |
| 78 | 0.3879 | 0.12 |
| 79 | 4.104 | 1.85 |
| 80 | 0.3202 | 0.46 |
| 81 | 5.583 | 4.49 |
| 82 | 1.23 | 0.78 |
| 83 | 5.723 | 6.94 |
| 84 | 0.3694 | 0.35 |
| 85 | 1.038 | 0.63 |
| 86 | 1.822 | 0.43 |
| 87 | 0.2571 | 0.16 |
| 88 | 2.863 | 0.89 |
| 89 | 0.3426 | 0.37 |
| 90 | 7.205 | 8.26 |
| 91 | 0.567 | 0.42 |
| 92 | 3.933 | 1.54 |
| 93 | 0.4665 | 12.5 |
| 94 | 3.56 | 3.43 |
| 95 | 0.9598 | 0.68 |
| 96 | 0.2567 | 0.21 |
| 97 | 3.91 | 3.25 |
| 98 | 0.4804 | 0.28 |
| 99 | 0.4787 | 0.31 |
| 100 | 0.1582 | 0.12 |
| 101 | 0.1998 | 0.08 |
| 102 | 0.3685 | 0.15 |
| 103 | 0.3982 | 0.33 |
| 104 | 0.2463 | 0.05 |
| 105 | 0.3861 | 0.19 |
| 106 | 0.4388 | 0.18 |
| 107 | 0.1889 | 0.12 |
| 108 | 0.3686 | 0.23 |
| 109 | 0.9479 | 0.21 |
| 110 | 0.9977 | 0.42 |
| 111 | 1.302 | 0.99 |
| 112 | 0.7167 | 0.4 |
| 113 | 0.8756 | 0.2 |
| 114 | 4.552 | 1.54 |
| 115 | 0.6321 | 0.44 |
| 116 | 2.188 | 0.75 |
| 117 | 1.984 | 0.48 |
| 118 | 1.164 | 0.57 |
| 119 | 2.198 | 0.86 |
| 120 | 4.512 | 1.88 |
| 121 | 0.2436 | 0.15 |
| 122 | 0.5346 | 0.25 |
| 123 | 8.793 | 11.06 |
| 124 | 0.462 | 0.64 |
| 125 | 9.677 | 9.97 |
| 126 | 0.8296 | 0.7 |
| 127 | 0.8525 | 0.47 |
| 128 | 0.3346 | 0.14 |
| 129 | 0.0866 | 0.08 |
| 130 | 0.119 | 0.05 |
| 131 | 0.1832 | 0.06 |
| 132 | 0.1871 | 0.12 |
| 133 | 0.1793 | 0.07 |
| 134 | 0.314 | 0.13 |
| 135 | 3.419 | 1.53 |
| 136 | 0.747 | 0.39 |
| 137 | 0.1883 | 0.21 |

| Example No. | IL23 | IFNα |
|---|---|---|
| 138 | 0.3541 | 0.22 |
| 139 | 0.3672 | 0.18 |
| 140 | 0.2814 | 0.12 |
| 141 | 0.4007 | 0.35 |
| 142 | 0.7424 | 0.41 |
| 143 | 0.7829 | 0.56 |
| 144 | 0.5169 | 0.23 |
| 145 | 0.7944 | 0.42 |
| 146 | 2.16 | 1.45 |
| 147 | 1.061 | 0.52 |
| 148 | 0.7509 | 0.3 |
| 149 | 1.189 | 0.33 |
| 150 | 2.701 | 1.52 |
| 151 | 1.138 | 0.24 |
| 152 | 0.499 | 0.37 |
| 153 | 1.334 | 0.97 |
| 154 | 0.7838 | 0.56 |
| 155 | 0.2748 | 0.19 |
| 156 | 1.654 | 0.72 |
| 157 | 5.201 | 9.86 |
| 158 | 4.44 | 2.1 |
| 159 | 1.146 | 1.4 |
| 160 | 1.238 | 1.07 |
| 161 | 0.7602 | 0.61 |
| 162 | 0.2154 | 0.46 |
| 163 | 0.3062 | 0.23 |
| 164 | 4.412 | 2.99 |
| 165 | 10.71 | 6.65 |
| 166 | 0.1572 | 0.09 |
| 167 | 0.51 | 0.31 |
| 168 | 1.415 | 1.22 |
| 169 | 0.3522 | 0.44 |
| 170 | 1.623 | 1.72 |
| 171 | 0.1748 | 0.09 |
| 172 | 0.0892 | 0.05 |
| 173 | 0.0819 | 0.05 |
| 174 | 1.035 | 0.56 |
| 175 | 0.4337 | 0.5 |
| 176 | 1.045 | 1.02 |
| 177 | 0.3876 | |
| 178 | 1.63 | 1.88 |
| 179 | 2.73 | 3.25 |
| 180 | 5.09 | 2.58 |
| 181 | 6.17 | 12.5 |
| 182 | 8.85 | 12.5 |
| 183 | 9.72 | 5.97 |
| 184 | 7.984 | 4.11 |
| 185 | 2.576 | 2.9 |
| 186 | 7.807 | 7.85 |
| 187 | 2.818 | 2.58 |
| 188 | 4.304 | 6.47 |
| 189 | 12.5 | 9.37 |
| 190 | 0.367 | 0.51 |
| 191 | 3.069 | 3.58 |
| 192 | 0.5651 | 0.54 |
| 193 | 3.673 | 3.2 |
| 194 | 3.219 | 8.66 |
| 195 | 3.128 | 3.52 |
| 196 | 4.379 | 6.97 |
| 197 | 11.86 | 5.83 |
| 198 | 4.534 | 5.3 |
| 199 | 0.8974 | 0.66 |
| 200 | 0.9041 | 1.3 |
| 201 | 2.671 | 6.97 |
| 202 | 12.5 | 6.56 |
| 203 | 1.46 | 1.17 |
| 204 | 9.32 | 8.13 |
| 205 | 0.3722 | 0.18 |
| 206 | 6.433 | 5.85 |
| 207 | 3.303 | 2.04 |
| 208 | 1.846 | 2.41 |
| 209 | 1.579 | 1.31 |
| 210 | 1.685 | 0.86 |
| 211 | 4.274 | 3.15 |
| 212 | 4.173 | 2.03 |
| 213 | 1.868 | 1.31 |
| 214 | 2.934 | 2.01 |
| 215 | 4.929 | 4.33 |
| 216 | 0.1518 | 0.12 |
| 217 | 3.31 | 1.48 |
| 218 | 0.8017 | 0.26 |
| 219 | 5.093 | 2.81 |
| 220 | 0.4924 | 0.21 |
| 221 | 0.4556 | 0.15 |
| 222 | 8.039 | 8.39 |
| 223 | 0.3863 | 0.19 |
| 224 | 5.612 | 4.6 |
| 225 | 0.1571 | 0.09 |
| 226 | 0.1514 | 0.14 |
| 227 | 4.599 | 3.24 |
| 228 | 0.1438 | 0.14 |
| 229 | 0.3099 | 0.26 |
| 230 | 0.2238 | 0.16 |
| 231 | 9.176 | 3.12 |
| 232 | 3.04 | 2.09 |
| 233 | 1.367 | 0.87 |
| 234 | 2.796 | 1.87 |
| 235 | 1.423 | 0.7 |
| 236 | 2.178 | 1.11 |
| 237 | 0.4699 | 0.46 |
| 238 | 4.25 | 2.36 |
| 239 | 0.2927 | 0.23 |
| 240 | 0.6247 | 0.41 |
| 241 | 0.9018 | 0.5 |
| 242 | 1.735 | 2.71 |
| 243 | 4.608 | 2.11 |
| 244 | 1.159 | 1.26 |
| 245 | 3.257 | 3.66 |
| 246 | 2.382 | 1.65 |
| 247 | 0.4092 | 0.26 |
| 248 | 0.5037 | 0.25 |
| 249 | 10.48 | 6.41 |
| 250 | 0.4716 | 0.3 |
| 251 | 1.082 | 0.67 |
| 252 | 1.291 | 0.43 |
| 253 | | 0.44 |
| 254 | 0.488 | 0.31 |
| 255 | 1.555 | 0.71 |
| 256 | 0.5678 | 0.7 |
| 257 | 0.5771 | 0.6 |
| 258 | 0.6465 | 0.31 |
| 259 | 0.4328 | 0.2 |
| 260 | 2.4 | 1.76 |
| 261 | 2.18 | 1.37 |
| 262 | 0.7272 | 0.41 |
| 263 | 5.061 | 3.6 |
| 264 | 0.5421 | 0.35 |
| 265 | 0.3188 | 0.21 |
| 266 | 0.3116 | 0.16 |
| 267 | 2.635 | 1.83 |
| 268 | 0.7851 | 0.74 |
| 269 | 1.085 | 0.9 |
| 270 | 0.2211 | 0.17 |
| 271 | 1.185 | 0.82 |
| 272 | 1.056 | 0.6 |
| 273 | 0.2234 | 0.16 |
| 274 | 0.3359 | 0.19 |
| 275 | 1.04 | 0.68 |
| 276 | 1.344 | 1.17 |
| 277 | 0.2698 | 0.24 |
| 278 | 0.3739 | 0.96 |
| 279 | 0.4755 | 0.14 |
| 280 | 5.046 | 5.99 |
| 281 | 0.14 | 0.14 |
| 282 | 0.511 | |
| 283 | 8.9 | 12.5 |
| 284 | 3 | 3.63 |
| 285 | | 9.29 |
| 286 | 4.22 | 1.98 |
| 287 | 7.94 | 10.18 |
| 288 | 3.15 | 1.31 |
| 289 | 12.5 | 7.3 |
| 290 | 11.36 | 6.59 |
| 291 | 3.73 | 3.57 |

| Example No. | IL23 | IFNα |
|---|---|---|
| 292 | 4.72 | 5.6 |
| 293 | 4.78 | 11.42 |
| 294 | 6.35 | 4.9 |
| 295 | 7.3 | 3.29 |
| 296 | 7.16 | 2.72 |
| 297 | 0.25 | 0.6 |
| 298 | 0.11 | 0.06 |
| 299 | 0.27 | 0.09 |
| 300 | 0.28 | 0.13 |
| 301 | 3.16 | 1.46 |
| 302 | 4.06 | 2.09 |
| 303 | 2.34 | 2.65 |
| 304 | 1.24 | 0.57 |
| 305 | 2.65 | 3.11 |
| 306 | 2.53 | 0.56 |
| 307 | 3.74 | 1.54 |
| 308 | 1.86 | 1.16 |
| 309 | 1.92 | 0.63 |
| 310 | 1.08 | 0.59 |
| 311 | 0.19 | 0.16 |
| 312 | 0.59 | 1.02 |
| 313 | 1.33 | 0.50 |
| 314 | 0.19 | 0.08 |
| 315 | 0.09 | 0.08 |
| 316 | 0.07 | 0.10 |
| 317 | 0.21 | 0.11 |
| 318 | 0.13 | 0.13 |
| 319 | 0.09 | 0.01 |
| 320 | 0.05 | 0.03 |
| 321 | 0.15 | 0.14 |
| 322 | 0.07 | 0.03 |
| 323 | 0.07 | 0.03 |
| 324 | 0.22 | 0.07 |
| 325 | 0.46 | 0.21 |
| 326 | 0.06 | 0.04 |
| 327 | 0.10 | 0.01 |
| 328 | 0.60 | 0.12 |
| 329 | 0.09 | 0.16 |
| 330 | 0.31 | 0.09 |
| 331 | 0.06 | 0.04 |
| 332 | 0.38 | 0.13 |
| 333 | 0.12 | 0.09 |
| 334 | 0.31 | 0.23 |
| 335 | 0.28 | 0.19 |
| 336 | 0.40 | 0.44 |
| 337 | 0.11 | 0.08 |
| 338 | 0.40 | 0.11 |
| 339 | 0.05 | 0.03 |
| 340 | 0.22 | 0.12 |
| 341 | 0.44 | 0.22 |
| 342 | 0.15 | 0.13 |
| 343 | 0.16 | 0.14 |
| 344 | 0.13 | 0.03 |
| 345 | 0.03 | 0.03 |
| 346 | 0.04 | 0.02 |
| 347 | 0.19 | 0.07 |
| 348 | 0.43 | 0.18 |
| 349 | 0.06 | 0.06 |
| 350 | 0.08 | 0.08 |
| 351 | 0.06 | 0.02 |
| 352 | 0.02 | 0.02 |
| 353 | 0.25 | 0.16 |
| 354 | 0.15 | 0.13 |
| 355 | 0.03 | 0.03 |
| 356 | 0.12 | 0.08 |
| 357 | 0.12 | 0.03 |
| 358 | 9.98E−03 | 0.01 |
| 359 | 0.02 | 0.01 |
| 360 | 0.03 | 7.74E−03 |
| 361 | 0.06 | 0.02 |
| 362 | 0.02 | 0.01 |
| 363 | 0.07 | 0.04 |
| 364 | 0.01 | 0.01 |
| 365 | 0.01 | 0.01 |
| 366 | 0.02 | 9.22E−03 |
| 367 | 0.02 | 0.03 |
| 368 | 9.45E−03 | 0.01 |
| 369 | 0.03 | 0.01 |
| 370 | 0.03 | 0.03 |
| 371 | 4.89E−03 | 3.99E−03 |
| 372 | 0.01 | 0.01 |
| 373 | 6.22E−03 | 8.34E−03 |
| 374 | 8.36E−03 | 6.98E−03 |
| 375 | 0.02 | 9.47E−03 |
| 376 | 9.35E−03 | 3.47E−03 |
| 377 | 0.02 | 0.02 |
| 378 | 0.05 | 0.01 |
| 379 | 0.08 | 0.03 |
| 380 | 0.04 | 0.03 |
| 381 | 0.05 | 0.02 |
| 382 | 0.01 | 5.07E−03 |
| 383 | 0.10 | 0.02 |
| 384 | 0.12 | 0.17 |
| 385 | 0.07 | 0.02 |
| 386 | 0.02 | 0.01 |
| 387 | 0.28 | 0.12 |
| 388 | 0.05 | 0.02 |
| 389 | 0.26 | 0.23 |
| 390 | 1.03 | 0.33 |
| 391 | 9.66E−03 | 0.01 |
| 392 | 0.17 | 0.07 |
| 393 | 5.83E−03 | 2.86E−03 |
| 394 | 0.08 | 0.03 |
| 395 | 0.03 | 0.02 |
| 396 | 0.11 | 0.06 |
| 397 | 0.06 | 8.77E−03 |
| 398 | 0.02 | 0.02 |
| 399 | 0.05 | 0.05 |
| 400 | 0.30 | 0.07 |
| 401 | 0.48 | 0.44 |
| 402 | 0.25 | 0.33 |
| 403 | 0.24 | 0.29 |
| 404 | 4.40E−03 | 8.63E−03 |
| 405 | 0.02 | 0.01 |
| 406 | 0.25 | 0.10 |
| 407 | 0.09 | 0.09 |
| 408 | 0.68 | 0.43 |
| 409 | 0.04 | 0.02 |
| 410 | 0.02 | 8.61E−03 |
| 411 | 0.37 | 0.21 |
| 412 | 0.45 | 0.24 |
| 413 | 0.47 | 0.46 |
| 414 | 0.65 | 0.28 |
| 415 | 0.32 | 0.21 |
| 416 | 0.09 | 0.08 |
| 417 | 0.26 | 0.33 |
| 418 | 0.35 | 0.21 |
| 419 | 0.17 | 0.35 |
| 420 | 0.08 | 0.12 |
| 421 | 0.46 | 0.48 |
| 422 | 0.31 | 0.18 |
| 423 | 0.38 | 0.37 |
| 424 | 0.49 | 0.46 |
| 425 | 0.67 | 0.38 |
| 426 | 0.01 | 0.01 |
| 427 | 0.14 | 0.15 |
| 428 | 0.09 | 0.11 |
| 429 | 0.25 | 0.15 |
| 430 | 0.16 | 0.05 |
| 431 | 0.04 | 0.08 |
| 432 | 0.03 | 0.02 |
| 433 | 0.29 | 0.22 |
| 434 | 0.10 | 0.05 |
| 435 | 0.03 | 0.05 |
| 436 | 0.24 | 0.12 |
| 437 | 0.36 | 0.19 |
| 438 | 0.15 | 0.08 |
| 439 | 0.21 | 0.11 |
| 440 | 0.25 | 0.26 |
| 441 | 0.46 | 0.24 |
| 442 | 0.45 | 0.13 |
| 443 | 0.05 | 0.02 |

| Example No. | IL23 | IFNα |
| --- | --- | --- |
| 444 | 0.25 | 0.18 |
| 445 | 0.53 | 0.32 |
| 446 | 0.15 | 0.18 |
| 447 | 0.20 | 0.16 |
| 448 | 0.011 | 0.017 |
| 449 | 0.02 | 0.01 |
| 450 | 0.02 | 0.01 |

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the preparations and examples section set out hereinafter. Several of the compounds described were chiral, some were prepared as racemic mixtures, while others were prepared as a single enantiomer. In each case the preparation of the homochiral examples, or the preparation of the opposite enantiomer, may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diaststereoselectivity of transformations, providing enantio-enriched products upon cleavage of the chiral auxiliary.

Scheme 1. Coupling of halo-pyridine II with amine III

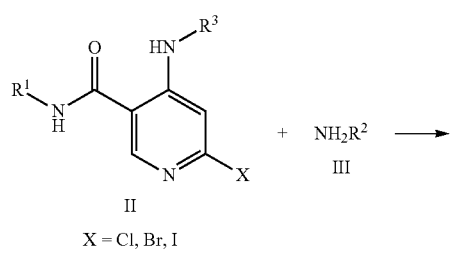

X = Cl, Br, I

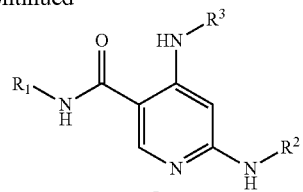

$R^1 = C_nR^{1a}$ (n = 1-3)
$R^{1a}$ = H/D/F
$R^2$ = cycloalkyl, heterocyclic, heteroaryl
$R^3 = C_{3-10}$ cycloalkyl, $C_{6-10}$ aryl, 5-10 membered heterocycle Scheme 1 illustrates the preparation of title compounds of the invention (I) from intermediate halo-pyridines (II) and amines (III). This coupling may be affected by many of the ways known to achieve displacement of 2-halo-pyridines by amines. This includes, but is not limited to, the palladium catalyzed N-arylation of amines, and nucleophilic displacement of the halide by the amine. A variety of palladium sources can be used to affect the coupling including both palladium(II) salts (for example palladium diacetate) as well as neutral palladium (such as tetrakis triphenylphosphine palladium or tris(dibenzylideneacetone)dipalladium). A large number of catalyst ligands are suitable for this transformation including bis(diphenylphosphino)-9,9-dimethylxanthene (Xantphos) and 2-(dicyclohexylphosphino)-3,6-dimethoxy-2',4',6'-tri-i-propyl-1,1'-biphenyl (BrettPhos) and many others that those versed in synthetic chemistry are familiar with (see Surry, D. S. et al., Chem. Sci., 2:27-50 (2011)). A variety of bases can be employed (such as potassium carbonate, sodium tert-butoxide, cesium carbonate and the like) as well as a number of solvents (such as 1,4-dioxane, toluene and dimethylacetamide and the like). Nucleophilic displacement is generally possible at elevated temperatures (typically >100° C.) in the presence or absence of either an acid or base catalyst. Heating can be accomplished using either a microwave or conventional heating. Amines are most typically, but not exclusively, aliphatic in such displacements.

Scheme 2. Coupling of halo-pyridine IV with amine V

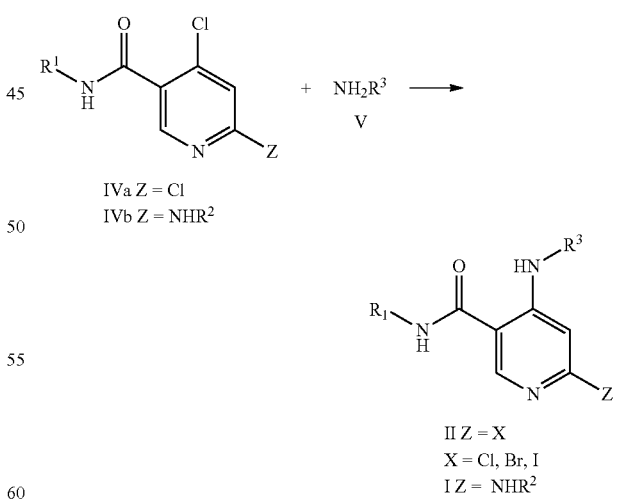

IVa Z = Cl
IVb Z = NHR²

II Z = X
X = Cl, Br, I
I Z = NHR²

Scheme 2 illustrates both the preparation of II as well as an alternative sequence to access I. The selective displacement of the 4-chloro group is possible both in the case of the dihalide (Z=Cl) and in the case where the Z group corresponds to an amine. In the former case displacement leads to intermediate II and in the latter in results in the formation of the title compound I. Displacement of the dihalide is most often accomplished in the presence of a base, such as sodium bis(trimethylsilyl)amide or N,N-diisopropylethylamine or related, but is also conceivable that it could be accomplished under elevated thermal conditions in the absence of a catalyst, or in the presence of an acid catalyst. In all cases a number of solvents were suitable, including tetrahydrofuran, dimethylformamide and N-methyl-2-pyrrolidone. Due to the increased reactivity of the 4-position relative to the 6-position of the 4,6-dichloronicotinamide it is reasonable to assume that alternative strategies could also be envisioned by someone skilled in the art of chemical synthesis. For the case of IVb the displacement can be accomplished under acidic conditions (using a protic acid such as hydrochloric acid), basic conditions (employing N,N-diisopropylethylamine or related) or using the aforementioned palladium-catalyzed N-arylation of amines.

Scheme 3 illustrates the preparation of intermediates IVb from commercially available (or prepared from diethyl 1,3-acetonedicarboxylate following: Platts, M. Y. et al., *Tetrahedron Lett.*, 52:512-514 (2011)) carboxylic acid VI. The amides IVb may be prepared from VI by many of the myriad ways known to prepare carboxamides by the dehydrative condensation of carboxylic acids and amines. For example, condensation of acid VI with amine ($NH_2R^1$, VII, where for these purposes $R^1$ is limited to substituted short aliphatic chains) may be effected by treatment of VI with an activating reagent, such as a water-soluble carbodiimide (EDC), in the presence of an N-hydroxy triazole (HOAt or HOBt, or the like) and amine in the presence of base (preferably triethylamine, diisopropylethylamine, or the like) in an appropriate polar aprotic solvent (N,N-dimethylformamide, acetonitrile, dichloromethane, or the like). Alternative combination reagents, reagents that combine an activating reagent and a hydroxy triazole, such as O-(7-azabenzotriazol-1-yl)-N,N,N',N'-tetramethyluronium hexafluorophosphate (HATU) or (benxotriazol-1-yloxy)tris(dimethylamino)phosphonium hexafluorophosphate (BOP) can be used in the presence of a base. The carboxylic acid VI may also be converted to an acid chloride by treatment with an appropriate chlorinating agent (thionyl chloride, oxalyl chloride, or the like). Similarly, VI may be converted to an acyl fluoride upon exposure to a fluorinating agent (such as cyanuric fluoride). Condensation of the acyl halide (chloride or fluoride) with the amine VII (typically carried out in the presence of a base such as pyridine or triethylamine in an aprotic solvent) may then provide the amide IVb.

Scheme 3. Coupling of carboxylic acid VI with amine VII

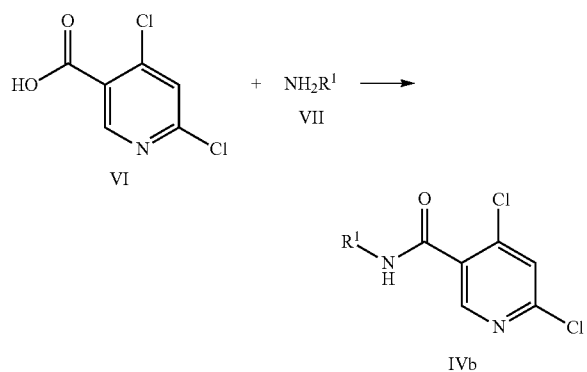

Scheme 4. Saponification and coupling of pendant carboxylates VIII/IX with amine X

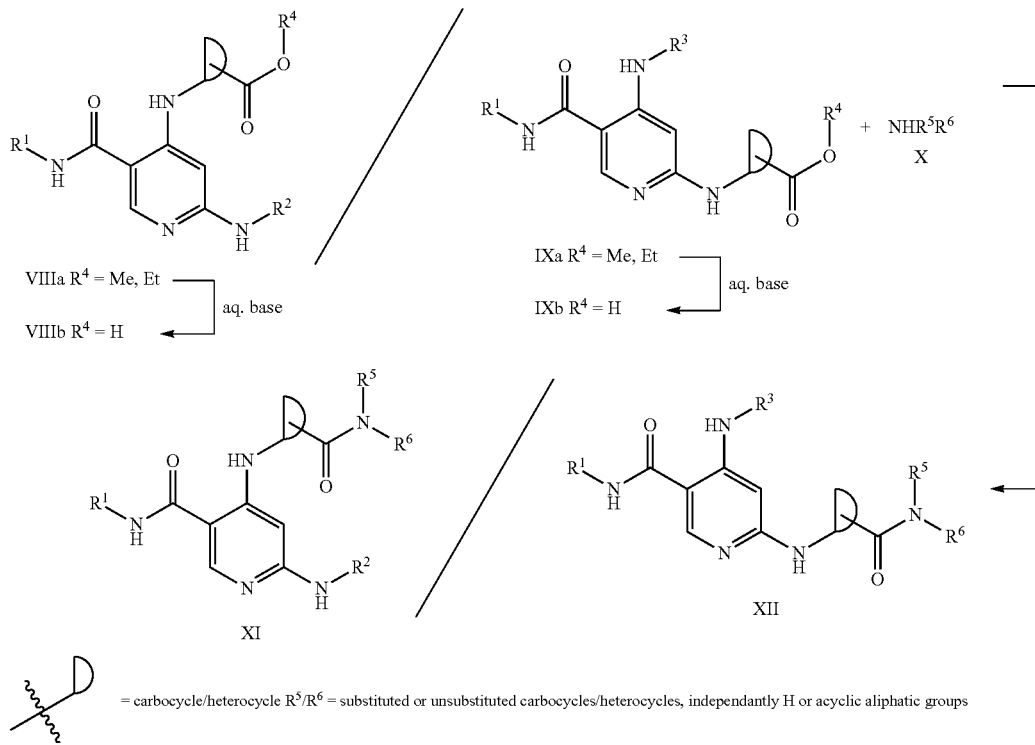

As illustrated in Scheme 4, in the case where $R^2$ or $R^3$ possess an acid/ester one can afford pendant amides via dehydrative condensation using standard chemistry techniques. If the carboxylate is a simple ester (as in VIIIa/IXa) saponification to the acid (VIIIb/IXb) can be accomplished using sodium, lithium, or potassium hydroxide under aqueous conditions with an organic co-solvent such as methanol and/or tetrahydrofuran. From the carboxylic acid, coupling to the amine X can be accomplished using the aforementioned coupling reagents (EDC/HOBt, HATU, etc.) or judicious activation of the acid by conversion to the acid chloride/fluoride and then combining the acid halide with the desired amine in the presence of a base such as pyridine.

-continued

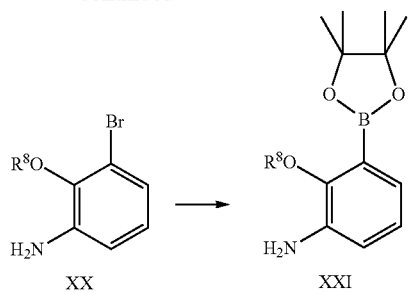

Scheme 5. Oxidation of pendant sulfides XIII and XIV

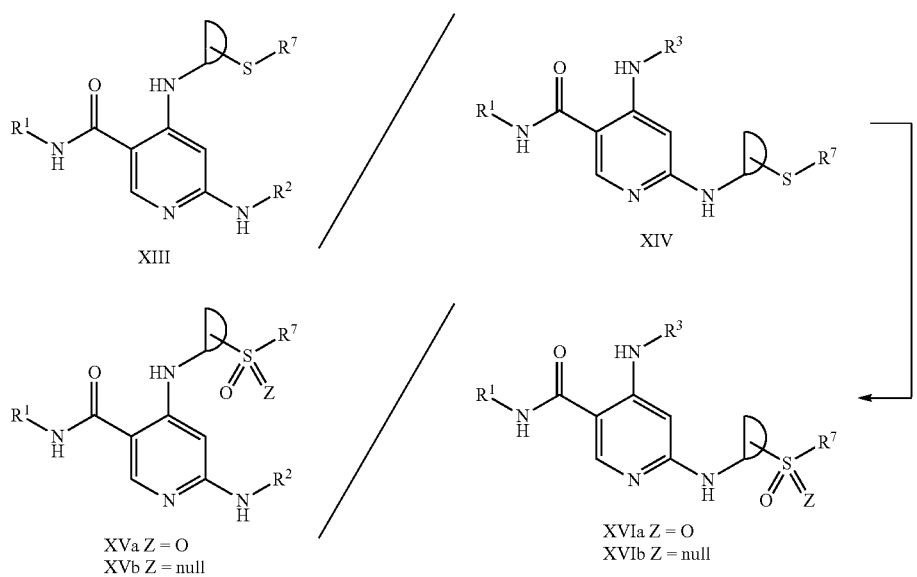

XVa Z = O
XVb Z = null

XVIa Z = O
XVIb Z = null $R^7$ = acyclic aliphatic chains with or without substition, amines bearing aliphatic substituents including hydrogen Scheme 5 illustrates how pendant sulfides can be oxidized to the corresponding sulfones or sulfoxides and, although not illustrated, it is also possible to perform these oxidations on II and then functionalize at the C6 position as shown in Scheme 1. The sulfides (XIII/XIV) can be oxidized to the sulfones (XVa/XVIa) using an oxidant such as sodium tungstate or 3-chloroperbenzoic acid in an organic solvent such as dichloromethane or acetic acid. The partial oxidation to the sulfoxides (XVb/XVIb) generally requires more mild conditions such as hydrogen peroxide in acetic acid; however, it is possible to use the same conditions as when targeting the sulfone if one quenches the reaction at the appropriate time.

Scheme 6. Synthesis of anilines V

-continued

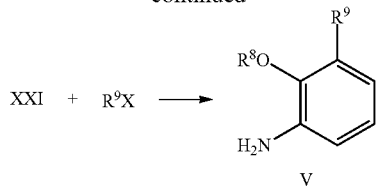

$R^8 = C_nR^{1a}$ $R^9$ = Aryl or heteraryl ring or bicycle X = halide

A large number of the anilines that were employed in Scheme 2 were commercially available; however, some were not. A strategy for the synthesis of many non-commercially available types of aniline is described in Scheme 6. The commercially available XVIII can be converted to the ether XIX using the Williamson ether synthesis. The Williamson ether formation is a common protocol for the synthesis of ethers, the reaction consists of the combination of an alcohol and a base—such as potassium carbonate, sodium hydride, triethylamine, or any number of others, followed by the addition of a compatible electrophile, such as an aliphatic, benzylic or allylic functional group featuring a leaving group —most commonly a halide, but mesylates/tosylates and other groups are also compatible, is added. The reaction is typically run in a polar aprotic solvent such as tetrahydrofuran or dimethylformamide. The nitro group of XIX is then reduced to the amine (XX) using a heterogeneous catalyst such as palladium, zinc or iron and a hydrogen source such as hydrogen (gas), ammonium chloride or hydrochloric acid, such reactions are typically run in alcoholic solvents. Borylation of the aryl bromide can be accomplished using palladium catalysis (see Ishiyama, T. et al., *J. Org. Chem.*, 60:7508 (1995)); however, metal halogen exchange followed by reaction with electrophilic borane is another common approach. The boronic ester (XXI) can be coupled via the Suzuki coupling to a wide variety of aryl and heteroaryl halides using a number of different catalysts, ligands, bases and solvents. One common combination of reagents is 1,1'-bis(di-tert-butylphosphino)ferrocene palladium dichloride, as the catalyst, tribasic potassium phosphate (in water), as the base, reacting with an aryl bromide using dioxane as the solvent; however, a great number of potential combinations exist, for a partial description see: Barder, T. E. et al., *J. Am. Chem. Soc.*, 127: 4685-4696 (2005); and Miyaura, N. et al., *Chem. Rev.*, 95:2457-2483 (1995).

Scheme 7. Alternative preparation of I

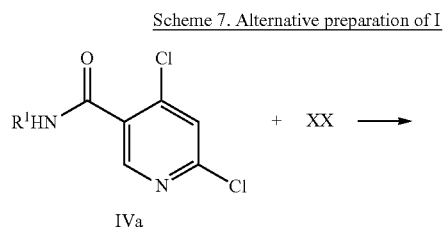

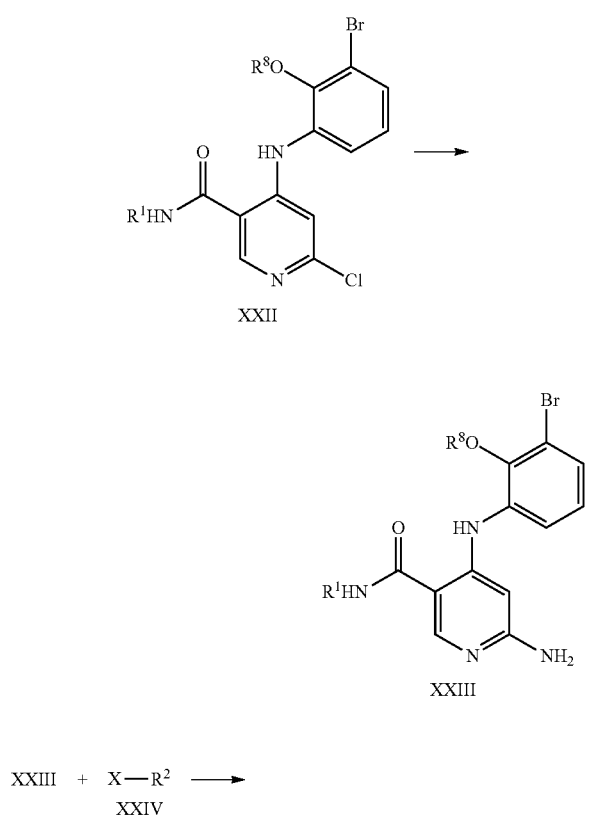

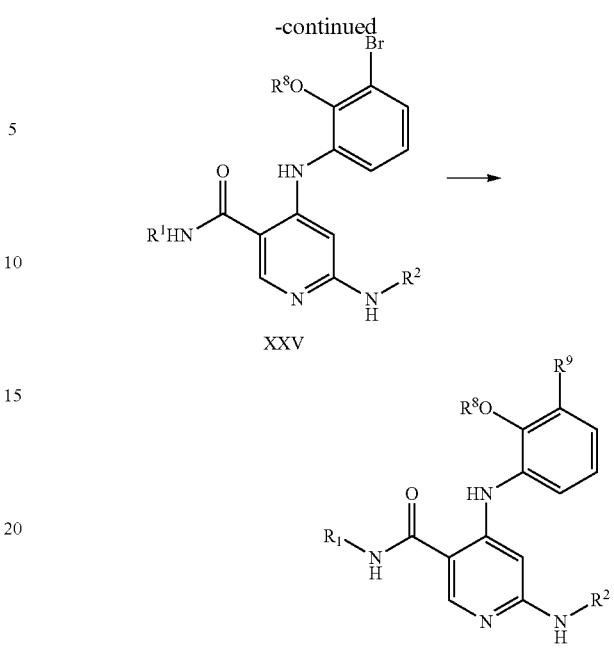

X = halide or leaving group; = O

Scheme 7 illustrates a means by which diversity at the $R^9$ (I) can be introduced at the end of the synthetic sequence. In this strategy IVa and XX can be coupled following the same procedures described in Scheme 2. Intermediate XXII can be converted to the primary amine via the addition of a protected amine (either via thermal, or selective palladium catalyzed N-arylation conditions) followed by deprotection, for example 4-methoxyphenyl)methanamine can be introduced under strictly thermal conditions followed by deprotection with a protic acid (such as trifluoroacetic acid) to provide XXIII. Addition of XXIII to XXIV can be accomplished in a variety of ways, depending on the nature of $R^2$. If $R^2$ is aliphatic (cyclic or acyclic), the amine XXIII can be added using a simple $S_N2$ displacement, usually performed using a single equivalent of a non-nucleophilic base such as sodium hydride. Such additions can be complicated by over alkylation of the amine, to which the standard solution is to use reductive amination of either the ketone or aldehyde version of XXIV. Reductive amination can be accomplished by first generating the imine (using removal of water to drive the reaction) and then using a common reducing agent such as sodium borohydride, or it can be accomplished using reducing agents, such as sodium cyanoborohydride, that are only reactive enough to reduce the imminium intermediate, for a thorough discussion see: Baxter, E. W. et al., *Organic Reactions, Vol.* 59, p 1, John Wiley & Sons, Inc., New York (2002). Alternatively if $R^3$ is aryl or heteroaryl the conversion can be accomplished using palladium-catalyzed N-arylation described in Scheme 1. Conversion of XXV to I can be accomplished using the Suzuki coupling reaction as described in Scheme 6, as well as other cross-coupling strategies such as Stille and Negishi cross-couplings (see: Stanforth, S. P., *Tetrahedron.*, 54:263-303 (1998)).

Scheme 8. Alternate synthesis of anilines V

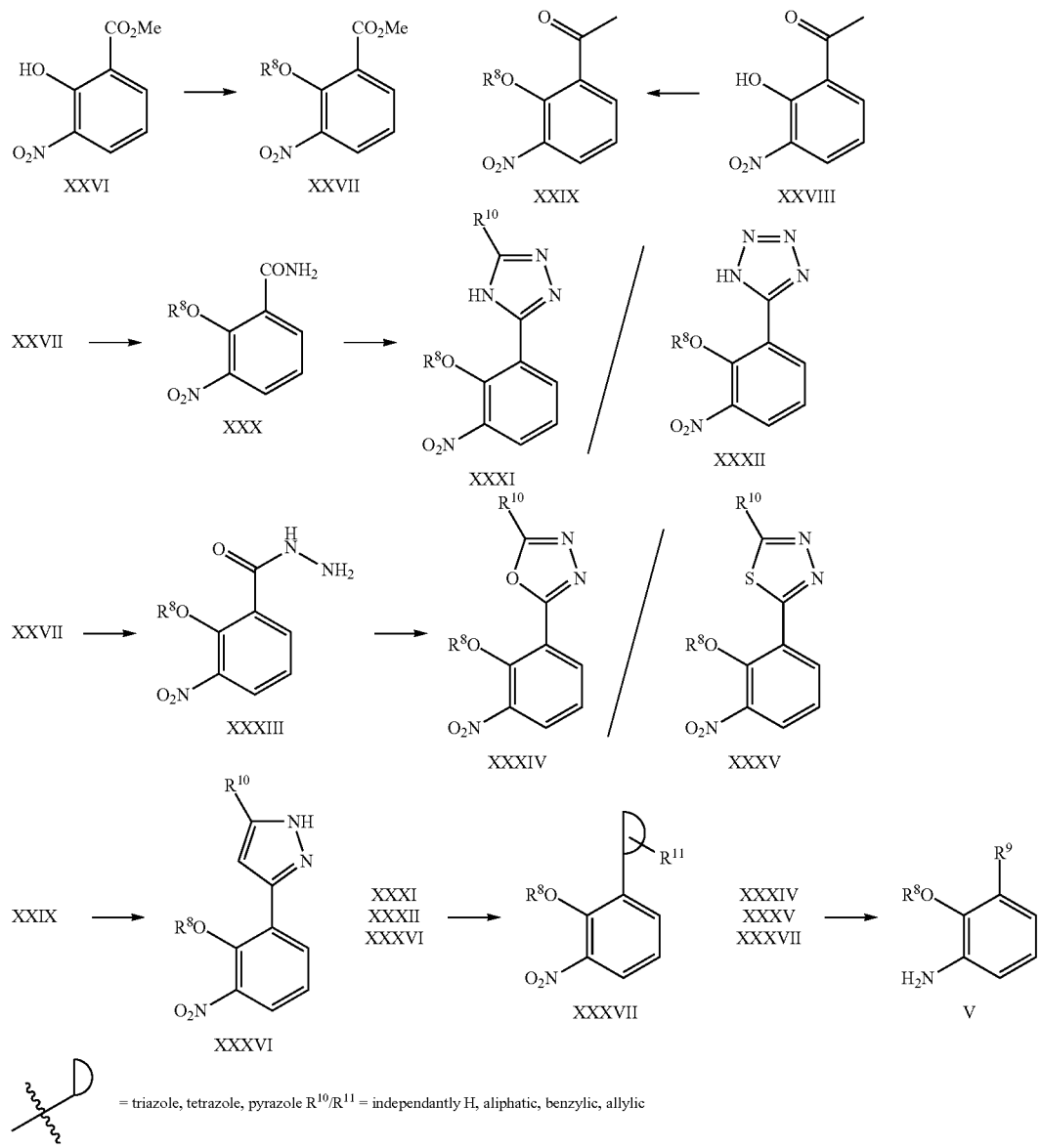

= triazole, tetrazole, pyrazole  $R^{10}/R^{11}$ = independantly H, aliphatic, benzylic, allylic Scheme 8 illustrates how some of heterocycles can be built directly off of carbonyl functionality to arrive at anilines V without the use of a transition metal catalyzed coupling reaction. The commercially available XXVI can be converted to the ether XXVII via the techniques described in Scheme 6, similarly XXVIII can be converted to XXIX. XXVII can be converted to the amide XXX directly using ammonia and ammonium hydroxide in methanol, or via saponification, accomplished using an aqueous base with a polar organic co-solvent like tetrahydrofuran and an alcohol co-solvent like methanol, and amide formation (described in Scheme 5). The amide XXX can be converted to a triazole via formation of the amidine using reagents such as N,N-dimethylacetamide dimethyl acetal or N,N-dimethylformamide dimethyl acetal followed by exposure to hydrazine in the presence of acetic acid. Alternatively the tetrazole XXXII can be prepared from XXX by reaction with triazidochlorosilane (generated in situ from tetrachlorosilane and sodium azide, see: El-Ahl, A-A. S. et al., Tetrahedron Lett., 38:1257-1260 (1997)). The hydrazide XXXIII can be converted to the oxadiazole via a condensation reaction with an orthoformate or orthoacetate under thermal or acid catalyzed conditions, often using the orthoformate/orthoacetate as the solvent. Alternatively the aceto variant of hydrazide XXXIII can be converted to the thiazole by exposure to a sulfonating reagent such as Lawesson's reagent and then condensation under thermal conditions, typically in polar aprotic solvent such as dioxane. The ketone XXIX can be converted to the pyrazole XXXVI by condensation with N,N-dimethylacetamide dimethyl acetal or N,N-dimethylformamide dimethyl acetal (or related) followed by reaction with hydrazine in the presence of acetic acid. In the cases of XXXI, XXXII, and XXXVI the heterocycle can further be reacted with an electrophile such as organo-halides, epoxides or activated carbonyl species (under basic conditions using an inorganic base such as potassium carbonate, a tertiary amine such as triethylamine, or a strong base such as sodium hydride) or with vinyl ethers such as ethoxyethene (under acidic conditions). Other electrophiles such as silyl halides would also be successful as would potentially a selective palladium catalyzed N-arylation. Finally the nitro compounds can be converted to the aniline V via reduction using conditions similar to those described in Scheme 6. This list is far from an exhaustive collection of the heterocycles available from common functional group manipulations of carbonyl moieties and their derivatives (such as cyanides) see: Caron, S., *Practical Synthetic Organic Chemistry*, 609-647 (2011) and references therein.

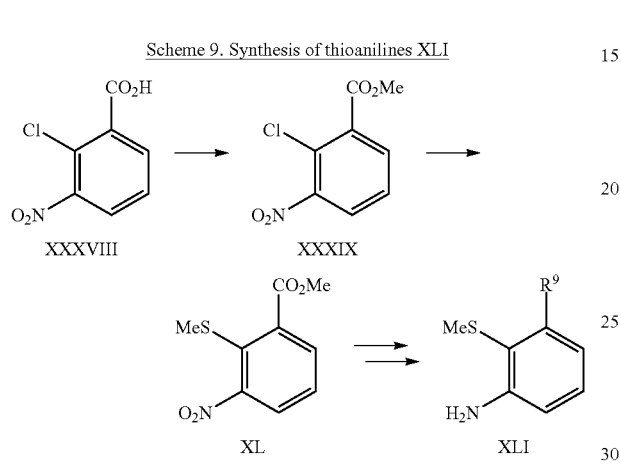

Scheme 9 illustrates the synthesis of the thio-variant of V. Starting from the commercially available acid XXXVIII, which can be converted to the ester via heating with methanol in the presence of a protic acid, as well as by any number of techniques available for the synthesis of esters from acids, such as formation of the acid halide (described in Scheme 5) followed by reaction with methanol. Displacement of the chloride to provide XL can be accomplished via nucleophilic addition using sodium thiomethoxide. Conversion to the functionalized aniline XLI follows the same techniques illustrated and described in Scheme 8. Additionally the final sulfide product can be oxidized to the sulfone using the oxidation conditions described in Scheme 5.

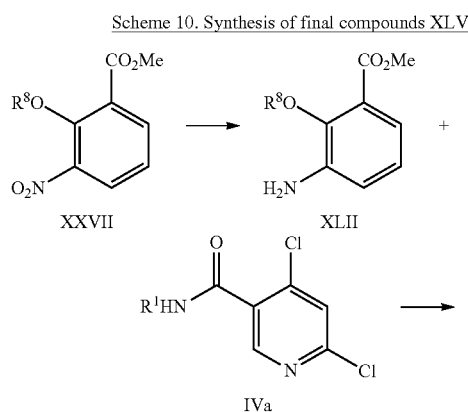

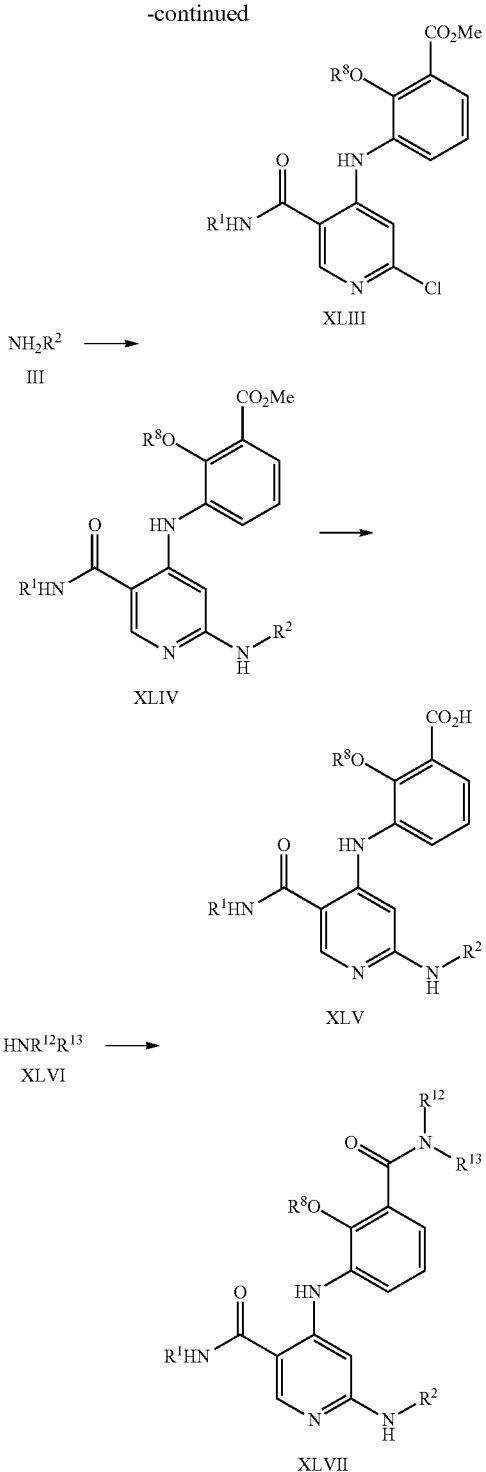

$R^{12}/R^{13}$ = independantly H, aliphatic, benzylic, allylic, also potentially linked to form a heterocycle Scheme 10 illustrates another form of the final compound I. In this strategy the aniline XLII (made via reduction of the nitro compound XXVII by analogy to Scheme 6) is added to the dichloride IVa using the techniques from Scheme 2. Conversion to XLIV can be accomplished using the same techniques described in Scheme 1. Saponification of the methyl ester (XLIV) to provide the acid XLV is typically accomplished under aqueous conditions employing a strong water soluble base such as potassium-, lithium-, or sodium hydroxide using tetrahydrofuran and an alcohol co-solvent. The acid XLV can be converted to various heterocycles using the techniques described in Scheme 8, or it can be coupled with an amine to generate the amide XLVII as the final product as described in Scheme 3.

Scheme 11. Synthesis of anilines L (variant of V)

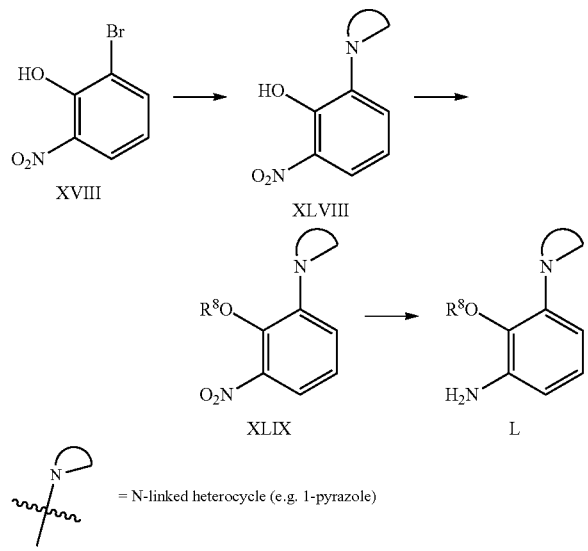

Scheme 11 illustrates another variant of V, where the aniline has been substituted with a heterocycle via a carbon-nitrogen bond. Starting from commercially available XVIII an Ullmann condensation (for a recent review see: Mannier, F. et al., *Angew. Chem. Int. Ed.*, 48:6954-6971 (2009)) can be used. This reaction is typically performed in the presence of a copper salt (such as copper(I) oxide), an inorganic base (such as cesium carbonate) and often a ligand (although some solvents such as DMF can take the role of the ligand). The phenol XLVIII can be converted to the ether XLIX using the Williamson ether conditions as described in Scheme 6. Conversion to the aniline (L) is accomplished by reduction of the nitro group as described in Scheme 6.

Scheme 12. Synthesis of anilines LI and LIV (variants of V)

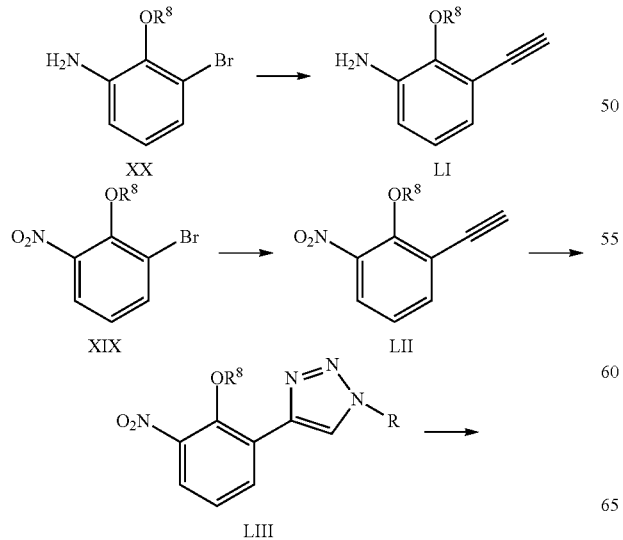

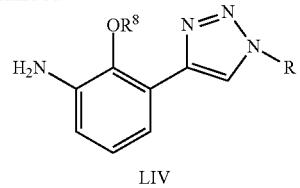

Scheme 12 describes the synthesis of anilines LI and LIV. A Sonogashira coupling of XX/XIX with ethynyltrimethylsilane followed by removal of the silyl group using a mild base (such as potassium carbonate in a protic solvent such as methanol) or a fluoride source (such as tetrabutylammonium fluoride or potassium fluoride) can be used to provide the terminal alkynes LI and LII. The Sonogashira coupling is performed using a palladium catalyst (such as tetrakis triphenylphosphine palladium), a copper catalyst such as copper (I) iodide, and a base (typically an amine base such as triethylamine or diisopropylamine) using either the base as the solvent or a polar solvent such as dimethylformamide; however, a great deal of work has been done running the reaction with different ligands and additives and even in the absence of the catalysts, see: Chinchilla, R. et al., *Chem. Rev.*, 107:874-923 (2007); Chinchilla, R. et al., *Chem. Soc. Rev.*, 40:5084-5121 (2011). The aniline LI can be coupled to IVa as described in Scheme 2 and then converted to the target ligand I as described in Scheme 1 or further elaborated using the techniques described for LIII (to follow). LII can be converted to the 1,2,3-triazole using the Huisgen cycloaddition (or "Click chemistry"), This reaction is run between an alkyne and an azide using a copper catalyst (commonly copper(II) sulfate), a reducing agent (such as sodium ascorbate), the reaction can be run in a number of solvents/co-solvents including water, tert-butyl alcohol, tetrahydrofuran and toluene. A great deal of work has been done describing the variety and versatility of this cycloaddition, for reviews see: Kolb, H. C. et al., *Angew. Chem. Int. Ed.*, 40:2004-2021 (2001), and Meldal, M. et al., *Chem. Rev.*, 108:2952-3015 (2008). If the Huisgen cycloaddition is performed with a removable group such as methyl pivalate this can be removed and the triazole alkylated as described in Scheme 8. Otherwise the nitro group can be reduced as described in Scheme 6 and LIV can be carried forward to react with IVa as described in Scheme 2.

Scheme 13. Synthesis of LVII

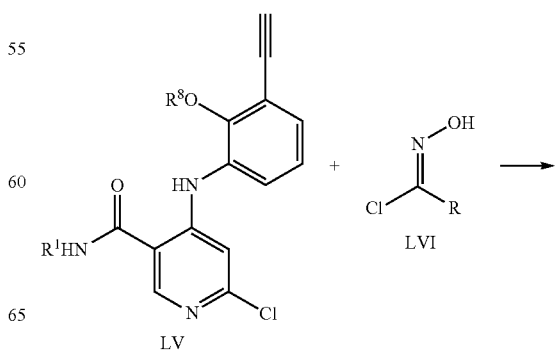

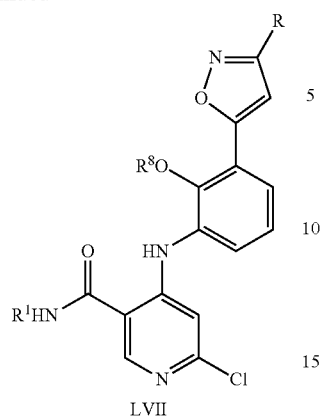

LVII

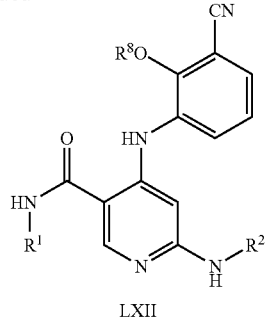

LXII

Scheme 13 illustrates the synthesis of penultimate compounds LVII (converted to target ligands using the coupling procedures described in Scheme 1). Intermediate LV (prepared using the techniques described in Scheme 12 and Scheme 2) can be converted to the isoxazole LVII using a [3+2] cycloaddition with a nitrile oxide (formed in situ from a N-hydroxyimidoyl chloride and a mild non-nucleophilic base). The reaction can be run thermally in aprotic solvents (such as dichloroethane) but recent work has described the utility of catalysts in the reaction, see: Grecian, S. et al., Angew. Chem. Int. Ed., 47:8285-8287 (2008).

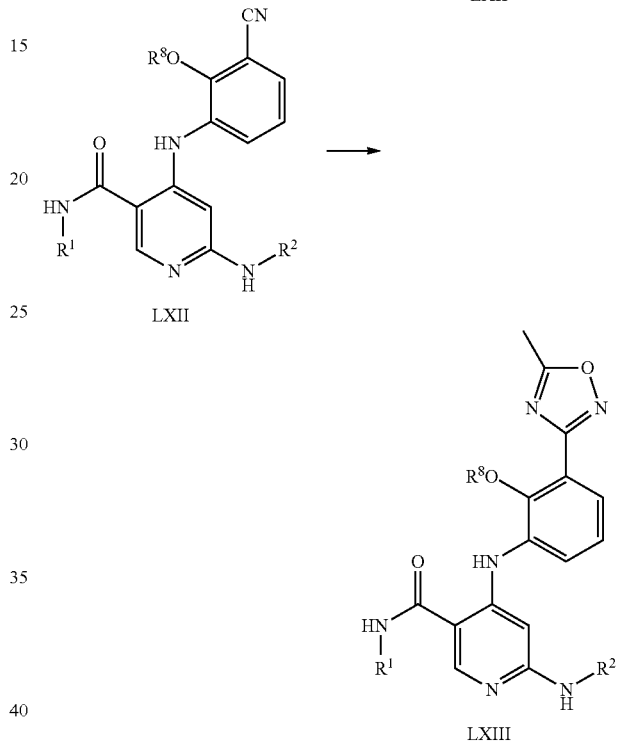

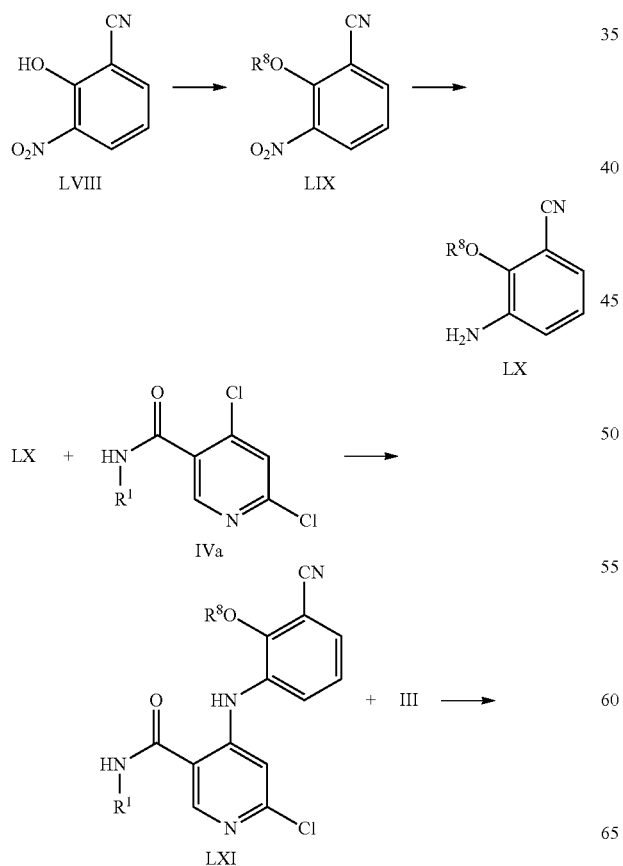

Scheme 14 illustrates the synthesis of target compounds LXII and LXIII. Commercially available LVIII can be converted to the aniline LX following the strategies outlined in Scheme 6. Addition of LX to IVa follows the techniques described in Scheme 2 to provide LXI, which can be coupled with III following the strategies described in Scheme 1. Conversion of the cyano-containing LXII to the oxadiazole LXIII can be accomplished via the nucleophilic addition of hydroxylamine to the cyanide, performed under basic conditions typically in a polar protic solvent such as water or alcohol, followed by acylation and condensation with acetic anhydride, done by heating the intermediate with acetic anhydride in a polar aprotic solvent.

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters SunFire $C_{18}$, Waters XBridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:
$NaHCO_3$ (aq)=saturated aqueous sodium bicarbonate
brine=saturated aqueous sodium chloride
DCM=dichloromethane
DIEA=N,N-diisopropylethylamine
DMAP=4-(N,N-dimethylamino)pyridine
DMF=N,N-dimethylformamide
DMSO=dimethyl sulfoxide
EDC=N-(3-dimethylaminopropyl)-N'-ethylcarbodiimide hydrochloride
EtOAc=ethyl acetate
HOAT=1-hydroxy-7-azabenzotriazole
HOBT=1-hydroxybenzotriazole hydrate
rt=ambient room temperature (generally about 20-25° C.)
TEA=triethylamine
TFA=trifluoroacetic acid
THF=tetrahydrofuran Analytical HPLC Method Employed in Characterization of Examples Analytical HPLC was performed on Shimadzu LC10AS liquid chromatographs using the following methods:
Method A (used in all cases, unless otherwise indicated):
  Linear gradient of 0 to 100% solvent B over 4 minutes ("min"), with 1 minute ("min") hold at 100% B
  Ultraviolet ("UV") visualization at 220 nanometers ("nm")
  Column: YMC S5 ODS Ballistic 4.6×50 mm
  Flow rate: 4 milliliters ("mL")/min
  Solvent A: 0.2% phosphoric acid, 90% water, 10% methanol
  Solvent B: 0.2% phosphoric acid, 90% methanol, 10% water
Method B:
  Column: PHENOMENEX® Luna C18(2), 4.6×50 mm×5 µm
  Mobile Phase: (A) 10:90 methanol:water; (B) 90:10 methanol:water
  Buffer: 0.1% TFA
  Gradient Range: 0-100% B
  Gradient Time: 4 min
  Flow Rate: 4 mL/min
  Analysis Time: 5 min
  Detection:
  Detector 1: UV at 220 nm
  Detector 2: MS(ESI$^+$)
  Detector 3: ELSD
Method C:
  Column: Waters SunFire C18, 4.6×50 mm×5 µm
  Mobile Phase: (A) 10:90 methanol:water; (B) 90:10 methanol:water
  Buffer: 0.1% TFA
  Gradient Range: 0-100% B
  Gradient Time: 4 min
  Flow Rate: 4 mL/min
  Analysis Time: 5 min
  Detection:
  Detector 1: UV at 220 nm
  Detector 2: MS(ESI$^+$)
  Detector 3: ELSD
Method D:
  Column: PHENOMENEX® Luna C18(2), 4.6×50 mm×5 µm
  Mobile Phase: (A) 10:90 methanol:water; (B) 90:10 methanol:water
  Buffer: 0.1% TFA
  Gradient Range: 0-100% B
  Gradient Time: 4 min
  Flow Rate: 4 mL/min
  Analysis Time: 5 min
  Detection:
  Detector 1: UV at 220 nm
  Detector 2: MS(ESI$^+$)
  Detector 3: ELSD
Method E:
  Column: Waters Acquity UPLC BEH C18, 2.1×50 mm, 1.7 µm particles
  Mobile Phase: (A) 5:95 acetonitrile:water; (B) 95:5 acetonitrile:water
  Buffer: 10 mM ammonium acetate
  Gradient Range: 0-100% B
  Gradient Time: 3 min
  Flow Rate: 1.11 mL/min
  Analysis Time: 4 min
  Detection:
  Detector 1: UV at 220 nm
  Detector 2: MS(ESI$^+$)
  Detector 3: ELSD
Method F:
  Column: Waters SunFire C18 (4.6×150 mm), 3.5 µm
  Mobile Phase: (A) 5:95 acetonitrile:water; (B) 95:5 acetonitrile:water
  Buffer: 0.1% TFA
  Gradient Range: 0-100% B
  Gradient Time: 12 min
  Flow Rate: 4 mL/min
  Analysis Time: 15 min
  Detection:
  Detector 1: UV at 220 nm
  Detector 2: UV at 254 nm
Method G:
  Column: Waters Acquity UPLC BEH C18, 2.1×50 mm, 1.7 µm particles
  Mobile Phase: (A) 5:95 acetonitrile:water; (B) 95:5 acetonitrile:water
  Buffer: 0.05% TFA
  Gradient Range: 0-100% B
  Gradient Time: 3 min
  Flow Rate: 1.11 mL/min
  Analysis Time: 4 min Detection:
Detector 1: UV at 220 nm
Detector 2: MS(ESI$^+$)
Detector 3: ELSD Method H:
Column: (LCMS) Ascentis Express C18, 4.6×50 mm, 2.7 µm particles
Mobile Phase: (A) 5:95 acetonitrile:water; (B) 95:5 acetonitrile:water
Buffer: 10 mM ammonium acetate
Gradient Range: 0-100% B
Gradient Time: 4 min
Flow Rate: 4 mL/min
Analysis Time: 5 min
Detection:
Detector 1: UV at 220 nm
Detector 2: MS(ESI$^+$)

Method I:
Column: Waters XBridge C18, 4.6×50 mm, 5 µm particles
Mobile Phase: (A) 5:95 acetonitrile:water; (B) 95:5 acetonitrile:water
Buffer: 0.05% TFA
Gradient Range: 0-100% B
Gradient Time: 4 min
Flow Rate: 4 mL/min
Analysis Time: 5 min
Detection:
Detector 1: UV at 220 nm
Detector 2: MS(ESI$^+$)

Method J:
Column: (LCMS) BEH C18, 2.1×50 mm, 1.7 µm particles
Mobile Phase: (A) water; (B) acetonitrile
Buffer: 0.05% TFA
Gradient Range: 2%-98% B (0 to 1 min) 98% B (to 1.5 min) 98%-2% B (to 1.6 min)
Gradient Time: 1.6 min
Flow Rate: 0.8 mL/min
Analysis Time: 2.2 min
Detection:
Detector 1: UV at 254 nm
Detector 2: MS(ESI$^+$)

Method K:
Column: (LCMS) BEH C18, 3.0×50 mm, 1.7 µm particles
Mobile Phase: (A) 5:95 acetonitrile:water; (B) 95:5 acetonitrile:water
Buffer: 10 mM ammonium acetate
Gradient Range: 0-100% B
Gradient Time: 1.8 min
Flow Rate: 1.2 mL/min
Analysis Time: 4 min
Detection:
Detector 1: UV at 220 nm
Detector 2: MS(ESI$^+$)

Method L:
Column: (LCMS) SunFire C18 2.1×30 mm, 2.5 µm particles
Mobile Phase: (A) 10:90 methanol:water; (B) 90:10 methanol:water
Buffer: 0.1% TFA
Gradient Range: 0-100% B
Gradient Time: 2 min
Flow Rate: 1 mL/min
Analysis Time: 3 min
Detection:
Detector 1: UV at 220 nm
Detector 2: MS(ESI$^+$)

Method M:
Column: (LCMS) SunFire C18 2.1×30 mm, 3.5 µm particles
Mobile Phase: (A) 10:90 methanol:water; (B) 90:10 methanol:water
Buffer: 0.1% TFA
Gradient Range: 0-100% B
Gradient Time: 4 min
Flow Rate: 1 mL/min
Analysis Time: 5 min
Detection:
Detector 1: UV at 220 nm
Detector 2: MS(ESI$^+$)

Method N:
Column: Waters SunFire C18 (3×150 mm), 3.5 µm
Mobile Phase: (A) 5:95 acetonitrile:water; (B) 95:5 acetonitrile:water
Buffer: 0.05% TFA
Gradient Range: 0-100% B
Gradient Time: 12 min
Flow Rate: 0.5 mL/min
Analysis Time: 15 min
Detection:
Detector 1: UV at 220 nm
Detector 2: UV at 254 nm Method O:
Column: Waters SunFire C18 (4.6×150 mm), 3.5 µm
Mobile Phase: (A) 5:95 acetonitrile:water; (B) 95:5 acetonitrile:water
Buffer: 0.05% TFA
Gradient Range: 0-50% B (0-15 min) 50-100% B (15-18 min)
Gradient Time: 18 min
Flow Rate: 1 mL/min
Analysis Time: 23 min
Detection:
Detector 1: UV at 220 nm
Detector 2: UV at 254 nm Method P:
Column: Waters XBridge Phenyl, 4.6×150 mm, 3.5 µm particles
Mobile Phase: (A) 5:95 acetonitrile:water; (B) 95:5 acetonitrile:water
Buffer: 0.05% TFA
Gradient Range: 0-100% B
Gradient Time: 12 min
Flow Rate: 1 mL/min
Analysis Time: 15 min
Detection:
Detector 1: UV at 220 nm
Detector 2: UV at 254 nm Preparation 1

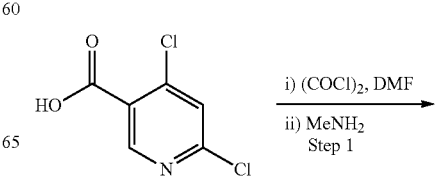

-continued

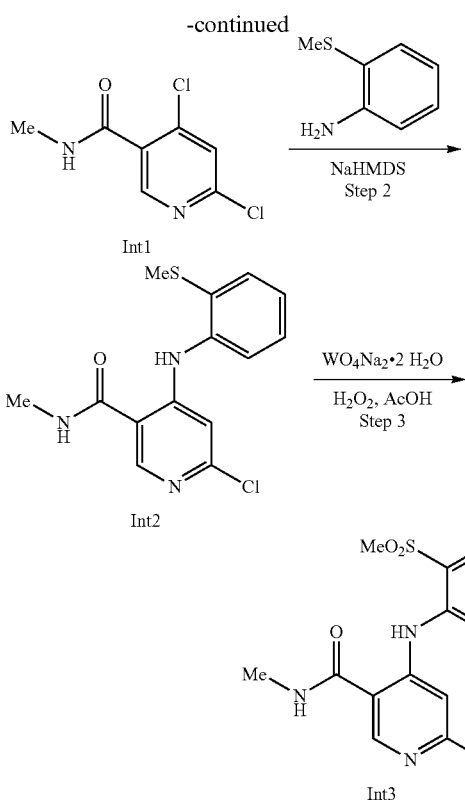

Step 1

To a round bottomed flask containing 4,6-dichloronicotinic acid (60 g, 313 mmol) was added chloroform (500 mL) and a single drop of N,N-dimethylformamide (DMF). The reaction was cooled to 0° C. and oxalyl chloride (82 mL, 938 mmol) was subsequently added over 5 minutes. The reaction was maintained at 0° C. for one hour and then concentrated under reduced pressure. The reaction vessel was recharged with chloroform and re-concentrated, this was repeated one additional time, yielding a brown oil. The oil was dissolved in chloroform (500 mL) and cooled to 0° C. To the chilled reaction vessel was added methylamine (2 M in THF, 390 mL, 780 mmol) in a gradual manner. Stirring was maintained at 0° C. for 1 hour and then the reaction was quenched via the addition of water. The product was extracted with chloroform and the combined organic layers were washed with water and brine (saturated aqueous sodium chloride solution) and then dried over sodium sulfate, filtered and concentrated. The crude product (52 g) was combined with another batch of crude material (27 g) and then purified using flash chromatography eluting with 40-50% ethyl acetate in petroleum ether, providing 73 g of the product Intermediate 1. $^1$H NMR (400 MHz, DMSO-$d_6$); δ 8.60 (bm, 1H), δ 8.47 (s, 1H), δ 7.89 (s, 1H), δ 2.78 (d, J=4.6 Hz, 3H). LC retention time 1.25 min [A]. Mass Spectrometry ("MS") (E+) m/z: 205 (MH$^+$).

Step 2

To a solution of Intermediate 1 (1.8 g, 8.78 mmol) in tetrahydrofuran (THF, 68 mL) was added 2-(methylthio) aniline (1.83 g, 13.2 mmol) followed by sodium bis(trimethylsilyl)amide solution (NaHMDS, 1M in THF, 61 mL, 61 mmol). The reaction was stirred at room temperature for 30 minutes and then quenched with water. The crude product was extracted with ethyl acetate, dried over sodium sulfate, filtered, concentrated and purified by automated chromatography (0-100% EtOAc/hexanes) to provide Intermediate 2 (2.16 g, 80% yield). $^1$H NMR (400 MHz, DMSO-$d_6$) δ 10.34 (s, 1H), 8.77 (d, J=4.4 Hz, 1H), 8.51 (s, 1H), 7.44-7.22 (m, 4H), 6.51 (s, 1H), 2.80 (d, J=4.6 Hz, 3H), 2.43 (s, 3H). LC retention time 0.86 min [J]. MS(E$^+$) m/z: 308 (MH$^+$).

Step 3

Intermediate 2 (900 mg, 2.92 mmol) was suspended in acetic acid (AcOH, 9.7 mL), and hydrogen peroxide (30% aqueous solution, 6.0 mL, 58.5 mmol) and sodium tungstate dihydrate (964 mg, 2.92 mmol) were subsequently added. The reaction was complete after 30 minutes, and was then diluted with water and ethyl acetate. The layers were separated and the aqueous layer extracted once with ethyl acetate. The combined organic layers were washed once with saturated aqueous sodium bisulfate and once with water. The combined organic layers were then dried over sodium sulfate, filtered, concentrated under reduced pressure and purified with automated silica gel chromatography (0-100% EtOAc/hexanes), yielding the sulfone product Intermediate 3. $^1$H NMR (400 MHz, DMSO-$d_6$) δ 10.76 (s, 1H), 8.79 (d, J=4.0 Hz, 1H), 8.57 (s, 1H), 7.96 (dd, J=7.9, 1.5 Hz, 1H), 7.79-7.73 (m, 1H), 7.70-7.66 (m, 1H), 7.46 (t, J=7.6 Hz, 1H), 6.97 (s, 1H), 3.17 (s, 3H), 2.79 (d, J=4.4 Hz, 3H). LC retention time 0.72 min [J]. MS(E$^+$) m/z: 339 (MH$^+$).

Example 1

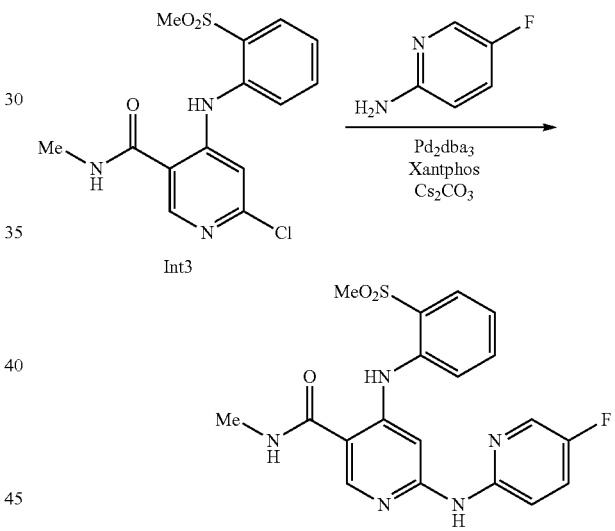

5-Fluoropyridin-2-amine (40 mg, 0.35 mmol) was combined with Intermediate 3 (80 mg, 0.24 mmol). To the vessel was added dimethylacetamide (DMA, 1 mL) followed by tris(dibenzylideneacetone)dipalladium(0) (Pd$_2$dba$_3$, 22 mg, 0.024 mmol), 4,5-bis(diphenylphosphino)-9,9-dimethylxanthene (Xantphos, 27 mg, 0.047 mmol) and cesium carbonate (153 mg, 0.47 mmol). The vessel was then evacuated and backfilled with nitrogen three times and then heated to 145° C. for 2 hours. The crude product was diluted with DMF and filtered, before being purified using preparative HPLC providing 50 mg (51% yield) of 1. $^1$H NMR (500 MHz, DMSO-$d_6$) δ 10.82 (s, 1H), 9.82 (s, 1H), 8.57-8.48 (m, 2H), 8.09 (d, J=2.5 Hz, 1H), 7.93 (dd, J=7.9, 1.5 Hz, 1H), 7.83-7.77 (m, 1H), 7.76-7.73 (m, 1H), 7.69-7.60 (m, 2H), 7.59 (s, 1H), 7.40-7.34 (m, 1H), 3.15 (s, 3H), 2.77 (d, J=4.5 Hz, 3H). LC retention time 1.23 min [E]. MS(E$^+$) m/z: 416 (MH$^+$).

Examples 2 to 61

The following Examples were prepared in a similar manner to the product of Example 1:

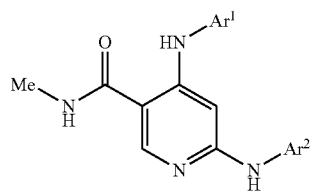
| Example No. | Ar¹ | Ar² | Rt (min) [Method] | m/z [M + H]⁺ |
|---|---|---|---|---|
| 2 | MeO₂S-phenyl | quinolin-2-yl | 1.56 [E] | 448 |
| 3 | MeO₂S-phenyl | pyridin-2-yl | 1.23 [E] | 398 |
| 4 | MeO₂S-phenyl | 4-Me-pyridin-2-yl | 1.31 [E] | 412 |
| 5 | MeO₂S-phenyl | 4-CN-pyridin-2-yl | 1.33 [E] | 423 |
| 6 | MeO₂S, OMe-phenyl | 5-F-pyridin-2-yl | 1.26 [E] | 446 |
| 7 | MeO₂S, OMe-phenyl | 5-morpholino-pyridin-2-yl | 1.14 [E] | 513 |
| 8 | MeO₂S, OMe-phenyl | pyridin-2-yl | 1.18 [E] | 428 |

-continued

| Example No. | Ar¹ | Ar² | Rt (min) [Method] | m/z [M + H]⁺ |
|---|---|---|---|---|
| 9 | MeO₂S-phenyl | 5-morpholino-pyridin-2-yl | 1.20 [E] | 483 |
| 10 | MeO₂S, F-phenyl | pyridin-2-yl | 1.22 [E] | 416 |
| 11 | MeO₂S, Cl-phenyl | 5-F-pyridin-2-yl | 1.46 [E] | 450 |
| 12 | MeO₂S, Cl-phenyl | pyridin-2-yl | 1.27 [E] | 432 |
| 13 | MeO₂S, F-phenyl | 5-F-pyridin-2-yl | 1.29 [E] | 434 |
| 14 | MeO₂S-phenyl | 4-CF₃-pyridin-2-yl | 0.94 [E] | 466 |
| 15 | MeO₂S-phenyl | 4-OMe-pyridin-2-yl | 1.03 [G] | 428 |
| 16 | MeO₂S-phenyl | 6-CF₃-pyridin-2-yl | 1.38 [G] | 466 |
| 17 | MeO₂S-phenyl | 5-Cl-pyridin-2-yl | 1.06 [G] | 432 |

-continued
| Example No. | Ar¹ | Ar² | Rt (min) [Method] | m/z [M + H]⁺ |
|---|---|---|---|---|
| 18 | 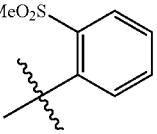 | 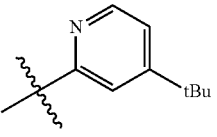 [SMILES: *c1cc(C(C)(C)C)ccn1] | 1.32 [G] | 454 |
| 19 | 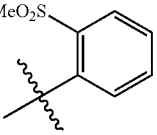 | 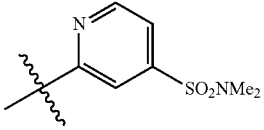 | 1.05 [G] | 505 |
| 20 | 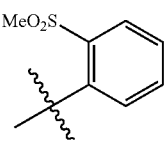 | 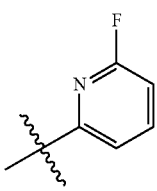 [SMILES: *c1cccc(F)n1] | 1.04 [G] | 416 |
| 21 | 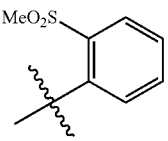 | 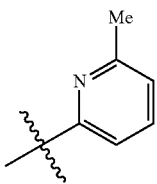 | 1.05 [G] | 412 |
| 22 | 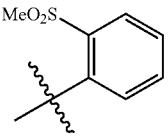 | 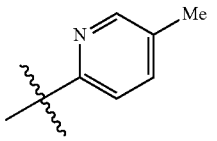 [SMILES: *c1ccc(C)cn1] | 1.05 [G] | 412 |
| 23 | 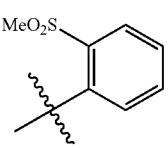 | 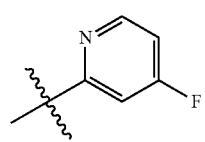 [SMILES: *c1cc(F)ccn1] | 1.35 [G] | 416 |
| 24 | 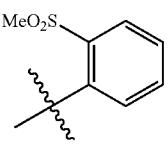 | 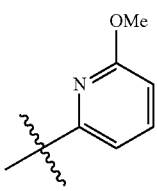 [SMILES: *c1cccc(OC)n1] | 1.42 [G] | 428 |
| 25 | 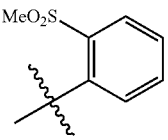 | 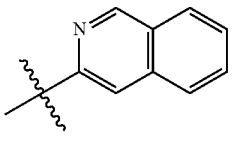 [SMILES: *c1cc2ccccc2cn1] | 1.21 [G] | 448 |
| 26 | 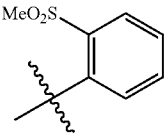 | 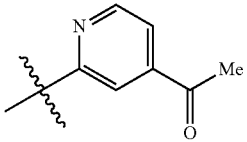 [SMILES: *c1cc(C(C)=O)ccn1] | 1.02 [G] | 440 |

| Example No. | Ar¹ | Ar² | Rt (min) [Method] | m/z [M + H]⁺ |
|---|---|---|---|---|
| 27 | MeO₂S-phenyl | 6-CN-pyridin-2-yl | 1.03 [G] | 423 |
| 28 | F₃CO₂S-phenyl | 5-F-pyridin-2-yl | 1.53 [E] | 470 |
| 29 | F₃CO₂S-phenyl | pyridin-2-yl | 1.46 [E] | 452 |
| 30 | MeO₂S-phenyl | 4-CN-pyridin-2-yl | 1.01 [G] | 423 |
| 31 | EtO₂S-phenyl | pyridin-2-yl | 1.24 [E] | 412 |
| 32 | EtO₂S-phenyl | 5-F-pyridin-2-yl | 1.30 [E] | 430 |
| 33 | EtO₂S-phenyl | 4-CN-pyridin-2-yl | 1.28 [E] | 437 |
| 34 | MeO₂S, F-phenyl | 4-CN-pyridin-2-yl | 1.44 [E] | 441 |
| 35 | SO₂Me, F-phenyl | 4-CN-pyridin-2-yl | 1.39 [E] | 441 |

-continued

| Example No. | Ar¹ | Ar² | Rt (min) [Method] | m/z [M + H]⁺ |
|---|---|---|---|---|
| 36 | MeO₂S-phenyl | pyridazin-3-yl | 1.04 [E] | 399 |
| 37 | MeO₂S-phenyl | pyrimidin-5-yl | 0.92 [E] | 399 |
| 38 | MeO₂S-phenyl | pyrazin-2-yl | 1.07 [E] | 399 |
| 39 | MeO₂S, F-phenyl | pyrazin-2-yl | 1.15 [E] | 417 |
| 40 | MeO₂S-phenyl | 5-Me-pyrazin-2-yl | 1.15 [E] | 413 |
| 41 | MeO₂S-phenyl | 5-CN-pyrazin-2-yl | 1.20 [E] | 424 |
| 42 | MeO₂S-phenyl | 6-Me-pyrazin-3-yl | 1.16 [E] | 413 |
| 43 | MeO, SO₂Me-phenyl | 4-CN-pyridin-2-yl | 1.35 [E] | 453 |
| 44 | MeO, SO₂Me-phenyl | 5-F-pyridin-2-yl | 1.22 [E] | 446 |

-continued

| Example No. | Ar¹ | Ar² | Rt (min) [Method] | m/z [M + H]⁺ |
|---|---|---|---|---|
| 45 | 3-MeO, 4-SO₂Me phenyl | 2-pyridyl | 1.17 [E] | 428 |
| 46 | 2-F, 3-MeO₂S phenyl | 2-pyridyl | 1.20 [E] | 416 |
| 47 | 2-F, 3-MeO₂S phenyl | 5-F-2-pyridyl | 1.30 [E] | 434 |
| 48 | 2-F, 3-MeO₂S phenyl | 4-CN-2-pyridyl | 1.28 [E] | 441 |
| 49 | 2-F, 3-MeO₂S phenyl | 4-Me-2-pyridyl | 1.30 [E] | 430 |
| 50 | 2-F, 3-MeO₂S phenyl | 4-F-2-pyridyl | 1.32 [E] | 434 |
| 51 | 2-MeO₂S, 4-F phenyl | 4-F-2-pyridyl | 1.30 [E] | 434 |
| 52 | 2-MeO₂S, 4-F phenyl | 4-Me-2-pyridyl | 1.42 [E] | 430 |

-continued

| Example No. | Ar¹ | Ar² | Rt (min) [Method] | m/z [M + H]⁺ |
|---|---|---|---|---|
| 53 | MeO₂S-phenyl-F | pyridin-2-yl | 1.36 [E] | 416 |
| 54 | MeO₂S-phenyl-F | 6-F-pyridin-2-yl | 1.46 [E] | 434 |
| 55 | MeO₂S-phenyl-F | 5-F-pyridin-2-yl | 1.32 [E] | 434 |
| 56 | MeO₂S-phenyl-F | 4-Me-pyridin-2-yl | 1.32 [E] | 430 |
| 57 | MeO₂S-phenyl-F | 4-F-pyridin-2-yl | 1.32 [E] | 434 |
| 58 | MeO₂S-phenyl-F | 4-CN-pyridin-2-yl | 1.31 [E] | 441 |
| 59 | MeO₂S-phenyl | 5-CF₃-pyridin-2-yl | 1.62 [E] | 466 |
| 60 | MeO₂S-phenyl | 5-F-4-Me-pyridin-2-yl | 1.44 [E] | 430 |
| 61 | MeO₂S-phenyl | 5-SO₂Me-pyridin-2-yl | 1.10 [E] | 476 |

Preparation 2

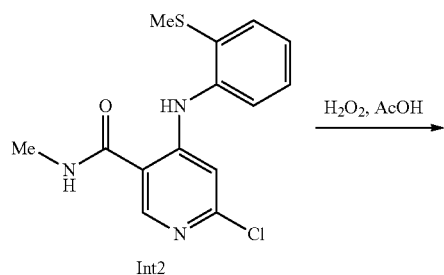

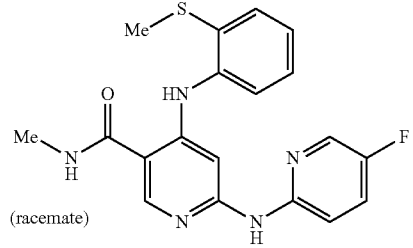
(racemate)

To a solution of Intermediate 2 (50 mg, 0.16 mmol) in acetic acid (0.9 mL) was added hydrogen peroxide (33% aqueous solution, 18 µL, 0.20 mmol) and the reaction allowed to run for 4 hours. One drop of saturated aqueous sodium bisulfite was added, the mixture was concentrated under reduced pressure, rendered neutral with saturated aqueous sodium bicarbonate and then extracted with DCM (3×). The combined organic layers were dried over $Na_2SO_4$ filtered and concentrated leaving Intermediate 4 as a colorless powder 55 mg, 100%). $^1$H NMR (400 MHz, DMSO-$d_6$) δ 10.38 (s, 1H), 8.81 (d, J=4.2 Hz, 1H), 8.53 (s, 1H), 7.87 (dd, J=7.6, 1.7 Hz, 1H), 7.66-7.61 (m, 1H), 7.59-7.55 (m, 1H), 7.48 (d, J=7.9 Hz, 1H), 6.60 (s, 1H), 2.80 (d, J=4.6 Hz, 3H), 2.70 (s, 3H). LC retention time 1.68 [A]. MS(E$^+$) m/z: 324 (MH$^+$).

Example 62

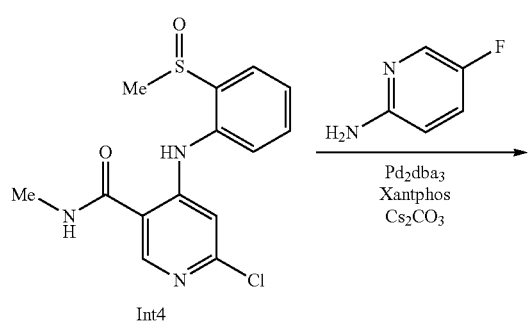

5-Fluoropyridin-2-amine (13.8 mg, 0.124 mmol) was combined with Intermediate 3 (20 mg, 0.062 mmol). To the vessel was added dimethylacetamide (DMA, 0.6 mL) followed by $Pd_2dba_3$ (5.7 mg, 0.0062 mmol), Xantphos (27 mg, 0.047 mmol) and cesium carbonate (80 mg, 0.247 mmol). The vessel was then evacuated and backfilled with nitrogen three times and then heated to 145° C. for 2 hours. The crude product was diluted with DMF and filtered, before being purified using preparative HPLC providing 5.2 mg (21% yield) of 62. $^1$H NMR (500 MHz, methanol-$d_4$) δ 8.37 (s, 1H), 7.98-7.92 (m, 2H), 7.67-7.62 (m, 1H), 7.59-7.52 (m, 2H), 7.43-7.37 (m, 1H), 7.35-7.29 (m, 2H), 2.95 (s, 3H), 2.81 (s, 3H). LC retention time 1.13 [E]. MS(E$^+$) m/z: 400 (MH$^+$).

Preparation 3

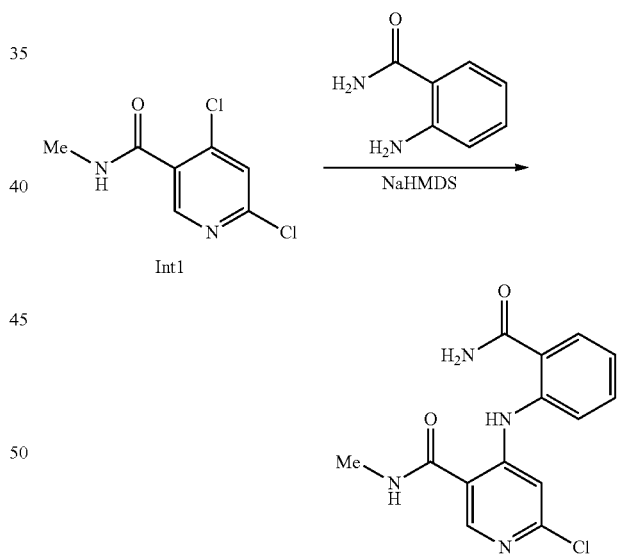

To a stirred solution of Intermediate 1 (800 mg, 3.90 mmol) was added 2-aminobenzamide (1.59 g, 11.7 mmol) followed by NaHMDS (1M in THF, 23.4 mL, 23.4 mmol) at 0° C. The reaction was warmed to room temperature and stirred for 2 hours at which point methanol was added to quench the reaction. The solvents were removed in vacuo and the crude material purified using flash chromatography (5-10% MeOH/chloroform) to provide Intermediate 5 (950 mg, 80% yield). $^1$H NMR (400 MHz, DMSO-$d_6$) δ 10.90 (s, 1H), 8.62 (d, J=3.3 Hz, 1H), 8.41 (s, 1H), 7.95 (br. s., 1H), 7.62 (d, J=7.7

Hz, 1H), 7.53-7.38 (m, 3H), 7.29-7.15 (m, 1H), 6.92 (s, 1H), 2.78 (d, J=4.4 Hz, 3H).). LC retention time 0.64 min [J]. MS(E$^+$) m/z: 305 (MH$^+$).

Example 63

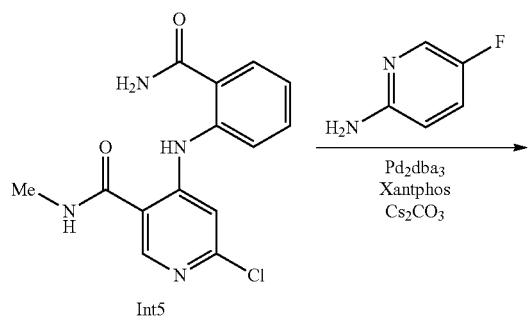

5-Fluoropyridin-2-amine (74 mg, 0.66 mmol) was combined with Intermediate 5 (100 mg, 0.328 mmol). To the vessel was added dimethylacetamide (3 mL) followed by Pd$_2$dba$_3$ (30 mg, 0.033 mmol), Xantphos (38 mg, 0.066 mmol) and cesium carbonate (214 mg, 0.656 mmol). The vessel was then evacuated and backfilled with nitrogen three times and then heated to 145° C. for 45 minutes. The crude product was diluted with DMF and filtered, before being purified using preparative HPLC providing 16.4 mg (12.5% yield) of 63. $^1$H NMR (500 MHz, DMSO-d$_6$) δ 10.89 (s, 1H), 9.73 (s, 1H), 8.37 (s, 1H), 8.33 (d, J=4.5 Hz, 1H), 8.08 (d, J=3.0 Hz, 1H), 7.92 (s, 1H), 7.68 (s, 1H), 7.67-7.62 (m, 1H), 7.62-7.59 (m, 1H), 7.57 (d, J=7.9 Hz, 2H), 7.52-7.45 (m, 1H), 7.40 (s, 1H), 7.13-7.06 (m, 1H), 4.05 (s, 1H), 3.90 (s, 1H), 2.75 (d, J=4.5 Hz, 3H). LC retention time 1.24 min [E]. MS(E$^+$) m/z: 381 (MH$^+$).

Examples 64 to 183

The following Examples were prepared in a similar manner to the product of Example 63:

| Example No. | Ar$^1$ | Ar$^2$ | Rt (min) [Method] | m/z [M + H]$^+$ |
|---|---|---|---|---|
| 64 | 2,5-difluorophenyl | 5-fluoropyridin-2-yl | 1.78 [E] | 374 |
| 65 | 2-(methylthio)phenyl | 5-fluoropyridin-2-yl | 1.72 [E] | 384 |
| 66 | 2-(2-hydroxyethyl)phenyl | 5-fluoropyridin-2-yl | 1.36 [E] | 382 |
| 67 | 2-carbamoylphenyl | 6-methylpyridin-2-yl | 1.17 [E] | 377 |

-continued

| Example No. | Ar¹ | Ar² | Rt (min) [Method] | m/z [M + H]⁺ |
|---|---|---|---|---|
| 68 | 2-carbamoylphenyl | pyridin-2-yl | 1.02 [E] | 363 |
| 69 | 2-carbamoylphenyl | 3-fluoropyridin-2-yl | 1.10 [E] | 381 |
| 70 | 2-carbamoylphenyl | 5-methoxypyridin-2-yl | 1.05 [E] | 393 |
| 71 | 2-carbamoylphenyl | 4-fluoropyridin-2-yl | 0.85 [G] | 381 |
| 72 | 2-carbamoylphenyl | 5-methylpyridin-2-yl | 0.91 [G] | 377 |
| 73 | 2-carbamoylphenyl | 6-methoxypyridin-2-yl | 0.92 [G] | 393 |
| 74 | 2-carbamoylphenyl | 6-fluoropyridin-2-yl | 0.85 [G] | 381 |
| 75 | 2-carbamoylphenyl | 4-phenylpyridin-2-yl | 1.50 [E] | 439 |

-continued
| Example No. | Ar¹ | Ar² | Rt (min) [Method] | m/z [M + H]⁺ |
|---|---|---|---|---|
| 76 | 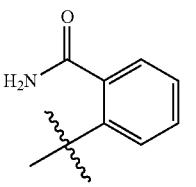 [SMILES: *c1ccccc1C(N)=O] | 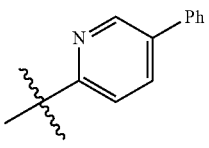 [SMILES: *c1ccc(-c2ccccc2)cn1] | 1.53 [E] | 439 |
| 77 | 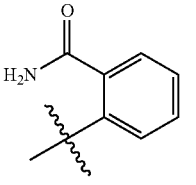 [SMILES: *c1ccccc1C(N)=O] | 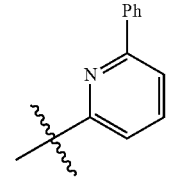 [SMILES: *c1cccc(-c2ccccc2)n1] | 1.52 [E] | 439 |
| 78 | 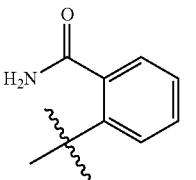 [SMILES: *c1ccccc1C(N)=O] | 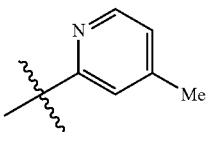 [SMILES: *c1cc(C)ccn1] | 0.91 [G] | 377 |
| 79 | 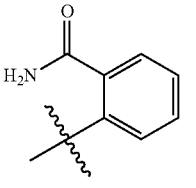 [SMILES: *c1ccccc1C(N)=O] | 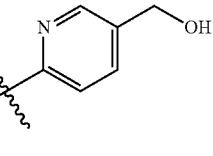 | 0.73 [G] | 393 |
| 80 | 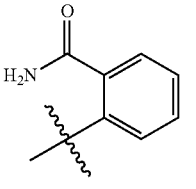 [SMILES: *c1ccccc1C(N)=O] | 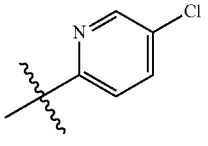 [SMILES: *c1ccc(Cl)cn1] | 0.97 [G] | 397 |
| 81 | 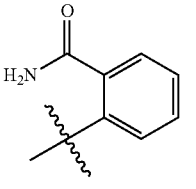 [SMILES: *c1ccccc1C(N)=O] | 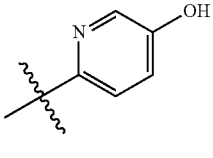 [SMILES: *c1ccc(O)cn1] | 0.77 [G] | 379 |
| 82 | 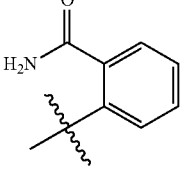 | 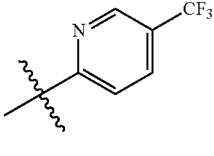 [SMILES: *c1ccc(C(F)(F)F)cn1] | 1.08 [G] | 431 |

-continued

| Example No. | Ar¹ | Ar² | Rt (min) [Method] | m/z [M + H]⁺ |
|---|---|---|---|---|
| 83 | 2-carbamoylphenyl | 3-methylpyridin-2-yl | 1.08 [G] | 377 |
| 84 | 2-carbamoylphenyl | 4-cyanopyridin-2-yl | 1.12 [G] | 388 |
| 85 | 2-carbamoylphenyl | 5-morpholinopyridin-2-yl | 0.90 [G] | 447 |
| 86 | 2-carbamoylphenyl | 2-methyl-3-cyanopyridin-6-yl | 1.18 [G] | 402 |
| 87 | 2-carbamoylphenyl | quinolin-2-yl | 1.37 [E] | 413 |
| 88 | 2-carbamoylphenyl | 5-(N,N-dimethylsulfamoyl)pyridin-2-yl | 1.12 [G] | 470 |
| 89 | 2-carbamoylphenyl | isoquinolin-3-yl | 1.31 [G] | 413 |

-continued

| Example No. | Ar¹ | Ar² | Rt (min) [Method] | m/z [M + H]⁺ |
|---|---|---|---|---|
| 90 | 2-carbamoylphenyl | 3-chloropyridin-2-yl | 0.91 [G] | 397 |
| 91 | 2-carbamoylphenyl | 4-(trifluoromethyl)pyridin-2-yl | 1.43 [E] | 431 |
| 92 | 2-carbamoylphenyl | 5-cyanopyridin-2-yl | 1.10 [G] | 388 |
| 93 | 2-carbamoylphenyl | 5-carbamoylpyridin-2-yl | 0.67 [G] | 406 |
| 94 | 2-carbamoylphenyl | 4-(hydroxymethyl)pyridin-2-yl | 0.74 [G] | 393 |
| 95 | 2-carbamoylphenyl | 6-(trifluoromethyl)pyridin-2-yl | 1.31 [G] | 431 |
| 96 | 2-methoxy-3,4-difluorophenyl | 5-fluoropyridin-2-yl | 1.78 [E] | 404 |
| 97 | 2-methoxy-4-chlorophenyl | 4-carbamoylpyridin-2-yl | 1.38 [E] | 427 |

| Example No. | Ar¹ | Ar² | Rt (min) [Method] | m/z [M + H]⁺ |
|---|---|---|---|---|
| 98 | 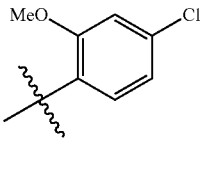 [SMILES: *c1ccc(Cl)cc1OC] | 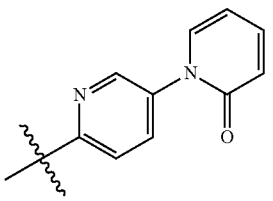 [SMILES: *c1ccc(-n2ccccc2=O)cn1] | 1.51 [E] | 477 |
| 99 | 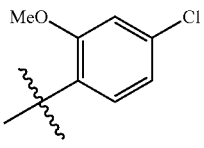 [SMILES: *c1ccc(Cl)cc1OC] | 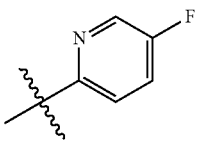 [SMILES: *c1ccc(F)cn1] | 1.83 [E] | 402 |
| 100 | 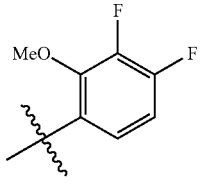 [SMILES: *c1ccc(F)c(F)c1OC] | 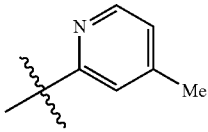 [SMILES: *c1cc(C)ccn1] | 1.76 [E] | 400 |
| 101 | 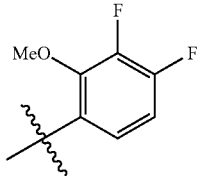 [SMILES: *c1ccc(F)c(F)c1OC] | 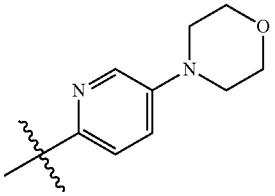 [SMILES: *c1ccc(N2CCOCC2)cn1] | 1.59 [E] | 471 |
| 102 | 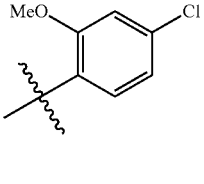 | 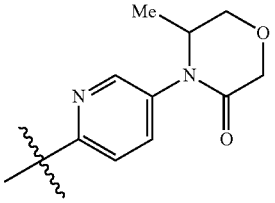 [SMILES: *c1ccc(N2C(=O)COCC2C)cn1] | 1.51 [E] | 497 |
| 103 | 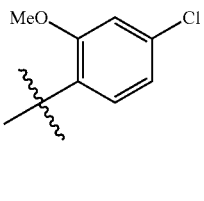 [SMILES: *c1ccc(Cl)cc1OC] | 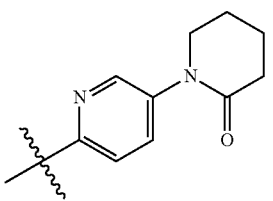 [SMILES: *c1ccc(N2CCCCC2=O)cn1] | 1.58 [E] | 481 |
| 104 | 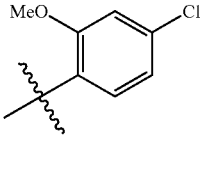 [SMILES: *c1ccc(Cl)cc1OC] | 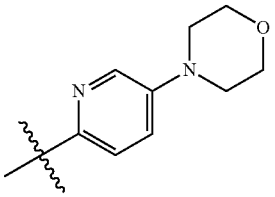 [SMILES: *c1ccc(N2CCOCC2)cn1] | 1.63 [E] | 469 |

-continued
| Example No. | Ar¹ | Ar² | Rt (min) [Method] | m/z [M + H]⁺ |
|---|---|---|---|---|
| 105 | 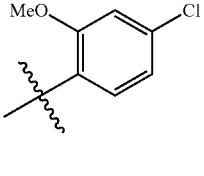 [SMILES: *c1ccc(Cl)cc1OC] | 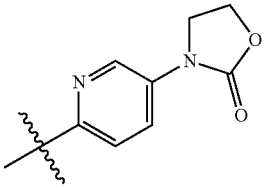 [SMILES: *c1ccc(N2CCOC2=O)cn1] | 1.52 [E] | 469 |
| 106 | 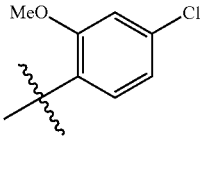 | 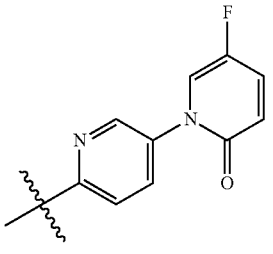 [SMILES: *c1ccc(-n2cc(F)ccc2=O)cn1] | 1.58 [E] | 495 |
| 107 | 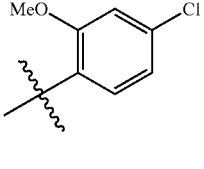 | 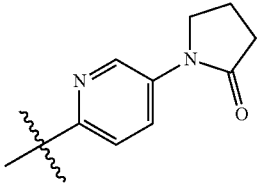 [SMILES: *c1ccc(N2CCCC2=O)cn1] | 1.59 [E] | 467 |
| 108 | 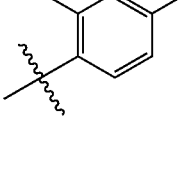 | 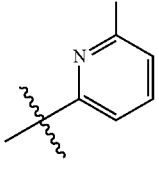 | 1.42 [G] | 414 |
| 109 | 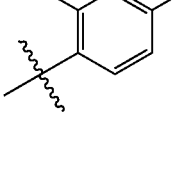 | 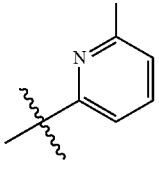 | 1.42 [G] | 398 |
| 110 | 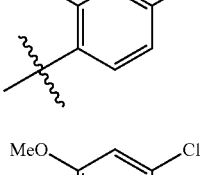 | 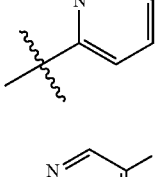 | 1.33 [G] | 383 |
| 111 | 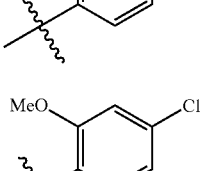 | 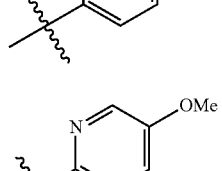 | 1.42 [G] | 398 |
| 112 | 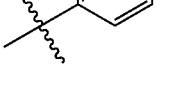 | 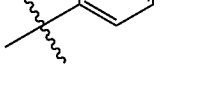 | 1.40 [G] | 414 |

-continued

| Example No. | Ar¹ | Ar² | Rt (min) [Method] | m/z [M + H]⁺ |
|---|---|---|---|---|
| 113 | MeO, Cl (phenyl) | pyridinyl-Me | 1.82 [G] | 398 |
| 114 | MeO, Cl (phenyl) | 1H-pyrrolo[3,2-b]pyridinyl | 1.33 [G] | 423 |
| 115 | MeO, Cl (phenyl) | pyridinyl-F | 1.84 [G] | 402 |
| 116 | MeO, Cl (phenyl) | pyridinyl-Ph | 2.15 [G] | 460 |
| 117 | MeO, Cl (phenyl) | pyridinyl-CF₃ | 2.02 [G] | 452 |
| 118 | MeO, Cl (phenyl) | pyridinyl-Me, CN | 1.42 [G] | 423 |
| 119 | MeO, F (phenyl) | pyridinyl-F | 1.41 [G] | 386 |
| 120 | MeO, Cl (phenyl) | pyridinyl-CF₃ | 2.07 [G] | 452 |
| 121 | MeO, Cl (phenyl) | pyridinyl-CN | 1.34 [G] | 409 |

-continued

| Example No. | Ar¹ | Ar² | Rt (min) [Method] | m/z [M + H]⁺ |
|---|---|---|---|---|
| 122 | 2-(OCHF₂)phenyl | 5-fluoropyridin-2-yl | 1.70 [E] | 404 |
| 123 | 2,2-difluorobenzo[d][1,3]dioxol-4-yl | 5-fluoropyridin-2-yl | 1.88 [E] | 418 |
| 124 | 4-fluoro-2-methoxyphenyl | 5-cyanopyridin-2-yl | 1.12 [G] | 393 |
| 125 | 4-chloro-2-methoxyphenyl | 6-ethylpyridin-2-yl | 1.88 [G] | 412 |
| 126 | 4-fluoro-2-methoxyphenyl | 6-(5-fluoro-2-oxopyridin-1(2H)-yl)pyridin-3-yl | 1.26 [E] | 479 |
| 127 | 4-fluoro-2-methoxyphenyl | 6-(2-oxopyrrolidin-1-yl)pyridin-3-yl | 1.40 [E] | 451 |
| 128 | 3,5-difluoro-2-methoxyphenyl | 5-methylpyridin-2-yl | 1.85 [E] | 400 |

-continued
| Example No. | Ar¹ | Ar² | Rt (min) [Method] | m/z [M + H]⁺ |
|---|---|---|---|---|
| 129 | 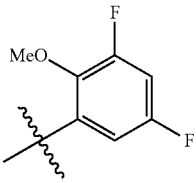 [SMILES: *c1cc(F)cc(F)c1OC] | 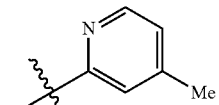 | 1.82 [E] | 400 |
| 130 | 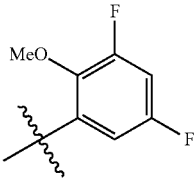 [SMILES: *c1cc(F)cc(F)c1OC] | 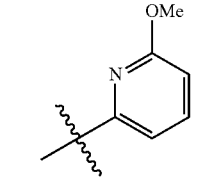 [SMILES: *c1cccc(OC)n1] | 1.83 [E] | 416 |
| 131 | 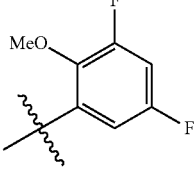 | 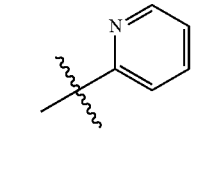 [SMILES: *c1ccccn1] | 1.73 [E] | 386 |
| 132 | 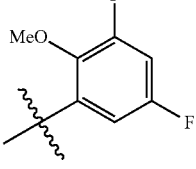 | 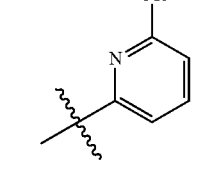 | 1.88 [E] | 400 |
| 133 | 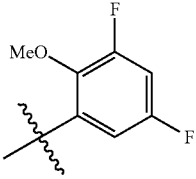 [SMILES: *c1cc(F)cc(F)c1OC] | 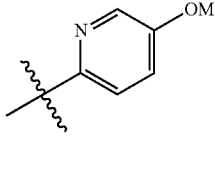 [SMILES: *c1ccc(C(F)(F)F)cn1] | 1.33 [G] | 416 |
| 134 | 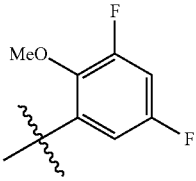 [SMILES: *c1cc(F)cc(F)c1OC] | 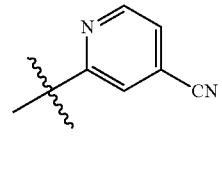 [SMILES: *c1cc(C#N)ccn1] | 1.81 [E] | 411 |
| 135 | 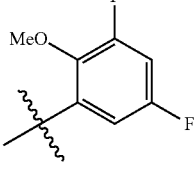 | 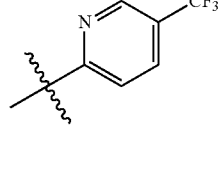 | 2.09 [E] | 454 |
| 136 | 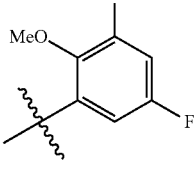 | 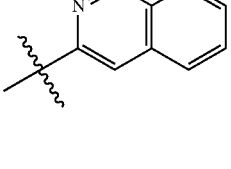 | 1.97 [E] | 436 |

-continued

| Example No. | Ar¹ | Ar² | Rt (min) [Method] | m/z [M + H]⁺ |
|---|---|---|---|---|
| 137 | F, MeO, F (difluoro-methoxyphenyl) | 4-fluoropyridin-2-yl | 1.84 [E] | 404 |
| 138 | F, MeO, F | 6-(CF₃)pyridin-2-yl | 1.95 [E] | 454 |
| 139 | F, MeO, F | 2-Me-3-CN-pyridin-6-yl | 1.84 [E] | 425 |
| 140 | F, MeO, F | 2-Me-3-CN-4-Me-pyridin-6-yl | 1.93 [E] | 438 |
| 141 | F, MeO, F | 6-Et-pyridin-2-yl | | 414 |
| 142 | F, OCH₂F, F (fluoromethoxy-fluorophenyl) | 5-(2-oxopyrrolidin-1-yl)pyridin-2-yl | 1.41 [E] | 469 |
| 143 | F, MeO, F | 6-Ph-pyridin-2-yl | 1.62 [G] | 462 |

-continued

| Example No. | Ar¹ | Ar² | Rt (min) [Method] | m/z [M + H]⁺ |
|---|---|---|---|---|
| 144 | MeO, F, F (phenyl) | 4-Cl pyridin-2-yl | 2.00 [E] | 420 |
| 145 | MeO, F, F (phenyl) | 5-CN pyridin-2-yl | 1.74 [E] | 411 |
| 146 | MeO, F (phenyl) | isoquinolin-3-yl | 1.45 [G] | 418 |
| 147 | MeO, F (phenyl) | pyridin-2-yl | 1.21 [G] | 368 |
| 148 | MeO, F (phenyl) | 4-Me pyridin-2-yl | 1.30 [G] | 382 |
| 149 | MeO, F (phenyl) | 4-F pyridin-2-yl | 1.23 [G] | 386 |
| 150 | MeO, F (phenyl) | 6-Ph pyridin-2-yl | 1.61 [G] | 444 |
| 151 | FCH₂O, F (phenyl) | 5-F pyridin-2-yl | 1.66 [E] | 404 |
| 152 | MeO, F (phenyl) | 2-Me-3-CN pyridin-6-yl | 1.44 [G] | 407 |

-continued

| Example No. | Ar¹ | Ar² | Rt (min) [Method] | m/z [M + H]⁺ |
|---|---|---|---|---|
| 153 | MeO, F (phenyl) | pyridyl-Cl | 1.21 [G] | 402 |
| 154 | MeO, F (phenyl) | pyridyl-OMe | 1.19 [G] | 398 |
| 155 | MeO, F (phenyl) | pyridyl-CN | 1.14 [G] | 393 |
| 156 | MeO, F (phenyl) | pyridyl-CF₃ | 1.28 [G] | 436 |
| 157 | MeO, F (phenyl) | pyridyl-CF₃ | 1.26 [G] | 436 |
| 158 | MeO, F (phenyl) | pyridyl-Cl | 1.33 [G] | 402 |
| 159 | MeO, F (phenyl) | pyridyl-Me | 1.40 [G] | 382 |
| 160 | MeO, F (phenyl) | 7-azaindolyl | 1.21 [G] | 407 |
| 161 | MeO, F (phenyl) | pyridyl-OMe | 1.28 [G] | 398 |

-continued

| Example No. | Ar¹ | Ar² | Rt (min) [Method] | m/z [M + H]⁺ |
|---|---|---|---|---|
| 162 | 2-(fluoromethoxy)-4-fluorophenyl | 6-(5-cyano)pyridin-2-yl | 1.58 [E] | 411 |
| 163 | 2-methoxy-4-fluorophenyl | 2,4-dimethyl-3-cyano-pyridin-6-yl | 1.22 [G] | 421 |
| 164 | 2-methoxy-3,5-difluorophenyl | 6-(2-oxopyridin-1-yl)pyridin-2-yl | 1.46 [E] | 478 |
| 165 | 2-methoxy-4-fluorophenyl | 6-(2-oxopyridin-1-yl)pyridin-2-yl | 1.35 [E] | 461 |
| 166 | 2-(fluoromethoxy)-4-fluorophenyl | 4-cyanopyridin-2-yl | 1.43 [E] | 411 |
| 167 | 2-methoxy-3,5-difluorophenyl | 4-(2-oxopyridin-1-yl)pyridin-2-yl | 1.34 [E] | 479 |
| 168 | 2-methoxy-4-fluorophenyl | 4-(2-oxopyridin-1-yl)pyridin-2-yl | 1.24 [E] | 461 |

-continued

| Example No. | Ar¹ | Ar² | Rt (min) [Method] | m/z [M + H]⁺ |
|---|---|---|---|---|
| 169 | 3,5-difluoro-2-methoxyphenyl (MeO, F, F) | 4-methoxypyridin-2-yl (OMe) | 1.52 [E] | 416 |
| 170 | 5-fluoro-2-methoxyphenyl (MeO, F) | 4-methoxypyridin-2-yl (OMe) | 1.34 [E] | 398 |
| 171 | 3-fluoro-2-methoxyphenyl (MeO, F) | 5-fluoropyridin-2-yl (F) | 1.70 [E] | 386 |
| 172 | 3-fluoro-2-methoxyphenyl (MeO, F) | pyridin-2-yl | 1.59 [E] | 368 |
| 173 | 3-fluoro-2-methoxyphenyl (MeO, F) | 4-cyanopyridin-2-yl (CN) | 1.68 [E] | 393 |
| 174 | 2-carbamoyl-3-methylphenyl (H₂N-C(O), Me) | 5-fluoropyridin-2-yl (F) | 1.24 [E] | 395 |
| 175 | 2-carbamoyl-3-fluorophenyl (H₂N-C(O), F) | 5-fluoropyridin-2-yl (F) | 1.23 [E] | 399 |
| 176 | 2-carbamoyl-3-fluorophenyl (H₂N-C(O), F) | 4-cyanopyridin-2-yl (CN) | 1.22 [E] | 406 |

-continued

| Example No. | Ar¹ | Ar² | Rt (min) [Method] | m/z [M + H]⁺ |
|---|---|---|---|---|
| 177 | 2-carbamoyl-6-methylphenyl | 4-cyanopyridin-2-yl | 1.23 [E] | 402 |
| 178 | 2-carbamoylphenyl | pyrazin-2-yl |  | 364 |
| 179 | 4-methoxypyridin-3-yl | 4-cyanopyridin-2-yl | 1.20 [E] | 376 |
| 180 | 2-(2-hydroxypropan-2-yl)phenyl | quinolin-2-yl | 1.63 [E] | 428 |
| 181 | 2-(2-hydroxypropan-2-yl)phenyl | 5-(trifluoromethyl)pyridin-2-yl | 1.50 [E] | 446 |
| 182 | 2-(2-hydroxypropan-2-yl)phenyl | pyridazin-3-yl | 1.06 [E] | 379 |
| 183 | 2-(2-hydroxypropan-2-yl)phenyl | pyridin-2-yl | 1.30 [E] | 378 |

Preparation 4

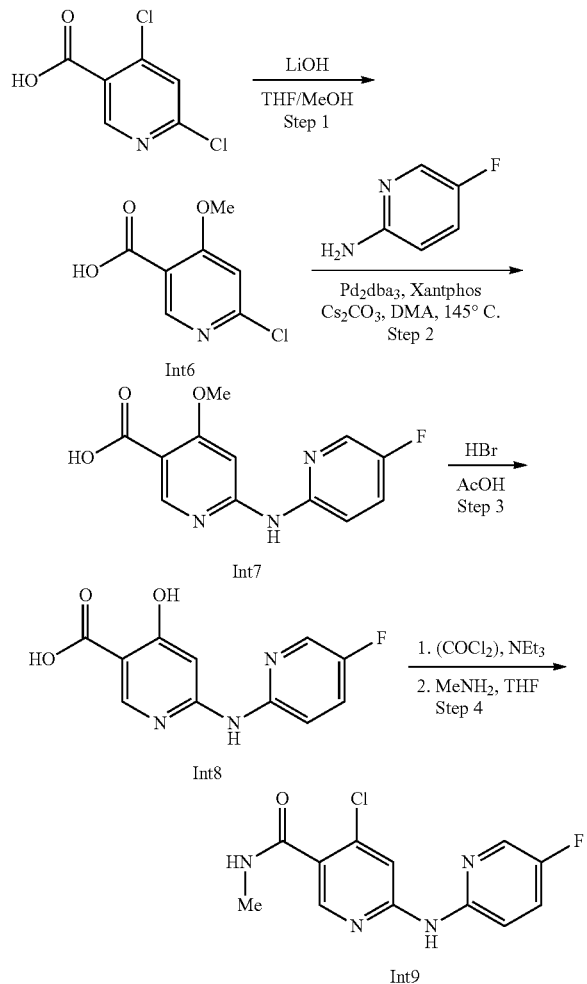

Step 1

To a solution of 4,6-dichloronicotinic acid (4 g, 20.8 mmol) in methanol (8 mL) and tetrahydrofuran (16 mL) was added lithium hydroxide mono-hydrate (2.62 g, 62.5 mmol) and the reaction was stirred at room temperature for 1 hour. The reaction was concentrated under reduced pressure and 12 mL of water was added, the solution was cooled to 0° C. and 1 N hydrochloric acid (aqueous) was added while the solution was agitated resulting in a precipitate. Gradual addition of the acid was continued until the pH measured (litmus paper) to be ~4. The suspension was then filtered and the solid collected and triturated with diethyl ether for 1 hour. The solid was filtered, dried and collected yielding Intermediate 6 (2.84 g, 73%). $^1$H NMR (400 MHz, DMSO-$d_6$) δ 13.23 (br. s., 1H), 8.54 (s, 1H), 7.32 (s, 1H), 3.94 (s, 3H). LC retention time 0.55 min [J]. MS(E$^+$) m/z: 188 (MH$^+$).

Step 2

5-Fluoropyridin-2-amine (1.195 g, 10.66 mmol) was combined with Intermediate 6 (1.00 g, 5.33 mmol). To the vessel was added DMA (20 mL) followed by Pd$_2$dba$_3$ (488 mg, 0.533 mmol), Xantphos (617 mg, 1.07 mmol) and cesium carbonate (3.47 g, 107 mmol). The vessel was then evacuated and backfilled with nitrogen three times and then heated to 145° C. for 30 minutes. The crude reaction was diluted with methanol and filtered (rinsing with methanol). The filtrate was concentrated to minimal volume using a rotary evaporator connected to an oil pump. To the viscous oil was added 1N HCl (aqueous) to a pH ~2 resulting in a precipitate which was then sonicated and filtered off, rinsing with cold water. The solid was collected, dried and suspended in diethyl ether. The slurry was sonicated and subsequently filtered, rinsing with diethyl ether. The solid was once again collected and this time suspended in 1:1 dichloromethane:ether and again sonicated. Filtration followed by a 1:1 dichloromethane:ether rinse and a hexanes rinse yielded the Intermediate 7 (1.31 g, 94%). $^1$H NMR (400 MHz, DMSO-$d_6$) δ 8.60 (s, 1H), 8.35 (d, J=3.1 Hz, 1H), 7.86 (td, J=8.6, 2.8 Hz, 1H), 7.57 (d, J=5.9 Hz, 1H), 7.16 (s, 1H), 3.96 (s, 3H). LC retention time 0.50 min [J]. MS(E$^+$) m/z: 264 (MH$^+$).

Step 3

To a suspension of Intermediate 7 (1.53 g, 5.81 mmol) in glacial acetic acid (50 mL) was added hydrobromic acid (48% in AcOH, 9.86 mL, 87 mmol)). The vessel was sealed and heated to 110° C. for 4 hours. The reaction was cooled to room temperature and the solvent removed under reduced pressure, the crude product was co-evaporated with toluene and then suspended in diethyl ether and filtered rinsing with ether. The resulting red powder (1.8 g, 100%) was carried on without further purification. LC retention time 0.55 min [J]. MS(E$^+$) m/z: 250 (MH$^+$).

Step 4

Intermediate 8 (1.1 g, 4.41 mmol) was dissolved in phosphorus oxychloride (POCl$_3$, 25 mL, 265 mmol), to this was added triethylamine (0.61 mL, 4.4 mmol)) and the reaction was sealed and heated to 110° C. for 2 hours. The reaction was concentrated under reduced pressure and dissolved in tetrahydrofuran (20 mL). The solution was cooled to 0° C. and methylamine (2M in THF, 4.42 mL, 8.84 mmol) was gradually added. The reaction was stirred at 0° C. for 1 hour, concentrated and then purified using flash chromatography providing Intermediate 9 (500 mg, 40% yield). $^1$H NMR (300 MHz, DMSO-$d_6$) δ 10.20 (s, 1H), 8.36 (m, 1H), 8.29 (m, 2H), 7.90 (s, 1H), 7.69 (m, 2H), 2.76 (d, J=4.5 Hz, 3H). LC retention time 0.57 min [J]. MS(E$^+$) m/z: 281 (MH$^+$).

Example 184

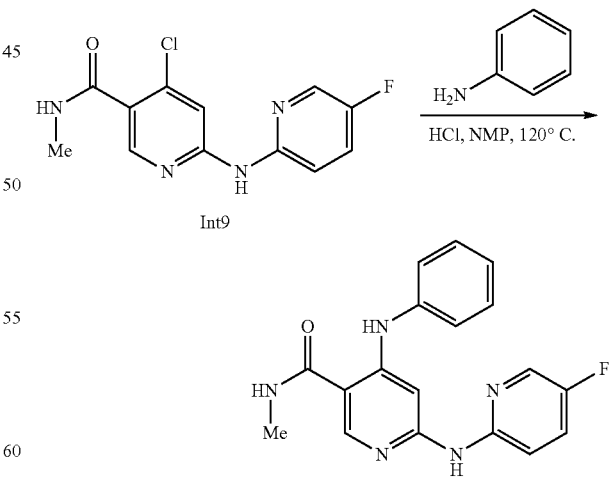

Intermediate 9 (20 mg, 0.071 mmol) was combined aniline (13 mg, 0.4 mmol) in NMP (1 mL), to this was added hydrochloric acid (4M in dioxane, 14 µL, 0.057 mmol) and the vessel was sealed and heated to 120° C. overnight. The crude reaction was filtered and purified using preparative HPLC providing 8.7 mg (36% yield) of 184. $^1$H NMR (500 MHz, methanol-d$_4$) δ 8.29 (s, 1H), 8.00 (d, J=3.0 Hz, 1H), 7.58 (s, 1H), 7.45-7.37 (m, 3H), 7.35-7.29 (m, 3H), 7.20-7.14 (m, 1H), 2.93 (s, 3H). LC retention time 1.62 min [E]. MS(E$^+$) m/z: 338 (MH$^+$).

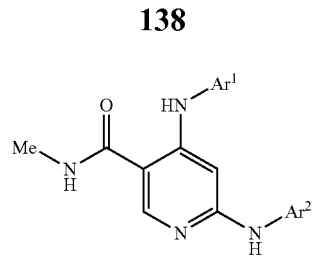

Examples 185 to 232

The following Examples were prepared in a similar manner to the product of Example 184:

| Example No. | Ar$^1$ | Ar$^2$ | Rt (min) [Method] | m/z [M + H]$^+$ |
|---|---|---|---|---|
| 185 | 2-cyclopropylphenyl | 5-fluoropyridin-2-yl | 1.87 [E] | 378 |
| 186 | 2-(4H-1,2,4-triazol-3-yl)phenyl | 5-fluoropyridin-2-yl | 1.24 [E] | 405 |
| 187 | 3-methoxy-4-morpholinophenyl | 5-fluoropyridin-2-yl | 1.46 [E] | 453 |
| 188 | naphthalen-1-yl | 5-fluoropyridin-2-yl | 1.88 [E] | 388 |
| 189 | 4-fluoro-2-methylphenyl | 5-fluoropyridin-2-yl | 1.74 [E] | 370 |
| 190 | 2-methoxyphenyl | 5-fluoropyridin-2-yl | 6.25 [F] | 368 |
| 191 | 4-(2-hydroxyethyl)phenyl | 5-fluoropyridin-2-yl | 1.00 [G] | 382 |

-continued

| Example No. | Ar¹ | Ar² | Rt (min) [Method] | m/z [M + H]⁺ |
|---|---|---|---|---|
| 192 | 2,4-dimethoxyphenyl | 5-fluoropyridin-2-yl | 1.23 [G] | 398 |
| 193 | 4-methylphenyl | 5-fluoropyridin-2-yl | 1.30 [G] | 352 |
| 194 | 4-phenylphenyl | 5-fluoropyridin-2-yl | 1.60 [G] | 414 |
| 195 | 4-methoxyphenyl | 5-fluoropyridin-2-yl | 1.18 [G] | 368 |
| 196 | 4-fluorophenyl | 5-fluoropyridin-2-yl | 1.18 [G] | 356 |
| 197 | 3-methylphenyl | 5-fluoropyridin-2-yl | 1.30 [G] | 352 |
| 198 | 4-cyclopropylphenyl | 5-fluoropyridin-2-yl | 1.46 [G] | 378 |
| 199 | 2-methoxy-5-fluorophenyl | 5-fluoropyridin-2-yl | 1.24 [G] | 386 |
| 200 | 4-(pyrrolidine-1-carbonyl)phenyl | 5-fluoropyridin-2-yl | 1.10 [G] | 435 |
| 201 | 4-(methylsulfonyl)phenyl | 5-fluoropyridin-2-yl | 0.94 [G] | 416 |

| Example No. | Ar¹ | Ar² | Rt (min) [Method] | m/z [M + H]⁺ |
|---|---|---|---|---|
| 202 | 3-OMe-phenyl | 5-F-pyridin-2-yl | 1.22 [G] | 368 |
| 203 | 2-MeO-5-Cl-phenyl | 5-F-pyridin-2-yl | 1.34 [G] | 402 |
| 204 | 3,4-diF-phenyl | 5-F-pyridin-2-yl | 1.21 [G] | 374 |
| 205 | 2-MeO-3,5-diF-phenyl | 5-F-pyridin-2-yl | 1.28 [G] | 404 |
| 206 | 2-MeO-5-OCF₃-phenyl | 5-F-pyridin-2-yl | 1.42 [G] | 436 |
| 207 | 2-MeS-4-F-phenyl | 5-F-pyridin-2-yl | 1.74 [E] | 402 |
| 208 | 2-HO-phenyl | 5-F-pyridin-2-yl | 7.46 [F] | 354 |
| 209 | 2-F₃CO-phenyl | 5-F-pyridin-2-yl | 2.55 [H] | 422 |
| 210 | 2-F₃CS-phenyl | 5-F-pyridin-2-yl | 2.64 [H] | 438 |

-continued

| Example No. | Ar¹ | Ar² | Rt (min) [Method] | m/z [M + H]⁺ |
|---|---|---|---|---|
| 211 | 4-(morpholin-4-yl)phenyl | 5-fluoropyridin-2-yl | 2.09 [H] | 423 |
| 212 | 1H-indol-4-yl | 5-fluoropyridin-2-yl | 6.22 [F] | 377 |
| 213 | 4-ethylphenyl | 5-(morpholin-4-yl)pyridin-2-yl | 1.28 [G] | 433 |
| 214 | 2-fluorophenyl | 5-(morpholin-4-yl)pyridin-2-yl | 1.12 [G] | 423 |
| 215 | 3-ethylphenyl | 5-(morpholin-4-yl)pyridin-2-yl | 1.25 [G] | 433 |
| 216 | 2-methoxyphenyl | 5-(morpholin-4-yl)pyridin-2-yl | 1.41 [G] | 435 |
| 217 | 2-methylphenyl | 5-(morpholin-4-yl)pyridin-2-yl | 1.50 [G] | 419 |

-continued

| Example No. | Ar¹ | Ar² | Rt (min) [Method] | m/z [M + H]⁺ |
|---|---|---|---|---|
| 218 | MeO, F (phenyl) | morpholine-pyridine | 1.28 [G] | 453 |
| 219 | MeO, F (phenyl) | morpholine-pyridine | 1.26 [G] | 453 |
| 220 | MeO, OMe (phenyl) | morpholine-pyridine | 1.16 [G] | 465 |
| 221 | MeO, Br (phenyl) | morpholine-pyridine | 1.25 [G] | 514 |
| 222 | MeO, SO₂Me (phenyl) | morpholine-pyridine | 1.04 [G] | 513 |
| 223 | EtO (phenyl) | morpholine-pyridine | 1.20 [G] | 449 |
| 224 | OH-ethyl (phenyl) | morpholine-pyridine | 1.19 [G] | 449 |

-continued

| Example No. | Ar¹ | Ar² | Rt (min) [Method] | m/z [M + H]⁺ |
|---|---|---|---|---|
| 225 | benzodioxine | pyridine-morpholine | 1.23 [G] | 463 |
| 226 | MeS-phenyl | pyridine-morpholine | 1.30 [G] | 451 |
| 227 | HO, F-phenyl | pyridine-morpholine | 1.14 [E] | 439 |
| 228 | F₂CHO-phenyl | pyridine-morpholine | 1.31 [E] | 171 |
| 229 | EtO, OEt-phenyl | pyridine-morpholine | 1.43 [E] | 493 |
| 230 | EtO, F, F-phenyl | pyridine-morpholine | 1.52 [E] | 485 |
| 231 | H₂N-phenyl | F-pyridine | 10.2 [F] | 352 |

-continued

| Example No. | Ar¹ | Ar² | Rt (min) [Method] | m/z [M + H]⁺ |
|---|---|---|---|---|
| 232 | EtO-, F (phenyl) | morpholine-pyridine | 1.36 [E] | 467 |

Preparation 5

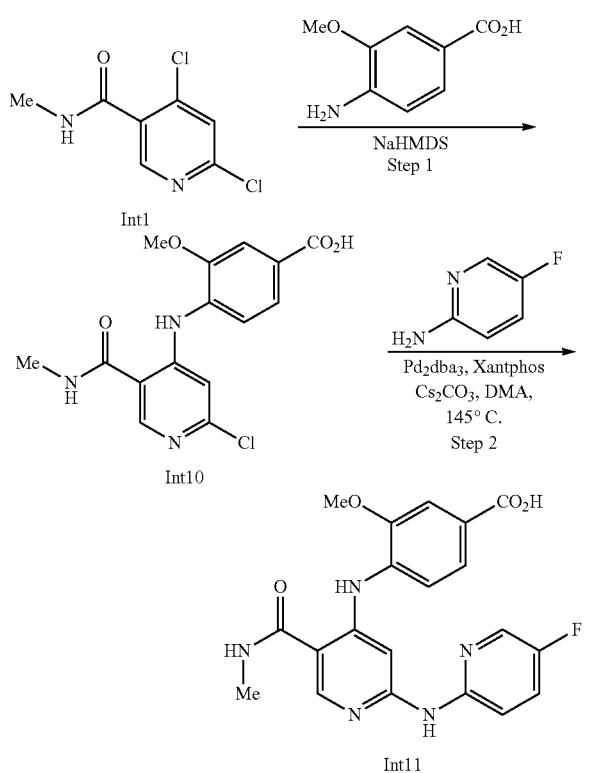

Step 1

To a stirred solution of Intermediate 1 (1.00 g, 4.88 mmol) in DMA (30 mL) was added 4-amino-3-methoxybenzoic acid (1.22 g, 7.32 mmol) followed by NaHMDS (1M in THF, 36.6 mL, 36.6 mmol). The reaction was stirred for 2 hours at which point the THF was removed in vacuo and HCl (1M aqueous) was added to adjust to pH to ~5, the resulting heterogeneous slurry was filtered off yielding Intermediate 10. The filtrate was extracted with DCM and washed with water (3×), dried, concentrated and purified by automated silica gel chromatography (0-100% MeOH/DCM) to yield additional material. Total yield=0.87 g, 53%. $^1$H NMR (400 MHz, DMSO-$d_6$) δ 12.86 (br. s., 1H), 10.64 (s, 1H), 8.81 (d, J=4.4 Hz, 1H), 8.52 (s, 1H), 7.65-7.50 (m, 3H), 7.14 (s, 1H), 3.91 (s, 3H), 2.80 (d, J=4.4 Hz, 3H). LC retention time 0.70 [J]. MS(E⁺) m/z: 336 (MH⁺).

Step 2

5-Fluoropyridin-2-amine (217 mg, 1.94 mmol) was combined with Intermediate 10 (500 mg, 1.49 mmol). To the vessel was added dimethylacetamide (10 mL) followed by Pd₂dba₃ (136 mg, 0.15 mmol), Xantphos (172 mg, 0.30 mmol) and cesium carbonate (0.970 g, 2.98 mmol). The vessel was then evacuated and backfilled with nitrogen three times and then heated to 145° C. for 2 hours. The crude product was filtered and then concentrated on rotary evaporator connected to an oil pump vacuum. The crude oil was absorbed onto silica gel, dried and then purified using automated chromatography (0-100% MeOH/DCM) to provide 300 mg (49% yield) of Intermediate 11. LC retention time 0.66 [J]. MS(E⁺) m/z: 412 (MH⁺).

Example 233

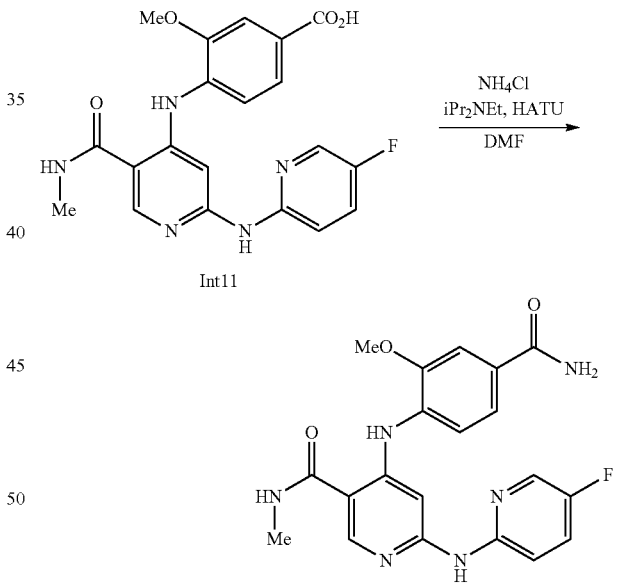

To a DMF (1 mL) solution containing Intermediate 11 (30 mg, 0.073 mmol), ammonium chloride (7.8 mg, 0.15 mmol) and N,N-diisopropylethylamine (51 µL, 0.29 mmol) was added O-(7-azabenzotriazol-1-yl)-N,N,N',N'-tetramethyluronium hexafluorophosphate (HATU, 36 mg, 0.095 mmol) and the reaction stirred for 1 hour. The reaction was filtered and purified by pHPLC providing 233 (12 mg, 40% yield). $^1$H NMR (500 MHz, DMSO-$d_6$) δ 10.66 (s, 1H), 9.86 (s, 1H), 8.56-8.44 (m, 2H), 8.20 (d, J=2.0 Hz, 1H), 7.95 (s, 1H), 7.87 (s, 1H), 7.72-7.62 (m, 2H), 7.61-7.55 (m, 3H), 7.31 (br. s., 1H), 3.91 (s, 3H), 2.77 (d, J=4.5 Hz, 3H). LC retention time 1.09 [E]. MS(E⁺) m/z: 411 (MH⁺).

Examples 234 to 253

The following Examples were prepared in a similar manner to the product of Example 233

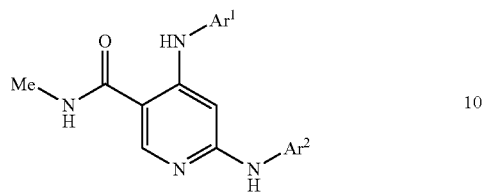

| Example No. | Ar¹ | Ar² | Rt (min) [Method] | m/z [M + H]⁺ |
|---|---|---|---|---|
| 234 | 3-Me-4-(CONH₂)-phenyl (Me, C(O)NH₂) | 5-F-pyridin-2-yl | 1.11 [E] | 395 |
| 235 | 3-Me-4-(piperidine-1-carbonyl)-phenyl | 5-F-pyridin-2-yl | 1.62 [E] | 463 |
| 236 | 3-Me-4-(morpholine-4-carbonyl)-phenyl | 5-F-pyridin-2-yl | 1.29 [E] | 465 |
| 237 | 3-MeO-4-(C(O)NHMe)-phenyl | 5-F-pyridin-2-yl | 1.20 [E] | 425 |
| 238 | 3-MeO-4-(C(O)NHCH₂CH₂OH)-phenyl | 5-F-pyridin-2-yl | 1.08 [E] | 455 |
| 239 | 3-MeO-4-(piperidine-1-carbonyl)-phenyl | 5-F-pyridin-2-yl | 1.57 [E] | 479 |

| Example No. | Ar¹ | Ar² | Rt (min) [Method] | m/z [M + H]⁺ |
|---|---|---|---|---|
| 240 | MeO-, N,N-diethyl benzamide | 5-F-pyridin-2-yl | 1.53 [E] | 467 |
| 241 | MeO-, morpholinyl benzamide | 5-F-pyridin-2-yl | 1.25 [E] | 481 |
| 242 | benzamide (NH₂) | 5-F-pyridin-2-yl | 1.03 [E] | 381 |
| 243 | N-methyl benzamide | 5-F-pyridin-2-yl | 1.13 [E] | 395 |
| 244 | piperidinyl benzamide | 5-F-pyridin-2-yl | 1.54 [E] | 449 |
| 245 | morpholinyl benzamide | 5-F-pyridin-2-yl | 1.22 [E] | 451 |
| 246 | N,N-diethyl benzamide | 5-F-pyridin-2-yl | 1.49 [E] | 437 |
| 247 | MeO-, 3,3-difluoropyrrolidinyl benzamide | 5-F-pyridin-2-yl | 1.49 [E] | 501 |

-continued
| Example No. | Ar¹ | Ar² | Rt (min) [Method] | m/z [M + H]⁺ |
|---|---|---|---|---|
| 248 | 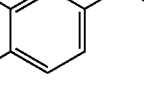 | 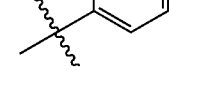 | 1.40 [E] | 465 |
| 249 | 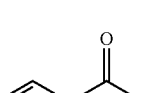 | 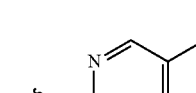 | 1.11 [E] | 505 |
| 250 | 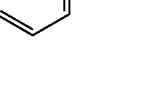 |  | 1.16 [E] | 411 |
| 251 | 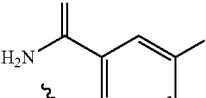 | 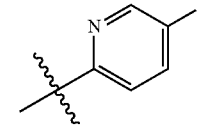 | 1.34 [E] | 409 |
| 252 | 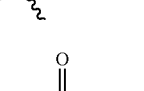 | 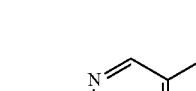 | 1.52 [E] | 465 |
| 253 | 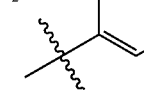 | 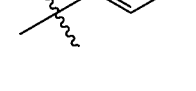 | 1.42 [E] | 430 |
Preparation 6
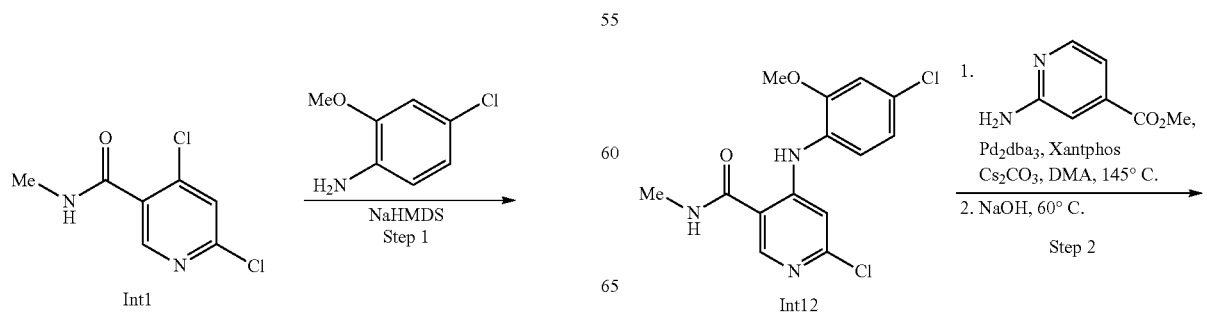

-continued

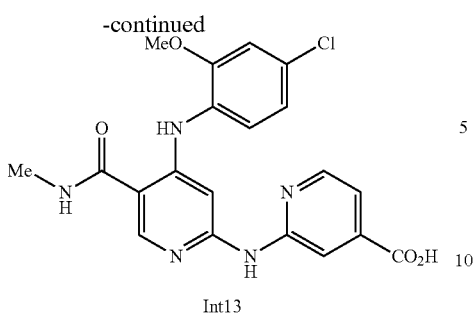

Int13

-continued

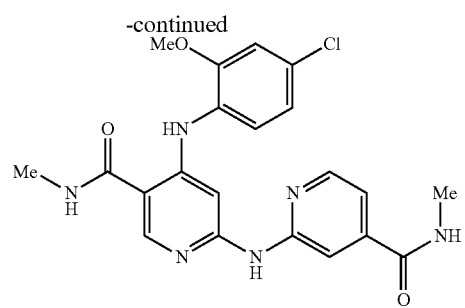

Step 1

To a stirred solution of Intermediate 1 (0.25 g, 1.22 mmol) in DMA (3 mL) was added 4-chloro-2-methoxyaniline (0.25 g, 1.58 mmol) followed by NaHMDS (1M in THF, 3.66 mL, 3.66 mmol). The reaction was stirred for 20 minutes and then water was gradually added resulting in the product crashing out as a precipitate. The product was collected by filtration, washed with additional water and then dried under vacuum providing Intermediate 12 (361 mg, 91% yield). LC retention time 3.44 min [A].

Step 2

Methyl 2-aminoisonicotinate (70 mg, 0.46 mmol) was combined with Intermediate 12 (100 mg, 0.31 mmol). To the vessel was added dimethylacetamide (0.6 mL) followed by $Pd_2dba_3$ (28 mg, 0.031 mmol), Xantphos (35 mg, 0.061 mmol) and cesium carbonate (0.25 g, 0.77 mmol). The vessel was then evacuated and backfilled with nitrogen three times and then heated to 145° C. for 1 hour. The reaction was cooled to room temperature and 0.1 mL of sodium hydroxide (1M in water, 0.1 mmol) was added and the reaction was reheated to 60° C. and stirred overnight. The reaction was diluted with MeOH (~5 mL) and the resulting solids filtered off, rinsing with MeOH, yielding Intermediate 13 (63 mg, 48% yield). $^1$H NMR (400 MHz, DMSO-$d_6$) δ 10.43 (s, 1H), 9.51 (s, 1H), 8.51-8.38 (m, 2H), 8.04 (d, J=5.1 Hz, 1H), 7.96 (s, 1H), 7.71 (s, 1H), 7.54 (d, J=8.6 Hz, 1H), 7.20-7.12 (m, 2H), 7.08 (dd, J=8.6, 2.2 Hz, 1H), 3.87 (s, 3H), 2.77 (d, J=4.4 Hz, 3H). LC retention time 2.83 min [A].

Intermediate 13 (20 mg, 0.047 mmol) was dissolved in DMF (0.2 mL) and methylamine hydrochloride (9.5 mg, 0.14 mmol) as well as N,N-diisopropylethylamine (24 μL, 0.14 mmol) were subsequently added to the reaction vessel. To this vessel was added (benxotriazol-1-yloxy)tris(dimethylamino) phosphonium hexafluorophosphate (BOP, 31 mg, 0.070 mmol) and the reaction was stirred at room temperature for 1 hour. The solution was diluted further with DMF, filtered and purified via pHPLC providing 254 (1.5 mg, 7.3% yield). $^1$H NMR (500 MHz, methanol-$d_4$) δ 8.32 (s, 1H), 8.28 (d, J=5.4 Hz, 1H), 7.71 (s, 1H), 7.64 (s, 1H), 7.51 (d, J=8.4 Hz, 1H), 7.19 (dd, J=5.0, 1.5 Hz, 1H), 7.03-6.96 (m, 2H), 3.92 (s, 3H), 2.96 (s, 3H), 2.94 (s, 3H). LC retention time 1.46 [E]. MS(E$^+$) m/z: 441 (MH$^+$).

Example 254

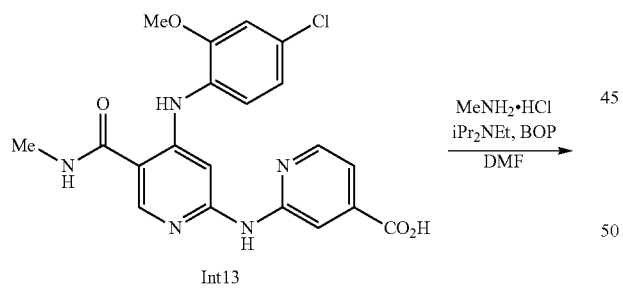

Int13

MeNH$_2$·HCl
iPr$_2$NEt, BOP
DMF
→

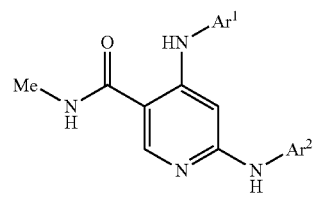

Examples 255 to 278

The following Examples were prepared in a similar manner to the product of Example 254:

| Example No. | Ar$^1$ | Ar$^2$ | Rt (min) [Method] | m/z [M + H]$^+$ |
|---|---|---|---|---|
| 255 | 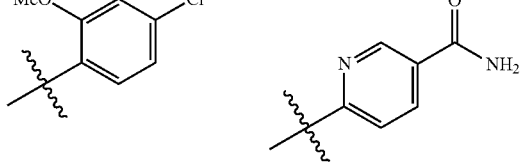 | | 1.40 [E] | 427 |

-continued

| Example No. | Ar¹ | Ar² | Rt (min) [Method] | m/z [M + H]⁺ |
|---|---|---|---|---|
| 256 | MeO, F, F (phenyl) | pyridine-C(O)NH₂ | 1.34 [E] | 429 |
| 257 | MeO, F, F (phenyl) | pyridine-C(O)NHMe | 1.42 [E] | 443 |
| 258 | MeO, F, F (phenyl) | pyridine-C(O)N(Me)Me | 1.48 [E] | 457 |
| 259 | MeO, Cl (phenyl) | pyridine-C(O)NH-cyclopropyl | 1.59 [E] | 467 |
| 260 | MeO, Cl (phenyl) | pyridine-C(O)NHMe | 1.52 [E] | 441 |
| 261 | MeO, Cl (phenyl) | pyridine-C(O)NH-cyclopropyl | 1.65 [E] | 467 |
| 262 | MeO, Cl (phenyl) | pyridine-C(O)N(Me)Me | 1.30 [E] | 455 |
| 263 | MeO, Cl (phenyl) | pyridine-C(O)-morpholine | 1.27 [E] | 497 |

-continued

| Example No. | Ar¹ | Ar² | Rt (min) [Method] | m/z [M + H]⁺ |
|---|---|---|---|---|
| 264 | MeO, F, F (phenyl) | pyridine-C(O)NH₂ | 1.26 [E] | 429 |
| 265 | MeO, F, F (phenyl) | pyridine-C(O)-morpholine | 1.35 [E] | 499 |
| 266 | MeO, F, F (phenyl) | pyridine-C(O)NH-CH₂CH₂-OMe | 1.35 [E] | 487 |
| 267 | MeO, F (phenyl) | pyridine-C(O)NH₂ | 1.15 [E] | 411 |
| 268 | MeO, F (phenyl) | pyridine-C(O)-pyrrolidine | 1.24 [E] | 465 |
| 269 | MeO, F (phenyl) | pyridine-C(O)-morpholine | 1.24 [E] | 481 |
| 270 | MeO, F, F (phenyl) | pyridine-C(O)-pyrrolidine | 1.47 [E] | 483 |
| 271 | MeO, F (phenyl) | pyridine-C(O)NH-CH₂CH₂-OMe | 1.24 [E] | 469 |
| 272 | MeO, F (phenyl) | pyridine-C(O)N(Me)₂ | 1.24 [E] | 439 |

-continued

| Example No. | Ar¹ | Ar² | Rt (min) [Method] | m/z [M + H]⁺ |
|---|---|---|---|---|
| 273 | MeO, F, F (difluoro-methoxyphenyl) | pyridine-C(O)NHMe | 1.30 [E] | 443 |
| 274 | MeO, F, F (difluoro-methoxyphenyl) | pyridine-C(O)NMe₂ | 1.36 [E] | 457 |
| 275 | MeO, F (methoxy-fluorophenyl) | pyridine-C(O)NHMe | 1.49 [I] | 425 |
| 276 | MeO, F (methoxy-fluorophenyl) | pyridine-C(O)NH₂ | 1.20 [E] | 411 |
| 277 | MeO, F (methoxy-fluorophenyl) | pyridine-C(O)NMe₂ | 1.30 [E] | 439 |
| 278 | MeO, F (methoxy-fluorophenyl) | pyridine-C(O)NH-CH₂-CN | 1.29 [E] | 450 |

Preparation 7

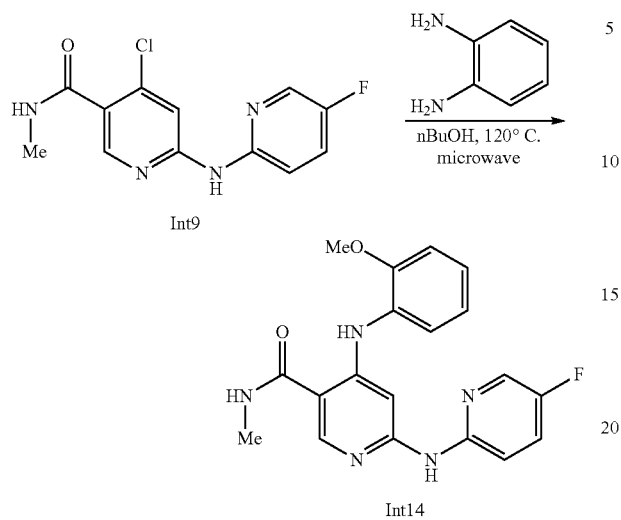

Int9

Int14

To Intermediate 9 (50 mg, 0.18 mmol) was added benzene-1,2-diamine (19 mg, 0.18 mmol) in n-butanol (2 mL). The mixture was heated under microwave irradiation to 120° C. for 3 hours, cooled to room temperature and then purified using pHPLC, providing Intermediate 14 (30 mg, 48% yield). $^1$H NMR (300 MHz, DMSO-$d_6$) δ 11.10 (bs, 1H), 10.15 (s, 1H), 8.86 (m, 1H), 8.35 (s, 1H), 8.32 (m, 1H), 7.85 (m, 1H), 7.15-7.06 (m, 3H), 6.86 (m, 1H), 6.67 (m, 1H), 2.82 (d, J=4.5 Hz, 3H). LC retention time 1.84 min [K]. MS(E$^+$) m/z: 352 (MH$^+$).

Intermediate 14 (40 mg, 0.11 mmol) was dissolved in DCM (1.5 mL) and to this triethylamine (47 μL, 0.34 mmol) was added. The vessel was cooled to 0° C. and methanesulfonyl chloride (13 mg, 0.11 mmol) was added to the reaction. The reaction was warmed to room temperature, stirred for 30 minutes, and then purified using pHPLC to provide 279 (5.2 mg, 10% yield). $^1$H NMR (400 MHz, DMSO-$d_6$) δ 10.46 (bs, 1H), 9.38 (bs, 1H), 8.40 (s, 1H), 8.26 (bs, 1H), 7.79 (m, 1H), 7.50 (m, 2H), 7.39 (m, 3H), 3.03 (s, 3H), 2.82 (d, J=4.4 Hz, 3H). LC retention time 10.27 min [F]. MS(E$^+$) m/z: 431 (MH$^+$)

Example 279

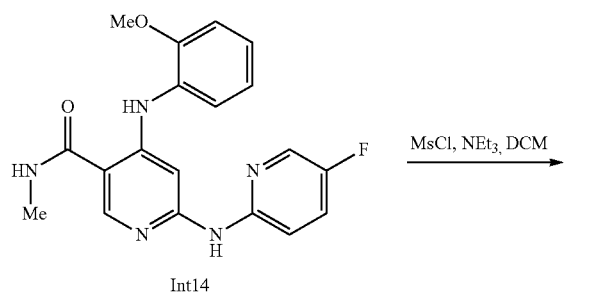

Int14

Examples 280 and 281

The following Examples was prepared in a similar manner to the product of Example 279:

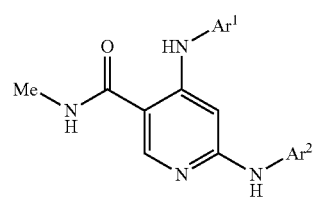

| Example No. | Ar$^1$ | Ar$^2$ | Rt (min) [Method] | m/z [M + H]$^+$ |
|---|---|---|---|---|
| 280 | Me-C(O)-NH-phenyl- | 5-F-pyridin-2-yl- | 7.28 [F] | 395 |

-continued

| Example No. | Ar¹ | Ar² | Rt (min) [Method] | m/z [M + H]⁺ |
|---|---|---|---|---|
| 281 | ![structure with SO₂Me and HN on benzene] | ![pyridine with CN] | 5.50 [F] | 438 |

Preparation 8

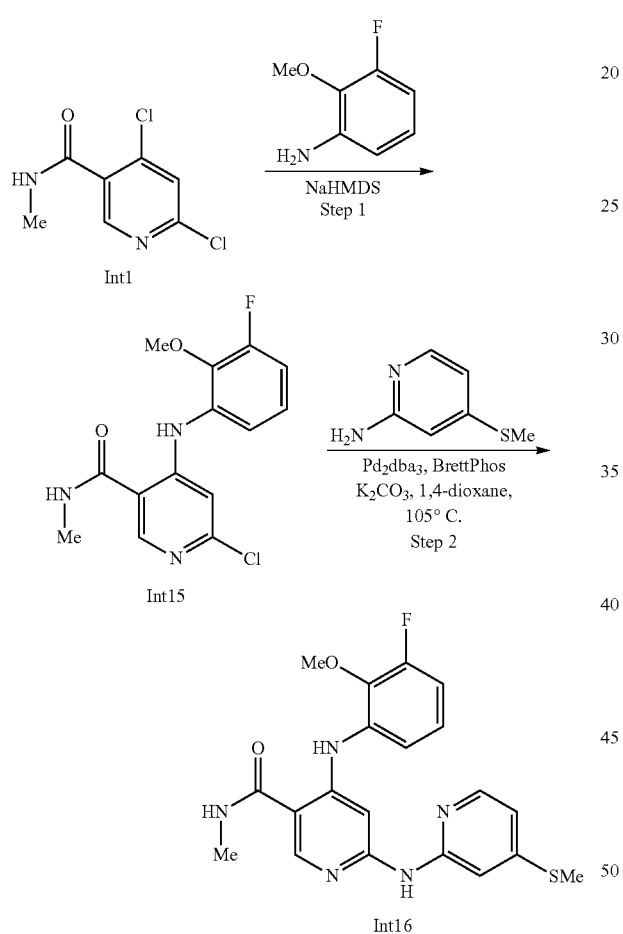

Step 1

To a stirred solution of Intermediate 1 (0.33 g, 1.61 mmol) in DMA (3 mL) was added 3-fluoro-2-methoxyaniline (0.27 g, 1.9 mmol) followed by NaHMDS (1M in THF, 4.83 mL, 4.83 mmol). The reaction was stirred for 30 minutes and then water (~30 mL) was gradually added resulting in the product crashing out as a precipitate. The product was collected by filtration, washed with additional water and then dried under vacuum providing Intermediate 15 (476 mg, 95% yield). LC retention time 3.22 min [A]. MS(E⁺) m/z: 310 (MH⁺).

Step 2

Intermediate 15 (30 mg, 0.097 mmol) was combined with 4-(methylthio)pyridin-2-amine (20.4 mg, 0.145 mmol) as well as palladium diacetate (4.4 mg, 0.019 mmol), 2-(dicyclohexylphosphino)-3,6-dimethoxy-2',4',6'-tri-i-propyl-1,1'-biphenyl (BrettPhos, 10.4 mg, 0.019 mmol), and potassium carbonate (20 mg, 0.14 mmol) and the vial was flushed with N2 for several minutes. 1,4-Dioxane (0.3 mL) was subsequently added and the heterogeneous mixture was sparged with N2, sealed and then heated to 105° C. for 1 hour. The reaction was cooled to room temperature and water was added resulting in the formation of a precipitate. The slurry was stirred at room temperature for 1 hour and then the solid was collected via filtration, washed with water and dried on the filter overnight, providing Intermediate 16 as a yellow powder (40 mg, 100% yield). LC retention time 2.89 min [A]. MS(E⁺) m/z: 414 (MH⁺).

Example 282

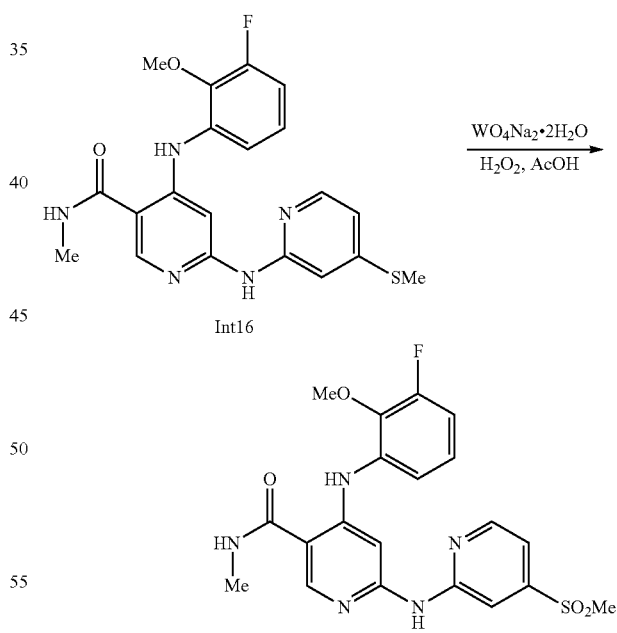

To Intermediate 16 (40 mg, 0.097 mmol) was added sodium tungstate dihydrate (32 mg, 0.097 mmol) and glacial acetic acid (0.3 mL). To this was added hydrogen peroxide (33% aqueous, 59 µL, 0.63 mmol) and the oxidation was allowed to occur over 30 minutes. The reaction was quenched by cooling the reaction to 0° C. and adding 25% aqueous sodium thiosulfate (~1 mL). This slurry was warmed to room temperature and stirred for 1 hour at which point the solid was filtered off and air dried. The resulting powder was re-dissolved in DMF and purified by pHPLC providing 282 (21 mg, 49% yield). $^1$H NMR (500 MHz, DMSO-d$_6$) δ 10.75 (s, 1H), 10.25 (s, 1H), 8.59 (d, J=4.5 Hz, 1H), 8.55 (s, 1H), 8.47 (d, J=5.4 Hz, 1H), 8.33 (s, 1H), 7.67 (s, 1H), 7.38 (d, J=8.4 Hz, 1H), 7.34 (dd, J=5.4, 1.5 Hz, 1H), 7.18 (td, J=8.2, 5.9 Hz, 1H), 7.04-6.96 (m, 1H), 3.85 (s, 3H), 3.27 (s, 3H), 2.79 (d, J=4.5 Hz, 3H). LC retention time 1.54 min [E]. MS(E$^+$) m/z: 446 (MH$^+$).

Preparation 9

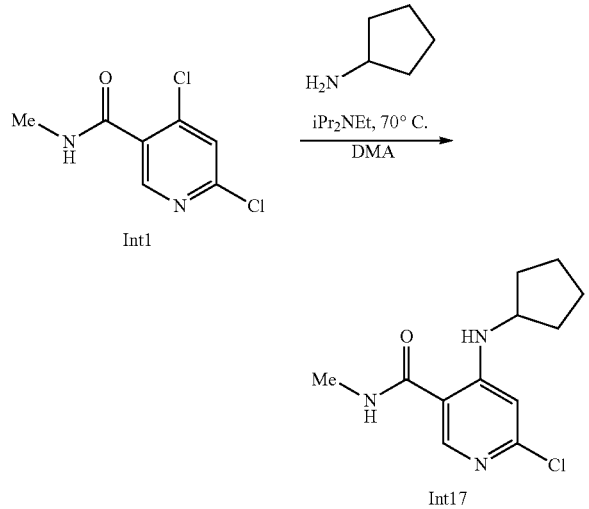

Int1

To a solution of Intermediate 1 (200 mg, 0.98 mmol) in DMA (0.2 mL) was added cyclopentanamine (125 mg, 1.46 mmol) and iPr$_2$NEt (138 mg, 1.07 mmol). The vessel was sealed and heated to 70° C. for two hours, cooled to room temperature and poured into water resulting in the formation of a precipitate. The slurry was stirred at room temperature for 4 hours and then filtered, rinsing with water. The solid was collected and dried, no further purification was performed.

Example 283

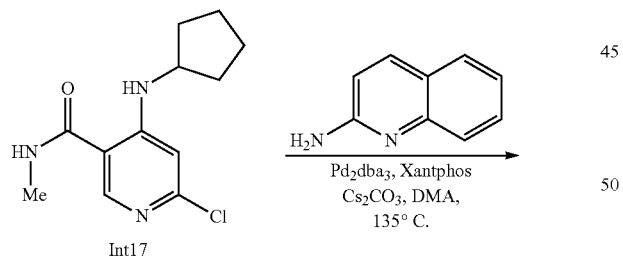

Int17

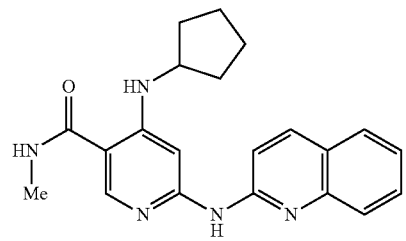

Intermediate 17 (25 mg, 0.099 mmol) was combined with quinolin-2-amine (28 mg, 0.20 mmol) within a reaction vessel. To the vessel was added DMA (0.5 mL) followed by Pd$_2$dba$_3$ (9.0 mg, 0.0098 mmol), Xantphos (11.4 mg, 0.020 mmol) and cesium carbonate (64 mg, 0.20 mmol). The vessel was then evacuated and backfilled with nitrogen three times and then heated to 135° C. for 2 hours. The crude product was then diluted with DMF and filtered, before being purified using preparative HPLC to provide 283 (25.6 mg, 71% yield). $^1$H NMR (500 MHz, methanol-d$_4$) δ 8.20 (s, 1H), 8.13-8.02 (m, 2H), 7.78 (d, J=8.4 Hz, 1H), 7.75-7.71 (m, 1H), 7.65 (td, J=7.7, 1.5 Hz, 1H), 7.42-7.36 (m, 1H), 7.20 (d, J=8.9 Hz, 1H), 4.01 (quin, J=5.9 Hz, 1H), 2.90 (s, 3H), 2.30-2.16 (m, 2H), 1.92-1.62 (m, 6H). LC retention time 1.89 min [E]. MS(E$^+$) m/z: 362 (MH$^+$)

Examples 284 to 293

The following Examples were prepared in a similar manner to the product of Example 283:

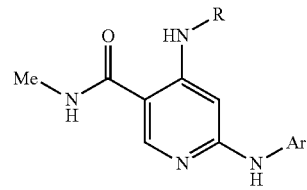

| Example No. | R | Ar | Rt (min) [Method] | m/z [M + H]$^+$ |
|---|---|---|---|---|
| 284 | ![F, Me cyclopentyl (±)] | ![quinolin-2-yl] | 1.86 [E] | 394 |

-continued

| Example No. | R | Ar | Rt (min) [Method] | m/z [M + H]+ |
|---|---|---|---|---|
| 285 | tBu, Me | quinolin-2-yl | 2.05 [E] | 378 |
| 286 | cyclohexyl-C(O)NH₂ (±) | quinolin-2-yl | 1.42 [E] | 419 |
| 287 | 4-F-cyclohexyl (±) | quinolin-2-yl | 1.78 [E] | 394 |
| 288 | cyclopentyl-C(O)NH₂ (±) | quinolin-2-yl | 1.33 [E] | 405 |
| 289 | cyclopentyl-C(O)NH₂ (±) | quinolin-2-yl | 1.27 [E] | 405 |
| 290 | cyclohexyl-C(O)NH₂ (±) | 5-CF₃-pyridin-2-yl | 1.32 [E] | 437 |
| 291 | cyclopentyl-C(O)NH₂ (±) | 5-CF₃-pyridin-2-yl | 1.42 [E] | 423 |
| 292 | 4,4-difluorocyclohexyl | quinolin-2-yl | 1.76 [E] | 412 |

-continued

| Example No. | R | Ar | Rt (min) [Method] | m/z [M + H]+ |
|---|---|---|---|---|
| 293 | HO,,,,, F F (±) | quinolin-2-yl | 1.34 [E] | 428 |

Preparation 10

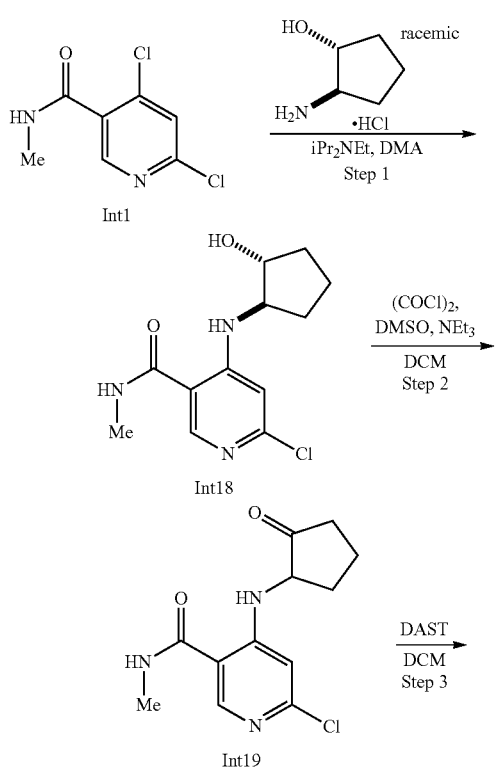

Step 1

To a solution of Intermediate 1 (150 mg, 0.73 mmol) in DMA (0.5 mL) was added (±)-trans-2-aminocyclopentanol hydrochloride (111 mg, 0.80 mmol) and iPr₂NEt (0.286 mL, 1.61 mmol), the reaction vessel was sealed and heated to 80° C. overnight. The reaction was diluted with ethyl acetate, washed with brine, dried and concentrated to give Intermediate 18 as the crude product (yield not determined). LC retention time 1.28 min [L]. MS(E⁺) m/z: 270 (MH⁺).

Step 2

To a solution of oxalyl chloride (0.097 mL, 1.12 mmol) in DCM (5 mL) was added DMSO (0.158 mL, 2.22 mmol) at −78° C. The mixture was stirred at −78° C. for 10 minutes and then Intermediate 18 (100 mg, 0.37 mmol) in DCM (1 mL) was added in a dropwise manner. The reaction was stirred at −78° C. for 5 hours and then triethylamine (0.31 mL, 2.22 mmol) was added and the reaction allowed to warm to room temperature overnight. The reaction was quenched with water and the product extracted with DCM, the combined organics were dried over MgSO₄, filtered, concentrated and carried on without further purification (100 mg, ~50% pdt/sm). Intermediate 19 LC retention time 0.63 min [J]. MS(E⁺) m/z: 268 (MH⁺).

Step 3

To a solution of the crude product of Step 1 (Intermediate 19) in DCM (5 mL) was added DAST (0.10 mL, 0.78 mmol) and the reaction allowed to stir at room temperature overnight. The reaction was quenched via the addition of water and the product extracted with DCM. The combined organic layers were washed with saturated aqueous NaHCO₃, dried over sodium sulfate, filtered and concentrated and then purified using automated chromatography (20-60% EtOAc/hexanes) providing Intermediate 20 (35 mg, 32% yield over 2 steps). LC retention time 2.34 min [M]. MS(E⁺) m/z: 290 (MH⁺).

Example 294

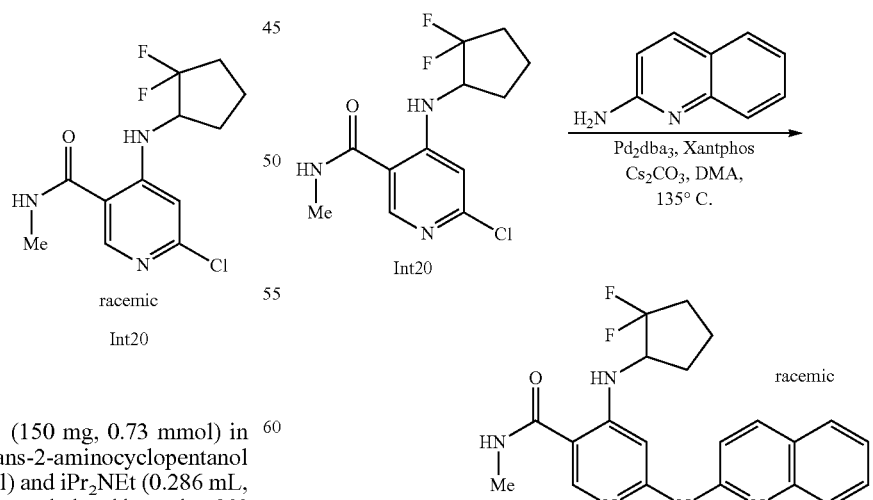

Intermediate 20 (10 mg, 0.035 mmol) was combined with quinolin-2-amine (10 mg, 0.069 mmol) within a reaction vessel. To the vessel was added DMA (0.5 mL) followed by Pd$_2$dba$_3$ (3.2 mg, 0.0034 mmol), Xantphos (3.6 mg, 0.0069 mmol) and cesium carbonate (34 mg, 0.10 mmol). The vessel was then evacuated and backfilled with nitrogen three times and then heated to 130° C. for 3 hours. The crude product was then diluted with DMF and filtered, before being purified using preparative HPLC to provide 294 (8.2 mg, 58% yield). $^1$H NMR (500 MHz, methanol-d$_4$) δ 8.27 (s, 1H), 8.17 (br. s., 1H), 8.06 (d, J=8.9 Hz, 1H), 7.81 (d, J=8.4 Hz, 1H), 7.76-7.71 (m, 1H), 7.68-7.60 (m, 1H), 7.43-7.35 (m, 1H), 7.23 (d, J=8.9 Hz, 1H), 4.23-4.10 (m, 1H), 2.96-2.85 (m, 3H), 2.55 (dtd, J=12.3, 7.9, 3.7 Hz, 1H), 2.41-2.17 (m, 2H), 2.06-1.86 (m, 2H), 1.86-1.75 (m, 1H) LC retention time 1.76 min [E]. MS(E m/z: 398 (MH$^+$)

Preparation 11

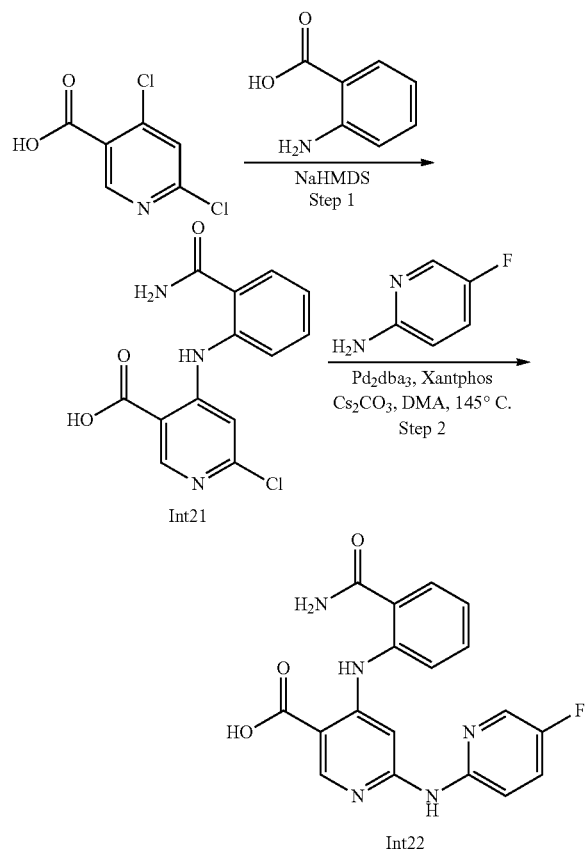

Step 1

To a solution of 4,6-dichloronicotinic acid in tetrahydrofuran (THF, 0.1-0.8M) was added a corresponding aniline (1.5 molar equivalents) followed by sodium bis(trimethylsilyl)amide solution (1M in THF, 8 molar equivalents). The reaction was stirred at room temperature until such time that LCMS and/or HPLC analysis of an aliquot of the reaction mixture revealed complete consumption of the starting material. The reaction was quenched with 1 M hydrochloric acid (HCl) in water and the crude reaction was concentrated. The crude product was absorbed onto silica gel and purified using automated silica gel chromatography (0-30% MeOH/DCM), providing Intermediate 21 (400 mg, 33% yield). LC retention time 0.83 min [J]. MS(E$^+$) m/z: 292 (MH$^+$).

Step 2

Intermediate 21 (380 mg, 1.30 mmol) was combined with 5-fluoropyridin-2-amine (219 mg, 1.95 mmol) within a reaction vessel. To the vessel was added DMA (15 mL) followed by Pd$_2$dba$_3$ (119 mg, 0.13 mmol), Xantphos (151 mg, 0.26 mmol) and cesium carbonate (849 mg, 2.61 mmol). The vessel was then evacuated and backfilled with nitrogen three times and then heated to 145° C. for 35 minutes. The reaction mixture was filtered, absorbed onto silica gel and then purified using automated chromatography (0-100% MeOH/DCM) to provide Intermediate 22 (350 mg, 73% yield). LC retention time 0.59 min [J]. MS(E$^+$) m/z: 368 (MH$^+$).

Example 295

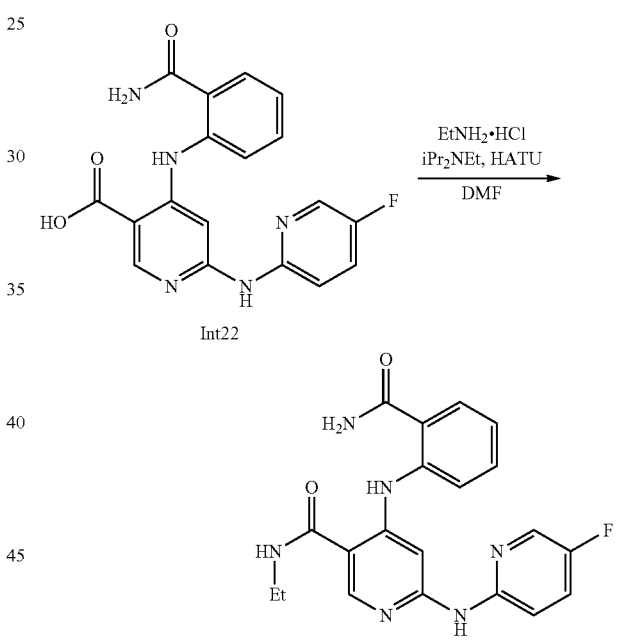

Intermediate 22 (20 mg, 0.054 mmol) was dissolved in DMF (1 mL) and combined with ethylamine hydrochloride (6.7 mg, 0.082 mmol) as well as N,N-diisopropylethylamine (38 μL, 0.22 mmol). To this was added HATU (27 mg, 0.071 mmol) and the reaction was stirred for one hour. The crude reaction was filtered and purified using pHPLC to provide 295 (6.9 mg, 32% yield). $^1$H NMR (500 MHz, methanol-d$_4$) δ 8.26 (s, 1H), 8.18 (br. s., 1H), 7.73 (d, J=7.4 Hz, 1H), 7.58-7.50 (m, 2H), 7.43-7.29 (m, 1H), 7.02 (br. s., 1H), 3.42 (q, J=7.3 Hz, 2H), 1.27-1.20 (m, 3H). LC retention time 1.24 min [E]. MS(E$^+$) m/z: 395 (MH$^+$).

Example 296

The following Example was prepared in a similar manner to the product of Example 295:

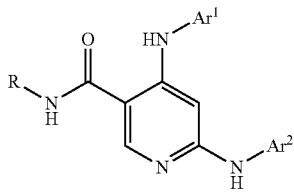

| Example No. | R | Ar¹ | Ar² | Rt (min) [Method] | m/z [M + H]⁺ |
|---|---|---|---|---|---|
| 296 | Et | MeO-phenyl | 5-F-pyridin-2-yl | 1.72 [E] | 382 |

Preparation 12

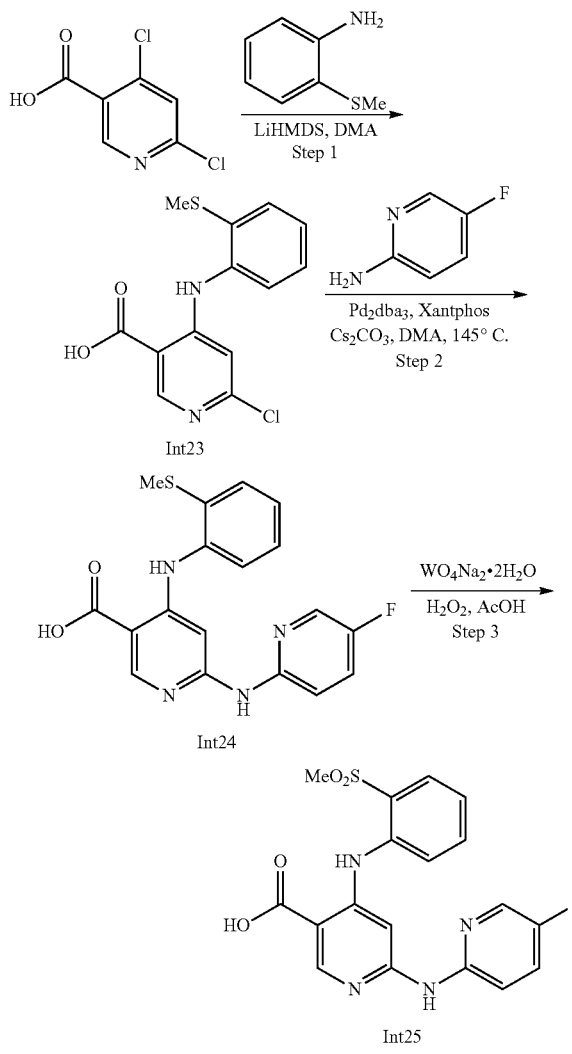

Step 1

To a solution of 4,6-dichloronicotinic acid (2 g, 10.42 mmol) and 2-(methylthioaniline) (1.74 g, 12.5 mmol) in DMA (30 mL) was added lithium bis(trimethylsilyl)amide (LiHMDS, 1M in THF, 25 mL, 25 mmol) resulting in a mild exotherm. The reaction was stirred for 1 hour at room temperature and then concentrated under reduced pressure to remove the THF, water was added to the residual oil (total volume ~80 mL), 6M HCl was added until the pH ~1-2 resulting in the product crashing out. The product was collected via filtration, washed with water and dried overnight, yielding Intermediate 23 as an off-white solid (3.17 g, ~100%). LC retention time 3.20 min [A]. MS(E⁺) m/z: 295 (MH⁺).

Step 2

5-Fluoropyridin-2-amine (57 mg, 0.51 mmol) was combined with Intermediate 23 (100 mg, 0.34 mmol). To the vessel was added dimethylacetamide (1 mL) followed by $Pd_2dba_3$ (31 mg, 0.034 mmol), Xantphos (39 mg, 0.068 mmol) and cesium carbonate (0.33 g, 1.0 mmol). The vessel was then evacuated and backfilled with nitrogen three times and then heated to 145° C. for 1 hour. The reaction was cooled to room temperature and then diluted with water (~3 mL) and 3N NaOH (1 mL). The resulting slurry was filtered and chloroform was added to the receiving flask and the flask was swirled, and the chloroform was decanted off via pipette. Chloroform was added and decanted twice more at which point the aqueous layer was rendered acidic with 6N HCl (aqueous) resulting in a tan precipitate. The precipitate was collected via filtration, washed with water and dried yielding Intermediate 24 (70 mg, 56% yield). ¹H NMR (400 MHz, DMSO-$d_6$) δ 9.97 (br. s., 1H), 8.65 (s, 1H), 8.11 (br. s., 1H), 7.67 (br. s., 1H), 7.49-7.35 (m, 3H), 7.36-7.27 (m, 2H), 2.44 (s, 3H). LC retention time 2.80 [A]. MS(E⁺) m/z: 371 (MH⁺)

Step 3

To a slurry of Intermediate 24 (85 mg, 0.23 mmol) and sodium tungstate dihydrate (76 mg, 0.23 mmol) in acetic acid (4 mL) was added hydrogen peroxide (30% aqueous solution, 0.70 mL, 6.9 mmol) and the reaction stirred at room temperature for 1 hour. The reaction was then cooled in an ice bath and 1 mL of sodium thiosulfate (25% aqueous solution) was added in a dropwise manner. The mixture was allowed to warm to room temperature and then diluted with water to a total volume of ~10 mL. The product was collected via filtration, washed with water and then air dried on the filter overnight providing 89 mg (96% yield) of Intermediate 25. ¹H NMR (400 MHz, DMSO-$d_6$) δ 10.54 (br. s., 1H), 8.72 (s, 1H), 8.18 (br. s., 1H), 8.00 (d, J=7.5 Hz, 1H), 7.91-7.84 (m, 1H), 7.83-7.78 (m, 1H), 7.72 (br. s., 1H), 7.51 (br. s., 2H), 3.16 (s, 3H). LC retention time 2.12 [A]. MS(E⁺) m/z: 403 (MH⁺).

Example 297

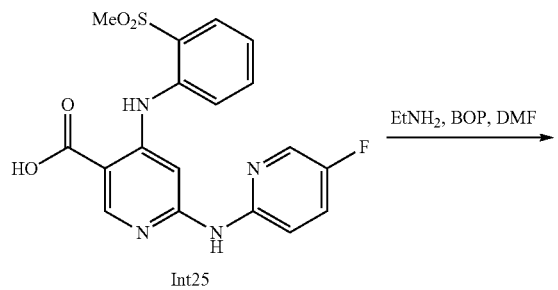

Int25

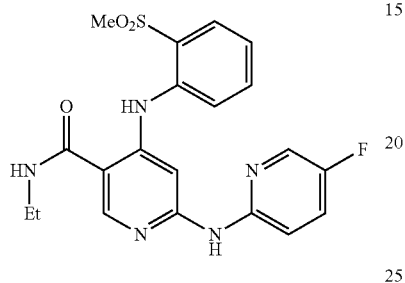

Intermediate 25 (30 mg, 0.075 mmol) was dissolved in DMF (0.3 mL) and an. To this vessel was added a slight excess of ethylamine (70% aqueous solution, several drops ~0.02, ~0.2 mmol) along with BOP (50 mg, 0.11 mmol) and the reaction was stirred at room temperature for 2 hours. The solution was diluted with DMSO, filtered and purified via pHPLC providing 297 (9.2 mg, 29% yield). $^1$H NMR (500 MHz, methanol-$d_4$) δ 8.40 (s, 1H), 8.03 (dd, J=8.4, 1.5 Hz, 1H), 7.98 (d, J=3.0 Hz, 1H), 7.82 (d, J=7.4 Hz, 1H), 7.80 (s, 1H), 7.73-7.68 (m, 1H), 7.45-7.38 (m, 1H), 7.36-7.29 (m, 2H), 3.44 (q, J=7.3 Hz, 2H), 3.14 (s, 3H), 1.25 (t, J=7.2 Hz, 3H). LC retention time 1.48 [E]. MS(E$^+$) m/z: 430 (MH$^+$).

Examples 298 to 301

The following Examples was prepared in a similar manner to the product of Example 297:

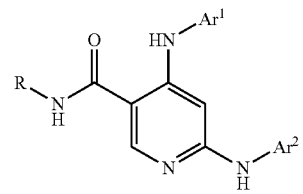

| Example No. | R | Ar$^1$ | Ar$^2$ | Rt (min) [Method] | m/z [M + H]$^+$ |
|---|---|---|---|---|---|
| 298 | CD$_3$ | MeO$_2$S-(2-phenyl) | 5-F-pyridin-2-yl | 1.38 [E] | 419 |
| 299 | CD$_3$ | MeO$_2$S-(4-F-phenyl) | pyridin-2-yl | 1.30 [E] | 419 |
| 300 | CD$_3$ | MeO$_2$S-(2-phenyl) | 2,6-dimethylpyrimidin-4-yl | 1.16 [E] | 430 |
| 301 | CD$_3$ | MeO$_2$S-(2-phenyl) | 6-(5-fluoro-2-oxopyridin-1(2H)-yl)pyridin-2-yl | 1.22 [E] | 512 |

Preparation 13

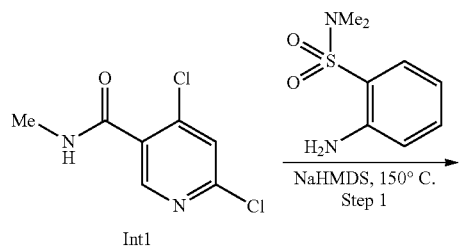

Step 1

To a microwave vessel equipped with a stir bar was added Intermediate 1 (50 mg, 0.24 mmol) and 2-amino-N,N-dimethylbenzenesulfonamide (68 mg, 0.34 mmol). The solids were dissolved in dioxane (0.7 mL), the vessel was sealed and purged with nitrogen and then NaHMDS (1M in THF, 0.24 mL, 0.24 mmol) was added via syringe. The vessel was subsequently heated to 150° C. in a microwave for 1 hour and then concentrated and purified by automated chromatography providing Intermediate 26 (3.4 mg, 3.4% yield). $^1$H NMR (400 MHz, chloroform-d) δ 10.61 (s, 1H), 8.35 (s, 1H), 7.99 (dd, J=7.9, 1.3 Hz, 1H), 7.63-7.56 (m, 1H), 7.56-7.50 (m, 1H), 7.34-7.28 (m, 1H), 7.05 (s, 1H), 6.22 (br. s., 1H), 3.04 (d, J=4.8 Hz, 3H), 2.76 (s, 6H). LC retention time 1.37 [A]. MS(E$^+$) m/z: 369 (MH$^+$).

Example 302

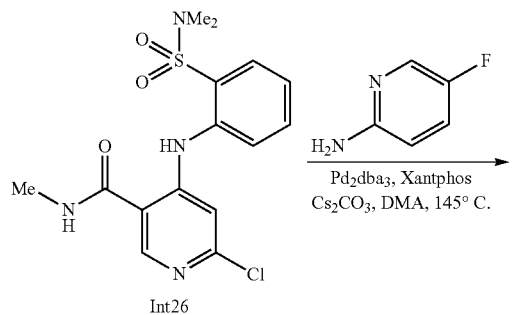

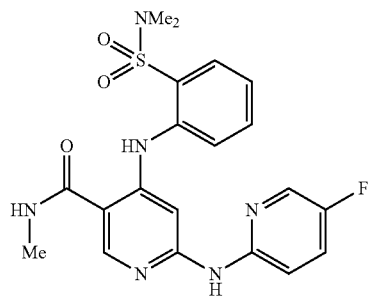

Intermediate 26 (10 mg, 0.027 mmol) was combined with 5-Fluoropyridin-2-amine (6.1 mg, 0.054 mmol) within a reaction vessel. To the vessel was added DMA (0.4 mL) followed by Pd$_2$dba$_3$ (2.4 mg, 0.0027 mmol), Xantphos (3.1 mg, 0.0054 mmol) and cesium carbonate (22 mg, 0.068 mmol). The vessel was then evacuated and backfilled with nitrogen three times and then heated to 145° C. for 1.5 hours. The crude product was then diluted with DMF and filtered, before being purified using preparative HPLC to provide 302 (1 mg, 8% yield). $^1$H NMR (500 MHz, methanol-d$_4$) δ 8.34 (br. s., 1H), 7.98 (br. s., 1H), 7.94 (dd, J=8.2, 1.2 Hz, 1H), 7.78 (d, J=7.9 Hz, 1H), 7.70 (br. s., 1H), 7.64 (t, J=7.7 Hz, 1H), 7.42 (br. s., 1H), 7.37-7.23 (m, 2H), 2.93 (s, 3H), 2.75 (s, 6H). LC retention time 0.68 [J]. MS(E$^+$) m/z: 445 (MH$^+$).

Preparation 14

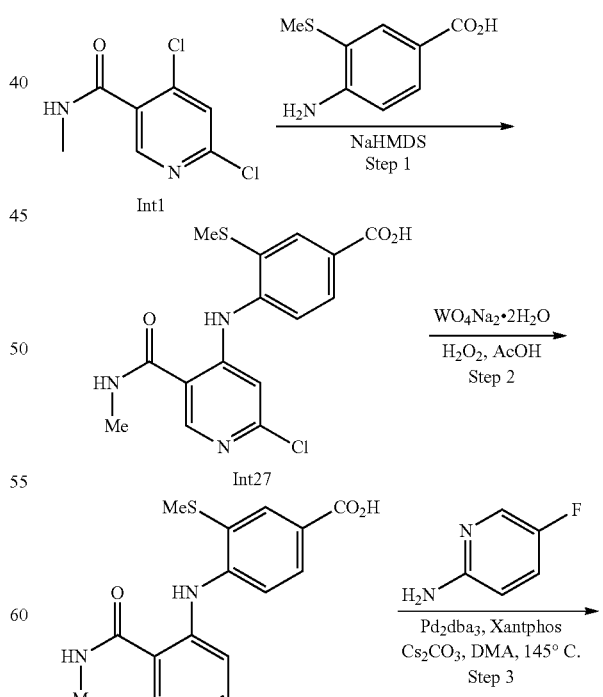

183

-continued

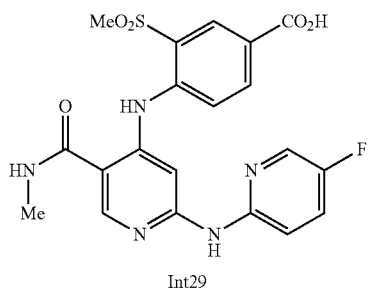

Int29

Step 1

To a stirred solution of Intermediate 1 (2.00 g, 9.75 mmol) in DMA (70 mL) was added 4-amino-3-(methylthio)benzoic acid (2.68 g, 14.6 mmol) followed by NaHMDS (1M in THF, 68 mL, 68 mmol). The reaction was stirred for 1 hour at which point HCl (1M aqueous) was added to adjust to pH to ~5, the resulting solution was concentrated, absorbed onto silica and purified using automated chromatography (0-100% MeOH/DCM) to yield Intermediate 27 (900 mg, 26%). LC retention time 0.76 [J]. MS(E$^+$) m/z: 352 (MH$^+$).

Step 2

To a slurry of Intermediate 27 (850 mg, 2.42 mmol) and sodium tungstate dihydrate (797 mg, 2.42 mmol) in acetic acid (5 mL) was added hydrogen peroxide (30% aqueous solution, 7.4 mL, 72 mmol) and the reaction stirred at room temperature for 1 hour. Water was added and the product was extracted with ethyl acetate (×3). The combined organic layers were washed with water, dried over sodium sulfate, filtered and concentrated providing Intermediate 28 (700 mg, 75% yield) which was carried on without further purification. LC retention time 0.65 [J]. MS(E$^+$) m/z: 384 (MH$^+$).

Step 3

5-Fluoropyridin-2-amine (169 mg, 1.51 mmol) was combined with Intermediate 28 (290 mg, 0.76 mmol). To the vessel was added dimethylacetamide (1 mL) followed by Pd$_2$dba$_3$ (69 mg, 0.076 mmol), Xantphos (87 mg, 0.15 mmol) and cesium carbonate (0.49 g, 1.5 mmol). The vessel was then evacuated and backfilled with nitrogen three times and then heated to 145° C. for 4 hours. The crude product was filtered and then concentrated on rotary evaporator connected to an oil pump vacuum. The crude oil was absorbed onto silica gel, dried and then purified using automated chromatography (0-100% MeOH/DCM) to provide 236 mg (68% yield) of Intermediate 29. A portion of this material was further purified by preparative HPLC. $^1$H NMR (500 MHz, methanol-d$_4$) δ 8.75 (br. s., 1H), 8.46 (s, 1H), 8.38 (d, J=7.4 Hz, 1H), 8.23 (br. s., 1H), 7.86 (d, J=8.4 Hz, 1H), 7.64-7.60 (m, 1H), 7.22-7.05 (m, 2H), 3.23 (s, 3H), 2.97 (s, 3H). LC retention time 0.88 [E]. MS(E$^+$) m/z: 460 (MH$^+$).

184

Example 303

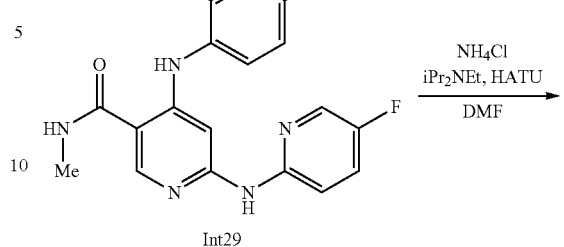

Int29

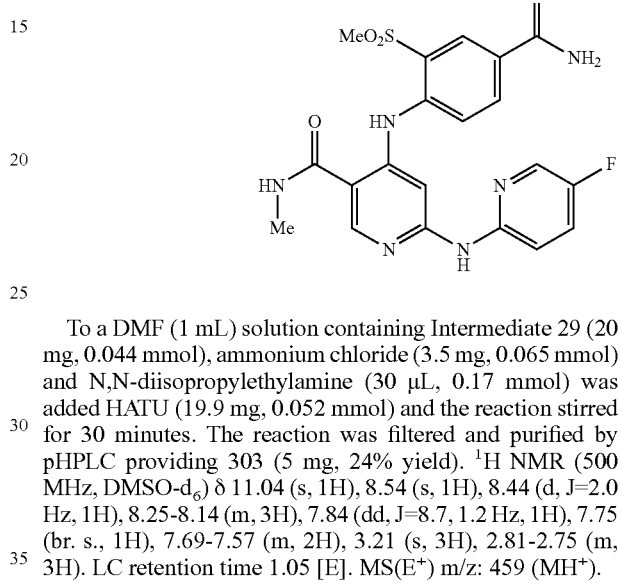

To a DMF (1 mL) solution containing Intermediate 29 (20 mg, 0.044 mmol), ammonium chloride (3.5 mg, 0.065 mmol) and N,N-diisopropylethylamine (30 µL, 0.17 mmol) was added HATU (19.9 mg, 0.052 mmol) and the reaction stirred for 30 minutes. The reaction was filtered and purified by pHPLC providing 303 (5 mg, 24% yield). $^1$H NMR (500 MHz, DMSO-d$_6$) δ 11.04 (s, 1H), 8.54 (s, 1H), 8.44 (d, J=2.0 Hz, 1H), 8.25-8.14 (m, 3H), 7.84 (dd, J=8.7, 1.2 Hz, 1H), 7.75 (br. s., 1H), 7.69-7.57 (m, 2H), 3.21 (s, 3H), 2.81-2.75 (m, 3H). LC retention time 1.05 [E]. MS(E$^+$) m/z: 459 (MH$^+$).

Examples 304 to 309

The following Examples was prepared in a similar manner to the product of Example 303:

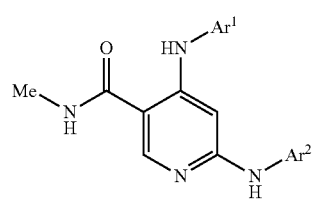

| Example No. | Ar1 | Ar2 | Rt (min) [Method] | m/z [M + H]+ |
|---|---|---|---|---|
| 304 | MeO₂S-C₆H₃-C(O)NHMe | 5-F-pyridin-2-yl | 1.13 [E] | 473 |

-continued

| Example No. | Ar1 | Ar2 | Rt (min) [Method] | m/z [M + H]+ |
|---|---|---|---|---|
| 305 | MeO₂S-phenyl-C(O)-morpholine | 5-F-pyridin-2-yl | 1.18 [E] | 529 |
| 306 | MeO₂S-phenyl-C(O)-N(Me)₂ | 5-F-pyridin-2-yl | 1.19 [E] | 487 |
| 307 | MeO₂S-phenyl-C(O)NH-(2-F-cyclopropyl) | 5-F-pyridin-2-yl | 1.22 [E] | 517 |
| 308 | MeO₂S-phenyl-C(O)-(3,3-difluoroazetidin-1-yl) | 5-F-pyridin-2-yl | 1.36 [E] | 535 |
| 309 | MeO₂S-phenyl-C(O)NH-cyclopropyl | 5-F-pyridin-2-yl | 1.01 [E] | 499 |

Example 310

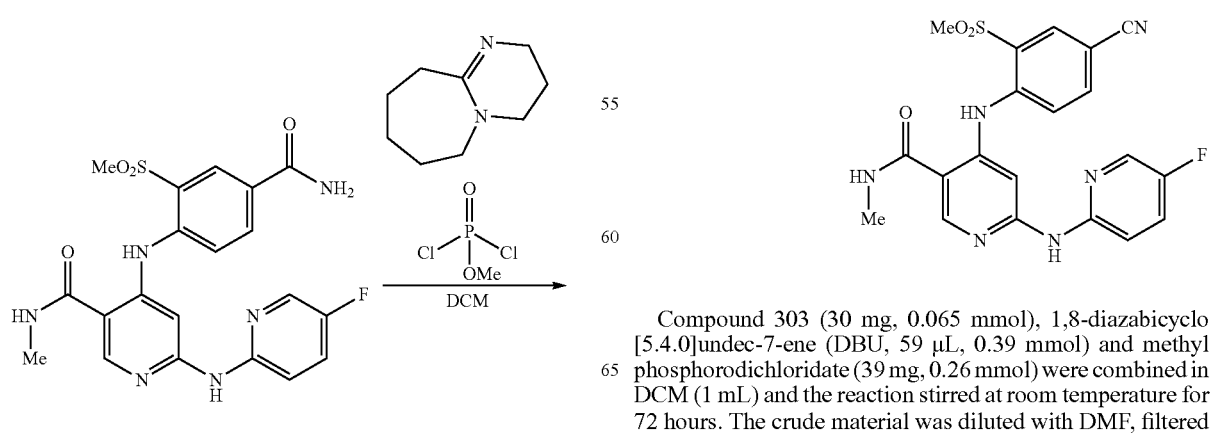

Compound 303 (30 mg, 0.065 mmol), 1,8-diazabicyclo[5.4.0]undec-7-ene (DBU, 59 μL, 0.39 mmol) and methyl phosphorodichloridate (39 mg, 0.26 mmol) were combined in DCM (1 mL) and the reaction stirred at room temperature for 72 hours. The crude material was diluted with DMF, filtered and purified using preparative HPLC providing 310 (1.6 mg, 5% yield). $^1$H NMR (500 MHz, methanol-$d_4$) δ 8.46 (s, 1H), 8.32 (d, J=2.0 Hz, 1H), 8.07-7.98 (m, 3H), 7.93 (dd, J=8.9, 2.0 Hz, 1H), 7.45 (td, J=8.4, 3.0 Hz, 1H), 7.35 (dd, J=8.9, 3.5 Hz, 1H), 3.23 (s, 3H), 2.93 (s, 3H). LC retention time 1.38 [E]. MS(E$^+$) m/z: 441 (MH$^+$).

Preparation 15

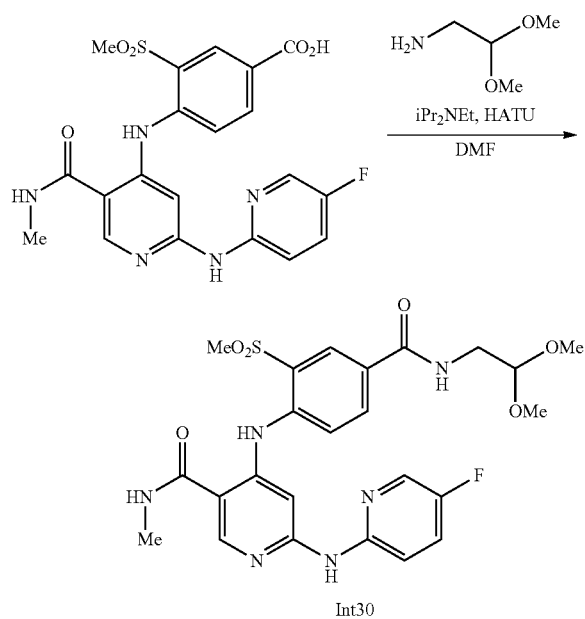

To a DMF (1 mL) solution containing Intermediate 29 (54 mg, 0.118 mmol), 2,2-dimethoxyethanamine (24.7 mg, 0.235 mmol) and N,N-diisopropylethylamine (82 µL, 0.47 mmol) was added HATU (53.6 mg, 0.141 mmol) and the reaction stirred for 60 minutes. The reaction was concentrated and purified by automated chromatography (0-25% MeOH/DCM) providing Intermediate 30 (40 mg, 62% yield). LC retention time 0.65 [J]. MS(E$^+$) m/z: 547 (MH$^+$).

Example 311

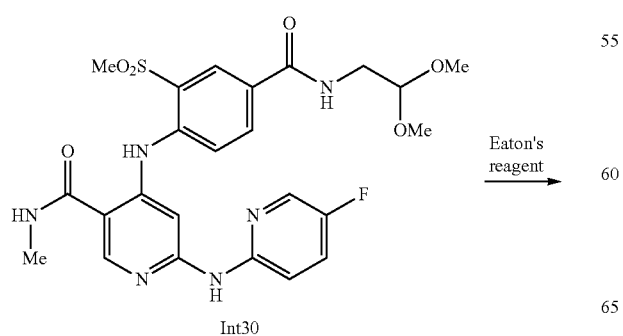

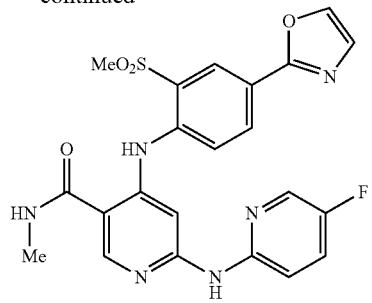

Intermediate 30 (60 mg, 0.11 mmol) was added to Eaton's reagent (phosphorus pentoxide, 7.7 wt. % in methanesulfonic acid, 0.7 mL, 4.4 mmol) and the reaction heated to 135° C. for 3.5 hours. The reaction was cooled to room temperature and then neutralized with 1N NaOH. The crude product was extracted with DCM, the combined organic layers were dried over sodium sulfate, filtered, concentrated and purified by preparative HPLC to give 311 (9.4 mg, 17% yield). $^1$H NMR (500 MHz, DMSO-$d_6$) δ 11.10 (s, 1H), 8.66 (br. s., 1H), 8.55 (s, 1H), 8.49 (d, J=2.0 Hz, 1H), 8.35-8.27 (m, 2H), 8.19 (d, J=2.5 Hz, 1H), 7.97-7.90 (m, 1H), 7.75-7.65 (m, 1H), 7.58 (br. s., 1H), 7.45 (s, 1H), 3.28 (s, 3H), 2.79 (d, J=4.5 Hz, 3H). LC retention time 1.42 [E]. MS(E$^+$) m/z: 483 (MH$^+$).

Preparation 16

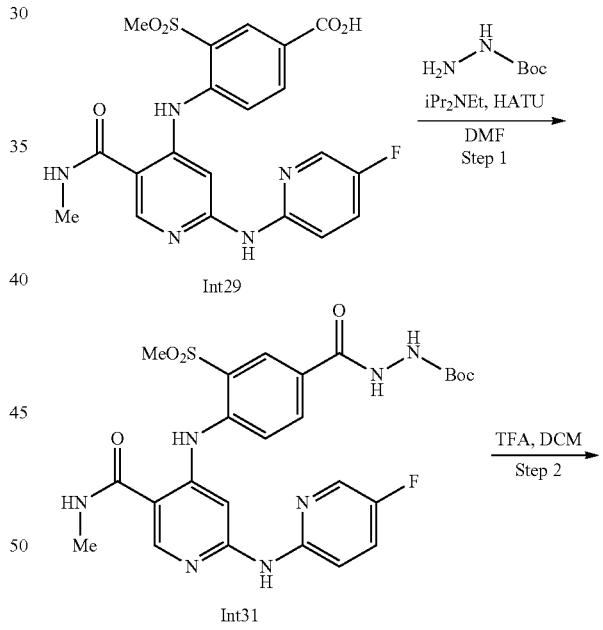

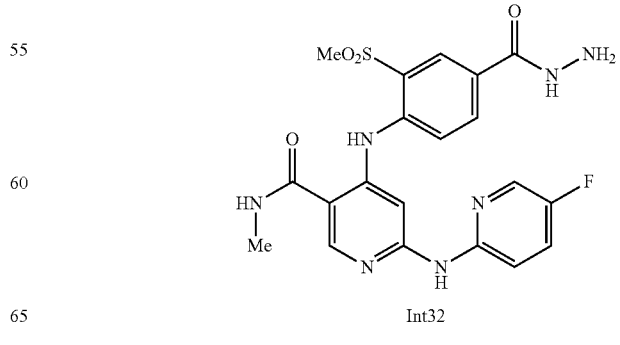

Step 1

To a DMF (1 mL) solution containing Intermediate 29 (60 mg, 0.131 mmol), tert-butyl hydrazinecarboxylate (34.5 mg, 0.26 mmol) and N,N-diisopropylethylamine (91 μL, 0.52 mmol) was added HATU (60 mg, 0.157 mmol) and the reaction stirred for 60 minutes. The reaction was concentrated and purified by automated chromatography (0-100% EtOAc/hexanes) providing Intermediate 31 (45 mg, 60% yield). LC retention time 0.71 [J]. MS(E$^+$) m/z: 574 (MH$^+$).

Step 2

To a solution of Intermediate 31 (45 mg, 0.078 mmol) in DCM (0.5 mL) was added TFA (0.30 mL, 3.92 mmol) and the reaction run for 5 minutes, at which point the solvent was removed in vacuo and the residue redissolved in DCM and reconcentrated (twice). Diethyl ether was added and the vessel sonicated resulting in a heterogeneous slurry, the precipitate was filtered off, rinsed with diethyl ether and collected, providing Intermediate 32 (40 mg, 87% yield) presumably as the TFA salt. LC retention time 0.55 [J]. MS(E$^+$) m/z: 474 (MH$^+$).

Example 312

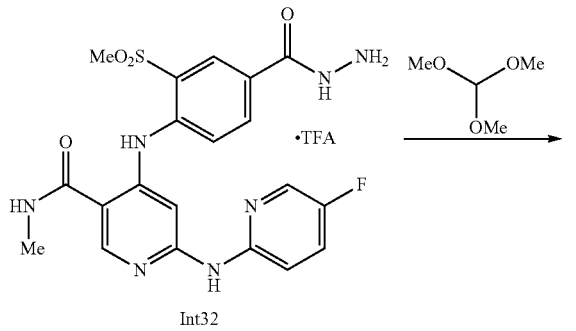

The intermediate salt Intermediate 32 (43 mg, 0.084 mmol) was combined with trimethoxymethane (179 mg, 1.69 mmol) in a sealed vessel. The vessel was heated to 105° C. for 45 minutes and then cooled to room temperature. The solution was concentrated and then redissolved in DMF and purified using preparative HPLC to provide 312 (12.3 mg, 30% yield). $^1$H NMR (500 MHz, methanol-d$_4$) δ 8.95 (s, 1H), 8.67 (d, J=2.0 Hz, 1H), 8.46 (s, 1H), 8.35 (dd, J=8.9, 2.0 Hz, 1H), 8.11-8.01 (m, 3H), 7.49-7.40 (m, 1H), 7.34 (dd, J=8.9, 3.5 Hz, 1H), 3.24 (s, 3H), 2.94 (s, 3H). LC retention time 1.22 [E]. MS(E$^+$) m/z: 484 (MH$^+$).

The following reagents were not available commercially and their preparations are shown below.

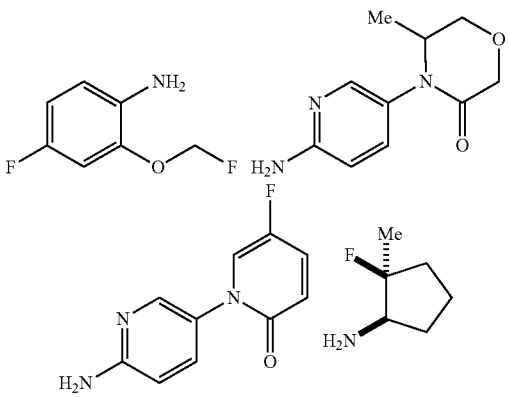

Intermediate 33

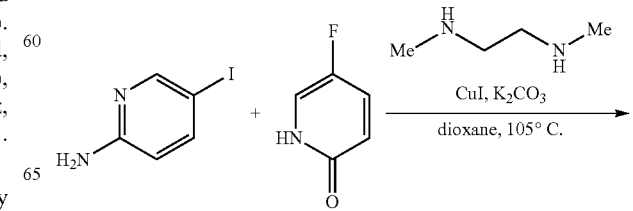

Reference: Xu, R. et al., *J. Med. Chem.*, 53:7035-7047 (2010).

To a cooled (−70° C.) 30 mL pressure tube containing 2-amino-5-fluorophenol (300 mg, 2.36 mmol), cesium carbonate (1.54 g, 4.72 mmol) and DMF (10 mL), was bubbled in chlorofluoromethane gas (14 minutes of bubbling time, ~0.6 g gas weight, ~9 mmol). The tube was sealed and allowed to gradually warm to room temperature and then stirred for 5 days. Nitrogen gas was bubbled through the solution to remove excess chlorofluoromethane gas and the reaction was partitioned between EtOAc (250 mL) and water (50 mL), the layers were separated and the aqueous layer extracted once with EtOAc. The combined organic layers were washed successively with water (2×), 10% aq. LiCl, water, and brine. The organic layer was then dried over Na$_2$SO$_4$, filtered, concentrated and Intermediate 33 was collected as a brown solid (298 mg, 79%). $^1$H NMR (400 MHz, chloroform-d) δ 6.88-6.80 (m, 1H), 6.72-6.63 (m, 2H), 5.83-5.62 (m, 2H).

Intermediate 34

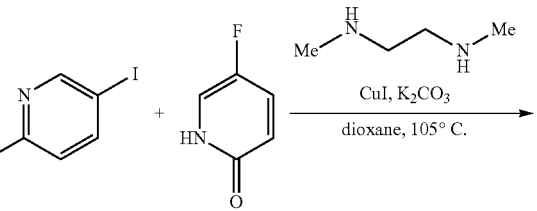

-continued

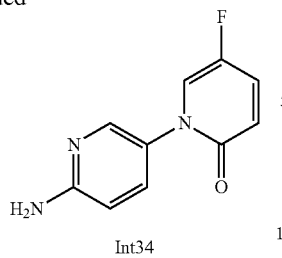

Int34

A vial was loaded with 5-iodopyridin-2-amine (817 mg, 3.71 mmol), 5-fluoropyridin-2(1H)-one (350 mg, 3.09 mmol), copper(I) iodide (118 mg, 0.619 mmol), potassium carbonate (855 mg, 6.19 mmol), N1,N2-dimethylethane-1,2-diamine (0.13 mL, 1.2 mmol) and dioxane (6.2 mL), flushed with nitrogen and then heated to 105° C. overnight. The reaction was cooled to room temperature, diluted with methanol (20 mL) and filtered, rinsing with warm methanol. The filtrate was concentrated and purified using automated chromatography (0%-12% MeOH/EtOAc) providing Intermediate 34 as a brown solid (212 mg, 33% yield). $^1$H NMR (400 MHz, methanol-$d_4$) δ 7.96 (br. s., 1H), 7.70 (ddd, J=4.1, 3.4, 0.7 Hz, 1H), 7.64 (ddd, J=10.1, 7.0, 3.3 Hz, 1H), 7.51 (dd, J=8.8, 2.6 Hz, 1H), 6.67 (d, J=8.4 Hz, 1H), 6.61 (ddd, J=10.1, 5.3, 0.7 Hz, 1H).

Intermediate 35

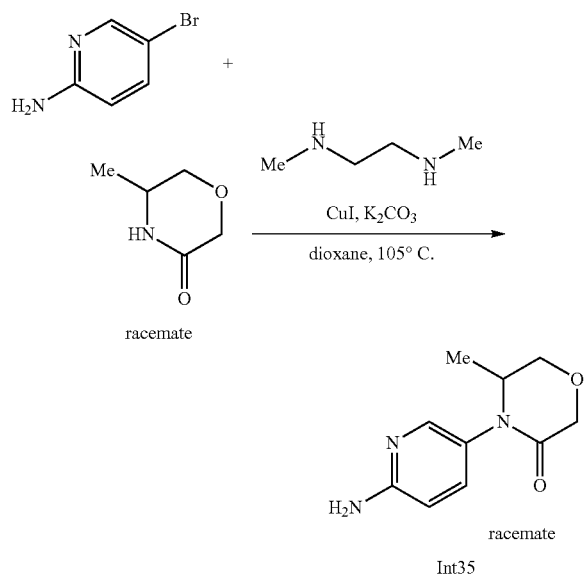

Int35

A vial was loaded with 5-bromopyridin-2-amine (400 mg, 2.3 mmol), 5-methylmorpholin-3-one (532 mg, 4.62 mmol), copper(I) iodide (88 mg, 0.46 mmol), potassium carbonate (1.28 g, 9.25 mmol), N1,N2-dimethylethane-1,2-diamine (0.10 mL, 0.92 mmol) and dioxane (5 mL), flushed with nitrogen and then heated to 105° C. overnight. The reaction was cooled to room temperature, poured into 10% MeOH/DCM and filtered through a pad of CELITE®. The filtrate was concentrated and then purified using automated chromatography (0-20% MeOH/EtOAc) to give Intermediate 35 as a tan oil (265 mg, 55% yield). $^1$H NMR (400 MHz, methanol-$d_4$) δ 7.82 (br. s., 1H), 7.35 (dd, J=8.7, 2.1 Hz, 1H), 6.65 (d, J=7.5 Hz, 1H), 4.36-4.15 (m, 2H), 4.07 (dd, J=11.8, 3.4 Hz, 1H), 3.88 (dt, J=6.6, 3.5 Hz, 1H), 3.79 (dd, J=11.8, 4.1 Hz, 1H), 1.18 (d, J=6.4 Hz, 3H). LC retention time 0.2 min [A]. MS(E$^+$) m/z: 208 (MH$^+$).

Intermediate 36

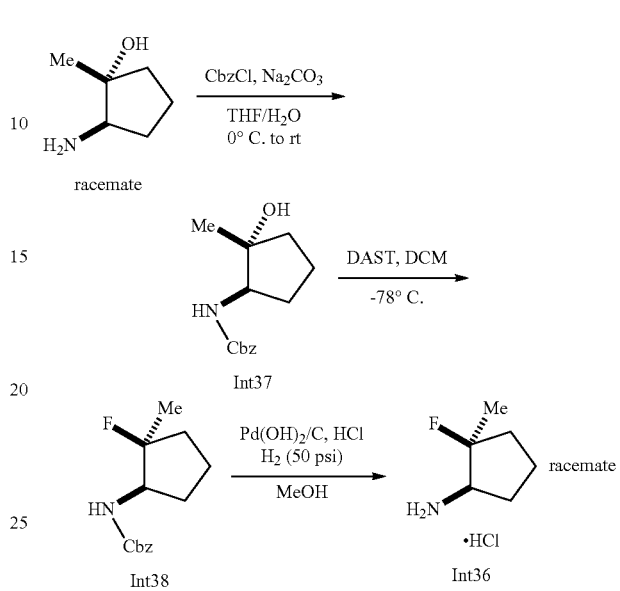

Using a dropping funnel carbobenzoxy chloride (38 mL, 266 mmol) was add dropwise to a rapidly stirred suspension of 2-amino-1-methylcyclopentanol (27.85 g, 242 mmol) in water:THF (1:1, 600 mL total) while the internal temperature was maintained at 5-10° C. via an ice bath. The reaction was warmed to room temperature and stirred for 5 hours at which point EtOAc was added and the layers separated. The organic layer was dried, filtered and purified by automated chromatography (0-60% EtOAc/hexanes) to give Intermediate 37 as a white solid (23.53 g, 39%). $^1$H NMR (400 MHz, chloroform-d) δ ppm 7.29-7.40 (5 H, m), 5.11 (2 H, s), 4.80 (1 H, br. s.), 3.86 (1H, ddd, J=9.68, 8.25, 6.05 Hz), 3.73 (1 H, s), 2.06-2.19 (1H, m, J=12.41, 8.32, 8.32, 3.74 Hz), 1.82-1.94 (1 H, m), 1.69-1.82 (2 H, m), 1.55-1.69 (1 H, m), 1.27-1.39 (1 H, m), 1.16 (3 H, s).

To a suspension of Intermediate 37 (8.48 g, 34 mmol) in DCM (340 mL) at −78° C. was added DAST (9.0 mL, 68 mmol) in a dropwise fashion. The reaction was stirred at −78° C. for 4 hours and then quenched with isopropanol (40 mL). The crude was concentrated and combined with two additional batches that were run in parallel (total mass of Intermediate 37=23.48 g, 94 mmol). The combined material was purified using automated chromatography (0-30% EtOAc/hexanes) to give Intermediate 38 as a white solid (17.26 g, 73% yield). $^1$H NMR (400 MHz, chloroform-d) δ ppm 7.29-7.40 (5 H, m), 5.12 (2 H, d, J=0.88 Hz), 4.97 (1 H, d, J=8.80 Hz), 3.75-3.91 (1H, m), 1.94-2.16 (2 H, m), 1.72-1.88 (2 H, m), 1.56-1.67 (2 H, m), 1.40 (3 H, d, J=21.80 Hz).

A solution of Intermediate 38 (6.38 g, 25.4 mmol), palladium hydroxide on carbon (20% by weight, 3.6 g, 5.13 mmol), and HCl (2M aq., 15.2 mL, 30.5 mmol) in MeOH (85 mL) was stirred overnight under 50 psi of hydrogen at room temperature. The reaction was depressurized, additional palladium hydroxide was added (0.5 g, 0.71 mmol), and the hydrogenation (50 psi, H$_2$) was continued for 4 more hours. The solids were filtered off and the filtrate was concentrated to provide Intermediate 36 (3.79 g, 97% yield). $^1$H NMR (400

MHz, methanol-d$_4$) δ 3.49-3.37 (m, 1H), 2.30-2.02 (m, 2H), 2.02-1.67 (m, 4H), 1.59-1.49 (m, 3H).

Preparation 17

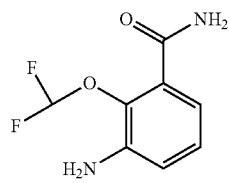

Step 1

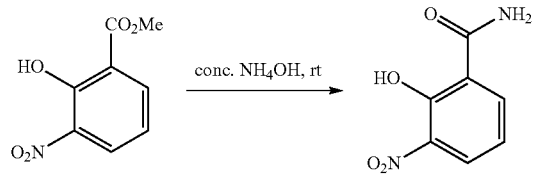 [SMILES: COC(=O)c1cccc([N+](=O)[O-])c1O ; NC(=O)c1cccc([N+](=O)[O-])c1O]

Concentrated (30-35%) aqueous ammonium hydroxide (100 mL) was added to methyl 2-hydroxy-3-nitrobenzoate (12 g, 60.9 mmol) and the resulting orange partial slurry was allowed to stir at room temperature overnight. The reaction was worked up by concentrating under vacuum to yield a red-orange semi-solid to which was added water (~200 mL) and acetic acid (~15 mL) and the slurry was stirred for 1-2 hrs and filtered to collect the solid which was rinsed with water and dried to afford 9.42 g (85%) of a pale yellow solid as the pure product.

Step 2

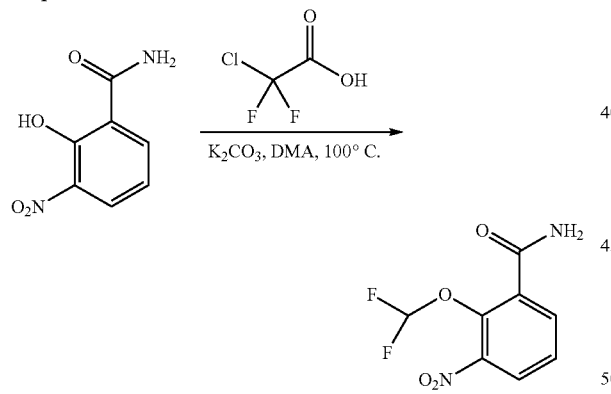

To a solution of 2-hydroxy-3-nitrobenzamide (1 g, 5.49 mmol) in DMF (10 mL) was added potassium carbonate (2.276 g, 16.47 mmol) and the mixture was stirred at room temperature for 5 minutes giving an orange slurry. 2-Chloro-2,2-difluoroacetic acid (0.603 mL, 7.14 mmol) was then slowly added causing some effervescence. Let stir at room temperature for an additional 5 minutes, then heated to 100° C. for c. 1 hour. The reaction was cooled to room temperature, diluted with water (~25 mL) and extracted with ethyl acetate (3×20 mL) and the combined extracts were dried over anhydrous sodium sulfate, filtered and concentrated to give the crude product as a brown liquid. The crude product was dissolved into a minimal amount of dichloromethane and purified using automated chromatography. Afforded 0.58 g (46%) of a yellow solid.

Step 3

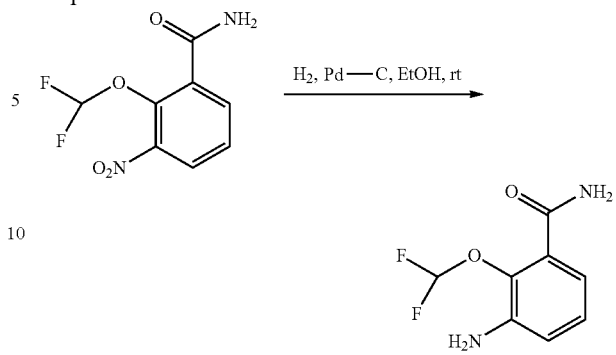

A solution of 2-(difluoromethoxy)-3-nitrobenzamide (0.58 g, 2.498 mmol) in ethanol (20 mL) was sparged with nitrogen for a few minutes at which point palladium on carbon (10% by weight, 0.266 g, 0.125 mmol) then the flask was purged with hydrogen gas using a balloon and the mixture was stirred at room temperature for ~2 h under hydrogen. The mixture was sparged with nitrogen to remove the hydrogen and the mixture was filtered through CELITE® and the resulting clear, nearly colorless filtrate was concentrated under vacuum overnight. Afforded 503 mg of a light grey colored solid as the product. $^1$H NMR (400 MHz, methanol-d$_4$) δ 7.13-7.02 (m, 1H), 6.94 (dd, J=8.0, 1.7 Hz, 1H), 6.90-6.84 (m, 1H)

Preparation 18

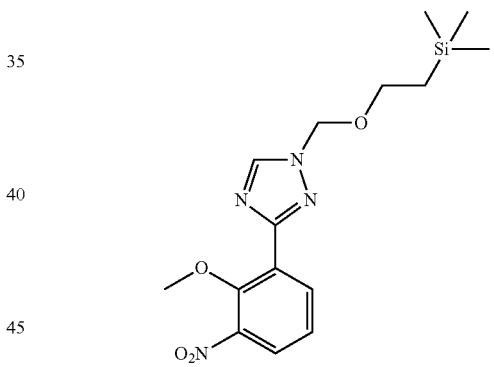

Step 1

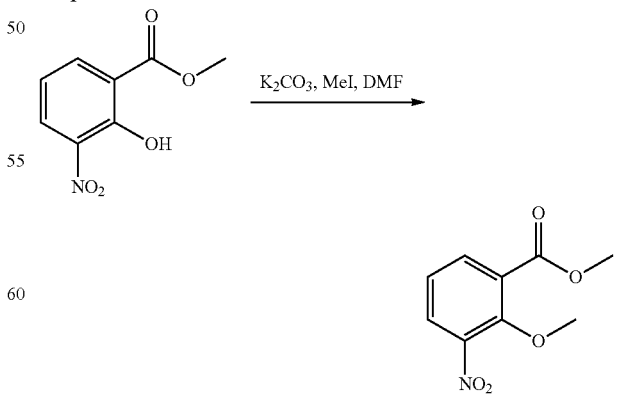

To a solution of methyl 2-hydroxy-3-nitrobenzoate (10 g, 50.7 mmol) in dimethylformamide (100 mL) at room temperature was added potassium carbonate (14.02 g, 101 mmol) followed by addition of methyl iodide (6.34 mL, 101 mmol) and the resulting orange mixture was heated to 60° C. for 1 h. The reaction was cooled to room temperature and added to crushed ice (~100 mL) and then further diluted with water to a total volume of ~400 mL causing a nice yellow solid to crystallize. The solid was collected by vacuum filtration and the resulting initially yellow solid was rinsed with additional water (~100 mL) until all of the yellow color was rinsed into the filtrate giving a near white solid in the funnel. Partially air-dried solid in funnel then transferred to a round-bottomed flask and further dried under vacuum overnight to afford 10.5 g (98%) of a yellow solid as the desired product. LCMS MH+212.

Step 2

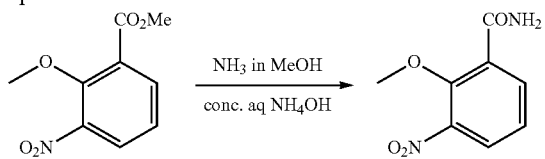

Methyl 2-methoxy-3-nitrobenzoate (11 g, 52.1 mmol) was dissolved in a cold solution of ammonia in methanol (7N, 250 mL) and concentrated aqueous ammonium hydroxide (100 mL) was added. The flask was sealed and the resulting solution was allowed to gently stir at room temperature overnight. The reaction mixture was concentrated on the rotovap to yield an aqueous slurry of the product. This slurry was diluted with additional water (~300 mL) and was sonicated briefly then the solid was collected by vacuum filtration and the resulting yellow solid was rinsed with additional water (~100 mL). The solid was air dried in the funnel for several hours then under vacuum to afford 7.12 g of a yellow solid as the pure product 2-methoxy-3-nitrobenzamide. A second crop of product was obtained by extracting the filtrate with ethyl acetate (3×100 mL) followed by washing the extracts with brine, drying over anhydrous. Sodium sulfate, decanting and concentration under vacuum to afford 1.67 g of additional product as a yellow solid (86% overall combined yield). LCMS observed MH+197.

Step 3

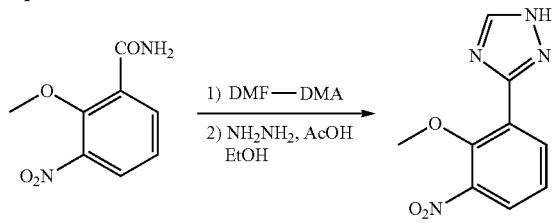

2-Methoxy-3-nitrobenzamide (7.1 g, 36.2 mmol) was slurried in N,N-dimethylformamide dimethyl acetal (DMF-DMA, 48.5 mL, 362 mmol) and the mixture was heated to 95° C. giving a clear, pale yellow solution. After heating for ~30 minutes at this temperature, the reaction was cooled to room temperature and concentrated. The resulting yellow oil was azeotroped twice with 1,2-dichloroethane (40 mL portions) to ensure complete removal of any residual DMF-DMA. The crude oil thus obtained was immediately dissolved in 35 mL of ethanol and was used in the following step.

In a separate flask was prepared a mixture of ethanol (150 mL) and acetic acid (35 mL) and the resulting solution was cooled in an ice bath. Once cooled, hydrazine hydrate (17.59 mL, 362 mmol) was added dropwise. At this time, the solution containing the crude DMF-DMA adduct of the substrate prepared above was transferred dropwise over ~15 minutes via cannula into the previously prepared well-stirred ice-cold mixture containing the hydrazine. During the addition, a pale yellow solid formed in the solution. After the addition was complete, the resulting cloudy yellow mixture was allowed to warm to room temperature and stir for ~4 h. The reaction mixture was concentrated to remove some of the ethanol, diluted with additional water and filtered to collect the solid. The solid was washed with additional portions of water, air dried in the funnel then under vacuum to afford 5.5 g (69%) of a pale yellow solid as the desired product. LC retention time 0.62 [J]. MS(E⁺) m/z: 221 (MH⁺).

Step 4

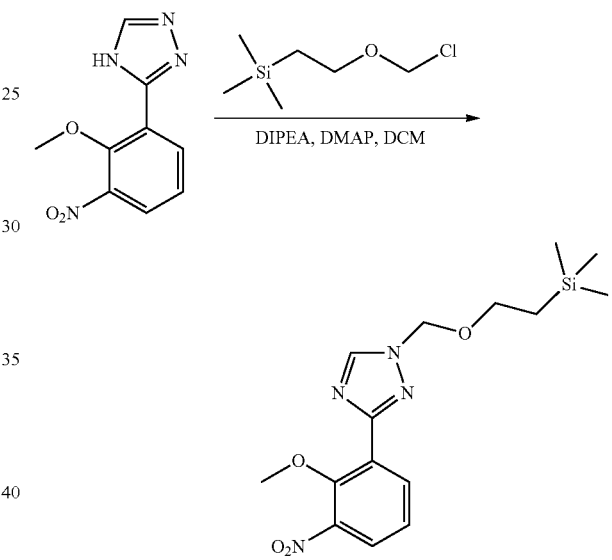

To a solution of 3-(2-methoxy-3-nitrophenyl)-4H-1,2,4-triazole (1.76 g, 7.99 mmol), diisopropylethylamine (1.954 mL, 11.19 mmol) and N,N'-dimethylaminopyridine (DMAP, 0.098 g, 0.799 mmol) in dichloromethane (25 mL) at room temperature was added 2-(trimethylsilyl)ethoxymethyl chloride (1.701 mL, 9.59 mmol) and the reaction mixture was stirred at room temperature for 3 h. Mixture was then concentrated to remove the solvent, water was added and the mixture was extracted with ethyl acetate (100 mL×4). The combined extracts were washed with brine, dried over anhydrous sodium sulfate, filtered and concentrated to afford a tan semi-solid as the crude product. This material was purified by silica gel chromatography (hex/ethyl acetate; 40 g column) to afford fractions containing the major product. These fractions were concentrated to afford 1.26 g (45%) of a clear oil as the desired product (Preparation 18) (1.26 g, 3.60 mmol, 45% yield) as an apparent 2:3 mixture of regioisomers. HPLC RT=3.44 and 3.53 minutes. LCMS (m+1)=351. Major isomer: $^1$H NMR (400 MHz, chloroform-d) δ 8.34 (s, 2H), 8.25 (dd, J=7.8, 1.7 Hz, 2H), 7.82 (dd, J=8.0, 1.7 Hz, 2H), 7.31 (t, J=8.0 Hz, 2H), 5.59 (s, 4H), 3.96 (s, 7H), 3.76-3.71 (m, 5H), 1.02-0.92 (m, 4H), 0.01 (s, 9H).

Step 5

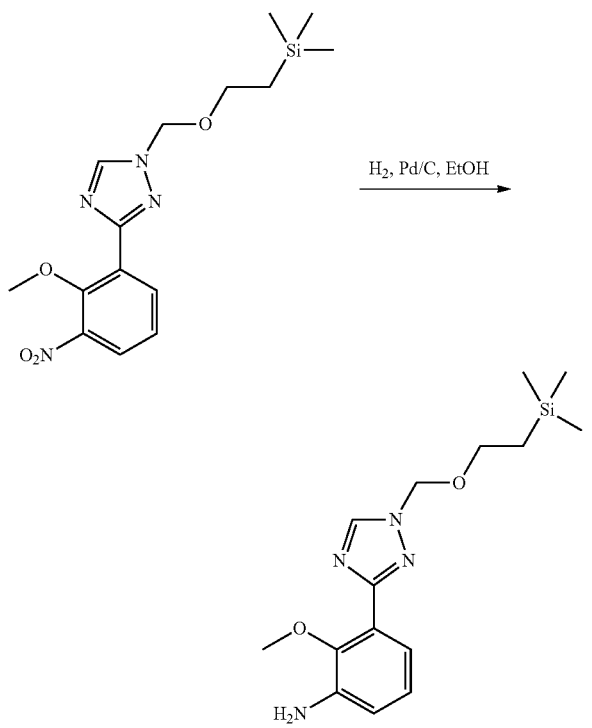

To a slurry of 3-(2-methoxy-3-nitrophenyl)-1-((2-(trimethylsilyl)ethoxy)methyl)-1H-1,2,4-triazole (1.26 g, 3.60 mmol) in ethanol (50 mL) was added palladium on carbon (10% on Carbon) (0.115 g, 0.108 mmol). The flask was evacuated and supplied with hydrogen gas from a balloon for 4 h. At this time, the balloon was removed and reaction was flushed with nitrogen, then filtered through a pad of CELITE® to remove the catalyst and the resulting clear colorless filtrate was concentrated to afford 1.12 g (97%) of the product Preparation 18 as a clear oil which solidified on standing. HPLC and LCMS analysis indicated an ~2:3 mixture of regioisomers. HPLC Peak RT=2.70 minutes (major) and 3.01 minutes (minor). LCMS (m+1)=321 for both isomers.

Preparation 19

Step 1

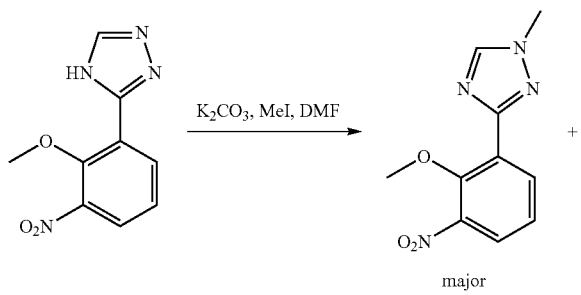

-continued

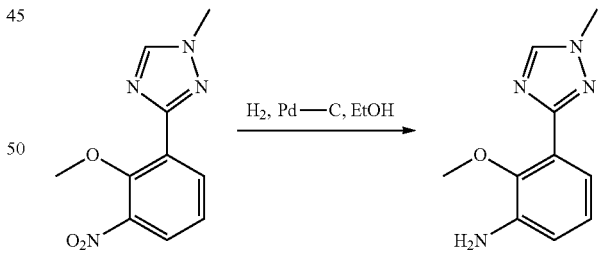

A solution of 3-(2-methoxy-3-nitrophenyl)-4H-1,2,4-triazole from Step 3 of Preparation 18 (2.23 g, 10.13 mmol) was prepared in DMF (20 mL) and potassium carbonate (4.20 g, 30.4 mmol) was added. After cooling the resulting mixture in an ice bath, a solution of iodomethane (0.855 mL, 13.67 mmol) in DMF (5 mL) was slowly added dropwise via syringe over 2 minutes. After the addition was complete, the ice bath was removed and the reaction mixture was allowed to warm to room temperature. After stirring at room temperature for ~4 hours, the reaction was cooled in an ice bath and was diluted with water (~50 mL) and the solution was extracted with ethyl acetate (3×40 mL) and the combined extracts were washed with 10% aq. LiCl (2×20 mL), water (20 mL) then brine before concentrating to afford 2.17 g (91%) of a yellow oil as the crude product which solidified to a yellow solid upon standing. This crude material was combined with another batch of additional crude product (~0.45 g) from a previous similar reaction and the material was purified by SFC chromatography to resolve the isomers (Conditions: column=chiral IC 3×25 cm, 5 μm; column temperature=35° C.; flow rate=200 mL/minutes; mobile phase=$CO_2$/methanol=80/20; injection program=stacked (2.3 minutes/cycle), 2.5 ml/per injection; sampler conc. (mg/mL): 60 mg/mL; detector wavelength=220 nm) to afford 1.87 g (65%) of the major isomer as a pale yellow solid. $^1$H NMR (400 MHz, methanol-$d_4$) δ 8.50 (s, 1H), 8.11 (dd, J=7.9, 1.8 Hz, 1H), 7.85 (dd, J=8.1, 1.8 Hz, 1H), 7.38 (t, J=8.0 Hz, 1H), 4.03 (s, 3H), 3.83 (s, 3H). LC retention time 0.74 [J]. MS($E^+$) m/z: 235 (MH$^+$).

Step 2

A solution of 3-(2-methoxy-3-nitrophenyl)-1-methyl-1H-1,2,4-triazole (1.87 g, 7.98 mmol) in ethanol (50 mL) was sparged with nitrogen for a few minutes before adding 5% Pd-C (0.850 g, 0.399 mmol) followed by sparging with hydrogen from a balloon for a few minutes then allowing the mixture to stir under a balloon of hydrogen for 1.5 hours at room temperature. The mixture was then sparged with nitrogen to deactivate the catalyst and the mixture was filtered through a pad of CELITE® washing with additional amounts of ethanol and the resulting clear, colorless filtrate containing the product was concentrated under vacuum to afford a colorless oil. This material was azeotroped with two portions of dry toluene (~25 mL each) to afford an off-white solid which was dried further under vacuum to afford 1.5 g (92%) of a free-flowing white solid as the pure product. $^1$H NMR (400 MHz, chloroform-d) δ 8.09 (s, 1H), 7.35 (dd, J=7.8, 1.7 Hz, 1H), 7.00 (t, J=7.8 Hz, 1H), 6.82 (dd, J=7.8, 1.7 Hz, 1H), 4.00 (s, 3H), 3.94 (br. s., 2H), 3.78 (s, 3H). LC retention time 0.44 [J]. MS(E$^+$) m/z: 205 (MH$^+$).

Preparation 20

Step 1

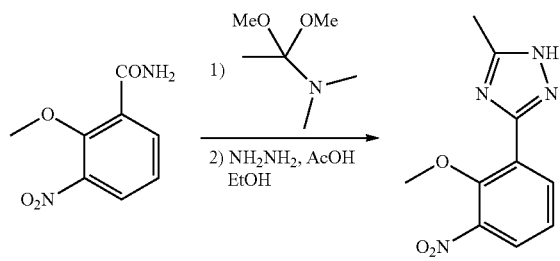

Prepared using the procedure previously described in Step 3 for the Preparation of Example 314 by replacing N,N-dimethylformamide dimethyl acetal with 1,1-dimethoxy-N,N-dimethylethanamine to afford 1.32 g (74%) of the product, 3-(2-methoxy-3-nitrophenyl)-5-methyl-4H-1,2,4-triazole, as a wine colored solid. $^1$H NMR (400 MHz, chloroform-d) δ 8.45 (dd, J=7.9, 1.5 Hz, 1H), 7.93 (dd, J=8.1, 1.8 Hz, 1H), 7.42-7.33 (m, 1H), 3.97 (s, 3H), 2.53 (s, 3H). LC retention time 1.58 [A]. MS(E$^+$) m/z: 235 (MH$^+$).

Step 2

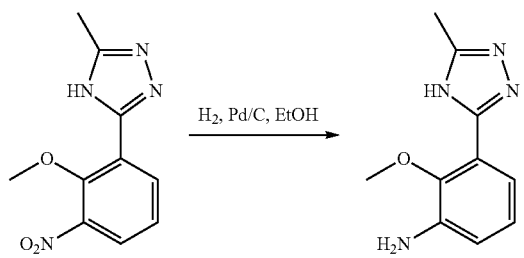 [SMILES: COc1c(-c2nnc(C)[nH]2)cccc1[N+](=O)[O-] ; COc1c(N)cccc1-c1nnc(C)[nH]1]

Prepared using the procedure previously described in Step 5 for the preparation of Example 314 to afford 0.97 g (86%) of the product as a clear oil which solidified upon standing. HPLC RT=0.44 minutes. LCMS (m+1)=205.

Preparation 21

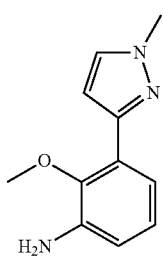

Step 1

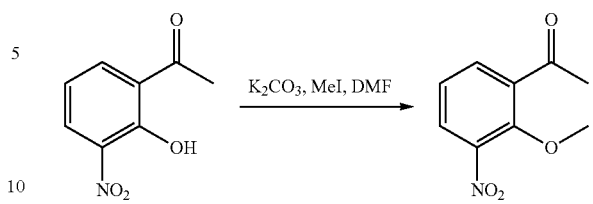

A slurry of 1-(2-hydroxy-3-nitrophenyl)ethanone (1.00 g, 5.52 mmol) and potassium carbonate (3.05 g, 22.08 mmol) in DMF (20 mL) was stirred at room temperature for 30 minutes, then iodomethane (1.338 mL, 16.56 mmol) was added dropwise and the resulting mixture was allowed to stir at room temperature overnight. LCMS indicated some un-reacted starting material remained, therefore additional iodomethane (1.338 mL, 16.56 mmol) was added and the mixture was warmed to 50° C. over 2 days. Reaction was quenched by the addition of water to give a solution followed by adjusting the pH with 1N HCl to ~7. The resulting solution was extracted with ethyl acetate (80 mL×3) and the combined organic extracts were washed with brine, dried over anhydrous sodium sulfate, filtered and concentrated to afford the product, 1-(2-methoxy-3-nitrophenyl)ethanone (1.05 g, 5.38 mmol, 97% yield) as a tan oil. HPLC (Method N) RT=1.86 minutes.

Step 2

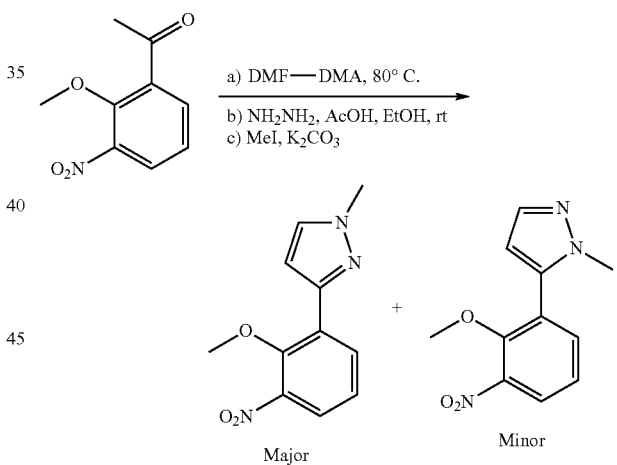

A slurry of 1-(2-methoxy-3-nitrophenyl)ethanone (450 mg, 2.306 mmol) in N,N-dimethylformamide dimethyl acetal (DMF-DMA, 8.148 g, 68.4 mmol) was heated to 80° C. giving a clear solution. After stirring at this temperature for ~30 minutes., the reaction was cooled, diluted with 100 mL of ethyl acetate, washed with water (3×), then brine, dried over Na$_2$SO$_4$, filtered and concentrated to afford tan oil as the crude intermediate (432 mg). To this material was added ethanol (4.0 mL) to make a homogeneous tan solution and followed by cooling in an ice bath. At this time, hydrazine hydrate (0.217 mL, 6.92 mmol) was slowly added dropwise via syringe with good stirring. After the addition was complete, the reaction was allowed to warm to room temperature then was heated to 80° C. for 1h then cooled to room temperature and allowed to stir at room temperature overnight. The resulting mixture was concentrated to remove the ethanol, diluted with 100 mL of ethyl acetate, washed with water for 3 times, then brine, dried over sodium sulfate, filtered and concentrated to afford a tan semi-solid as the crude pyrazole intermediate. To this intermediate was added 4 mL of acetone and potassium carbonate (956 mg, 6.92 mmol), and the resulting mixture was stirred at room temperature for 10 minutes before adding iodomethane (0.577 mL, 9.22 mmol). After stirring at room temperature overnight, the reaction mixture was concentrated and was partitioned between ethyl acetate and water. The layers were separated and the organic portion was washed with water (3×), dried over sodium sulfate, filtered and concentrated under vacuum to afford tan oil as the crude product. This material was purified by flash silica gel chromatography using hexanes/ethyl acetate mixtures as the eluent. Fractions containing the major component were combined and concentrated under vacuum to afford 155 mg (29% overall yield) of a tan oil which was determined to be the desired product as a mixture of regioisomers (~4-5:1). HPLC (Method N) RT=2.50 minutes (regioisomers unresolved). LCMS (m+1)=235. $^1$H NMR (400 MHz, methanol-$d_4$) δ 8.07 (dd, J=7.9, 1.5 Hz, 1H), 7.76 (dd, J=8.0, 1.7 Hz, 1H), 7.72 (d, J=2.4 Hz, 1H), 7.36 (t, J=7.9 Hz, 1H), 6.80 (d, J=2.2 Hz, 1H), 4.01 (s, 3H), 3.77 (s, 3H).

Step 3

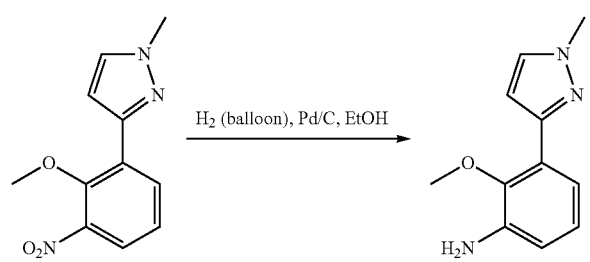

To a clear solution of product from Step 2 (0.15 g, 0.643 mmol) in ethanol (10 mL) was added Pd/C (10% on Carbon) (0.021 g, 0.019 mmol). The flask was evacuated and supplied with hydrogen gas from a balloon for 3 h. The hydrogen balloon was removed and reaction was flashed with nitrogen, 50 mL of ethanol was added, and the reaction mixture was filtered and the filtrate was concentrated to afford 2-methoxy-3-(1-methyl-1H-pyrazol-3-yl)aniline (120 mg, 0.590 mmol, 92% yield) which contained ~20% of a minor regioisomer. HPLC (Method N) RT=0.96 minutes. (major) and 1.12 minutes (minor). LCMS (m+1)=204.

Preparation 22

Step 1

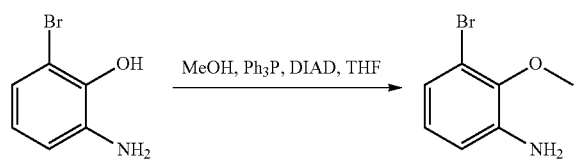

To a slurry of 2-amino-6-bromophenol (4.00 g, 21.27 mmol) in methanol (2.152 mL, 53.2 mmol) and THF (10 mL) at room temperature was added triphenylphosphine (11.16 g, 42.5 mmol). After stirring for a few minutes, diisopropyl azodicarboxylate (DIAD, 12.41 mL, 63.8 mmol) was then added dropwise via syringe over ~5 minutes. After the addition was complete, the reaction was allowed to stir at room temperature for ~1 h. The resulting mixture was then concentrated to remove the volatiles and the resulting residue was purified by silica gel flash chromatography using hexanes/ethyl acetate as the eluent. Fractions containing the major UV-active product were combined and concentrated under vacuum to afford 2.35 g (55%) of a dark brown oil as the desired product. HPLC (Method N) RT=1.33 minutes. LCMS MH+202/204 (observed bromide isotope pattern).

Preparation 23

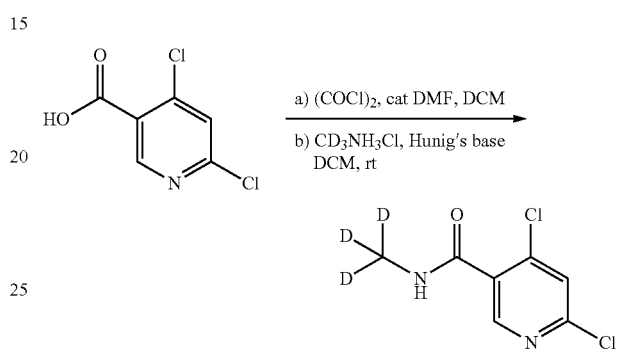

To a slurry of 4,6-dichloronicotinic acid (3 g, 15.63 mmol) in dichloromethane (90 mL) at room temperature was added oxalyl chloride (1.778 mL, 20.31 mmol) followed by 3 drops of DMF causing some effervescence. Let mixture stir at room temperature for ~1.5 h at which time mixture became a nearly clear solution. The reaction was concentrated and the residue was dissolved in dichloroethane (~20 mL) and re-concentrated and the process was repeated to ensure complete removal of the excess oxalyl chloride. The resulting crude acid chloride was dissolved in dichloromethane (~100 mL) and methyl-d3-ammonium chloride (1.433 g, 20.31 mmol) was added and the mixture was cooled in an ice bath whereupon diisopropylethylamine (Hunig's base, 8.19 mL, 46.9 mmol) was added dropwise via syringe. After the addition was complete, the ice bath was removed and the resulting mixture was allowed to warm to room temperature and stirred overnight. The mixture was diluted with dichloromethane (~100 mL) and was washed with 1 N aq. HCl (3×100 mL) then brine before drying over anhydrous sodium sulfate, decanting and concentrating under vacuum. This afforded 2.7 g of an off-white solid which was purified by preparative silica gel flash chromatography using ethyl acetate/hexanes as the eluent. Fractions containing the major UV-active product were collected and concentrated under vacuum to afford 2.42 g (74%) of a white solid as the pure product. LCMS MH+209.2.

Step 2

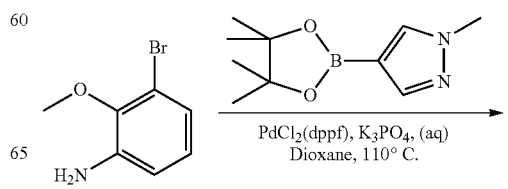

-continued

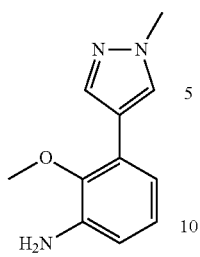

To a reaction vial charged with 3-bromo-2-methoxyaniline (1.12 g, 5.54 mmol), 1-methyl-4-(4,4,5,5-tetramethyl-1,3,2-dioxaborolan-2-yl)-1H-pyrazole (1.499 g, 7.21 mmol) in dioxane (6 mL) was added aqueous potassium phosphate (2.0 M) (5.54 ml, 11.09 mmol). The resulting mixture was deoxygenated by bubbling argon through the mixture for ~5 minutes. [1,1'-Bis(diphenylphosphino)ferrocene]dichloropalladium(II) (PdCl$_2$(dppf), 0.122 g, 0.166 mmol) was then added and the mixture was heated at 110° C. for 2 hours. The reaction was cooled, diluted with ethyl acetate (200 mL), washed with water, brine, dried over anhydrous sodium sulfate, filtered and concentrated to afford tan oil as the crude product mixture. This material was purified by silica gel flash chromatography using hexanes/ethyl acetate mixtures as the eluent. Fractions containing the desired product were collected, combined, and concentrated under vacuum to afford 0.87 g (77%) of the desired product as an oil which solidified upon standing. HPLC (Method N)=0.89 minutes. LCMS MH+204.1.

Example 313

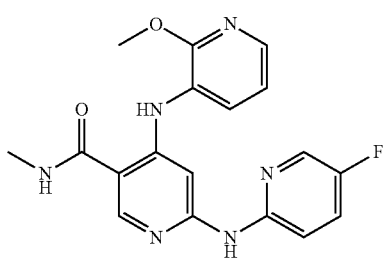 [SMILES: CNC(=O)c1cnc(Nc2ccc(F)cn2)cc1Nc1cccnc1OC]

Step 1

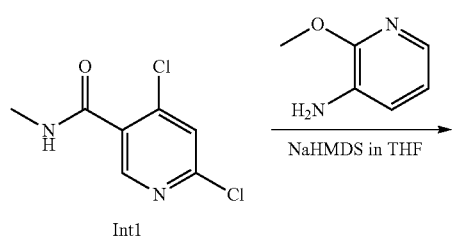

-continued

Step 1 was performed using Int1 and commercially available 3-amino-2-methoxypyridine using similar conditions as described in Step 2 of Example 1. This afforded a 70% yield of the desired product, 6-chloro-4-((2-methoxypyridin-3-yl)amino)-N-methylnicotinamide, as a tan solid. HPLC RT (Method A)=2.60 minutes. LCMS MH+293/295 (~3:1 chloride isotope pattern).

Step 2

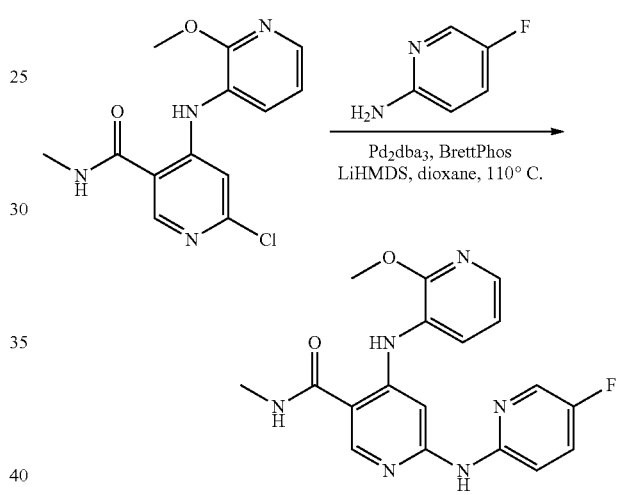

A reaction vial was charged with 6-chloro-4-((2-methoxypyridin-3-yl)amino)-N-methylnicotinamide (15 mg, 0.051 mmol), 5-fluoropyridin-2-amine (8.04 mg, 0.072 mmol), 2-(dicyclohexylphosphino)3,6-dimethoxy-2',4',6'-triisopropyl-1,1'-biphenyl (BrettPhos, 4.13 mg, 7.69 μmol) and tris(dibenzylideneacetone)dipalladium(0) (Pd$_2$dba$_3$, 4.69 mg, 5.12 μmol). After flushing the contents with nitrogen, dioxane (0.3 mL) was added followed by the addition of LiHMDS (1 M in THF) (0.113 mL, 0.113 mmol) affording a dark amber colored solution. This solution was heated in a preheated heating block at 110° C. for 1.5 h, then cooled to room temperature. The reaction mixture was quenched with 0.1 mL of methanol, concentrated to remove the residual solvents, diluted with DMF, filtered through a Millipore filter, and the crude material was purified via preparative LC/MS. Fractions containing the desired product were combined and dried via centrifugal evaporation to afford 18.9 mg (97%) of Example 313. LCMS (Method E) RT=1.39 minutes; LCMS (Method G) R=0.97 minutes. LCMS observed MH+=369.1. $^1$H NMR (500 MHz, DMSO-d$_6$) δ 10.50 (s, 1H), 9.80 (s, 1H), 8.50 (d, J=4.3 Hz, 1H), 8.46 (s, 1H), 8.16 (d, J=2.4 Hz, 1H), 7.86 (d, J=4.9 Hz, 1H), 7.83 (d, J=7.3 Hz, 1H), 7.74-7.57 (m, 3H), 7.09 (dd, J=7.3, 5.5 Hz, 1H), 3.94 (s, 3H), 2.77 (d, J=4.3 Hz, 3H).

Example 314

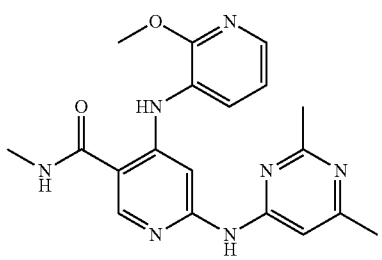

Example 314 was prepared using similar conditions as described for the preparation of Example 313. These conditions afforded 20.4 mg (93%) of Example 314. LCMS (Method E) RT=1.16 minutes; LCMS (Method G) R=0.75 minutes. LCMS observed MH+=380.1. $^1$H NMR (500 MHz, DMSO-$d_6$) δ 10.53 (s, 1H), 10.02 (s, 1H), 8.55 (d, J=4.3 Hz, 1H), 8.50 (s, 1H), 8.08 (br. s., 1H), 7.92-7.83 (m, 2H), 7.14-6.97 (m, 2H), 3.93 (s, 3H), 2.78 (d, J=4.3 Hz, 3H), 2.37 (s, 3H), 2.27 (s, 3H).

Example 315

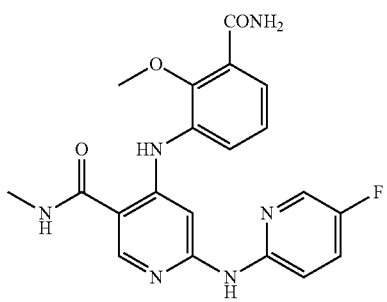 [SMILES: CNC(=O)c1cnc(Nc2ccc(F)cn2)cc1Nc1cccc(C(N)=O)c1OC]

Step 1

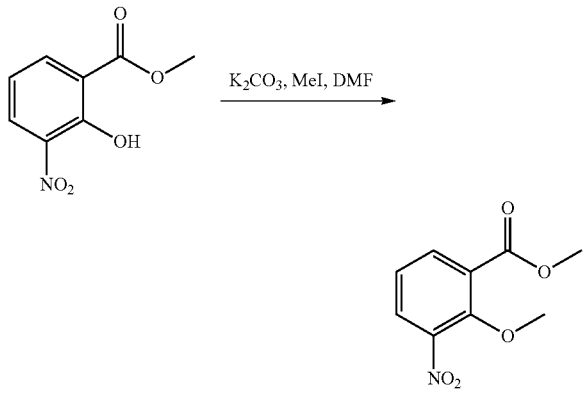

To a solution of methyl 2-hydroxy-3-nitrobenzoate (10 g, 50.7 mmol) in DMF (100 mL) at room temperature was added potassium carbonate (14.02 g, 101 mmol) followed by addition of methyl iodide (6.34 mL, 101 mmol) and the resulting orange mixture was heated to 60° C. for 1 hour. The reaction was cooled to room temperature and added to crushed ice (~100 mL) followed by dilution with water to a total volume of ~400 mL causing a yellow solid to crystallize from solution. The slurry was stirred for a few minutes and then collected solid by vacuum filtration and the resulting initially yellow solid was rinsed with additional water (~100 mL) until all of the yellow color was rinsed into the filtrate giving a white solid in the funnel. Partially air-dried solid in funnel then transferred to a round-bottomed flask and further dried under vacuum overnight to afford 10.5 g (98%) of a yellow solid as methyl 2-hydroxy-3-nitrobenzoate. LCMS MH+ 212.

Step 2

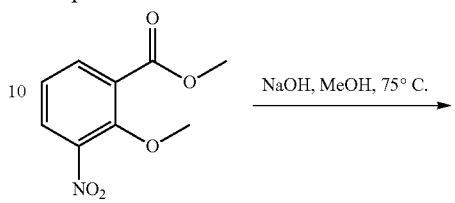

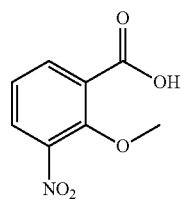

Methyl 2-hydroxy-3-nitrobenzoate (2.85 g, 13.50 mmol) was dissolved in hot methanol (10 mL) at 75° C. to make clear solution and 1N aq. sodium hydroxide (28.3 mL, 28.3 mmol) was added dropwise. The mixture was heated under reflux for 15 minutes and then cooled to room temperature, concentrated to remove the methanol and then cooled in an ice bath. The solution was acidified via the dropwise addition of 1M (aq.) HCl until the pH was ~1, resulting in the product precipitating out of solution. The solid was collected by filtration, rinsed with water, and dried on the filter to afford the product 2-methoxy-3-nitrobenzoic acid (2.48 g, 12.58 mmol, 93% yield) as a white solid. HPLC (Method N) RT=1.57 minutes.

Step 3

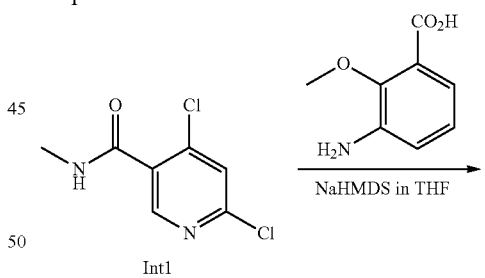

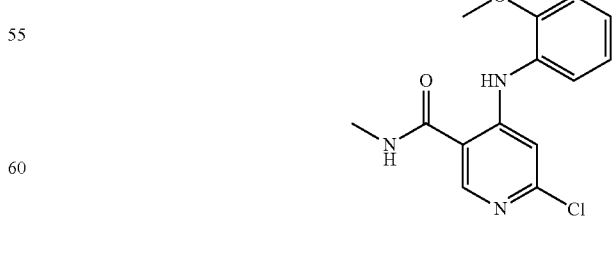

Step 3 was performed using Int1 and 2-methoxy-3-nitrobenzoic acid from Step 2 and using similar conditions as described in Step 2 of Example 1 to afford a 64% yield of the desired product, 3-((2-chloro-5-(methylcarbamoyl)pyridin- 4-yl)amino)-2-methoxybenzoic acid as a tan solid. HPLC RT (Method N)=2.57 minutes. LCMS MH+ 336.1.

Step 4

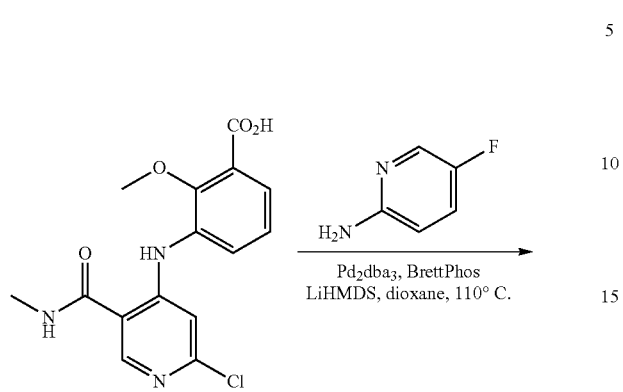

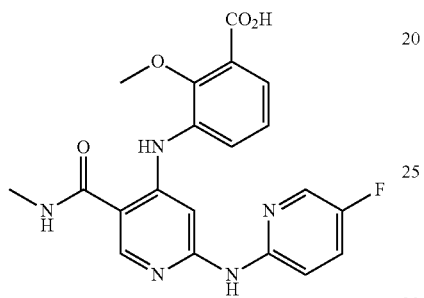

A reaction vial was charged with 3-((2-chloro-5-(methylcarbamoyl)pyridin-4-yl)amino)-2-methoxybenzoic acid (600 mg, 1.787 mmol), 5-fluoro-4-methylpyridin-2-amine (316 mg, 2.502 mmol), BrettPhos (38.4 mg, 0.071 mmol) and Pd$_2$(dba)$_3$ (32.7 mg, 0.036 mmol) and the contents were flushed with nitrogen before adding dioxane (2 mL) and DMA (1 mL). The resulting slurry was sparged with additional nitrogen for ~1 minutes, then LiHMDS (1 M in THF) (3.93 mL, 3.93 mmol) was added and the resulting dark amber colored solution was heated in a preheated heating block at 110° C. for 2 h, then cooled to room temperature. The reaction mixture was added to water (80 mL) and the pH was adjusted with aq. 1N HCl to ~3 causing a solid to precipitate from solution. After stirring the slurry at room temperature for ~4 h, the solid was collected by vacuum filtration, rinsed with water, and dried on the filter to afford 3-((2-((5-fluoro-4-methylpyridin-2-yl)amino)-5-(methylcarbamoyl)pyridin-4-yl)amino)-2-methoxybenzoic acid (736 mg, 1.730 mmol, 97% yield) as a beige solid. HPLC (Method N) RT=2.45 minutes. LCMS (m+1)=426.

Step 5

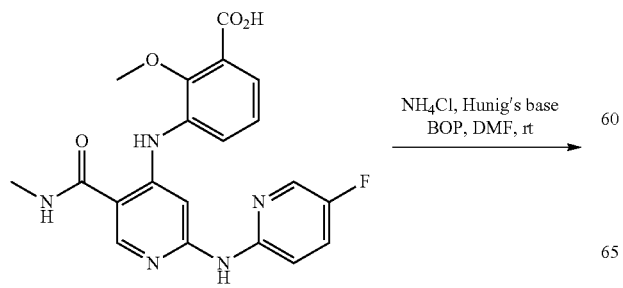

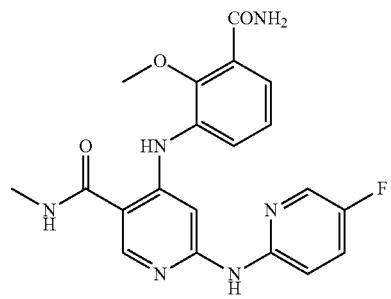

3-((2-((5-Fluoro-4-methylpyridin-2-yl)amino)-5-(methylcarbamoyl)pyridin-4-yl)amino)-2-methoxybenzoic acid (15 mg, 0.036 mmol), Hunig's base (0.019 mL, 0.109 mmol) and ammonium chloride (3.90 mg, 0.073 mmol) were stirred in DMF at room temperature for a few minutes then BOP (20.96 mg, 0.047 mmol) was added to the resulting slurry and the mixture was stirred at room temperature for 1 h. The reaction mixture was then quenched with 0.1 mL of methanol, diluted with DMF, filtered through a Millipore filter, and was subjected to purification by reverse-phase preparative LCMS using the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-100% B over 20 minutes, then a 5-minute hold at 100% B; Flow: 25 mL/minutes. Fractions containing the desired product were combined and dried via centrifugal evaporation to afford the 7.6 mg (47%) of the desired product (Example 315). HPLC (Method E) RT=1.23 minutes. HPLC (Method G) RT=0.96 minutes. LCMS observed MH+=411.2.
$^1$H NMR (500 MHz, DMSO-d$_6$) δ 10.64 (s, 1H), 8.45 (s, 1H), 8.15 (s, 1H), 7.75 (br. s., 1H), 7.63 (dd, J=7.6, 1.5 Hz, 4H), 7.56 (br. s., 1H), 7.38-7.21 (m, 2H), 3.73 (s, 3H), 2.78 (d, J=4.3 Hz, 3H).

The following examples were prepared using commercially available reagents in a similar manner to Example 315:

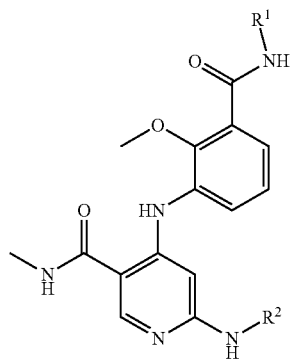

| Example No. | R¹ | R² | Rt (minutes) [Method] | m/z [M + H]⁺ |
|---|---|---|---|---|
| 316 | Me | 5-F pyridin-2-yl | 1.17 [E] | 425 |
| 317 | cyclopropyl | 5-F pyridin-2-yl | 1.31 [E] | 451 |
| 318 | cyclopropyl | 5-F, 4-Me pyridin-2-yl | 1.42 [E] | 465 |
| 319 | H | 5-F, 4-Me pyridin-2-yl | 1.20 [E] | 425 |
| 320 | Me | 5-F, 4-Me pyridin-2-yl | 1.29 [E] | 439 |
| 321 | C(Me)(NMe)... | 5-F, 4-Me pyridin-2-yl | 0.69 [J] | 453 |
| 322 | CH₂CH₂-morpholine | 5-F, 4-Me pyridin-2-yl | 1.32 [E] | 538 |
| 323 | isopropyl-branched | 5-F, 4-Me pyridin-2-yl | 1.53 [E] | 467 |
| 324 | CH₂-cyclopropyl | 5-F, 4-Me pyridin-2-yl | 1.57 [E] | 479 |
| 325 | CH₂-cyclohexyl | 5-F, 4-Me pyridin-2-yl | 1.93 [E] | 521 |

-continued

| Example No. | R¹ | R² | Rt (minutes) [Method] | m/z [M + H]⁺ |
|---|---|---|---|---|
| 326 | butyl | 2-(5-F-4-Me-pyridyl) | 1.68 [E] | 481 |
| 327 | (pyridin-2-yl)methyl | 2-(5-F-4-Me-pyridyl) | 1.44 [E] | 516 |
| 328 | Ph | 2-(5-F-4-Me-pyridyl) | 1.80 [E] | 501 |
| 329 | 5-hydroxypentyl | 2-(5-F-4-Me-pyridyl) | 1.31 [E] | 511 |
| 330 | hexyl | 2-(5-F-4-Me-pyridyl) | 1.81 [E] | 495 |
| 331 | 2-hydroxy-2-phenylethyl | 2-(5-F-4-Me-pyridyl) | 1.52 [E] | 545 |
| 332 | cyclobutylmethyl | 2-(5-F-4-Me-pyridyl) | 1.72 [E] | 493 |
| 333 | 3-hydroxy-3-methylbutyl | 2-(5-F-4-Me-pyridyl) | 1.36 [E] | 511 |
| 334 | 3-ethylpentyl | 2-(5-F-4-Me-pyridyl) | 1.91 [E] | 509 |

-continued

| Example No. | R¹ | R² | Rt (minutes) [Method] | m/z [M + H]⁺ |
|---|---|---|---|---|
| 335 | (2-hydroxypropyl with gem-dimethyl) | 5-F, 4-Me pyridin-2-yl | 1.24 [E] | 483 |
| 336 | (3-hydroxypropyl with gem-dimethyl) | 5-F, 4-Me pyridin-2-yl | 1.18 [E] | 469 |
| 337 | (2-phenylethyl with gem-dimethyl) | 5-F, 4-Me pyridin-2-yl | 1.78 [E] | 529 |
| 338 | (isopentyl with gem-dimethyl) | 5-F, 4-Me pyridin-2-yl | 1.78 [E] | 495 |
| 339 | (n-propyl with gem-dimethyl) | 5-F, 4-Me pyridin-2-yl | 1.53 [E] | 467 |
| 340 | (neopentyl with gem-dimethyl) | 5-F, 4-Me pyridin-2-yl | 1.78 [E] | 495 |
| 341 | (2-(5-methoxy-1H-indol-3-yl)ethyl with gem-dimethyl) | 5-F, 4-Me pyridin-2-yl | 1.65 [E] | 598 |
| 342 | (1-hydroxycyclobutylmethyl with gem-dimethyl) | 5-F, 4-Me pyridin-2-yl | 1.41 [E] | 509 |
| 343 | ((3-methyloxetan-3-yl)methyl with gem-dimethyl) | 5-F, 4-Me pyridin-2-yl | 1.38 [E] | 509 |
| 344 | ((tetrahydrofuran-2-yl)methyl with gem-dimethyl) (chiral) | 5-F, 4-Me pyridin-2-yl | 1.46 [E] | 509 |

-continued

| Example No. | R¹ | R² | Rt (minutes) [Method] | m/z [M + H]⁺ |
|---|---|---|---|---|
| 345 | thiazol-2-ylmethyl | 5-fluoro-4-methylpyridin-2-yl | 1.44 [E] | 522 |
| 346 | 2,2,2-trifluoroethyl (CH₂CF₃) with methyl branch | 5-fluoro-4-methylpyridin-2-yl | 1.63 [E] | 507 |
| 347 | 2-hydroxy-2-methylpropyl | 5-fluoro-4-methylpyridin-2-yl | 1.32 [E] | 497 |
| 348 | 3-hydroxypropyl | 5-fluoro-4-methylpyridin-2-yl | 1.19 [E] | 483 |
| 349 | 3-methoxypropyl | 5-fluoro-4-methylpyridin-2-yl | 1.39 [E] | 497 |
| 350 | isobutyl | 5-fluoro-4-methylpyridin-2-yl | 1.66 [E] | 481 |
| 351 | benzyl | 5-fluoro-4-methylpyridin-2-yl | 1.72 [E] | 515 |
| 352 | 2-methoxyethyl | 5-fluoro-4-methylpyridin-2-yl | 1.38 [E] | 483 |
| 353 | (1H-indol-3-yl)methyl | 5-fluoro-4-methylpyridin-2-yl | 1.48 [G] | 554 |
| 354 | (1-cyanocyclopropyl)methyl | 5-fluoro-4-methylpyridin-2-yl | NA | NA |

-continued

| Example No. | R¹ | R² | Rt (minutes) [Method] | m/z [M + H]⁺ |
|---|---|---|---|---|
| 355 | | | 1.56 [E] | 453 |
| 356 | | | 1.55 [E] | 471 |

Example 357

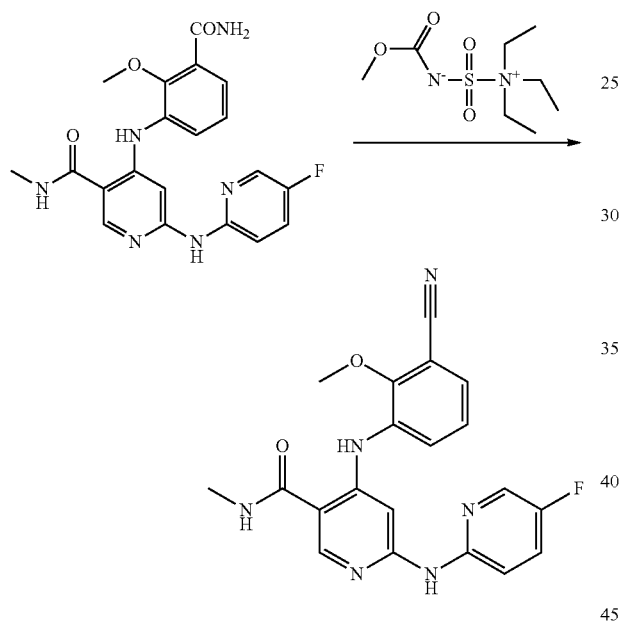

To a suspension of 4-((3-carbamoyl-2-methoxyphenyl) amino)-6-((5-fluoropyridin-2-yl)amino)-N-methylnicotinamide (Example 315, 21 mg, 0.051 mmol) in dichloromethane (0.2 mL) and THF (0.2 mL) was added Burgess reagent (24.39 mg, 0.102 mmol) in one portion under nitrogen and the resulting mixture was allowed to stir overnight at room temperature. HPLC and LCMS indicated only ~15% conversion of starting material to afford the desired product (observed MH+ of 393). Therefore, the reaction was concentrated to remove the THF and dichloromethane and acetonitrile (0.3 mL) was added followed by additional Burgess Reagent (24.39 mg, 0.102 mmol). After 4 h at room temperature, the reaction mixture became a clear solution and HPLC indicated completed conversion of starting material to the desired product. The reaction was concentrated, diluted with DMF, filtered, and was purified by reverse phase preparative LCMS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 20 minutes, then a 5-minute hold at 100% B; Flow: 25 mL/minutes. Fractions containing the desired product were combined and dried via centrifugal evaporation. The yield of the product was 7.2 mg (35%). HPLC (Method E) RT=1.53 minutes; HPLC (Method G) RT=1.08 minutes. LCMS observed MH+=393.1. ¹H NMR (500 MHz, DMSO-d₆) δ 10.79 (s, 1H), 9.87 (br. s., 1H), 8.58 (br. s., 1H), 8.50 (s, 1H), 8.17 (d, J=3.1 Hz, 1H), 7.87 (d, J=6.7 Hz, 1H), 7.66 (d, J=7.9 Hz, 2H), 7.50 (d, J=7.9 Hz, 1H), 7.44-7.35 (m, 1H), 3.92 (s, 3H), 2.79 (d, J=4.9 Hz, 3H).

Example 358

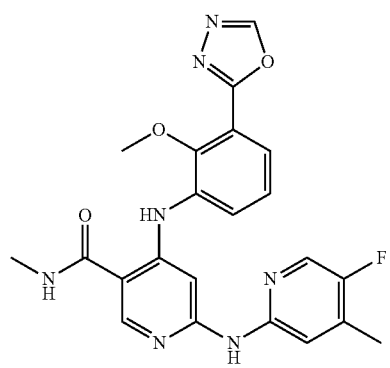 [SMILES: CNC(=O)c1cnc(Nc2cc(C)c(F)cn2)cc1Nc1cccc(-c2nnco2)c1OC]

Step 1

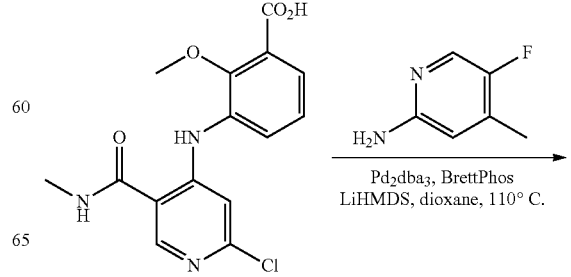

-continued

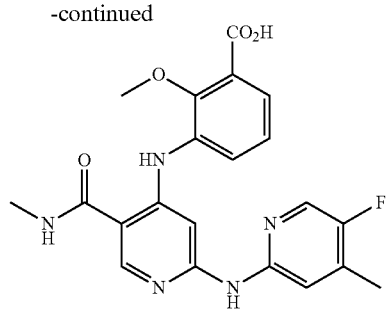

Step 1 was performed in a similar manner to Step 4 of Example 315 to afford a 97% yield of the desired product. HPLC (Method N) RT=2.45 minutes. LCMS (m+1)=426.

Step 2

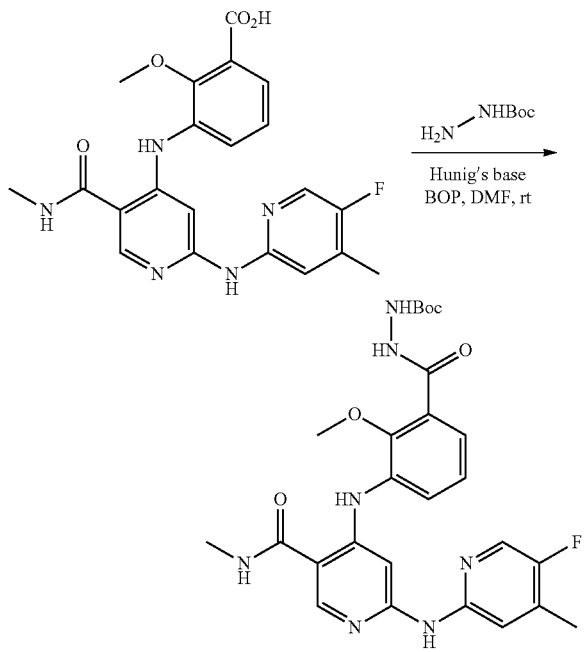

The product from the previous Step 1 (60 mg, 0.141 mmol), Hunig's base (0.074 mL, 0.423 mmol) and tert-butyl hydrazinecarboxylate (22.37 mg, 0.169 mmol) was stirred in DMF (0.6 mL) for a few minutes at room temperature then (benzotriazol-1-yloxy)tris(dimethylamino)phosphonium hexafluorophosphate (BOP, 81 mg, 0.183 mmol) was added to the resulting slurry. Let slurry stir at room temperature for 1 h. The reaction mixture was slowly diluted with water (~3 mL) and the resulting suspension was sonicated briefly then the precipitated solid was collected by vacuum filtration and air dried on the funnel to afford light tan solid as the product tert-butyl 2-(3-((2-((5-fluoro-4-methylpyridin-2-yl)amino)-5-(methylcarbamoyl)pyridin-4-yl)amino)-2-methoxybenzoyl)hydrazinecarboxylate (64 mg, 0.119 mmol, 84% yield). HPLC (Method N) RT=2.74 minutes. LCMS (m+1)=540.

Step 3

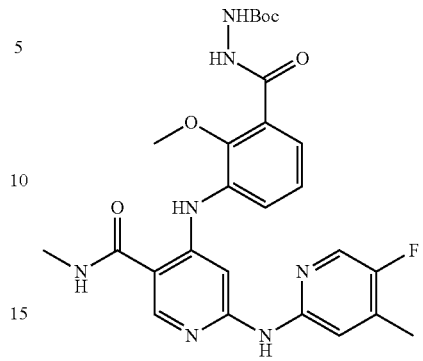

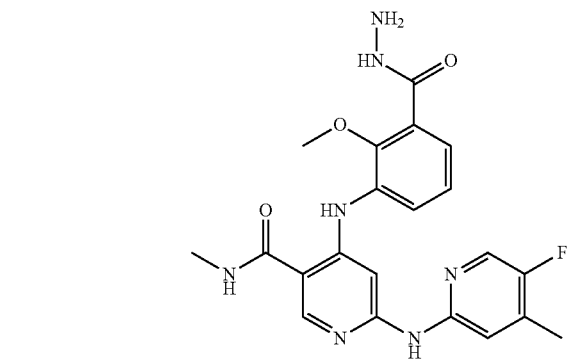

To a slurry of the product from the previous Step 2 (64 mg, 0.119 mmol) in dichloromethane (0.5 mL) was added trifluoroacetic acid (TFA, 0.183 mL, 2.372 mmol) to make clear solution and this solution was stirred at room temperature for 1 hour. The mixture was concentrated and then re-concentrated from dichloromethane (10 mL) twice. The resulting material was triturated with ether (5 mL×2) to give an oil which foamed and solidified under high vacuum to afford the product 6-((5-fluoro-4-methylpyridin-2-yl)amino)-4-((3-(hydrazinecarbonyl)-2-methoxyphenyl)amino)-N-methylnicotinamide, as its TFA salt (55 mg, 0.099 mmol, 84% yield). HPLC (Method N) RT=2.02 minutes. LCMS (m+1)=440.1.

Step 4

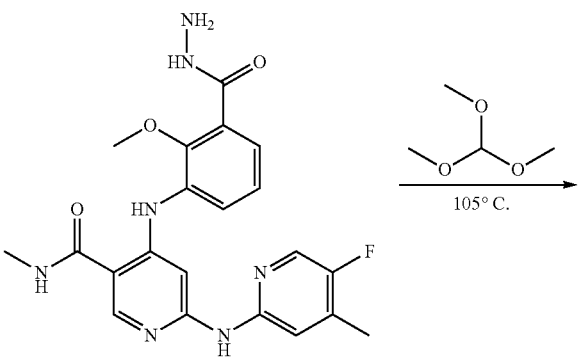

-continued

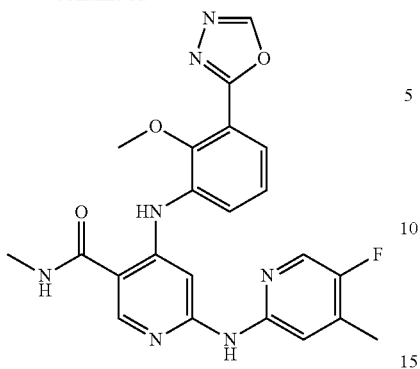

The product from the previous Step 3 (15 mg, 0.027 mmol) in trimethoxymethane (144 mg, 1.355 mmol) was heated on heating block at 105° C. After 2h, HPLC and LCMS indicated complete conversion to a major product consistent with the desired product (observed MH+ of 450). The reaction mixture was concentrated to remove excess trimethoxymethane, diluted with DMF, filtered through a Millipore filter, and was purified by preparative reverse phase LCMS to afford with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 20 minutes, then a 5-minute hold at 100% B; Flow: 25 mL/minutes. Fractions containing the desired product were combined and dried via centrifugal evaporation.

The yield of the product (Example 358) was 7.2 mg (59%). HPLC (Method E) RT=1.40 minutes; HPLC (Method G) RT=1.06 minutes. LCMS MH+=450.2. $^1$H NMR (500 MHz, DMSO-$d_6$) δ 10.82 (s, 1H), 9.75 (br. s., 1H), 9.41 (s, 1H), 8.55 (br. s., 1H), 8.50 (s, 1H), 8.07 (s, 1H), 7.87-7.78 (m, 1H), 7.72 (br. s., 1H), 7.63 (d, J=8.5 Hz, 1H), 7.56 (br. s., 1H), 7.43 (t, J=7.9 Hz, 1H), 3.79 (s, 3H), 3.16 (s, 3H), 2.79 (d, J=4.3 Hz, 3H), 2.24 (s, 3H).

Example 359

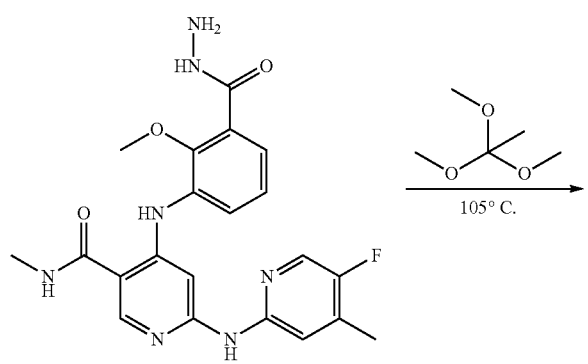

-continued

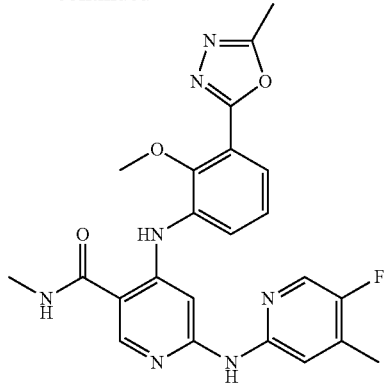

Example 359 was prepared from the product of Step 3 in Example 358 using the conditions described in Step 4 of Example 358 and by replacing trimethoxyorthoformate with trimethoxyorthoacetate to afford a 60% yield of Example 359. HPLC (Method E) RT=1.46 minutes; HPLC (Method G) RT=1.11 minutes. LCMS (m+1)=464.2. $^1$H NMR (500 MHz, DMSO-$d_6$) δ 10.82 (s, 1H), 9.73 (s, 1H), 8.53 (d, J=4.9 Hz, 1H), 8.50 (s, 1H), 8.06 (s, 1H), 7.82-7.77 (m, 1H), 7.73 (s, 1H), 7.61-7.53 (m, 2H), 7.41 (t, J=7.9 Hz, 1H), 3.78 (s, 3H), 3.16 (d, J=4.9 Hz, 3H), 2.79 (d, J=4.3 Hz, 3H), 2.24 (s, 3H).

Example 360

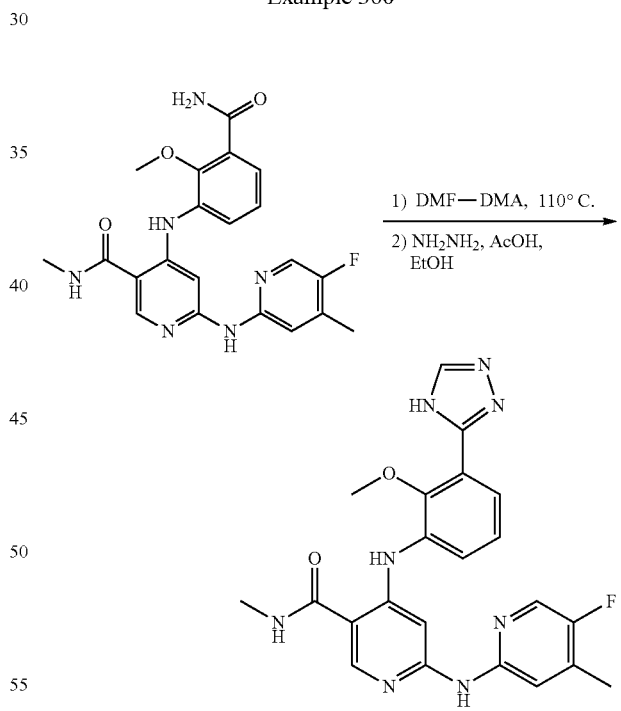

A slurry of Example 319 (25 mg, 0.059 mmol) in DMF-DMA (1.5 mL, 11.20 mmol) was heated to 110° C. giving a clear solution initially then eventually became a heterogeneous slurry. Let stir at this temperature for 30 minutes, then cooled slightly and concentrated to remove the DMF-DMA to afford a solid after concentrating further under high vacuum. To this residue was added acetic acid (0.12 mL) and ethanol (0.6 mL) to make clear solution and followed immediately by cooling the resulting slurry to −10° C. in a brine/ice bath and adding 60 μL (~10 equiv) of hydrazine hydrate dropwise via syringe with good stirring to afford light pink slurry. After addition was complete, the reaction was slowly heated to 60° C. and stirring was continued for 2 hours. The reaction mixture was then cooled to room temperature and allowed to stir overnight. The reaction mixture was diluted with ~2 mL of DMSO and was subjected to reverse phase preparative LCMS purification with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 25 minutes, then a 5-minute hold at 100% B; Flow: 25 mL/minutes. Fractions containing the desired product were combined and dried via centrifugal evaporation. The yield of the product was 8.6 mg (33%). HPLC (Method E) RT=1.25 minutes; HPLC (Method G) RT=0.99 minutes. LCMS (m+1)=448.2. $^1$H NMR (500 MHz, DMSO-$d_6$) δ 10.76 (s, 1H), 9.72 (br. s., 1H), 8.58-8.40 (m, 2H), 8.06 (d, J=19.5 Hz, 1H), 7.77-7.63 (m, 2H), 7.63-7.53 (m, 2H), 7.44-7.22 (m, 1H), 3.81-3.61 (m, 3H), 2.79 (br. s., 3H), 2.24 (s, 3H).

Example 361

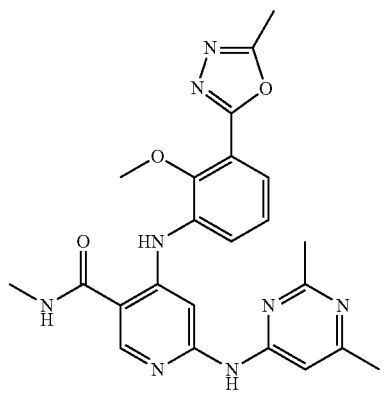

Step 1

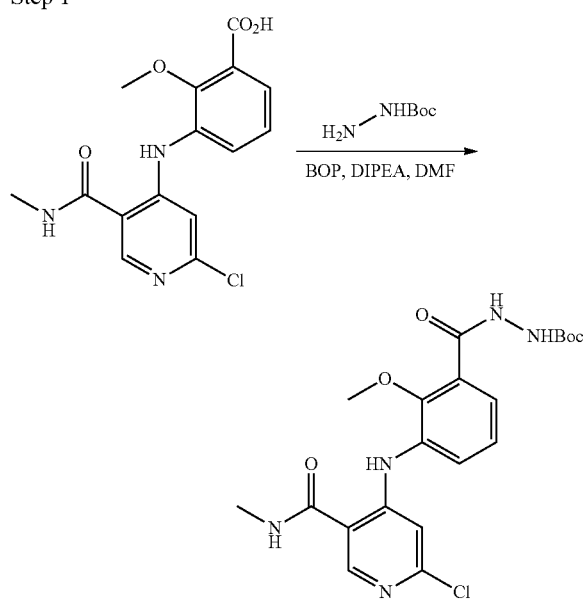

Dissolved the product from Step 3 of Example 315 (300 mg, 0.894 mmol), tert-butyl hydrazinecarboxylate (142 mg, 1.072 mmol) and diisopropylethylamine (DIPEA, 0.187 mL, 1.072 mmol) in DMF (3 mL) and let stir for a few minutes before adding BOP reagent (435 mg, 0.983 mmol). After stirring at room temperature for ~30 minutes, cold water was added causing a solid to precipitate. The slurry was briefly sonicated and the solid was collected by filtration and dried on the filter to afford the product, tert-butyl 2-(3-((2-chloro-5-(methylcarbamoyl)pyridin-4-yl)amino)-2-methoxybenzoyl)hydrazinecarboxylate (356 mg, 0.791 mmol, 89% yield). HPLC (Method N) RT=2.81 minutes. LCMS (m+1)=450/452.

Step 2

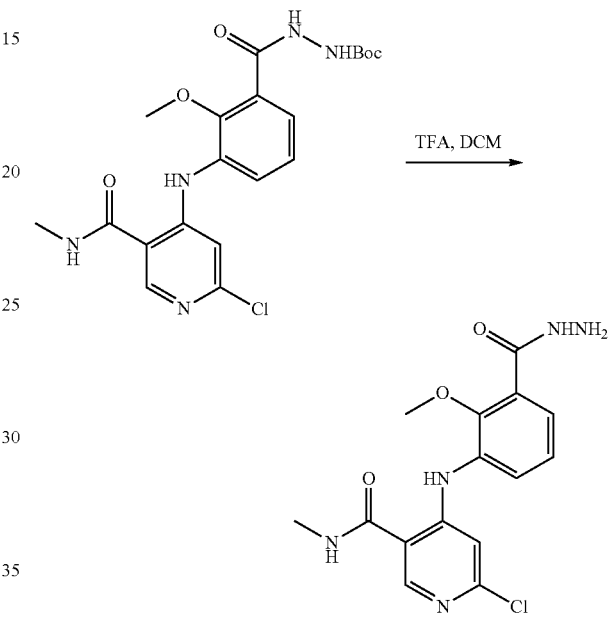

To slurry of the product from the previous step (356 mg, 0.791 mmol) in dichloromethane (2 mL) was added TFA (0.610 mL, 7.91 mmol) to make clear solution followed by stirring at room temperature for 1 h. The resulting mixture was then concentrated to remove the dichloromethane and TFA, and dichloromethane (10 mL) was added and the mixture was concentrated to dryness again followed by repeating this process one additional time. The resulting pale yellow oil obtained was triturated with ether (30 mL×2) to afford a near white solid as the presumed TFA salt of the final product, 6-chloro-4-((3-(hydrazinecarbonyl)-2-methoxyphenyl)amino)-N-methylnicotinamide (356 mg, 0.768 mmol, 97% yield). HPLC (Method N) RT=1.81 minutes. LCMS (m+1)=350.

Step 3

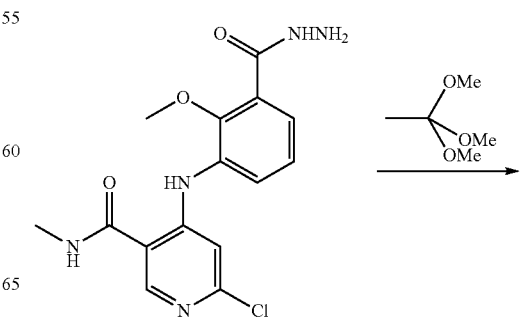

-continued

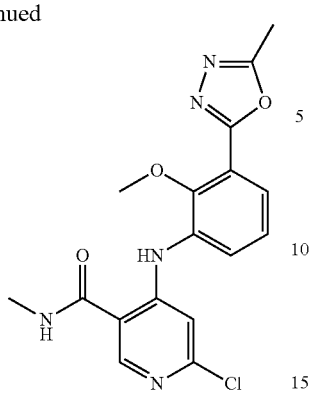

The product from the previous step (356 mg, 0.768 mmol) in 1,1,1-trimethoxyethane (1844 mg, 15.35 mmol) was heated at 90° C. for 4h then cooled down and concentrated to remove excess 1,1,1-trimethoxyethane. After cooling the residue in an ice bath, aq. sat. sodium bicarbonate (4 mL) was added and the mixture was sonicated to give a slurry and the solid was collected by vacuum filtration, rinsed with water, and dried on the filter to afford the product as a tan solid (186 mg, 0.498 mmol, 64.8% yield). HPLC (Method N) RT=2.81 minutes. LCMS (m+1)=375.

Step 4

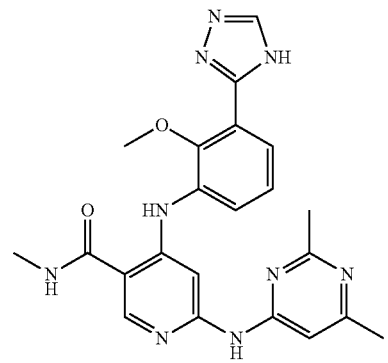

Step 4 was performed in a similar manner to Step 4 of Example 315 to afford a 60% yield of Example 361. HPLC (Method E) RT=1.17 minutes; HPLC (Method G) RT=0.81 minutes. LCMS (m+1)=461. $^1$H NMR (500 MHz, DMSO-d$_6$) δ10.86 (s, 1H), 8.67 (d, J=4.3 Hz, 1H), 8.57 (s, 1H), 7.81 (d, J=7.9 Hz, 1H), 7.64 (d, J=7.3 Hz, 1H), 7.40 (t, J=7.9 Hz, 1H), 3.79 (s, 3H), 2.81 (d, J=4.9 Hz, 3H), 2.60 (s, 3H), 2.43 (s, 3H), 2.35 (s, 3H).

Example 362

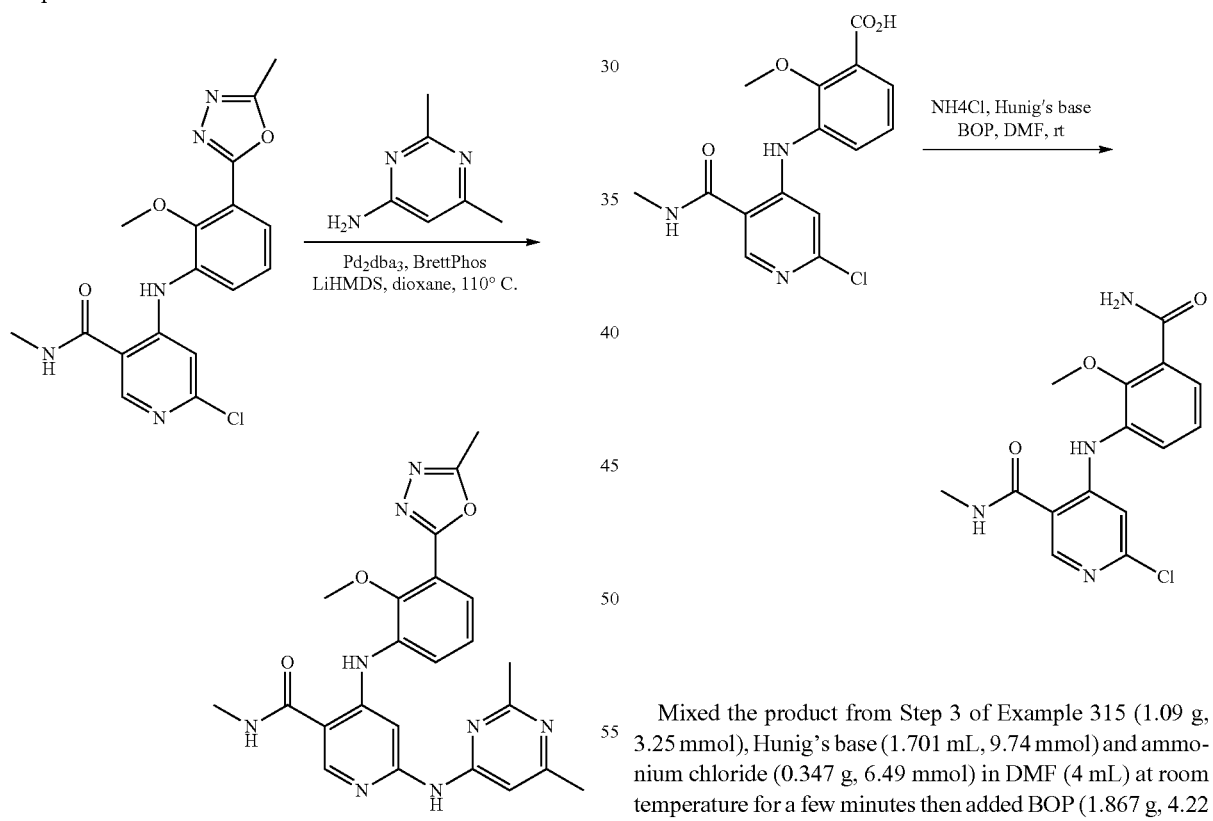

Step 1

Mixed the product from Step 3 of Example 315 (1.09 g, 3.25 mmol), Hunig's base (1.701 mL, 9.74 mmol) and ammonium chloride (0.347 g, 6.49 mmol) in DMF (4 mL) at room temperature for a few minutes then added BOP (1.867 g, 4.22 mmol) to the resulting slurry. Let slurry stir at room temperature for 1 h then crushed ice was added to the reaction mixture and the resulting suspension was sonicated briefly then the precipitated solid was collected by vacuum filtration and air dried in the funnel to afford the product, 4-((3-carbamoyl-2-methoxyphenyl)amino)-6-chloro-N-methylnicotinamide (1.07 g, 3.20 mmol, 98% yield) as a light tan solid. HPLC (Method N) RT=2.24 minutes. LCMS (m+1)=335.

Step 2

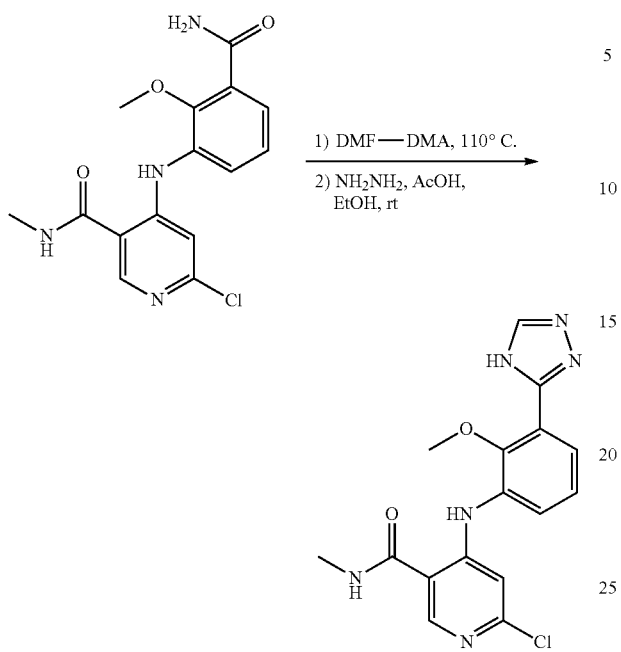

1) DMF—DMA, 110° C.
2) NH₂NH₂, AcOH, EtOH, rt

Step 2 was performed in a similar manner described for the preparation of Example 360 to afford an 87% yield of the desired product. HPLC (Method N) RT=2.51 minutes. LCMS (m+1)=359/361.

Step 3

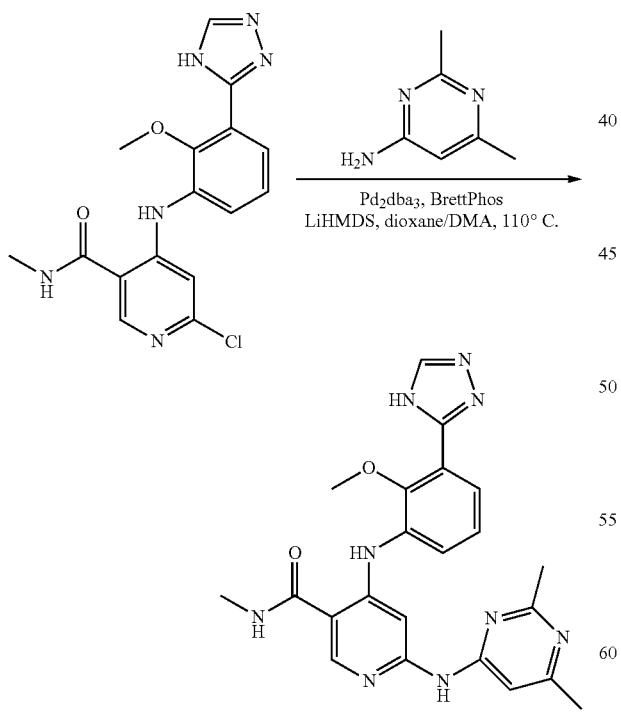

Pd₂dba₃, BrettPhos
LiHMDS, dioxane/DMA, 110° C.

To a reaction vial was added the product from the previous Step 2 (20 mg, 0.056 mmol), 2,6-dimethylpyrimidin-4-amine (10.30 mg, 0.084 mmol) and BrettPhos ligand (3.59 mg, 6.69 μmol) and the contents were purged with nitrogen before adding DMA (0.100 mL) and dioxane (0.20 mL). The resulting slurry was sparged with nitrogen for an additional minute, then Pd₂(dba)₃ (5.10 mg, 5.57 μmol) followed by LiHMDS (1 M in THF) (0.139 mL, 0.139 mmol) was added and the reaction vial was capped under nitrogen and placed into a preheated 110° C. heating block and the mixture was allowed to stir at that temperature for 1.5 h. The reaction was cooled, concentrated to remove the THF, diluted with methanol, and the residue was purified by reverse phase preparative HPLC to afford 9.8 mg (38%) of Example 362 as a tan solid. HPLC (Method N) RT=1.84 minutes. LCMS (m+1)=446.3. $^1$H NMR (500 MHz, DMSO-$d_6$) δ 10.86 (s, 1H), 8.67 (d, J=4.3 Hz, 1H), 8.57 (s, 1H), 7.81 (d, J=7.9 Hz, 1H), 7.64 (d, J=7.3 Hz, 1H), 7.40 (t, J=7.9 Hz, 1H), 3.79 (s, 3H), 2.81 (d, J=4.9 Hz, 3H), 2.60 (s, 3H), 2.43 (s, 3H), 2.35 (s, 3H).

Example 363

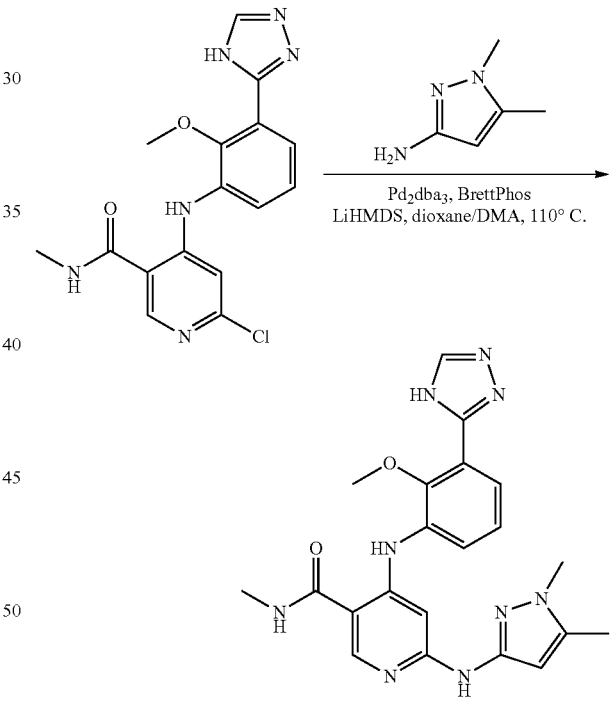

Pd₂dba₃, BrettPhos
LiHMDS, dioxane/DMA, 110° C.

Example 363 was prepared from the product of Step 2 in Example 362 using similar conditions as described in Step 3 of Example 362 to afford a 25% yield of Example 363 as a white solid. HPLC (Method N) RT=2.26 minutes. LCMS (m+1)=434.2. $^1$H NMR (400 MHz, methanol-$d_4$) δ 8.73 (br. s., 1H), 8.37 (s, 1H), 8.37-8.36 (m, 1H), 7.96 (dd, J=7.9, 1.5 Hz, 1H), 7.71-7.58 (m, 1H), 7.44 (t, J=7.9 Hz, 1H), 6.48 (s, 1H), 5.79 (d, J=0.7 Hz, 1H), 3.82 (s, 3H), 3.79 (s, 3H), 3.08-2.92 (m, 3H), 2.32 (s, 3H).

Example 364

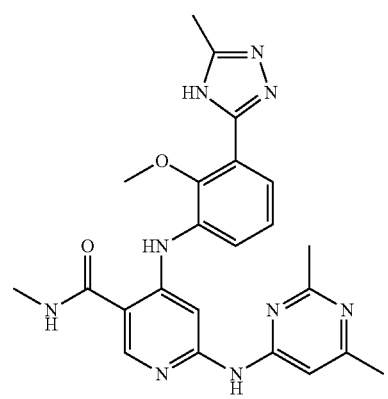

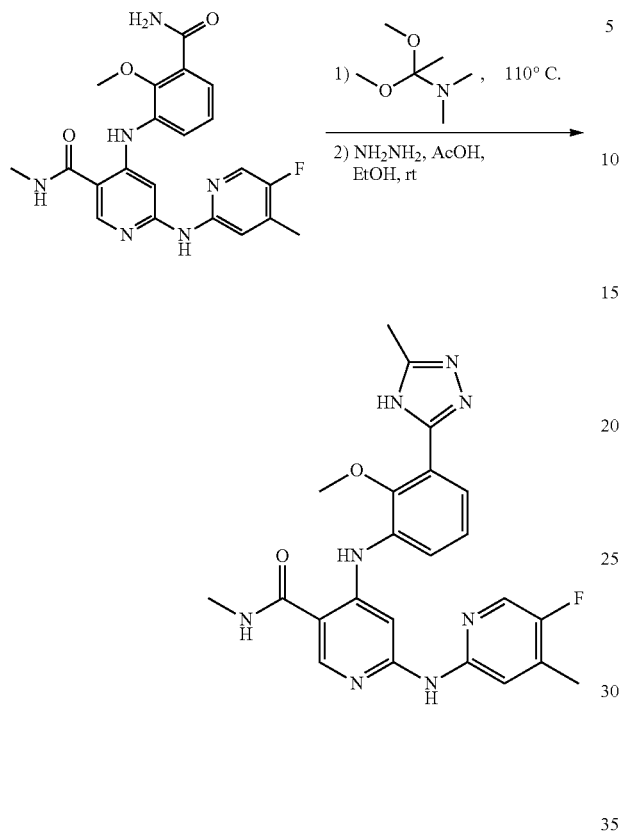

A slurry of Example 319 (30 mg, 0.071 mmol) in 1,1-dimethoxy-N,N-dimethylethanamine (94 mg, 0.707 mmol) was heated to 110° C. giving a clear solution. The reaction was stirred at this temperature for 1 hour, and then cooled to room temperature and concentrated to afford a semi-solid. To this residue was added ethanol (0.1 mL) and acetic acid (0.500 mL) resulting in a clear solution that was immediately cooled to 0° C.; whereupon, hydrazine hydrate (0.022 mL, 0.707 mmol) was slowly added dropwise via syringe with good stirring to afford light tan slurry which was allowed to warm to room temperature and stirred overnight. At this time, the mixture was concentrated to remove the ethanol and acetic acid, diluted methanol and was purified by reverse phase preparative HPLC using the conditions: Column: C18 PHENOMENEX® Luna Axia, 21×250 mm, Mobile Phase A: 5:95 acetonitrile:water with 10-mM ammonium acetate; Mobile Phase B: 95:5 acetonitrile:water with 10-mM ammonium acetate; Gradient: 20-100% B over 15 minutes. Flow: 20 mL/minutes. Fractions containing the desired product were combined and dried via centrifugal evaporation. This afforded the product, 6-((5-fluoro-4-methylpyridin-2-yl) amino)-4-((2-methoxy-3-(5-methyl-4H-1,2,4-triazol-3-yl) phenyl)amino)-N-methylnicotinamide (12.3 mg, 0.024 mmol, 34.2% yield) as a white solid. HPLC (Method N) RT=2.48 minutes. LCMS (m+1)=463. $^1$H NMR (400 MHz, methanol-$d_4$) δ 8.43 (s, 1H), 7.99 (s, 1H), 7.74 (d, J=7.7 Hz, 2H), 7.64 (br. s., 1H), 7.44-7.31 (m, 2H), 3.79 (s, 3H), 3.00 (s, 3H), 2.54 (s, 3H), 2.34 (s, 3H).

Example 365

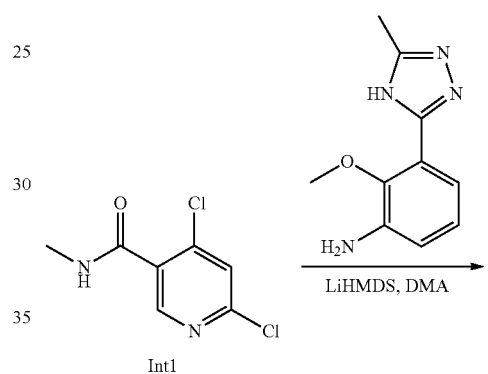

Step 1

Int1 200 mg, 0.975 mmol) and 2-methoxy-3-(5-methyl-4H-1,2,4-triazol-3-yl)aniline (Preparation 20, 219 mg, 1.073 mmol) were dissolved in N,N-dimethylacetamide (DMA, 2 mL) and to this was added LiHMDS (1 M in THF) (2.439 mL, 2.439 mmol) dropwise via syringe at room temperature over ~5 minutes. The reaction was stirred at room temperature for 30 minutes and then additional LiHMDS (1 M in THF) (1 mL, 1.0 mmol) was added, causing some solid to precipitate. HPLC indicated complete conversion of starting material.

Reaction was cooled in an ace bath and water was added to form clear solution, saturated aq. ammonium chloride solution was added causing a solid to precipitate. After diluting with additional water (40 mL), the resulting slurry was stirred for 1 h then the solid was collected by vacuum filtration, rinsed with water, and dried to 287 mg (79%) of the desired product as a tan solid. HPLC (Method N) RT=2.42 minutes. LCMS (m+1)=373.

Step 2

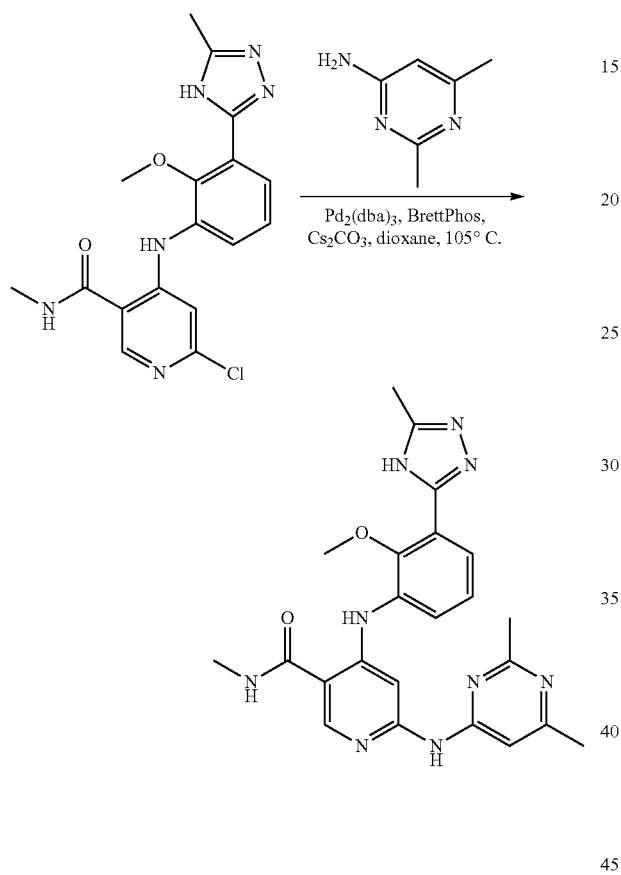

A slurry of the product from Step 1 (30 mg, 0.080 mmol), 2,6-dimethylpyrimidin-4-amine (14.87 mg, 0.121 mmol), cesium carbonate (52.4 mg, 0.161 mmol) and BrettPhos (6.48 mg, 0.012 mmol) in dioxane (0.5 mL) was sparged with nitrogen for 5 minutes., then $Pd_2(dba)_3$ (11.05 mg, 0.012 mmol) was added and the reaction was placed into a preheated 105° C. heating block for 1 h. The reaction was cooled to room temperature, diluted with DMSO, filtered through a Millipore filter and was purified by reverse phase preparative LCMS. Fractions containing the desired product were combined and dried via centrifugal evaporation. The yield of the product Example 365 was 11.2 mg (30%). HPLC (Method E) RT=1.07 minutes; HPLC (Method G) RT=0.67 minutes. LCMS MH+=460.2. HPLC (E) RT=1.07 minutes. LCMS (m+1)=460. $^1H$ NMR (500 MHz, DMSO-$d_6$) δ 10.78 (br. s., 1H), 10.11 (br. s., 1H), 8.67-8.47 (m, 2H), 8.11 (br. s., 1H), 7.78-7.52 (m, 2H), 7.26 (br. s., 1H), 7.10 (br. s., 1H), 3.71 (br. s., 3H), 2.80 (d, J=4.3 Hz, 3H), 2.48-2.31 (m, 6H), 2.28 (s, 3H).

Example 366 and Example 367

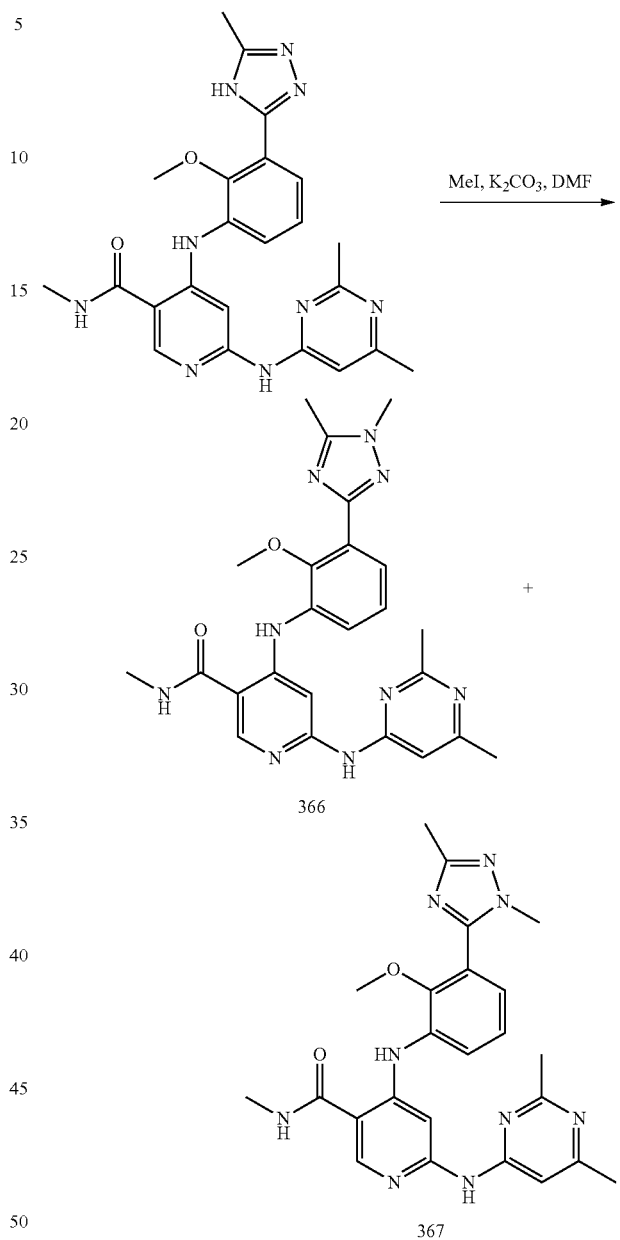

To a slurry of Example 365 (40 mg, 0.061 mmol) and potassium carbonate (25.3 mg, 0.183 mmol) in DMF (0.5 mL) at room temperature was added solution of iodomethane (4.57 µl, 0.073 mmol) in 0.3 mL of DMF. After stirring at room temperature for 3 h, the reaction was quenched with MeOH, diluted with DMSO, filtered through a Millipore (0.45µ), and subjected to purification by reverse phase preparative LCMS with the following conditions: Column: Waters XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 5-45% B over 25 minutes, then a 10-minute hold at 45% B; Flow: 20 mL/minutes. Fractions containing the desired product were combined and dried via centrifugal evaporation.

233

The yield of the product Example 366 was 4.2 mg (14%). HPLC (Method E) RT=1.15 minutes; HPLC (Method G) RT=0.77 minutes. LCMS MH+=474.2. $^1$H NMR (500 MHz, DMSO-d$_6$) δ 10.82 (s, 1H), 10.09 (br. s., 1H), 8.59 (d, J=4.3 Hz, 1H), 8.53 (s, 1H), 8.15 (br. s., 1H), 7.78 (d, J=7.9 Hz, 1H), 7.33 (t, J=7.9 Hz, 1H), 7.18 (d, J=7.9 Hz, 1H), 7.10 (br. s., 1H), 3.64 (s, 3H), 3.47 (s, 3H), 2.79 (d, J=3.7 Hz, 3H), 2.40 (s, 3H), 2.29 (d, J=3.1 Hz, 6H).

The yield of the isomeric product Example 55 was 5.4 mg (15%). HPLC (Method E) RT=1.11 minutes; HPLC (Method G) RT=0.77 minutes. $^1$H NMR (500 MHz, DMSO-d$_6$) δ 11.38 (br. s., 1H), 10.77 (br. s., 1H), 8.75 (d, J=4.3 Hz, 1H), 8.60 (s, 1H), 7.59 (dd, J=19.8, 7.6 Hz, 2H), 7.33-7.21 (m, 1H), 3.84 (s, 3H), 3.73 (s, 3H), 2.82 (d, J=4.3 Hz, 3H), 2.54 (s, 3H), 2.46 (s, 6H).

Example 368

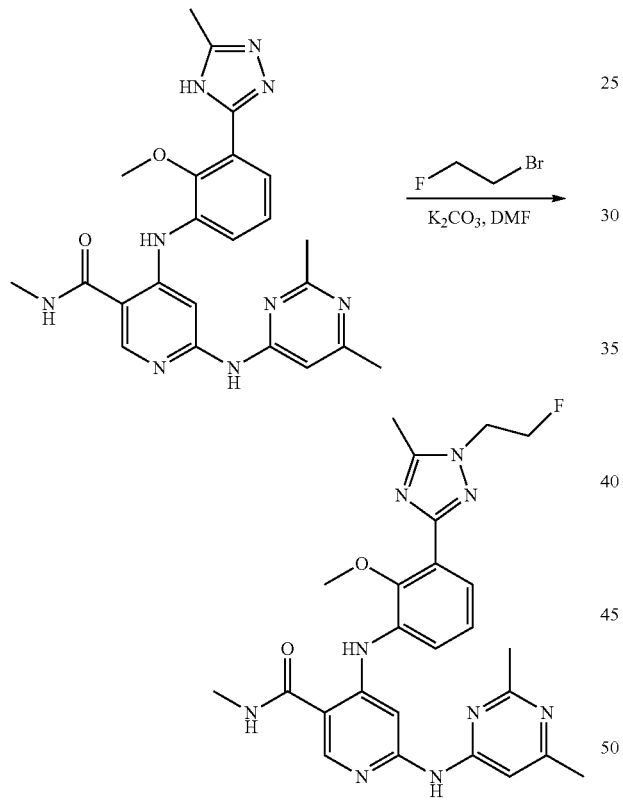

Example 368 was prepared from Example 365 similar to the method described for the preparation of Example 366 and Example 367 and by replacing iodomethane with 2-fluoromethylbromide as the alkylating agent. This afforded Example 368 as the major product along with a regioisomeric product as an inseparable 5:2 mixture respectively in 40% overall yield. HPLC (Method E) RT=1.21 minutes; HPLC (Method G) RT=0.85 minutes. LCMS MH+506.2. $^1$H NMR (500 MHz, DMSO-d$_6$) δ 10.85-10.68 (m, 1H), 8.70-8.39 (m, 2H), 8.22-8.10 (m, 1H), 7.70-7.47 (m, 1H), 7.40-7.21 (m, 1H), 7.19-7.01 (m, 1H), 4.92-4.70 (m, 2H), 4.59-4.43 (m, 1H), 3.97-3.66 (m, 1H), 2.79 (d, J=4.0 Hz, 3H), 2.44-2.36 (m, 3H), 2.35-2.22 (m, 3H).

234

Example 369

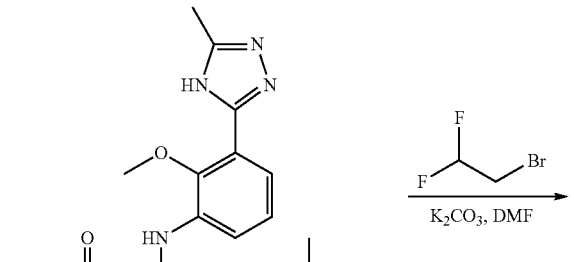

Example 369 was prepared from Example 365 similar to the method described for the preparation of Example 366 and Example 367 and by replacing iodomethane with 2,2-difluoromethylbromide as the alkylating agent. This afforded Example 369 as an inseparable 5:2 mixture respectively in 40% overall yield. HPLC (Method E) RT=1.28 minutes; HPLC (Method G) RT=0.92 minutes. $^1$H NMR (500 MHz, DMSO-d$_6$) δ10.86-10.72 (m, 1H), 10.14-9.97 (m, 1H), 8.65-8.47 (m, 2H), 8.24-8.09 (m, 1H), 7.95 (s, 1H), 7.71-7.51 (m, 2H), 7.41-7.23 (m, 1H), 7.07 (br. s., 1H), 4.74 (td, J=15.3, 3.1 Hz, 2H), 3.73 (s, 3H), 2.80 (d, J=4.3 Hz, 3H), 2.44-2.35 (m, 3H), 2.32-2.23 (m, 3H).

Example 370

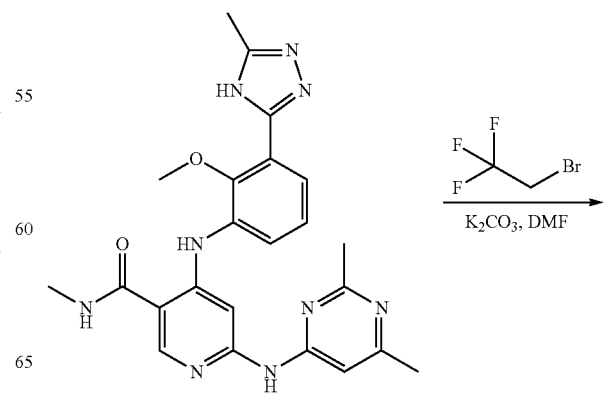

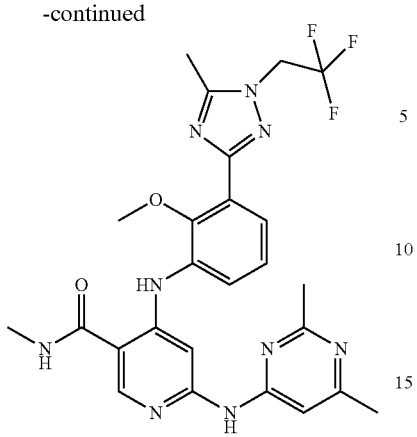

Example 370 was prepared from Example 365 similar to the method described for the preparation of Example 366 and Example 367 and by replacing iodomethane with 2,2,2-trifluoromethylbromide as the alkylating agent. This afforded Example 370 as the major product in 25% isolated yield. HPLC (Method E) RT=1.41 minutes; HPLC (Method G) RT=0.99 minutes. $^1$H NMR (500 MHz, DMSO-$d_6$) δ 10.84-10.71 (m, 1H), 10.16-9.94 (m, 1H), 8.68-8.37 (m, 2H), 8.25-8.08 (m, 1H), 7.67 (d, J=7.4 Hz, 1H), 7.56 (d, J=7.7 Hz, 1H), 7.27 (t, J=7.9 Hz, 1H), 7.07 (br. s., 1H), 5.30 (q, J=9.0 Hz, 2H), 2.79 (d, J=4.0 Hz, 3H), 2.54 (s, 3H), 2.42-2.32 (m, 3H), 2.31-2.24 (m, 3H).

Example 371

Step 1

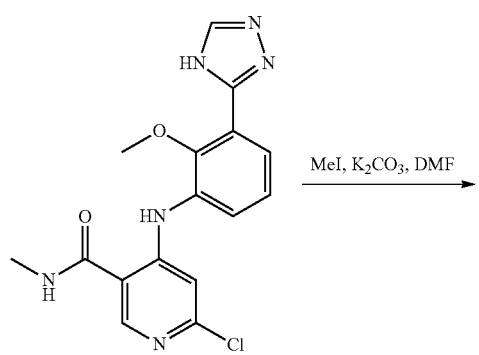

To slurry of product from Step 2 of Example 362 (80 mg, 0.223 mmol) and potassium carbonate (61.6 mg, 0.446 mmol) in DMF (0.5 mL) at room temperature was added 0.3 mL solution of iodomethane (240 mg in 2 mL of acetonitrile). The resulting mixture was allowed to stir at room temperature for 30 minutes before quenching with cold water. Brief sonication of the resulting slurry and vacuum filtration gave a solid which was rinsed with water and dried to afford 39 mg (47%) of the product as an off-white solid. HPLC (Method N) RT=2.61 minutes. LCMS (m+1)=373.

Step 2

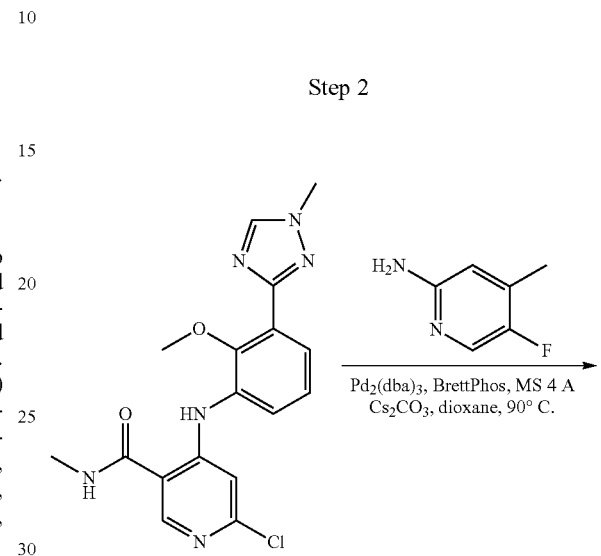

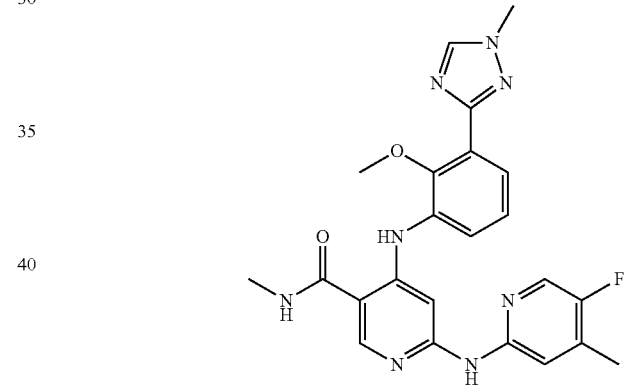

A mixture of the product from Step 1 (35 mg, 0.094 mmol), 5-fluoro-4-methylpyridin-2-amine (17.76 mg, 0.141 mmol), BrettPhos (7.56 mg, 0.014 mmol), 4 Å powdered molecular sieves (20 mg) and cesium carbonate (61.2 mg, 0.188 mmol) in dioxane (0.5 mL) was sparged with nitrogen for 5 minutes, then $Pd_2(dba)_3$ (17.19 mg, 0.019 mmol) was added and the reaction was placed into a preheated 90° C. heating block. After stirring at this temp for 4 h, the reaction was cooled to room temperature and water was added and the resulting solid which precipitated from solution was collected by vacuum filtration, rinsed with water, and dried to afford tan solid as the crude product mixture. To remove the molecular sieves, this material was slurried in 0.5 mL of DMSO and 5 mL of MeOH, filtered through CELITE®, and the resulting filtrate was concentrated and purified by reverse phase preparative LCMS. The yield of the product was 6.9 mg (35%). HPLC (Method E) RT=1.32 minutes; HPLC (Method G) RT=1.07 minutes. ¹H NMR (400 MHz, methanol-d₄) δ 8.75 (br. s., 1H), 8.55 (s, 1H), 8.38 (s, 1H), 8.21 (d, J=1.5 Hz, 1H), 7.87 (dd, J=7.8, 1.7 Hz, 1H), 7.60 (dd, J=7.9, 1.5 Hz, 1H), 7.47-7.36 (m, 1H), 6.92 (d, J=5.3 Hz, 1H), 6.50 (s, 1H), 4.07 (s, 3H), 3.77 (s, 3H), 3.03-2.97 (m, 3H), 2.38 (s, 3H).

The following Examples were prepared from the product of Step 2 of Example 362 using commercially available reagents and using similar conditions as described in Step 3 of Example 362:

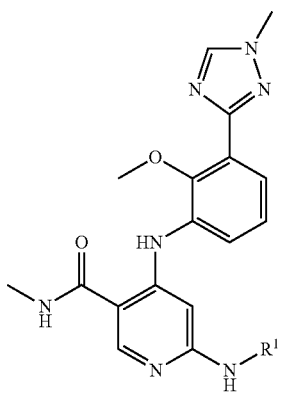

| Example No. | R¹ | Rt (minutes) [Method] | m/z [M + H]⁺ |
|---|---|---|---|
| 372 | 2,6-dimethylpyrimidin-4-yl | 1.95 [N] | 460 |
| 373 | 5-fluoropyridin-2-yl | 2.37 [N] | 449 |
| 374 | pyridin-2-yl | 2.35 [N] | 431 |
| 375 | 5-(trifluoromethyl)pyridin-2-yl | 2.65 [N] | 499 |
| 376 | 5-cyanopyridin-2-yl | 2.27 [N] | 456 |

Example 377

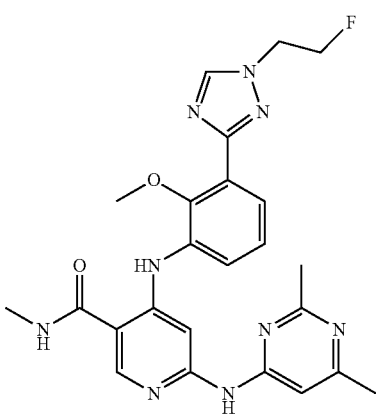

Step 1

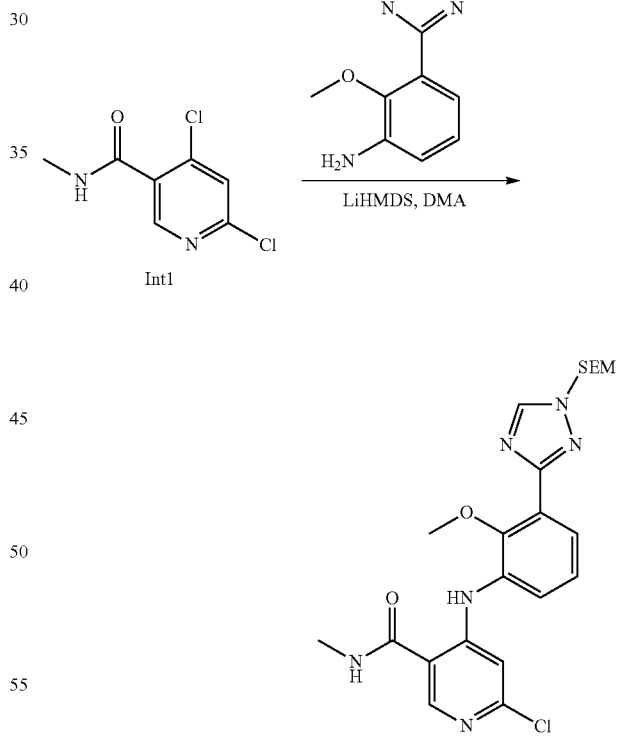

Step 1 of Example 377 was performed similar to previously described in Step 1 of Example 365 to afford the desired product (98% yield) as a tan solid. HPLC (Method N) RT=3.67 minutes. LCMS MH+489.

Step 2

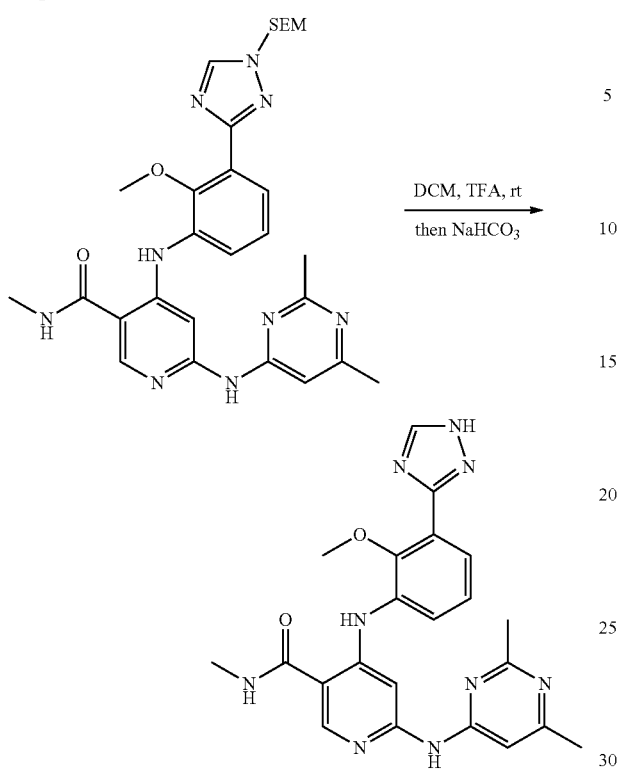

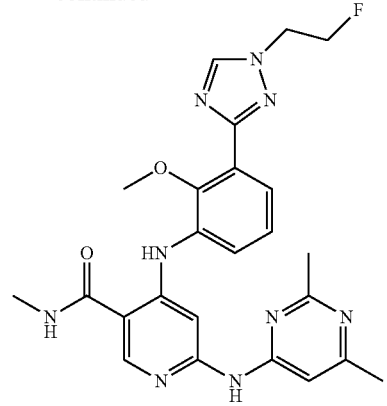

To a solution of the product from Step 1 (495 mg, 0.859 mmol) in dichloromethane (3 mL) at room temperature was added trifluoroacetic acid (TFA, 1.324 mL, 17.18 mmol) and the resulting mixture was stirred at room temperature for 2 hours then the mixture was concentrated and the resulting residue was co-evaporated twice with additional dichloromethane (15 mL) to afford tan oil. Trituration with ether (30 mL) afforded a solid and the clear ether layer was decanted and the trituration was repeated twice with additional ether. The remaining solid was then slurried in 10 mL of aqueous sat. NaHCO$_3$ and was briefly sonicated before collecting the resulting solid by vacuum filtration. The solid was rinsed with water and dried on the filter to afford the product (Example 362, 320 mg, 0.718 mmol, 84% yield) as a tan solid. HPLC (Method N) RT=1.86 minutes. LCMS MH+446. $^1$H NMR (400 MHz, methanol-d$_4$) δ 8.47 (s, 1H), 8.26 (br. s., 1H), 8.20 (s, 1H), 7.85-7.74 (m, 2H), 7.41 (t, J=7.9 Hz, 1H), 7.00 (s, 1H), 3.78 (s, 3H), 2.98 (s, 3H), 2.44 (s, 3H), 2.39 (s, 3H).

Step 3

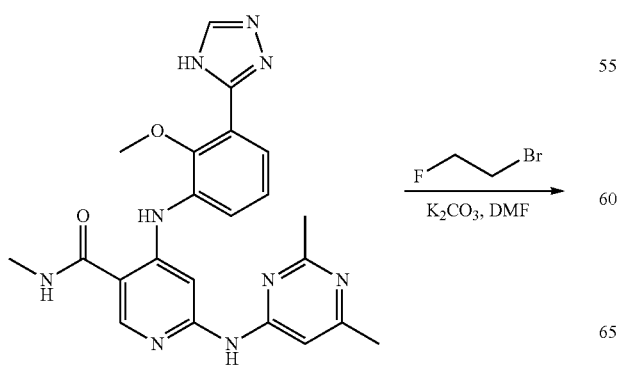

Example 377 was prepared from Example 362 (prepared from Step 2) using a similar method as described for the preparation of Example 366 and Example 367 and by replacing iodomethane with 2-fluoroethylbromide as the alkylating agent. This afforded Example 377 as an inseparable regioisomeric mixture (3:1) in 44% isolated yield. HPLC (Method E) RT=1.18 minutes; HPLC (Method G) RT=0.82 minutes. LCMS MH+ 492.2. $^1$H NMR (500 MHz, DMSO-d$_6$) δ 10.86-10.67 (m, 1H), 10.12-9.88 (m, 1H), 8.69-8.37 (m, 3H), 8.15 (d, J=9.8 Hz, 1H), 7.86-7.53 (m, 2H), 7.42-7.22 (m, 1H), 7.19-6.95 (m, 1H), 4.99-4.73 (m, 2H), 4.71-4.45 (m, 2H), 4.43-4.25 (m, 1H), 2.79 (d, J=4.0 Hz, 2H), 2.44-2.32 (m, 3H), 2.31-2.20 (m, 3H).

Example 378 and Example 379

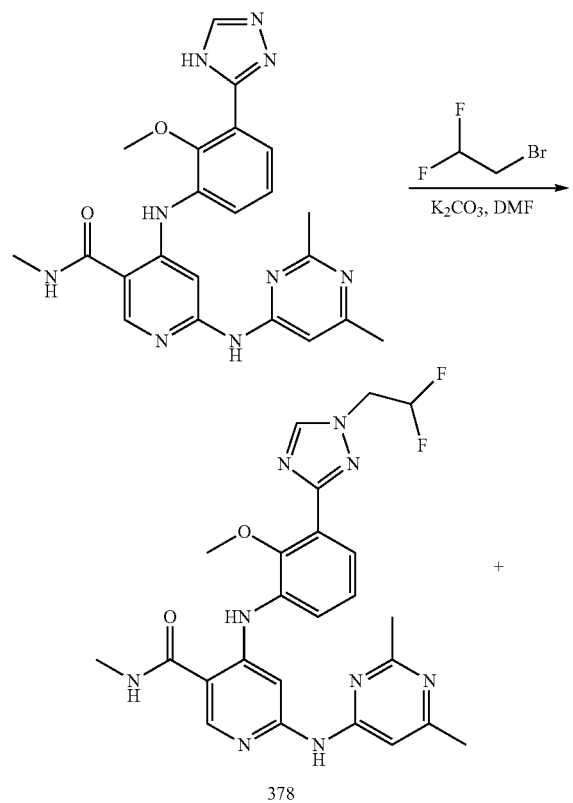

378

-continued

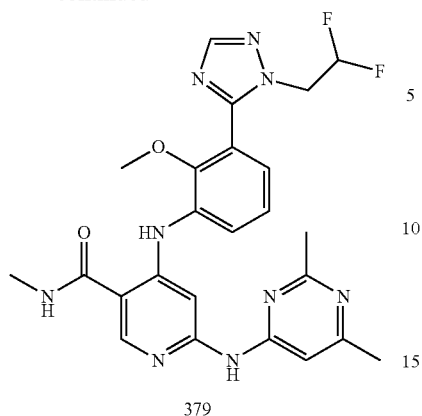

379

Example 378 and Example 379 were prepared from Example 362 (prepared from Step 2 of Example 377) using a similar method as described for the preparation of Example 366 and Example 367 and by replacing iodomethane with 2,2-difluoroethylbromide as the alkylating agent. This afforded Example 378 as the major product in 35% yield and Example 379 as the minor product in 10% yield.

Example 378 (major product): HPLC (Method E) RT=1.24 minutes; HPLC (Method G) RT=0.88 minutes. LCMS MH+510.2. $^1$H NMR (500 MHz, DMSO-$d_6$) δ 10.74 (s, 1H), 10.01 (s, 1H), 8.67 (s, 1H), 8.56 (d, J=4.4 Hz, 1H), 8.49 (s, 1H), 8.14 (br. s., 1H), 7.67 (d, J=7.7 Hz, 1H), 7.58 (d, J=7.4 Hz, 1H), 7.28 (t, J=7.9 Hz, 1H), 7.05 (s, 1H), 6.64-6.29 (m, 1H), 4.82 (td, J=15.3, 3.4 Hz, 3H), 2.79 (d, J=4.4 Hz, 3H), 2.37 (s, 3H), 2.27 (s, 4H).

Example 379 (minor product): HPLC (Method E) RT=1.25 minutes; HPLC (Method G) RT=0.89 minutes. LCMS MH+510.2. $^1$H NMR (500 MHz, DMSO-$d_6$) δ 10.79 (s, 1H), 10.05 (s, 1H), 8.60 (d, J=4.4 Hz, 1H), 8.52 (s, 1H), 8.19 (d, J=17.2 Hz, 2H), 7.82 (d, J=7.7 Hz, 1H), 7.37 (t, J=7.9 Hz, 1H), 7.18 (d, J=7.4 Hz, 1H), 7.07 (br. s., 1H), 6.55-6.17 (m, 1H), 4.64-4.46 (m, 2H), 3.89 (s, 3H), 2.79 (d, J=4.0 Hz, 3H), 2.39 (s, 3H), 2.28 (s, 3H).

Example 380 and Example 381

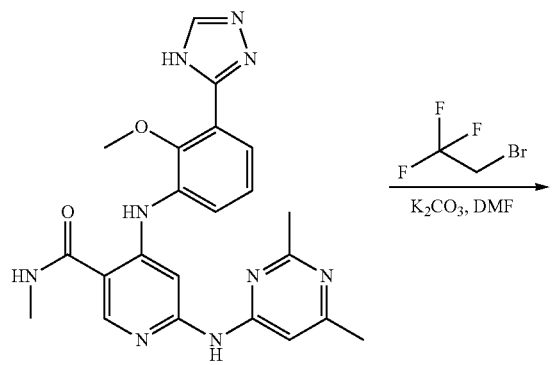

-continued

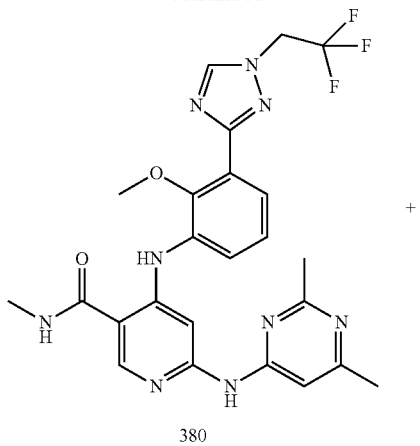

380

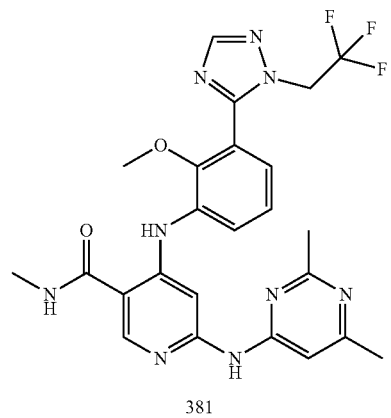

381

Example 380 and Example 381 were prepared from Example 362 (prepared from Step 2 of Example 377) using a similar method as described for the preparation of Example 366 and Example 367 and by replacing iodomethane with 2,2,2-trifluoroethylbromide as the alkylating agent. This afforded Example 380 as the major product in 31% yield and Example 381 as the minor product in 8% yield.

Example 380 (major product): HPLC (Method E) RT=1.37 minutes; HPLC (Method G) RT=1.00 minutes. LCMS MH+528.2. $^1$H NMR (500 MHz, DMSO-$d_6$) δ 10.78 (s, 1H), 10.04 (s, 1H), 8.78 (s, 1H), 8.62-8.49 (m, 2H), 8.15 (br. s., 1H), 7.70 (d, J=7.9 Hz, 1H), 7.65-7.51 (m, 1H), 7.30 (t, J=7.9 Hz, 1H), 7.07 (s, 1H), 5.38 (q, J=9.2 Hz, 2H), 3.73 (s, 3H), 2.80 (d, J=4.9 Hz, 3H), 2.38 (s, 3H), 2.27 (s, 3H).

Example 381 (minor product): HPLC (Method E) RT=1.38 minutes; HPLC (Method G) RT=1.01 minutes. LCMS MH+528.2. $^1$H NMR (500 MHz, DMSO-$d_6$) δ 10.81 (s, 1H), 10.17-9.98 (m, 1H), 8.60 (d, J=4.3 Hz, 1H), 8.55-8.46 (m, 1H), 8.27 (s, 1H), 8.18 (br. s., 1H), 7.95 (s, 1H), 7.84 (d, J=8.5 Hz, 1H), 7.38 (t, J=7.9 Hz, 1H), 7.20 (d, J=6.7 Hz, 1H), 7.09 (br. s., 1H), 5.10 (q, J=9.0 Hz, 2H), 3.48 (s, 3H), 2.79 (d, J=4.9 Hz, 3H), 2.40 (s, 3H), 2.29 (s, 3H).

Example 382 and Example 383

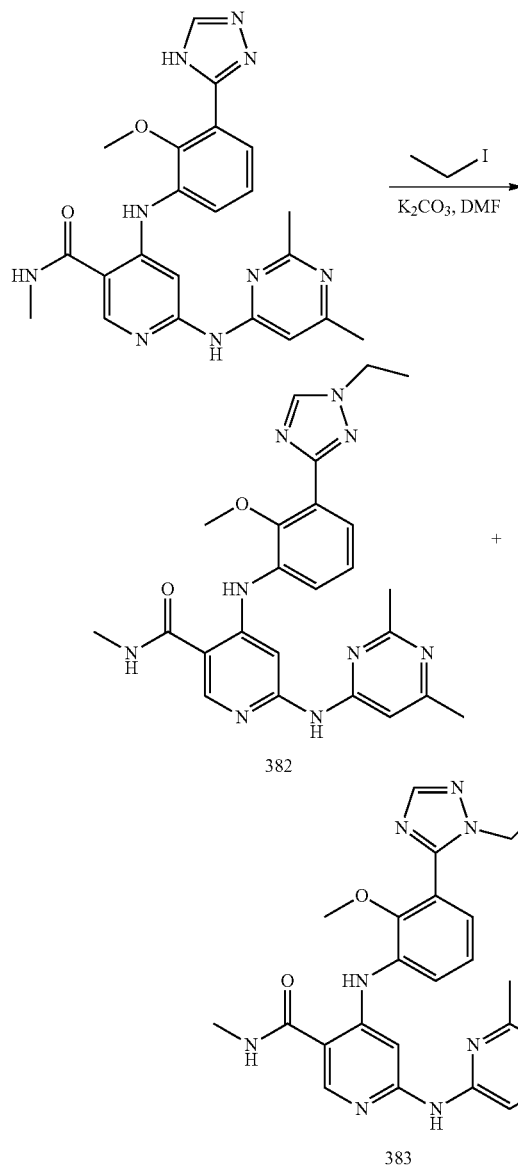

Example 382 and Example 383 were prepared from Example 362 (prepared from Step 2 of Example 377) using a similar method as described for the preparation of Example 366 and Example 367 and by replacing iodomethane with iodoethane as the alkylating agent. This afforded Example 382 as the major product in 18% yield and Example 383 as the minor product in 9% yield.

Example 382 (major product): HPLC (Method E) RT=1.23 minutes; HPLC (Method G) RT=0.97 minutes. LCMS MH+474.2. $^1$H NMR (500 MHz, DMSO-$d_6$) δ 10.67 (s, 1H), 9.97 (s, 1H), 8.56 (s, 2H), 8.47 (s, 1H), 8.13 (br. s., 1H), 7.63 (d, J=7.9 Hz, 1H), 7.56 (d, J=7.9 Hz, 1H), 7.27 (t, J=7.9 Hz, 1H), 7.02 (br. s., 1H), 4.25 (q, J=6.9 Hz, 2H), 2.78 (d, J=4.3 Hz, 3H), 2.35 (s, 3H), 2.26 (s, 3H), 1.43 (t, J=7.3 Hz, 3H).

Example 383 (minor product): HPLC (Method E) RT=1.24 minutes; HPLC (Method G) RT=0.98 minutes. LCMS MH+474.2. $^1$H NMR (500 MHz, DMSO-$d_6$) δ 10.72 (s, 1H), 10.01 (s, 1H), 8.58 (d, J=4.3 Hz, 1H), 8.49 (s, 1H), 8.14 (br. s., 1H), 8.08 (s, 1H), 7.78 (d, J=7.3 Hz, 1H), 7.35 (t, J=7.9 Hz, 1H), 7.16 (d, J=7.3 Hz, 1H), 7.04 (s, 1H), 3.98 (q, J=7.3 Hz, 2H), 3.44 (s, 3H), 2.78 (d, J=4.3 Hz, 3H), 2.37 (s, 3H), 2.27 (s, 3H), 1.27 (t, J=7.3 Hz, 3H).

Example 384

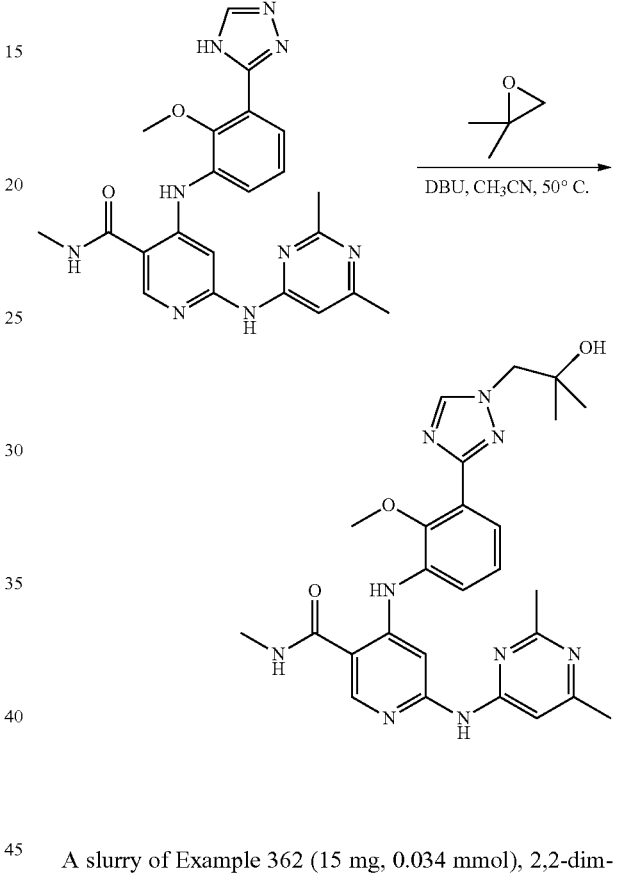

A slurry of Example 362 (15 mg, 0.034 mmol), 2,2-dimethyloxirane (12.14 mg, 0.168 mmol) and 1,8-diazabicyclo[5.4.0]undec-7-ene (DBU, 0.015 mL, 0.101 mmol) in acetonitrile (0.2 mL) was heated at 50° C. for overnight (~16 h). The resulting reaction mixture was then cooled to room temperature, was diluted with DMSO and was purified by reverse-phase preparative LCMS 10-mM ammonium acetate; Mobile Phase B: 95:5 acetonitrile: water with 10-mM ammonium acetate; Gradient: 0-100% B over 20 minutes, then a 0-minute hold at 100% B; Flow: 20 mL/minutes. Fractions containing the desired product were combined and dried via centrifugal evaporation. The yield of the product, Example 384, was 1.5 mg (8%). HPLC (Method E) RT=1.13 minutes; HPLC (Method G) RT=0.81 minutes. LCMS MH+518.2. $^1$H NMR (500 MHz, DMSO-$d_6$) δ 10.76 (s, 1H), 10.03 (s, 1H), 8.56 (d, J=4.3 Hz, 1H), 8.50 (s, 1H), 8.47 (s, 1H), 8.16 (br. s., 1H), 7.66 (d, J=7.9 Hz, 1H), 7.58 (d, J=7.9 Hz, 1H), 7.27 (t, J=7.9 Hz, 1H), 7.07 (s, 1H), 4.87 (br. s., 1H), 4.15 (s, 2H), 3.73 (s, 3H), 2.79 (d, J=4.3 Hz, 3H), 2.27 (s, 3H), 1.88 (s, 3H), 1.14 (s, 6H).

Example 385

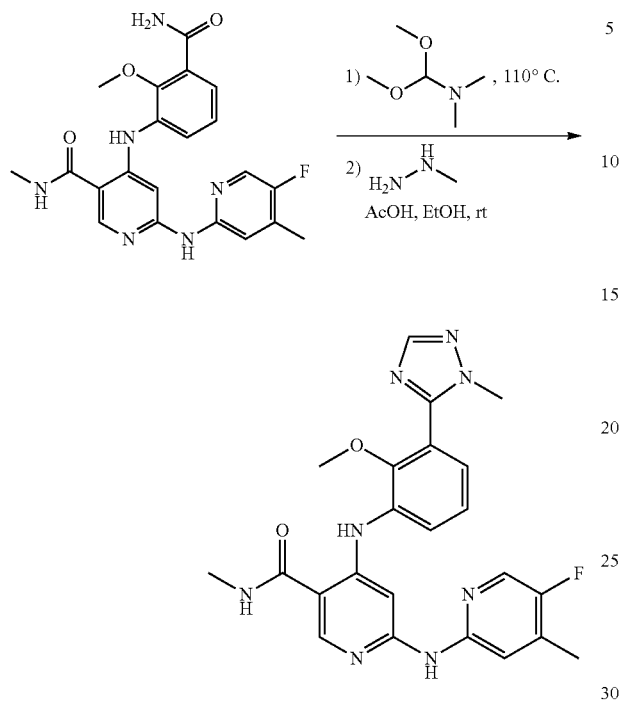

A slurry of Example 319 (30 mg, 0.071 mmol) in 1,1-dimethoxy-N,N-dimethylmethanamine (84 mg, 0.707 mmol) was heated to 110° C. giving a clear solution. Let stir at this temp. for 1 h, then the resulting solution was concentrated to remove the DMF-DMA and the resulting semi-solid residue was dissolved in ethanol (1.0 mL) and acetic acid (5.00 mL) to make clear solution followed by cooling the resulting mixture to 0° C. in an ice bath. At this time, methylhydrazine (16.28 mg, 0.353 mmol) was slowly added dropwise via syringe with good stirring to afford light pink slurry which was allowed to warm to room temperature and stir overnight (~16 h). HPLC and LCMS analysis of the resulting slurry indicated complete conversion to a clean triazole product near 2.46 minutes with expected MH+ of 463. Concentrated to remove ethanol and acetic acid, diluted with MeOH, and the mixture was purified by reverse-phase preparative HPLC [Conditions=Column: C18 PHENOMENEX® Luna Axia, 21×250 mm, Mobile Phase A: 5:95 acetonitrile:water with 10-mM ammonium acetate; Mobile Phase B: 95:5 acetonitrile:water with 10-mM ammonium acetate; Gradient: 20-100% B over 15 minutes. Flow: 20 mL/minutes.]. Fractions containing the desired product were combined and dried via centrifugal evaporation to afford Example 385 (15 mg, 0.030 mmol, 42.2% yield) as an off-white solid. HPLC RT (Method N)=2.48 minutes. LCMS (m+1)=463.2. $^1$H NMR (400 MHz, methanol-$d_4$) δ 8.43 (s, 1H), 8.11 (s, 1H), 8.03 (br. s., 1H), 8.01 (s, 1H), 7.88 (d, J=7.7 Hz, 1H), 7.78 (s, 1H), 7.43 (t, J=7.8 Hz, 1H), 7.34 (d, J=5.5 Hz, 1H), 7.29 (d, J=7.7 Hz, 1H), 3.86 (s, 3H), 3.59 (s, 3H), 2.97 (s, 3H), 2.35 (s, 3H).

Example 386

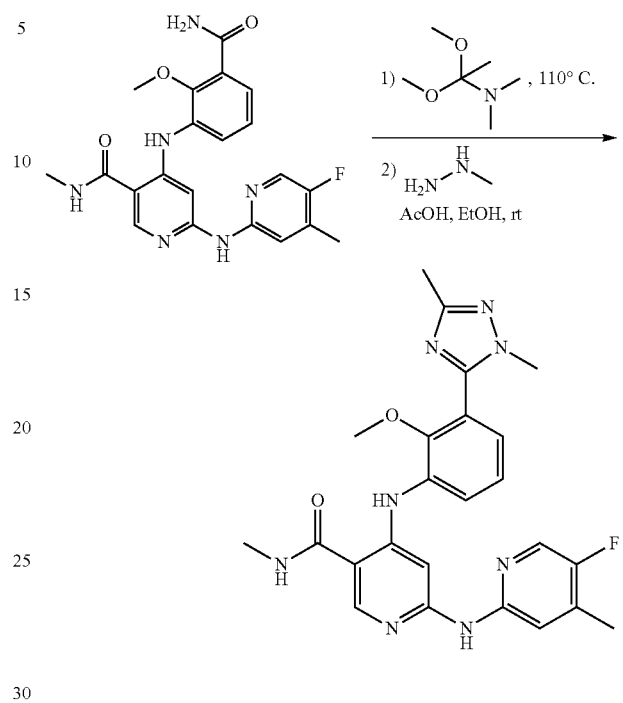

Example 386 was prepared from Example 319 using the same procedure as described for the preparation of Example 385 and replacing 1,1-dimethoxy-N,N-dimethylmethanamine with 1,1-dimethoxy-N,N-dimethylethanamine as a reagent. This afforded Example 386 in 10% yield as an off-white solid. HPLC RT (Method N)=2.52 minutes. LCMS (m+1)=477.4. $^1$H NMR (400 MHz, methanol-$d_4$) δ 8.40 (s, 1H), 7.99 (d, J=1.1 Hz, 1H), 7.84 (dd, J=8.1, 1.6 Hz, 1H), 7.74 (s, 1H), 7.40 (t, J=7.9 Hz, 1H), 7.31 (d, J=5.5 Hz, 1H), 7.26 (dd, J=7.7, 1.6 Hz, 1H), 3.76 (s, 3H), 3.58 (s, 3H), 2.94 (s, 3H), 2.43 (s, 3H), 2.33 (s, 3H).

Example 387

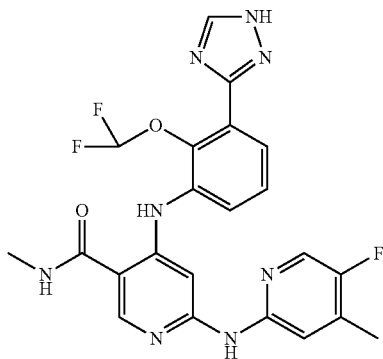 [SMILES: CNC(=O)c1cnc(Nc2cc(C)c(F)cn2)cc1Nc1cccc(-c2nc[nH]n2)c1OC(F)F]

Step 1

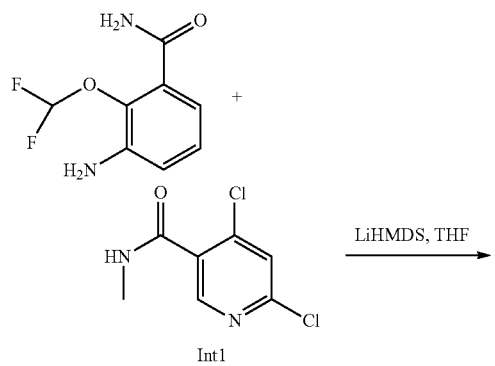

Step 2

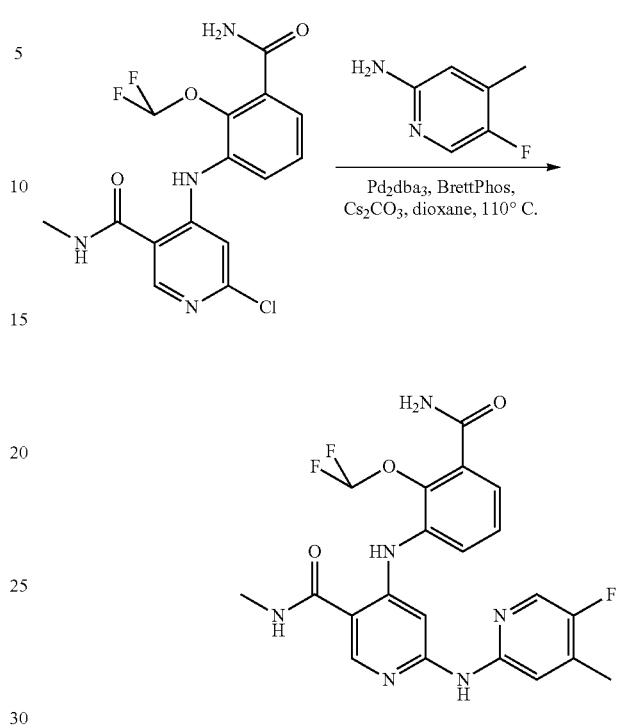

3-Amino-2-(difluoromethoxy)benzamide (Preparation 17, 155 mg, 0.768 mmol) and 4,6-dichloro-N-methylnicotinamide (Int1, 150 mg, 0.732 mmol) were dissolved in tetrahydrofuran (THF, 3 mL) at room temperature and the amber-colored solution was cooled in an ice bath whereupon LiHMDS (1 M in THF) (1.829 mL, 1.829 mmol) was added dropwise via syringe over ~1 minute. After addition was complete, the ice bath was removed and the reaction was allowed to stir at room temperature for ~15 minutes. LCMS analysis of the reaction mixture containing a dark brown semi-solid residue which adhered to the sides of the flask showed only ~60% conversion to the desired coupled product. Therefore, at this time, an additional amount of LiHMDS (1 M in THF) (1.829 mL, 1.829 mmol) was added dropwise while stirring at room temperature. This caused additional solid to precipitate from solution. The mixture was sonicated to give a dispersed heterogeneous slurry that was stirred at room temperature for an additional 15 minutes. The reaction was cooled in an ice bath and 1N HCl was added dropwise followed by removal of the THF on the rotovap giving a heterogeneous slurry of a thick oil, additional 1 M aq. HCl was added until the solution was acidic. The product was extracted into ethyl acetate (3×30 mL). The combined extracts were washed with brine, dried over anhydrous sodium sulfate, filtered, and concentrated under vacuum to afford 315 mg of a yellow brown solid as the crude product. This material was slurried in ~10 mL of dichloromethane and CELITE® was added followed by concentrating and dry loading onto a 12 g silica gel cartridge using dichloromethane/methanol mixture as the eluent. Fractions containing the major product were combined and concentrated to afford 155 mg (75%) of the desired product. LCMS MH+371.3.

A mixture of 4-((3-carbamoyl-2-(difluoromethoxy)phenyl)amino)-6-chloro-N-methylnicotinamide from Step 1 (155 mg, 0.418 mmol), 5-fluoro-4-methylpyridin-2-amine (79 mg, 0.627 mmol), BrettPhos (33.7 mg, 0.063 mmol) and cesium carbonate (272 mg, 0.836 mmol) in dioxane (3 mL) was sparged with nitrogen for a few minutes before adding Pd$_2$(dba)$_3$ (57.4 mg, 0.063 mmol) and heating to reflux in a preheated 115° C. oil bath. After 1.5 h, the reaction mixture was cooled and concentrated and the resulting solids were slurried in water (~10 mL) and 1 N aq. HCl was slowly added until pH was ~3. The resulting rust-brown colored solid was collected by vacuum filtration and air dried then slurried in dichloromethane, added CELITE® and concentrated. This material was dry loaded onto a 4 g silica gel column and eluted with dichloromethane/methanol in dichloromethane mixtures. Fractions containing the major product were concentrated to yield 135 mg (70%). LCMS MH+461.2.

Step 3

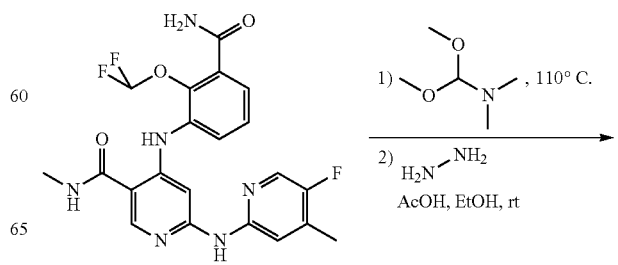

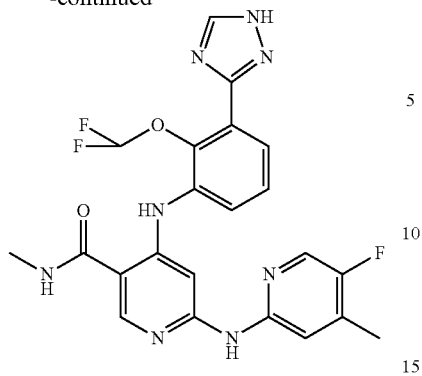

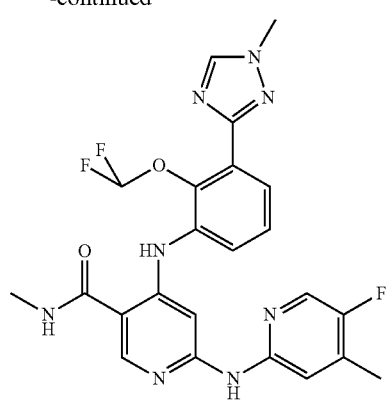

The product from Step 2 (135 mg, 0.293 mmol) and N,N-dimethylformamide dimethyl acetal (2 mL, 14.94 mmol) was refluxed at 110° C. for ~1 hour then the resulting mixture was cooled and concentrated under vacuum to afford a brown semi-solid to which was added ethanol (1.5 mL) and acetic acid (0.3 mL) followed by a slow dropwise addition of hydrazine (monohydrate) (0.091 mL, 2.93 mmol). The resulting mixture was allowed to stir at room temperature for ~2 hours giving a dark brown mixture. The reaction was cooled room temperature, and then water (~6 mL) was added dropwise. After stirring for ~5 minutes, the solid that had precipitated was collected by vacuum filtration and air dried in the funnel to afford 146 mg of a brown solid as the crude product. Approximately 40 mg of this material was dissolved in DMSO and was purified by reverse phase preparative LCMS. Fractions containing the desired product were combined and dried via centrifugal evaporation. The yield of the product Example 387 was 2.4 mg. LCMS (m+1)=484.2. HPLC (Method E) RT=1.34 minutes; HPLC (Method G) RT=1.11 minutes. $^1$H NMR (500 MHz, DMSO-$d_6$) δ 10.66 (br. s., 1H), 8.61-8.36 (m, 2H), 7.84-7.35 (m, 5H), 7.19-6.81 (m, 1H), 2.78 (d, J=4.4 Hz, 3H), 2.23 (s, 3H).

Example 388 and Example 389 were prepared from Example 387 using a similar method as previously described for the preparation of Example 366 and Example 367. This afforded Example 388 as the major product in 16% yield and Example 389 as the minor product in 5% yield. Example 388 (major): HPLC (Method E) RT=1.48 minutes; HPLC (Method G) RT=1.22 minutes. LCMS MH+498.2. $^1$H NMR (500 MHz, DMSO-$d_6$) δ 10.65 (s, 1H), 9.68 (s, 1H), 8.60 (s, 1H), 8.51-8.41 (m, 2H), 8.02 (s, 1H), 7.76-7.65 (m, 2H), 7.63-7.52 (m, 2H), 7.48 (t, J=7.9 Hz, 1H), 7.28-6.81 (m, 1H), 3.94 (s, 3H), 2.78 (d, J=4.3 Hz, 3H), 2.23 (s, 3H).

Example 389 (minor): HPLC (Method E) RT=1.46 minutes; HPLC (Method G) RT=1.18 minutes. LCMS MH+498.2. $^1$H NMR (500 MHz, DMSO-$d_6$) δ 10.74 (s, 1H), 9.73 (s, 1H), 8.50 (s, 2H), 8.06 (d, J=4.3 Hz, 2H), 7.83 (d, J=7.3 Hz, 1H), 7.64 (s, 1H), 7.61-7.52 (m, 2H), 7.34 (d, J=7.9 Hz, 1H), 7.04-6.62 (m, 1H), 3.76 (s, 3H), 2.77 (d, J=4.3 Hz, 3H), 2.24 (s, 3H).

Example 388 and Example 389

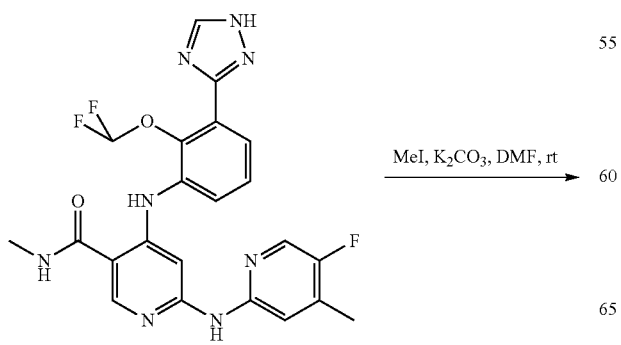

Example 390

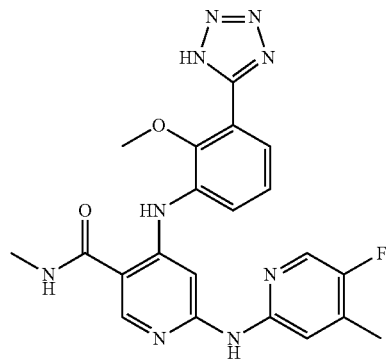 [SMILES: CNC(=O)c1cnc(Nc2cc(C)c(F)cn2)cc1Nc1cccc(-c2nnn[nH]2)c1OC]

Step 1

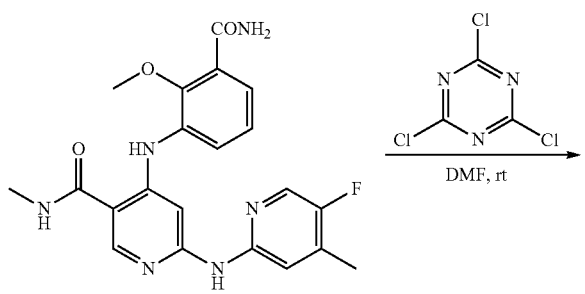

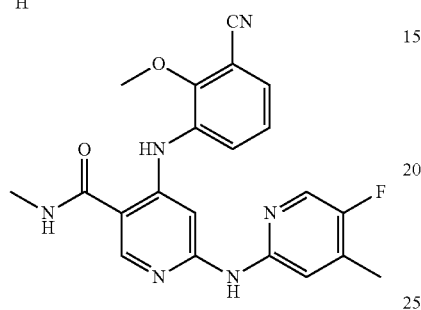

To solution of Example 319 (75 mg, 0.177 mmol) in DMF was added 2,4,6-trichloro-1,3,5-triazine (98 mg, 0.530 mmol) and the resulting mixture was allowed to stir for 3 hours before diluting with water causing a solid to precipitate. The slurry was stirred at room temperature for a few hours then the solid was collected and rinsed with water, dried on filter to afford the desired product as a bright yellow solid (60 mg, 0.148 mmol, 84% yield). HPLC RT (Method N)=2.56 minutes. LCMS (m+1)=407.

Step 2

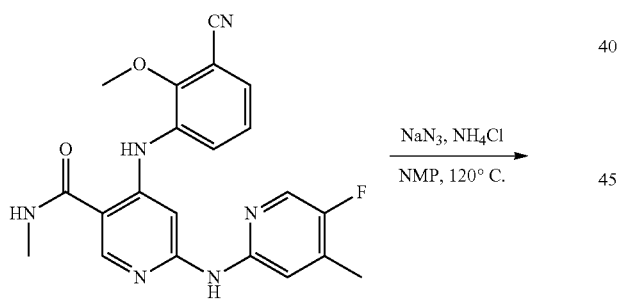

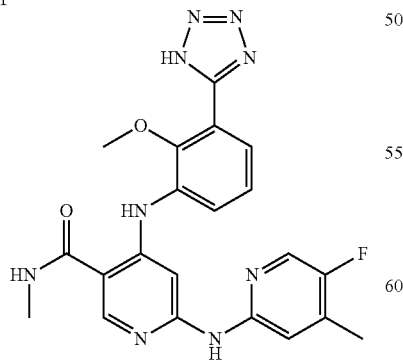

A slurry of the product from Step 1 (20 mg, 0.049 mmol), ammonium chloride (13.16 mg, 0.246 mmol) and sodium azide (16.00 mg, 0.246 mmol) in NMP was heated at 120° C. for 16 h then at 150° C. for 3 days. After cooling to room temperature, the reaction mixture was concentrated and diluted with ~2 mL of DMSO and the resulting solution was subjected to reverse phase LCMS purification. Fractions containing the desired product were combined and dried via centrifugal evaporation. The yield of the product, Example 390, was 2.0 mg (7%). HPLC (Method E) RT=1.68 minutes; HPLC (Method G) RT=1.17 minutes. LCMS MH+450.2. $^1$H NMR (500 MHz, DMSO-$d_6$) δ 10.59 (s, 1H), 9.95 (s, 1H), 8.42 (s, 1H), 8.16 (br. s., 1H), 7.79 (br. s., 1H), 7.59 (d, J=7.9 Hz, 1H), 7.18 (t, J=7.9 Hz, 2H), 4.49 (s, 3H), 2.82 (d, J=4.9 Hz, 3H), 2.28 (s, 3H).

Example 391 and Example 392

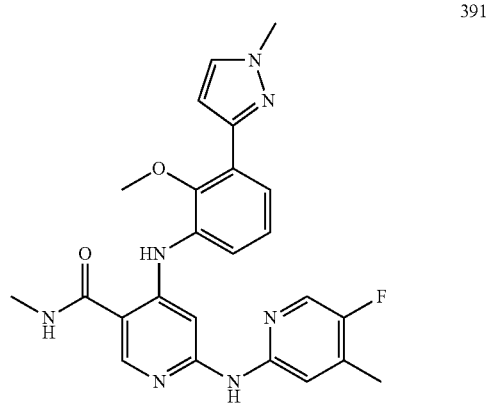

391

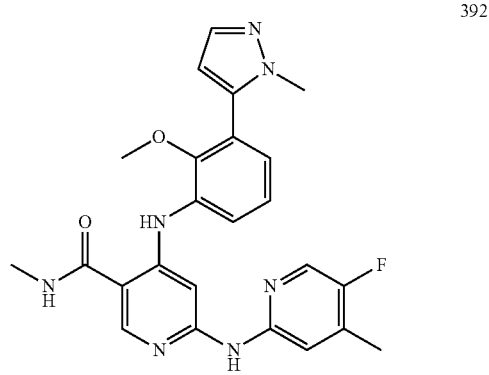

392

Step 1

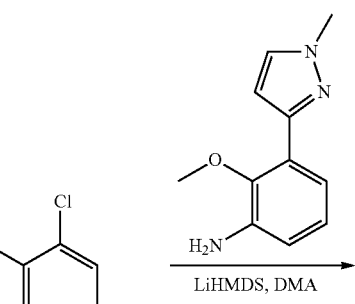

-continued

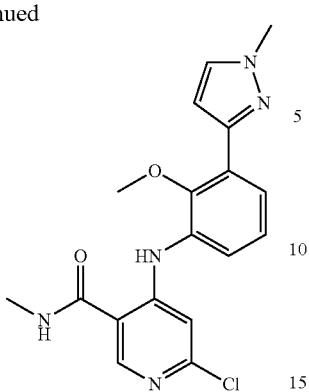

To a solution of 4,6-dichloro-N-methylnicotinamide (Int1, 110 mg, 0.536 mmol) and 2-methoxy-3-(1-methyl-1H-pyrazol-3-yl)aniline (Preparation 21, 120 mg, 0.590 mmol) in DMA (1 mL) was added LiHMDS (1 M in THF) (1.341 mL, 1.341 mmol) dropwise via syringe at room temperature over ~5 minutes. After 30 minutes at room temperature additional LiHMDS (1 M in THF) (0.6 mL, 0.6 mmol) was added and the mixture was stirred for an additional 30 minutes. Water was then added and the resulting mixture was concentrated to remove most of the volatile material. The resulting aqueous solution was acidified to a pH of ~4 by slowly adding 1N aq. HCl dropwise with stirring causing a solid to precipitate from solution. The resulting slurry was stirred at room temperature for ~1 h, then the solid was collected by vacuum filtration, rinsed with water and dried to afford a tan solid of the desired product (155 mg, 0.417 mmol, 78% yield) which contained ~20% of a minor regioisomer. HPLC RT (Method N)=3.04 (major) and 3.12 minutes (minor). LCMS (m+1)=372.2 for both regioisomers.

Step 2

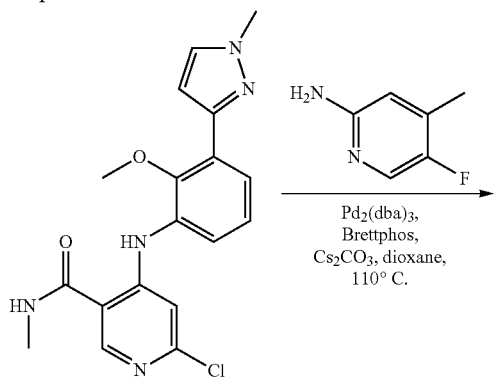

+

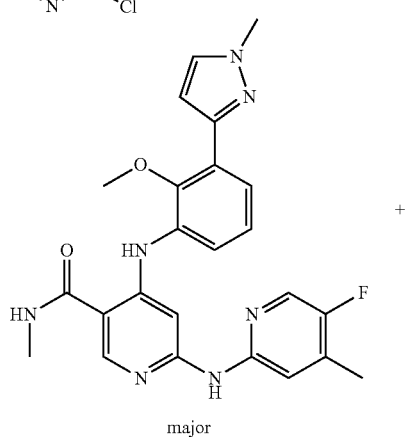

minor

-continued

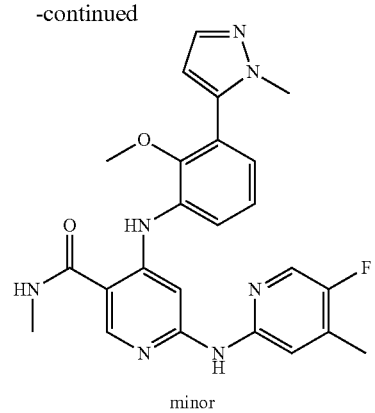

A mixture of the products from Step 1 (25 mg, 0.067 mmol), 5-fluoro-4-methylpyridin-2-amine (12.72 mg, 0.101 mmol), cesium carbonate (43.8 mg, 0.134 mmol) and 2-(dicyclohexylphosphino)3,6-dimethoxy-2',4',6'-triisopropyl-1,1'-biphenyl (BrettPhos, 5.41 mg, 10.09 μmol) in dioxane (0.5 mL) was sparged with nitrogen for 5 minutes, then $Pd_2(dba)_3$ (9.24 mg, 10.09 μmol) was added and the reaction was placed into a preheated 110° C. heating block for 1 h. The reaction was cooled to room temperature, diluted with DMSO, filtered through a Millipore (0.45 g), and was subjected to purification by reverse phase preparative LCMS. The yield of the major product, Example 391, was 13.2 mg (40%) and the yield of the minor product, Example 392, was 3.0 mg (9%).

Example 391 (major product): HPLC (Method E) RT=1.66 minutes; HPLC (Method G) RT=1.35 minutes. LCMS MH+462.2. $^1$H NMR (500 MHz, DMSO-$d_6$) δ 10.79-10.59 (m, 1H), 9.68 (s, 1H), 8.49 (d, J=4.9 Hz, 1H), 8.48 (s, 1H), 8.04 (s, 1H), 7.77 (d, J=1.8 Hz, 1H), 7.72 (s, 1H), 7.63-7.55 (m, 2H), 7.49 (d, J=7.9 Hz, 1H), 7.23 (t, J=7.9 Hz, 1H), 6.73 (d, J=2.4 Hz, 1H), 3.91 (s, 3H), 3.64-3.58 (m, 3H), 2.79 (d, J=4.3 Hz, 3H), 2.24 (s, 3H).

Example 392 (minor product): HPLC (Method E) RT=1.65 minutes; HPLC (Method G) RT=1.26 minutes. LCMS MH+462.2. $^1$H NMR (500 MHz, DMSO-$d_6$) δ 10.76 (s, 1H), 9.85 (br. s., 1H), 8.56 (br. s., 1H), 8.47 (s, 1H), 8.09 (s, 1H), 7.67 (d, J=8.5 Hz, 2H), 7.51 (s, 2H), 7.32 (t, J=7.6 Hz, 1H), 7.07 (d, J=7.3 Hz, 1H), 6.38 (s, 1H), 3.69 (s, 3H), 3.47 (br. s., 3H), 2.78 (d, J=3.7 Hz, 3H), 2.25 (s, 3H).

Example 393 and Example 394

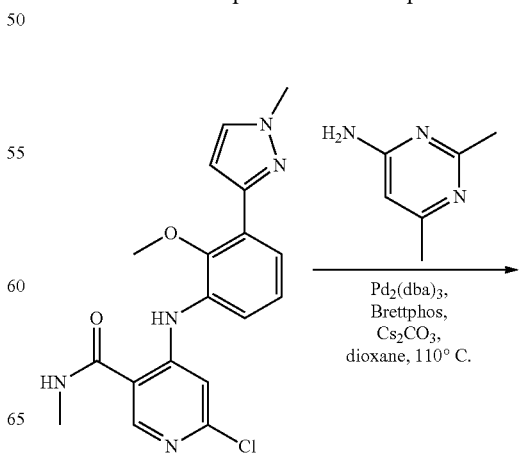

255
-continued major minor

Example 393 and Example 394 were prepared from the product of Step 1 in Example 391 and Example 392 using the similar procedure as described in Step 2 for the preparation of Example 391 and Example 392. This afforded Example 393 as the major product in 31% yield and Example 394 as the minor product in 12% yield.

Example 393 (major product): HPLC (Method E) RT=1.30 minutes; HPLC (Method G) RT=0.92 minutes. LCMS MH+459.2. $^1$H NMR (500 MHz, DMSO-d$_6$) δ 10.75 (s, 1H), 10.07 (br. s., 1H), 8.57 (d, J=4.3 Hz, 1H), 8.51 (s, 1H), 8.14 (br. s., 1H), 7.77 (d, J=1.8 Hz, 1H), 7.61 (d, J=7.9 Hz, 1H), 7.53 (d, J=7.9 Hz, 1H), 7.21 (t, J=7.9 Hz, 1H), 7.08 (br. s., 1H), 6.73 (d, J=1.8 Hz, 1H), 3.91 (s, 3H), 3.61 (s, 3H), 2.80 (d, J=4.3 Hz, 3H), 2.38 (s, 3H), 2.28 (s, 3H).

Example 394 (minor product): HPLC (Method E) RT=1.36 minutes; HPLC (Method G) RT=0.94 minutes. LCMS MH+459.2. $^1$H NMR (500 MHz, DMSO-d$_6$) δ 10.82 (s, 1H), 10.16 (br. s., 1H), 8.59 (d, J=4.3 Hz, 1H), 8.52 (s, 1H), 8.14 (br. s., 1H), 7.72 (d, J=7.9 Hz, 1H), 7.51 (d, J=1.8 Hz, 1H), 7.29 (t, J=7.9 Hz, 1H), 7.16-7.05 (m, 2H), 6.38 (d, J=1.2 Hz, 1H), 3.69 (s, 3H), 3.30 (s, 3H, overlapping with water peak), 2.79 (d, J=4.3 Hz, 3H), 2.42 (s, 3H), 2.30 (s, 3H).

256
Example 395

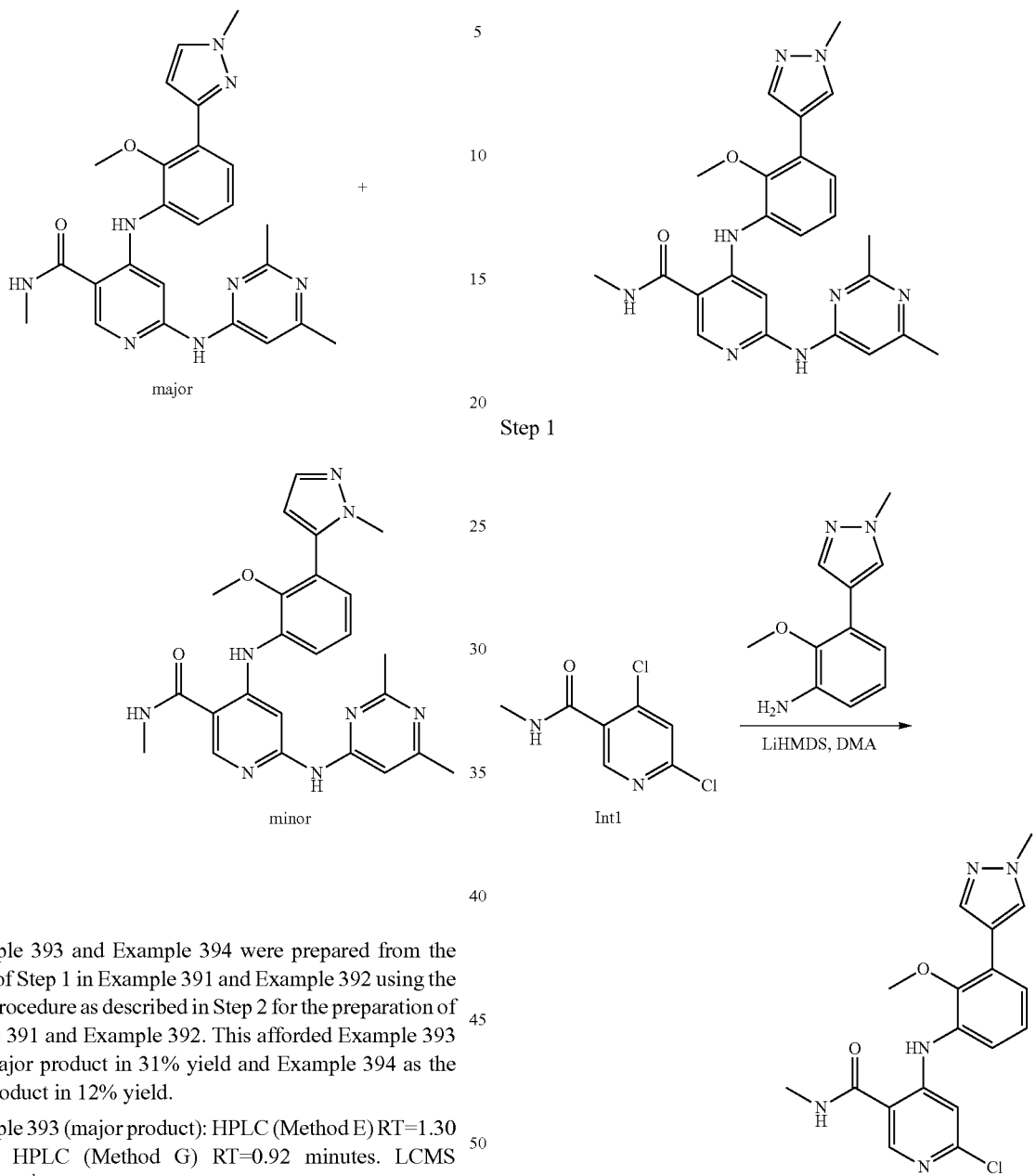

Step 1

To a solution of 4,6-dichloro-N-methylnicotinamide (Int1, 75 mg, 0.366 mmol) and 2-methoxy-3-(1-methyl-1H-pyrazol-4-yl)aniline (Preparation 22, (82 mg, 0.402 mmol) in DMA (1 mL) was added LiHMDS (1 M in THF) (1.280 mL, 1.280 mmol) dropwise via syringe at room temperature over ~5 minutes. The reaction was stirred at room temperature for 30 minutes then the mixture was cooled in an ice bath and water was added to form clear solution. The THF was removed under vacuum and 1N aq. HCl was added to adjust the pH of the aqueous portion to ~3 causing a solid to precipitate from solution. The mixture was diluted with water to a total volume of ~40 mL and the suspension was stirred at room temperature for ~1 h. The solid was collected by vacuum filtration, rinsed with water, and dried to afford a tan Step 2

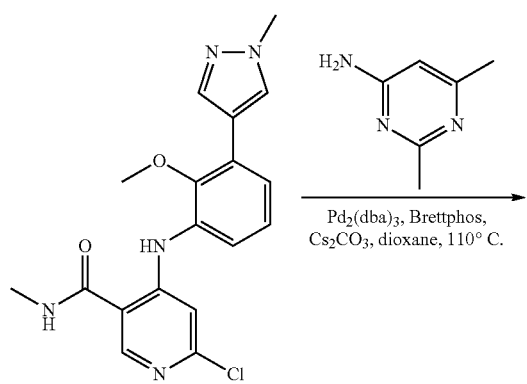

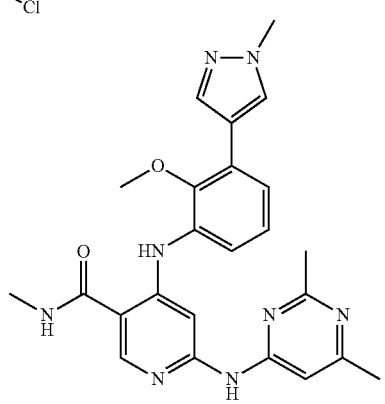

Example 395 was prepared using the similar procedure as described in Step 2 for the preparation of Example 391 and Example 392 to afford Example 395 in 65% yield. HPLC (Method E) RT=1.31 minutes; HPLC (Method G) RT=0.94 minutes. LCMS MH+459.2. $^1$H NMR (500 MHz, DMSO-$d_6$) δ 10.73 (s, 1H), 10.03 (s, 1H), 8.56 (d, J=4.9 Hz, 1H), 8.50 (s, 1H), 8.17 (s, 1H), 8.13 (br. s., 1H), 7.91 (s, 1H), 7.44 (d, J=7.9 Hz, 1H), 7.36 (d, J=7.9 Hz, 1H), 7.18 (t, J=7.9 Hz, 1H), 7.06 (s, 1H), 3.89 (s, 3H), 3.60 (s, 3H), 2.80 (d, J=4.3 Hz, 3H), 2.37 (s, 3H), 2.27 (s, 3H).

Example 396

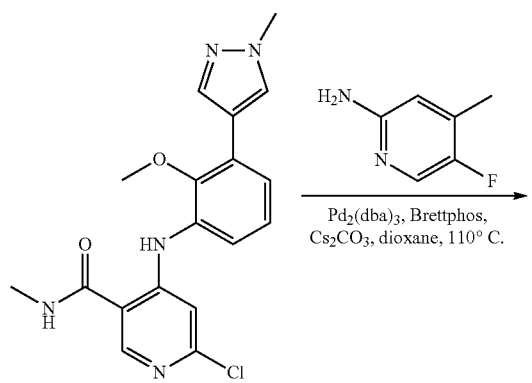

-continued

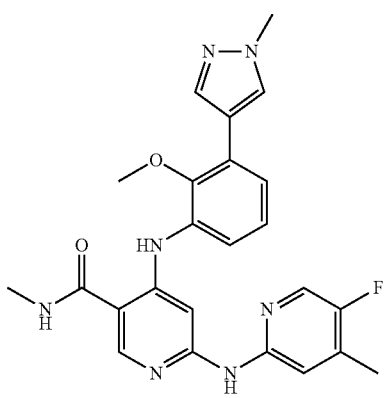

Example 396 was prepared using the similar procedure as described in Step 2 for the preparation of Example 391 and Example 392 to afford Example 396 in 62% yield. HPLC (Method E) RT=1.63 minutes; HPLC (Method G) RT=1.31 minutes. LCMS MH+461.2. $^1$H NMR (500 MHz, DMSO-$d_6$) δ 10.67 (s, 1H), 9.67 (s, 1H), 8.49 (d, J=4.9 Hz, 1H), 8.47 (s, 1H), 8.16 (s, 1H), 8.04 (s, 1H), 7.91 (s, 1H), 7.71 (s, 1H), 7.57 (d, J=6.1 Hz, 1H), 7.39 (d, J=7.9 Hz, 1H), 7.32 (d, J=7.3 Hz, 1H), 7.23-7.15 (m, 1H), 3.90 (s, 3H), 3.60 (s, 3H), 2.79 (d, J=4.9 Hz, 3H), 2.23 (s, 3H).

Example 397

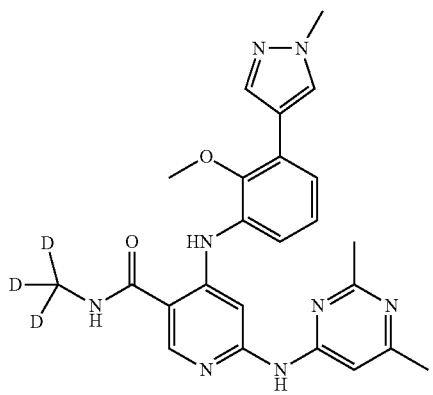 [SMILES: [2H]C([2H])([2H])NC(=O)c1cnc(Nc2cc(C)nc(C)n2)cc1Nc1cccc(-c2cnn(C)c2)c1OC]

Step 1

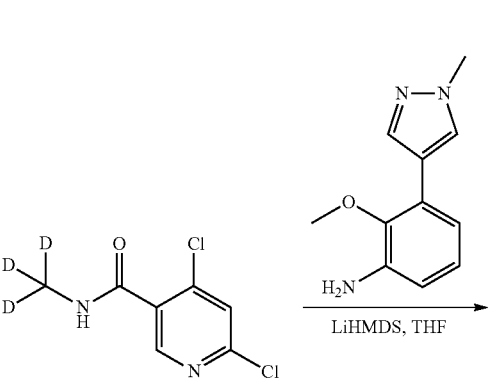

-continued

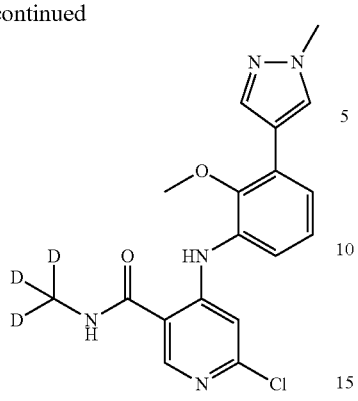

To a solution of 4,6-dichloro-N-trideutero-methylpyridazine-3-carboxamide (Preparation 22, 250 mg, 1.230 mmol) and 2-methoxy-3-(1-methyl-1H-pyrazol-4-yl)aniline (Preparation 23, 244 mg, 1.171 mmol) in THF (3 mL) at room temperature and the resulting solution was cooled in an ice bath whereupon LiHMDS (1 M in THF) (2.93 mL, 2.93 mmol) was added dropwise via syringe over ~1 minute. After addition was complete, the ice bath was removed and the reaction was allowed to stir at room temperature for ~15 minutes. The reaction was quenched with a few drops of methanol and the solution was allowed to stir at room temperature overnight. The reaction was concentrated and the resulting solid was dissolved into a minimal amount of dichloromethane (~5 mL) and purified using automated chromatography. Fractions containing product were concentrated and dried in vacuo to afford 356 mg (81%) of a pale yellow solid as the desired product. LCMS MH+375.
Step 2

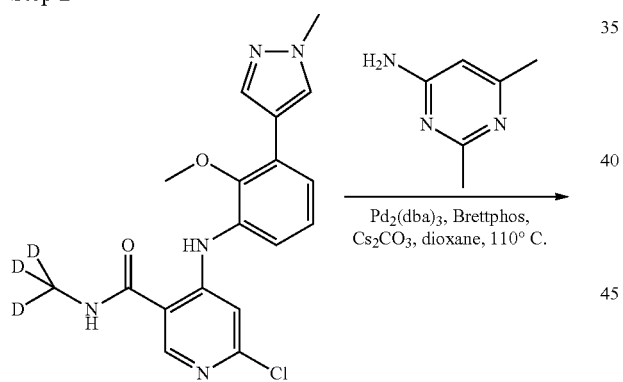

Example 397 was prepared from the product of the previous Step 1 using a similar procedure as described in Step 2 for the preparation of Example 391 and Example 392 to afford Example 397 in 65% yield. HPLC (Method E) RT=1.32 minutes; HPLC (Method G) RT=0.92 minutes. LCMS MH+462.3. $^1$H NMR (500 MHz, DMSO-d$_6$) δ 10.73 (s, 1H), 10.02 (s, 1H), 8.60-8.45 (m, 2H), 8.20-8.05 (m, 2H), 7.91 (s, 1H), 7.49-7.31 (m, 2H), 7.18 (t, J=7.9 Hz, 1H), 7.05 (br. s., 1H), 3.89 (s, 3H), 3.60 (s, 3H), 2.37 (s, 3H), 2.27 (s, 3H).

Example 398

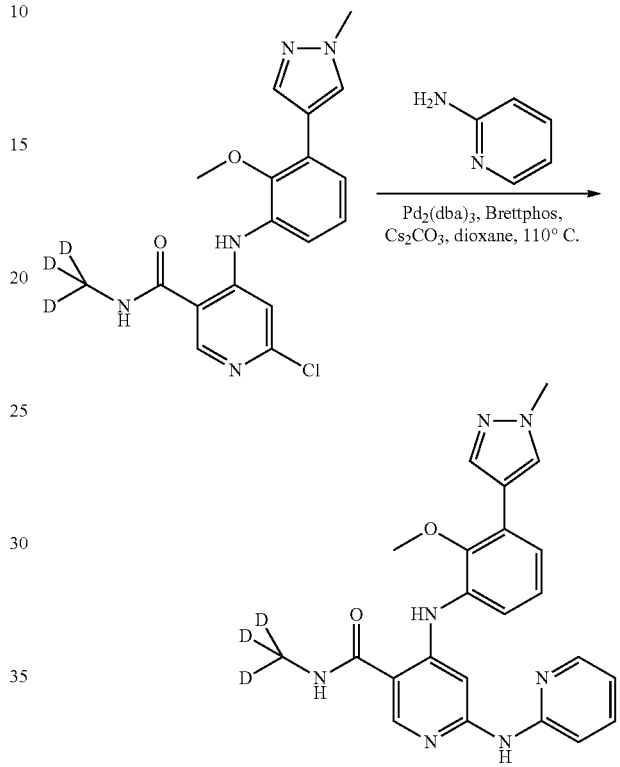

Example 398 was prepared from the product of Step 1 in Example 397 using a similar procedure as described in Step 2 for the preparation of Example 391 and Example 392 to afford Example 398 in 69% yield. HPLC (Method E) RT=1.41 minutes; HPLC (Method G) RT=1.23 minutes. LCMS MH+433.4. $^1$H NMR (500 MHz, DMSO-d$_6$) δ 10.65 (s, 1H), 9.66 (br. s., 1H), 8.47 (d, J=11.0 Hz, 2H), 8.14 (s, 2H), 7.92 (d, J=16.5 Hz, 2H), 7.67-7.57 (m, 1H), 7.52 (d, J=8.5 Hz, 1H), 7.43 (d, J=7.9 Hz, 1H), 7.31 (d, J=7.3 Hz, 1H), 7.24-7.13 (m, 1H), 6.85 (t, J=5.5 Hz, 1H), 3.89 (s, 3H), 3.60 (s, 3H).

Example 399

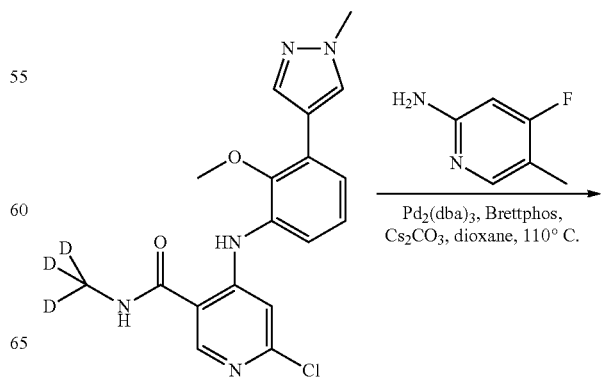

261

-continued

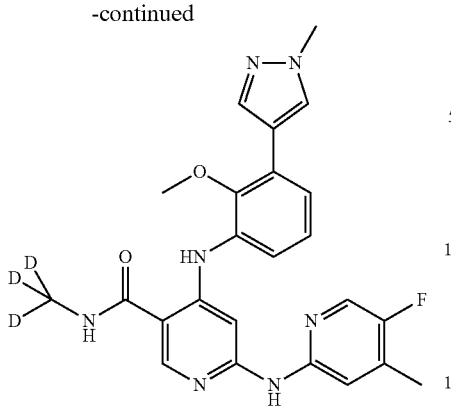

Example 399 was prepared from the product of Step 1 in Example 397 using a similar procedure as described in Step 2 for the preparation of Example 391 and Example 392 to afford Example 399 in 58% yield. HPLC (Method E) RT=1.63 minutes; HPLC (Method G) RT=1.32 minutes. LCMS MH+465.3. $^1$H NMR (500 MHz, DMSO-$d_6$) δ 10.65 (s, 1H), 9.65 (s, 1H), 8.46 (d, J=3.1 Hz, 2H), 8.15 (s, 1H), 8.02 (s, 1H), 7.91 (s, 1H), 7.70 (s, 1H), 7.55 (d, J=5.5 Hz, 1H), 7.39 (d, J=7.3 Hz, 1H), 7.32 (d, J=7.9 Hz, 1H), 7.25-7.14 (m, 1H), 3.89 (s, 3H), 3.59 (s, 3H), 2.23 (s, 3H).

Example 400

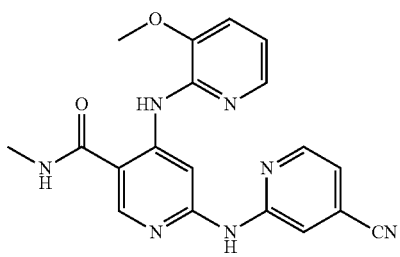 [SMILES: CNC(=O)c1cnc(Nc2cc(C#N)ccn2)cc1Nc1ncccc1OC]

Step 1

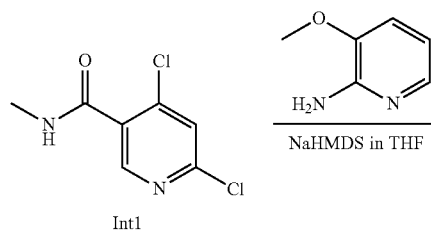

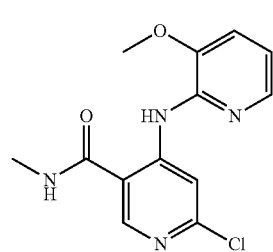

To a solution of 4,6-dichloro-N-methylnicotinamide (Int1, 100 mg, 0.488 mmol) and 3-methoxypyridin-2-amine (72.7

262 mg, 0.585 mmol) in DMA (1.5 mL) was added NaHMDS (1.0 M in THF) (1.463 mL, 1.463 mmol) dropwise via syringe at room temperature over ~5 minutes. The reaction was run for 4.5 hours and then slowly diluted with ~20 mL of water causing the product to precipitate. The solid was collected by vacuum filtration and rinsed with additional water. Drying afforded off-white solid as final product (35 mg, 0.120 mmol, 24% yield). HPLC RT (Method N)=3.14 minutes. LCMS (m+1)=293/295 (3:1).

Step 2

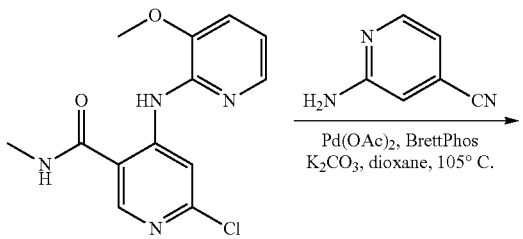

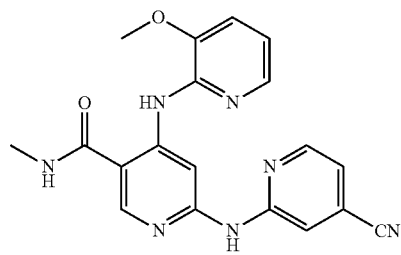

Example 400 was prepared from the product of Step 1 using a similar procedure as described in Step 2 for the preparation of Example 391 and Example 392 and by replacing cesium carbonate with potassium carbonate as the base to afford Example 400 in 23% yield. HPLC (Method E) RT=1.20 minutes; HPLC (Method G) RT=0.94 minutes. LCMS MH+406.1. $^1$H NMR (500 MHz, DMSO-$d_6$) δ 11.63 (s, 1H), 10.29 (s, 1H), 9.15 (s, 1H), 8.64-8.50 (m, 2H), 8.48 (d, J=5.0 Hz, 1H), 8.24 (s, 1H), 7.91 (dd, J=5.0, 1.0 Hz, 1H), 7.35 (dd, J=7.9, 1.0 Hz, 1H), 7.28 (dd, J=5.2, 1.2 Hz, 1H), 6.96 (dd, J=7.9, 5.0 Hz, 1H), 3.91 (s, 3H), 2.80 (d, J=4.5 Hz, 3H).

Example 401

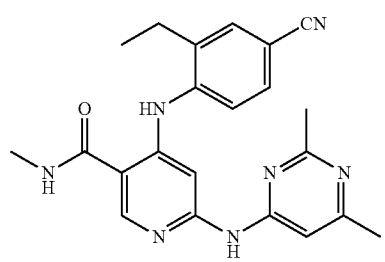

Step 1

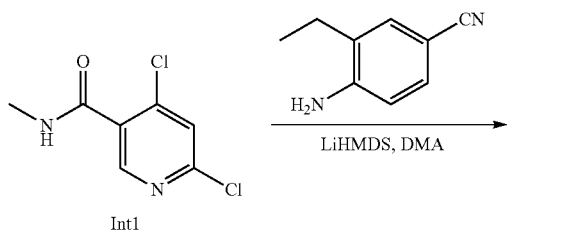

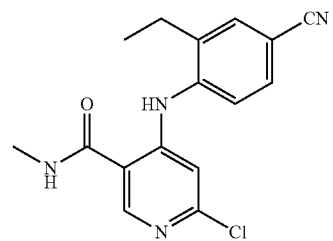

The coupling of Int1 and 4-amino-3-ethylbenzonitrile was performed similar to the previously described procedure in Step 1 of the preparation of Example 391 and Example 392. This afforded the desired product in 67% yield as an off-white solid. LCMS MH+436/438 (3:1).

Step 2

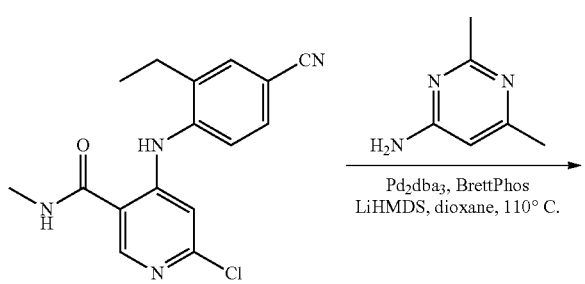

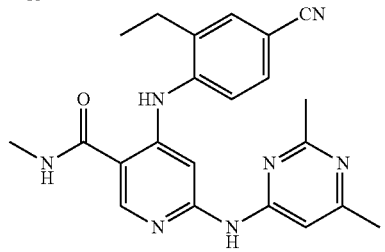

Step 2 was performed similar to the previously described procedure in Step 4 of Example 315 to afford a 53% yield of Example 401. HPLC (Method E) RT=1.47 minutes; HPLC (Method G) RT=1.05 minutes. LCMS (m+1)=401.2. $^1$H NMR (500 MHz, DMSO-$d_6$) δ 10.93 (br. s., 1H), 8.80 (br. s., 1H), 8.64 (s, 1H), 7.85-7.72 (m, 2H), 7.63 (d, J=8.4 Hz, 1H), 2.81 (d, J=4.4 Hz, 3H), 2.66 (d, J=7.7 Hz, 2H), 2.54 (s, 3H), 2.45 (br. s., 3H), 1.19 (t, J=7.4 Hz, 3H).

Example 402

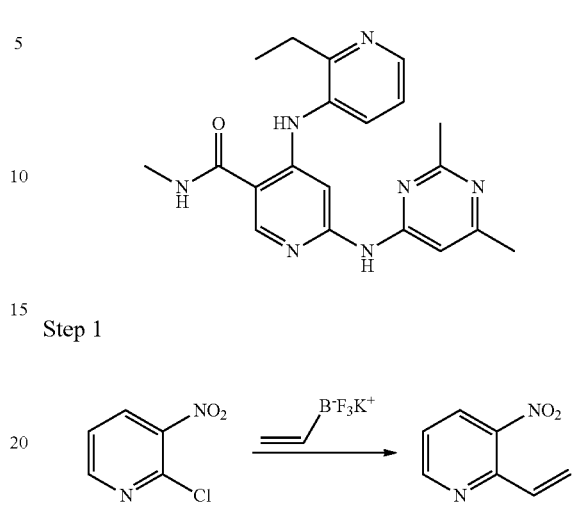

Step 1

A solution of 2-chloro-3-nitropyridine (0.20 g, 1.261 mmol), potassium trifluoro(vinyl)borate (0.203 g, 1.514 mmol) and PdCl$_2$(dppf) (0.018 g, 0.025 mmol) dissolved in isopropanol (4 mL) and triethylamine (0.211 mL, 1.514 mmol) was gently purged with stream of nitrogen for a few minutes then heated at 100° C. for 4 h. The reaction was cooled and filtered through CELITE® and the solvent was removed under vacuum. The resulting residue was purified via automated flash chromatography (40 gram silica gel, hex/ethyl acetate). Fractions containing the desired product were collected, combined, and evaporated in vacuo to afford tan oil as final product, 3-nitro-2-vinylpyridine (100 mg, 0.666 mmol, 52.8% yield). HPLC RT (Method N)=1.75 minutes.

Step 2

To 3-nitro-2-vinylpyridine from Step 1 (100 mg, 0.666 mmol) in methanol (5 ml) was added 30 mg of 10% palladium on charcoal. The flask was evacuated and supplied with hydrogen gas from a balloon while stirring the mixture. After 4 h at room temperature, the hydrogen balloon was removed and reaction was flushed with nitrogen to deactivate the catalyst then the mixture was filtered through CELITE® and concentrated to remove the solvent to afford the desired product (46 mg, 0.377 mmol, 56.5% yield) as an off-white solid.

Step 3

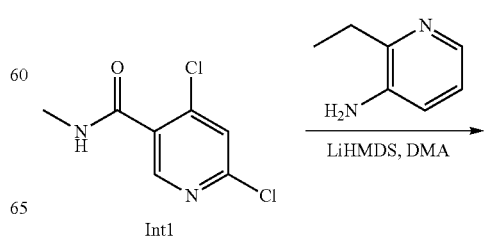

-continued

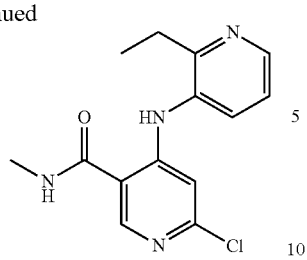

To a solution of 4,6-dichloro-N-methylnicotinamide (Int1, 70 mg, 0.341 mmol) and 2-ethylpyridin-3-amine from Step 2 (45.9 mg, 0.376 mmol) in DMA (1 mL) was added LiHMDS (1 M in THF) (0.853 mL, 0.853 mmol) dropwise via syringe at room temperature over ~5 minutes. The reaction was stirred at room temperature for 2 hours and then crushed ice was added, the slurry was stirred for 30 minutes, and then the pH was adjusted with aqueous 1N HCl to ~1. The resulting solution was concentrated to remove the THF and then stirred at 0° C. for two hours resulting in the precipitation of a beige solid. The solid was collected by vacuum filtration, rinsed with water, and dried on the filter to afford tan solid as the desired product (75 mg, 0.258 mmol, 76% yield). HPLC RT (Method N)=1.38 minutes. LCMS (m+1)=291.1.

Step 4

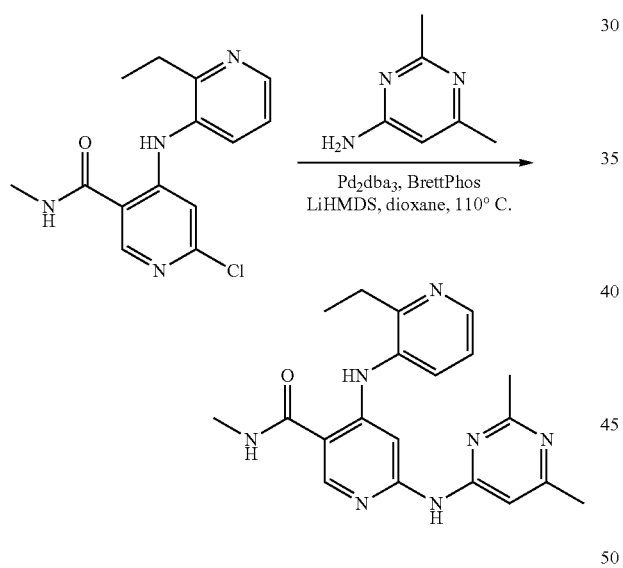

A reaction vial was charged with the product from Step 3 (15 mg, 0.052 mmol), 2,6-dimethylpyrimidin-4-amine (8.90 mg, 0.072 mmol), 2-(dicyclohexylphosphino)3,6-dimethoxy-2',4',6'-triisopropyl-1,1'-biphenyl (BrettPhos, 4.15 mg, 7.74 µmol) and Pd$_2$(dba)$_3$ (4.72 mg, 5.16 µmol) and the contents were flushed with nitrogen before adding dioxane (0.3 mL). The resulting slurry was sparged with additional nitrogen for ~1 minutes, then LiHMDS (1 M in THF) (0.114 mL, 0.114 mmol) was added and the resulting dark amber colored solution was heated in a preheated heating block at 110° C. for 1 h, then cooled to room temperature. The reaction mixture was quenched with 0.1 mL of MeOH, concentrated to remove THF and diluted with DMF, filtered through a Millipore filter and was purified by reverse phase preparative LCMS. Fractions containing the desired product were combined and dried via centrifugal evaporation. The yield of the product was 17.9 mg (88%). HPLC (Method E) RT=1.20 minutes; HPLC (Method G) RT=0.64 minutes. LCMS (m+1)=378.2. $^1$H NMR (500 MHz, DMSO-d$_6$) δ 10.51 (s, 1H), 9.99 (br. s., 1H), 8.65-8.50 (m, 2H), 8.37 (d, J=4.0 Hz, 1H), 7.79 (d, J=8.1 Hz, 1H), 7.69 (br. s., 1H), 7.33 (dd, J=8.1, 4.7 Hz, 1H), 7.02 (br. s., 1H), 2.82-2.70 (m, 5H), 2.26 (s, 6H), 1.20 (t, J=7.6 Hz, 3H).

Example 403

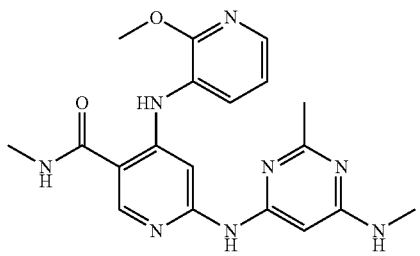

Step 1

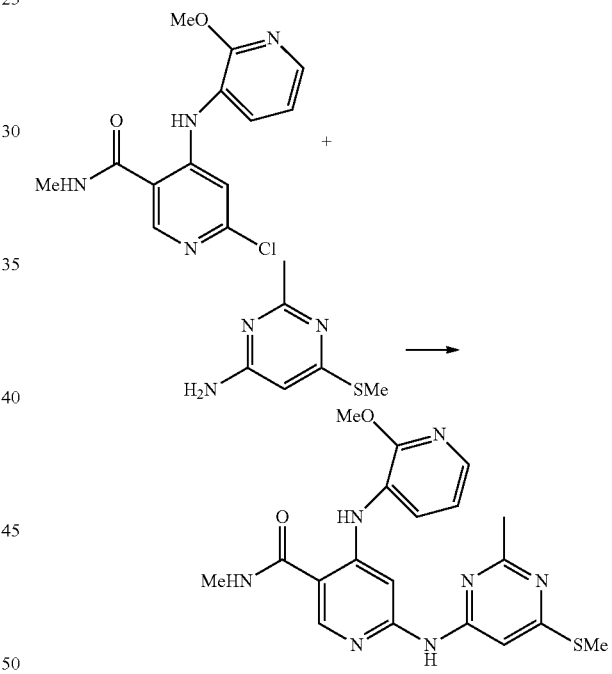

To a 100 mL reaction tube was added 6-chloro-4-((2-methoxypyridin-3-yl)amino)-N-methylnicotinamide from Step 1 of Example 313 (260 mg, 0.888 mmol), 2-methyl-6-(methylthio)pyrimidin-4-amine (207 mg, 1.332 mmol) followed by Pd$_2$(dba)$_3$ (81 mg, 0.089 mmol) and 2-(dicyclohexylphosphino)3,6-dimethoxy-2',4',6'-triisopropyl-1,1'-biphenyl (BrettPhos, 95 mg, 0.178 mmol) and the resulting mixture was dissolved in dioxane (10 mL) and was flushed with nitrogen for ~10 minutes. To the reaction mixture was added LiHMDS (446 mg, 2.66 mmol) and the reaction was heated to 110° C. for 5 hours. After cooling to room temperature, the crude reaction mixture was coated onto CELITE® and was purified through flash column chromatography to afford fractions containing the desired product (210 mg, 0.510 mmol, 57.5% yield) as an off-white solid. LCMS MH+412.0.

Step 2

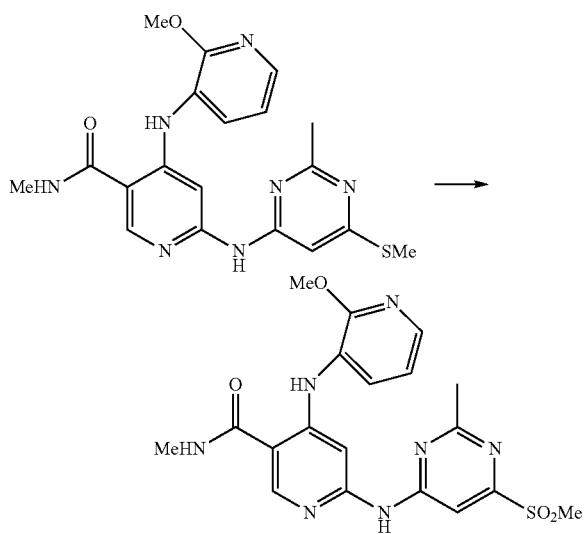

To a solution of the product from Step 1 (210 mg, 0.510 mmol) in acetic acid (5 mL) at room temperature was added sodium tungstate dihydrate (168 mg, 0.510 mmol) followed by hydrogen peroxide solution (0.313 mL, 10.21 mmol). The resulting reaction mixture was stirred at room temperature for 1 hour and then the reaction was quenched with water and extracted with ethyl acetate. The organic phase was dried over anhydrous sodium sulfate and concentrated under reduce pressure to afford the desired product (200 mg, 0.451 mmol, 88% yield) as a yellow solid. LCMS MH+444.2.

Step 3

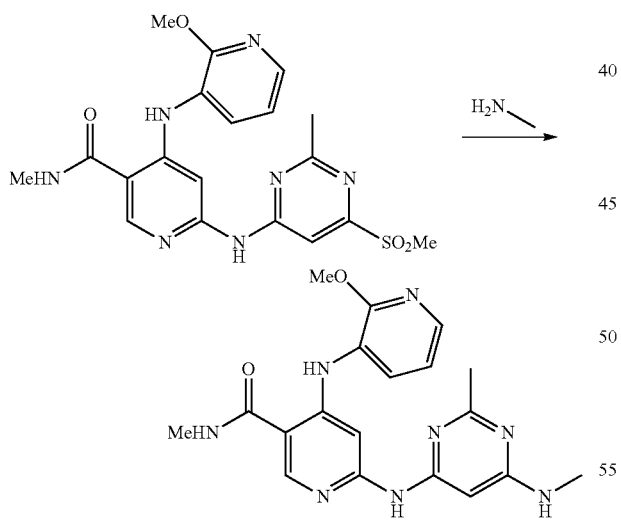

In a sealed tube, a solution of the product from Step 2 (50 mg, 0.113 mmol) and methylamine (10.50 mg, 0.338 mmol) in THF (2 mL) was heated for 100° C. for 24 hours. After cooling to room temperature, the solvent was evaporated under reduced pressure and the product was partitioned between water and chloroform. The organic phase was dried over anhydrous sodium sulfate, filtered, concentrated and then purified by reverse phase preparative HPLC to afford the product, Example 403 (3.5 mg, 8.87 μmol, 7.87% yield). LC retention time 8.98 [O]. MS(E+) m/z: 395 (MH+). $^1$H NMR (400 MHz, DMSO-$d_6$) δ 10.54 (s, 1H), 9.54 (s., 1H), 8.50 (bs, 1H), 8.46 (s, 1H), 7.92 (br. s, 1H), 7.86 (m, 2H), 7.03 (dd, J=7.6, 4.8 Hz, 1H), 6.87 (br. s., 1H), 6.36 (br. s., 1H), 3.95 (s, 3H), 2.78 (d, J=4.4 Hz, 3H), 2.72 (d, J=4.8 Hz, 3H), 2.23 (s, 3H).

Example 404

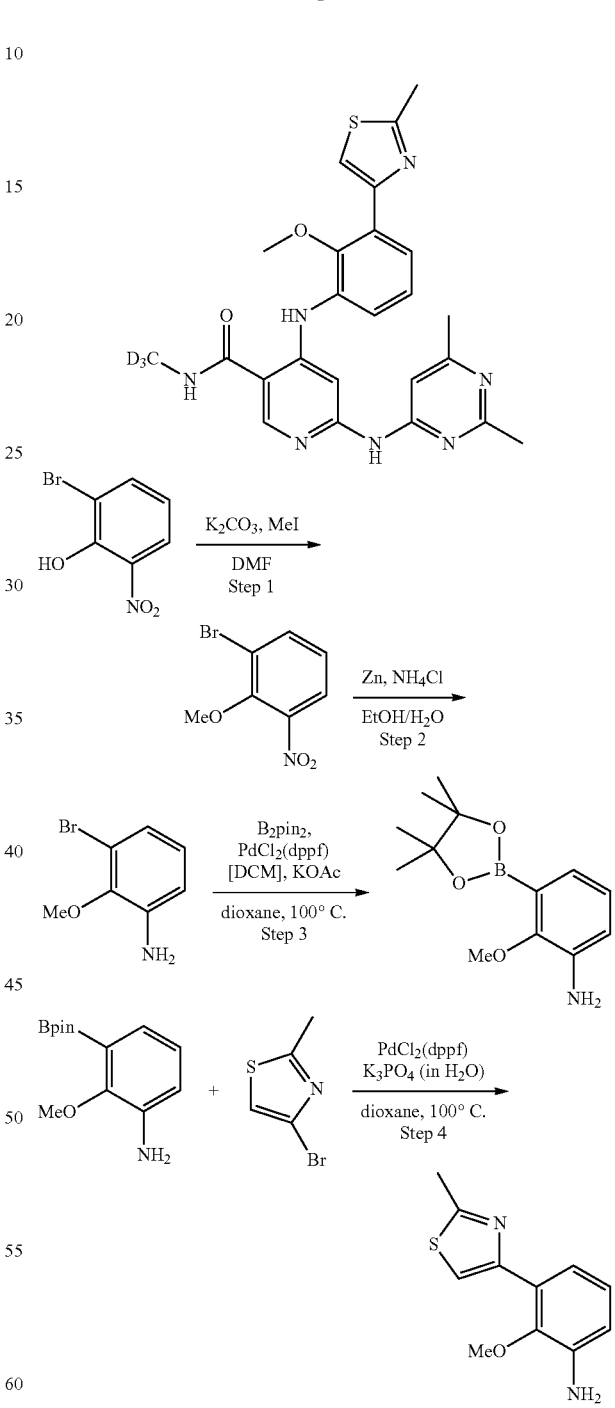

Step 1

2-Bromo-6-nitrophenol (5.0 g, 22.9 mmol) was dissolved in DMF (3 mL), potassium carbonate (4.75 g, 34.4 mmol) was added and the reaction was stirred for 30 minutes. Next iodomethane (2.15 mL, 34.4 mmol) was added and the reaction was stirred overnight. The crude reaction was filtered, diluted with ethyl acetate and washed with brine (twice) and water (twice). The organic layer was dried over sodium sulfate, filtered and concentrated to provide 1-bromo-2-methoxy-3-nitrobenzene (5.12 g, 96%). LC retention time 0.92 [J].

Step 2

1-Bromo-2-methoxy-3-nitrobenzene (5.12 g, 22.1 mmol) was dissolved in ethyl alcohol (150 mL) and water (50 mL). To this was added zinc (5.77 g, 88 mmol) and ammonium chloride (2.36 g, 44.1 mmol). The reaction was stirred for 1 hour, filtered and then concentrated. The crude material was dissolved in ethyl acetate and washed with water three times, the organic layer was then dried over sodium sulfate, filtered, concentrated and collected (4.3 g, 96%). LC retention time 0.75 [J]. m/z: 201.8 (MH$^+$).

Step 3

3-Bromo-2-methoxyaniline (2.0 g, 9.9 mmol) was dissolved in dioxane (40 mL) and the vessel purged with nitrogen for 5 minutes. Next bis(pinacolato)diborone (3.77 g, 14.85 mmol), [1,1'-bis(diphenylphosphino)ferrocene]dichloropalladium (II) complex with dichloromethane (404 mg, 0.49 mmol) and potassium acetate (2.91 g, 29.7 mmol) were added. The flask was evacuated and backfilled with nitrogen, and then heated to 100° C. for 15 hours. Water was added to quench the reaction and the product was then extracted with EtOAc. The combined organic layers were washed with brine (×3), dried over sodium sulfate, filtered, concentrated and purified using automated chromatography (elutes at ~40% ethyl acetate) to provide 2-methoxy-3-(4,4,5,5-tetramethyl-1,3,2-dioxaborolan-2-yl)aniline (2.0 g, 81%). $^1$H NMR (400 MHz, chloroform-d) δ 7.12 (dd, J=7.3, 1.8 Hz, 1H), 6.96-6.89 (m, 1H), 6.88-6.83 (m, 1H), 3.82 (s, 3H), 1.37 (s, 12H). LC retention time 0.65 [J]. m/z: 250 (MH$^+$).

Step 4

A stirred mixture of 4-bromo-2-methylthiazole (128 mg, 0.719 mmol), 2-methoxy-3-(4,4,5,5-tetramethyl-1,3,2-dioxaborolan-2-yl)aniline (197 mg, 0.791 mmol) and 1,1'-bis(di-tert-Butylphosphino)ferrocene palladium dichloride (14.06 mg, 0.022 mmol) in dioxane (4 mL) was degassed by bubbling nitrogen through the mixture for 5 minutes. To this was added aqueous potassium phosphate (K$_3$PO$_4$, 2M, 1.078 mL, 2.157 mmol) and the reaction mixture was heated to 100° C. for one hour. The reaction mixture was cooled to room temperature, then diluted with ethyl acetate (75 mL). This solution was then dried over sodium sulfate, filtered, concentrated and purified by flash chromatography, eluting with 0-100% EtOAc in hexanes. Afforded 2-methoxy-3-(2-methylthiazol-4-yl)aniline (122 mg, 0.543 mmol, 75% yield) as a yellow oil. LC retention time 0.60 [J]. m/z: 221 (MH$^+$).

Step 5

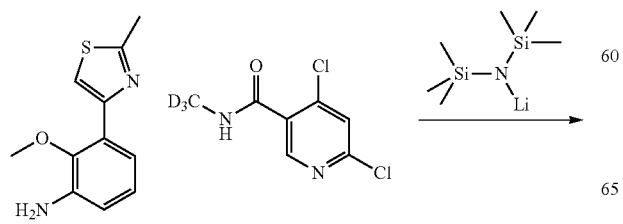

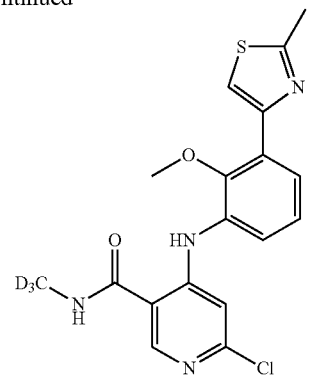

To a solution of 4,6-dichloro-N-trideuteromethylpyridazine-3-carboxamide (80 mg, 0.385 mmol) and 2-methoxy-3-(2-methylthiazol-4-yl)aniline (89 mg, 0.404 mmol) in tetrahydrofuran (3 mL) was added lithium bis(trimethylsilyl)amide (1M in THF, 0.961 mL, 0.961 mmol) in a dropwise manner (<2 min) using a needle and syringe, the reaction was for 10 minutes and then HCl (1M aqueous) (0.577 mL, 0.577 mmol) was added to quench the residual base. Then the reaction was partitioned between ethyl acetate and water. The water layer was extracted once with ethyl acetate, and then the combined organic layers were washed with saturated ammonium chloride and brine. The organic layer was then dried over sodium sulfate, filtered and concentrated to afford the crude product as a tan solid. The crude product was purified using automated chromatography to afford 6-chloro-4-((2-methoxy-3-(2-methylthiazol-4-yl)phenyl)amino)-N-trideuteromethylnicotinamide (119 mg, 0.298 mmol, 77% yield) as an off-white solid. $^1$H NMR (400 MHz, chloroform-d) δ 10.24 (s, 1H), 8.32 (s, 1H), 7.95 (dd, J=7.8, 1.7 Hz, 1H), 7.81 (s, 1H), 7.32-7.29 (m, 1H), 7.25-7.20 (m, 1H), 7.03 (s, 1H), 6.30 (br. s., 1H), 3.69 (s, 3H), 2.79 (s, 3H).

Step 6

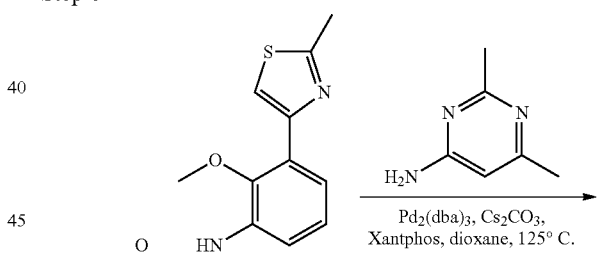

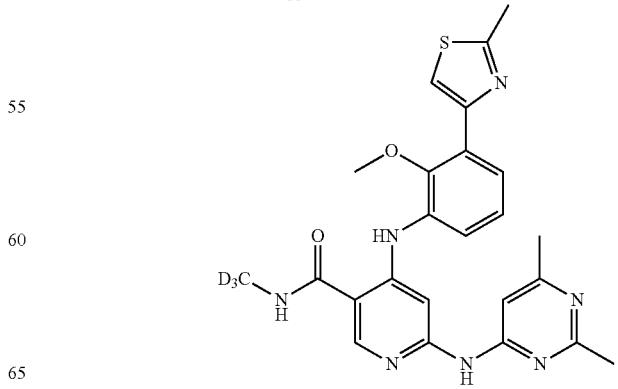

A solution of 6-chloro-4-((2-methoxy-3-(2-methylthiazol-4-yl)phenyl)amino)-N-trideuteromethylnicotinamide (16 mg, 0.041 mmol), Xantphos (4.72 mg, 8.17 μmol), and 2,6-dimethylpyrimidin-4-amine (10.06 mg, 0.082 mmol) in dioxane (1 mL) was degassed by bubbling nitrogen through the solution for 5 minutes. Then cesium carbonate (53.2 mg, 0.163 mmol) and $Pd_2(dba)_3$ (3.74 mg, 4.08 μmol) were added, the vessel was sealed, and the reaction was stirred at 125° C. for 75 minutes. The reaction was diluted with dichloromethane, filtered and concentrated. The material was then re-dissolved in DMF and purified via preparative LC/MS. Fractions containing the desired product were combined and dried via centrifugal evaporation to afford 6-((2,6-dimethylpyrimidin-4-yl)amino)-4-((2-methoxy-3-(2-methylthiazol-4-yl)phenyl)amino)-N-trideuteromethylnicotinamide (6.1 mg, 0.013 mmol, 30.9% yield). $^1$H NMR (500 MHz, DMSO-$d_6$) δ 10.78 (s, 1H), 10.05 (s, 1H), 8.56 (s, 1H), 8.53 (s, 1H), 8.14 (br. s., 1H), 7.99 (s, 1H), 7.82 (d, J=7.7 Hz, 1H), 7.58 (d, J=7.7 Hz, 1H), 7.28 (t, J=7.9 Hz, 1H), 7.08 (br. s., 1H), 3.66 (s, 3H), 2.74 (s, 3H), 2.38 (s, 3H), 2.28 (s, 3H). LC retention time 1.50 [E]. MS($E^+$) m/z: 479 (MH$^+$).

Example 405

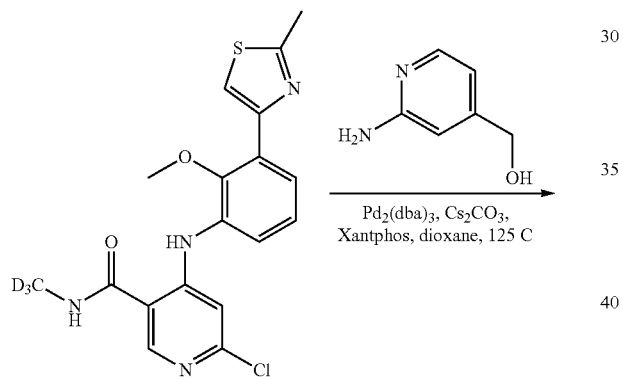

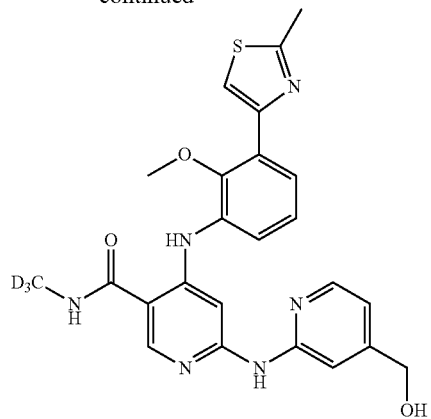

6-((4-(Hydroxymethyl)pyridin-2-yl)amino)-4-((2-methoxy-3-(thiazol-4-yl)phenyl)amino)-N-trideuteromethylnicotinamide (2.6 mg) was prepared and purified in the identical manner to Example 404, except substituting (2-aminopyridin-4-yl)methanol in place of the 2,6-dimethylpyrimidin-4-amine. $^1$H NMR (500 MHz, DMSO-$d_6$) δ 11.17 (d, J=13.5 Hz, 1H), 10.77 (s, 1H), 8.91 (br. s., 1H), 8.49 (s, 1H), 8.26 (d, J=5.4 Hz, 1H), 8.00 (s, 2H), 7.49 (d, J=7.4 Hz, 1H), 7.38-7.33 (m, 1H), 7.10 (d, J=16.8 Hz, 2H), 6.77 (br. s., 1H), 4.58 (s, 2H), 3.68 (s, 3H), 3.45 (br. s., 1H), 2.74 (s, 3H). LC retention time 1.47 [E]. MS($E^+$) m/z: 480 (MH$^+$).

The following Examples were prepared in a similar manner to the product of Example 63:

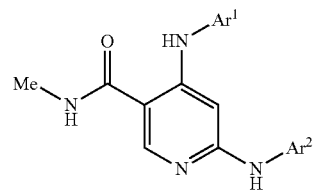

| Example No. | Ar$^1$ | Ar$^2$ | Rt (min) [Method] | m/z [M + H]$^+$ |
|---|---|---|---|---|
| 406 | 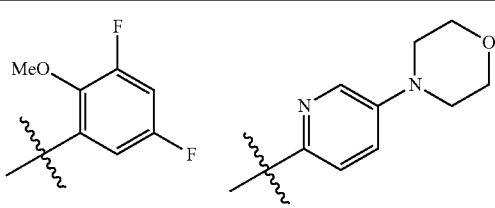 | | 1.65 [E] | 471 |
| 407 | 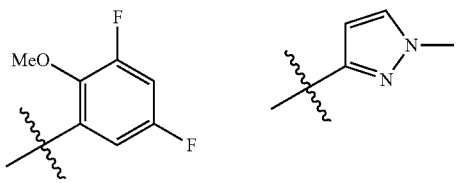 | | 1.53 [E] | 389 |

-continued

| Example No. | Ar¹ | Ar² | Rt (min) [Method] | m/z [M + H]⁺ |
|---|---|---|---|---|
| 408 | MeO, F, F (phenyl) | N-isopropyl pyrazole | 1.77 [E] | 417 |
| 409 | MeO, F, F (phenyl) | 2,6-dimethylpyrimidine | 1.51 [E] | 415 |
| 410 | MeO, F (phenyl) | 2,6-dimethylpyrimidine | 1.39 [E] | 397 |

The following Examples were prepared in a similar manner to the product of Example 303:

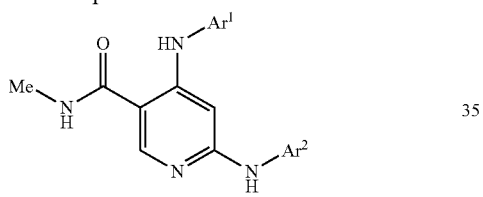

| Example No. | Ar¹ | Ar² | Rt (min) [Method] | m/z [M + H]⁺ |
|---|---|---|---|---|
| 411 | MeO₂S, phenyl with pyrrolidine amide | 5-fluoro-4-methylpyridine | 1.34 [E] | 527 |
| 412 | MeO₂S, phenyl with N,N-dimethyl amide | 5-fluoro-4-methylpyridine | 1.26 [E] | 501 |
| 413 | MeO₂S, phenyl with 3,3-difluoroazetidine amide | 5-fluoro-4-methylpyridine | 1.45 [E] | 549 |

The following Examples were prepared in a similar manner to the product of Example 1:

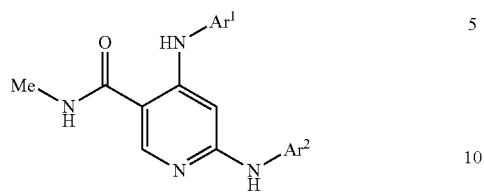

| Example No. | Ar¹ | Ar² | Rt (min) [Method] | m/z [M + H]⁺ |
|---|---|---|---|---|
| 414 | 2-MeO₂S-phenyl | 6-methylpyridazin-3-yl | 1.08 [E] | 413 |
| 415 | 2-MeO₂S-phenyl | 5,6-dimethylpyridazin-3-yl | 1.15 [E] | 427 |
| 416 | 2-MeO₂S-phenyl | 5,6-dimethylpyrazin-2-yl | 1.30 [E] | 427 |
| 417 | 2-MeO₂S-phenyl | 1,6-naphthyridin-2-yl | 1.20 [E] | 449 |
| 418 | 2-MeO₂S-phenyl | 2-methyl-6-(methoxymethyl)pyrimidin-4-yl | 1.12 [E] | 457 |
| 419 | 2-MeO₂S-phenyl | 6-methoxypyrimidin-4-yl | 1.17 [E] | 429 |
| 420 | 2-MeO₂S-phenyl | 6-ethylpyrimidin-4-yl | 1.15 [E] | 427 |

| Example No. | Ar¹ | Ar² | Rt (min) [Method] | m/z [M + H]⁺ |
|---|---|---|---|---|
| 421 | MeO₂S-phenyl | tert-butyl-pyrimidine | 1.49 [E] | 455 |
| 422 | MeO₂S-phenyl | isopropoxy-pyrimidine | 1.53 [E] | 457 |
| 423 | MeO₂S-phenyl | 2-methyl-pyrimidine-NH-(CH₂)₃-NEt₂ | 0.96 [E] | 541 |
| 424 | MeO₂S-phenyl | pyrimidine-NH-CH₂-Ph | 1.42 [E] | 504 |
| 425 | MeO₂S-phenyl | pyrimidine-N(CH₃)-CH₂-Ph | 1.67 [E] | 518 |

Intermediate 39

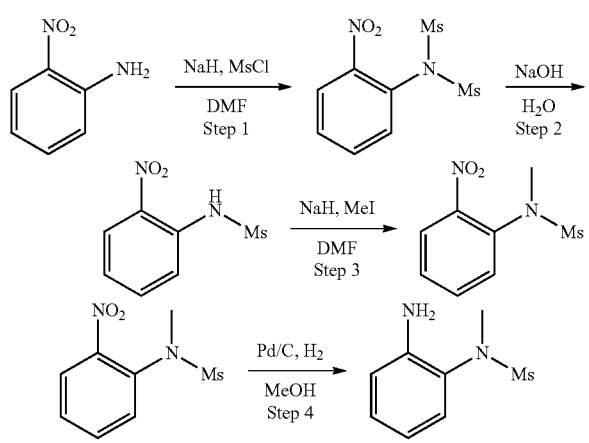

Step 1

To a cooled (0° C.) solution of 2-nitroaniline (1 g, 7.25 mmol) in dimethylformamide (DMF, 10 mL) was added sodium hydride (608 mg, 25 mmol). After addition was complete methanesulfonyl chloride (1.69 mL, 21.8 mmol) was added and the reaction was warmed to room temperature and stirred for 1 hour. The reaction was then diluted with water and the product extracted with ethyl acetate. The organic layer was concentrated and purified by chromatography to provide N-(methylsulfonyl)-N-(2-nitrophenyl)methanesulfonamide (1.5 g, 70% yield). ¹H NMR (400 MHz, DMSO-$d_6$) δ 8.17 (s, 1H), 7.89 (m, 1H), 7.80 (m, 2H), 3.58 (s, 6H).

Step 2

N-(Methylsulfonyl)-N-(2-nitrophenyl)methanesulfonamide (1.5 g, 5.1 mmol) was dissolved in 3N aqueous sodium hydroxide solution (10 mL) and stirred at 90° C. overnight. The crude reaction was acidified, to pH ~2, using aqueous hydrochloric acid solution resulting in the product precipitating out. The solid was collected via filtration and carried on. ¹H NMR (400 MHz, DMSO-$d_6$) δ 9.79 (s, 1H), 8.03 (dd, J=8.4, 1.6 Hz, 1H), 7.75 (m, 1H), 7.65 (dd, J=8.4, 1.2 Hz, 1H), 7.42 (m, 1H), 3.15 (s, 3H).

Step 3

To a cooled (0° C.) solution of N-(2-nitrophenyl)methanesulfonamide (50 mg, 0.231 mmol) in DMF (2 mL) was added sodium hydride (11 mg, 0.46 mmol) and the reaction was warmed to room temperature and stirred for 20 minutes. The reaction was then re-cooled to 0° C. and iodomethane (0.029 mL 0.46 mmol) was added. The reaction was warmed to room temperature and stirred for 3 hours. The crude reaction was concentrated and purified by silica gel chromatography to provide N-methyl-N-(2-nitrophenyl)methanesulfonamide (20 mg, 38% yield). ¹H NMR (300 MHz, CDCl₃) δ 7.91 (m, 1H), 7.70-7.50 (m, 3H), 3.34 (s, 3H), 3.01 (s, 3H).

Step 4

To a solution of N-methyl-N-(2-nitrophenyl)methanesulfonamide (900 mg, 3.91 mmol) in methanol (5 mL) was added palladium on carbon (10% by weight, 416 mg, 0.39 mmol). The solution was purged with hydrogen and then stirred for 4 hours under 1 atm of hydrogen. The crude reaction was filtered, concentrated and purified by chromatography to provide N-(2-aminophenyl)-N-methylmethanesulfonamide (540 mg, 60% yield). Product not characterized.

Intermediate 40

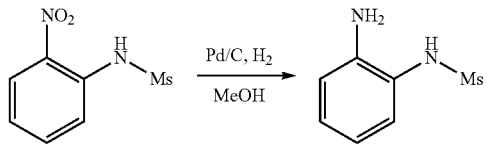 [SMILES: "MeOH" ; CS(=O)(=O)Nc1ccccc1[N+](=O)[O-] ; CS(=O)(=O)Nc1ccccc1N]

To a solution of N-(2-nitrophenyl)methanesulfonamide (800 mg, 3.70 mmol) in methanol (20 mL) was added palladium on carbon (10% by weight, 394 mg, 0.37 mmol). The vessel was purged with hydrogen and then stirred for 4 hours under 1 atm of hydrogen. The reaction was filtered, concentrated and purified by chromatography to provide N-(2-aminophenyl)methanesulfonamide (600 mg, 87% yield). $^1$H NMR (300 MHz, DMSO-$d_6$) δ 8.67 (bs, 1H), 7.05 (dd, J=7.8, 1.5 Hz, 1H), 6.98 (m, 1H), 6.73 (dd, J=7.8, 1.5 Hz, 1H), 6.54 (m, 1H), 5.11 (bs, 2H), 2.90 (s, 3H).

The following Examples were prepared using Intermediates 39 and 40 and in a manner to the product of Example 184:

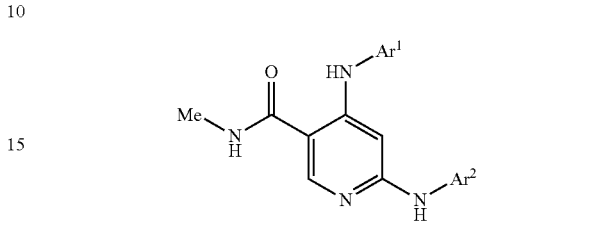

| Example No. | Ar$^1$ | Ar$^2$ | Rt (min) [Method] | m/z [M + H]$^+$ |
|---|---|---|---|---|
| 426 | 2-(N-methyl-methanesulfonamido)phenyl | 5-fluoropyridin-2-yl | 5.28 [F] | 445 |
| 427 | 2-(methanesulfonamido)phenyl | 4-fluoropyridin-2-yl | 5.66 [P] | 431 |
| 428 | 2-(methanesulfonamido)phenyl | pyridin-2-yl | 5.61 [P] | 413 |
| 429 | 2-sulfamoylphenyl | 5-fluoropyridin-2-yl | 4.83 [F] | 417 |
| 430 | 2-sulfamoylphenyl | pyridin-2-yl | 5.37 [P] | 399 |

| Example No. | Ar¹ | Ar² | Rt (min) [Method] | m/z [M + H]⁺ |
|---|---|---|---|---|
| 431 | 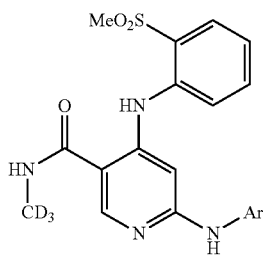 | 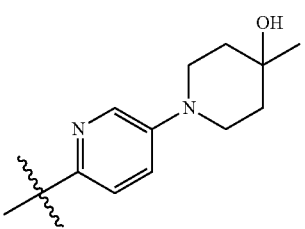 [SMILES: *c1ccc(N2CCC(C)(O)CC2)cn1] | 6.28 [P] | 431 |
The following Examples were prepared in a similar manner to the product of Example 1, employing 4,6-dichloro-N-trideutero-methylpyridazine-3-carboxamide (Preparation 22) instead of Int1:
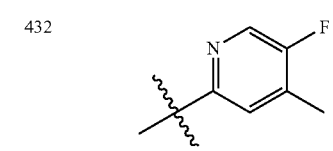
| Example No. | Ar | Rt (min) [Method] | m/z [M + H]⁺ |
|---|---|---|---|
| 432 | 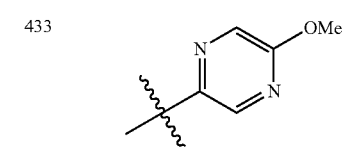 | 1.44 [E] | 433 |
| 433 | 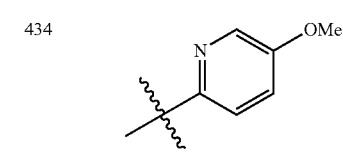 | 1.28 [E] | 432 |
| 434 | 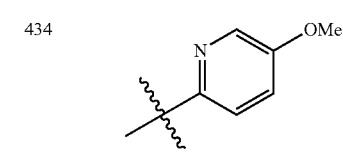 | 1.08 [G] | 431 |
| 435 | 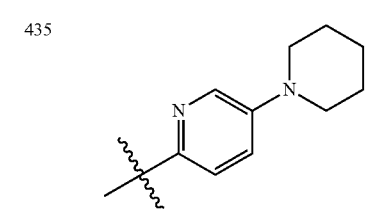 | 1.61 [E] | 484 |
| 436 | 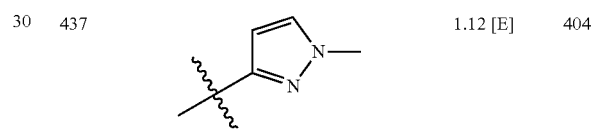 | 1.18 [E] | 514 |
| 437 | 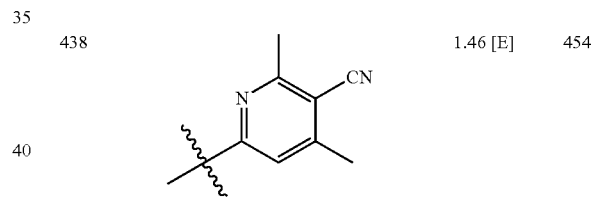 | 1.12 [E] | 404 |
| 438 | 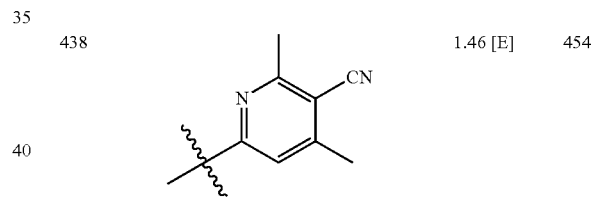 | 1.46 [E] | 454 |
| 439 | 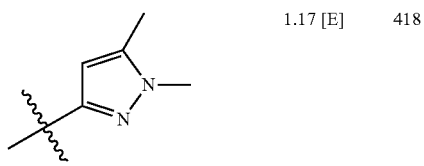 | 1.17 [E] | 418 |
| 440 | 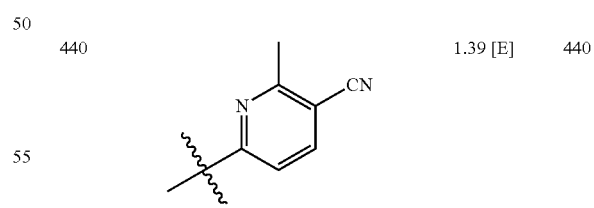 | 1.39 [E] | 440 |
| 441 | 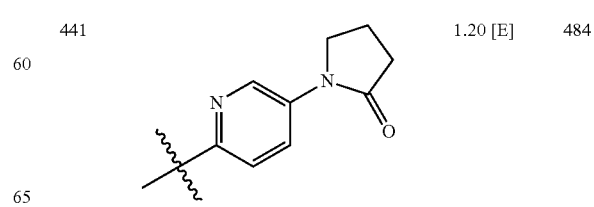 | 1.20 [E] | 484 |

| Example No. | Ar | Rt (min) [Method] | m/z [M + H]+ |
|---|---|---|---|
| 442 | (1-isopropyl-pyrazol-3-yl) | 1.32 [E] | 432 |
| 443 | (2,4-dimethylpyridin-6-yl) | 1.45 [E] | 429 |
| 444 | (3-ethoxypyridazin-6-yl) | 1.29 [E] | 446 |
| 445 | (5-cyclobutyl-1H-pyrazol-3-yl) | 1.33 [E] | 444 |
| 446 | (1-(4-chlorophenyl)-1H-pyrazol-3-yl) | 1.67 [E] | 500 |
| 447 | (5-cyano-4-methylpyridin-2-yl) | 1.31 [E] | 440 |

The following Examples were prepared in a manner to the product of Example 404:

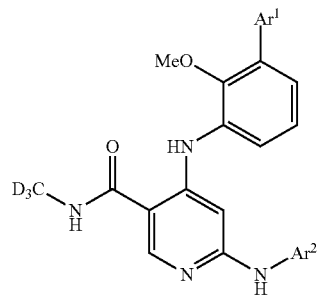

| Example No. | Ar¹ | Ar² | Rt (min) [Method] | m/z [M + H]+ |
|---|---|---|---|---|
| 448 | (2-methylthiazol-4-yl) | (6-methylpyridazin-3-yl) | 1.40 [E] | 465 |
| 449 | (5-fluoropyrimidin-2-yl) | (pyridin-2-yl) | 0.69 [J] | 449 |
| 450 | (5-fluoropyrimidin-2-yl) | (4-(2-hydroxypropan-2-yl)pyridin-2-yl) | 0.69 [J] | 507 |

| Compound | ¹H NMR (methanol-d₄ equates CDCl₃:MeOD ~1:1 unless otherwise noted) Occasionally water suppression is used in DMSO-d₆ spectra |
|---|---|
| 2 | ¹H NMR (500 MHz, DMSO-d₆) δ 10.94 (s, 1H), 10.18 (s, 1H), 8.67 (s, 1H), 8.60 (s, 1H), 8.56 (d, J = 4.5 Hz, 1H), 8.11 (d, J = 8.9 Hz, 1H), 8.02 (d, J = 7.4 Hz, 1H), 7.95 (s, 1H), 7.93-7.87 (m, 2H), 7.75 (d, J = 6.9 Hz, 1H), 7.62-7.56 (m, 1H), 7.50 (ddd, J = 8.3, 5.8, 2.7 Hz, 1H), 7.39-7.27 (m, 3H), 3.17 (s, 3H), 2.80 (d, J = 4.5 Hz, 3H) |
| 3 | ¹H NMR (500 MHz, DMSO-d₆) δ 10.84 (s, 1H), 9.77 (br. s., 1H), 8.53 (s, 2H), 8.10 (br. s., 1H), 7.94 (d, J = 7.9 Hz, 1H), 7.78 (d, J = 3.5 Hz, 2H), 7.65 (br. s., 1H), 7.49 (br. s., 1H), 7.38 (br. s., 1H), 6.86 (br. s., 1H), 3.17 (s, 3H), 2.78 (d, J = 4.5 Hz, 3H) |
| 4 | ¹H NMR (500 MHz, DMSO-d₆) δ 10.83 (s, 1H), 9.67 (br. s., 1H), 8.57-8.47 (m, 2H), 8.01-7.89 (m, 2H), 7.84-7.71 (m, 3H), 7.42-7.24 (m, 2H), 6.70 (d, J = 5.0 Hz, 1H), 3.16 (s, 3H), 2.77 (d, J = 4.5 Hz, 3H), 2.24 (s, 3H) |
| 5 | ¹H NMR (500 MHz, DMSO-d₆) δ 10.83 (s, 1H), 10.17 (s, 1H), 8.59 (s, 1H), 8.55 (d, J = 4.5 Hz, 1H), 8.35 (d, J = 5.0 Hz, 1H), 8.11 (s, 1H), 7.98-7.91 (m, 1H), 7.82-7.71 (m, 2H), 7.51 (s, 1H), 7.43-7.35 (m, 1H), 7.25 (dd, J = 5.0, 1.5 Hz, 1H), 3.16 (s, 3H), 2.78 (d, J = 4.5 Hz, 3H) |
| 6 | ¹H NMR (500 MHz, methanol-d₄) δ 8.36 (s, 1H), 7.97 (d, J = 3.0 Hz, 1H), 7.67 (d, J = 8.4 Hz, 1H), 7.56 (d, J = 3.0 Hz, 1H), 7.52 (s, 1H), 7.45-7.38 (m, |

| Compound | ¹H NMR (methanol-d₄ equates CDCl₃:MeOD ~1:1 unless otherwise noted) Occasionally water suppression is used in DMSO-d₆ spectra |
|---|---|
|  | 1H), 7.32 (dd, J = 9.2, 3.7 Hz, 1H), 7.27 (dd, J = 8.9, 3.0 Hz, 1H), 3.92 (s, 3H), 3.12 (s, 3H), 2.94 (s, 3H) |
| 7 | ¹H NMR (500 MHz, DMSO-d₆) δ 10.56 (s, 1H), 9.41 (s, 1H), 8.47 (s, 1H), 8.42 (q, J = 4.5 Hz, 1H), 7.78 (d, J = 3.0 Hz, 1H), 7.63 (d, J = 8.4 Hz, 1H), 7.50 (d, J = 9.4 Hz, 1H), 7.43-7.34 (m, 3H), 7.31 (s, 1H), 3.86 (s, 3H), 3.78-3.69 (m, 4H), 3.14 (s, 3H), 3.06-2.97 (m, 4H), 2.76 (d, J = 5.0 Hz, 3H) |
| 8 | ¹H NMR (500 MHz, DMSO-d₆) δ 10.67 (s, 1H), 8.87 (br. s., 1H), 8.49 (s, 1H), 8.31 (br. s., 1H), 7.87 (br. s., 1H), 7.63 (d, J = 8.9 Hz, 1H), 7.50 (d, J = 3.0 Hz, 1H), 7.45 (dd, J = 8.9, 3.0 Hz, 1H), 7.13 (br. s., 2H), 3.90 (s, 3H), 3.23 (s, 3H), 2.82 (d, J = 5.0 Hz, 3H) |
| 9 | ¹H NMR (500 MHz, DMSO-d₆) δ 10.82 (s, 1H), 9.51 (s, 1H), 8.49 (s, 1H), 8.46 (d, J = 4.0 Hz, 1H), 7.96-7.89 (m, 1H), 7.81-7.72 (m, 3H), 7.60 (br. s., 1H), 7.47 (d, J = 8.9 Hz, 1H), 7.42-7.32 (m, 2H), 3.76-3.68 (m, 4H), 3.16 (s, 3H), 3.07-2.98 (m, 4H), 2.77 (d, J = 4.5 Hz, 3H) |
| 10 | ¹H NMR (500 MHz, DMSO-d₆) δ 10.81 (s, 1H), 8.83 (br. s., 1H), 8.52 (s, 1H), 8.29 (br. s., 1H), 7.92-7.69 (m, 4H), 7.25-7.06 (m, 2H), 3.27 (s, 3H), 2.81 (d, J = 4.5 Hz, 3H) |
| 11 | ¹H NMR (500 MHz, DMSO-d₆) δ 10.95 (s, 1H), 8.80 (br. s., 1H), 8.50 (s, 1H), 8.26 (d, J = 2.5 Hz, 1H), 8.02-7.90 (m, 2H), 7.85-7.71 (m, 2H), 7.35 (br. s., 1H), 7.01-6.85 (m, 1H), 3.27 (s, 3H), 2.80 (d, J = 4.5 Hz, 3H) |
| 12 | ¹H NMR (500 MHz, DMSO-d₆) δ 10.93 (s, 1H), 8.86 (br. s., 1H), 8.53 (s, 1H), 8.31 (d, J = 4.5 Hz, 1H), 7.99-7.91 (m, 2H), 7.88 (t, J = 7.2 Hz, 1H), 7.80 (d, J = 8.4 Hz, 1H), 7.23-7.18 (m, 1H), 7.12 (d, J = 7.9 Hz, 1H), 3.28 (s, 3H), 2.81 (d, J = 4.5 Hz, 3H) |
| 13 | ¹H NMR (500 MHz, DMSO-d₆) δ 10.76 (s, 1H), 9.81 (s, 1H), 8.57-8.45 (m, 2H), 8.12 (t, J = 1.7 Hz, 1H), 7.81-7.77 (m, 1H), 7.74 (dd, J = 7.9, 3.0 Hz, 1H), 7.72-7.67 (m, 1H), 7.64-7.61 (m, 2H), 7.49 (s, 1H), 3.20 (s, 3H), 2.77 (d, J = 4.5 Hz, 3H) |
| 14 | ¹H NMR (500 MHz, DMSO-d₆) δ 10.84 (s, 1H), 10.16 (s, 1H), 8.59 (s, 1H), 8.55 (q, J = 4.5 Hz, 1H), 8.37 (d, J = 5.4 Hz, 1H), 8.14 (s, 1H), 7.95 (dd, J = 8.2, 1.2 Hz, 1H), 7.83-7.72 (m, 2H), 7.54 (s, 1H), 7.39 (ddd, J = 7.9, 6.4, 2.0 Hz, 1H), 7.17 (dd, J = 5.2, 1.2 Hz, 1H), 3.16 (s, 3H), 2.78 (d, J = 4.5 Hz, 3H) |
| 15 | ¹H NMR (500 MHz, DMSO-d₆) δ 10.80 (s, 1H), 9.56 (br. s., 1H), 8.53-8.39 (m, 2H), 7.97-7.90 (m, 1H), 7.83 (d, J = 3.0 Hz, 1H), 7.81-7.70 (m, 2H), 7.63-7.47 (m, 2H), 7.41-7.30 (m, 2H), 3.76 (s, 3H), 3.15 (s, 3H), 2.77 (d, J = 4.5 Hz, 3H) |
| 16 | ¹H NMR (500 MHz, methanol-d₄) δ 8.41 (s, 1H), 8.21 (s, 1H), 8.05 (dd, J = 8.2, 1.2 Hz, 1H), 7.77-7.71 (m, 2H), 7.70-7.65 (m, 1H), 7.36 (t, J = 7.4 Hz, 1H), 7.26 (d, J = 8.4 Hz, 1H), 7.18 (d, J = 7.4 Hz, 1H), 3.12 (s, 3H), 2.95 (s, 3H) |
| 17 | ¹H NMR (500 MHz, methanol-d₄) δ 8.40 (s, 1H), 8.09-8.01 (m, 2H), 7.87 (s, 1H), 7.83 (d, J = 8.4 Hz, 1H), 7.74-7.68 (m, 1H), 7.58 (dd, J = 8.9, 3.0 Hz, 1H), 7.35 (t, J = 7.7 Hz, 1H), 7.28 (d, J = 8.9 Hz, 1H), 3.14 (s, 3H), 2.94 (s, 3H) |
| 18 | ¹H NMR (500 MHz, DMSO-d₆) δ 10.84 (s, 1H), 9.63 (s, 1H), 8.54 (s, 1H), 8.50 (d, J = 5.0 Hz, 1H), 7.99 (d, J = 5.4 Hz, 1H), 7.93 (d, J = 7.4 Hz, 1H), 7.86 (s, 1H), 7.80-7.73 (m, 2H), 7.52 (s, 1H), 7.36 (ddd, J = 8.1, 5.6, 2.7 Hz, 1H), 6.89 (dd, J = 5.4, 1.5 Hz, 1H), 3.16 (s, 3H), 2.77 (d, J = 4.5 Hz, 3H), 1.24 (s, 9H) |
| 19 | ¹H NMR (500 MHz, DMSO-d₆) δ 10.85 (s, 1H), 10.38 (s, 1H), 8.63-8.52 (m, 2H), 8.38 (d, J = 2.0 Hz, 1H), 7.96 (ddd, J = 11.3, 8.8, 1.7 Hz, 2H), 7.82 (d, J = 8.9 Hz, 1H), 7.80-7.73 (m, 2H), 7.69 (s, 1H), 7.45-7.33 (m, 1H), 3.17 (s, 3H), 2.79 (d, J = 4.5 Hz, 3H), 2.61 (s, 6H) |
| 20 | ¹H NMR (500 MHz, DMSO-d₆) δ 10.85 (s, 1H), 10.02 (s, 1H), 8.55 (s, 2H), 7.94 (dd, J = 7.9, 1.5 Hz, 1H), 7.84-7.76 (m, 2H), 7.76-7.69 (m, 1H), 7.63 (s, 1H), 7.44 (dd, J = 7.9, 1.5 Hz, 1H), 7.40-7.33 (m, 1H), 3.16 (s, 3H), 2.78 (d, J = 4.5 Hz, 3H) |
| 21 | ¹H NMR (500 MHz, DMSO-d₆) δ 10.83 (s, 1H), 9.72 (br. s., 1H), 8.59-8.48 (m, 2H), 8.06 (br. s., 1H), 7.95 (d, J = 7.4 Hz, 1H), 7.77 (d, J = 4.0 Hz, 2H), 7.50 (t, J = 7.7 Hz, 1H), 7.41-7.35 (m, 1H), 7.12 (d, J = 7.9 Hz, 1H), 6.68 (d, J = 7.4 Hz, 1H), 3.15 (s, 3H), 2.78 (d, J = 4.5 Hz, 3H), 2.18 (s, 3H) |
| 22 | ¹H NMR (500 MHz, DMSO-d₆) δ 10.83 (s, 1H), 9.65 (s, 1H), 8.51 (s, 1H), 8.48 (d, J = 4.5 Hz, 1H), 8.02-7.89 (m, 2H), 7.83-7.72 (m, 3H), 7.52-7.45 (m, 1H), 7.43-7.39 (m, 1H), 7.36 (ddd, J = 8.1, 4.8, 3.5 Hz, 1H), 3.16 (s, 3H), 2.77 (d, J = 4.5 Hz, 3H), 2.18 (s, 3H) |
| 23 | ¹H NMR (500 MHz, DMSO-d₆) δ 10.82 (s, 1H), 9.82 (s, 1H), 8.56-8.46 (m, 2H), 8.09 (d, J = 3.0 Hz, 1H), 7.93 (dd, J = 7.9, 1.0 Hz, 1H), 7.82-7.77 (m, 1H), 7.77-7.74 (m, 1H), 7.70-7.60 (m, 2H), 7.59 (s, 1H), 7.40-7.34 (m, 1H), 3.16 (s, 3H), 2.77 (d, J = 4.5 Hz, 3H) |
| 24 | ¹H NMR (500 MHz, methanol-d₄) δ 8.40 (s, 1H), 8.11 (s, 1H), 8.04 (dd, J = 8.2, 1.2 Hz, 1H), 7.76-7.71 (m, 1H), 7.69-7.64 (m, 1H), 7.49 (t, J = 7.9 Hz, 1H), 7.38-7.32 (m, 1H), 6.61 (d, J = 7.9 Hz, 1H), 6.25 (d, J = 7.9 Hz, 1H), 3.31 (s, 3H), 3.14 (s, 3H), 2.94 (s, 3H) |

| Compound | ¹H NMR (methanol-d₄ equates CDCl₃:MeOD ~1:1 unless otherwise noted) Occasionally water suppression is used in DMSO-d₆ spectra |
|---|---|
| 25 | ¹H NMR (500 MHz, DMSO-d₆) δ 10.77 (s, 1H), 9.82 (s, 1H), 9.02 (s, 1H), 8.61 (s, 1H), 8.53 (q, J = 4.3 Hz, 1H), 8.30 (s, 1H), 7.95 (dd, J = 14.9, 7.9 Hz, 2H), 7.83-7.71 (m, 3H), 7.67-7.57 (m, 1H), 7.45-7.34 (m, 2H), 7.26 (s, 1H), 3.17 (s, 3H), 2.79 (d, J = 4.5 Hz, 3H) |
| 26 | ¹H NMR (500 MHz, DMSO-d₆) δ 10.92 (s, 1H), 8.72 (br. s., 1H), 8.55 (s, 1H), 8.39 (d, J = 4.5 Hz, 1H), 7.99 (d, J = 7.4 Hz, 1H), 7.95 (s, 1H), 7.87-7.80 (m, 1H), 7.79-7.73 (m, 1H), 7.48 (br. s., 1H), 7.39 (br. s., 1H), 3.20 (s, 3H), 2.80 (d, J = 4.5 Hz, 3H), 2.59 (s, 3H) |
| 27 | ¹H NMR (500 MHz, DMSO-d₆) δ 10.96 (s, 1H), 10.48 (br. s., 1H), 8.67 (d, J = 4.0 Hz, 1H), 8.56 (s, 1H), 8.01-7.93 (m, 2H), 7.90-7.86 (m, 1H), 7.85-7.81 (m, 1H), 7.80-7.74 (m, 1H), 7.62 (d, J = 8.9 Hz, 1H), 7.55-7.47 (m, 2H), 7.44 (t, J = 7.4 Hz, 1H), 3.18 (s, 3H), 2.79 (d, J = 4.5 Hz, 3H) |
| 28 | ¹H NMR (500 MHz, DMSO-d₆) δ 11.20 (s, 1H), 9.89 (br. s., 1H), 8.65-8.43 (m, 2H), 8.14 (s, 1H), 8.07 (d, J = 7.9 Hz, 1H), 8.04-7.98 (m, 1H), 7.90 (d, J = 8.4 Hz, 1H), 7.76-7.56 (m, 3H), 7.45 (t, J = 7.7 Hz, 1H), 2.77 (d, J = 4.5 Hz, 3H) |
| 29 | ¹H NMR (500 MHz, DMSO-d₆) δ 11.20 (s, 1H), 9.82 (br. s., 1H), 8.55 (s, 2H), 8.13 (br. s., 1H), 8.07 (d, J = 7.9 Hz, 1H), 8.03-7.96 (m, 1H), 7.95-7.89 (m, 1H), 7.67 (br. s., 1H), 7.54 (br. s., 1H), 7.45 (t, J = 7.4 Hz, 1H), 6.88 (br. s., 1H), 2.78 (d, J = 4.5 Hz, 3H) |
| 30 | ¹H NMR (500 MHz, DMSO-d₆) δ 10.90 (s, 1H), 10.57 (br. s., 1H), 8.66 (br. s., 1H), 8.61-8.54 (m, 2H), 8.08 (dd, J = 8.9, 2.0 Hz, 1H), 8.00-7.93 (m, 2H), 7.88-7.79 (m, 1H), 7.76 (d, J = 7.9 Hz, 1H), 7.63 (d, J = 7.9 Hz, 1H), 7.52 (br. s., 1H), 7.44 (t, J = 7.7 Hz, 1H), 3.18 (s, 3H), 2.79 (d, J = 4.5 Hz, 3H) |
| 31 | ¹H NMR (500 MHz, DMSO-d₆) δ 10.74 (s, 1H), 9.73 (br. s., 1H), 8.55-8.44 (m, 2H), 8.07 (d, J = 3.5 Hz, 1H), 7.90 (dd, J = 7.9, 1.5 Hz, 1H), 7.81-7.72 (m, 3H), 7.67-7.59 (m, 1H), 7.52 (d, J = 8.4 Hz, 1H), 7.42-7.33 (m, 1H), 6.88-6.81 (m, 1H), 3.23 (q, J = 7.3 Hz, 2H), 2.77 (d, J = 4.5 Hz, 3H), 1.05 (t, J = 7.4 Hz, 3H) |
| 32 | ¹H NMR (500 MHz, methanol-d₄) δ 8.38 (s, 1H), 8.00 (dd, J = 8.2, 1.2 Hz, 1H), 7.97 (d, J = 3.0 Hz, 1H), 7.81 (d, J = 8.4 Hz, 1H), 7.76 (s, 1H), 7.73-7.68 (m, 1H), 7.45-7.39 (m, 1H), 7.37-7.30 (m, 2H), 3.25 (q, J = 7.4 Hz, 2H), 2.94 (s, 3H), 1.23 (t, J = 7.4 Hz, 3H) |
| 33 | ¹H NMR (500 MHz, methanol-d₄) δ 8.45 (s, 1H), 8.31-8.25 (m, 1H), 8.00 (dd, J = 7.9, 1.5 Hz, 1H), 7.89 (s, 1H), 7.79 (d, J = 7.9 Hz, 1H), 7.73-7.68 (m, 1H), 7.63 (s, 1H), 7.38-7.30 (m, 1H), 7.06 (dd, J = 5.2, 1.2 Hz, 1H), 3.25 (q, J = 7.4 Hz, 2H), 2.95 (s, 3H), 1.23 (t, J = 7.4 Hz, 3H) |
| 34 | ¹H NMR (500 MHz, DMSO-d₆) δ 10.76 (d, J = 3.5 Hz, 1H), 10.15 (d, J = 3.5 Hz, 1H), 8.66-8.50 (m, 2H), 8.36 (t, J = 4.7 Hz, 1H), 8.08 (d, J = 2.5 Hz, 1H), 7.86-7.75 (m, 1H), 7.75-7.67 (m, 2H), 7.40 (d, J = 4.0 Hz, 1H), 7.29-7.21 (m, 1H), 3.21 (d, J = 4.5 Hz, 3H), 2.78 (t, J = 4.2 Hz, 3H) |
| 35 | ¹H NMR (500 MHz, DMSO-d₆) δ 10.79 (br. s., 1H), 10.22 (s, 1H), 8.65 (br. s., 1H), 8.58 (d, J = 3.0 Hz, 1H), 8.39 (dd, J = 4.5, 3.0 Hz, 1H), 8.12 (br. s., 1H), 8.01-7.88 (m, 2H), 7.60 (d, J = 5.4 Hz, 1H), 7.56-7.48 (m, 2H), 7.27 (d, J = 1.5 Hz, 1H), 2.80 (d, J = 2.5 Hz, 3H) |
| 36 | ¹H NMR (500 MHz, DMSO-d₆) δ 10.83 (s, 1H), 10.12 (s, 1H), 8.73 (d, J = 4.5 Hz, 1H), 8.60-8.50 (m, 2H), 7.95 (dd, J = 13.6, 8.7 Hz, 2H), 7.77-7.70 (m, 2H), 7.65 (s, 1H), 7.53 (dd, J = 8.9, 4.5 Hz, 1H), 7.41-7.35 (m, 1H), 3.17 (s, 4H), 2.78 (d, J = 4.0 Hz, 3H) |
| 37 | ¹H NMR (500 MHz, DMSO-d₆) δ 10.84 (s, 1H), 10.22 (s, 1H), 8.65-8.54 (m, 3H), 8.41 (d, J = 5.9 Hz, 1H), 7.94 (dd, J = 8.2, 1.2 Hz, 1H), 7.82-7.78 (m, 1H), 7.77-7.74 (m, 1H), 7.67 (s, 1H), 7.63 (d, J = 5.4 Hz, 1H), 7.47-7.36 (m, 1H), 3.16 (s, 3H), 2.78 (d, J = 4.5 Hz, 3H) |
| 38 | ¹H NMR (500 MHz, DMSO-d₆) δ 10.85 (s, 1H), 10.09 (s, 1H), 8.93 (d, J = 1.5 Hz, 1H), 8.60-8.52 (m, 2H), 8.12 (dd, J = 2.5, 1.5 Hz, 1H), 8.06 (d, J = 2.5 Hz, 1H), 7.98-7.92 (m, 1H), 7.82-7.73 (m, 2H), 7.63 (s, 1H), 7.38 (ddd, J = 8.2, 6.4, 1.7 Hz, 1H), 3.16 (s, 3H), 2.78 (d, J = 4.5 Hz, 3H) |
| 39 | ¹H NMR (500 MHz, DMSO-d₆) δ 10.83 (s, 1H), 10.44 (br. s., 1H), 8.77 (s, 1H), 8.69 (d, J = 3.5 Hz, 1H), 8.55 (s, 1H), 8.20 (s, 1H), 8.14 (d, J = 2.5 Hz, 1H), 7.82-7.77 (m, 1H), 7.76-7.69 (m, 2H), 7.22 (d, J = 6.4 Hz, 1H), 3.23 (s, 3H), 2.79 (d, J = 4.5 Hz, 3H) |
| 40 | ¹H NMR (500 MHz, DMSO-d₆) δ 10.84 (s, 1H), 9.93 (s, 1H), 8.84 (s, 1H), 8.63-8.46 (m, 2H), 8.02 (s, 1H), 7.94 (d, J = 6.9 Hz, 1H), 7.81-7.71 (m, 2H), 7.55 (s, 1H), 7.38 (t, J = 7.4 Hz, 1H), 3.16 (s, 4H), 2.77 (d, J = 4.5 Hz, 3H), 2.36 (s, 3H) |
| 41 | ¹H NMR (500 MHz, DMSO-d₆) δ 10.98-10.79 (m, 1H), 8.95 (br. s., 1H), 8.75-8.57 (m, 3H), 8.01-7.91 (m, 1H), 7.86-7.79 (m, 1H), 7.75 (dd, J = 8.2, 2.2 Hz, 1H), 7.64 (br. s., 1H), 7.45-7.38 (m, 1H), 3.16 (d, J = 3.5 Hz, 3H), 2.79 (t, J = 3.5 Hz, 3H) |
| 42 | ¹H NMR (500 MHz, DMSO-d₆) δ 10.86 (d, J = 3.5 Hz, 1H), 10.08 (d, J = 4.0 Hz, 1H), 8.62-8.50 (m, 3H), 8.00-7.92 (m, 2H), 7.89 (d, J = 4.0 Hz, 1H), 7.82-7.72 (m, 2H), 7.48-7.34 (m, 1H), 3.18-3.12 (m, 3H), 2.78 (t, J = 4.5 Hz, 3H), 2.22 (d, J = 3.5 Hz, 3H) |
| 43 | ¹H NMR (500 MHz, DMSO-d₆) δ 10.85 (s, 1H), 10.26 (s, 1H), 8.63-8.58 (m, 1H), 8.57 (s, 1H), 8.46 (d, J = 5.0 Hz, 1H), 8.13 (s, 1H), 7.95 (s, 1H), 7.84 (s, 2H), 7.75 (d, J = 8.4 Hz, 2H), 7.57 (dd, J = 8.4, 2.0 Hz, 2H), 7.52 (d, |

| Compound | ¹H NMR (methanol-d₄ equates CDCl₃:MeOD ~1:1 unless otherwise noted) Occasionally water suppression is used in DMSO-d₆ spectra |
|---|---|
| | J = 2.0 Hz, 2H), 7.29 (dd, J = 5.0, 1.5 Hz, 2H), 3.98 (s, 6H), 3.24 (s, 6H), 2.79 (d, J = 4.5 Hz, 6H) |
| 44 | ¹H NMR (500 MHz, DMSO-d₆) δ 10.88 (s, 1H), 9.92 (s, 1H), 8.56 (d, J = 4.5 Hz, 1H), 8.51 (s, 1H), 8.25 (d, J = 2.5 Hz, 1H), 7.99-7.89 (m, 2H), 7.76 (d, J = 8.4 Hz, 1H), 7.70-7.63 (m, 2H), 7.60 (dd, J = 8.4, 2.0 Hz, 1H), 7.51 (d, J = 2.0 Hz, 1H), 3.98 (s, 3H), 3.24 (s, 3H), 2.78 (d, J = 4.5 Hz, 3H) |
| 45 | ¹H NMR (500 MHz, methanol-d₄) δ 8.45 (s, 1H), 8.36 (dd, J = 5.4, 1.0 Hz, 1H), 7.91-7.85 (m, 1H), 7.75-7.69 (m, 1H), 7.67-7.63 (m, 1H), 7.60 (d, J = 2.0 Hz, 1H), 7.22-7.15 (m, 1H), 7.11 (d, J = 8.4 Hz, 1H), 7.01 (br. s., 1H), 4.07 (s, 4H), 3.18 (s, 4H), 2.98 (s, 4H) |
| 46 | ¹H NMR (500 MHz, DMSO-d₆) δ 10.88 (s, 1H), 9.77 (s, 1H), 8.54-8.42 (m, 2H), 8.11 (dd, J = 5.0, 1.0 Hz, 1H), 7.86 (s, 1H), 7.71 (td, J = 8.3, 6.2 Hz, 1H), 7.67-7.59 (m, 1H), 7.55 (d, J = 8.4 Hz, 1H), 7.50 (d, J = 7.9 Hz, 1H), 7.11 (dd, J = 10.4, 8.4 Hz, 1H), 6.85 (ddd, J = 6.9, 5.0, 1.0 Hz, 1H), 3.33 (s, 3H), 2.76 (d, J = 4.5 Hz, 3H) |
| 47 | ¹H NMR (500 MHz, DMSO-d₆) δ 10.86 (s, 1H), 9.84 (s, 1H), 8.51-8.43 (m, 2H), 8.11 (d, J = 2.0 Hz, 1H), 7.78-7.68 (m, 1H), 7.68-7.59 (m, 3H), 7.52 (d, J = 8.4 Hz, 1H), 7.12 (dd, J = 10.9, 8.4 Hz, 1H), 3.34 (s, 3H), 2.76 (d, J = 4.5 Hz, 3H) |
| 48 | ¹H NMR (500 MHz, methanol-d₄) δ 8.50 (d, J = 5.0 Hz, 1H), 8.43 (s, 1H), 7.77 (td, J = 8.2, 5.9 Hz, 1H), 7.51 (d, J = 7.9 Hz, 1H), 7.43 (s, 1H), 7.32 (d, J = 5.0 Hz, 1H), 7.28 (t, J = 9.4 Hz, 1H), 6.95 (br. s., 1H), 3.37 (d, J = 1.0 Hz, 3H), 2.97 (s, 3H) |
| 49 | ¹H NMR (500 MHz, methanol-d₄) δ 8.36 (s, 1H), 8.00 (d, J = 5.0 Hz, 1H), 7.83 (s, 1H), 7.63-7.58 (m, 2H), 7.09 (s, 1H), 6.99-6.92 (m, 1H), 6.75 (d, J = 5.0 Hz, 1H), 3.31 (s, 3H), 2.93 (s, 3H), 2.33 (s, 3H) |
| 50 | ¹H NMR (500 MHz, methanol-d₄) δ 8.36 (s, 1H), 8.00 (d, J = 3.0 Hz, 1H), 7.87 (s, 1H), 7.61-7.59 (m, 2H), 7.46-7.39 (m, 1H), 7.32 (dd, J = 9.2, 3.7 Hz, 1H), 6.96 (ddd, J = 10.5, 6.1, 3.2 Hz, 1H), 3.32 (s, 3H), 2.93 (s, 3H) |
| 51 | ¹H NMR (500 MHz, methanol-d₄) δ 8.43 (s, 1H), 8.24 (d, J = 3.0 Hz, 1H), 7.89 (dd, J = 7.9, 3.0 Hz, 1H), 7.70 (dd, J = 8.9, 4.5 Hz, 1H), 7.66-7.61 (m, 1H), 7.60-7.55 (m, 1H), 7.08 (dd, J = 9.2, 3.7 Hz, 1H), 6.55 (br. s., 1H), 3.23 (s, 3H), 2.98 (s, 3H) |
| 52 | ¹H NMR (500 MHz, methanol-d₄) δ 8.39 (s, 1H), 7.98 (d, J = 5.4 Hz, 1H), 7.82 (dd, J = 8.9, 4.5 Hz, 1H), 7.76 (dd, J = 7.9, 3.0 Hz, 1H), 7.67 (s, 1H), 7.45 (ddd, J = 8.9, 7.4, 3.0 Hz, 1H), 7.08 (s, 1H), 6.75 (d, J = 5.0 Hz, 1H), 3.15 (s, 3H), 2.94 (s, 3H), 2.33 (s, 3H) |
| 53 | ¹H NMR (500 MHz, methanol-d₄) δ 8.42 (s, 1H), 8.20 (d, J = 4.0 Hz, 1H), 8.08-7.99 (m, 2H), 7.72-7.61 (m, 2H), 7.22 (d, J = 8.4 Hz, 1H), 7.05-6.95 (m, 1H), 6.94-6.86 (m, 1H), 3.15 (s, 3H), 2.94 (s, 3H) |
| 54 | ¹H NMR (500 MHz, methanol-d₄) δ 8.43 (br. s., 1H), 8.11 (s, 1H), 8.05 (dd, J = 8.9, 5.9 Hz, 1H), 7.70 (q, J = 8.3 Hz, 1H), 7.62-7.58 (m, 1H), 7.09-6.93 (m, 1H), 6.46 (dd, J = 7.9, 2.0 Hz, 1H), 3.15 (s, 3H), 2.94 (s, 3H) |
| 55 | ¹H NMR (500 MHz, methanol-d₄) δ 8.41 (s, 1H), 8.07-8.01 (m, 2H), 7.97 (s, 1H), 7.65 (dd, J = 10.9, 2.5 Hz, 1H), 7.43 (ddd, J = 8.9, 7.9, 3.0 Hz, 1H), 7.26 (dd, J = 9.2, 3.7 Hz, 1H), 7.06-6.96 (m, 1H), 3.15 (s, 3H), 2.94 (s, 3H) |
| 56 | ¹H NMR (500 MHz, methanol-d₄) δ 8.41 (s, 1H), 8.07-8.00 (m, 2H), 7.95 (s, 1H), 7.66 (dd, J = 10.9, 2.5 Hz, 1H), 7.05 (s, 1H), 7.02-6.95 (m, 1H), 6.77 (d, J = 5.0 Hz, 1H), 3.14 (s, 3H), 2.94 (s, 3H), 2.34 (s, 3H) |
| 57 | ¹H NMR (500 MHz, methanol-d₄) δ 8.41 (s, 1H), 8.09-8.01 (m, 2H), 7.98 (s, 1H), 7.65 (dd, J = 10.9, 2.5 Hz, 1H), 7.43 (td, J = 8.4, 3.0 Hz, 1H), 7.26 (dd, J = 9.2, 3.7 Hz, 1H), 7.07-6.97 (m, 1H), 3.15 (s, 3H), 2.94 (s, 3H) |
| 58 | ¹H NMR (500 MHz, methanol-d₄) δ 8.48 (s, 1H), 8.35 (d, J = 5.4 Hz, 1H), 8.05 (dd, J = 8.9, 6.4 Hz, 1H), 7.90 (s, 1H), 7.78 (s, 1H), 7.62 (dd, J = 10.9, 2.5 Hz, 1H), 7.10 (dd, J = 5.2, 1.2 Hz, 1H), 7.02 (ddd, J = 9.2, 7.4, 2.2 Hz, 1H), 3.15 (s, 3H), 2.95 (s, 3H) |
| 59 | ¹H NMR (500 MHz, methanol-d₄) δ 8.44 (s, 1H), 8.35 (s, 1H), 8.05 (dd, J = 7.9, 1.5 Hz, 1H), 8.00 (s, 1H), 7.84 (d, J = 7.9 Hz, 1H), 7.80 (dd, J = 8.9, 2.0 Hz, 1H), 7.76-7.70 (m, 1H), 7.43 (d, J = 8.4 Hz, 1H), 7.37 (t, J = 7.7 Hz, 1H), 3.15 (s, 3H), 2.95 (s, 3H) |
| 60 | ¹H NMR (500 MHz, methanol-d₄) δ 8.38 (s, 1H), 8.07-8.01 (m, 1H), 7.88 (s, 1H), 7.81 (d, J = 7.9 Hz, 1H), 7.70 (t, J = 7.2 Hz, 2H), 7.34 (t, J = 7.7 Hz, 1H), 7.15 (d, J = 5.0 Hz, 1H), 3.14 (s, 3H), 2.94 (s, 3H), 2.30 (s, 3H) |
| 61 | ¹H NMR (500 MHz, DMSO-d₆) δ 10.88 (s, 1H), 10.52 (br. s., 1H), 8.63 (br. s., 1H), 8.60-8.49 (m, 2H), 8.11 (dd, J = 8.9, 2.0 Hz, 1H), 7.96 (d, J = 8.9 Hz, 1H), 7.87-7.74 (m, 2H), 7.73-7.58 (m, 2H), 7.43 (t, J = 7.4 Hz, 2H), 3.22 (s, 3H), 3.17 (s, 3H), 2.79 (d, J = 4.5 Hz, 3H) |
| 64 | ¹H NMR (500 MHz, methanol-d₄) δ 8.36 (s, 1H), 8.08 (d, J = 3.0 Hz, 1H), 7.91 (s, 1H), 7.61 (s, 1H), 7.48 (ddd, J = 10.2, 6.7, 3.0 Hz, 1H), 7.43 (ddd, J = 8.9, 7.9, 3.0 Hz, 1H), 7.28 (dd, J = 9.2, 3.7 Hz, 1H), 7.20-7.10 (m, 1H), 6.85-6.75 (m, 1H), 2.93 (s, 3H) |
| 65 | ¹H NMR (500 MHz, DMSO-d₆) δ 10.39 (s, 1H), 9.72 (s, 1H), 8.47 (s, 2H), 8.06 (d, J = 3.0 Hz, 1H), 7.72-7.66 (m, 1H), 7.64-7.58 (m, 1H), 7.47-7.41 (m, 1H), 7.40-7.35 (m, 2H), 7.28 (t, J = 7.7 Hz, 1H), 7.23-7.16 (m, 1H), 2.80-2.76 (m, 3H), 2.43 (s, 3H) |

| Compound | ¹H NMR (methanol-d₄ equates CDCl₃:MeOD ~1:1 unless otherwise noted) Occasionally water suppression is used in DMSO-d₆ spectra |
|---|---|
| 66 | ¹H NMR (500 MHz, methanol-d₄) δ 8.29 (s, 1H), 7.98 (s, 2H), 7.46-7.36 (m, 4H), 7.35-7.19 (m, 4H), 3.85-3.68 (m, 4H), 2.95 (s, 3H), 2.92-2.86 (m, 4H) |
| 67 | ¹H NMR (500 MHz, methanol-d₄) δ 8.28 (s, 1H), 7.84 (s, 1H), 7.71 (dd, J = 7.7, 1.2 Hz, 1H), 7.67 (d, J = 7.9 Hz, 1H), 7.55-7.47 (m, 2H), 7.20 (t, J = 7.7 Hz, 1H), 6.91 (d, J = 8.4 Hz, 1H), 6.74 (d, J = 7.4 Hz, 1H), 2.94 (s, 3H), 2.34 (s, 3H) |
| 68 | ¹H NMR (500 MHz, methanol-d₄) δ 8.29 (s, 1H), 8.12 (dd, J = 5.0, 1.5 Hz, 1H), 7.73-7.61 (m, 3H), 7.54-7.45 (m, 1H), 7.29 (d, J = 8.4 Hz, 1H), 7.18 (t, J = 7.2 Hz, 1H), 6.88 (dd, J = 6.9, 5.4 Hz, 1H), 4.29 (s, 1H), 2.94 (s, 3H) |
| 69 | ¹H NMR (500 MHz, DMSO-d₆) δ 10.96 (s, 1H), 9.05 (s, 1H), 8.42-8.33 (m, 2H), 8.05-7.84 (m, 3H), 7.67-7.54 (m, 3H), 7.48 (t, J = 7.7 Hz, 1H), 7.40 (br. s., 1H), 7.09 (t, J = 7.4 Hz, 1H), 6.96 (ddd, J = 7.9, 4.5, 3.5 Hz, 1H), 2.78-2.74 (m, 3H) |
| 70 | ¹H NMR (500 MHz, methanol-d₄) δ 8.26 (s, 1H), 7.85 (d, J = 3.0 Hz, 1H), 7.70 (dd, J = 7.7, 1.2 Hz, 1H), 7.62 (d, J = 8.4 Hz, 1H), 7.50 (td, J = 7.9, 1.5 Hz, 1H), 7.33-7.27 (m, 2H), 7.25-7.16 (m, 2H), 3.84 (s, 3H), 2.93 (s, 3H) |
| 71 | ¹H NMR (500 MHz, DMSO-d₆) δ 10.89 (s, 1H), 9.73 (s, 1H), 8.37 (s, 1H), 8.35-8.30 (m, 1H), 8.08 (d, J = 3.0 Hz, 1H), 7.97-7.89 (m, 2H), 7.70-7.59 (m, 3H), 7.57 (d, J = 7.9 Hz, 2H), 7.52-7.46 (m, 1H), 7.39 (br. s., 1H), 7.09 (t, J = 7.9 Hz, 1H), 2.75 (d, J = 4.5 Hz, 3H) |
| 72 | ¹H NMR (500 MHz, methanol-d₄) δ 8.27 (s, 1H), 7.97 (d, J = 2.0 Hz, 1H), 7.70 (dd, J = 7.9, 1.5 Hz, 1H), 7.62 (d, J = 7.9 Hz, 1H), 7.55-7.45 (m, 2H), 7.38 (s, 1H), 7.26-7.19 (m, 1H), 7.16 (d, J = 8.4 Hz, 1H), 2.94 (s, 3H), 2.27 (s, 3H), 2.01 (s, 2H) |
| 73 | ¹H NMR (500 MHz, methanol-d₄) δ 8.38 (s, 1H), 7.77 (dd, J = 7.7, 1.2 Hz, 1H), 7.69 (t, J = 7.9 Hz, 1H), 7.60-7.57 (m, 1H), 7.56-7.53 (m, 1H), 7.45-7.37 (m, 1H), 6.81 (br. s., 1H), 6.57 (d, J = 7.9 Hz, 1H), 6.54 (d, J = 8.4 Hz, 1H), 3.88 (s, 3H), 2.96 (s, 3H) |
| 74 | ¹H NMR (500 MHz, methanol-d₄) δ 8.29 (s, 1H), 7.85 (s, 1H), 7.76 (d, J = 7.9 Hz, 1H), 7.71-7.65 (m, 2H), 7.59-7.48 (m, 1H), 7.20-7.13 (m, 1H), 7.02 (dd, J = 7.9, 2.0 Hz, 1H), 6.42 (dd, J = 7.9, 2.5 Hz, 1H), 2.93 (s, 3H) |
| 75 | ¹H NMR (500 MHz, methanol-d₄) δ 8.34 (s, 1H), 8.27 (d, J = 5.4 Hz, 1H), 7.73 (dd, J = 7.9, 1.5 Hz, 1H), 7.66 (dd, J = 7.9, 1.5 Hz, 2H), 7.60 (s, 1H), 7.55-7.45 (m, 4H), 7.39 (br. s., 1H), 7.32-7.21 (m, 2H), 2.95 (s, 3H) |
| 76 | ¹H NMR (500 MHz, DMSO-d₆) δ 11.18 (br. s., 1H), 8.74 (br. s., 1H), 8.58 (br. s., 1H), 8.41 (s, 1H), 8.16 (d, J = 6.9 Hz, 1H), 8.04 (br. s., 1H), 7.73-7.65 (m, 3H), 7.65-7.47 (m, 5H), 7.45-7.38 (m, 1H), 7.36-7.19 (m, 2H), 2.80 (d, J = 4.5 Hz, 3H) |
| 77 | ¹H NMR (500 MHz, methanol-d₄) δ 8.31 (s, 1H), 8.07 (s, 1H), 7.76-7.71 (m, 2H), 7.70-7.64 (m, 2H), 7.57 (dd, J = 7.9, 1.0 Hz, 1H), 7.38-7.33 (m, 1H), 7.30 (t, J = 8.2 Hz, 3H), 7.07 (d, J = 7.9 Hz, 1H), 7.02-6.97 (m, 1H), 6.96 (dd, J = 7.9, 1.5 Hz, 1H), 2.94 (s, 3H) |
| 78 | ¹H NMR (500 MHz, methanol-d₄) δ 8.29 (s, 1H), 7.99 (d, J = 5.0 Hz, 1H), 7.69 (dd, J = 7.9, 1.5 Hz, 1H), 7.63 (d, J = 7.9 Hz, 1H), 7.50 (td, J = 7.7, 1.5 Hz, 1H), 7.44 (s, 1H), 7.19 (td, J = 7.4, 1.0 Hz, 1H), 7.10 (s, 1H), 6.75 (d, J = 5.0 Hz, 1H), 2.94 (s, 3H), 2.33 (s, 3H) |
| 79 | ¹H NMR (500 MHz, methanol-d₄) δ 8.29 (s, 1H), 8.11 (d, J = 2.0 Hz, 1H), 7.70 (dd, J = 7.9, 1.5 Hz, 1H), 7.67-7.62 (m, 2H), 7.55 (s, 1H), 7.51 (td, J = 7.9, 1.5 Hz, 1H), 7.27 (d, J = 8.4 Hz, 1H), 7.19 (td, J = 7.4, 1.0 Hz, 1H), 4.56 (s, 2H), 2.94 (s, 3H) |
| 80 | ¹H NMR (500 MHz, methanol-d₄) δ 8.30 (s, 1H), 8.06 (d, J = 2.5 Hz, 1H), 7.70 (dd, J = 7.7, 1.2 Hz, 1H), 7.64 (br. s., 1H), 7.58 (dd, J = 8.9, 3.0 Hz, 1H), 7.54-7.48 (m, 1H), 7.32 (d, J = 8.9 Hz, 1H), 7.23-7.16 (m, 1H), 2.93 (s, 3H) |
| 81 | ¹H NMR (500 MHz, methanol-d₄) δ 8.24 (s, 1H), 7.78 (d, J = 3.0 Hz, 1H), 7.69 (dd, J = 7.9, 1.5 Hz, 1H), 7.65-7.63 (m, 1H), 7.60 (d, J = 7.9 Hz, 1H), 7.49 (t, J = 7.7 Hz, 1H), 7.23-7.16 (m, 3H), 7.15-7.09 (m, 1H), 2.93 (s, 3H) |
| 82 | ¹H NMR (500 MHz, DMSO-d₆) δ 10.93 (s, 1H), 10.18 (s, 1H), 8.44-8.36 (m, 3H), 8.01-7.91 (m, 2H), 7.82-7.73 (m, 2H), 7.62-7.55 (m, 2H), 7.54-7.47 (m, 1H), 7.40 (br. s., 1H), 7.16-7.07 (m, 1H), 2.76 (d, J = 4.5 Hz, 3H) |
| 83 | ¹H NMR (500 MHz, methanol-d₄) δ 8.29 (s, 1H), 8.05-7.99 (m, 2H), 7.71 (d, J = 7.9 Hz, 1H), 7.68 (dd, J = 7.7, 1.2 Hz, 1H), 7.55-7.46 (m, 2H), 7.21-7.14 (m, 1H), 6.87 (dd, J = 7.4, 5.0 Hz, 1H), 2.93 (s, 3H), 2.30 (s, 3H) |
| 84 | ¹H NMR (500 MHz, methanol-d₄) δ 8.35 (s, 1H), 8.28 (d, J = 5.4 Hz, 1H), 7.92 (s, 1H), 7.70 (dd, J = 7.9, 1.5 Hz, 1H), 7.65-7.60 (m, 1H), 7.54-7.48 (m, 1H), 7.45 (s, 1H), 7.19 (t, J = 7.9 Hz, 1H), 7.04 (dd, J = 5.2, 1.2 Hz, 1H), 2.94 (s, 3H) |
| 85 | ¹H NMR (500 MHz, methanol-d₄) δ 8.26 (s, 1H), 7.84 (d, J = 3.0 Hz, 1H), 7.70 (dd, J = 7.7, 1.2 Hz, 1H), 7.62 (d, J = 7.4 Hz, 1H), 7.51 (td, J = 7.8, 1.7 Hz, 1H), 7.37 (dd, J = 9.2, 3.2 Hz, 1H), 7.25 (s, 1H), 7.23-7.16 (m, 2H), 3.90-3.85 (m, 4H), 3.15-3.09 (m, 4H), 2.93 (s, 3H) |
| 86 | ¹H NMR (500 MHz, DMSO-d₆) δ 10.96 (s, 1H), 10.25 (s, 1H), 8.43-8.37 (m, 2H), 8.07 (s, 1H), 7.96-7.90 (m, 2H), 7.64-7.56 (m, 2H), 7.53-7.45 (m, 1H), 7.41 (s, 1H), 7.36 (d, J = 8.4 Hz, 1H), 7.19-7.10 (m, 1H), 2.76 (d, J = 5.0 Hz, 3H), 2.41 (s, 3H) |

| Compound | ¹H NMR (methanol-d₄ equates CDCl₃:MeOD ~1:1 unless otherwise noted) Occasionally water suppression is used in DMSO-d₆ spectra |
|---|---|
| 87 | ¹H NMR (500 MHz, methanol-d₄) δ 8.53 (s, 1H), 8.31 (d, J = 8.9 Hz, 1H), 8.00 (d, J = 8.4 Hz, 1H), 7.87 (d, J = 7.9 Hz, 1H), 7.84-7.75 (m, 2H), 7.60-7.54 (m, 2H), 7.42-7.37 (m, 1H), 7.15 (d, J = 8.9 Hz, 1H), 6.81 (br. s., 1H), 2.99 (s, 3H) |
| 88 | ¹H NMR (500 MHz, DMSO-d₆) δ 10.94 (s, 1H), 10.30 (s, 1H), 8.45-8.35 (m, 3H), 7.98-7.90 (m, 2H), 7.83 (d, J = 8.9 Hz, 1H), 7.77 (s, 1H), 7.62-7.56 (m, 2H), 7.48 (t, J = 7.7 Hz, 1H), 7.41 (br. s., 1H), 7.13 (t, J = 7.4 Hz, 1H), 2.79-2.75 (m, 3H), 2.60 (s, 6H) |
| 89 | ¹H NMR (500 MHz, DMSO-d₆) δ 10.85 (s, 1H), 9.73 (s, 1H), 9.01 (s, 1H), 8.46 (s, 1H), 8.34 (d, J = 4.5 Hz, 1H), 8.29 (s, 1H), 8.01-7.87 (m, 2H), 7.74 (d, J = 8.4 Hz, 1H), 7.65-7.55 (m, 3H), 7.52-7.43 (m, 1H), 7.42-7.36 (m, 2H), 7.32 (s, 1H), 7.10 (t, J = 7.7 Hz, 1H), 2.79-2.75 (m, 3H) |
| 90 | ¹H NMR (500 MHz, methanol-d₄) δ 8.45 (s, 1H), 8.32 (s, 1H), 8.04 (dd, J = 5.0, 1.0 Hz, 1H), 7.78-7.60 (m, 4H), 7.51 (t, J = 7.7 Hz, 1H), 7.18 (t, J = 7.7 Hz, 1H), 6.87 (dd, J = 7.9, 5.0 Hz, 1H), 2.94 (s, 3H) |
| 91 | ¹H NMR (500 MHz, methanol-d₄) δ 8.54 (d, J = 5.4 Hz, 1H), 8.35 (s, 1H), 7.78 (dd, J = 7.7, 1.2 Hz, 1H), 7.64-7.59 (m, 1H), 7.58-7.54 (m, 1H), 7.45-7.39 (m, 1H), 7.34 (d, J = 5.0 Hz, 1H), 7.23 (s, 1H), 6.71 (br. s., 1H), 2.97 (s, 3H) |
| 92 | N/A |
| 93 | ¹H NMR (500 MHz, DMSO-d₆) δ 11.17 (br. s., 1H), 8.74 (br. s., 2H), 8.41 (s, 1H), 8.20 (d, J = 7.9 Hz, 1H), 8.11-8.00 (m, 2H), 7.67 (d, J = 7.4 Hz, 1H), 7.63-7.44 (m, 4H), 7.33-7.14 (m, 2H), 2.80 (d, J = 4.5 Hz, 3H) |
| 94 | ¹H NMR (500 MHz, methanol-d₄) δ 8.29 (s, 1H), 8.07 (d, J = 5.0 Hz, 1H), 7.69 (dd, J = 7.9, 1.5 Hz, 1H), 7.65 (d, J = 8.4 Hz, 1H), 7.56 (s, 1H), 7.52-7.46 (m, 1H), 7.28 (s, 1H), 7.21-7.15 (m, 1H), 6.86 (d, J = 5.0 Hz, 1H), 4.62 (s, 2H), 2.93 (s, 3H) |
| 95 | ¹H NMR (500 MHz, methanol-d₄) δ 8.31 (s, 1H), 8.02 (s, 1H), 7.74 (t, J = 7.9 Hz, 1H), 7.68 (dd, J = 7.9, 1.5 Hz, 1H), 7.65 (d, J = 8.4 Hz, 1H), 7.49 (t, J = 7.7 Hz, 1H), 7.36 (d, J = 8.4 Hz, 1H), 7.20-7.14 (m, 2H), 2.94 (s, 3H) |
| 96 | ¹H NMR (500 MHz, methanol-d₄) δ 8.32 (s, 1H), 8.05 (d, J = 3.0 Hz, 1H), 7.52 (s, 1H), 7.44 (td, J = 8.4, 3.0 Hz, 1H), 7.31 (dd, J = 9.2, 3.7 Hz, 1H), 7.27 (ddd, J = 9.2, 5.2, 2.5 Hz, 1H), 7.04-6.96 (m, 1H), 4.00 (d, J = 1.5 Hz, 3H), 2.94 (s, 3H) |
| 97 | ¹H NMR (500 MHz, DMSO-d₆) δ 10.42 (s, 1H), 9.85 (s, 1H), 8.53-8.45 (m, 2H), 8.27 (d, J = 5.4 Hz, 1H), 8.11 (s, 1H), 8.01-7.91 (m, 1H), 7.72 (s, 1H), 7.61 (s, 1H), 7.50 (d, J = 8.4 Hz, 1H), 7.21 (dd, J = 5.2, 1.2 Hz, 1H), 7.17 (d, J = 2.5 Hz, 1H), 7.08 (dd, J = 8.4, 2.5 Hz, 1H), 3.87 (s, 3H), 2.77 (d, J = 4.5 Hz, 3H) |
| 98 | ¹H NMR (500 MHz, DMSO-d₆) δ 10.46 (s, 1H), 9.97 (s, 1H), 8.57-8.45 (m, 2H), 8.22 (d, J = 3.0 Hz, 1H), 7.81 (s, 1H), 7.75-7.71 (m, 1H), 7.70-7.65 (m, 2H), 7.55-7.49 (m, 2H), 7.17 (d, J = 2.5 Hz, 1H), 7.11 (dd, J = 8.4, 2.0 Hz, 1H), 6.49 (d, J = 8.9 Hz, 1H), 6.33 (td, J = 6.8, 1.2 Hz, 1H), 3.87 (s, 3H), 2.77 (d, J = 4.5 Hz, 3H) |
| 99 | ¹H NMR (500 MHz, methanol-d₄) δ 8.29 (s, 1H), 8.05 (d, J = 3.0 Hz, 1H), 7.64 (s, 1H), 7.49 (d, J = 7.9 Hz, 1H), 7.42 (td, J = 8.4, 3.0 Hz, 1H), 7.31 (dd, J = 9.2, 3.7 Hz, 1H), 7.03-6.96 (m, 2H), 3.92 (s, 3H), 2.93 (s, 3H) |
| 100 | ¹H NMR (500 MHz, methanol-d₄) δ 8.32 (s, 1H), 8.04 (d, J = 5.4 Hz, 1H), 7.48 (br. s., 1H), 7.28 (ddd, J = 9.2, 5.2, 2.5 Hz, 1H), 7.11 (s, 1H), 7.02-6.93 (m, 1H), 6.77 (d, J = 5.0 Hz, 1H), 4.00 (d, J = 1.5 Hz, 3H), 2.94 (s, 3H), 2.34 (s, 3H) |
| 101 | ¹H NMR (500 MHz, methanol-d₄) δ 8.29 (s, 1H), 7.87 (d, J = 3.0 Hz, 1H), 7.36 (dt, J = 5.9, 3.0 Hz, 2H), 7.29-7.20 (m, 2H), 7.03-6.93 (m, 1H), 4.00 (d, J = 1.5 Hz, 3H), 3.92-3.86 (m, 4H), 3.17-3.10 (m, 4H), 2.93 (s, 3H) |
| 102 | ¹H NMR (500 MHz, methanol-d₄) δ 8.32 (s, 1H), 8.09 (d, J = 2.5 Hz, 1H), 7.81 (s, 1H), 7.54-7.48 (m, 2H), 7.37 (d, J = 8.4 Hz, 1H), 7.03-6.95 (m, 2H), 4.39-4.33 (m, 1H), 4.31-4.24 (m, 1H), 4.13 (dd, J = 12.1, 3.2 Hz, 1H), 3.97 (td, J = 6.6, 3.2 Hz, 1H), 3.92 (s, 3H), 3.83 (dd, J = 11.9, 4.5 Hz, 1H), 2.93 (s, 3H), 1.22 (d, J = 6.4 Hz, 3H) |
| 103 | ¹H NMR (500 MHz, methanol-d₄) δ 8.31 (s, 1H), 8.10 (d, J = 2.5 Hz, 1H), 7.81 (s, 1H), 7.56-7.48 (m, 2H), 7.32 (d, J = 8.4 Hz, 1H), 7.03-6.96 (m, 2H), 3.92 (s, 3H), 3.68 (t, J = 5.4 Hz, 2H), 2.93 (s, 3H), 2.56 (t, J = 6.2 Hz, 2H), 2.06-1.96 (m, 4H) |
| 104 | ¹H NMR (500 MHz, methanol-d₄) δ 8.27 (s, 1H), 7.89 (d, J = 3.0 Hz, 1H), 7.46 (d, J = 8.4 Hz, 1H), 7.40-7.33 (m, 2H), 7.21 (d, J = 8.9 Hz, 1H), 7.04-6.95 (m, 2H), 3.93-3.87 (m, 7H), 3.16-3.11 (m, 4H), 2.93 (s, 3H) |
| 105 | ¹H NMR (500 MHz, methanol-d₄) δ 8.33-8.26 (m, 2H), 7.97 (dd, J = 9.2, 2.7 Hz, 1H), 7.49 (d, J = 8.4 Hz, 1H), 7.33 (d, J = 8.9 Hz, 1H), 7.03-6.96 (m, 2H), 4.62-4.53 (m, 2H), 4.18-4.08 (m, 2H), 3.92 (s, 3H), 2.94 (s, 3H) |
| 106 | ¹H NMR (500 MHz, DMSO-d₆) δ 10.47 (s, 1H), 9.99 (s, 1H), 8.56-8.44 (m, 2H), 8.25 (d, J = 3.0 Hz, 1H), 8.02-7.97 (m, 1H), 7.82 (s, 1H), 7.75 (dd, J = 8.9, 3.0 Hz, 1H), 7.72-7.63 (m, 2H), 7.52 (d, J = 8.4 Hz, 1H), 7.18 (d, J = 2.0 Hz, 1H), 7.11 (dd, J = 8.4, 2.5 Hz, 1H), 6.52 (dd, J = 10.4, 5.4 Hz, 1H), 3.88 (s, 3H), 2.77 (d, J = 4.5 Hz, 3H) |

-continued

| Compound | ¹H NMR (methanol-d₄ equates CDCl₃:MeOD ~1:1 unless otherwise noted) Occasionally water suppression is used in DMSO-d₆ spectra |
|---|---|
| 107 | N/A |
| 108 | ¹H NMR (500 MHz, methanol-d₄) δ 8.28 (s, 1H), 7.81 (s, 1H), 7.48 (t, J = 7.9 Hz, 1H), 7.38 (d, J = 8.4 Hz, 1H), 7.00 (d, J = 2.5 Hz, 1H), 6.94 (dd, J = 8.4, 2.5 Hz, 1H), 6.58 (d, J = 7.4 Hz, 1H), 6.26 (d, J = 8.4 Hz, 1H), 3.88 (s, 3H), 3.46 (s, 3H), 2.93 (s, 3H) |
| 109 | ¹H NMR (500 MHz, methanol-d₄) δ 8.29 (s, 1H), 7.93 (s, 1H), 7.57-7.45 (m, 2H), 7.04-6.96 (m, 2H), 6.88 (d, J = 8.4 Hz, 1H), 6.77 (d, J = 7.4 Hz, 1H), 3.91 (s, 3H), 2.93 (s, 3H), 2.42 (s, 3H) |
| 110 | ¹H NMR (500 MHz, methanol-d₄) δ 8.28 (s, 1H), 8.20 (dd, J = 5.0, 1.0 Hz, 1H), 7.67 (s, 1H), 7.63 (ddd, J = 8.5, 7.1, 1.7 Hz, 1H), 7.50 (d, J = 8.9 Hz, 1H), 7.24 (d, J = 8.4 Hz, 1H), 7.03-6.97 (m, 2H), 6.93-6.88 (m, 1H), 3.91 (s, 3H), 2.94 (s, 3H) |
| 111 | ¹H NMR (500 MHz, methanol-d₄) δ 8.29 (s, 1H), 8.03 (s, 1H), 7.54-7.43 (m, 3H), 7.16 (d, J = 8.4 Hz, 1H), 7.05-6.95 (m, 2H), 3.92 (s, 3H), 2.93 (s, 3H), 2.29 (s, 3H) |
| 112 | ¹H NMR (500 MHz, methanol-d₄) δ 8.27 (s, 1H), 7.91 (d, J = 3.0 Hz, 1H), 7.46 (d, J = 8.4 Hz, 1H), 7.36 (s, 1H), 7.31 (dd, J = 8.9, 3.0 Hz, 1H), 7.20 (d, J = 8.9 Hz, 1H), 7.04-6.97 (m, 2H), 3.91 (s, 3H), 3.86 (s, 3H), 2.93 (s, 3H) |
| 113 | ¹H NMR (500 MHz, methanol-d₄) δ 8.30 (s, 1H), 8.05 (d, J = 5.4 Hz, 1H), 7.53-7.45 (m, 2H), 7.08 (s, 1H), 7.03-6.97 (m, 2H), 6.78 (d, J = 5.0 Hz, 1H), 3.91 (s, 3H), 2.93 (s, 3H), 2.34 (s, 3H) |
| 114 | ¹H NMR (500 MHz, methanol-d₄) δ 8.54 (s, 1H), 8.20 (d, J = 8.9 Hz, 1H), 7.66 (d, J = 3.5 Hz, 1H), 7.38 (d, J = 8.4 Hz, 1H), 7.07 (d, J = 2.0 Hz, 1H), 7.02 (dd, J = 8.4, 2.0 Hz, 1H), 6.93 (s, 1H), 6.55 (d, J = 8.9 Hz, 1H), 6.51 (d, J = 3.5 Hz, 1H), 3.92 (s, 3H), 2.97 (s, 3H) |
| 115 | ¹H NMR (500 MHz, methanol-d₄) δ 8.29 (s, 1H), 8.06 (d, J = 3.0 Hz, 1H), 7.57 (br. s., 1H), 7.48 (d, J = 8.4 Hz, 1H), 7.46-7.39 (m, 1H), 7.29 (dd, J = 9.2, 3.7 Hz, 1H), 7.05-6.97 (m, 2H), 3.92 (s, 3H), 2.93 (s, 3H) |
| 116 | ¹H NMR (500 MHz, methanol-d₄) δ 8.31 (s, 1H), 8.23 (s, 1H), 7.80-7.74 (m, 2H), 7.68 (t, J = 7.9 Hz, 1H), 7.44-7.37 (m, 1H), 7.36-7.26 (m, 4H), 7.00 (d, J = 7.9 Hz, 1H), 6.93 (d, J = 2.0 Hz, 1H), 6.27 (dd, J = 8.4, 2.0 Hz, 1H), 3.90 (s, 3H), 2.93 (s, 3H) |
| 117 | ¹H NMR (500 MHz, methanol-d₄) δ 8.41 (s, 1H), 7.96 (t, J = 7.9 Hz, 1H), 7.45 (d, J = 7.4 Hz, 1H), 7.37 (d, J = 8.4 Hz, 1H), 7.29 (d, J = 8.4 Hz, 1H), 7.26 (s, 1H), 7.11 (d, J = 2.0 Hz, 1H), 7.07 (dd, J = 8.2, 2.2 Hz, 1H), 3.91 (s, 3H), 2.96 (s, 3H) |
| 118 | ¹H NMR (500 MHz, methanol-d₄) δ 8.33 (s, 1H), 8.14 (s, 1H), 7.72 (d, J = 8.9 Hz, 1H), 7.50 (d, J = 8.4 Hz, 1H), 7.07-7.02 (m, 2H), 7.00 (dd, J = 8.4, 2.0 Hz, 1H), 3.92 (s, 3H), 2.94 (s, 3H), 2.56 (s, 3H) |
| 119 | ¹H NMR (500 MHz, DMSO-d₆) δ 10.36 (br. s., 1H), 8.79 (br. s., 1H), 8.40 (s, 1H), 8.25 (br. s., 1H), 7.77 (br. s., 1H), 7.43 (dd, J = 8.7, 6.2 Hz, 1H), 7.14 (d, J = 9.9 Hz, 1H), 6.92 (td, J = 8.5, 2.7 Hz, 1H), 3.84 (s, 3H), 2.79 (d, J = 4.5 Hz, 3H) |
| 120 | ¹H NMR (500 MHz, methanol-d₄) δ 8.63 (s, 1H), 8.41 (s, 1H), 8.01 (dd, J = 8.7, 2.2 Hz, 1H), 7.37 (d, J = 8.4 Hz, 1H), 7.19-7.12 (m, 2H), 7.08 (dd, J = 8.4, 2.0 Hz, 1H), 6.69 (br. s., 1H), 3.93 (s, 3H), 2.98 (s, 3H) |
| 121 | ¹H NMR (500 MHz, methanol-d₄) δ 8.53 (d, J = 5.4 Hz, 1H), 8.39 (s, 1H), 7.40-7.33 (m, 2H), 7.31 (s, 1H), 7.15 (d, J = 2.0 Hz, 1H), 7.08 (dd, J = 8.4, 2.5 Hz, 1H), 6.62 (br. s., 1H), 3.92 (s, 3H), 2.97 (s, 3H) |
| 122 | ¹H NMR (500 MHz, methanol-d₄) δ 8.32 (s, 1H), 8.01 (d, J = 2.5 Hz, 1H), 7.67-7.62 (m, 2H), 7.45-7.37 (m, 1H), 7.36-7.26 (m, 3H), 7.22-7.13 (m, 1H), 6.88-6.52 (m, 1H), 2.93 (s, 3H) |
| 123 | ¹H NMR (500 MHz, methanol-d₄) δ 8.36 (s, 1H), 8.00 (d, J = 3.0 Hz, 1H), 7.45-7.38 (m, 1H), 7.32 (dd, J = 9.2, 3.7 Hz, 1H), 7.27 (d, J = 8.4 Hz, 1H), 7.17 (t, J = 8.4 Hz, 1H), 6.95 (d, J = 7.4 Hz, 1H), 2.94 (s, 3H) |
| 124 | ¹H NMR (500 MHz, DMSO-d₆) δ 10.28 (s, 1H), 10.25 (s, 1H), 8.60 (d, J = 1.5 Hz, 1H), 8.53 (d, J = 4.5 Hz, 1H), 8.48 (s, 1H), 8.02 (dd, J = 8.9, 2.0 Hz, 1H), 7.73 (d, J = 8.9 Hz, 1H), 7.54 (s, 1H), 7.43 (dd, J = 8.9, 5.9 Hz, 1H), 7.07 (dd, J = 10.9, 3.0 Hz, 1H), 6.90 (td, J = 8.5, 2.7 Hz, 1H), 3.84 (s, 3H), 2.77 (d, J = 4.5 Hz, 3H) |
| 125 | N/A |
| 126 | ¹H NMR (500 MHz, DMSO-d₆) δ 10.26 (s, 1H), 9.93 (s, 1H), 8.51-8.43 (m, 2H), 8.20 (d, J = 2.5 Hz, 1H), 8.01-7.95 (m, 1H), 7.73 (dd, J = 8.9, 2.5 Hz, 1H), 7.71-7.59 (m, 3H), 7.45 (dd, J = 8.9, 5.9 Hz, 1H), 7.05 (dd, J = 10.9, 3.0 Hz, 1H), 6.88 (td, J = 8.5, 2.7 Hz, 1H), 6.52 (dd, J = 10.2, 5.7 Hz, 1H), 3.84 (s, 3H), 2.77 (d, J = 4.5 Hz, 3H) |
| 127 | ¹H NMR (500 MHz, DMSO-d₆) δ 10.23 (s, 1H), 9.66 (s, 1H), 8.48-8.40 (m, 2H), 8.37 (d, J = 2.5 Hz, 1H), 7.94 (dd, J = 9.2, 2.7 Hz, 1H), 7.63 (d, J = 9.4 Hz, 1H), 7.51 (s, 1H), 7.43 (dd, J = 8.7, 6.2 Hz, 1H), 7.05 (dd, J = 10.7, 2.7 Hz, 1H), 6.84 (td, J = 8.5, 2.7 Hz, 1H), 3.84 (s, 3H), 3.81 (t, J = 6.9 Hz, 2H), 2.76 (d, J = 4.5 Hz, 3H), 2.46 (t, J = 8.2 Hz, 2H), 2.07 (quin, J = 7.6 Hz, 2H) |
| 128 | ¹H NMR (500 MHz, DMSO-d₆) δ 11.02 (s, 1H), 9.78 (s, 1H), 8.59-8.52 (m, 1H), 8.50 (s, 1H), 8.01 (s, 2H), 7.57-7.42 (m, 2H), 7.35 (dd, J = 11.1, 2.2 Hz, 1H), 6.97 (ddd, J = 11.3, 8.8, 2.7 Hz, 1H), 3.84 (s, 3H), 2.78 (d, J = 4.5 Hz, 3H), 2.21 (s, 3H) |

| Compound | ¹H NMR (methanol-d₄ equates CDCl₃:MeOD ~1:1 unless otherwise noted) Occasionally water suppression is used in DMSO-d₆ spectra |
|---|---|
| 129 | ¹H NMR (500 MHz, DMSO-d₆) δ 11.03 (s, 1H), 9.80 (s, 1H), 8.56 (d, J = 4.5 Hz, 1H), 8.53 (s, 1H), 8.10-7.99 (m, 2H), 7.42-7.30 (m, 2H), 6.97 (ddd, J = 11.5, 8.8, 3.0 Hz, 1H), 6.76 (d, J = 4.5 Hz, 1H), 3.84 (s, 3H), 2.78 (d, J = 4.5 Hz, 3H), 2.27 (s, 3H) |
| 130 | ¹H NMR (500 MHz, DMSO-d₆) δ 10.85 (s, 1H), 9.74 (s, 1H), 8.57 (d, J = 4.5 Hz, 1H), 8.51 (s, 1H), 7.75 (s, 1H), 7.57 (t, J = 7.9 Hz, 1H), 7.27-7.17 (m, 2H), 7.05-6.97 (m, 1H), 6.29 (d, J = 7.9 Hz, 1H), 3.81 (s, 3H), 3.62 (s, 3H), 2.78 (d, J = 4.5 Hz, 3H) |
| 131 | ¹H NMR (500 MHz, DMSO-d₆) δ 11.01 (s, 1H), 8.65 (br. s., 1H), 8.52 (s, 1H), 8.22 (br. s., 1H), 7.73 (br. s., 1H), 7.49 (br. s., 1H), 7.35 (d, J = 10.4 Hz, 1H), 7.12-6.87 (m, 2H), 3.84 (s, 3H), 2.79 (d, J = 4.5 Hz, 3H) |
| 132 | ¹H NMR (500 MHz, DMSO-d₆) δ 11.05 (s, 1H), 8.78-8.44 (m, 2H), 7.62 (br. s., 1H), 7.31 (d, J = 10.4 Hz, 1H), 7.24-6.96 (m, 2H), 6.83 (br. s., 1H), 3.84 (s, 4H), 2.80 (d, J = 4.5 Hz, 4H), 1.91 (s, 1H) |
| 133 | ¹H NMR (500 MHz, DMSO-d₆) δ 11.00 (s, 1H), 9.72 (br. s., 1H), 8.54 (d, J = 4.5 Hz, 1H), 8.49 (s, 1H), 7.90 (d, J = 3.0 Hz, 1H), 7.82 (br. s., 1H), 7.62 (d, J = 8.9 Hz, 1H), 7.40 (dd, J = 8.9, 3.0 Hz, 1H), 7.32 (dd, J = 10.9, 2.0 Hz, 1H), 6.97 (ddd, J = 11.3, 8.8, 2.7 Hz, 1H), 3.83 (s, 3H), 3.78 (s, 3H), 2.78 (d, J = 4.5 Hz, 3H) |
| 134 | ¹H NMR (500 MHz, DMSO-d₆) δ 11.00 (s, 1H), 10.33 (br. s., 1H), 8.70-8.54 (m, 2H), 8.41 (d, J = 5.0 Hz, 1H), 8.17 (br. s., 1H), 7.70 (br. s., 1H), 7.35-7.25 (m, 2H), 7.08-6.91 (m, 1H), 3.84 (s, 3H), 2.79 (d, J = 4.5 Hz, 3H) |
| 135 | ¹H NMR (500 MHz, DMSO-d₆) δ 11.00 (s, 1H), 10.39 (s, 1H), 8.65 (d, J = 4.5 Hz, 1H), 8.56 (s, 1H), 8.50 (d, J = 1.0 Hz, 1H), 8.04 (dd, J = 8.9, 2.5 Hz, 1H), 7.93-7.84 (m, 2H), 7.34 (dd, J = 10.7, 2.2 Hz, 1H), 7.01 (ddd, J = 11.3, 8.8, 2.7 Hz, 1H), 3.84 (s, 3H), 2.80 (d, J = 4.5 Hz, 3H) |
| 136 | ¹H NMR (500 MHz, DMSO-d₆) δ 10.98 (s, 1H), 9.98 (s, 1H), 9.07 (s, 1H), 8.67-8.53 (m, 2H), 8.40 (s, 1H), 8.00 (d, J = 8.4 Hz, 1H), 7.78 (d, J = 8.4 Hz, 1H), 7.70-7.61 (m, 1H), 7.46 (s, 1H), 7.45-7.39 (m, 1H), 7.32 (dd, J = 10.7, 2.2 Hz, 1H), 6.98 (ddd, J = 11.3, 8.8, 2.7 Hz, 1H), 3.84 (s, 3H), 2.80 (d, J = 4.5 Hz, 3H) |
| 137 | ¹H NMR (500 MHz, DMSO-d₆) δ 10.99 (s, 1H), 9.97 (br. s., 1H), 8.59 (br. s., 1H), 8.51 (s, 1H), 8.14 (d, J = 3.0 Hz, 1H), 7.77 (br. s., 2H), 7.68 (td, J = 8.7, 3.0 Hz, 1H), 7.31 (dd, J = 10.9, 2.0 Hz, 1H), 6.99 (t, J = 8.9 Hz, 1H), 3.83 (s, 3H), 2.79 (d, J = 4.5 Hz, 3H) |
| 138 | ¹H NMR (500 MHz, DMSO-d₆) δ 10.96 (s, 1H), 10.28 (s, 1H), 8.63 (d, J = 5.0 Hz, 1H), 8.55 (s, 1H), 7.99-7.81 (m, 4H), 7.34 (d, J = 7.9 Hz, 1H), 7.19 (dd, J = 10.4, 2.0 Hz, 1H), 7.01 (ddd, J = 11.4, 8.9, 3.0 Hz, 1H), 3.82 (s, 3H), 2.79 (d, J = 4.5 Hz, 3H) |
| 139 | ¹H NMR (500 MHz, DMSO-d₆) δ 11.04 (s, 1H), 10.42 (s, 1H), 8.65 (d, J = 4.5 Hz, 1H), 8.56 (s, 1H), 8.12 (s, 1H), 8.02-7.93 (m, 1H), 7.49 (d, J = 8.4 Hz, 1H), 7.29 (d, J = 10.4 Hz, 1H), 7.11-6.97 (m, 1H), 3.83 (s, 3H), 2.79 (d, J = 4.5 Hz, 3H), 2.53 (s, 3H) |
| 140 | ¹H NMR (500 MHz, DMSO-d₆) δ 11.05 (s, 1H), 10.32 (s, 1H), 8.63 (d, J = 4.5 Hz, 1H), 8.56 (s, 1H), 8.09 (s, 1H), 7.40 (s, 1H), 7.33-7.22 (m, 1H), 7.12-6.97 (m, 1H), 3.83 (s, 3H), 2.79 (d, J = 4.5 Hz, 3H), 2.52 (s, 3H), 2.38 (s, 3H) |
| 141 | ¹H NMR (500 MHz, DMSO-d₆) δ 10.99 (s, 1H), 9.79 (s, 1H), 8.57 (d, J = 4.5 Hz, 1H), 8.51 (s, 1H), 8.22 (s, 1H), 7.59-7.49 (m, 1H), 7.26 (d, J = 8.4 Hz, 2H), 7.00 (ddd, J = 11.4, 8.9, 3.0 Hz, 1H), 6.75 (d, J = 7.4 Hz, 1H), 3.82 (s, 3H), 2.78 (d, J = 4.5 Hz, 3H), 2.61 (q, J = 7.4 Hz, 2H), 1.10 (t, J = 7.7 Hz, 3H) |
| 142 | ¹H NMR (500 MHz, DMSO-d₆) δ 10.38 (s, 1H), 8.74-8.35 (m, 3H), 8.00 (d, J = 8.9 Hz, 1H), 7.54 (dd, J = 8.7, 6.2 Hz, 2H), 7.32-7.21 (m, 1H), 7.15-6.99 (m, 1H), 6.02-5.82 (m, 2H), 3.82 (t, J = 6.9 Hz, 2H), 2.78 (d, J = 4.5 Hz, 3H), 2.48-2.45 (m, 1H), 2.08 (quin, J = 7.6 Hz, 2H) |
| 143 | ¹H NMR (500 MHz, DMSO-d₆) δ 11.00 (br. s., 1H), 8.76 (br. s., 1H), 8.60 (s, 1H), 7.97-7.77 (m, 3H), 7.55 (d, J = 6.9 Hz, 1H), 7.41 (dd, J = 14.4, 6.9 Hz, 3H), 7.25 (d, J = 9.9 Hz, 1H), 7.15-6.94 (m, 1H), 3.85 (s, 3H), 2.81 (d, J = 4.5 Hz, 3H) |
| 144 | ¹H NMR (500 MHz, DMSO-d₆) δ 11.00 (s, 1H), 8.76 (br. s., 1H), 8.53 (s, 1H), 8.23 (d, J = 5.4 Hz, 1H), 7.65 (br. s., 1H), 7.46 (br. s., 1H), 7.32 (d, J = 10.4 Hz, 1H), 7.18-7.05 (m, 2H), 3.84 (s, 3H), 2.80 (d, J = 4.5 Hz, 3H) |
| 145 | ¹H NMR (500 MHz, DMSO-d₆) δ 10.98 (s, 1H), 10.49 (s, 1H), 8.66 (d, J = 5.0 Hz, 1H), 8.60-8.53 (m, 2H), 8.09 (dd, J = 8.9, 2.0 Hz, 1H), 7.89 (d, J = 8.9 Hz, 1H), 7.82 (s, 1H), 7.37-7.23 (m, 1H), 7.02 (ddd, J = 11.3, 8.8, 2.7 Hz, 1H), 3.84 (s, 3H), 2.80 (d, J = 4.5 Hz, 3H) |
| 146 | ¹H NMR (500 MHz, DMSO-d₆) δ 10.19 (br. s., 1H), 9.06 (br. s., 1H), 8.50 (s, 2H), 7.99 (d, J = 6.9 Hz, 1H), 7.76 (d, J = 7.9 Hz, 1H), 7.64 (t, J = 7.4 Hz, 1H), 7.49-7.37 (m, 2H), 7.07 (d, J = 9.4 Hz, 2H), 6.86 (td, J = 8.4, 2.5 Hz, 1H), 3.85 (s, 3H), 2.78 (d, J = 4.5 Hz, 3H) |
| 147 | ¹H NMR (500 MHz, DMSO-d₆) δ 10.23 (s, 1H), 9.65 (br. s., 1H), 8.49-8.38 (m, 2H), 8.13 (d, J = 3.5 Hz, 1H), 7.73-7.58 (m, 2H), 7.51 (d, J = 8.4 Hz, 1H), 7.45 (dd, J = 8.7, 6.2 Hz, 1H), 7.05 (dd, J = 10.9, 2.5 Hz, 1H), 6.92-6.78 (m, 2H), 3.84 (s, 3H), 2.77 (d, J = 4.5 Hz, 3H) |

| Compound | ¹H NMR (methanol-d₄ equates CDCl₃:MeOD ~1:1 unless otherwise noted) Occasionally water suppression is used in DMSO-d₆ spectra |
|---|---|
| 148 | ¹H NMR (500 MHz, DMSO-d₆) δ 10.23 (s, 1H), 9.54 (s, 1H), 8.47-8.37 (m, 2H), 7.99 (d, J = 5.4 Hz, 1H), 7.67 (s, 1H), 7.44 (dd, J = 8.7, 6.2 Hz, 1H), 7.34 (s, 1H), 7.04 (dd, J = 10.9, 2.5 Hz, 1H), 6.85 (td, J = 8.5, 2.7 Hz, 1H), 6.69 (d, J = 4.5 Hz, 1H), 3.84 (s, 3H), 2.76 (d, J = 4.5 Hz, 3H), 2.24 (s, 3H) |
| 149 | ¹H NMR (500 MHz, DMSO-d₆) δ 10.22 (s, 1H), 9.71 (s, 1H), 8.49-8.37 (m, 2H), 8.13 (d, J = 3.0 Hz, 1H), 7.68-7.64 (m, 1H), 7.64-7.59 (m, 1H), 7.46 (s, 1H), 7.42 (dd, J = 8.9, 5.9 Hz, 1H), 7.05 (dd, J = 10.9, 3.0 Hz, 1H), 6.88 (td, J = 8.5, 2.7 Hz, 1H), 3.84 (s, 3H), 2.76 (d, J = 4.5 Hz, 3H) |
| 150 | ¹H NMR (500 MHz, DMSO-d₆) δ 10.30 (br. s., 1H), 8.49 (s, 2H), 7.89-7.64 (m, 4H), 7.48-7.23 (m, 6H), 7.05 (d, J = 10.4 Hz, 1H), 6.42 (br. s., 1H), 3.84 (s, 3H), 2.78 (d, J = 4.5 Hz, 3H) |
| 151 | ¹H NMR (500 MHz, DMSO-d₆) δ 10.35 (s, 1H), 9.75 (s, 1H), 8.54-8.41 (m, 2H), 8.14 (d, J = 3.0 Hz, 1H), 7.72-7.57 (m, 2H), 7.53 (dd, J = 8.9, 5.9 Hz, 1H), 7.47 (s, 1H), 7.23 (dd, J = 10.2, 2.7 Hz, 1H), 7.09 (td, J = 8.5, 2.7 Hz, 1H), 5.99 (s, 1H), 5.88 (s, 1H), 2.77 (d, J = 4.5 Hz, 3H) |
| 152 | ¹H NMR (500 MHz, DMSO-d₆) δ 10.25 (s, 1H), 10.23 (s, 1H), 8.56-8.43 (m, 1H), 7.99-7.89 (m, 1H), 7.83 (s, 1H), 7.43 (dd, J = 8.7, 6.2 Hz, 1H), 7.35 (d, J = 8.4 Hz, 1H), 7.08 (dd, J = 10.9, 2.5 Hz, 1H), 6.85 (td, J = 8.4, 3.0 Hz, 1H), 3.83 (s, 3H), 2.77 (d, J = 4.5 Hz, 3H), 2.42 (s, 3H) |
| 153 | ¹H NMR (500 MHz, methanol-d₄) δ 8.31 (s, 1H), 8.05 (d, J = 5.4 Hz, 1H), 7.50 (d, J = 2.0 Hz, 1H), 7.42 (dd, J = 8.9, 5.9 Hz, 1H), 7.33 (s, 1H), 6.88 (dd, J = 5.4, 1.5 Hz, 1H), 6.80 (dd, J = 10.4, 3.0 Hz, 1H), 6.72 (td, J = 8.3, 2.7 Hz, 1H), 3.89 (s, 3H), 2.94 (s, 3H) |
| 154 | ¹H NMR (500 MHz, methanol-d₄) δ 8.27 (s, 1H), 7.65 (s, 1H), 7.46 (t, J = 7.9 Hz, 1H), 7.34 (dd, J = 8.7, 6.2 Hz, 1H), 6.79 (dd, J = 10.4, 3.0 Hz, 1H), 6.68 (td, J = 8.3, 2.7 Hz, 1H), 6.56 (d, J = 7.9 Hz, 1H), 6.24 (d, J = 7.9 Hz, 1H), 3.85 (s, 3H), 3.41 (s, 3H), 2.93 (s, 3H) |
| 155 | ¹H NMR (500 MHz, methanol-d₄) δ 8.34 (s, 1H), 8.30 (d, J = 4.5 Hz, 1H), 7.87 (s, 1H), 7.42 (dd, J = 8.9, 5.9 Hz, 1H), 7.32 (s, 1H), 7.04 (dd, J = 5.2, 1.2 Hz, 1H), 6.81 (dd, J = 10.4, 2.5 Hz, 1H), 6.73 (td, J = 8.3, 2.7 Hz, 1H), 3.89 (s, 3H), 2.94 (s, 3H) |
| 156 | ¹H NMR (500 MHz, DMSO-d₆) δ 10.67-10.35 (m, 1H), 8.67 (br. s., 1H), 8.51 (s, 1H), 7.95 (t, J = 7.9 Hz, 1H), 7.56 (d, J = 7.9 Hz, 1H), 7.44-7.34 (m, 2H), 7.31 (br. s., 1H), 7.09 (dd, J = 10.9, 2.5 Hz, 1H), 6.80 (td, J = 8.4, 2.5 Hz, 1H), 3.82 (s, 3H), 2.79 (d, J = 4.5 Hz, 3H) |
| 157 | ¹H NMR (500 MHz, DMSO-d₆) δ 10.42 (br. s., 1H), 8.81 (br. s., 1H), 8.58 (br. s., 1H), 8.45 (s, 1H), 8.11 (d, J = 7.9 Hz, 1H), 7.44 (dd, J = 8.9, 6.4 Hz, 2H), 7.15 (dd, J = 10.7, 2.2 Hz, 1H), 6.93 (td, J = 8.4, 3.0 Hz, 1H), 3.85 (s, 3H), 2.80 (d, J = 4.5 Hz, 3H) |
| 158 | ¹H NMR (500 MHz, DMSO-d₆) δ 10.39 (br. s., 1H), 8.81 (br. s., 1H), 8.41 (s, 1H), 8.29 (br. s., 1H), 7.89 (d, J = 6.4 Hz, 1H), 7.43 (dd, J = 8.7, 6.2 Hz, 1H), 7.34-7.06 (m, 2H), 6.92 (td, J = 8.5, 2.7 Hz, 1H), 3.84 (s, 3H), 2.80 (d, J = 4.5 Hz, 3H) |
| 159 | ¹H NMR (500 MHz, DMSO-d₆) δ 10.23 (s, 1H), 9.53 (s, 1H), 8.47-8.35 (m, 2H), 7.97 (d, J = 2.0 Hz, 1H), 7.66 (s, 1H), 7.52-7.35 (m, 3H), 7.05 (dd, J = 10.9, 2.5 Hz, 1H), 6.86 (td, J = 8.7, 3.0 Hz, 1H), 3.84 (s, 3H), 2.76 (d, J = 4.5 Hz, 3H), 2.18 (s, 3H) |
| 160 | ¹H NMR (500 MHz, DMSO-d₆) δ 10.32 (s, 1H), 8.86 (br. s., 1H), 8.54 (br. s., 1H), 8.10-7.91 (m, 1H), 7.70 (br. s., 1H), 7.47 (br. s., 1H), 7.26-7.13 (m, 1H), 6.93 (td, J = 8.5, 2.7 Hz, 1H), 6.84 (br. s., 1H), 3.85 (s, 6H), 2.81 (d, J = 4.0 Hz, 5H) |
| 161 | ¹H NMR (500 MHz, DMSO-d₆) δ 10.35 (s, 1H), 8.85 (br. s., 1H), 8.37 (s, 1H), 7.99 (br. s., 1H), 7.54 (d, J = 7.4 Hz, 1H), 7.43 (dd, J = 8.7, 6.2 Hz, 1H), 7.17 (d, J = 10.4 Hz, 1H), 7.10 (d, J = 5.9 Hz, 1H), 6.92 (td, J = 8.5, 2.7 Hz, 1H), 3.85 (s, 3H), 3.83 (s, 3H), 2.80 (d, J = 4.5 Hz, 3H) |
| 162 | ¹H NMR (500 MHz, methanol-d₄) δ 8.44 (d, J = 2.0 Hz, 1H), 8.36 (s, 1H), 7.80 (dd, J = 8.9, 2.5 Hz, 1H), 7.59 (s, 1H), 7.55-7.45 (m, 2H), 7.06 (dd, J = 9.4, 2.5 Hz, 1H), 6.94 (td, J = 8.4, 2.5 Hz, 1H), 5.86-5.72 (m, 2H), 2.94 (s, 3H) |
| 163 | ¹H NMR (500 MHz, DMSO-d₆) δ 10.25 (s, 1H), 10.13 (s, 1H), 8.54-8.43 (m, 2H), 7.79 (s, 1H), 7.42 (dd, J = 8.7, 6.2 Hz, 1H), 7.26 (s, 1H), 7.07 (dd, J = 10.9, 3.0 Hz, 1H), 6.84 (td, J = 8.5, 2.7 Hz, 1H), 3.83 (s, 3H), 2.77 (d, J = 4.5 Hz, 3H), 2.42 (s, 3H), 2.35 (s, 3H) |
| 164 | ¹H NMR (500 MHz, methanol-d₄) δ 8.38 (s, 1H), 8.14 (br. s., 1H), 7.78 (t, J = 8.2 Hz, 1H), 7.69 (dd, J = 6.9, 1.5 Hz, 1H), 7.51 (ddd, J = 9.2, 6.7, 2.0 Hz, 1H), 7.27 (dd, J = 13.1, 7.7 Hz, 2H), 7.00 (dt, J = 9.8, 2.5 Hz, 1H), 6.65 (d, J = 8.9 Hz, 1H), 6.48 (ddd, J = 10.9, 8.4, 2.5 Hz, 1H), 6.22 (td, J = 6.8, 1.2 Hz, 1H), 3.94 (d, J = 1.0 Hz, 3H), 2.94 (s, 3H) |
| 165 | ¹H NMR (500 MHz, DMSO-d₆) δ 10.25 (s, 1H), 9.93 (s, 1H), 8.50-8.42 (m, 2H), 7.79 (t, J = 7.9 Hz, 1H), 7.65 (dd, J = 6.9, 1.5 Hz, 1H), 7.58-7.45 (m, 3H), 7.27 (dd, J = 8.7, 6.2 Hz, 1H), 7.09 (d, J = 7.4 Hz, 1H), 6.94 (dd, J = 10.9, 2.5 Hz, 1H), 6.49 (d, J = 8.9 Hz, 1H), 6.44 (td, J = 8.4, 3.0 Hz, 1H), 6.18 (td, J = 6.8, 1.2 Hz, 1H), 3.80 (s, 3H), 2.76 (d, J = 4.5 Hz, 3H) |
| 166 | ¹H NMR (500 MHz, DMSO-d₆) δ 10.33 (s, 1H), 10.10 (s, 1H), 8.58-8.48 (m, 2H), 8.37 (d, J = 4.5 Hz, 1H), 8.13 (s, 1H), 7.52 (dd, J = 8.9, 5.9 Hz, 1H), |

| Compound | ¹H NMR (methanol-d₄ equates CDCl₃:MeOD ~1:1 unless otherwise noted) Occasionally water suppression is used in DMSO-d₆ spectra |
|---|---|
| | 7.34 (s, 1H), 7.26-7.19 (m, 2H), 7.07 (td, J = 8.4, 3.0 Hz, 1H), 6.04-5.82 (m, 2H), 2.78 (d, J = 4.5 Hz, 3H) |
| 167 | ¹H NMR (500 MHz, DMSO-d₆) δ 11.01 (s, 1H), 10.13 (s, 1H), 8.58 (d, J = 4.5 Hz, 1H), 8.53 (s, 1H), 8.31 (d, J = 5.4 Hz, 1H), 7.89 (s, 1H), 7.81 (s, 1H), 7.69 (dd, J = 6.7, 1.7 Hz, 1H), 7.55 (ddd, J = 9.2, 6.7, 2.0 Hz, 1H), 7.34 (d, J = 10.4 Hz, 1H), 7.08-6.92 (m, 2H), 6.52 (d, J = 9.4 Hz, 1H), 6.38 (td, J = 6.7, 1.5 Hz, 1H), 3.84 (s, 3H), 2.78 (d, J = 4.5 Hz, 3H) |
| 168 | ¹H NMR (500 MHz, DMSO-d₆) δ 10.21 (s, 1H), 9.89 (s, 1H), 8.48-8.41 (m, 2H), 8.27 (d, J = 5.4 Hz, 1H), 7.75 (s, 1H), 7.66 (dd, J = 6.9, 2.0 Hz, 1H), 7.54 (ddd, J = 9.0, 6.8, 2.0 Hz, 1H), 7.48 (s, 1H), 7.44 (dd, J = 8.7, 6.2 Hz, 1H), 7.06 (dd, J = 10.9, 3.0 Hz, 1H), 6.94 (dd, J = 5.2, 1.7 Hz, 1H), 6.86 (td, J = 8.5, 2.7 Hz, 1H), 6.51 (d, J = 9.4 Hz, 1H), 6.36 (td, J = 6.7, 1.0 Hz, 1H), 3.84 (s, 3H), 2.76 (d, J = 4.5 Hz, 3H) |
| 169 | ¹H NMR (500 MHz, DMSO-d₆) δ 11.01 (s, 1H), 9.77 (s, 1H), 8.62-8.55 (m, 1H), 8.52 (s, 1H), 8.03-7.98 (m, 2H), 7.34 (dd, J = 10.9, 2.0 Hz, 1H), 7.23 (d, J = 2.0 Hz, 1H), 6.97 (ddd, J = 11.5, 8.8, 3.0 Hz, 1H), 6.56 (dd, J = 5.9, 2.5 Hz, 1H), 3.83 (s, 3H), 3.79 (s, 3H), 2.78 (d, J = 4.5 Hz, 3H) |
| 170 | ¹H NMR (500 MHz, DMSO-d₆) δ 10.20 (s, 1H), 9.52 (s, 1H), 8.47-8.40 (m, 2H), 7.96 (d, J = 5.9 Hz, 1H), 7.59 (s, 1H), 7.43 (dd, J = 8.7, 6.2 Hz, 1H), 7.20 (br. s., 1H), 7.04 (dd, J = 10.7, 2.7 Hz, 1H), 6.84 (td, J = 8.7, 3.0 Hz, 1H), 6.49 (dd, J = 5.9, 2.0 Hz, 1H), 3.83 (s, 3H), 3.77 (s, 3H), 2.76 (d, J = 4.5 Hz, 3H) |
| 171 | ¹H NMR (500 MHz, DMSO-d₆) δ 10.75 (s, 1H), 9.85 (s, 1H), 8.53 (d, J = 4.5 Hz, 1H), 8.48 (s, 1H), 8.17 (d, J = 3.0 Hz, 1H), 7.76 (s, 1H), 7.73-7.67 (m, 1H), 7.67-7.61 (m, 1H), 7.39 (d, J = 8.4 Hz, 1H), 7.19 (td, J = 8.2, 5.9 Hz, 1H), 6.98 (ddd, J = 10.9, 8.4, 1.0 Hz, 1H), 3.85 (s, 3H), 2.78 (d, J = 4.5 Hz, 3H) |
| 172 | ¹H NMR (500 MHz, DMSO-d₆) δ 10.76 (s, 1H), 9.77 (s, 1H), 8.52 (d, J = 4.5 Hz, 1H), 8.49 (s, 1H), 8.18 (dd, J = 5.0, 1.5 Hz, 1H), 7.98 (s, 1H), 7.68-7.61 (m, 1H), 7.54 (d, J = 8.4 Hz, 1H), 7.43 (d, J = 8.4 Hz, 1H), 7.17 (td, J = 8.3, 6.2 Hz, 1H), 7.01-6.93 (m, 1H), 6.91-6.82 (m, 1H), 3.85 (d, J = 1.0 Hz, 3H), 2.78 (d, J = 4.5 Hz, 3H) |
| 173 | ¹H NMR (500 MHz, DMSO-d₆) δ 10.73 (s, 1H), 10.20 (s, 1H), 8.57 (d, J = 4.5 Hz, 1H), 8.54 (s, 1H), 8.41 (d, J = 5.9 Hz, 1H), 8.15 (s, 1H), 7.64 (s, 1H), 7.38 (d, J = 8.4 Hz, 1H), 7.27 (dd, J = 5.2, 1.2 Hz, 1H), 7.17 (td, J = 8.2, 5.9 Hz, 1H), 7.00 (ddd, J = 10.9, 8.4, 1.5 Hz, 1H), 3.85 (s, 3H), 2.79 (d, J = 4.5 Hz, 3H) |
| 174 | ¹H NMR (500 MHz, methanol-d₄) δ 8.28 (s, 1H), 7.93 (d, J = 3.0 Hz, 1H), 7.46-7.37 (m, 2H), 7.37-7.31 (m, 3H), 7.31-7.23 (m, 2H), 7.12 (t, J = 4.2 Hz, 1H), 2.91 (s, 3H), 2.44 (s, 3H) |
| 175 | ¹H NMR (500 MHz, DMSO-d₆) δ 10.65 (s, 1H), 9.79 (s, 1H), 8.48-8.36 (m, 2H), 8.08 (d, J = 19.3 Hz, 2H), 7.77 (s, 1H), 7.68 (s, 1H), 7.65-7.56 (m, 2H), 7.52-7.43 (m, 1H), 7.39 (d, J = 7.9 Hz, 1H), 6.98 (t, J = 8.7 Hz, 1H), 2.75 (d, J = 4.5 Hz, 3H) |
| 176 | ¹H NMR (500 MHz, DMSO-d₆) δ 10.65 (s, 1H), 10.15 (s, 1H), 8.51 (s, 1H), 8.49-8.43 (m, 1H), 8.38-8.33 (m, 1H), 8.13-8.02 (m, 2H), 7.79 (s, 1H), 7.58 (s, 1H), 7.51-7.41 (m, 1H), 7.38 (d, J = 7.9 Hz, 1H), 7.24 (dd, J = 5.2, 1.2 Hz, 1H), 7.00 (t, J = 8.7 Hz, 1H), 2.76 (d, J = 4.5 Hz, 3H) |
| 177 | ¹H NMR (500 MHz, DMSO-d₆) δ 10.62 (br. s., 1H), 8.71 (br. s., 1H), 8.52-8.36 (m, 3H), 8.05-7.87 (m, 2H), 7.64 (br. s., 2H), 7.46-7.27 (m, 4H), 7.16 (br. s., 1H), 2.79 (d, J = 3.5 Hz, 3H), 2.32 (s, 3H) |
| 178 | ¹H NMR (500 MHz, DMSO-d₆) δ 11.14 (br. s., 1H), 8.64 (br. s., 2H), 8.40 (s, 1H), 8.22 (d, J = 12.9 Hz, 2H), 8.01 (br. s., 1H), 7.65 (d, J = 7.4 Hz, 1H), 7.61-7.45 (m, 3H), 7.26 (t, J = 6.9 Hz, 2H), 2.79 (d, J = 4.5 Hz, 3H) |
| 179 | ¹H NMR (500 MHz, methanol-d₄) δ 8.65 (s, 1H), 8.44-8.37 (m, 2H), 8.27 (d, J = 5.4 Hz, 1H), 7.80 (br. s., 1H), 7.55 (br. s., 1H), 7.09 (d, J = 5.9 Hz, 2H), 4.02 (s, 3H), 2.95 (s, 3H) |
| 180 | ¹H NMR (500 MHz, methanol-d₄) δ 8.33 (br. s., 1H), 8.04 (d, J = 8.4 Hz, 1H), 7.70 (d, J = 7.4 Hz, 1H), 7.60 (d, J = 6.9 Hz, 3H), 7.54 (br. s., 1H), 7.42 (t, J = 6.9 Hz, 1H), 7.37 (t, J = 7.2 Hz, 1H), 7.28 (t, J = 7.2 Hz, 1H), 7.13 (d, J = 8.4 Hz, 1H), 2.95 (s, 3H), 1.64 (s, 6H) |
| 181 | ¹H NMR (500 MHz, methanol-d₄) δ 8.62 (br. s., 1H), 8.34 (s, 1H), 8.00 (d, J = 8.4 Hz, 1H), 7.60 (d, J = 7.9 Hz, 1H), 7.45-7.36 (m, 2H), 7.35-7.29 (m, 1H), 7.11 (d, J = 8.4 Hz, 1H), 6.70 (br. s., 1H), 2.97 (s, 3H), 1.62 (s, 6H) |
| 182 | ¹H NMR (500 MHz, methanol-d₄) δ 8.67 (dd, J = 4.5, 1.5 Hz, 1H), 8.32 (s, 1H), 8.07-8.01 (m, 1H), 7.54 (dd, J = 7.9, 1.0 Hz, 1H), 7.48 (dd, J = 9.2, 4.7 Hz, 1H), 7.44 (d, J = 7.9, 1.5 Hz, 1H), 7.33 (td, J = 7.6, 1.2 Hz, 1H), 7.21-7.14 (m, 1H), 7.00 (s, 1H), 2.94 (s, 3H), 1.63 (s, 6H) |
| 183 | ¹H NMR (500 MHz, methanol-d₄) δ 8.34 (dd, J = 5.4, 1.0 Hz, 1H), 8.32 (s, 1H), 7.83-7.77 (m, 1H), 7.59 (dd, J = 7.7, 1.2 Hz, 1H), 7.43-7.35 (m, 2H), 7.34-7.28 (m, 1H), 7.13 (dd, J = 6.9, 5.4 Hz, 1H), 6.97 (d, J = 8.4 Hz, 1H), 6.53 (s, 1H), 2.96 (s, 3H), 1.62 (s, 6H) |
| 185 | ¹H NMR (500 MHz, methanol-d₄) δ 8.29 (s, 1H), 7.97 (d, J = 3.0 Hz, 1H), 7.61 (s, 2H), 7.43 (dd, J = 7.9, 1.0 Hz, 1H), 7.41-7.36 (m, 1H), 7.35-7.31 (m, 2H), 7.24 (td, J = 7.6, 1.7 Hz, 1H), 7.17-7.11 (m, 1H), 7.10-7.05 (m, 1H), 2.95 (s, 3H), 1.96 (tt, J = 8.5, 5.4 Hz, 1H), 1.06-0.94 (m, 2H), 0.72-0.60 (m, 2H) |

| Compound | ¹H NMR (methanol-d₄ equates CDCl₃:MeOD ~1:1 unless otherwise noted) Occasionally water suppression is used in DMSO-d₆ spectra |
|---|---|
| 186 | ¹H NMR (500 MHz, methanol-d₄) δ 8.25 (s, 1H), 8.01 (d, J = 3.0 Hz, 1H), 7.71 (d, J = 7.9 Hz, 1H), 7.48 (br. s., 1H), 7.44-7.38 (m, 1H), 7.34-7.22 (m, 2H), 2.96 (s, 3H) |
| 187 | ¹H NMR (500 MHz, methanol-d₄) δ 8.25 (s, 1H), 8.04 (d, J = 3.0 Hz, 1H), 7.50-7.40 (m, 1H), 7.34 (d, J = 8.9 Hz, 1H), 7.28 (dd, J = 9.2, 3.7 Hz, 1H), 7.21 (s, 1H), 6.66 (d, J = 2.5 Hz, 1H), 6.60 (dd, J = 8.4, 2.5 Hz, 1H), 3.92-3.89 (m, 4H), 3.88 (s, 3H), 3.26-3.15 (m, 4H), 2.93 (s, 3H) |
| 188 | ¹H NMR (500 MHz, methanol-d₄) δ 8.43 (s, 1H), 8.21 (d, J = 2.5 Hz, 1H), 8.02-7.92 (m, 3H), 7.66-7.53 (m, 4H), 6.90 (dd, J = 9.2, 3.7 Hz, 1H), 6.14 (s, 1H), 3.03 (s, 3H) |
| 189 | ¹H NMR (500 MHz, methanol-d₄) δ 8.30 (s, 1H), 7.96 (d, J = 3.0 Hz, 1H), 7.44-7.37 (m, 1H), 7.31 (ddd, J = 15.9, 8.7, 4.7 Hz, 2H), 7.05 (dd, J = 9.4, 3.0 Hz, 1H), 6.98 (td, J = 8.4, 3.0 Hz, 1H), 6.95 (s, 1H), 2.94 (s, 3H), 2.30 (s, 3H) |
| 190 | ¹H NMR (400 MHz, DMSO-d₆) δ 10.54 (s, 1H), 8.41 (s, 1H), 8.28 (m, 1H), 7.80 (bs, 1H), 7.46 (d, J = 8.0 Hz, 1H), 7.28-7.20 (m, 3H), 7.07 (m, 1 H), 3.86 (s, 3H), 2.82 (d, J = 4.4 Hz, 3H) |
| 191 | ¹H NMR (500 MHz, methanol-d₄) δ 8.28 (s, 1H), 8.02 (d, J = 3.0 Hz, 1H), 7.47 (s, 1H), 7.41 (ddd, J = 8.9, 7.9, 3.0 Hz, 1H), 7.32 (dd, J = 9.2, 3.7 Hz, 1H), 7.29-7.23 (m, 4H), 3.81 (t, J = 7.2 Hz, 2H), 2.93 (s, 3H), 2.87 (t, J = 7.2 Hz, 2H) |
| 192 | ¹H NMR (500 MHz, methanol-d₄) δ 8.25 (s, 1H), 8.00 (d, J = 3.0 Hz, 1H), 7.45-7.37 (m, 1H), 7.35 (d, J = 8.4 Hz, 1H), 7.31 (dd, J = 8.9, 4.0 Hz, 1H), 7.28 (s, 1H), 6.61 (d, J = 3.0 Hz, 1H), 6.56 (dd, J = 8.7, 2.7 Hz, 1H), 3.86 (s, 6H), 2.93 (s, 3H) |
| 193 | ¹H NMR (500 MHz, methanol-d₄) δ 8.27 (s, 1H), 8.00 (d, J = 3.0 Hz, 1H), 7.47 (s, 1H), 7.43-7.37 (m, 1H), 7.35-7.30 (m, 1H), 7.21 (s, 4H), 2.93 (s, 3H), 2.37 (s, 3H) |
| 194 | ¹H NMR (500 MHz, methanol-d₄) δ 8.31 (s, 1H), 8.04 (d, J = 3.0 Hz, 1H), 7.67-7.62 (m, 5H), 7.46 (t, J = 7.7 Hz, 2H), 7.41 (d, J = 8.9 Hz, 3H), 7.37-7.31 (m, 2H), 2.95 (s, 3H) |
| 195 | ¹H NMR (500 MHz, methanol-d₄) δ 8.26 (s, 1H), 7.98 (d, J = 3.0 Hz, 1H), 7.43-7.37 (m, 1H), 7.34-7.30 (m, 1H), 7.27 (s, 1H), 7.24 (d, J = 8.9 Hz, 2H), 6.97 (d, J = 8.9 Hz, 2H), 3.85 (s, 3H), 2.93 (s, 3H) |
| 196 | ¹H NMR (500 MHz, methanol-d₄) δ 8.29 (s, 1H), 8.00 (d, J = 3.0 Hz, 1H), 7.45-7.36 (m, 2H), 7.33-7.28 (m, 3H), 7.17-7.09 (m, 2H), 2.93 (s, 3H) |
| 197 | ¹H NMR (500 MHz, methanol-d₄) δ 8.28 (s, 1H), 8.02 (d, J = 3.0 Hz, 1H), 7.59 (s, 1H), 7.45-7.37 (m, 1H), 7.32-7.25 (m, 2H), 7.17 (s, 1H), 7.11 (d, J = 7.9 Hz, 1H), 6.99 (d, J = 7.4 Hz, 1H), 2.93 (s, 3H), 2.40 (s, 3H) |
| 198 | ¹H NMR (500 MHz, methanol-d₄) δ 8.27 (s, 1H), 8.00 (d, J = 3.0 Hz, 1H), 7.43-7.37 (m, 2H), 7.35-7.31 (m, 1H), 7.22-7.19 (m, 2H), 7.15-7.10 (m, 2H), 2.92 (s, 3H), 1.98-1.88 (m, 1H), 1.03-0.95 (m, 2H), 0.73-0.66 (m, 2H) |
| 199 | ¹H NMR (500 MHz, methanol-d₄) δ 8.31 (s, 1H), 8.10 (d, J = 3.0 Hz, 1H), 7.99 (s, 1H), 7.50-7.37 (m, 2H), 7.25 (dd, J = 9.2, 3.7 Hz, 1H), 6.93 (dd, J = 8.9, 5.0 Hz, 1H), 6.76 (td, J = 8.4, 3.0 Hz, 1H), 3.92 (s, 3H), 2.94 (s, 3H) |
| 200 | ¹H NMR (500 MHz, methanol-d₄) δ 8.33 (s, 1H), 8.06 (d, J = 3.0 Hz, 1H), 7.82 (s, 1H), 7.59 (d, J = 8.9 Hz, 2H), 7.47-7.36 (m, 3H), 7.32 (dd, J = 9.2, 3.7 Hz, 1H), 3.65 (t, J = 6.9 Hz, 2H), 3.58 (t, J = 6.4 Hz, 2H), 2.93 (s, 3H), 2.08-1.99 (m, 3H), 2.00-1.91 (m, 2H) |
| 201 | ¹H NMR (500 MHz, methanol-d₄) δ 8.39 (s, 1H), 8.10 (d, J = 3.0 Hz, 1H), 8.02 (s, 1H), 7.96-7.90 (m, 2H), 7.56-7.51 (m, 2H), 7.48-7.40 (m, 1H), 7.34 (dd, J = 8.9, 3.5 Hz, 1H), 3.14 (s, 3H), 2.94 (s, 3H) |
| 202 | ¹H NMR (500 MHz, methanol-d₄) δ 8.29 (s, 1H), 8.04 (d, J = 3.0 Hz, 1H), 7.68 (s, 1H), 7.46-7.38 (m, 1H), 7.34-7.25 (m, 2H), 6.95-6.87 (m, 2H), 6.73 (dd, J = 8.4, 2.0 Hz, 1H), 3.84 (s, 3H), 2.93 (s, 3H) |
| 203 | N/A |
| 204 | ¹H NMR (500 MHz, methanol-d₄) δ 8.32 (s, 1H), 8.04 (d, J = 3.0 Hz, 1H), 7.63 (s, 1H), 7.43 (td, J = 8.4, 3.0 Hz, 1H), 7.35-7.28 (m, 2H), 7.28-7.18 (m, 1H), 7.10-7.01 (m, 1H), 2.92 (s, 3H) |
| 205 | ¹H NMR (500 MHz, methanol-d₄) δ 8.36 (s, 1H), 8.10 (d, J = 3.0 Hz, 1H), 8.06 (s, 1H), 7.44 (td, J = 8.7, 3.0 Hz, 1H), 7.32 (dt, J = 10.8, 2.3 Hz, 1H), 7.29 (dd, J = 9.2, 3.7 Hz, 1H), 6.62 (ddd, J = 11.0, 8.5, 2.7 Hz, 1H), 3.95 (s, 3H), 2.93 (s, 3H) |
| 206 | ¹H NMR (500 MHz, DMSO-d₆) δ 10.72 (s, 1H), 9.94 (s, 1H), 8.53-8.43 (m, 1H), 8.30 (s, 1H), 7.99 (d, J = 2.5 Hz, 2H), 7.79 (s, 1H), 7.63 (td, J = 8.8, 3.2 Hz, 1H), 7.51 (dd, J = 9.2, 3.7 Hz, 1H), 7.44-7.40 (m, 1H), 7.28 (d, J = 8.4 Hz, 1H), 3.94 (s, 3H), 2.81-2.75 (m, 3H) |
| 207 | ¹H NMR (500 MHz, DMSO-d₆) δ 10.20 (s, 1H), 9.67 (s, 1H), 8.46 (s, 1H), 8.30 (s, 1H), 8.06 (d, J = 3.0 Hz, 1H), 7.73-7.66 (m, 1H), 7.59 (td, J = 8.8, 3.2 Hz, 1H), 7.42-7.35 (m, 1H), 7.21-7.13 (m, 2H), 7.08 (td, J = 8.5, 2.7 Hz, 1H), 2.80-2.75 (m, 3H), 2.45 (s, 3H) |
| 208 | ¹H NMR (400 MHz, DMSO-d₆) δ 10.43 (bs, 1H), 10.03 (m, 1H), 8.83 (m, 1H), 8.39 (s, 1H), 8.29 (bs, 1H), 7.82 (m, 1H), 7.36 (d, J = 7.2 Hz, 1H), 7.22-6.92 (m, 3H), 2.82 (d, J = 4.8 Hz, 3H) |

| Compound | ¹H NMR (methanol-d₄ equates CDCl₃:MeOD ~1:1 unless otherwise noted) Occasionally water suppression is used in DMSO-d₆ spectra |
|---|---|
| 209 | ¹H NMR (400 MHz, DMSO-d₆) δ 10.83 (s, 1H), 9.82 (s, 1H), 8.52 (m, 2H), 8.15 (d, J = 2.8 Hz, 1H), 7.73-7.61 (m, 4 H), 7.53-7.47 (m, 2H), 7.22 (m, 1H), 2.79 (d, J = 4.4 Hz, 3H) |
| 210 | ¹H NMR (400 MHz, DMSO-d₆) δ 11.03 (s, 1H), 9.81 (s, 1H), 8.51 (m, 2H), 8.13 (d, J = 3.2 Hz, 1H), 7.80 (d, J = 8.0 Hz, 1H), 7.74-7.62 (m, 5 H), 7.24 (m, 1H), 2.80 (d, J = 4.4 Hz, 3H) |
| 211 | ¹H NMR (400 MHz, DMSO-d₆) δ 10.24 (s, 1H), 9.65 (s, 1H), 8.42 (m, 2H), 8.12 (d, J = 3.2 Hz, 1H), 7.69 (m, 1H), 7.59 (m, 1H), 7.42 (s, 1H), 7.15 (m, 2H), 7.01 (m, 2H), 3.77 (m, 4H), 3.12 (m, 4H), 2.77 (d, J = 4.8 Hz, 3H) |
| 212 | ¹H NMR (400 MHz, DMSO-d₆) δ 11.42 (bs, 1H), 10.97 (bs, 1H), 8.96 (m, 1H), 8.44 (s, 1H), 8.28 (bs, 1H), 7.80 (m, 1 H), 7.42 (m, 2H), 7.22 (t, J = 8.0 Hz, 1H), 7.09 (d, J = 7.2 Hz, 1H), 6.36 (bs, 1H), 2.86 (d, J = 4.4 Hz, 3H) |
| 213 | ¹H NMR (500 MHz, methanol-d₄) δ 8.25 (s, 1H), 7.85 (d, J = 3.0 Hz, 1H), 7.34 (dd, J = 9.4, 3.0 Hz, 1H), 7.28-7.19 (m, 5H), 7.15 (s, 1H), 3.92-3.84 (m, 4H), 3.17-3.07 (m, 4H), 2.93 (s, 3H), 2.67 (q, J = 7.8 Hz, 2H), 1.26 (t, J = 7.7 Hz, 3H) |
| 214 | ¹H NMR (500 MHz, methanol-d₄) δ 8.30 (s, 1H), 7.85 (d, J = 3.0 Hz, 1H), 7.59-7.51 (m, 1H), 7.35 (dd, J = 8.9, 3.0 Hz, 1H), 7.30-7.13 (m, 5H), 3.92-3.86 (m, 4H), 3.16-3.09 (m, 4H), 2.93 (s, 3H) |
| 215 | ¹H NMR (500 MHz, methanol-d₄) δ 8.26 (s, 1H), 7.86 (d, J = 3.0 Hz, 1H), 7.38-7.28 (m, 3H), 7.22-7.14 (m, 2H), 7.12 (d, J = 7.9 Hz, 1H), 7.02 (d, J = 7.9 Hz, 1H), 3.93-3.84 (m, 4H), 3.15-3.07 (m, 4H), 2.93 (s, 3H), 2.68 (q, J = 7.6 Hz, 2H), 1.26 (t, J = 7.7 Hz, 3H) |
| 216 | ¹H NMR (500 MHz, DMSO-d₆) δ 10.37 (s, 1H), 9.43 (s, 1H), 8.45-8.34 (m, 2H), 7.82 (d, J = 3.0 Hz, 1H), 7.69 (s, 1H), 7.55-7.46 (m, 2H), 7.38 (dd, J = 8.9, 3.0 Hz, 1H), 7.13-6.95 (m, 3H), 3.84 (s, 3H), 3.77-3.69 (m, 4H), 3.07-3.01 (m, 4H), 2.76 (d, J = 4.5 Hz, 3H) |
| 217 | ¹H NMR (500 MHz, DMSO-d₆) δ 10.37 (s, 1H), 9.39 (s, 1H), 8.49-8.35 (m, 2H), 7.76 (d, J = 3.0 Hz, 1H), 7.48 (d, J = 8.9 Hz, 1H), 7.42-7.34 (m, 3H), 7.33-7.24 (m, 2H), 7.13-7.05 (m, 1H), 3.79-3.67 (m, 4H), 3.08-2.98 (m, 4H), 2.77 (d, J = 4.5 Hz, 3H), 2.24 (s, 3H) |
| 218 | ¹H NMR (500 MHz, DMSO-d₆) δ 10.23 (s, 1H), 9.39 (s, 1H), 8.43-8.33 (m, 2H), 7.82 (d, J = 3.0 Hz, 1H), 7.54-7.46 (m, 2H), 7.43 (dd, J = 8.7, 6.2 Hz, 1H), 7.37 (dd, J = 9.2, 3.2 Hz, 1H), 7.04 (dd, J = 10.9, 3.0 Hz, 1H), 6.86 (td, J = 8.5, 2.7 Hz, 1H), 3.84 (s, 3H), 3.78-3.69 (m, 4H), 3.08-3.00 (m, 4H), 2.75 (d, J = 4.5 Hz, 3H) |
| 219 | ¹H NMR (500 MHz, methanol-d₄) δ 8.27 (s, 1H), 7.81 (d, J = 3.0 Hz, 1H), 7.35 (dd, J = 8.9, 3.0 Hz, 1H), 7.28-7.21 (m, 2H), 6.91-6.78 (m, 2H), 6.48 (d, J = 3.5 Hz, 1H), 3.91-3.85 (m, 7H), 3.15-3.07 (m, 4H), 2.94 (s, 3H) |
| 220 | ¹H NMR (500 MHz, DMSO-d₆) δ 10.04 (s, 1H), 9.31 (s, 1H), 8.40-8.29 (m, 2H), 7.80 (d, J = 3.0 Hz, 1H), 7.51 (d, J = 8.9 Hz, 1H), 7.36 (dd, J = 8.9, 3.0 Hz, 1H), 7.33-7.23 (m, 2H), 6.69 (d, J = 3.0 Hz, 1H), 6.59 (dd, J = 8.9, 2.5 Hz, 1H), 3.80 (s, 3H), 3.79 (s, 3H), 3.76-3.70 (m, 4H), 3.05-2.99 (m, 4H), 2.75 (d, J = 4.5 Hz, 3H) |
| 221 | ¹H NMR (500 MHz, DMSO-d₆) δ 10.44 (s, 1H), 9.46 (s, 1H), 8.47-8.35 (m, 2H), 7.87 (d, J = 3.0 Hz, 1H), 7.63 (s, 1H), 7.51 (d, J = 8.9 Hz, 1H), 7.44 (d, J = 8.9 Hz, 1H), 7.38 (dd, J = 8.9, 3.0 Hz, 1H), 7.26 (d, J = 2.0 Hz, 1H), 7.21 (dd, J = 8.4, 2.0 Hz, 1H), 3.87 (s, 3H), 3.76-3.71 (m, 4H), 3.09-3.02 (m, 4H), 2.76 (d, J = 4.5 Hz, 3H) |
| 222 | ¹H NMR (500 MHz, DMSO-d₆) δ 10.75 (s, 1H), 9.60 (s, 1H), 8.53-8.42 (m, 2H), 8.01-7.91 (m, 3H), 7.61 (dd, J = 8.9, 2.0 Hz, 1H), 7.43-7.35 (m, 2H), 7.32 (d, J = 8.4 Hz, 1H), 3.97 (s, 3H), 3.76-3.71 (m, 4H), 3.21 (s, 3H), 3.06-2.98 (m, 4H), 2.77 (d, J = 4.5 Hz, 3H) |
| 223 | ¹H NMR (500 MHz, methanol-d₄) δ 8.30 (s, 1H), 7.98 (d, J = 3.0 Hz, 1H), 7.47 (dd, J = 9.4, 3.0 Hz, 1H), 7.39 (dd, J = 7.4, 1.5 Hz, 1H), 7.32-7.25 (m, 1H), 7.09 (d, J = 7.4 Hz, 1H), 7.04 (td, J = 7.7, 1.0 Hz, 1H), 6.93 (d, J = 8.9 Hz, 1H), 6.49 (s, 1H), 4.15 (q, J = 6.9 Hz, 2H), 3.94-3.85 (m, 4H), 3.22-3.13 (m, 4H), 2.97 (s, 3H), 1.44 (t, J = 6.9 Hz, 3H) |
| 224 | ¹H NMR (500 MHz, DMSO-d₆) δ 10.47 (br. s., 1H), 8.39 (s, 1H), 7.89 (br. s., 1H), 7.57 (br. s., 1H), 7.47-7.28 (m, 4H), 7.22 (s, 3H), 7.11 (s, 3H), 7.01 (s, 3H), 3.80-3.71 (m, 4H), 3.59 (t, J = 6.7 Hz, 2H), 3.10 (br. s., 4H), 2.81 (d, J = 4.5 Hz, 3H), 2.72 (t, J = 6.7 Hz, 2H) |
| 225 | ¹H NMR (500 MHz, DMSO-d₆) δ 10.35 (s, 1H), 9.44 (s, 1H), 8.46-8.35 (m, 2H), 7.82 (d, J = 3.0 Hz, 1H), 7.66 (s, 1H), 7.50 (d, J = 8.9 Hz, 1H), 7.38 (dd, J = 8.9, 3.0 Hz, 1H), 7.06 (dd, J = 8.2, 1.2 Hz, 1H), 6.87 (t, J = 8.2 Hz, 1H), 6.61 (dd, J = 8.2, 1.2 Hz, 1H), 4.37-4.22 (m, 4H), 3.78-3.68 (m, 4H), 3.07-2.99 (m, 4H), 2.76 (d, J = 4.5 Hz, 3H) |
| 226 | ¹H NMR (500 MHz, DMSO-d₆) δ 10.51 (s, 1H), 8.86 (br. s., 1H), 8.43 (s, 1H), 7.90 (br. s., 1H), 7.58 (br. s., 1H), 7.49-7.26 (m, 4H), 7.14-6.96 (m, 1H), 3.79-3.72 (m, 4H), 3.13-3.08 (m, 4H), 2.81 (d, J = 4.5 Hz, 3H), 2.45 (s, 3H) |
| 227 | ¹H NMR (500 MHz, DMSO-d₆) δ 10.61 (s, 1H), 10.23 (s, 1H), 8.87 (br. s., 1H), 8.36 (s, 1H), 7.93 (d, J = 3.0 Hz, 1H), 7.62 (dd, J = 9.2, 2.7 Hz, 1H), 7.34 (dd, J = 8.9, 6.4 Hz, 1H), 7.05-6.92 (m, 1H), 6.88-6.73 (m, 2H), 3.81-3.72 (m, 4H), 3.16-3.05 (m, 4H), 2.81 (d, J = 4.5 Hz, 3H) |

-continued

| Compound | ¹H NMR (methanol-d₄ equates CDCl₃:MeOD ~1:1 unless otherwise noted) Occasionally water suppression is used in DMSO-d₆ spectra |
|---|---|
| 228 | ¹H NMR (500 MHz, DMSO-d₆) δ 10.60 (s, 1H), 9.49 (s, 1H), 8.44 (s, 2H), 7.82 (d, J = 3.0 Hz, 1H), 7.69 (s, 1H), 7.66-7.61 (m, 1H), 7.49 (d, J = 8.9 Hz, 1H), 7.38 (dd, J = 9.9, 3.5 Hz, 1H), 7.35-7.26 (m, 2H), 7.22 (s, 1H), 7.17-7.11 (m, 1H), 3.77-3.68 (m, 4H), 3.08-2.97 (m, 4H), 2.77 (d, J = 4.5 Hz, 3H) |
| 229 | ¹H NMR (500 MHz, DMSO-d₆) δ 10.50 (s, 1H), 9.54 (br. s., 1H), 8.50-8.31 (m, 2H), 7.93 (br. s., 1H), 7.82 (d, J = 2.0 Hz, 1H), 7.47-7.35 (m, 2H), 7.14 (d, J = 2.5 Hz, 1H), 6.97 (d, J = 8.9 Hz, 1H), 6.55 (dd, J = 8.7, 2.7 Hz, 1H), 4.06-3.95 (m, 4H), 3.78-3.71 (m, 4H), 3.07-3.00 (m, 4H), 2.76 (d, J = 4.5 Hz, 3H), 1.33 (td, J = 6.9, 4.0 Hz, 6H) |
| 230 | ¹H NMR (500 MHz, DMSO-d₆) δ 10.95 (s, 1H), 9.65 (s, 1H), 8.51 (d, J = 5.0 Hz, 1H), 8.46 (s, 1H), 7.94-7.81 (m, 2H), 7.55 (d, J = 9.4 Hz, 1H), 7.43 (dd, J = 9.4, 3.0 Hz, 1H), 7.33 (d, J = 10.9 Hz, 1H), 6.95 (ddd, J = 11.1, 8.7, 3.0 Hz, 1H), 4.02 (q, J = 7.1 Hz, 2H), 3.77-3.71 (m, 4H), 3.11-3.00 (m, 4H), 2.78 (d, J = 4.5 Hz, 3H), 1.36 (t, J = 6.9 Hz, 3H) |
| 231 | ¹H NMR (400 MHz, DMSO-d₆) δ 14.08 (bs, 1H), 11.08 (bs, 1H), 10.14 (bs, 1H), 8.84 (bs, 1H), 8.36 (s, 1H), 8.30 (bs, 1H), 7.84 (m, 1 H), 7.12 (m, 3H), 6.87 (d, J = 8.0 Hz, 1H), 6.71 (m, 1H), 2.83 (d, J = 4.4 Hz, 3H) |
| 232 | ¹H NMR (500 MHz, DMSO-d₆) δ 10.15 (s, 1H), 8.49-8.38 (m, 2H), 7.79 (d, J = 2.5 Hz, 1H), 7.50 (d, J = 7.4 Hz, 1H), 7.42-7.34 (m, 2H), 7.15 (br. s., 1H), 6.99 (dd, J = 12.6, 2.7 Hz, 1H), 6.86 (dd, J = 8.7, 2.2 Hz, 1H), 4.07 (q, J = 6.9 Hz, 2H), 3.77-3.66 (m, 4H), 3.07-2.98 (m, 4H), 2.77 (d, J = 4.5 Hz, 3H), 1.34 (t, J = 6.9 Hz, 3H) |
| 234 | ¹H NMR (500 MHz, DMSO-d₆) δ 10.64 (s, 1H), 9.81 (s, 1H), 8.56 (d, J = 4.5 Hz, 1H), 8.50 (s, 1H), 8.14 (d, J = 3.0 Hz, 1H), 7.90 (br. s., 1H), 7.83 (s, 1H), 7.80 (d, J = 8.4 Hz, 1H), 7.70-7.58 (m, 3H), 7.55-7.49 (m, 1H), 7.26 (br. s., 1H), 2.79 (d, J = 4.0 Hz, 3H), 2.29 (s, 3H) |
| 235 | ¹H NMR (500 MHz, methanol-d₄) δ 8.33 (s, 1H), 7.99 (d, J = 3.0 Hz, 1H), 7.54 (d, J = 7.9 Hz, 1H), 7.49 (s, 1H), 7.44-7.38 (m, 1H), 7.34 (s, 1H), 7.33-7.27 (m, 2H), 3.73 (br. s., 2H), 3.49 (br. s., 2H), 2.94 (s, 4H), 2.37 (s, 4H), 1.82-1.57 (m, 6H) |
| 236 | ¹H NMR (500 MHz, methanol-d₄) δ 8.34 (s, 1H), 8.01-7.96 (m, 1H), 7.58 (d, J = 7.9 Hz, 1H), 7.54 (s, 1H), 7.44-7.38 (m, 1H), 7.37 (s, 1H), 7.35-7.29 (m, 2H), 3.89-3.56 (m, 8H), 2.94 (s, 3H), 2.38 (s, 3H) |
| 237 | ¹H NMR (500 MHz, methanol-d₄) δ 8.32 (s, 1H), 8.12 (d, J = 3.0 Hz, 1H), 7.91 (s, 1H), 7.67 (d, J = 8.4 Hz, 1H), 7.54-7.48 (m, 2H), 7.47-7.41 (m, 1H), 7.29 (dd, J = 9.2, 3.7 Hz, 1H), 4.00 (s, 3H), 2.97 (s, 3H), 2.94 (s, 3H) |
| 238 | ¹H NMR (500 MHz, methanol-d₄) δ 8.33 (s, 1H), 8.13 (d, J = 3.0 Hz, 1H), 7.94 (s, 1H), 7.68 (d, J = 7.9 Hz, 1H), 7.56-7.51 (m, 2H), 7.44 (td, J = 8.4, 3.0 Hz, 1H), 7.29 (dd, J = 9.2, 3.7 Hz, 1H), 4.01 (s, 3H), 3.82-3.74 (m, 2H), 3.57 (t, J = 5.7 Hz, 2H), 2.94 (s, 3H) |
| 239 | ¹H NMR (500 MHz, methanol-d₄) δ 8.31 (s, 1H), 8.05 (d, J = 3.0 Hz, 1H), 7.86 (s, 1H), 7.67-7.63 (m, 1H), 7.46-7.39 (m, 1H), 7.31 (dd, J = 9.2, 3.7 Hz, 1H), 7.07-7.03 (m, 2H), 3.97 (s, 3H), 3.73 (d, J = 3.5 Hz, 2H), 3.52 (br. s., 2H), 2.94 (s, 3H), 1.82-1.55 (m, 6H) |
| 240 | ¹H NMR (500 MHz, methanol-d₄) δ 8.31 (s, 1H), 8.06 (d, J = 3.0 Hz, 1H), 7.86 (s, 1H), 7.65 (d, J = 7.9 Hz, 1H), 7.46-7.40 (m, 1H), 7.31 (dd, J = 9.2, 3.7 Hz, 1H), 7.07-7.01 (m, 2H), 3.97 (s, 3H), 3.65-3.40 (m, 4H), 2.94 (s, 3H), 1.26 (d, J = 12.9 Hz, 6H) |
| 241 | ¹H NMR (500 MHz, methanol-d₄) δ 8.32 (s, 1H), 8.06 (d, J = 3.0 Hz, 1H), 7.87 (s, 1H), 7.67 (d, J = 8.4 Hz, 1H), 7.43 (td, J = 8.4, 3.0 Hz, 1H), 7.31 (dd, J = 9.2, 3.7 Hz, 1H), 7.08 (dd, J = 4.0, 2.5 Hz, 2H), 3.98 (s, 3H), 3.87-3.57 (m, 8H), 2.94 (s, 3H) |
| 242 | ¹H NMR (500 MHz, DMSO-d₆) δ 10.74 (s, 1H), 9.86 (s, 1H), 8.59-8.54 (m, 1H), 8.49 (s, 1H), 8.19 (d, J = 2.5 Hz, 1H), 7.96-7.89 (m, 3H), 7.84 (s, 1H), 7.71-7.61 (m, 2H), 7.34 (d, J = 8.9 Hz, 2H), 7.28 (br. s., 1H), 2.78 (d, J = 4.5 Hz, 3H) |
| 243 | ¹H NMR (500 MHz, methanol-d₄) δ 8.34 (s, 1H), 8.10 (d, J = 3.0 Hz, 1H), 7.90-7.82 (m, 3H), 7.47-7.37 (m, 3H), 7.30 (dd, J = 9.2, 3.7 Hz, 1H), 2.96 (s, 3H), 2.93 (s, 3H) |
| 244 | ¹H NMR (500 MHz, methanol-d₄) δ 8.33 (s, 1H), 8.05 (d, J = 3.0 Hz, 1H), 7.77 (s, 1H), 7.49-7.38 (m, 5H), 7.35-7.27 (m, 1H), 3.79-3.67 (m, 2H), 3.49 (br. s., 2H), 2.93 (s, 3H), 1.84-1.52 (m, 6H) |
| 245 | ¹H NMR (500 MHz, methanol-d₄) δ 8.34 (s, 1H), 8.06 (d, J = 3.0 Hz, 1H), 7.78 (s, 1H), 7.52-7.47 (m, 2H), 7.46-7.39 (m, 3H), 7.32 (dd, J = 8.9, 3.5 Hz, 1H), 3.76 (s, 8H), 2.93 (s, 3H) |
| 246 | ¹H NMR (500 MHz, methanol-d₄) δ 8.38 (s, 1H), 8.25 (d, J = 2.5 Hz, 1H), 7.67-7.62 (m, 1H), 7.55-7.49 (m, 2H), 7.43 (d, J = 8.4 Hz, 2H), 7.05 (dd, J = 9.4, 3.5 Hz, 1H), 6.71 (br. s., 1H), 3.59 (d, J = 6.4 Hz, 2H), 3.37 (br. s., 2H), 2.98 (s, 3H), 1.30 (d, J = 6.4 Hz, 3H), 1.20 (br. s., 3H) |
| 247 | ¹H NMR (500 MHz, DMSO-d₆) δ 10.64 (s, 1H), 9.85 (s, 1H), 8.50 (q, J = 4.3 Hz, 1H), 8.47 (s, 1H), 8.19 (s, 1H), 7.95 (s, 1H), 7.84 (s, 1H), 7.68-7.63 (m, 2H), 7.59 (d, J = 7.9 Hz, 1H), 7.31-7.21 (m, 2H), 3.94 (d, J = 5.4 Hz, 2H), 3.90 (s, 3H), 3.85-3.62 (m, 2H), 2.77 (d, J = 4.5 Hz, 3H), 2.46 (d, J = 6.4 Hz, 2H) |

| Compound | ¹H NMR (methanol-d₄ equates CDCl₃:MeOD ~1:1 unless otherwise noted) Occasionally water suppression is used in DMSO-d₆ spectra |
|---|---|
| 248 | ¹H NMR (500 MHz, methanol-d₄) δ 8.32 (s, 1H), 8.07 (d, J = 3.0 Hz, 1H), 7.89 (s, 1H), 7.66 (d, J = 7.9 Hz, 1H), 7.43 (ddd, J = 8.9, 7.9, 3.0 Hz, 1H), 7.31 (dd, J = 9.2, 3.7 Hz, 1H), 7.23-7.17 (m, 2H), 3.98 (s, 3H), 3.65 (t, J = 6.9 Hz, 2H), 3.60 (t, J = 6.4 Hz, 2H), 2.94 (s, 3H), 2.11-2.01 (m, 2H), 1.97 (q, J = 6.4 Hz, 2H) |
| 249 | ¹H NMR (500 MHz, methanol-d₄) δ 8.31 (s, 1H), 8.10 (d, J = 2.5 Hz, 1H), 7.81 (s, 1H), 7.55-7.48 (m, 2H), 7.32 (d, J = 8.4 Hz, 1H), 7.03-6.97 (m, 2H), 3.92 (s, 3H), 3.68 (t, J = 5.4 Hz, 2H), 2.93 (s, 3H), 2.56 (t, J = 6.2 Hz, 2H), 2.09-1.95 (m, 4H) |
| 250 | ¹H NMR (500 MHz, DMSO-d₆) δ 10.56 (s, 1H), 9.63 (s, 1H), 8.35 (s, 1H), 8.32-8.27 (m, 1H), 8.07 (d, J = 3.0 Hz, 1H), 7.95 (s, 1H), 7.89 (s, 1H), 7.69-7.63 (m, 1H), 7.63-7.56 (m, 1H), 7.46-7.37 (m, 3H), 7.14-7.07 (m, 2H), 3.81 (s, 3H), 2.89 (s, 2H), 2.78-2.72 (m, 5H) |
| 251 | ¹H NMR (500 MHz, DMSO-d₆) δ 8.41 (s, 1H), 8.25 (br. s., 1H), 7.77 (br. s., 1H), 7.56 (d, J = 3.5 Hz, 2H), 7.47-7.28 (m, 2H), 2.96 (s, 3H), 2.82 (s, 3H), 2.79 (d, J = 4.5 Hz, 3H) |
| 252 | ¹H NMR (500 MHz, DMSO-d₆) δ 10.95 (s, 1H), 9.77 (s, 1H), 8.40 (s, 1H), 8.38-8.34 (m, 1H), 8.31 (s, 1H), 8.09 (d, J = 3.0 Hz, 2H), 7.70-7.65 (m, 4H), 7.65-7.57 (m, 2H), 7.55-7.48 (m, 3H), 2.77-2.74 (m, 3H) |
| 253 | ¹H NMR (500 MHz, DMSO-d₆) δ 10.90 (s, 1H), 9.76 (s, 1H), 8.42 (s, 1H), 8.36 (d, J = 4.5 Hz, 1H), 8.31 (s, 1H), 8.16-8.11 (m, 1H), 8.01 (s, 1H), 7.97-7.91 (m, 1H), 7.90-7.82 (m, 3H), 7.73-7.66 (m, 1H), 7.63-7.54 (m, 2H), 7.51-7.43 (m, 1H), 2.79-2.76 (m, 3H) |
| 255 | ¹H NMR (500 MHz, methanol-d₄) δ 8.35 (s, 1H), 7.80-7.74 (m, 1H), 7.66 (d, J = 6.9 Hz, 1H), 7.59 (d, J = 7.9 Hz, 1H), 7.40 (d, J = 8.4 Hz, 1H), 7.33 (s, 1H), 7.03 (d, J = 2.0 Hz, 1H), 6.97 (dd, J = 8.4, 2.5 Hz, 1H), 3.91 (s, 3H), 2.94 (s, 3H) |
| 256 | ¹H NMR (500 MHz, DMSO-d₆) δ 10.59 (s, 1H), 9.90 (br. s., 1H), 8.59-8.46 (m, 2H), 8.28 (d, J = 5.4 Hz, 1H), 8.10 (s, 1H), 8.03-7.91 (m, 1H), 7.74-7.58 (m, 2H), 7.43-7.15 (m, 3H), 3.90 (d, J = 1.0 Hz, 3H), 2.78 (d, J = 4.5 Hz, 3H) |
| 257 | ¹H NMR (500 MHz, methanol-d₄) δ 8.35 (s, 1H), 8.26 (d, J = 5.4 Hz, 1H), 7.65 (s, 2H), 7.30 (ddd, J = 9.2, 5.2, 2.5 Hz, 1H), 7.19 (dd, J = 5.2, 1.2 Hz, 1H), 7.06-6.92 (m, 1H), 4.00 (d, J = 1.0 Hz, 3H), 2.95 (s, 3H), 2.94 (s, 3H) |
| 258 | ¹H NMR (500 MHz, DMSO-d₆) δ 10.56 (s, 1H), 9.89 (s, 1H), 8.61-8.46 (m, 2H), 8.24 (d, J = 5.0 Hz, 1H), 7.68 (s, 1H), 7.60 (s, 1H), 7.39-7.31 (m, 1H), 7.31-7.22 (m, 1H), 6.84 (dd, J = 5.2, 1.2 Hz, 1H), 3.90 (d, J = 1.0 Hz, 3H), 2.98 (s, 3H), 2.88 (s, 3H), 2.78 (d, J = 4.5 Hz, 3H) |
| 259 | ¹H NMR (500 MHz, methanol-d₄) δ 8.32 (s, 1H), 8.27 (d, J = 5.4 Hz, 1H), 7.65 (s, 1H), 7.50 (d, J = 7.9 Hz, 1H), 7.20-7.17 (m, 1H), 7.03-6.97 (m, 2H), 3.92 (s, 3H), 2.94 (s, 3H), 2.90-2.85 (m, 1H), 0.90-0.81 (m, 2H), 0.72-0.64 (m, 2H) |
| 260 | ¹H NMR (500 MHz, methanol-d₄) δ 8.35 (s, 1H), 7.79-7.73 (m, 1H), 7.65 (d, J = 6.9 Hz, 1H), 7.52 (d, J = 8.4 Hz, 1H), 7.43 (d, J = 8.4 Hz, 1H), 7.03 (d, J = 2.5 Hz, 1H), 6.91 (dd, J = 8.4, 2.5 Hz, 1H), 3.94 (s, 3H), 2.94 (s, 3H), 2.77 (s, 3H) |
| 261 | ¹H NMR (500 MHz, methanol-d₄) δ 8.35 (s, 1H), 7.81-7.74 (m, 1H), 7.65 (d, J = 6.9 Hz, 1H), 7.58 (d, J = 7.9 Hz, 1H), 7.49 (s, 1H), 7.41 (d, J = 8.4 Hz, 1H), 7.03 (d, J = 2.0 Hz, 1H), 6.92 (dd, J = 8.4, 2.0 Hz, 1H), 3.94 (s, 3H), 2.94 (s, 3H), 2.73 (tt, J = 7.3, 3.8 Hz, 1H), 0.81-0.69 (m, 2H), 0.47-0.37 (m, 2H) |
| 262 | ¹H NMR (500 MHz, methanol-d₄) δ 8.31 (s, 1H), 8.25 (s, 1H), 7.70 (dd, J = 8.4, 7.4 Hz, 1H), 7.50 (d, J = 8.4 Hz, 1H), 7.16 (d, J = 7.9 Hz, 1H), 7.05 (d, J = 6.9 Hz, 1H), 7.01 (d, J = 2.0 Hz, 1H), 6.96 (dd, J = 8.4, 2.5 Hz, 1H), 3.93 (s, 3H), 3.04 (s, 3H), 2.93 (s, 3H), 2.84 (s, 3H) |
| 263 | ¹H NMR (500 MHz, DMSO-d₆) δ 10.53 (s, 1H), 9.92 (s, 1H), 8.56-8.41 (m, 2H), 7.91 (s, 1H), 7.79-7.70 (m, 1H), 7.55 (d, J = 8.4 Hz, 1H), 7.47 (d, J = 8.4 Hz, 1H), 7.17 (d, J = 2.0 Hz, 1H), 6.99 (d, J = 7.4 Hz, 1H), 6.94 (dd, J = 8.7, 2.2 Hz, 1H), 3.87 (s, 3H), 3.54 (d, J = 4.5 Hz, 2H), 3.49 (d, J = 4.0 Hz, 2H), 3.38 (d, J = 4.5 Hz, 2H), 3.22 (d, J = 4.5 Hz, 2H), 2.77 (d, J = 4.5 Hz, 3H) |
| 264 | ¹H NMR (500 MHz, DMSO-d₆) δ 11.03 (s, 1H), 10.05 (s, 1H), 8.60 (d, J = 4.5 Hz, 1H), 8.56 (s, 1H), 8.26 (d, J = 5.4 Hz, 1H), 8.11 (s, 1H), 8.03 (s, 1H), 7.94 (s, 1H), 7.63 (s, 1H), 7.34 (d, J = 10.9 Hz, 1H), 7.26 (dd, J = 5.2, 1.2 Hz, 1H), 6.99 (ddd, J = 11.3, 8.8, 2.7 Hz, 1H), 3.84 (s, 3H), 2.79 (d, J = 4.5 Hz, 3H) |
| 265 | ¹H NMR (500 MHz, DMSO-d₆) δ 11.02 (s, 1H), 10.06 (s, 1H), 8.59 (d, J = 4.5 Hz, 1H), 8.54 (s, 1H), 8.25 (d, J = 5.0 Hz, 1H), 7.91 (s, 1H), 7.68 (s, 1H), 7.33 (d, J = 11.4 Hz, 1H), 6.99 (ddd, J = 11.3, 8.8, 2.7 Hz, 1H), 6.93-6.89 (m, 1H), 3.84 (s, 3H), 3.64 (d, J = 12.4 Hz, 4H), 3.56 (br. s., 2H), 2.79 (d, J = 4.5 Hz, 3H) |
| 266 | ¹H NMR (500 MHz, DMSO-d₆) δ 11.03 (s, 1H), 10.06 (s, 1H), 8.70 (t, J = 5.2 Hz, 1H), 8.60 (d, J = 4.5 Hz, 1H), 8.55 (s, 1H), 8.27 (d, J = 5.0 Hz, 1H), 8.01 (s, 1H), 7.95 (s, 1H), 7.34 (d, J = 10.9 Hz, 1H), 7.24 (d, J = 5.0 Hz, 1H), 7.03-6.95 (m, 1H), 3.84 (s, 3H), 3.49-3.39 (m, 4H), 3.27 (s, 3H), 2.79 (d, J = 4.5 Hz, 3H) |
| 267 | ¹H NMR (500 MHz, DMSO-d₆) δ 10.24 (s, 1H), 9.80 (s, 1H), 8.51-8.43 (m, 2H), 8.23 (d, J = 5.0 Hz, 1H), 8.08 (s, 1H), 8.01-7.90 (m, 1H), 7.61 (s, 1H), |

| Compound | ¹H NMR (methanol-d₄ equates CDCl₃:MeOD ~1:1 unless otherwise noted) Occasionally water suppression is used in DMSO-d₆ spectra |
|---|---|
| | 7.56 (s, 1H), 7.44 (dd, J = 8.7, 6.2 Hz, 1H), 7.20 (dd, J = 5.2, 1.2 Hz, 1H), 7.05 (dd, J = 10.9, 2.5 Hz, 1H), 6.86 (td, J = 8.4, 2.5 Hz, 1H), 3.84 (s, 3H), 2.77 (d, J = 4.0 Hz, 3H) |
| 268 | ¹H NMR (500 MHz, DMSO-d₆) δ 10.22 (s, 1H), 9.80 (s, 1H), 8.49-8.38 (m, 2H), 8.20 (d, J = 5.4 Hz, 1H), 7.70 (s, 1H), 7.53 (s, 1H), 7.44 (dd, J = 8.7, 6.2 Hz, 1H), 7.06 (dd, J = 10.7, 2.7 Hz, 1H), 6.90 (dd, J = 5.0, 1.5 Hz, 1H), 6.86 (td, J = 8.5, 2.7 Hz, 1H), 3.84 (s, 3H), 3.46 (t, J = 6.7 Hz, 3H), 2.76 (d, J = 4.5 Hz, 3H), 1.93-1.75 (m, 5H) |
| 269 | ¹H NMR (500 MHz, DMSO-d₆) δ 10.21 (s, 1H), 9.81 (s, 1H), 8.50-8.41 (m, 2H), 8.21 (d, J = 5.0 Hz, 1H), 7.63 (s, 1H), 7.50 (s, 1H), 7.43 (dd, J = 8.7, 6.2 Hz, 1H), 7.05 (dd, J = 10.9, 3.0 Hz, 1H), 6.90-6.78 (m, 2H), 3.84 (s, 3H), 3.71-3.59 (m, 4H), 3.55 (br. s., 2H), 3.32 (d, J = 4.5 Hz, 3H), 2.77 (d, J = 4.5 Hz, 3H) |
| 270 | ¹H NMR (500 MHz, DMSO-d₆) δ 11.02 (s, 1H), 10.04 (s, 1H), 8.59 (q, J = 4.3 Hz, 1H), 8.54 (s, 1H), 8.24 (d, J = 5.0 Hz, 1H), 7.93 (s, 1H), 7.75 (s, 1H), 7.38-7.31 (m, 1H), 7.05-6.94 (m, 2H), 3.84 (s, 3H), 3.47 (t, J = 6.7 Hz, 2H), 3.37 (d, J = 2.5 Hz, 1H), 2.79 (d, J = 4.5 Hz, 3H), 1.94-1.75 (m, 4H) |
| 271 | ¹H NMR (500 MHz, DMSO-d₆) δ 10.24 (s, 1H), 9.81 (s, 1H), 8.67 (t, J = 5.4 Hz, 1H), 8.50-8.43 (m, 2H), 8.23 (d, J = 5.4 Hz, 1H), 7.94 (s, 1H), 7.57 (s, 1H), 7.44 (dd, J = 8.9, 6.4 Hz, 1H), 7.17 (dd, J = 5.0, 1.5 Hz, 1H), 7.05 (dd, J = 10.9, 2.5 Hz, 1H), 6.86 (td, J = 8.5, 2.7 Hz, 1H), 3.84 (s, 3H), 3.49-3.39 (m, 4H), 3.27 (s, 3H), 2.77 (d, J = 4.5 Hz, 3H) |
| 272 | ¹H NMR (500 MHz, DMSO-d₆) δ 10.21 (s, 1H), 9.80 (s, 1H), 8.49-8.39 (m, 2H), 8.19 (d, J = 5.4 Hz, 1H), 7.58 (s, 1H), 7.54 (s, 1H), 7.44 (dd, J = 8.7, 6.2 Hz, 1H), 7.05 (dd, J = 10.9, 3.0 Hz, 1H), 6.86 (td, J = 8.4, 3.0 Hz, 1H), 6.81 (dd, J = 5.0, 1.5 Hz, 1H), 3.84 (s, 3H), 2.98 (s, 3H), 2.87 (s, 3H), 2.76 (d, J = 4.5 Hz, 3H) |
| 273 | ¹H NMR (500 MHz, DMSO-d₆) δ 11.03 (s, 1H), 10.06 (s, 1H), 8.61 (t, J = 4.7 Hz, 2H), 8.55 (s, 1H), 8.27 (d, J = 5.0 Hz, 1H), 8.01 (s, 1H), 7.94 (s, 1H), 7.34 (d, J = 10.9 Hz, 1H), 7.21 (dd, J = 5.2, 1.2 Hz, 1H), 6.99 (ddd, J = 11.3, 8.8, 2.7 Hz, 1H), 3.84 (s, 3H), 2.79 (dd, J = 4.5, 3.0 Hz, 6H) |
| 274 | ¹H NMR (500 MHz, DMSO-d₆) δ 11.01 (s, 1H), 10.05 (s, 1H), 8.58 (q, J = 4.5 Hz, 1H), 8.54 (s, 1H), 8.24 (d, J = 5.4 Hz, 1H), 7.94 (s, 1H), 7.63 (s, 1H), 7.34 (d, J = 10.9 Hz, 1H), 6.99 (ddd, J = 11.5, 8.8, 3.0 Hz, 1H), 6.88 (dd, J = 5.0, 1.0 Hz, 1H), 3.84 (s, 3H), 2.99 (s, 3H), 2.89 (s, 3H), 2.78 (d, J = 4.5 Hz, 3H) |
| 275 | ¹H NMR (500 MHz, DMSO-d₆) δ 10.24 (s, 1H), 9.82 (s, 1H), 8.58 (q, J = 4.3 Hz, 1H), 8.51-8.40 (m, 2H), 8.23 (d, J = 5.0 Hz, 1H), 7.95 (s, 1H), 7.57 (s, 1H), 7.44 (dd, J = 8.7, 6.2 Hz, 1H), 7.15 (dd, J = 5.2, 1.2 Hz, 1H), 7.05 (dd, J = 10.9, 2.5 Hz, 1H), 6.86 (td, J = 8.4, 3.0 Hz, 1H), 3.84 (s, 3H), 2.77 (dd, J = 4.5, 2.5 Hz, 6H) |
| 276 | ¹H NMR (500 MHz, DMSO-d₆) δ 10.76 (d, J = 3.5 Hz, 1H), 9.94 (br. s., 1H), 8.59-8.46 (m, 2H), 8.27 (t, J = 4.2 Hz, 1H), 8.11 (br. s., 1H), 7.99 (br. s., 1H), 7.86 (br. s., 1H), 7.62 (br. s., 1H), 7.45-7.36 (m, 1H), 7.26-7.10 (m, 2H), 7.01-6.94 (m, 1H), 3.85 (d, J = 3.5 Hz, 3H), 2.83-2.75 (m, 3H) |
| 277 | ¹H NMR (500 MHz, DMSO-d₆) δ 10.75 (d, J = 3.5 Hz, 1H), 9.94 (d, J = 3.5 Hz, 1H), 8.61-8.44 (m, 2H), 8.24 (t, J = 4.5 Hz, 1H), 7.85 (d, J = 3.5 Hz, 1H), 7.61 (d, J = 2.5 Hz, 1H), 7.41 (dd, J = 8.4, 2.5 Hz, 1H), 7.25-7.12 (m, 1H), 7.05-6.94 (m, 1H), 6.84 (t, J = 4.0 Hz, 1H), 3.85 (d, J = 3.5 Hz, 3H), 2.99 (d, J = 4.0 Hz, 3H), 2.88 (d, J = 4.0 Hz, 3H), 2.78 (t, J = 4.2 Hz, 3H) |
| 278 | ¹H NMR (500 MHz, DMSO-d₆) δ 10.76 (d, J = 3.5 Hz, 1H), 10.01 (d, J = 3.5 Hz, 1H), 9.46-9.28 (m, 1H), 8.60-8.48 (m, 2H), 8.38-8.27 (m, 1H), 8.06 (br. s., 1H), 7.82 (d, J = 3.5 Hz, 1H), 7.41 (d, J = 7.9 Hz, 1H), 7.28-7.13 (m, 2H), 7.05-6.91 (m, 1H), 4.36-4.28 (m, 2H), 3.85 (d, J = 3.5 Hz, 3H), 2.82-2.76 (m, 3H) |
| 280 | ¹H NMR (400 MHz, DMSO-d₆) δ 10.14 (bs, 1H), 9.74 (bs, 1H), 9.53 (bs, 1H), 8.41 (m, 2H), 8.11 (bs, 1H), 7.64 (m, 2H), 7.47 (m, 3H), 7.30 (t, J = 7.6 Hz, 1H), 7.15 (m, 1H), 2.78 (d, J = 4.4 Hz, 3H), 2.04 (s, 3H) |
| 281 | ¹H NMR (400 MHz, DMSO-d₆) δ 10.33 (s, 1H), 10.10 (s, 1H), 9.28 (bs, 1H), 8.51 (bs, 2H), 8.36 (dd, J = 5.2, 0.8 Hz, 1H), 8.17 (s, 1H), 7.52 (d, J = 8.0 Hz, 1H), 7.50 (m, 2H), 7.40 (m, 2H), 7.34 (m, 1H), 7.24 (dd, J = 5.2, 1.2 Hz, 1H), 7.18 (t, J = 7.0 Hz, 1H) 3.00 (s, 3 H), 2.80 (d, J = 4.4 Hz, 3H). |
| 284 | ¹H NMR (500 MHz, methanol-d₄) δ 8.26 (s, 1H), 8.10 (d, J = 8.9 Hz, 1H), 7.91 (br. s., 1H), 7.77 (dd, J = 7.7, 4.2 Hz, 2H), 7.70-7.65 (m, 1H), 7.42 (t, J = 7.7 Hz, 1H), 7.21 (d, J = 8.9 Hz, 1H), 3.86-3.68 (m, 1H), 2.91 (s, 3H), 2.61-2.47 (m, 1H), 2.28-2.10 (m, 1H), 2.07-1.92 (m, 2H), 1.90-1.71 (m, 2H), 1.60-1.50 (m, 3H) |
| 285 | ¹H NMR (500 MHz, methanol-d₄) δ 8.43 (s, 1H), 8.30 (d, J = 8.9 Hz, 1H), 8.03 (d, J = 8.4 Hz, 1H), 7.86 (d, J = 7.9 Hz, 1H), 7.81-7.74 (m, 1H), 7.54 (t, J = 7.4 Hz, 1H), 7.17 (d, J = 8.9 Hz, 1H), 3.46 (q, J = 6.6 Hz, 1H), 2.95 (s, 3H), 1.27 (d, J = 6.4 Hz, 3H), 1.07 (s, 9H) |
| 286 | ¹H NMR (500 MHz, methanol-d₄) δ 8.28-8.21 (m, 1H), 8.13-8.08 (m, 1H), 7.84 (d, J = 8.4 Hz, 1H), 7.75 (d, J = 7.4 Hz, 1H), 7.71-7.65 (m, 1H), 7.42 (t, J = 7.4 Hz, 1H), 7.21 (d, J = 8.9 Hz, 1H), 4.23 (br. s., 1H), 2.91 (s, 3H), 2.84-2.75 (m, 1H), 2.32-2.22 (m, 1H), 1.97-1.86 (m, 3H), 1.74 (ddd, J = 13.3, 8.8, 3.7 Hz, 1H), 1.68-1.58 (m, 2H), 1.56-1.44 (m, 1H) |

-continued

| Compound | ¹H NMR (methanol-d₄ equates CDCl₃:MeOD ~1:1 unless otherwise noted) Occasionally water suppression is used in DMSO-d₆ spectra |
|---|---|
| 287 | ¹H NMR (500 MHz, methanol-d₄) δ 8.24 (s, 1H), 8.09 (d, J = 8.9 Hz, 1H), 7.93 (br. s., 1H), 7.76 (d, J = 7.9 Hz, 2H), 7.68-7.64 (m, 1H), 7.41 (t, J = 7.4 Hz, 1H), 7.19 (d, J = 8.9 Hz, 1H), 4.95-4.78 (m, 1H), 3.62 (br. s., 1H), 2.91 (s, 3H), 2.22-2.03 (m, 4H), 1.95-1.73 (m, 4H) |
| 288 | ¹H NMR (500 MHz, DMSO-d₆) δ 9.92 (s, 1H), 8.69 (d, J = 6.9 Hz, 1H), 8.34 (s, 1H), 8.23 (s, 1H), 8.19 (q, J = 4.3 Hz, 1H), 8.12 (d, J = 8.9 Hz, 1H), 7.95 (s, 1H), 7.78 (d, J = 7.4 Hz, 1H), 7.71-7.63 (m, 2H), 7.43 (d, J = 8.9 Hz, 1H), 7.36 (td, J = 7.3, 1.2 Hz, 1H), 7.28 (s, 1H), 6.82 (s, 1H), 4.15 (quin, J = 6.3 Hz, 1H), 3.09-2.98 (m, 1H), 2.71 (d, J = 4.5 Hz, 3H), 2.17-1.96 (m, 2H), 1.93-1.75 (m, 3H), 1.74-1.57 (m, 1H) |
| 289 | ¹H NMR (500 MHz, methanol-d₄) δ 8.25 (s, 1H), 8.11 (d, J = 8.9 Hz, 1H), 7.89 (d, J = 8.4 Hz, 1H), 7.76 (d, J = 7.9 Hz, 1H), 7.70-7.65 (m, 1H), 7.42 (t, J = 7.4 Hz, 1H), 7.25 (d, J = 8.9 Hz, 1H), 4.29 (q, J = 6.9 Hz, 1H), 2.91 (s, 3H), 2.74 (q, J = 7.6 Hz, 2H), 2.52-2.38 (m, 1H), 2.25-2.11 (m, 1H), 1.99-1.85 (m, 3H), 1.79-1.66 (m, 1H) |
| 290 | ¹H NMR (500 MHz, DMSO-d₆) δ 10.01 (d, J = 3.0 Hz, 1H), 8.86 (d, J = 7.9 Hz, 1H), 8.59-8.46 (m, 1H), 8.38-8.30 (m, 1H), 8.26 (d, J = 4.0 Hz, 1H), 8.01-7.90 (m, 1H), 7.82 (d, J = 8.4 Hz, 1H), 7.28-7.08 (m, 2H), 6.78-6.67 (m, 1H), 4.01-3.86 (m, 1H), 2.72 (t, J = 4.5 Hz, 3H), 2.56 (d, J = 5.9 Hz, 1H), 2.05-1.97 (m, 1H), 1.78-1.58 (m, 3H), 1.55-1.25 (m, 4H) |
| 291 | ¹H NMR (500 MHz, DMSO-d₆) δ 9.99 (d, J = 4.0 Hz, 1H), 8.69-8.49 (m, 2H), 8.31 (d, J = 4.0 Hz, 1H), 8.22 (t, J = 4.2 Hz, 1H), 7.98 (d, J = 8.9 Hz, 1H), 7.87 (dd, J = 8.9, 3.5 Hz, 1H), 7.22 (br. s., 1H), 7.14 (d, J = 3.5 Hz, 1H), 6.78 (br. s., 1H), 3.98 (d, J = 4.5 Hz, 1H), 2.97-2.83 (m, 1H), 2.76-2.66 (m, 3H), 1.95 (d, J = 8.4 Hz, 2H), 1.88-1.67 (m, 3H), 1.61 (d, J = 9.4 Hz, 1H) |
| 292 | ¹H NMR (500 MHz, methanol-d₄) δ 8.25 (s, 1H), 8.07 (d, J = 8.9 Hz, 2H), 7.78-7.71 (m, 2H), 7.68-7.64 (m, 1H), 7.43-7.36 (m, 1H), 7.21 (d, J = 8.9 Hz, 1H), 3.74 (t, J = 8.9 Hz, 1H), 2.90 (s, 3H), 2.32-2.13 (m, 4H), 2.11-1.97 (m, 2H), 1.92-1.81 (m, 2H) |
| 293 | ¹H NMR (500 MHz, methanol-d₄) δ 8.26 (s, 1H), 8.09 (d, J = 8.9 Hz, 1H), 7.91 (br. s., 1H), 7.79-7.72 (m, 2H), 7.67 (t, J = 7.7 Hz, 1H), 7.41 (t, J = 7.4 Hz, 1H), 7.21 (d, J = 8.9 Hz, 1H), 4.29-4.21 (m, 1H), 3.92 (br. s., 1H), 2.91 (s, 3H), 2.36-2.22 (m, 2H), 2.18-1.90 (m, 4H) |
| 296 | ¹H NMR (500 MHz, methanol-d₄) δ 8.29 (s, 1H), 8.03 (d, J = 3.0 Hz, 1H), 7.53 (dd, J = 7.7, 1.7 Hz, 1H), 7.44-7.38 (m, 1H), 7.31 (dd, J = 9.2, 3.7 Hz, 1H), 7.17-7.10 (m, 1H), 7.07-6.98 (m, 2H), 3.91 (s, 3H), 3.43 (q, J = 7.1 Hz, 2H), 1.26 (t, J = 1.4 Hz, 3H) |
| 298 | ¹H NMR (500 MHz, DMSO-d₆) δ 10.83 (br. s., 1H), 9.83 (br. s., 1H), 8.56-8.43 (m, 2H), 8.09 (d, J = 3.0 Hz, 1H), 7.93 (dd, J = 7.9, 3.0 Hz, 1H), 7.85-7.72 (m, 2H), 7.69-7.54 (m, 3H), 7.42-7.34 (m, 1H), 3.20-3.11 (m, 3H) |
| 299 | ¹H NMR (500 MHz, methanol-d₄) δ 8.40 (s, 1H), 8.12 (dd, J = 5.0, 1.0 Hz, 1H), 7.83 (dd, J = 9.2, 4.7 Hz, 1H), 7.78-7.73 (m, 2H), 7.67-7.62 (m, 1H), 7.46 (ddd, J = 8.9, 7.4, 3.0 Hz, 1H), 7.26 (d, J = 8.4 Hz, 1H), 6.89 (td, J = 6.2, 1.0 Hz, 1H), 3.16 (s, 3H) |
| 300 | ¹H NMR (500 MHz, methanol-d₄) δ 8.44 (s, 1H), 8.19 (s, 1H), 8.07 (dd, J = 7.9, 1.5 Hz, 1H), 7.84 (d, J = 7.4 Hz, 1H), 7.76-7.69 (m, 1H), 7.43-7.31 (m, 1H), 6.84 (s, 1H), 3.14 (s, 3H), 2.38 (d, J = 6.9 Hz, 6H) |
| 301 | ¹H NMR (500 MHz, methanol-d₄) δ 8.47 (s, 1H), 8.42 (d, J = 2.5 Hz, 1H), 8.17 (dd, J = 7.9, 1.5 Hz, 1H), 7.89 (dd, J = 8.7, 2.7 Hz, 1H), 7.87-7.81 (m, 1H), 7.71 (d, J = 1.4 Hz, 1H), 7.65-7.58 (m, 3H), 7.18 (d, J = 8.9 Hz, 1H), 6.81 (br. s., 1H), 6.73-6.65 (m, 1H), 3.21 (s, 3H) |
| 304 | ¹H NMR (500 MHz, methanol-d₄) δ 8.48 (d, J = 2.0 Hz, 1H), 8.43 (br. s., 1H), 8.13 (dd, J = 8.4, 2.0 Hz, 1H), 8.06 (br. s., 1H), 7.98 (br. s., 1H), 7.93 (d, J = 8.4 Hz, 1H), 7.43 (d, J = 7.4 Hz, 1H), 7.32 (br. s., 1H), 3.19 (s, 3H), 2.98 (s, 3H), 2.94 (s, 3H) |
| 305 | ¹H NMR (500 MHz, methanol-d₄) δ 8.43 (br. s., 1H), 8.09 (d, J = 1.5 Hz, 1H), 8.03 (br. s., 1H), 7.99-7.87 (m, 2H), 7.75 (d, J = 7.4 Hz, 1H), 7.43 (br. s., 1H), 7.34 (br. s., 1H), 4.39 (br. s., 2H), 3.76 (s, 4H), 3.60 (br. s., 2H), 3.19 (s, 3H), 2.94 (s, 3H) |
| 306 | ¹H NMR (500 MHz, methanol-d₄) δ 8.43 (s, 1H), 8.14 (s, 2H), 7.90-7.84 (m, 1H), 7.80 (d, J = 8.4 Hz, 1H), 7.53 (br. s., 1H), 7.23 (br. s., 1H), 3.21 (s, 3H), 3.18-3.10 (m, 6H), 2.96 (s, 3H) |
| 307 | ¹H NMR (500 MHz, DMSO-d₆) δ 11.02 (s, 1H), 9.87 (s, 1H), 8.82 (d, J = 3.5 Hz, 1H), 8.59-8.51 (m, 2H), 8.43 (d, J = 2.0 Hz, 1H), 8.21 (dd, J = 8.4, 2.0 Hz, 1H), 8.14 (d, J = 3.0 Hz, 1H), 7.95 (s, 1H), 7.84 (d, J = 8.4 Hz, 1H), 7.73-7.58 (m, 3H), 4.89-4.68 (m, 1H), 3.22 (s, 3H), 2.88-2.83 (m, 1H), 2.78 (d, J = 4.5 Hz, 3H), 1.28-1.07 (m, 2H) |
| 308 | ¹H NMR (500 MHz, methanol-d₄) δ 8.47 (s, 1H), 8.39 (d, J = 2.0 Hz, 1H), 8.24 (d, J = 3.0 Hz, 1H), 8.08 (dd, J = 8.4, 2.0 Hz, 1H), 7.87 (d, J = 8.4 Hz, 1H), 7.67-7.61 (m, 1H), 7.17 (dd, J = 8.9, 3.5 Hz, 1H), 7.12 (br. s., 1H), 3.23 (s, 3H), 2.98 (s, 3H) |
| 309 | ¹H NMR (500 MHz, methanol-d₄) δ 11.78-11.69 (m, 2H), 11.43 (dd, J = 8.7, 2.2 Hz, 1H), 11.37 (d, J = 3.0 Hz, 1H), 11.30-11.24 (m, 1H), 11.22 (d, J = 8.9 Hz, 1H), 10.79-10.69 (m, 1H), 10.62 (dd, J = 8.9, 3.5 Hz, 1H), 7.59 (br. s., 2H), 6.49 (s, 3H), 6.25 (s, 3H), 4.22-4.11 (m, 2H), 4.04-3.96 (m, 2H) |

-continued

| Compound | $^1$H NMR (methanol-d$_4$ equates CDCl$_3$:MeOD ~1:1 unless otherwise noted) Occasionally water suppression is used in DMSO-d$_6$ spectra |
|---|---|
| 316 | $^1$H NMR (500 MHz, DMSO-d$_6$) δ 10.64 (s, 1H), 9.78 (s, 1H), 8.51 (d, J = 4.3 Hz, 1H), 8.45 (s, 1H), 8.24 (d, J = 4.9 Hz, 1H), 8.14 (d, J = 3.1 Hz, 1H), 7.94 (s, 1H), 7.71-7.58 (m, 4H), 7.31-7.20 (m, 2H), 3.16 (d, J = 4.9 Hz, 3H), 2.78 (dd, J = 8.2, 4.6 Hz, 6H) |
| 317 | $^1$H NMR (500 MHz, DMSO-d$_6$) δ 10.65 (s, 1H), 9.79 (s, 1H), 8.51 (d, J = 4.3 Hz, 1H), 8.45 (s, 1H), 8.30 (d, J = 4.3 Hz, 1H), 8.14 (d, J = 3.1 Hz, 1H), 7.72 (s, 1H), 7.68-7.55 (m, 3H), 7.25 (t, J = 7.9 Hz, 1H), 7.15 (dd, J = 7.9, 1.2 Hz, 1H), 3.16 (d, J = 5.5 Hz, 2H), 2.85 (td, J = 7.2, 4.0 Hz, 1H), 2.78 (d, J = 4.3 Hz, 3H), 0.74-0.66 (m, 2H), 0.58-0.52 (m, 2H) |
| 318 | $^1$H NMR (500 MHz, DMSO-d$_6$) δ 10.67 (s, 1H), 8.55-8.43 (m, 2H), 8.30 (d, J = 4.4 Hz, 1H), 8.04 (s, 1H), 7.70 (br. s., 1H), 7.61 (d, J = 7.1 Hz, 1H), 7.55 (d, J = 5.0 Hz, 1H), 7.24 (t, J = 7.7 Hz, 1H), 7.14 (d, J = 6.7 Hz, 1H), 2.85 (td, J = 7.3, 3.9 Hz, 1H), 2.77 (d, J = 4.4 Hz, 3H), 2.23 (s, 3H), 0.76-0.64 (m, 2H), 0.59-0.49 (m, 2H) |
| 319 | $^1$H NMR (500 MHz, DMSO-d$_6$) δ 10.66 (s, 1H), 9.69 (s, 1H), 8.53-8.43 (m, 2H), 8.04 (s, 1H), 7.77-7.66 (m, 2H), 7.63 (dd, J = 7.6, 1.5 Hz, 1H), 7.58-7.53 (m, 2H), 7.32-7.23 (m, 2H), 3.74 (s, 3H), 2.78 (d, J = 4.3 Hz, 3H), 2.23 (s, 3H) |
| 320 | $^1$H NMR (500 MHz, DMSO-d$_6$) δ 10.69 (s, 1H), 8.55 (br. s., 1H), 8.46 (s, 1H), 8.24 (d, J = 4.9 Hz, 1H), 8.07 (s, 1H), 7.65-7.58 (m, 2H), 7.26 (d, J = 4.9 Hz, 2H), 3.72 (s, 3H), 3.16 (s, 3H), 2.82-2.75 (m, 6H) |
| 321 | N/A |
| 322 | $^1$H NMR (500 MHz, DMSO-d$_6$) δ 10.68 (s, 1H), 9.71 (s, 1H), 8.57-8.41 (m, 2H), 8.33 (br. s., 1H), 8.04 (s, 1H), 7.74-7.61 (m, 2H), 7.56 (d, J = 5.5 Hz, 1H), 7.39-7.31 (m, 1H), 7.31-7.25 (m, 1H), 3.76 (s, 3H), 3.57 (br. s., 3H), 3.44-3.38 (m, 2H), 2.78 (d, J = 4.3 Hz, 3H), 2.42 (br. s., 3H), 2.24 (s, 3H) |
| 323 | $^1$H NMR (500 MHz, DMSO-d$_6$) δ 10.70 (s, 1H), 9.72 (br. s., 1H), 8.59-8.41 (m, 2H), 8.11 (d, J = 7.9 Hz, 1H), 8.05 (s, 1H), 7.72 (br. s., 1H), 7.66-7.49 (m, 2H), 7.30-7.22 (m, 1H), 7.19 (d, J = 7.3 Hz, 1H), 4.21-3.96 (m, 1H), 3.72 (s, 3H), 2.78 (d, J = 3.7 Hz, 3H), 2.24 (s, 3H), 1.17 (d, J = 6.7 Hz, 6H) |
| 324 | $^1$H NMR (500 MHz, DMSO-d$_6$) δ10.72 (s, 1H), 9.72 (br. s., 1H), 8.58-8.44 (m, 2H), 8.37 (t, J = 5.5 Hz, 1H), 8.05 (s, 1H), 7.71 (br. s., 1H), 7.64 (dd, J = 7.6, 2.1 Hz, 1H), 7.55 (br. s., 1H), 7.33-7.17 (m, 2H), 3.74 (s, 3H), 3.16 (t, J = 6.4 Hz, 2H), 2.78 (d, J = 4.3 Hz, 3H), 2.24 (s, 3H), 1.13-0.94 (m, 1H), 0.55-0.39 (m, 2H), 0.31-0.17 (m, 2H) |
| 325 | $^1$H NMR (500 MHz, DMSO-d$_6$) δ 10.69 (s, 1H), 9.72 (br. s., 1H), 8.58-8.44 (m, 2H), 8.27 (t, J = 5.8 Hz, 1H), 8.05 (s, 1H), 7.71 (br. s., 1H), 7.62 (d, J = 7.9 Hz, 1H), 7.56 (br. s., 1H), 7.29-7.22 (m, 1H), 7.23-7.14 (m, 1H), 3.71 (s, 1H), 3.11 (t, J = 6.4 Hz, 1H), 2.78 (d, J = 4.3 Hz, 2H), 2.24 (s, 2H), 1.80-1.64 (m, 3H), 1.62 (d, J = 9.8 Hz, 1H), 1.54 (br. s., 1H), 1.29-1.07 (m, 2H), 1.00-0.89 (m, 1H) |
| 326 | $^1$H NMR (500 MHz, DMSO-d$_6$) δ 10.69 (s, 1H), 9.71 (br. s., 1H), 8.59-8.43 (m, 2H), 8.27 (t, J = 5.8 Hz, 1H), 8.05 (s, 1H), 7.71 (br. s., 1H), 7.62 (dd, J = 7.9, 1.2 Hz, 1H), 7.56 (d, J = 5.5 Hz, 1H), 7.31-7.22 (m, 1H), 7.22-7.14 (m, 1H), 3.71 (s, 1H), 3.26 (q, J = 6.7 Hz, 1H), 2.78 (d, J = 4.3 Hz, 1H), 2.24 (s, 1H), 1.51 (quin, J = 7.3 Hz, 1H), 1.36 (sxt, J = 7.4 Hz, 1H), 0.91 (t, J = 7.3 Hz, 1H) |
| 327 | $^1$H NMR (500 MHz, DMSO-d$_6$) δ 10.72 (s, 1H), 9.72 (br. s., 1H), 9.02 (t, J = 5.8 Hz, 1H), 8.59-8.45 (m, 3H), 8.05 (s, 1H), 7.85-7.75 (m, 1H), 7.73-7.63 (m, 2H), 7.57 (d, J = 4.9 Hz, 1H), 7.42 (d, J = 7.3 Hz, 1H), 7.37 (d, J = 6.7 Hz, 1H), 7.33-7.22 (m, 2H), 4.61 (d, J = 5.5 Hz, 1H), 3.75 (s, 1H), 2.79 (d, J = 4.3 Hz, 1H), 2.24 (s, 1H) |
| 328 | $^1$H NMR (500 MHz, DMSO-d$_6$)δ 10.76 (s, 1H), 10.33 (s, 1H), 9.74 (br. s., 1H), 8.58-8.43 (m, 2H), 8.07 (s, 1H), 7.75 (d, J = 7.9 Hz, 3H), 7.69 (d, J = 7.9 Hz, 1H), 7.56 (br. s., 1H), 7.39-7.29 (m, 3H), 7.25 (d, J = 7.3 Hz, 1H), 7.10 (t, J = 7.3 Hz, 1H), 3.77 (s, 1H), 2.78 (d, J = 4.3 Hz, 1H), 2.24 (s, 1H) |
| 329 | $^1$H NMR (500 MHz, DMSO-d$_6$) δ 10.69 (s, 1H), 9.70 (s, 1H), 8.52-8.44 (m, 2H), 8.27 (t, J = 5.8 Hz, 1H), 8.04 (s, 1H), 7.71 (s, 1H), 7.62 (d, J = 73 Hz, 1H), 7.56 (d, J = 5.5 Hz, 1H), 7.29-7.22 (m, 1H), 7.23-7.15 (m, 1H), 4.39 (t, J = 5.2 Hz, 1H), 3.72 (s, 1H), 3.25 (q, J = 6.7 Hz, 1H), 2.78 (d, J = 4.9 Hz, 1H), 2.24 (s, 1H), 1.62-1.49 (m, 1H), 1.49-1.38 (m, 1H), 1.38-1.28 (m, 1H) |
| 330 | $^1$H NMR (500 MHz, DMSO-d$_6$) δ 10.69 (s, 1H), 9.70 (s, 1H), 8.57-8.43 (m, 2H), 8.27 (t, J = 5.8 Hz, 1H), 8.04 (s, 1H), 7.71 (s, 1H), 7.62 (d, J = 7.3 Hz, 1H), 7.56 (d, J = 5.5 Hz, 1H), 7.32-7.22 (m, 1H), 7.22-7.12 (m, 1H), 3.71 (s, 1H), 3.25 (q, J = 6.7 Hz, 1H), 2.78 (d, J = 4.3 Hz, 1H), 2.24 (s, 1H), 1.53 (t, J = 6.7 Hz, 1H), 1.37-1.26 (m, 2H), 1.00-0.82 (m, 2H) |
| 331 | $^1$H NMR (500 MHz, DMSO-d$_6$) δ 10.68 (s, 1H), 9.70 (s, 1H), 8.54-8.46 (m, 2H), 8.37 (t, J = 5.5 Hz, 1H), 8.04 (s, 1H), 7.72-7.62 (m, 2H), 7.57 (d, J = 5.5 Hz, 1H), 7.47-7.38 (m, 2H), 7.38-7.29 (m, 3H), 7.31-7.22 (m, 2H), 5.63 (d, J = 4.9 Hz, 1H), 4.84-4.74 (m, 1H), 3.65 (s, 3H), 3.63-3.53 (m, 1H), 2.78 (d, J = 4.9 Hz, 3H), 2.24 (s, 3H) |
| 332 | $^1$H NMR (500 MHz, DMSO-d$_6$) δ10.69 (s, 1H), 9.71 (s, 1H), 8.50 (d, J = 4.3 Hz, 1H), 8.48 (s, 1H), 8.28 (t, J = 5.8 Hz, 1H), 8.04 (s, 1H), 7.71 (s, 1H), 7.62 (d, J = 6.7 Hz, 1H), 7.56 (d, J = 4.9 Hz, 1H), 7.29-7.23 (m, 1H), 7.23-7.15 (m, 1H), 3.71 (s, 3H), 3.30 (t, J = 6.7 Hz, 2H), 2.78 (d, J = 4.3 Hz, 3H), 2.59- |

| Compound | ¹H NMR (methanol-d₄ equates CDCl₃:MeOD ~1:1 unless otherwise noted) Occasionally water suppression is used in DMSO-d₆ spectra |
|---|---|
| | 2.52 (m, 1H), 2.24 (s, 3H), 2.07-1.95 (m, 2H), 1.88-1.79 (m, 2H), 1.79-1.68 (m, 2H) |
| 333 | ¹H NMR (500 MHz, DMSO-d₆) δ 10.67 (s, 1H), 9.70 (s, 1H), 8.55-8.41 (m, 2H), 8.35 (t, J = 5.5 Hz, 1H), 8.04 (s, 1H), 7.70 (s, 1H), 7.63 (dd, J = 6.1, 3.7 Hz, 1H), 7.56 (d, J = 5.5 Hz, 1H), 7.33-7.21 (m, 2H), 4.44 (s, 1H), 3.72 (s, 3H), 2.78 (d, J = 4.3 Hz, 3H), 2.24 (s, 3H), 1.70-1.58 (m, 2H), 1.15 (s, 6H) |
| 334 | ¹H NMR (500 MHz, DMSO-d₆)δ 10.68 (s, 1H), 9.71 (br. s., 1H), 8.60-8.42 (m, 2H), 8.22 (t, J = 5.8 Hz, 1H), 8.04 (s, 1H), 7.72 (s, 1H), 7.62 (d, J = 8.5 Hz, 1H), 7.55 (d, J = 5.5 Hz, 1H), 7.30-7.23 (m, 1H), 7.19 (d, J = 6.7 Hz, 1H), 3.71 (s, 3H), 3.21 (t, J = 6.1 Hz, 2H), 2.78 (d, J = 4.3 Hz, 3H), 2.24 (s, 3H), 1.56-1.43 (m, 1H), 1.40-1.27 (m, 4H), 0.88 (t, J = 7.3 Hz, 6H) |
| 335 | ¹H NMR (500 MHz, DMSO-d₆) δ10.71 (s, 1H), 9.71 (s, 1H), 8.56-8.42 (m, 2H), 8.30 (t, J = 5.8 Hz, 1H), 8.05 (s, 1H), 7.70 (s, 1H), 7.65 (d, J = 6.7 Hz, 1H), 7.57 (d, J = 5.5 Hz, 1H), 7.38-7.31 (m, 1H), 7.32-7.23 (m, 3H), 4.82 (d, J = 4.9 Hz, 1H), 3.79 (dt, J = 11.6, 5.8 Hz, 1H), 3.73 (s, 3H), 3.33-3.25 (m, 1H), 3.25-3.12 (m, 1H), 2.78 (d, J = 4.9 Hz, 3H), 2.24 (s, 3H), 1.10 (d, J = 6.1 Hz, 3H) |
| 336 | ¹H NMR (500 MHz, DMSO-d₆) δ 10.69 (s, 1H), 9.71 (br. s., 1H), 8.60-8.43 (m, 2H), 8.28 (t, J = 5.8 Hz, 1H), 8.05 (s, 1H), 7.71 (s, 1H), 7.62 (dd, J = 7.9, 1.2 Hz, 1H), 7.56 (d, J = 6.1 Hz, 1H), 7.29-7.22 (m, 1H), 7.22-7.16 (m, 1H), 3.72 (s, 1H), 3.22 (q, J = 6.7 Hz, 1H), 2.78 (d, J = 4.3 Hz, 1H), 2.24 (s, 1H), 1.64-1.43 (m, 1H), 0.92 (t, J = 7.6 Hz, 2H) |
| 337 | ¹H NMR (500 MHz, DMSO-d₆) δ 10.66 (s, 1H), 9.71 (br. s., 1H), 8.58-8.43 (m, 2H), 8.36 (t, J = 5.8 Hz, 1H), 8.04 (s, 1H), 7.68 (br. s., 1H), 7.62 (d, J = 7.9 Hz, 1H), 7.56 (br. s., 1H), 7.36-7.14 (m, 7H), 3.60 (s, 3H), 3.56-3.47 (m, 2H), 2.88-2.83 (m, 2H), 2.78 (d, J = 4.3 Hz, 3H), 2.24 (s, 3H) |
| 338 | ¹H NMR (500 MHz, DMSO-d₆) δ10.69 (s, 1H), 9.70 (s, 1H), 8.50 (d, J = 4.9 Hz, 1H), 8.48 (s, 1H), 8.25 (t, J = 5.8 Hz, 1H), 8.04 (s, 1H), 7.71 (s, 1H), 7.65-7.59 (m, 1H), 7.56 (d, J = 6.1 Hz, 1H), 7.29-7.22 (m, 1H), 7.21-7.15 (m, 1H), 3.71 (s, 1H), 3.31-3.21 (m, 1H), 2.78 (d, J = 4.3 Hz, 1H), 2.24 (s, 1H), 1.66 (dt, J = 13.4, 6.7 Hz, 1H), 1.42 (q, J = 7.1 Hz, 2H), 0.91 (d, J = 6.7 Hz, 6H) |
| 339 | ¹H NMR (500 MHz, DMSO-d₆) δ10.69 (s, 1H), 9.71 (br. s., 1H), 8.58-8.42 (m, 2H), 8.28 (t, J = 5.8 Hz, 1H), 8.05 (s, 1H), 7.71 (s, 1H), 7.62 (dd, J = 7.9, 1.2 Hz, 1H), 7.56 (d, J = 6.1 Hz, 1H), 7.30-7.23 (m, 1H), 7.22-7.15 (m, 1H), 3.72 (s, 1H), 3.22 (q, J = 6.7 Hz, 1H), 2.78 (d, J = 4.3 Hz, 1H), 2.24 (s, 1H), 1.62-1.46 (m, 1H), 0.92 (t, J = 7.6 Hz, 2H) |
| 340 | ¹H NMR (500 MHz, DMSO-d₆) δ 10.68 (s, 1H), 9.70 (s, 1H), 8.55-8.43 (m, 2H), 8.23 (t, J = 6.4 Hz, 1H), 8.04 (s, 1H), 7.72 (s, 1H), 7.63 (d, J = 6.7 Hz, 1H), 7.55 (d, J = 5.5 Hz, 1H), 7.31-7.25 (m, 1H), 7.24-7.20 (m, 1H), 3.73 (s, 1H), 3.11 (d, J = 6.1 Hz, 1H), 2.78 (d, J = 4.3 Hz, 1H), 2.24 (s, 1H), 0.93 (s, 3H) |
| 341 | ¹H NMR (500 MHz, DMSO-d₆) δ 10.67 (s, 1H), 9.70 (s, 1H), 8.54-8.45 (m, 2H), 8.39 (t, J = 5.5 Hz, 1H), 8.05 (s, 1H), 7.95 (s, 1H), 7.69 (s, 1H), 7.63 (dd, J = 6.1, 3.7 Hz, 1H), 7.56 (d, J = 5.5 Hz, 1H), 7.30-7.21 (m, 3H), 7.18 (s, 1H), 7.08 (s, 1H), 6.72 (dd, J = 8.5, 2.4 Hz, 1H), 3.75 (s, 1H), 3.63 (s, 1H), 3.61-3.51 (m, 1H), 2.94 (t, J = 7.3 Hz, 1H), 2.78 (d, J = 4.3 Hz, 2H), 2.24 (s, 2H) |
| 342 | ¹H NMR (500 MHz, DMSO-d₆)δ 10.72 (s, 1H), 9.71 (s, 1H), 8.57-8.42 (m, 2H), 8.26 (t, J = 5.2 Hz, 1H), 8.05 (s, 1H), 7.75-7.63 (m, 2H), 7.57 (d, J = 5.0 Hz, 1H), 7.44 (d, J = 1.4 Hz, 1H), 7.31 (t, J = 7.9 Hz, 1H), 3.73 (s, 3H), 2.79 (d, J = 4.0 Hz, 1H), 2.24 (s, 3H), 2.10-1.86 (m, 2H), 1.71-1.58 (m, 1H), 1.58-1.43 (m, 1H) |
| 343 | ¹H NMR (500 MHz, DMSO-d₆) δ10.71 (s, 1H), 9.71 (s, 1H), 8.62-8.40 (m, 3H), 8.05 (s, 1H), 7.74 (s, 1H), 7.64 (d, J = 7.7 Hz, 1H), 7.56 (d, J = 5.4 Hz, 1H), 7.34-7.23 (m, 1H), 7.20 (d, J = 7.1 Hz, 1H), 4.49 (d, J = 5.7 Hz, 1H), 4.23 (d, J = 5.7 Hz, 1H), 3.72 (s, 1H), 2.78 (d, J = 4.0 Hz, 1H), 2.24 (s, 1H), 1.29 (s, 1H) |
| 344 | ¹H NMR (500 MHz, DMSO-d₆)δ 10.70 (s, 1H), 9.70 (s, 1H), 8.55-8.44 (m, 3H), 8.34 (t, J = 5.6 Hz, 1H), 8.04 (s, 1H), 7.70 (s, 1H), 7.64 (d, J = 7.1 Hz, 1H), 7.57 (d, J = 5.4 Hz, 1H), 7.32-7.22 (m, 3H), 3.98 (t, J = 6.2 Hz, 1H), 3.79 (q, J = 7.2 Hz, 1H), 3.73 (s, 3H), 3.65 (q, J = 7.4 Hz, 1H), 2.78 (d, J = 4.0 Hz, 3H), 2.24 (s, 3H), 1.99-1.77 (m, 4H), 1.67-1.54 (m, 1H) |
| 345 | ¹H NMR (500 MHz, DMSO-d₆) δ10.73 (s, 1H), 9.73 (br. s., 1H), 9.19 (t, J = 5.9 Hz, 1H), 8.58-8.43 (m, 2H), 8.05 (s, 1H), 7.78-7.62 (m, 3H), 7.56 (d, J = 4.4 Hz, 1H), 7.31 (d, J = 4.7 Hz, 2H), 4.77 (d, J = 6.1 Hz, 2H), 3.74 (s, 2H), 2.78 (d, J = 4.4 Hz, 3H), 2.24 (s, 3H) |
| 346 | ¹H NMR (500 MHz, DMSO-d₆) δ 10.75 (s, 1H), 9.73 (br. s., 1H), 8.93 (t, J = 6.4 Hz, 1H), 8.57-8.43 (m, 2H), 8.05 (s, 1H), 7.69 (d, J = 8.1 Hz, 2H), 7.55 (br. s., 1H), 7.35-7.26 (m, 1H), 7.26-7.18 (m, 1H), 4.17-4.04 (m, 2H), 3.71 (s, 3H), 2.78 (d, J = 4.4 Hz, 3H), 2.24 (s, 3H) |
| 347 | ¹H NMR (500 MHz, DMSO-d₆) δ 10.71 (s, 1H), 9.71 (s, 1H), 8.57-8.42 (m, 2H), 8.25 (t, J = 5.6 Hz, 1H), 8.04 (s, 1H), 7.74-7.63 (m, 2H), 7.57 (d, J = 5.4 Hz, 1H), 7.39 (d, J = 7.4 Hz, 1H), 7.34-7.23 (m, 1H), 3.74 (s, 2H), 2.78 (d, J = 4.0 Hz, 3H), 2.24 (s, 3H), 1.15 (s, 6H) |
| 348 | ¹H NMR (500 MHz, DMSO-d₆) δ 10.69 (s, 1H), 9.70 (s, 1H), 8.56-8.42 (m, 2H), 8.32 (t, J = 5.4 Hz, 1H), 8.04 (s, 1H), 7.70 (s, 1H), 7.63 (d, J = 5.7 Hz, |

| Compound | ¹H NMR (methanol-d₄ equates CDCl₃:MeOD ~1:1 unless otherwise noted) Occasionally water suppression is used in DMSO-d₆ spectra |
|---|---|
| | 1H), 7.56 (d, J = 5.4 Hz, 1H), 7.25 (q, J = 8.0 Hz, 2H), 3.72 (s, 3H), 2.78 (d, J = 4.4 Hz, 3H), 2.24 (s, 3H), 1.68 (quin, J = 6.5 Hz, 2H) |
| 349 | ¹H NMR (500 MHz, DMSO-d₆) δ 10.69 (s, 1H), 9.70 (s, 1H), 8.57-8.42 (m, 2H), 8.32 (t, J = 5.4 Hz, 1H), 8.04 (s, 1H), 7.71 (s, 1H), 7.63 (d, J = 7.1 Hz, 1H), 7.56 (d, J = 5.4 Hz, 1H), 7.36-7.07 (m, 2H), 3.72 (s, 3H), 3.25 (s, 3H), 2.78 (d, J = 4.0 Hz, 3H), 2.24 (s, 3H), 1.82-1.66 (m, 2H) |
| 350 | ¹H NMR (500 MHz, DMSO-d₆) δ 10.69 (s, 1H), 9.70 (s, 1H), 8.56-8.40 (m, 2H), 8.30 (t, J = 5.7 Hz, 1H), 8.04 (s, 1H), 7.72 (s, 1H), 7.62 (d, J = 7.7 Hz, 1H), 7.56 (d, J = 5.7 Hz, 1H), 7.34-7.22 (m, 1H), 7.22-7.10 (m, 1H), 3.72 (s, 2H), 3.09 (t, J = 6.2 Hz, 1H), 2.78 (d, J = 4.4 Hz, 2H), 1.84 (dt, J = 13.5, 6.7 Hz, 1H), 0.92 (d, J = 6.7 Hz, 6H) |
| 351 | ¹H NMR (500 MHz, DMSO-d₆) δ 10.70 (s, 1H), 9.71 (s, 1H), 8.83 (t, J = 5.7 Hz, 1H), 8.57-8.40 (m, 2H), 8.05 (s, 1H), 7.72 (s, 1H), 7.65 (d, J = 7.1 Hz, 1H), 7.56 (d, J = 5.0 Hz, 1H), 7.40-7.30 (m, 4H), 7.30-7.17 (m, 3H), 4.48 (d, J = 5.7 Hz, 2H), 3.68 (s, 3H), 2.78 (d, J = 4.0 Hz, 3H), 2.24 (s, 3H) |
| 352 | ¹H NMR (500 MHz, DMSO-d₆) δ 10.70 (s, 1H), 9.70 (s, 1H), 8.56-8.43 (m, 2H), 8.34 (t, J = 5.0 Hz, 1H), 8.04 (s, 1H), 7.70 (s, 1H), 7.65 (dd, J = 7.1, 2.0 Hz, 1H), 7.57 (d, J = 5.4 Hz, 1H), 7.33-7.21 (m, 2H), 3.72 (s, 3H), 2.78 (d, J = 4.4 Hz, 3H), 2.24 (s, 3H) |
| 353 | ¹H NMR (500 MHz, DMSO-d₆) δ 10.93 (br. s., 1H), 10.65 (s, 1H), 9.69 (s, 1H), 8.61-8.52 (m, 1H), 8.50-8.38 (m, 2H), 7.95 (s, 1H), 7.73-7.65 (m, 2H), 7.66-7.51 (m, 2H), 7.41-7.28 (m, 2H), 7.27-7.17 (m, 2H), 7.13-7.05 (m, 1H), 7.03-6.96 (m, 1H), 4.62 (d, J = 5.4 Hz, 2H), 3.59 (s, 3H), 2.76 (d, J = 4.4 Hz, 3H), 2.23 (s, 3H) |
| 354 | ¹H NMR (500 MHz, DMSO-d₆) δ 10.87-10.75 (m, 1H), 8.89-8.66 (m, 2H), 8.46 (s, 1H), 8.16 (s, 1H), 7.70-7.59 (m, 1H), 7.40 (d, J = 6.9 Hz, 1H), 7.38-7.29 (m, 1H), 7.22 (br. s., 1H), 3.79 (s, 3H), 2.82 (d, J = 4.4 Hz, 3H), 2.29 (s, 3H), 1.28-1.19 (m, 2H), 1.17-1.09 (m, 2H) |
| 355 | ¹H NMR (500 MHz, DMSO-d₆) δ 10.70 (s, 1H), 9.71 (br. s., 1H), 8.56-8.41 (m, 2H), 8.29 (br. s., 1H), 8.05 (s, 1H), 7.81-7.43 (m, 3H), 7.37-7.08 (m, 2H), 3.72 (s, 3H), 2.78 (d, J = 4.0 Hz, 3H), 2.24 (s, 3H), 1.13 (t, J = 7.1 Hz, 3H) |
| 356 | ¹H NMR (500 MHz, DMSO-d₆) δ 10.72 (s, 1H), 9.71 (br. s., 1H), 8.50 (d, J = 17.5 Hz, 3H), 8.05 (s, 1H), 7.74-7.59 (m, 2H), 7.56 (br. s., 1H), 7.39-7.13 (m, 2H), 4.70-4.39 (m, 2H), 3.73 (s, 3H), 2.78 (d, J = 4.0 Hz, 3H), 2.24 (s, 3H) |
| 372 | ¹H NMR (400 MHz, methanol-d₄) δ 8.53 (s, 1H), 8.53 (s, 1H), 7.75 (d, J = 7.9 Hz, 1H), 7.64 (d, J = 7.9 Hz, 1H), 7.37 (t, J = 7.9 Hz, 1H), 4.06 (s, 3H), 3.77 (s, 3H), 2.99 (s, 3H), 2.62 (s, 3H), 2.51 (s, 3H) |
| 373 | ¹H NMR (400 MHz, methanol-d₄) δ 8.55 (s, 1H), 8.40 (s, 1H), 8.32 (d, J = 3.1 Hz, 1H), 7.86 (dd, J = 7.7, 1.5 Hz, 1H), 7.76 (ddd, J = 9.0, 8.0, 3.0 Hz, 1H), 7.60 (dd, J = 7.9, 1.5 Hz, 1H), 7.45-7.36 (m, 1H), 7.08 (dd, J = 9.0, 3.5 Hz, 1H), 6.56 (s, 1H), 4.06 (s, 3H), 3.77 (s, 3H), 3.00 (s, 3H) |
| 374 | ¹H NMR (400 MHz, methanol-d₄) δ 8.50 (s, 1H), 8.39 (s, 1H), 8.23 (d, J = 4.0 Hz, 1H), 7.75-7.67 (m, 2H), 7.64 (dd, J = 7.7, 1.5 Hz, 1H), 7.59 (s, 1H), 7.37-7.29 (m, 2H), 7.03-6.93 (m, 1H), 4.05 (s, 3H), 3.77 (s, 3H), 2.95 (s, 4H) |
| 375 | ¹H NMR (400 MHz, methanol-d₄) δ 8.51 (s, 1H), 8.47-8.45 (m, 1H), 8.45 (s, 1H), 7.89 (dd, J = 8.7, 2.3 Hz, 1H), 7.82 (s, 1H), 7.74-7.62 (m, 3H), 7.34 (t, J = 7.9 Hz, 1H), 4.06 (s, 3H), 3.78 (s, 3H), 2.97 (s, 3H) |
| 376 | ¹H NMR (400 MHz, methanol-d₄) δ 8.54-8.51 (m, 2H), 8.45 (s, 1H), 7.91 (dd, J = 8.8, 2.4 Hz, 1H), 7.78 (s, 1H), 7.71-7.70 (m, 1H), 7.68 (d, J = 1.1 Hz, 1H), 7.64 (dd, J = 7.9, 1.5 Hz, 1H), 7.35 (t, J = 7.9 Hz, 1H), 4.06 (s, 3H), 3.77 (s, 3H), 2.96 (s, 3H) |
| 406 | ¹H NMR (500 MHz, methanol-d₄) δ 8.28 (s, 1H), 7.93 (d, J = 3.0 Hz, 1H), 7.89 (s, 1H), 7.33 (dd, J = 8.9, 3.0 Hz, 1H), 7.28 (dt, J = 10.7, 2.1 Hz, 1H), 7.14 (d, J = 8.9 Hz, 1H), 6.55 (ddd, J = 11.1, 8.4, 2.7 Hz, 1H), 3.91 (s, 3H), 3.88-3.82 (m, 4H), 3.15-3.07 (m, 4H), 2.90 (s, 3H) |
| 407 | ¹H NMR (500 MHz, DMSO-d₆) δ 11.09 (s, 1H), 9.64 (br. s., 1H), 8.54 (br. s., 1H), 8.44 (s, 1H), 7.76-7.51 (m, 2H), 7.33 (d, J = 10.9 Hz, 1H), 7.00 (t, J = 8.7 Hz, 1H), 6.06 (br. s., 1H), 3.83 (s, 3H), 3.75 (s, 3H), 2.77 (d, J = 4.5 Hz, 3H) |
| 408 | ¹H NMR (500 MHz, DMSO-d₆) δ 11.05 (s, 1H), 9.55 (br. s., 1H), 8.50 (br. s., 1H), 8.44 (s, 1H), 7.59 (d, J = 2.0 Hz, 2H), 7.26 (d, J = 10.4 Hz, 1H), 7.04-6.91 (m, 1H), 6.05 (br. s., 1H), 4.36 (dt, J = 13.4, 6.7 Hz, 1H), 3.83 (s, 3H), 2.77 (d, J = 4.5 Hz, 3H), 1.35 (d, J = 6.9 Hz, 6H) |
| 409 | ¹H NMR (500 MHz, DMSO-d₆) δ 11.04 (s, 1H), 10.14 (s, 1H), 8.63 (d, J = 4.9 Hz, 1H), 8.55 (s, 1H), 8.17 (br. s., 1H), 7.29 (d, J = 10.4 Hz, 1H), 7.15 (br. s., 1H), 7.07-6.94 (m, 1H), 3.83 (s, 3H), 2.79 (d, J = 43 Hz, 3H), 2.41 (s, 3H), 2.29 (s, 3H) |
| 410 | ¹H NMR (500 MHz, DMSO-d₆) δ 10.78 (s, 1H), 10.07 (s, 1H), 8.58 (d, J = 4.4 Hz, 1H), 8.52 (s, 1H), 8.14 (br. s., 1H), 7.42 (d, J = 8.1 Hz, 1H), 7.22-7.08 (m, 1H), 7.09-6.94 (m, 2H), 3.85 (s, 3H), 2.79 (d, J = 4.0 Hz, 3H), 2.38 (s, 3H), 2.28 (s, 3H) |
| 411 | ¹H NMR (500 MHz, methanol-d₄) δ 8.38 (s, 1H), 8.17 (d, J = 2.0 Hz, 1H), 7.88 (d, J = 5.9 Hz, 3H), 7.81 (dd, J = 8.4, 2.0 Hz, 1H), 7.12 (d, J = 5.0 Hz, 1H), |

| Compound | $^1$H NMR (methanol-d$_4$ equates CDCl$_3$:MeOD ~1:1 unless otherwise noted) Occasionally water suppression is used in DMSO-d$_6$ spectra |
|---|---|
| | 3.63 (t, J = 6.9 Hz, 2H), 3.55 (t, J = 6.4 Hz, 2H), 3.15 (s, 3H), 2.90 (s, 3H), 2.27 (s, 3H), 2.06-1.91 (m, 4H) |
| 412 | $^1$H NMR (500 MHz, methanol-d$_4$) δ 8.38 (s, 1H), 8.07 (d, J = 2.0 Hz, 1H), 7.93-7.85 (m, 2H), 7.83 (br. s., 1H), 7.71 (dd, J = 8.4, 1.5 Hz, 1H), 7.11 (d, J = 5.0 Hz, 1H), 3.20-3.03 (m, 9H), 2.91 (s, 3H), 2.27 (s, 3H) |
| 413 | $^1$H NMR (500 MHz, methanol-d$_4$) δ 8.40 (br. s., 1H), 8.24 (s, 1H), 7.99-7.86 (m, 4H), 7.13 (br. s., 1H), 3.16 (s, 3H), 2.90 (s, 3H), 2.46-2.19 (m, 4H) |
| 414 | $^1$H NMR (500 MHz, methanol-d$_4$) δ 8.40 (s, 1H), 8.00 (d, J = 7.9 Hz, 1H), 7.82 (d, J = 9.4 Hz, 1H), 7.77-7.73 (m, 1H), 7.72-7.66 (m, 1H), 7.34 (d, J = 9.4 Hz, 1H), 7.30 (t, J = 7.2 Hz, 1H), 3.11 (s, 3H), 2.91 (s, 3H), 2.54 (s, 3H) |
| 415 | $^1$H NMR (500 MHz, methanol-d$_4$) δ 8.39 (s, 1H), 7.99 (dd, J = 8.2, 1.2 Hz, 1H), 7.76-7.72 (m, 1H), 7.71-7.66 (m, 1H), 7.61 (s, 1H), 7.57 (s, 1H), 7.35-7.24 (m, 1H), 3.11 (s, 3H), 2.91 (s, 3H), 2.49 (s, 3H), 2.29 (s, 3H) |
| 416 | $^1$H NMR (500 MHz, methanol-d$_4$) δ 8.38 (s, 1H), 8.21 (s, 1H), 8.02 (dd, J = 7.9, 1.5 Hz, 1H), 7.99 (s, 1H), 7.79 (d, J = 7.9 Hz, 1H), 7.72-7.65 (m, 1H), 7.38-7.28 (m, 1H), 3.10 (s, 3H), 2.91 (s, 3H), 2.40 (s, 3H), 2.28 (s, 3H) |
| 417 | $^1$H NMR (500 MHz, methanol-d$_4$) δ 8.99-8.82 (m, 1H), 8.48 (s, 1H), 8.19-8.08 (m, 1H), 7.98 (d, J = 7.9 Hz, 1H), 7.88-7.81 (m, 1H), 7.47 (t, J = 7.7 Hz, 1H), 7.33-7.25 (m, 2H), 3.17 (s, 3H), 2.97 (s, 3H) |
| 418 | $^1$H NMR (500 MHz, DMSO-d$_6$) δ 10.86 (s, 1H), 10.17 (s, 1H), 8.58 (br. s., 2H), 8.10-7.86 (m, 2H), 7.78 (br. s., 2H), 7.51-7.34 (m, 1H), 7.28 (br. s., 1H), 4.33 (s, 2H), 3.17 (s, 3H), 2.79 (br. s., 3H), 2.29 (s, 3H). |
| 419 | $^1$H NMR (500 MHz, DMSO-d$_6$) δ 10.79 (s, 1H), 10.05 (s, 1H), 8.64-8.54 (m, 2H), 8.36 (s, 1H), 7.99-7.91 (m, 1H), 7.82-7.76 (m, 1H), 7.75-7.67 (m, 1H), 7.44-7.35 (m, 2H), 7.26 (s, 1H), 3.87 (s, 3H), 3.17 (s, 3H), 2.79 (d, J = 4.3 Hz, 3H) |
| 420 | $^1$H NMR (500 MHz, DMSO-d$_6$) δ 10.85 (s, 1H), 10.12 (s, 1H), 8.62-8.56 (m, 2H), 8.53 (s, 1H), 7.96 (s, 1H), 7.84-7.74 (m, 2H), 7.68 (s, 1H), 7.52 (s, 1H), 7.40 (t, J = 7.6 Hz, 1H), 3.17 (s, 3H), 2.79 (d, J = 4.3 Hz, 3H), 2.62 (q, J = 7.3 Hz, 2H), 1.20 (t, J = 7.6 Hz, 3H). |
| 421 | $^1$H NMR (500 MHz, DMSO-d$_6$) δ 10.86 (s, 1H), 10.10 (s, 1H), 8.64-8.54 (m, 3H), 7.98-7.92 (m, 1H), 7.85-7.75 (m, 2H), 7.74 (s, 1H), 7.67 (s, 1H), 7.43-7.37 (m, 1H), 3.17 (s, 3H), 2.79 (d, J = 4.3 Hz, 3H), 1.27 (s, 9H). |
| 422 | $^1$H NMR (500 MHz, DMSO-d$_6$) δ 10.78 (s, 1H), 10.01 (s, 1H), 8.63-8.52 (m, 2H), 8.33 (s, 1H), 7.98-7.90 (m, 1H), 7.82-7.70 (m, 2H), 7.47-7.35 (m, 2H), 7.16 (s, 1H), 5.33-5.17 (m, 1H), 3.17 (s, 3H), 2.80 (d, J = 4.3 Hz, 3H), 1.29 (d, J = 6.1 Hz, 6H). |
| 423 | $^1$H NMR (500 MHz, DMSO-d$_6$) δ 10.79 (s, 1H), 9.54 (s, 1H), 8.53 (d, J = 4.3 Hz, 1H), 8.51 (s, 1H), 7.94 (s, 1H), 7.81 (br. s., 1H), 7.78-7.69 (m, 2H), 7.38 (t, J = 7.3 Hz, 1H), 6.97 (br. s., 1H), 6.33 (br. s., 1H), 3.16 (m, 5H), 2.78 (d, J = 4.3 Hz, 3H), 2.58-2.38 (m, 6H), 1.91 (s, 3H), 1.69-1.55 (m, 2H), 0.95 (t, J = 7.0 Hz, 6H). |
| 424 | $^1$H NMR (500 MHz, DMSO-d$_6$) δ 10.76 (s, 1H), 9.60 (s, 1H), 8.56 (d, J = 4.3 Hz, 1H), 8.52 (s, 1H), 8.05 (s, 1H), 7.98-7.89 (m, 1H), 7.82-7.63 (m, 3H), 7.47 (br. s., 1H), 7.40-7.28 (m, 5H), 7.23 (d, J = 4.9 Hz, 1H), 6.85 (br. s., 1H), 4.46 (br. s., 2H), 3.16 (s, 3H), 2.79 (d, J = 4.3 Hz, 3H). |
| 425 | $^1$H NMR (500 MHz, DMSO-d$_6$) δ 10.89 (s, 2H), 8.83 (d, J = 4.3 Hz, 1H), 8.54 (s, 1H), 8.43 (s, 1H), 8.01 (d, J = 7.9 Hz, 1H), 7.86-7.77 (m, 1H), 7.72 (d, J = 7.9 Hz, 1H), 7.52 (t, J = 7.6 Hz, 1H), 7.40-7.31 (m, 2H), 7.31-7.25 (m, 1H), 7.23 (d, J = 7.3 Hz, 2H), 6.74 (br. s., 1H), 6.27 (br. s., 1H), 4.84 (br. s., 2H), 3.20 (s, 3H), 3.10 (br. s., 3H), 2.81 (d, J = 4.3 Hz, 3H). |
| 426 | $^1$H NMR (400 MHz, DMSO-d$_6$) δ 10.57 (s, 1H), 9.77 (s, 1H), 8.47 (m, 2H), 8.15 (d, J = 3.2 Hz, 1H), 7.71-7.61 (m, 4H), 7.54 (dd, J = 8.0, 1.2 Hz, 1H), 7.47 (m, 1H), 7.18 (m, 1H), 3.16 (s, 3H), 3.15 (s, 3H), 2.78 (d, J = 4.4 Hz, 3H) |
| 427 | $^1$H NMR (400 MHz, DMSO-d$_6$) δ 10.06 (bs, 1H), 9.81 (bs, 1H), 8.38 (m, 2H), 8.16 (dd, J = 9.4, 5.8 Hz, 1H), 7.64 (dd, J = 12.6, 2.2 Hz, 1H), 7.54 (s, 1H), 7.38 (m, 1H), 7.27 (m, 2H), 6.90 (bm, 1H), 6.75 (m, 1H), 2.77 (bs, 6H) |
| 428 | $^1$H NMR (400 MHz, DMSO-d$_6$) δ 10.57 (s, 1H), 9.68 (bs, 1H), 9.26 (bs, 1H), 8.46 (m, 2H), 8.12 (dd, J = 4.8, 1.2 Hz, 1H), 7.76-7.51 (m, 4H), 7.36 (m, 2H), 7.17 (m, 1H), 6.85 (m, 1H), 3.02 (s, 3H), 2.80 (d, J = 4.4 Hz, 3H) |
| 429 | $^1$H NMR (400 MHz, DMSO-d$_6$) δ 10.56 (s, 1H), 9.75 (s, 1H), 8.48 (s, 1H), 8.41 (m, 1H), 8.07 (d, J = 3.2 Hz, 1H), 7.89 (m, 1H), 7.68-7.37 (m, 5H), 7.27 (s, 2H), 7.23 (m, 1H), 2.77 (d, J = 4.4 Hz, 3H) |
| 430 | $^1$H NMR (400 MHz, DMSO-d$_6$) δ 10.57 (s, 1H), 9.67 (s, 1H), 8.48 (s, 1H), 8.41 (m, 1H), 8.08 (d, J = 3.6 Hz, 1H), 7.89 (dd, J = 8.0, 1.2 Hz, 1H), 7.82 (s, 1H), 7.69 (m, 1H), 7.63 (m, 2H), 7.52 (d, J = 8.4 Hz, 1H), 7.36 (m, 1H), 7.24 (t, J = 7.2 Hz, 1H), 6.83 (m, 1H), 2.77 (m, 3H) |
| 431 | $^1$H NMR (400 MHz, DMSO-d$_6$) δ 10.56 (s, 1H), 9.64 (s, 1H), 8.49 (s, 1H), 8.40 (bs, 1H), 7.97 (s, 1H), 7.88 (dd, J = 8.0, 1.6 Hz, 1H), 7.68-7.54 (m, 4H), 7.37 (bs, 2H), 7.24 (m, 1H), 2.76(s, 3H), 2.30 (s, 3H) |
| 432 | $^1$H NMR (500 MHz, methanol-d$_4$) δ 8.35 (s, 1H), 8.01 (d, J = 7.9 Hz, 1H), 7.86 (br. s., 1H), 7.67 (d, J = 8.9 Hz, 3H), 7.33 (t, J = 7.2 Hz, 1H), 7.11 (br. s., 1H), 3.11 (s, 3H), 2.27 (s, 3H). |

-continued

| Compound | ¹H NMR (methanol-d₄ equates CDCl₃:MeOD ~1:1 unless otherwise noted) Occasionally water suppression is used in DMSO-d₆ spectra |
|---|---|
| 433 | ¹H NMR (500 MHz, methanol-d₄) δ 8.36 (s, 1H), 8.32 (d, J = 1.0 Hz, 1H), 8.04-7.96 (m, 1H), 7.80 (d, J = 1.0 Hz, 1H), 7.75 (d, J = 7.9 Hz, 1H), 7.68-7.63 (m, 1H), 7.39 (s, 1H), 7.29 (t, J = 7.7 Hz, 1H), 3.90 (s, 3H), 3.10 (s, 3H) |
| 434 | ¹H NMR (500 MHz, methanol-d₄) δ 8.33 (s, 1H), 8.00 (dd, J = 7.9, 1.5 Hz, 1H), 7.80 (d, J = 2.5 Hz, 1H), 7.78 (d, J = 7.9 Hz, 1H), 7.71-7.62 (m, 1H), 7.55 (s, 1H), 7.30 (t, J = 7.7 Hz, 1H), 7.28-7.23 (m, 1H), 7.22-7.17 (m, 1H), 3.80 (s, 3H), 3.10 (s, 3H) |
| 435 | ¹H NMR (500 MHz, methanol-d₄) δ 8.32 (s, 1H), 7.99 (dd, J = 7.9, 1.5 Hz, 1H), 7.80-7.76 (m, 2H), 7.70-7.63 (m, 1H), 7.53 (s, 1H), 7.33 (dd, J = 8.9, 3.0 Hz, 1H), 7.30-7.26 (m, 1H), 7.17 (d, J = 8.9 Hz, 1H), 3.10 (s, 3H), 3.07-3.01 (m, 4H), 1.71 (quin, J = 5.7 Hz, 4H), 1.57 (q, J = 5.6 Hz, 2H) |
| 436 | N/A |
| 437 | ¹H NMR (500 MHz, methanol-d₄) δ 8.29 (s, 1H), 7.99 (dd, J = 7.9, 1.5 Hz, 1H), 7.75 (d, J = 7.9 Hz, 1H), 7.34-7.25 (m, 2H), 7.23 (s, 1H), 3.72 (s, 3H), 3.09 (s, 3H) |
| 438 | ¹H NMR (500 MHz, DMSO-d₆) δ 10.87 (s, 1H), 10.29 (br. s., 1H), 8.62-8.51 (m, 2H), 8.02-7.91 (m, 2H), 7.87 (br. s., 1H), 7.83-7.70 (m, 3H), 7.42 (t, J = 7.4 Hz, 1H), 7.23 (s, 1H), 3.16 (s, 3H), 2.37 (s, 3H), 2.35 (s, 3H) |
| 439 | N/A |
| 440 | ¹H NMR (500 MHz, DMSO-d₆) δ 10.86 (s, 1H), 10.34 (s, 1H), 8.65-8.51 (m, 2H), 7.99-7.89 (m, 4H), 7.83-7.68 (m, 2H), 7.45-7.38 (m, 1H), 7.34 (d, J = 8.9 Hz, 1H), 3.16 (s, 3H), 2.36 (s, 3H) |
| 445 | ¹H NMR (500 MHz, methanol-d₄) δ 8.30 (s, 1H), 7.98 (dd, J = 7.9, 1.5 Hz, 1H), 7.74-7.68 (m, 1H), 7.66-7.60 (m, 1H), 7.29-7.22 (m, 1H), 6.91 (s, 1H), 5.87 (s, 1H), 3.46 (quin, J = 8.7 Hz, 1H), 3.09 (s, 3H), 2.39-2.26 (m, 2H), 2.13 (td, J = 9.0, 2.2 Hz, 2H), 2.06-1.94 (m, 2H) |
| 446 | ¹H NMR (500 MHz, methanol-d₄) δ 8.36 (s, 1H), 8.10 (dd, J = 7.9, 1.0 Hz, 1H), 7.96 (d, J = 2.5 Hz, 1H), 7.81 (d, J = 7.9 Hz, 1H), 7.67 (t, J = 7.7 Hz, 1H), 7.59 (s, 1H), 7.45 (t, J = 7.7 Hz, 1H), 7.41-7.34 (m, 2H), 7.33-7.28 (m, 2H), 6.21 (d, J = 2.5 Hz, 1H), 3.13 (s, 3H) |
| 447 | ¹H NMR (500 MHz, DMSO-d₆) δ 10.83 (s, 1H), 10.25 (s, 1H), 8.57 (s, 1H), 8.54 (s, 1H), 8.46 (s, 1H), 7.94 (d, J = 6.1 Hz, 1H), 7.85-7.78 (m, 1H), 7.77-7.71 (m, 1H), 7.63 (d, J = 7.9 Hz, 2H), 7.39 (t, J = 7.3 Hz, 1H), 3.15 (s, 3H), 2.39 (s, 3H) |
| 448 | ¹H NMR (500 MHz, DMSO-d₆) δ 10.80 (br. s., 1H), 8.86 (br. s., 1H), 8.53 (br. s., 1H), 8.09-7.88 (m, 2H), 7.72-7.54 (m, 2H), 7.49 (d, J = 7.4 Hz, 1H), 7.32 (d, J = 7.7 Hz, 1H), 3.67 (br. s., 3H), 2.73 (br. s., 3H), 2.56 (br. s., 3H) |
| 449 | ¹H NMR (400 MHz, DMSO-d₆) δ 10.70 (s, 1H), 9.04 (d, J = 0.7 Hz, 2H), 8.49 (s, 2H), 8.18 (d, J = 4.2 Hz, 1H), 7.72 (dd, J = 8.0, 1.4 Hz, 1H), 7.69-7.61 (m, 1H), 7.53 (d, J = 7.9 Hz, 1H), 7.42 (d, J = 7.3 Hz, 1H), 7.37-7.26 (m, 1H), 6.88 (t, J = 5.8 Hz, 1H), 3.70 (s, 3H) |
| 450 | ¹H NMR (400 MHz, DMSO-d₆) δ 10.71 (s, 1H), 9.04 (d, J = 0.7 Hz, 2H), 8.50 (s, 2H), 8.10 (d, J = 5.3 Hz, 1H), 7.72 (d, J = 6.6 Hz, 1H), 7.62 (br. s., 1H), 7.40 (br. s., 1H), 7.35-7.27 (m, 1H), 6.96 (br. s., 1H), 3.70 (s, 3H), 1.40 (s, 6H) |

What is claimed is:

1. A compound having the following formula (I):

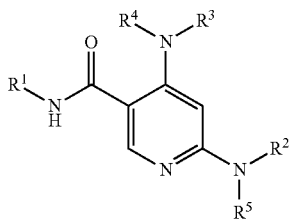

or a stereoisomer or pharmaceutically-acceptable salt thereof, wherein:

$R^1$ is $C_{1-3}$ alkyl optionally substituted by 0-7 $R^{1a}$;

$R^{1a}$ at each occurrence is independently hydrogen, deuterium, F, Cl, Br, $CF_3$ or CN;

$R^2$ is pyridyl substituted with 0-3 $R^{2a}$;

$R^{2a}$ at each occurrence is independently hydrogen, =O, halo, $OCF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $CH_2)_rNR^{11}R^{11}$, $-(CH_2)_rC(O)NR^{11}R^{11}$, $-(CH_2)_r NR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, $-(CH_2)_r$-3-14 membered carbocycle substituted with 0-1 $R^a$, $-(CH_2)_r$-5-7 membered heteroaryl comprising carbon atoms and 1-4 heteroatoms selected from N, O, and $S(O)_p$ substituted with 0-2 $R^a$; and $-(CH_2)_r$-5-7 membered heterocycle comprising carbon atoms or 1-4 heteroatoms selected from N, O, and $S(O)_p$ substituted with 0-2 $R^a$;

$R^3$ is phenyl, pyridyl, cyclopentyl, cyclohexyl, furanyl, pyridyl or pyranyl, each substituted with 0-3 $R^{3a}$;

$R^{3a}$ at each occurrence is independently hydrogen, =O, halo, $OCF_3$, $OCHF_2$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, $-(CH_2)_r$-3-14 membered carbocycle substituted with 0-3 $R^a$, a $-(CH_2)_r$-5-7 membered heteroaryl comprising carbon atoms and 1-4 heteroatoms selected from N, S or O substituted with 0-3 $R^a$, or a —$(CH_2)_r$-5-10 membered heterocycle comprising carbon atoms and 1-4 heteroatoms selected from N, O, and $S(O)_p$ substituted with 0-3 $R^a$;

or two $R^{3a}$, together with the atoms to which they are attached, combine to form a fused ring wherein said ring is selected from phenyl and a 5-7 membered heterocycle or heteroaryl, each comprising carbon atoms and 1-4 heteroatoms selected from N, S or O;

$R^4$ and $R^5$ are independently hydrogen, $C_{1-4}$ alkyl substituted with 0-1 $R^f$, $(CH_2)_r$-phenyl substituted with 0-3 $R^d$, or a —$(CH_2)$-5-7 membered heterocycle comprising carbon atoms and 1-4 heteroatoms selected from N, O, and $S(O)_p$;

$R^{11}$ at each occurrence is independently hydrogen, $C_{1-6}$ alkyl substituted with 0-3 $R^f$, $CF_3$, $C_{3-10}$ cycloalkyl substituted with 0-3 $R^f$, $(CH)_r$-phenyl substituted with 0-3 $R^d$, or —$(CH_2)_r$-5-7 membered heterocycle comprising carbon atoms and 1-4 heteroatoms selected from N, O, and $S(O)_p$ substituted with 0-3 $R^d$;

$R^a$ at each occurrence is independently hydrogen, =O, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle, —$(CH_2)_r$-5-7 membered heteroaryl comprising carbon atoms and 1-4 heteroatoms selected from N, O, and $S(O)_p$ substituted with 0-3 $R^f$; or —$(CH_2)_r$-5-7 membered heterocycle comprising carbon atoms and 1-4 heteroatoms selected from N, O, and $S(O)_p$ substituted with 0-3 $R^f$, alternatively two $R^a$ on adjacent or the same carbon atom form a cyclic acetal of the formula —O—$(CH_2)_n$—O—, or —O—$CF_2$—O—, wherein n is selected from 1 or 2;

$R^b$ is hydrogen, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle comprising carbon atoms and 1-4 heteroatoms selected from N, O, and $S(O)_p$ substituted with 0-3 $R^f$, or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$, $(CH_2)_r$-phenyl substituted with 0-3 $R^f$; or $R^d$ at each occurrence is independently hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl, or $(CH_2)_r$-phenyl substituted with 0-3 $R^f$;

$R^e$ is selected from hydrogen, $C_{1-6}$ alkyl, $C_{3-6}$ cycloalkyl, and $(CH_2)_r$-phenyl substituted with 0-3 $R^f$;

$R^f$ independently at each occurrence is hydrogen, halo, CN, $NH_2$, $NH(C_{1-6}alkyl)$, $N(C_{1-6}alkyl)_2$, OH, $C_{3-6}$ cycloalkyl, $CF_3$, $O(C_{1-6}alkyl)$, phenyl;

or $R^f$ independently at each occurrence is an optionally substituted —$(CH_2)_r$-5-10 membered heteroaryl comprising carbon atoms and 1-4 heteroatoms selected from N, O, and S(O) or $C_{3-6}$ cycloalkyl, each group optionally substituted with halo, CN, $CF_3$, $C_{1-6}$ alkyl or $O(C_{1-6}$ alkyl);

p is 0, 1, or 2; and r is 0, 1, 2, 3, or 4;

provided that the compound of formula (I) is not

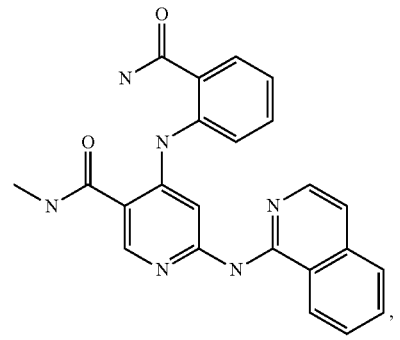

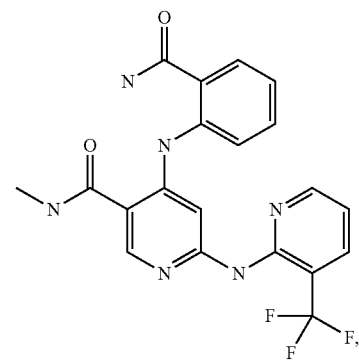

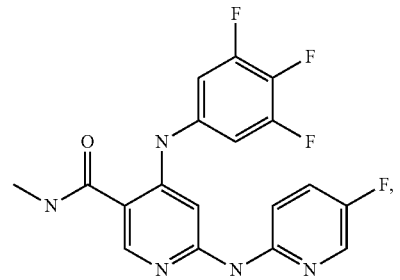

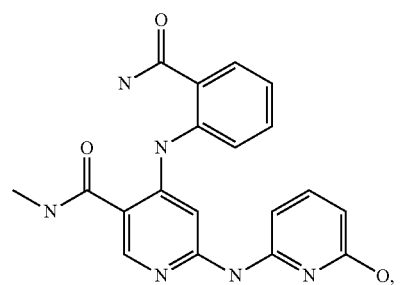

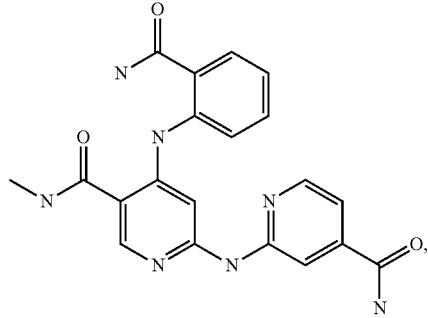

327
-continued
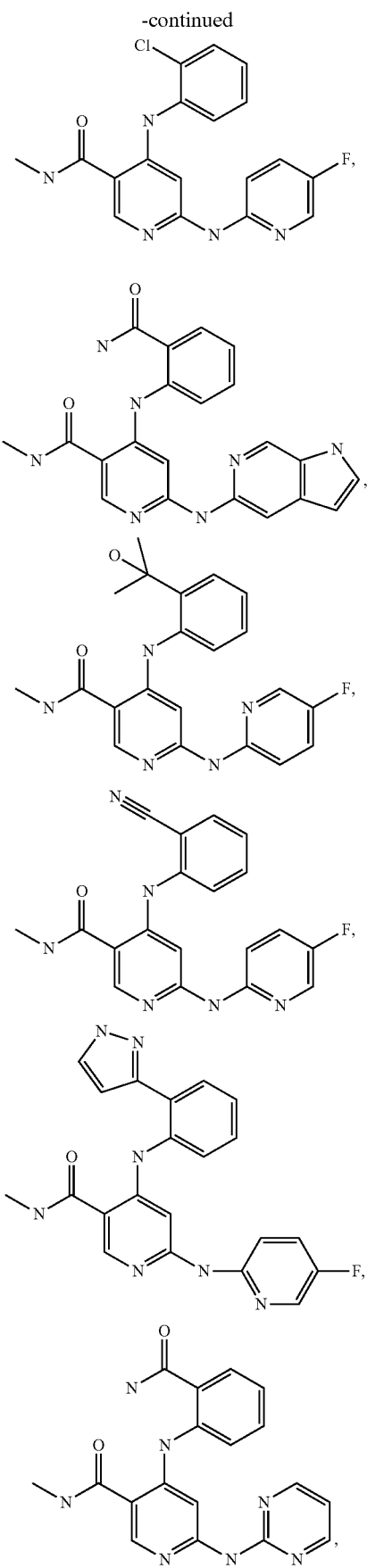
328
-continued
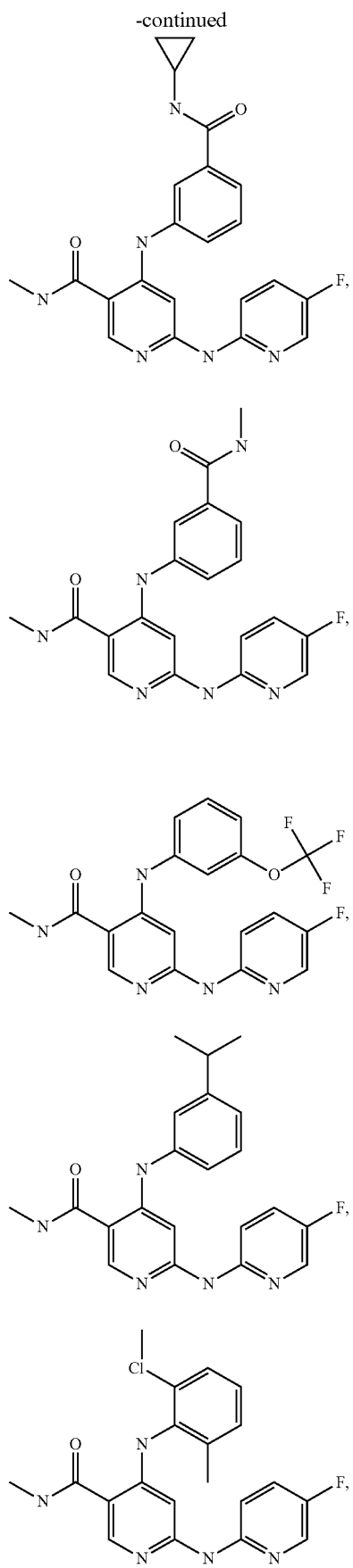

329
-continued
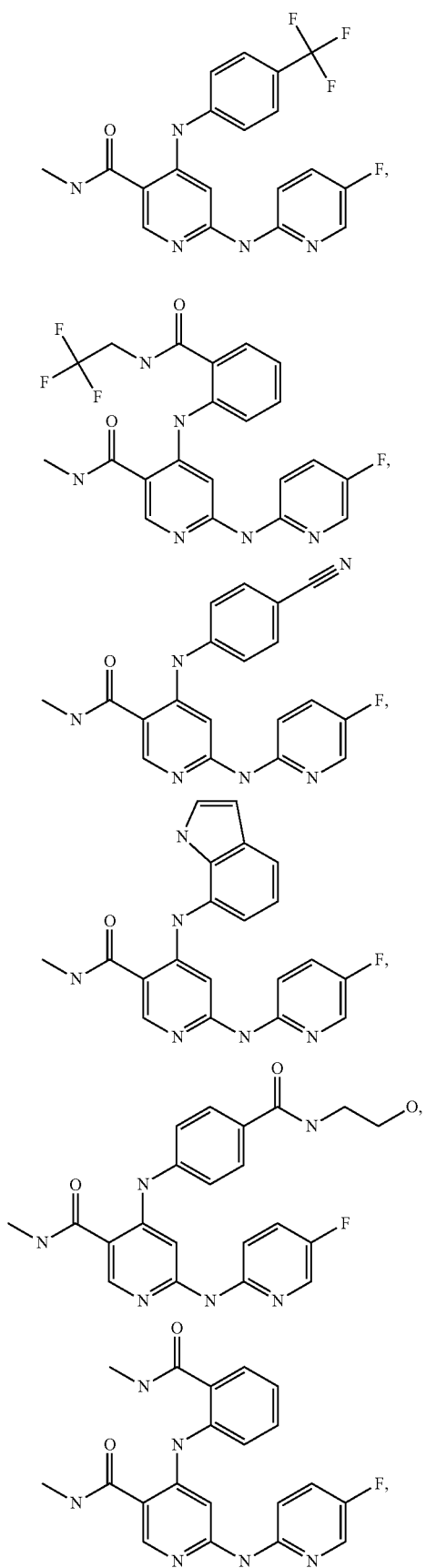
330
-continued
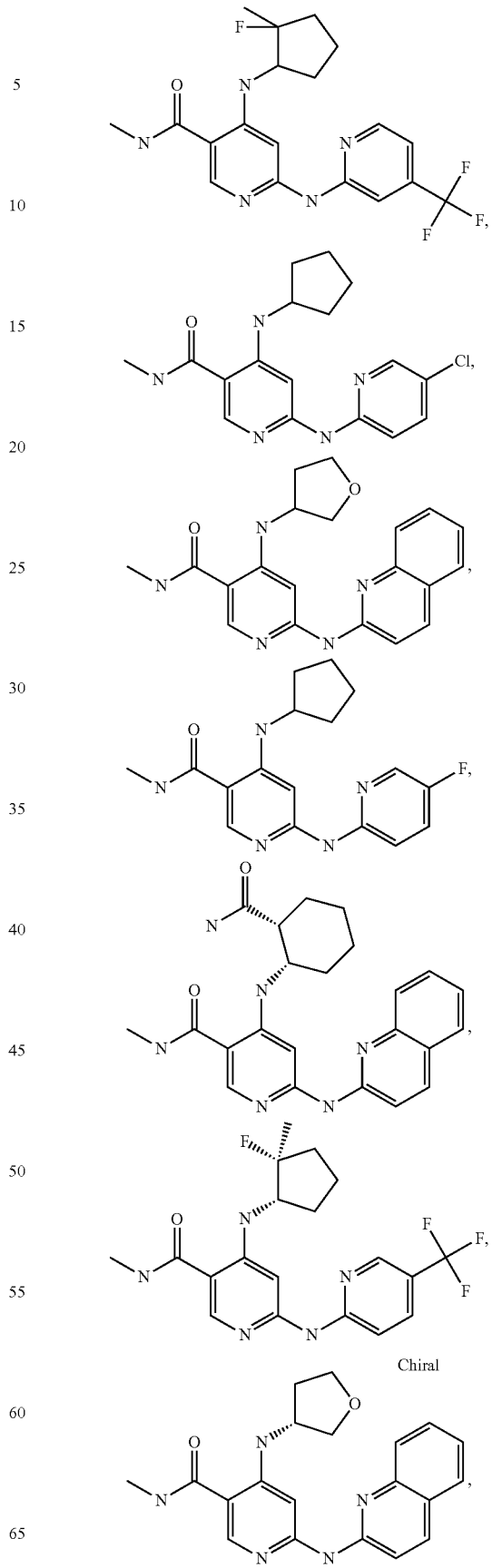

-continued
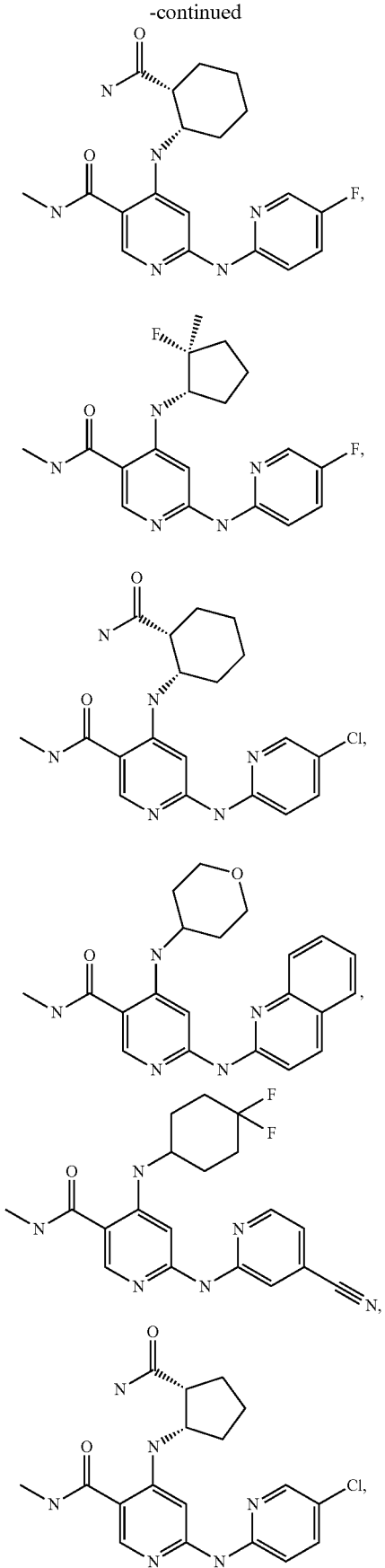
-continued
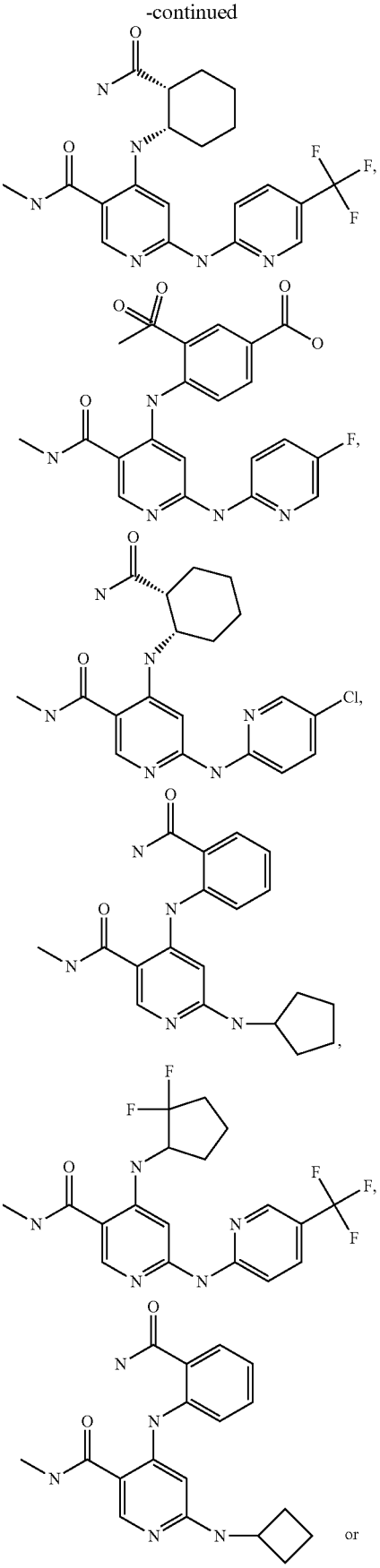
or

-continued

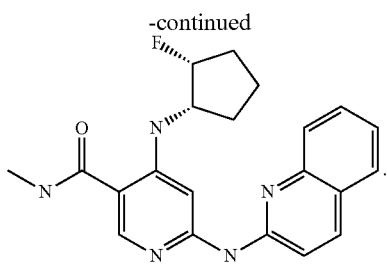

2. The compound of claim 1, or a stereoisomer or pharmaceutically-acceptable salt thereof, wherein both $R^4$ and $R^5$ are hydrogen.

3. A compound according claim 1 having the following formula

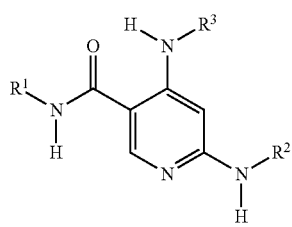

or a stereoisomer or pharmaceutically-acceptable salt thereof, wherein:
 $R^1$ is $C_{1-3}$alkyl substituted by 0-7 deuterium atoms;
 $R^2$ is pyridyl substituted with 0-3 $R^{2a}$;
 $R^{2a}$ at each occurrence is independently halo, CN, —$(CH_2)_rOR^b$, —$(CH_2)_rC(O)R^b$, —$(CH_2)_rC(O)NR^{11}R^{11}$, —$(CH_2)_r$ $NR^{11}R^{11}$, —$S(O)_pNR^{11}R^{11}$, —$C_{1-6}$alkyl substituted with 0-3 $R^a$, $C_{1-6}$ haloalkyl, —$(CH_2)_r$-3-14 membered carbocycle substituted with 0-1 $R^a$, a —$(CH_2)_r$-5-10 membered heteroaryl comprising carbon atoms and 1-4 heteroatoms selected from N, O, and $S(O)_p$ substituted with 0-2 $R^a$; or a —$(CH_2)_r$-5-7 membered heterocycle comprising carbon atoms and 1-4 heteroatoms selected from N, O, and $S(O)_p$ substituted with 0-2 $R^a$;
 $R^3$ is phenyl, pyridyl, cyclopentyl, cyclohexyl, furanyl, pyridyl or pyranyl, each substituted with 0-3 $R^{3a}$;
 $R^{3a}$ at each occurrence is independently hydrogen, halo, $OCF_3$, $OCHF_2$, $CF_3$, $CHF_2$, CN, —$(CH_2)_rOR^b$, —$(CH_2)_rSR^b$, —$(CH_2)_rC(O)R^b$, —$(CH_2)_rNR^{11}R^{11}$, —$(CH_2)_rC(O)NR^{11}R^{11}$, —$(CH_2)_rNR^bC(O)R^c$, —$S(O)_pNR^{11}R^{11}$, —$NR^bS(O)_pR^c$, —$S(O)_pR^c$, $C_{1-6}$ alkyl substituted with 0-3 $R^a$, $C_{1-6}$ haloalkyl, a —$(CH_2)_r$-3-14 membered carbocycle substituted with 0-3 $R^a$, a —$(CH_2)_r$-5-7 membered heteroaryl comprising carbon atoms and 1-4 heteroatoms selected from N, S or O substituted with 0-3 $R^a$, or a —$(CH_2)_r$-5-10 membered heterocycle comprising carbon atoms and 1-4 heteroatoms selected from N, O, and $S(O)_p$ substituted with 0-3 $R^a$;
 or two $R^{3a}$, together with the atoms to which they are attached, combine to form a fused ring wherein that ring is selected from phenyl, or a 5-7 membered heterocycle or heteroaryl, each comprising carbon atoms and 1-4 heteroatoms selected from N, S or O; and
 $R^{11}$ at each occurrence is independently hydrogen;
 or $R^{11}$ at each occurrence is independently phenyl, $C_{1-6}$ alkyl, or $C_{3-10}$ cycloalkyl, each group substituted with 0-3 $R^f$.

4. A compound of claim 1, or a stereoisomer or pharmaceutically-acceptable salt thereof, wherein $R^2$ is

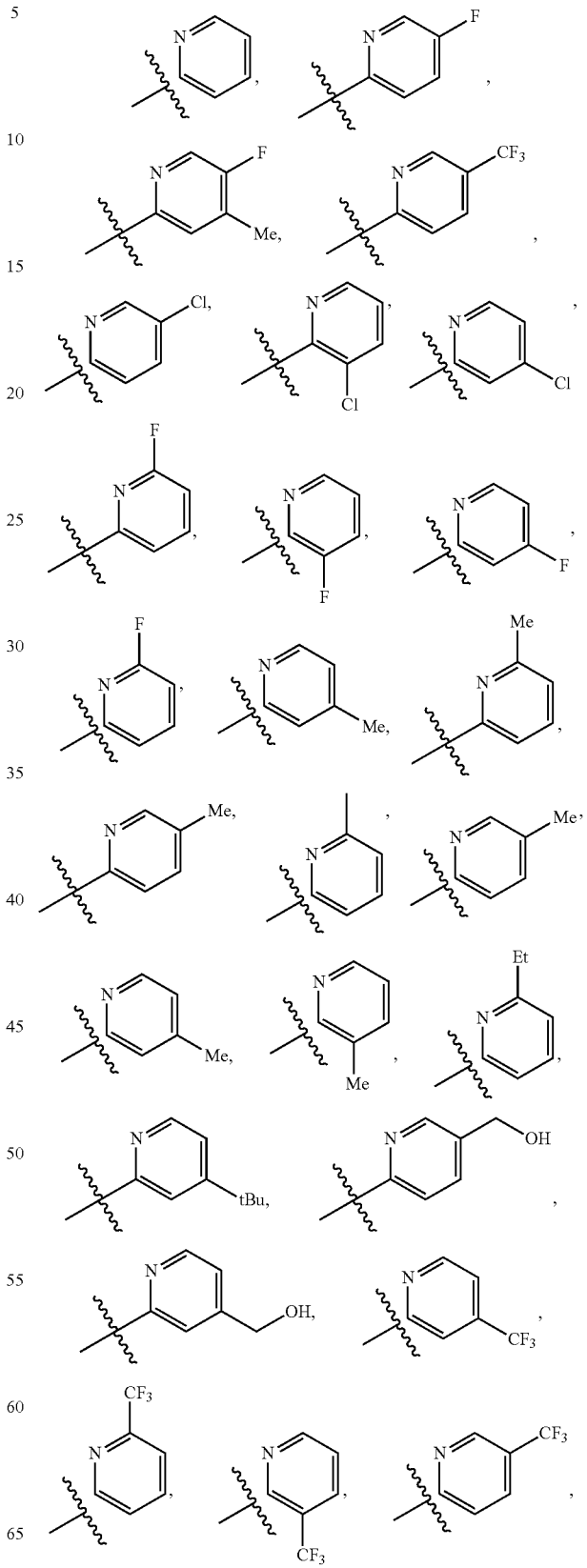

335
-continued
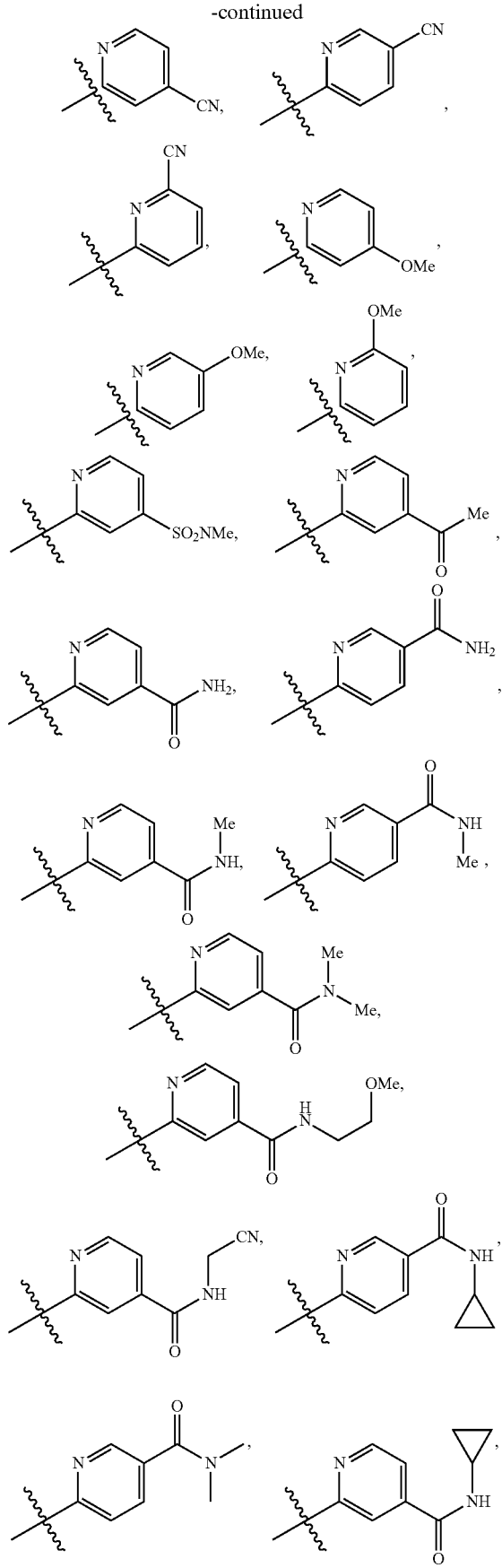
336
-continued
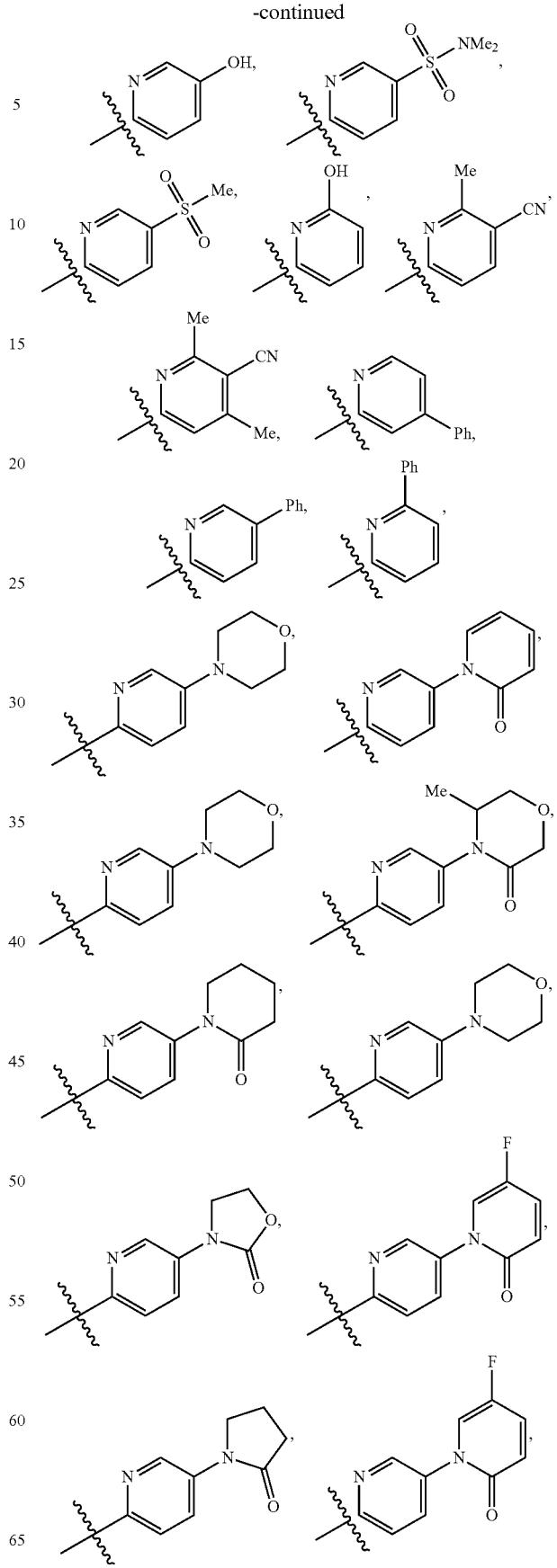

337
-continued
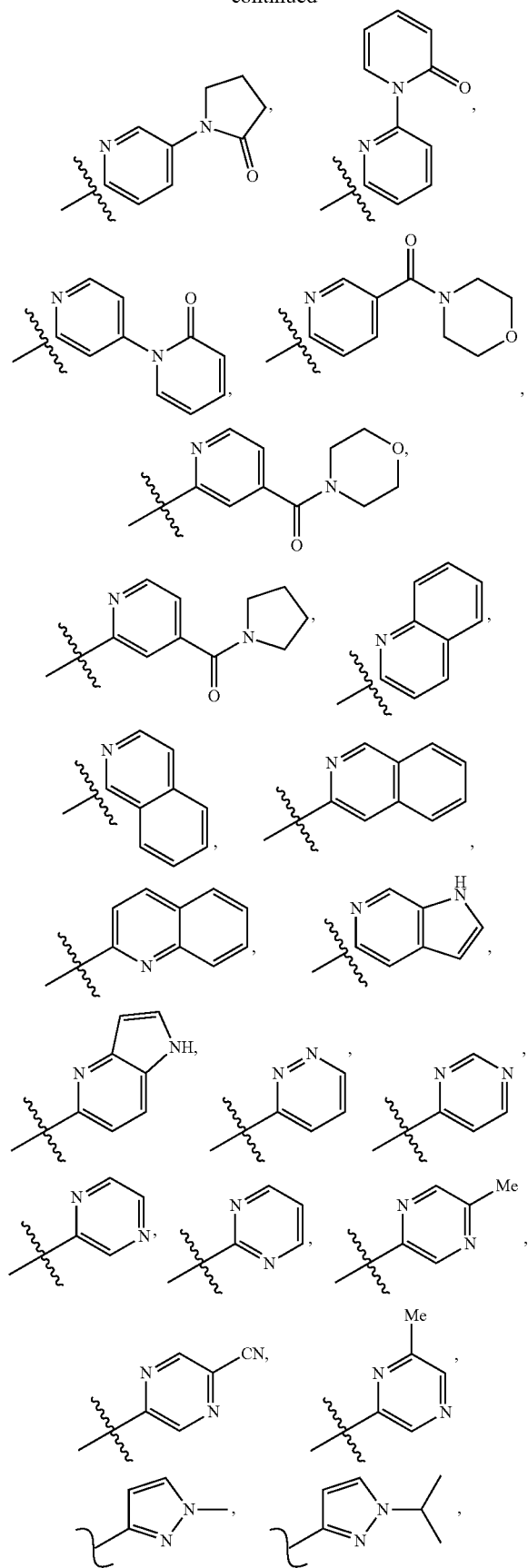
338
-continued
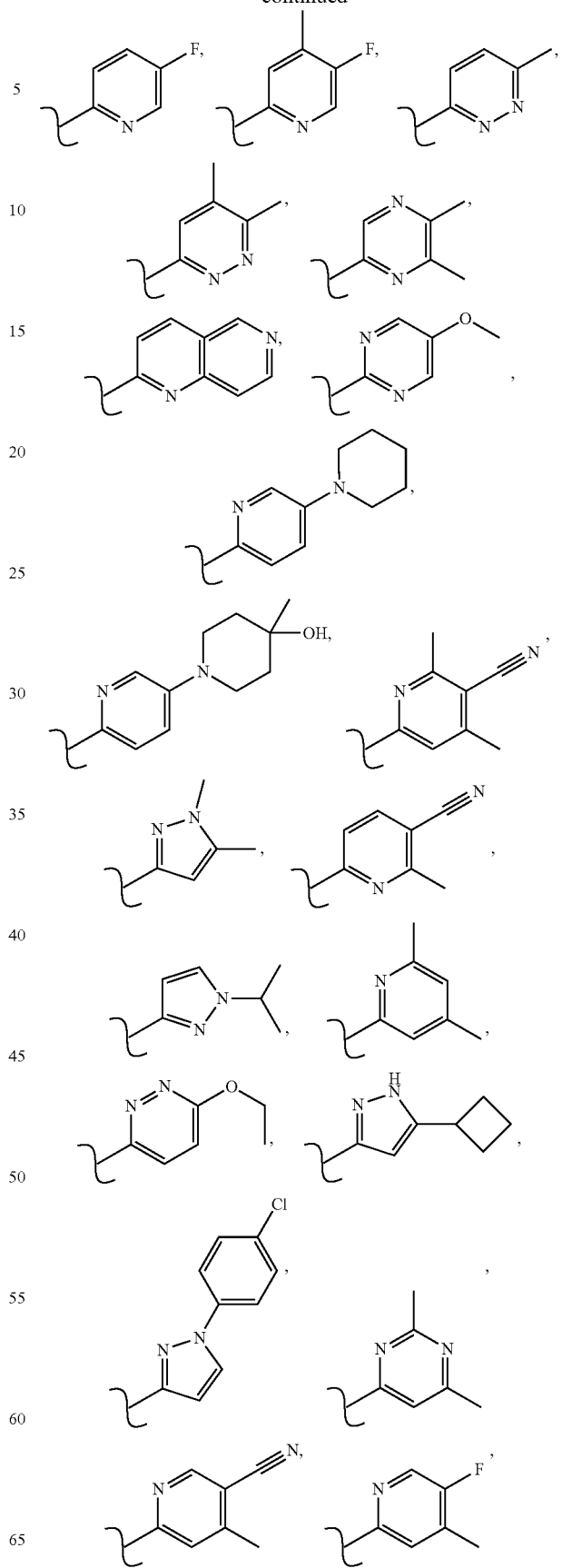

-continued

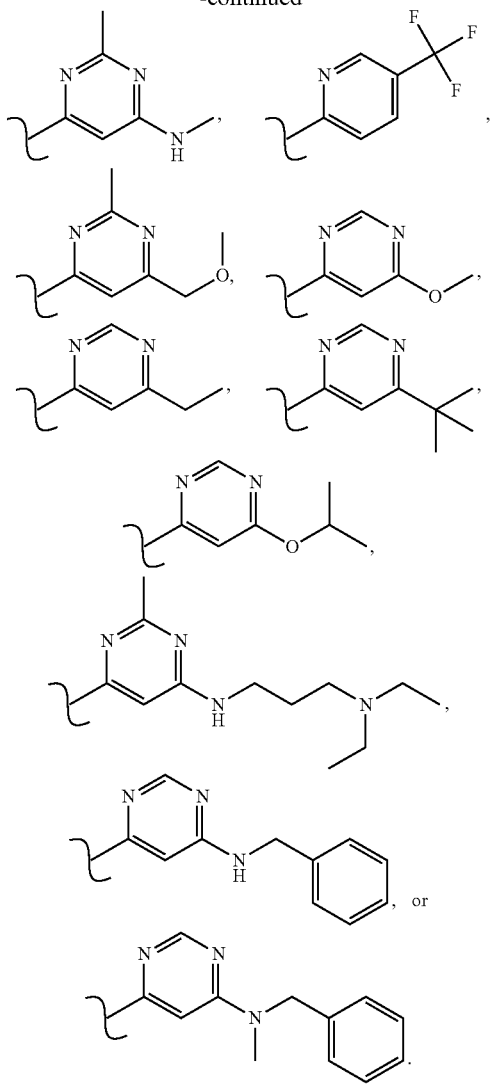

5. A compound of claim 1, or a stereoisomer or pharmaceutically-acceptable salt thereof, wherein:
R$^{3a}$ at each occurrence independently is hydrogen, Ph, CN, NH$_2$, OCF$_3$, OCHF$_2$, OR$^b$, halo, C$_{3-6}$cycloalkyl, C(O)NR$^{11}$R$^{11}$ S(O)$_2$NR$_{11}$R$_{11}$, C(O)R$^b$, SO$_p$R$^c$, NR$^b$SO$_p$R$^c$, NR$^b$C(O)R$^c$, haloalkyl, CN, a 5-10 membered heterocycle containing 1-4 heteroatoms selected from N, O, and S substituted with 0-3 R$^a$ and C$_{1-6}$ alkyl substituted with 0-3 R$^a$;
or one R$^{3a}$ and a second R$^{3a}$, together with the atoms to which they are attached, combine to form a fused 5-7 membered heterocycle containing 1-4 heteroatoms selected from N, O, and S or fused phenyl;
R$^{11}$ is at each occurrence independently hydrogen, phenyl, cyclopropyl, or C$_{1-6}$alkyl substituted with 0-3 R$^f$;
R$^a$ is at each occurrence independently halo or OR$^b$;
R$^b$ is at each occurrence independently hydrogen, a 5-10 membered heterocycle containing 1-4 heteroatoms selected from N, O, and S substituted with 0-3 R$^f$ or C$_{1-6}$ alkyl substituted with 0-3 R$^d$;
R$^d$ is at each occurrence independently halo or OH;
R$^c$ is at each occurrence independently C$_{1-6}$ alkyl substituted with 0-3 R$^f$;

R$^f$ is at each occurrence independently hydrogen, halo or OH;
or R$^f$ is at each occurrence independently cyclopropyl, cyclohexyl, pyridyl, thiazolyl, indolyl or imidazolyl, each group optionally substituted with CN or OMe; and
p is 2.

6. A compound of claim 1, or a stereoisomer or pharmaceutically-acceptable salt thereof, wherein:
R$^3$ is

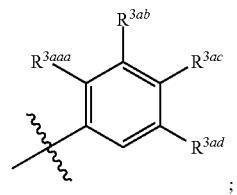

R$^{3aa}$ is S(O)$_p$R$^c$, OR$^b$, OCHF$_2$, chloro, F, CN, NH$_2$, C(O)NR$^{11}$R$^{11}$, NR$^b$SO$_p$R$^c$, NR$^b$C(O)R$^c$, C$_{1-6}$ alkyl substituted with 0-3 R$^a$ or a 5- to 6-membered heteroaryl containing 1-3 heteroatoms selected from N, O, and S substituted with 0-3 R$^a$;
R$^{3ab}$, R$^{3ac}$, or R$^{3ad}$ are independently hydrogen, Cl, F, Br, CN, OR$^b$, C$_{1-6}$ alkyl substituted 0-3 R$^a$; C(O)NR$^{11}$R$^{11}$, C(O)R$^b$, S(O)pRc, or a 4- to 7-membered heterocycle containing 1-3 heteroatoms selected from N, O, and S substituted with 0-3 R$^a$; and
p is 0-2.

7. A compound of claim 6, or a stereoisomer or pharmaceutically-acceptable salt thereof, wherein R$^{3aa}$ is OR$^b$.

8. A compound of claim 6, or a stereoisomer or pharmaceutically-acceptable salt thereof, wherein R$^{3aa}$ is S(O)$_p$R$^c$.

9. The compound of claim 1, or a stereoisomer or pharmaceutically-acceptable salt thereof, wherein R$^3$ is

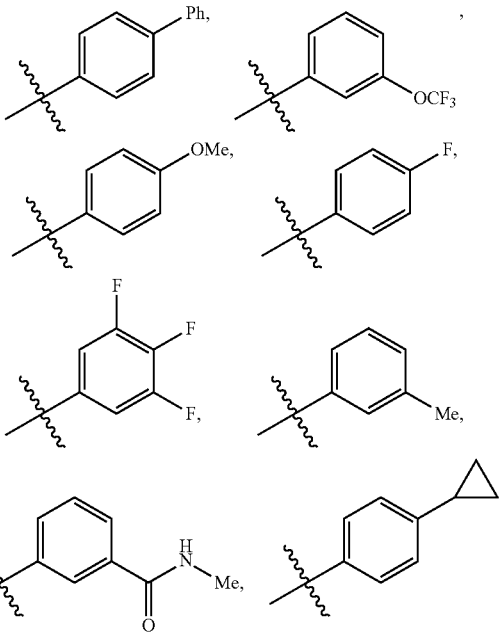

341
-continued
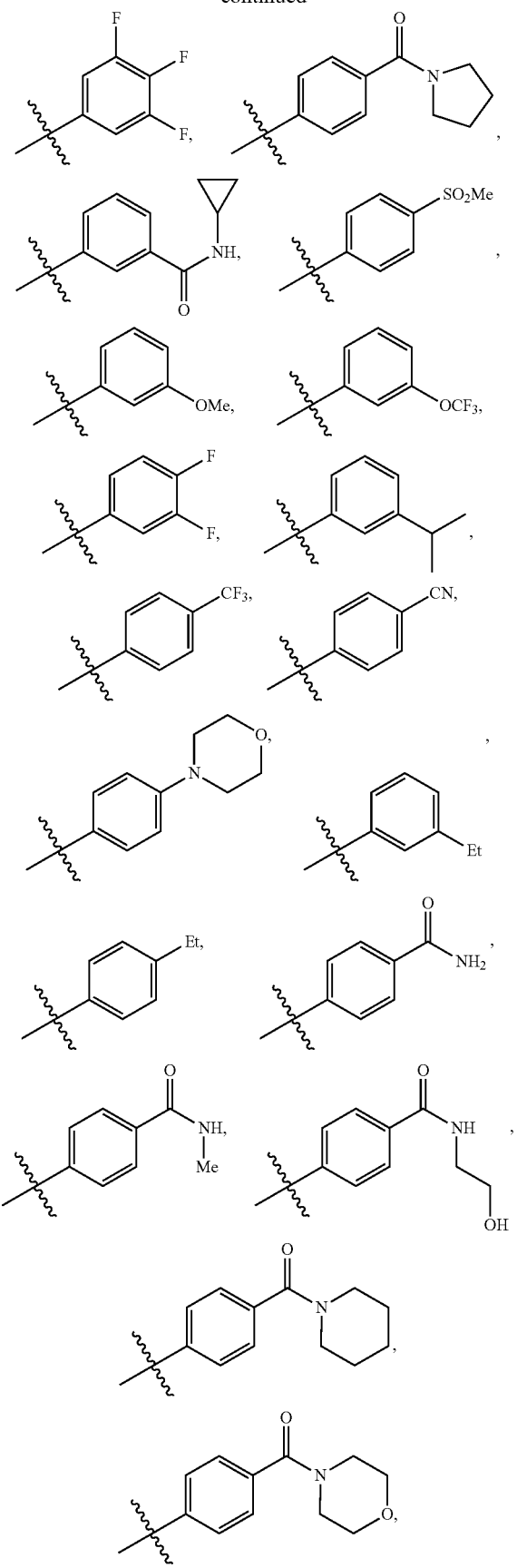
342
-continued
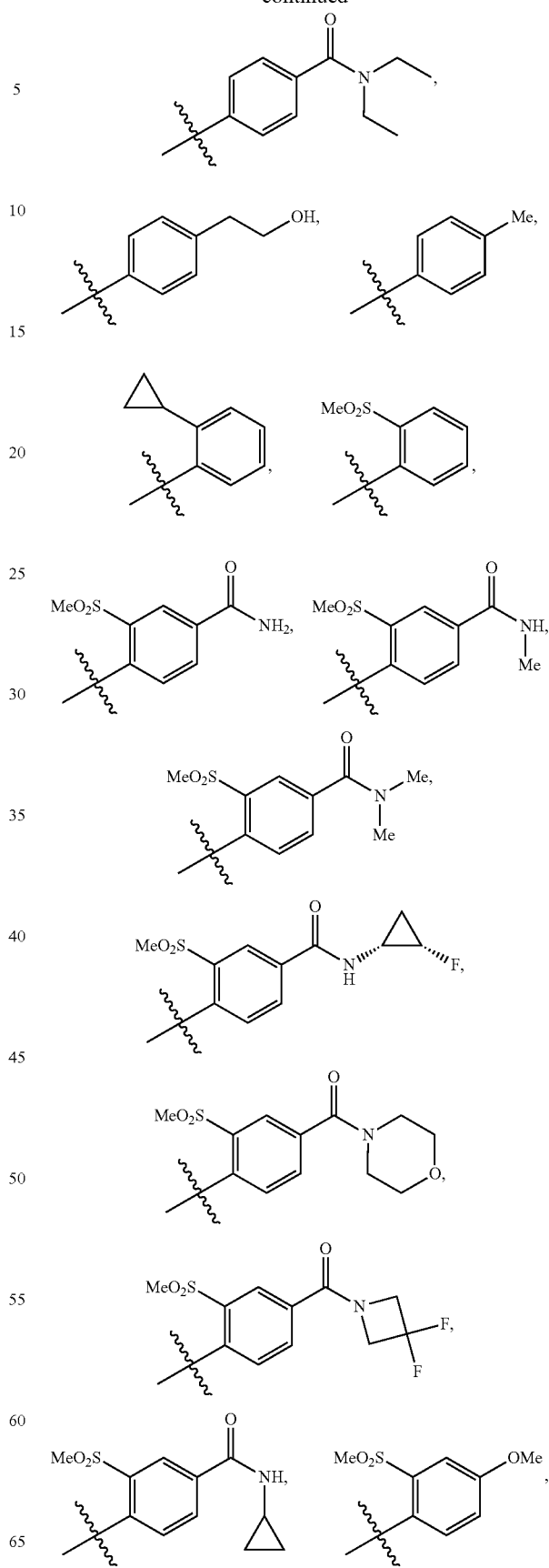

-continued
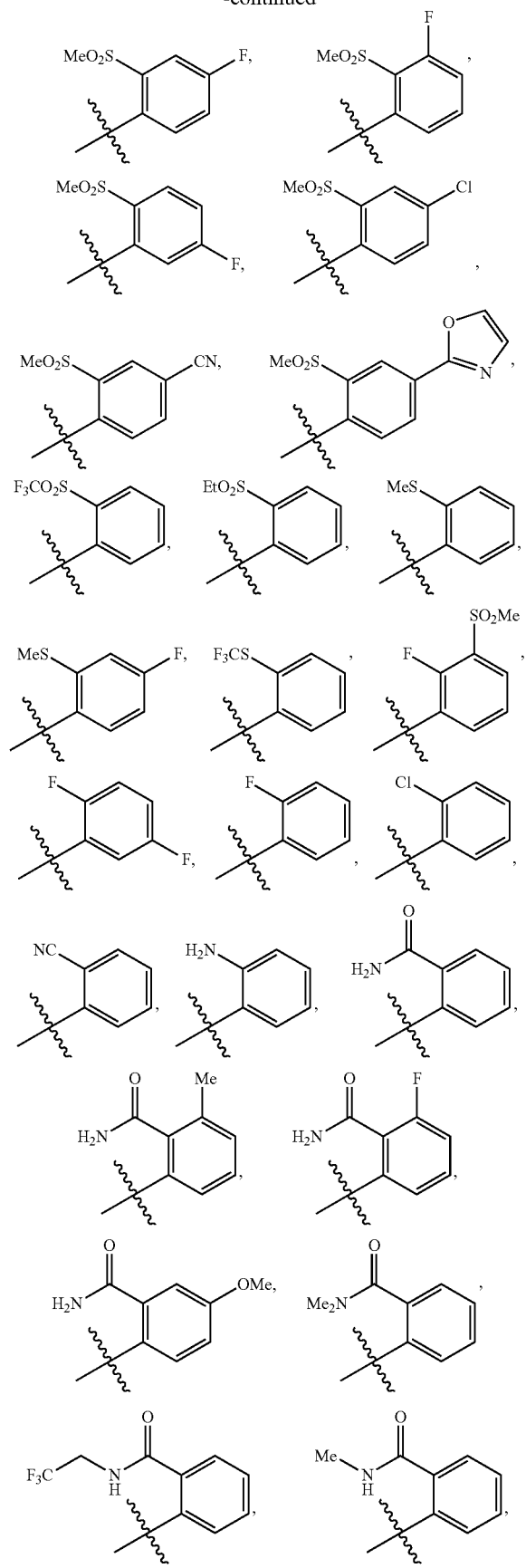
-continued
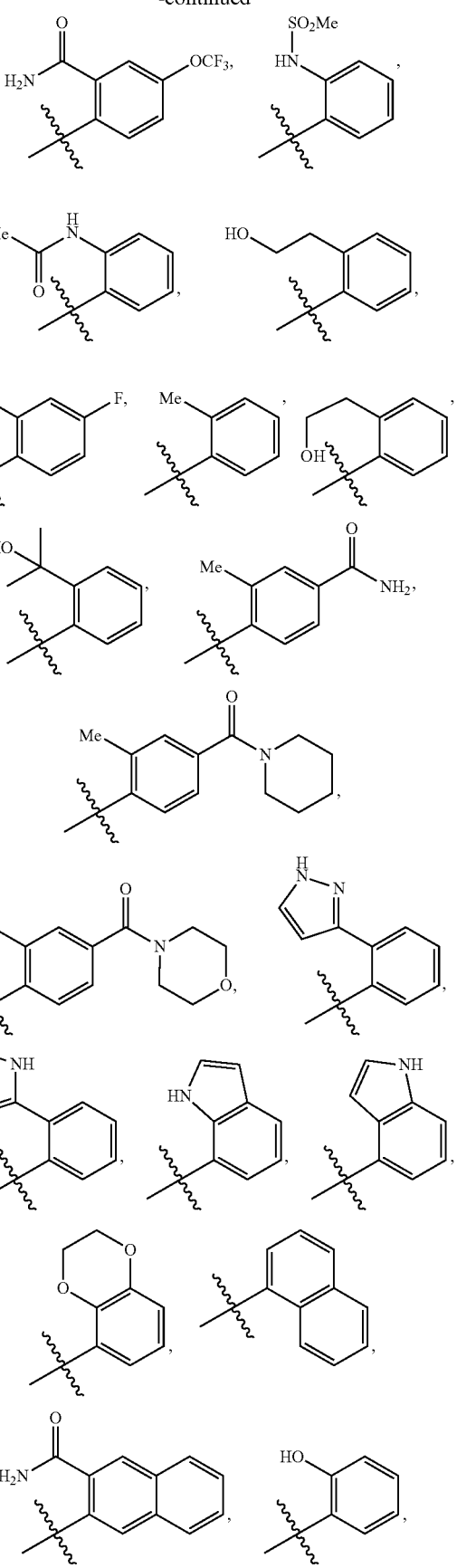

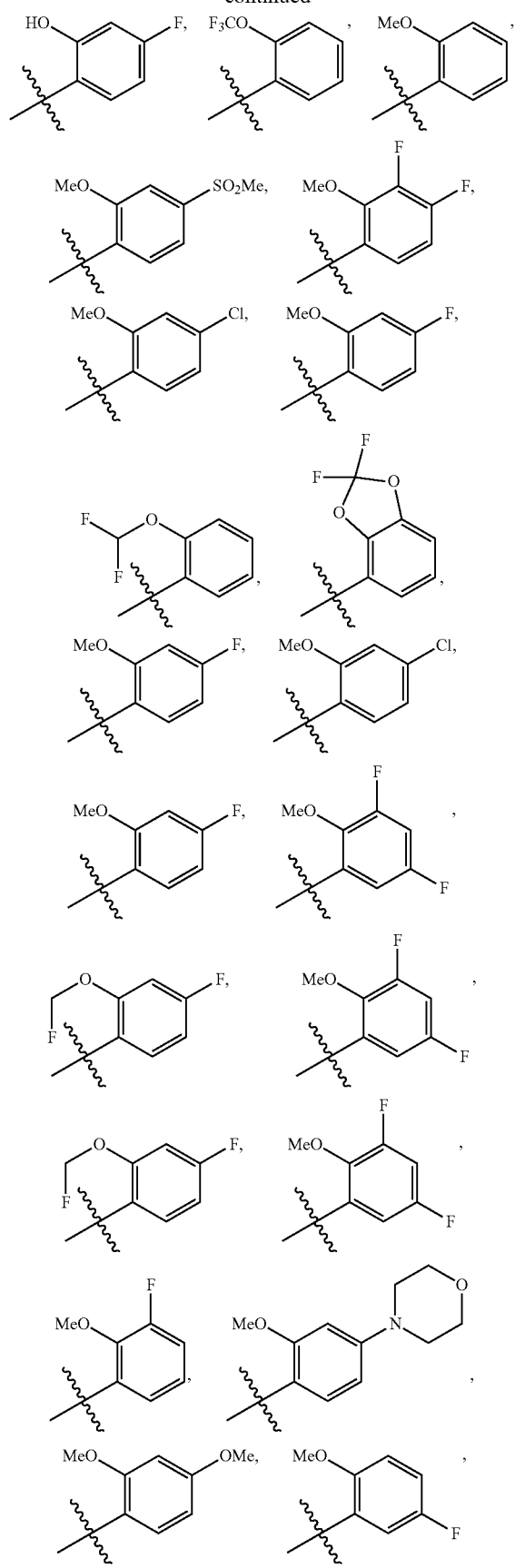
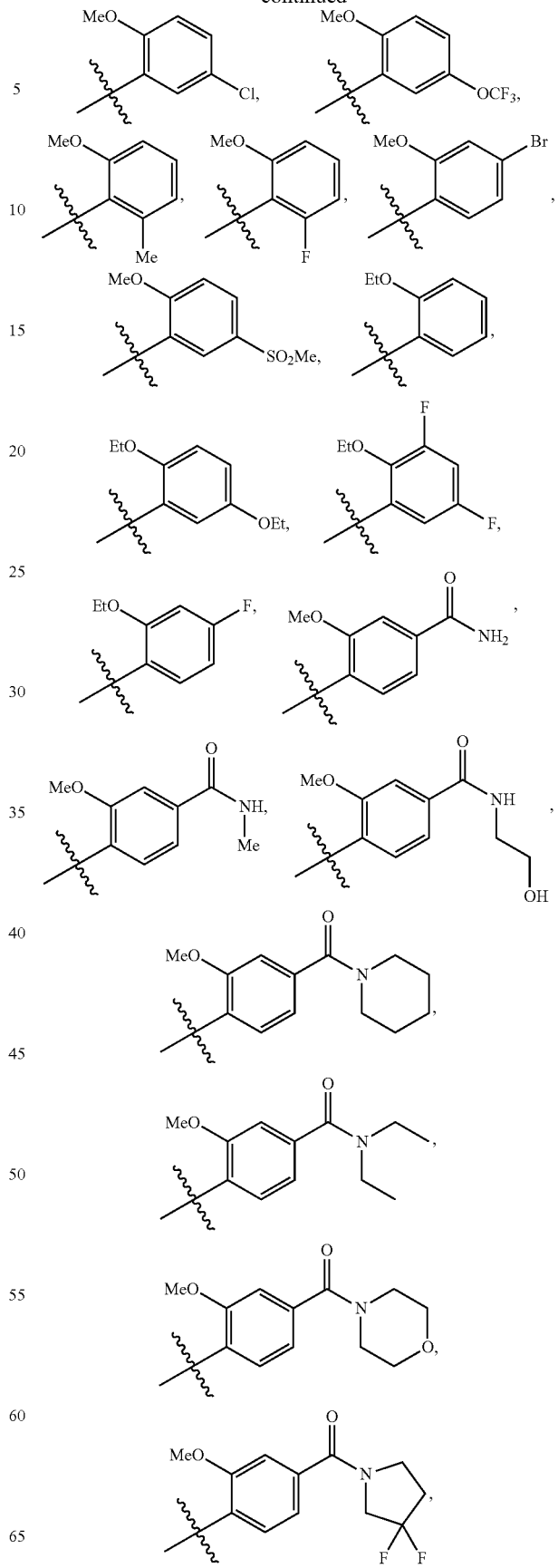

347
-continued
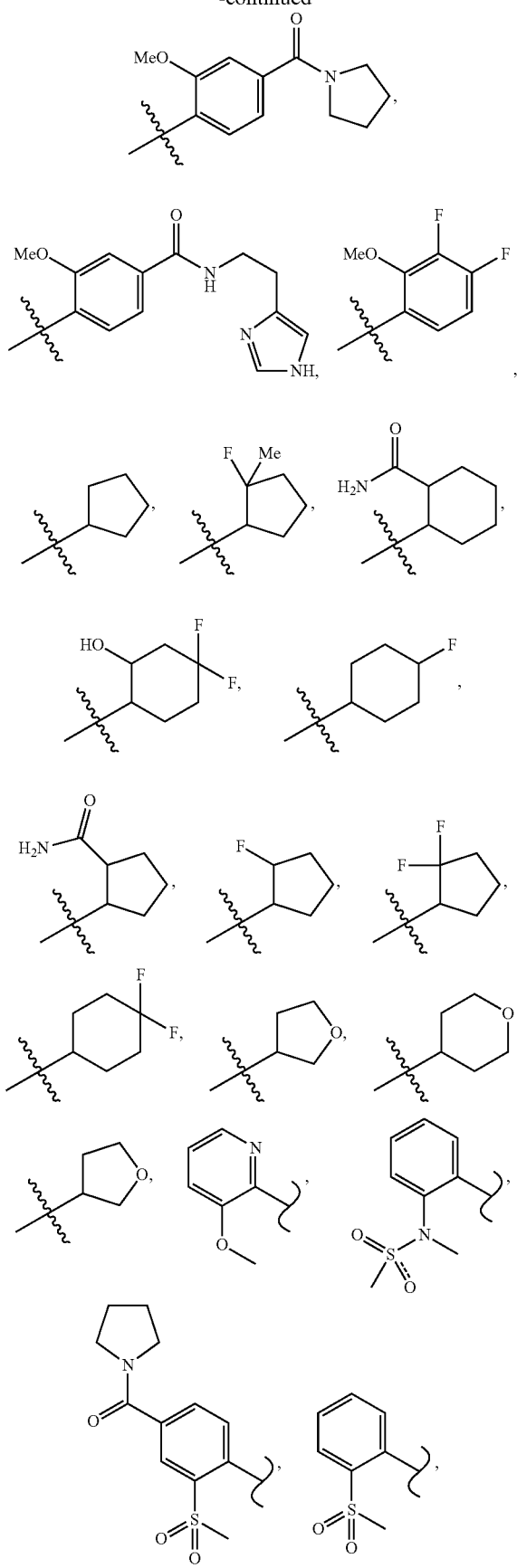
348
-continued
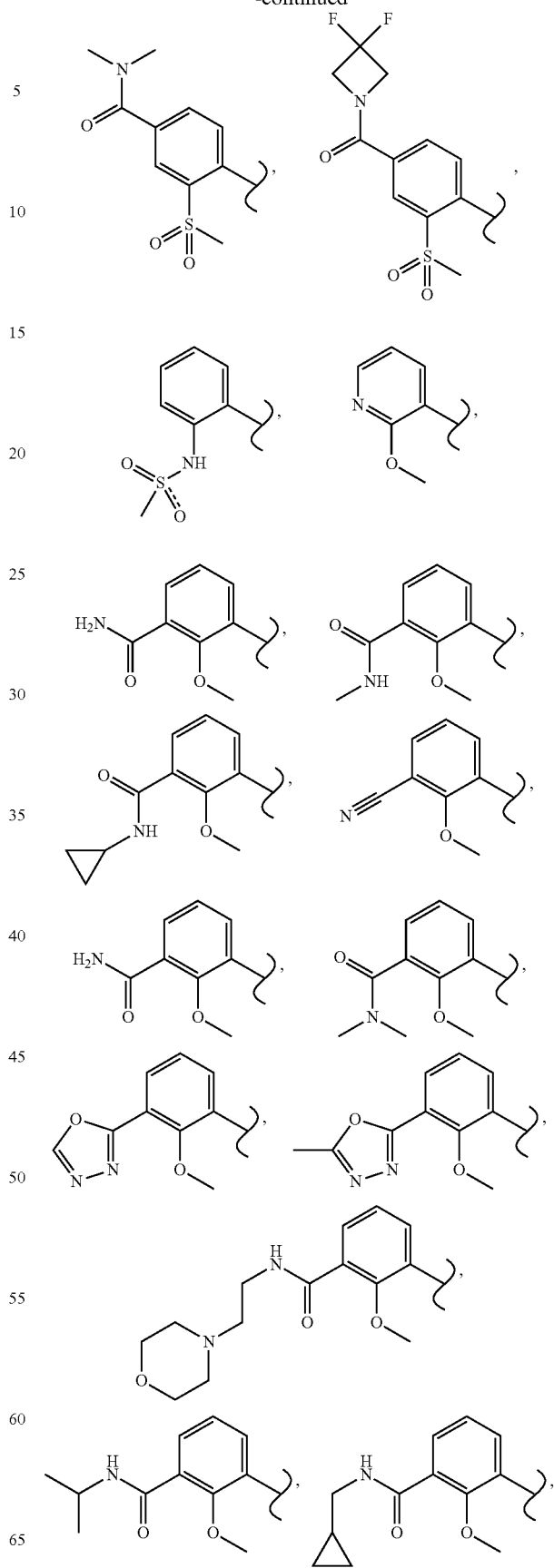

349
-continued
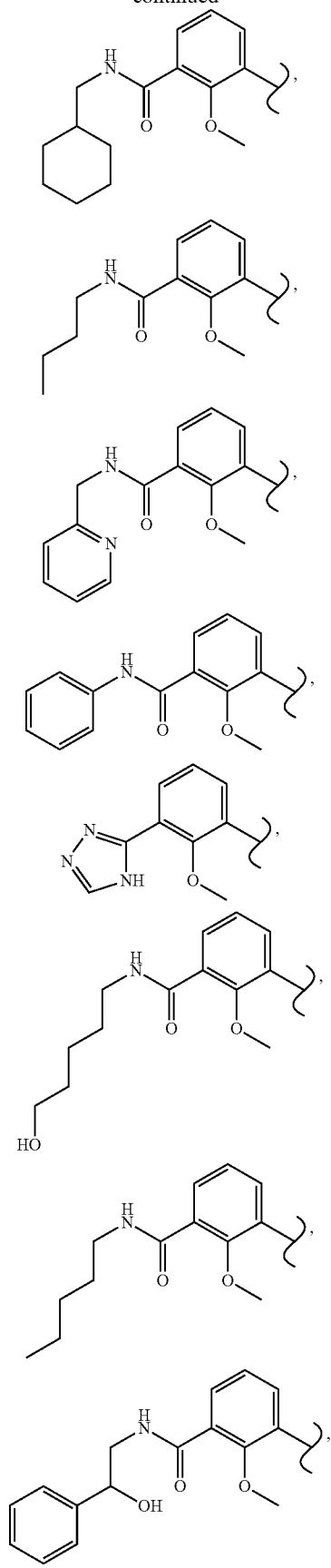
350
-continued
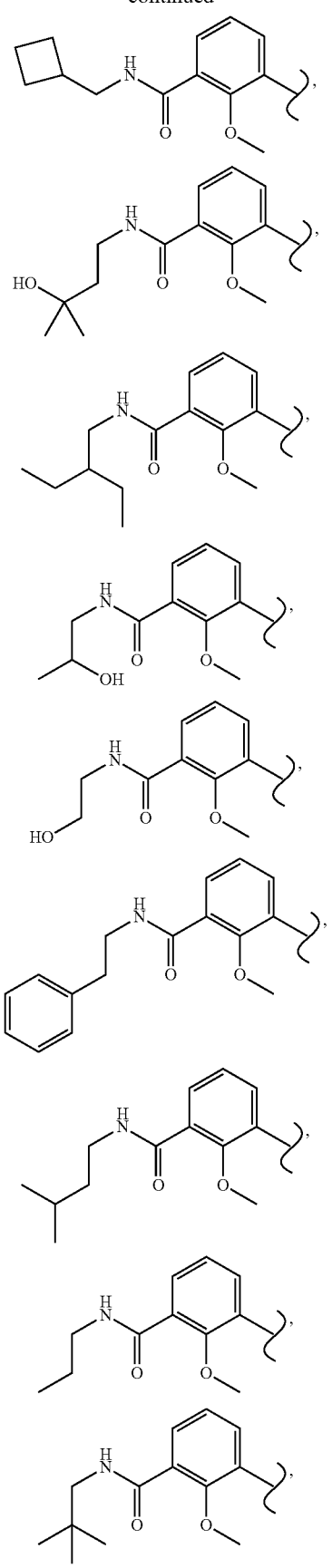

351
-continued
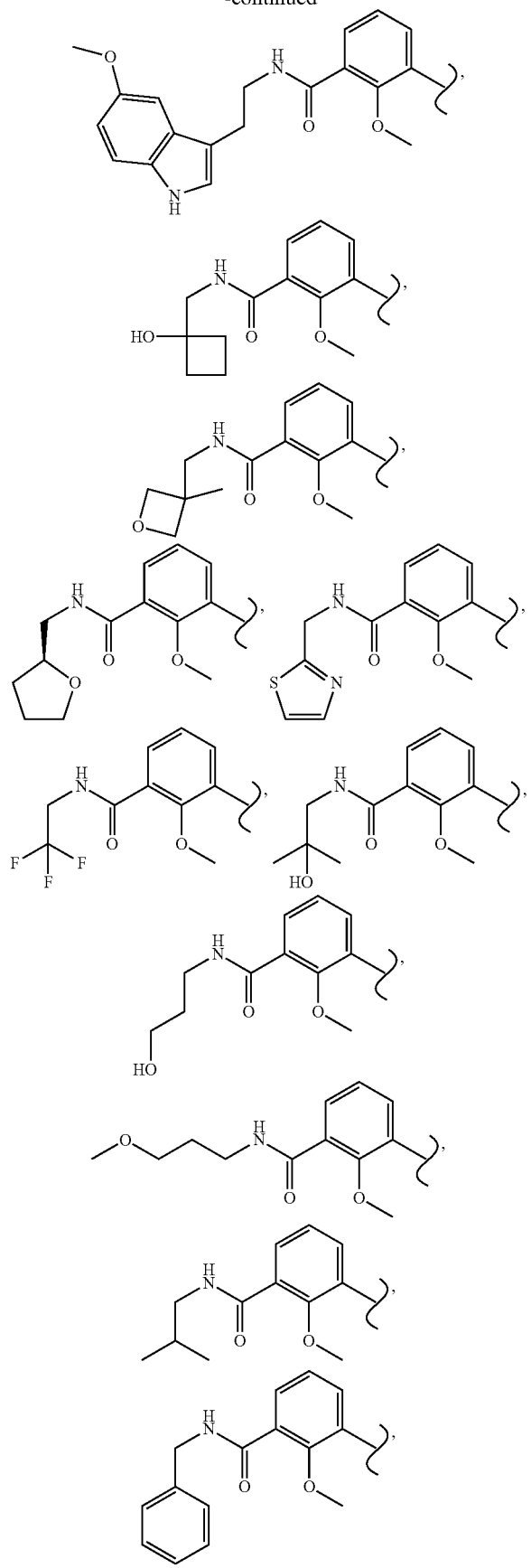
352
-continued
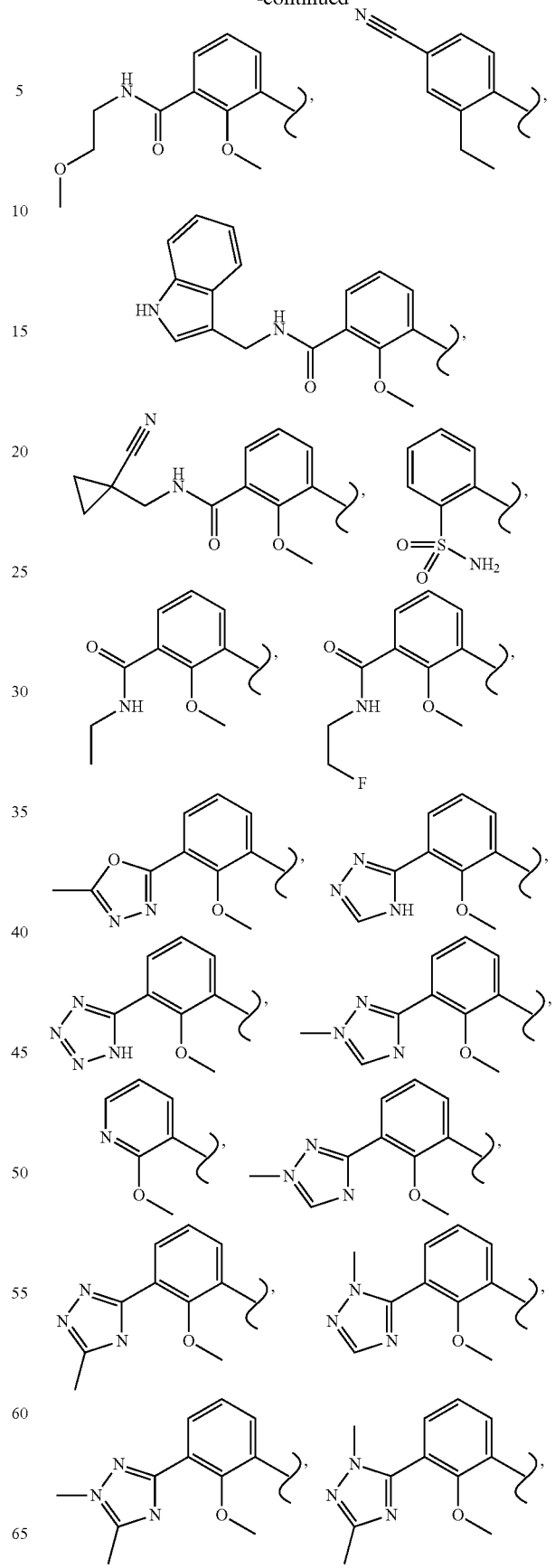

353
-continued
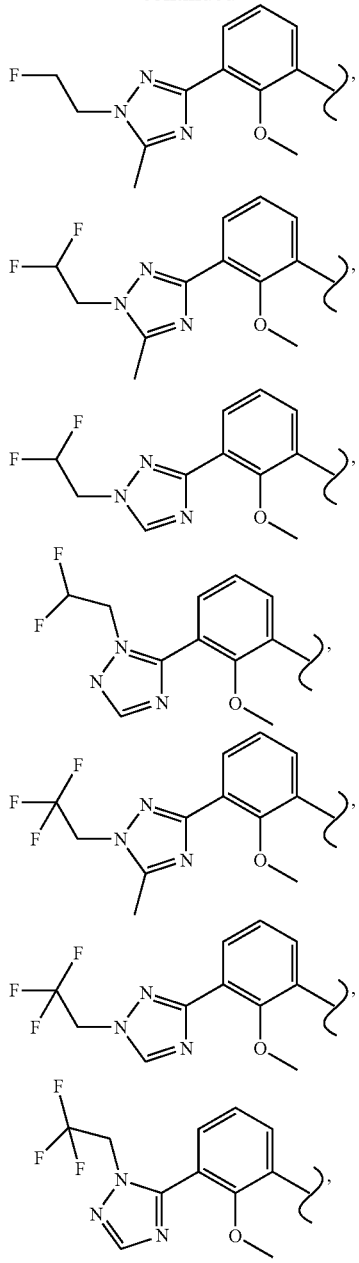
354
-continued
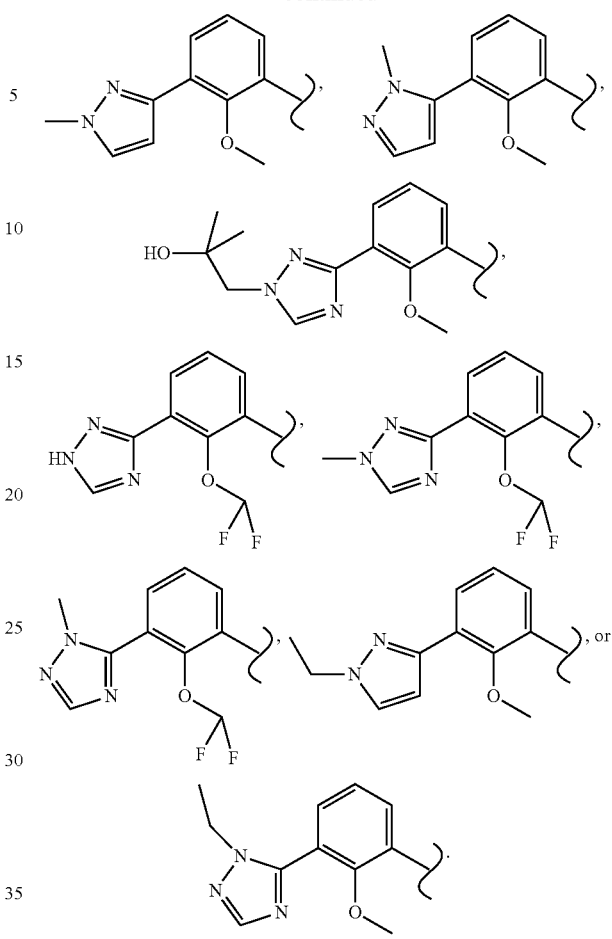
10. A compound of claim 1, or a stereoisomer or pharmaceutically-acceptable salt thereof, wherein $R^1$ is $CH_3$, $C_2H_5$, $CD_3$ or $CD_2CD_3$.
11. A pharmaceutical composition comprising a compound according to claim 1 and a pharmaceutically acceptable carrier or diluent.
* * * * *